US011672829B2

(12) United States Patent
Bhatnagar et al.

(10) Patent No.: US 11,672,829 B2
(45) Date of Patent: Jun. 13, 2023

(54) GENETICALLY ENGINEERED CORONAVIRUS-SPECIFIC EFFECTOR CELLS FOR IN SITU SYNTHESIS OF ANTIVIRAL PROTEINS

(71) Applicant: SRI International, Menlo Park, CA (US)

(72) Inventors: Parijat Bhatnagar, Belmont, CA (US); Marvin A. Ssemadaali, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 0 days.

(21) Appl. No.: 17/586,749

(22) Filed: Jan. 27, 2022

(65) Prior Publication Data

US 2022/0143093 A1 May 12, 2022

Related U.S. Application Data

(63) Continuation-in-part of application No. 15/263,078, filed on Sep. 12, 2016.

(60) Provisional application No. 62/249,986, filed on Nov. 3, 2015, provisional application No. 62/216,538, filed on Sep. 10, 2015, provisional application No. 63/255,380, filed on Oct. 13, 2021, provisional application No. 63/222,784, filed on Jul. 16, 2021, provisional application No. 63/142,315, filed on Jan. 27, 2021.

(51) Int. Cl.
| | |
|---|---|
| *A61K 35/17* | (2015.01) |
| *C07K 14/725* | (2006.01) |
| *C12N 5/0783* | (2010.01) |
| *A61P 31/12* | (2006.01) |
| *C07K 16/28* | (2006.01) |
| *A61K 38/00* | (2006.01) |

(52) U.S. Cl.
CPC .............. *A61K 35/17* (2013.01); *A61P 31/12* (2018.01); *C07K 14/7051* (2013.01); *C07K 16/2803* (2013.01); *C12N 5/0636* (2013.01); *A61K 38/00* (2013.01)

(58) Field of Classification Search
None
See application file for complete search history.

(56) References Cited

FOREIGN PATENT DOCUMENTS

| | | | |
|---|---|---|---|
| CN | 111675765 | * | 9/2020 |
| WO | 2016126608 A1 | | 8/2016 |

OTHER PUBLICATIONS

Chmielewski et al. Cancer Res. 2011, 71(17)5697-5706.*
Bhatnagar et al., "Imaging of Genetically Engineered T cells by PET using Gold Nanoparticles Complexed to Copper-64," Integrative Biology 5(1):231-238 (2013).
Bhatnagar et al., "Tumor Lysing Genetically Engineered T Cells Loaded with Multi-Modal Imaging Agents," Sci Rep. 4(4502):1-6 (Mar. 28, 2014).
Brenner et al., "Adoptive T cell Therapy of Cancer," Curr. Opin. Immunol. 22(2):251-257 (2010).
Chmielewski et al., "IL-12 Release by Engineered T Cells Expressing Chimeric Antigen Receptors Can Effectively Muster an Antigen-Independent Macrophage Response on Tumor Cells That Have Shut Down Tumor Antigen Expression," Cancer Res. 71(17):5697-5706; (Sep. 1, 2011).
Choi et al., "Current and emerging strategies for the prevention of graft-versus-host disease," Nat. Rev. Clin. Oncol. 11(9):536-547. (Sep. 2014).
Crabtree et al., "NFAT Signaling: Choreographing the Social Lives of Cells," Cell 109(2)(Suppl 1): S67-S79. (Apr. 2002).
Hinrichs et al. "Reassessing target antigens for adoptive T-cell therapy," Nat. Biotechnol. 31(11):999-1008. (Nov. 2013).
Kalos et al. "Adoptive T Cell Transfer for Cancer Immunotherapy in the Era of Synthetic Biology," Immunity 39:49-60. (Jul. 25, 2013).
Kershaw et al., "Gene-engineered T cells for cancer therapy," Nature Reviews: Cancer 13:525-541 (Aug. 2013) (Abstract).
Murphy et al., "Disparate Intracellular Processing of Human IL-12 Preprotein Subunits: Atypical Processing of the P35 Signal Peptide," J. Immunol 164:839-847 (2000).
Oh-Hora et al., "Calcium signaling in lymphocytes," Curr. Opin. Immunol. 20(3):250-258 (Jun. 2008).
Repellin et al., "Modular Antigen-Specific T-cell Biofactories for Calibrated In Vivo Synthesis of Engineered Proteins," Adv Biosyst, 2(12):1800210 (Dec. 2018).
Repellin et al., "NK-Cell Biofactory as an Off-the-Shelf Cell-based Vector for Targeted In Situ Synthesis of Engineered Proteins," Advanced BioSystems, 5(7): 2000398 (Jul. 2021).

(Continued)

*Primary Examiner* — James D Schultz
(74) *Attorney, Agent, or Firm* — Dicke, Billig & Czaja, PLLC

(57) ABSTRACT

An example genetically engineered effector cell comprises an exogenous polynucleotide sequence that includes a receptor element, an actuator element, and an effector element. The receptor element encodes a chimeric antigen receptor (CAR) comprising an extracellular antigen binding domain operably linked to a transmembrane domain, and an intracellular signaling domain, wherein the extracellular antigen binding domain recognizes an antigen on a surface of a Severe Acute Respiratory Syndrome Coronavirus 2 (SARS-CoV-2)-infected cell. The actuator element encodes a transcription factor binding site that upregulates synthesis of an antiviral protein. The effector element encodes the antiviral protein operably linked to a signal peptide, wherein, in response to the antigen binding domain of the CAR binding to the antigen of SARS-CoV-2-infected cell, the engineered effector cell is configured to activate and, to synthesize and secrete the antiviral protein.

19 Claims, 47 Drawing Sheets
(41 of 47 Drawing Sheet(s) Filed in Color)
Specification includes a Sequence Listing.

(56) References Cited

OTHER PUBLICATIONS

Roybal et al., "Engineering T Cells with Customized Therapeutic Response Programs Using Synthetic Notch Receptors," Cell 167:419-432, (Oct. 6, 2016).
Sadelain et al., "The basic principles of chimeric antigen receptor design," Cancer Discov. 3(4):388-398. (Apr. 2, 2013).
Schmidt et al., "Peptide Inhibitors of Flavivirus Entry Derived from the E Protein Stem," J. Virol. 84(24):12549-12554, (Dec. 2010).
Sharma et al., "Dephosphorylation of the nuclear factor of activated T cells (NFAT) transcription factor is regulated by an RNA-protein scaffold complex," PNAS 108(28):11381-11386 (Jul. 12, 2011).
Song et al., "In vivo rersistence, tumor localization, and antitumor activity of CAR engineered T cells Is enhanced by costimulatory signaling through CD137 (4-1BB)," Cancer Res 71(13):4617-4627 (Jul. 1, 2011).

* cited by examiner

SEQUENCE LISTING

<160> NUMBER OF SEQ ID NOS: 56

<210> SEQ ID NO 1
<211> LENGTH: 3819
<212> TYPE: DNA
<213> ORGANISM: Artificial sequence
<220> FEATURE:
<223> OTHER INFORMATION: Synthetic

<400> SEQUENCE: 1

| | | | | | |
|---|---|---|---|---|---|
| atgtttgtct | tcctcgtcct | cctgcctctc | gtttcttctc | agtgtgtgaa | cctcacaact | 60 |
| cgcactcagc | tgcctcctgc | ttacacaaac | agcttcacta | gaggcgtcta | ctacccagac | 120 |
| aaggtcttca | ggtcctctgt | cctgcactcc | acccaggatc | tgttcctccc | attctttagc | 180 |
| aatgtcacat | ggttccatgc | tatccatgtg | agcggaacta | atggtacaaa | gaggttcgac | 240 |
| aaccctgtgc | tcccttcaa | tgatggcgtc | tactttgcct | ccacagagaa | atctaacatc | 300 |
| attagaggtt | ggatcttcgg | cacaactctg | gacagcaaga | cccagagcct | cctgatcgtg | 360 |
| aacaacgcta | caaatgtcgt | catcaaggtg | tgcgagtttc | aattctgtaa | tgatcccttc | 420 |
| ctgggagtgt | actaccacaa | gaacaacaag | tcttggatgg | agtccgagtt | cagagtgtac | 480 |
| tcctctgcca | caattgtac | tttcgaatac | gtgtcccagc | cttcctcat | ggatctggag | 540 |
| ggtaaacagg | gaaacttcaa | gaacctgaga | gagttcgtgt | tcaagaacat | cgacggctac | 600 |
| ttcaagatct | acagcaaaca | cactccaatc | aatctggtga | gggacctccc | tcagggtttc | 660 |
| tccgctctgg | aacctctcgt | ggatctccct | attggcatca | acattactag | atttcagacc | 720 |
| ctcctggcac | tgcaccgctc | ttatctgaca | ccaggcgact | cttctagcgg | ttggactgca | 780 |
| ggtgctgcag | cctactacgt | gggataccctc | caacctcgca | ccttcctgct | gaagtacaac | 840 |
| gagaacggca | ctatcacaga | tgccgtggat | tgtgcactgg | accctctcag | cgagacaaag | 900 |
| tgtacactga | agagctttac | tgtggagaag | ggtatctatc | agacctctaa | cttcagggtt | 960 |
| cagcccaccg | agtctattgt | gaggttccca | acattacta | acctctgtcc | ctttggcgag | 1020 |
| gtcttcaacg | ccacaagatt | cgcttctgtg | tatgcttgga | acagaaagag | gatttccaat | 1080 |
| tgtgttgccg | actattccgt | cctctacaac | tccgcttctt | tctctacatt | caagtgctat | 1140 |
| ggcgtgagcc | ctaccaagct | caacgacctg | tgctttacaa | atgtctatgc | cgacagcttc | 1200 |
| gtgatcagag | gtgacgaggt | caggcagatc | gctcctggtc | aaacaggaaa | gattgccgac | 1260 |
| tacaactaca | aactgccaga | cgatttcact | ggctgtgtga | tcgcctggaa | tagcaacaac | 1320 |
| ctggatagca | agttggagg | caactacaac | tacctgtaca | gactgtttag | gaagagcaac | 1380 |
| ctgaagccat | ttgagagaga | cattagcacc | gaaatctacc | aagctggcag | cactccctgt | 1440 |
| aatggagttg | agggcttcaa | ctgctacttc | cctctgcagt | cttatggctt | ccagcccact | 1500 |
| aatggcgttg | ctaccaacc | ttacagggtc | gtggtcctca | gcttcgagct | gctgcacgct | 1560 |
| ccagctaccg | tctgtggtcc | caagaaatct | accaacctgg | tgaagaacaa | gtgtgttaac | 1620 |
| ttcaacttca | acggactgac | cggaaccgga | gtgctgaccg | agagcaacaa | gaagttcctc | 1680 |
| ccattccaac | agttcggaag | agatatcgct | gatactacag | acgctgtgag | agatccacag | 1740 |
| accctggaga | tcctggacat | cacaccctgc | tcctttggtg | gagtgtccgt | gattacacct | 1800 |
| ggtacaaaca | cctctaacca | ggtcgctgtg | ctgtaccagg | acgttaactg | cacagaagtt | 1860 |
| cccgttgcta | ttcacgcaga | ccagctgaca | ccaacttgga | gggtctactc | cactggctcc | 1920 |
| aacgtcttcc | aaaccagagc | tggatgcctc | atcggtgccg | agcacgtcaa | caacagctac | 1980 |
| gaatgtgaca | tcccaattgg | agcaggaatc | tgtgcctcct | atcagacaca | gaccaactct | 2040 |
| cccaggagag | ctaggtctgt | tgccagccag | tccatcatcg | cttacaccat | gagcctcgga | 2100 |
| gcagagaaca | gcgtggctta | cagcaacaat | tccattgcca | tcccaaccaa | cttcaccatt | 2160 |
| agcgttacta | ccgagattct | gcctgttagc | atgaccaaga | cttccgtcga | ttgcaccatg | 2220 |

```
tacatttgtg gtgatagcac cgagtgctct aatctgctgc tccagtacgg ttccttctgt    2280
acccagctca ataggctct gacaggcatc gcagtggaac aggacaagaa cactcaagaa    2340
gtgttcgctc aggtgaagca aatctacaag acacctccca tcaaggactt tggaggcttc    2400
aacttcagcc agatcctgcc tgacccaagc aagccatcca gcgctcctt cattgaggac    2460
ctgctcttca caaggtgac actggcagac gctggcttca tcaagcagta cggagactgc    2520
ctgggagata tcgcagctag ggacctgatt tgtgctcaga gttcaacgg tctgactgtg    2580
ctgcctcctc tgctcaccga cgaaatgatc gctcagtaca aagcgcact gctcgctggc    2640
accattacct ctggctggac attcggagct ggagctgctc tccagatccc tttcgccatg    2700
cagatggcct acaggttcaa cggaattggc gttactcaga atgtgctgta tgagaatcag    2760
aaactgatcg ccaaccagtt caactccgct attggaaaga tccaggattc cctctccagc    2820
acagcctctg ctctgggaaa gctccaagat gttgtcaacc agaacgctca agctctcaac    2880
accctcgtga agcagctgtc ctctaacttt ggtgccatct ccagcgtgct gaacgacatt    2940
ctgtccaggc tcgacaaagt ggaagccgag gttcaaatcg acaggctcat tactggcaga    3000
ctccagagcc tgcaaaccta cgtcacccag cagctgatta gggcagcaga gatcagggct    3060
tctgctaacc tggctgctac caagatgtcc gaatgcgtcc tgggtcagtc caagagggtt    3120
gacttctgtg gtaagggata ccacctgatg tccttcccac agtccgctcc acacggagtg    3180
gtgtttctcc atgtcactta cgtgcctgcc caggagaaga ctttaccac agcacctgct    3240
atctgtcacg acggtaaagc ccatttccca cgcgaaggcg tcttcgtttc caacggtaca    3300
cactggtttg tgactcaaag aaacttctac gagcctcaga tcatcaccac tgacaacaca    3360
ttcgtctctg gcaattgtga cgtcgtcatc ggaattgtga acaataccgt gtacgatcct    3420
ctgcagccag aactcgattc tttcaaggag gagctggaca agtacttcaa gaaccacacc    3480
tctcccgatg tggacctcgg tgacatttct ggtatcaacg cttctgtggt caacatccag    3540
aaggagatcg acaggctcaa cgaggttgca aagaatctca acgaatccct cattgatctg    3600
caggagctgg gaaagtatga gcaatacatc aagtggcctt ggtacatctg gctgggattc    3660
atcgctggac tcatcgctat cgtgatggtc actatcatgc tctgttgcat gacctcttgt    3720
tgtagctgtc tgaaaggatg ttgctcctgt ggatcttgtt gtaagttcga cgaggatgac    3780
tccgaacctg ttctcaaggg tgtcaaactg cactacact                          3819
```

```
<210> SEQ ID NO 2
<211> LENGTH: 3765
<212> TYPE: DNA
<213> ORGANISM: Artificial Sequence
<220> FEATURE:
<223> OTHER INFORMATION: Synthetic

<400> SEQUENCE: 2
```

```
atgttcatct ttttgctgtt cctgactctg accagtggta gtgatctgga tcgctgtacc      60
acattcgatg atgtgcaggc tcccaactac acacagcata cctccagtat gagaggagtg     120
tattaccctg acgaaatttt ccgctccgat accttgtacc tgacacagga cctcttcttg     180
cctttttatt ccaatgtcac cggctttcat acgatcaatc atacattcga caatcctgtg     240
attcccttca aggatggcat ttatttcgca gctacggaaa agtctaacgt ggtccgcggg     300
tgggtattcg gaagcaccat gaataataag tcacagtctg ttatcatcat caataatagt     360
actaatgttg taatccgcgc ttgcaacttt gaactgtgcg ataatccctt cttcgcagta     420
agcaagccca tggggacaca gactcacacg atgattttg acaatgcctt caattgtacg     480
```

-continued

| | |
|---|---|
| tttgagtaca tttctgatgc cttcagcttg gacgtgagcg agaaatctgg aaacttcaaa | 540 |
| caccttcgcg agttcgtgtt taaaaacaaa gacgggttct tgtacgtata taagggctat | 600 |
| cagcctattg acgtagttcg ggacttgccg agcgggttta atactctcaa acctatcttc | 660 |
| aagctccccc tgggaattaa cataactaat ttccgcgcaa tcctgacggc atttagccca | 720 |
| gcacaggata cttggggaac ctccgccgca gcctacttcg tgggctatct gaagcctacc | 780 |
| accttcatgc tgaagtacga tgagaatggc acgatcactg atgctgttga ctgttcacag | 840 |
| aaccccctcg ctgagctgaa gtgcagcgtg aagtcctttg agatcgacaa ggggatatac | 900 |
| cagacgagta actttcgcgt cgtcccttcc ggtgatgttg tgcgctttcc gaatattacc | 960 |
| aatctgtgcc cgtttggaga ggtctttaac gctacaaagt tcccctctgt gtacgcttgg | 1020 |
| gagaggaaga aaatatccaa ttgcgttgct gactattccg tattgtataa ctccaccttc | 1080 |
| ttttcaactt ttaaatgcta tggggtgtcc gctaccaaat tgaacgatct gtgtttttca | 1140 |
| aacgttatg ccgactcttt tgtagtgaaa ggtgacgacg tgcgccaaat cgctcctggg | 1200 |
| caaaccggcg tcatcgctga ttacaattac aagctccctg atgacttcat ggggtgcgtg | 1260 |
| ctcgcttgga atacgcgaaa tatagatgcc acatcaaccg ggaactacaa ctacaaatat | 1320 |
| cgctatttgc ggcacggaaa attgcgcccc ttcgaacggg atatatctaa cgtgcccttc | 1380 |
| agcccggatg ggaaaccgtg cactccgcct gcacttaact gttactggcc cctgaacgac | 1440 |
| tatggctttt acacaactac tggcatcgga tatcagccct ataggggttgt agtgctgagc | 1500 |
| ttcgagctgc tgaacgcccc tgctacggtg tgtggaccca agctgagcac ggatctgatc | 1560 |
| aaaaatcaat gcgtgaactt caatttaac ggccttactg gtaccggcgt gctcacacca | 1620 |
| tcaagcaaac ggtttcaacc ctttcagcaa ttcggaagag acgtaagcga cttcacggat | 1680 |
| tccgtcagag atcctaaaac aagcgagata ctggatatct ccccttgctc cttcggcggc | 1740 |
| gttagcgtga ttacacctgg aaccaatgcg agctccgaag tagctgtgct ctaccaggat | 1800 |
| gttaactgca cggacgtaag taccgccatc catgccgacc aactcacccc agcttggagg | 1860 |
| atatactcta cggggaacaa tgtgttccag acacaagcag gatgcttgat tggtgctgag | 1920 |
| cacgttgata cctcttatga atgcgacata cccatagggg ccggtatatg cgcctcatat | 1980 |
| cataccgtct ccctgctgcg gtccaccagt cagaaatcaa tcgttgcata caccatgagc | 2040 |
| ctgggcgcag actcatccat tgcctatagc aataatacta tcgcaatccc aacaaatttc | 2100 |
| agtatcagca taactaccga ggtcatgcca gtgtcaatgg caaaaacctc tgttgactgc | 2160 |
| aacatgtaca tctgtggcga ttccacagag tgtgctaatt tgctgttgca atacgggtct | 2220 |
| ttttgcaccc agttgaacag ggccctgagc ggaatcgcgg ccgagcagga tagaaacacc | 2280 |
| cgagaggtct tcgcccaggt caagcagatg tataagactc caactctgaa atacttcggc | 2340 |
| gggtttaact ttctctcaaat tctgcccgat cctctgaaac ccacaaagag atcattcatc | 2400 |
| gaagatctcc tgttcaataa ggtgaccctc gccgatgccg gcttcatgaa acaatacggc | 2460 |
| gaatgtctgg gggatatcaa cgcccgcgac ctgatctgtg cccaaaagtt caatggactg | 2520 |
| acagtgcttc cccctctgct tacggatgac atgattgctg catacactgc tgccctcgtc | 2580 |
| tctggcaccg ccactgctgg gtggaccttc ggcgcagggg cagccctgca gatcccctt | 2640 |
| gccatgcaga tggcttacag attcaatggt attggcgtca cgcagaacgt cctctatgaa | 2700 |
| aaccagaaac agattgccaa ccagttcaat aaagcgatca gtcaaattca ggagagcctg | 2760 |
| actaccacca gcactgctct gggaaagctc caggatgtgg tcaatcagaa tgcccaggcc | 2820 |

```
ctcaatactt tggtgaaaca actttctagc aattttggcg caatttcatc tgttcttaat    2880
gacattctgt caagactgga caaggtagag gctgaggttc aaatagatag gcttattaca    2940
ggacgcctgc agagcctgca gacttacgtt acgcagcagc tgattagggc agccgagatc    3000
cgcgctagtg ccaacctggc tgcgactaaa atgtccgagt gcgtcttggg ccaatccaaa    3060
cgcgtagact tttgcggaaa agggtaccat ctgatgtcct ttccccaggc tgcgcctcac    3120
ggtgttgtct tcctgcacgt gacctatgtg ccctcccagg aaagaaactt caccaccgca    3180
cctgccattt gtcacgaggg taaggcttac tttccccgcg agggtgtgtt tgtatttaat    3240
gggactagct ggttcatcac acagcgcaat ttcttctctc cccagatcat cacaaccgac    3300
aatacattcg tctcaggaaa ctgtgacgtg gtgattggaa tcatcaacaa taccgtgtac    3360
gaccctcttc agcccgaact cgattcattc aaggaagaac tcgacaagta ctttaagaac    3420
catacttctc ccgacgtgga tctcggggac atttctggaa taaatgctag tgtcgtaaat    3480
attcagaagg agatagaccg cctgaatgaa gtcgcaaaga atctcaatga aagcctcatc    3540
gacctgcaag agctggggaa gtacgagcag tatatcaaat ggccatggta cgtgtggctt    3600
gggtttatcg caggcctgat cgctatagtg atggtgacta tcctcctgtg ctgtatgacc    3660
tcatgttgtt cctgtctgaa gggcgcatgc agctgtgggc cttgttgtaa atttgacgaa    3720
gatgattcag aacccgtttt gaaggggggtc aaattgcact acacc             3765
```

<210> SEQ ID NO 3
<211> LENGTH: 381
<212> TYPE: DNA
<213> ORGANISM: Artificial Sequence
<220> FEATURE:
<223> OTHER INFORMATION: Synthetic
<400> SEQUENCE: 3

```
caagtgcaac tgcaggaatc tggaggtggc ctcgtgcaag ctggaggcag cctgaggctg      60
agctgtgctg catccggtcg cacctttagc gagtatgcaa tgggttggtt cgccaggca     120 ccaggtaagg agagggagtt tgtggcaacc atctcctggt ctggtggctc cacatactac     180
acagattccg tcaagggaag attcactatc tccagggaca acgcaaagaa cacagtgtat     240
ctgcagatga atagcctcaa gccagatgac acagccgtct actattgcgc tgcagctggt     300
ctgggcaccg tggtgtccga atgggattac gactacgatt actggggtca aggcactcag     360
gtgactgtgt ctagcggtag c                                              381
```

<210> SEQ ID NO 4
<211> LENGTH: 600
<212> TYPE: DNA
<213> ORGANISM: Artificial Sequence
<220> FEATURE:
<223> OTHER INFORMATION: Synthetic
<400> SEQUENCE: 4

```
atgaaactcg atatgactgg tgattgtact cctgttctgg tgctgatggc tgctgtgctc      60
actgttactg gtgccgtccc tgtggccaga ctgcacggag ccctccctga cgctagagga     120
tgccacatcg ctcagttcaa gtctctctct cctcaggaac tccaagcctt caagagagca     180
aaggatgctc tggaggaaag cctgctgctg aaagactgca gatgtcattc cagactgttt     240
cctagaacat gggacctcag gcagctgcag gtcaggagaa ggccaatggc tctggaggct     300
gagctggcac tcacactcaa agtgctcgaa gctaccgctg acaccgaccc agccctcgtt     360
gatgtcctcg atcagcctct gcacacactg caccacatcc tctcccagtt cagggcatgt     420
```

```
atccagcctc agcctactgc aggaccacgc actagaggaa gactccatca ctggctgtac    480
aggctgcagg aagcaccaaa gaaagagagc cctggatgcc tggaagcttc cgtcactttc    540
aatctgttca gactgctgac tagggacctg aactgtgtcg caagcggtga tctgtgcgtg    600
```

<210> SEQ ID NO 5
<211> LENGTH: 600
<212> TYPE: DNA
<213> ORGANISM: Artificial Sequence
<220> FEATURE:
<223> OTHER INFORMATION: Synthetic

<400> SEQUENCE: 5

```
atggctgcag cttggacagt tgttctcgtt acactcgttc tgggtctggc tgtggctggt     60
cctgtgccta cctccaaacc taccacaaca ggtaagggtt gtcacattgg acgcttcaaa    120
tccctcagcc acaggagct ggcctccttc aagaaagcta gagatgccct cgaagagagc    180
ctgaaactca gaactggtc ctgttctagc ccagtgttcc caggaaactg ggacctgagg    240
ctcctccaag ttcgcgagag gccagtggca ctggaggcag agctggctct cactctcaaa    300
gttctggagg ctgctgctgg accagctctg gaagacgtgc tcgaccagcc actgcatact    360
ctgcaccata tcctgagcca actgcaggct tgcatccagc cacagcctac agcaggtcct    420
agacccagag gtcgcctgca ccactggctg cacaggctcc aagaagctcc aaagaaggag    480
tctgcaggtt gcctggaggc cagcgttaca ttcaatctgt tcagactcct gactagggat    540
ctgaagtacg tggcagacgg taatctgtgt ctgcgcacct ctactcatcc cgagagcact    600
```

<210> SEQ ID NO 6
<211> LENGTH: 498
<212> TYPE: DNA
<213> ORGANISM: Artificial Sequence
<220> FEATURE:
<223> OTHER INFORMATION: Synthetic

<400> SEQUENCE: 6

```
atgtgtgatc tgcctcagac ccatagcctg ggctccagaa gaaccctgat gctgctggct     60
caaatgagac gcatttccct gttctcctgt ctgaaggaca gacacgactt tggcttccct    120
caagaagagt ttggaaacca attccagaag gctgagacaa tcccagtcct gcacgaaatg    180
atccaacaaa tcttcaatct gttctccacc aaggattcct ctgctgcttg ggacgagaca    240
ctcctcgaca gttctatac cgaactctat cagcaactga cgatctcga agcctgcgtg    300 atccaaggtg tgggtgtgac cgaaactcca ctgatgaagg aagatagcat cctggcagtg    360
aggaagtact ccaaaggat cactctctat ctgaaggaga agaagtactc tccatgcgca    420
tgggaagttg tgagagctga gatcatgcgc tctttcagcc tgagcaccaa cctccaggaa    480
tccctcaggt ctaaagag                                                  498
```

<210> SEQ ID NO 7
<211> LENGTH: 561
<212> TYPE: DNA
<213> ORGANISM: Artificial Sequence
<220> FEATURE:
<223> OTHER INFORMATION: Synthetic

<400> SEQUENCE: 7

```
atgactaaca aatgtctcct ccagattgca ctgctgctgt gtttctctac cactgctctc     60
tccatgagct acaacctgct gggcttcctc caacgctcct ccaactttca atgtcagaaa    120
```

```
ctcctgtggc agctgaatgg tcgcctcgaa tactgcctca aggataggat gaacttcgac    180
atccctgagg aaatcaaaca gctccagcaa ttccagaagg aagatgcagc tctgaccatc    240
tatgagatgc tccagaacat cttcgctatc tttagacaag actcctccag cacaggatgg    300
aatgagacaa tcgttgagaa cctgctcgct aacgtctacc atcagatcaa ccacctgaag    360
accgtgctgg aggagaagct ggagaaggaa gactttacca gaggcaagct gatgagcagc    420
ctgcacctga gaggtacta cggcagaatc ctgcactatc tgaaggccaa ggaatactcc    480
cattgcgcat ggaccattgt cagagtggag atcctccgca acttctactt catcaacagg    540
ctgactggct acctgagaaa c                                              561

<210> SEQ ID NO 8
<211> LENGTH: 1650
<212> TYPE: DNA
<213> ORGANISM: Artificial Sequence
<220> FEATURE:
<223> OTHER INFORMATION: Synthetic

<400> SEQUENCE: 8
atggaagatg ccaaaaacat taagaagggc ccagcgccat tctacccact cgaagacggg     60
accgccggcg agcagctgca caaagccatg aagcgctacg ccctggtgcc cggcaccatc    120
gcctttaccg acgcacatat cgaggtggac attacctacg ccgagtactt cgagatgagc    180
gttcggctgg cagaagctat gaagcgctat gggctgaata caaaccatcg gatcgtggtg    240
tgcagcgaga atagcttgca gttcttcatg cccgtgttgg gtgccctgtt catcggtgtg    300
gctgtggccc cagctaacga catctacaac gagcgcgagc tgctgaacag catgggcatc    360
agccagccca ccgtcgtatt cgtgagcaag aaagggctgc aaaagatcct caacgtgcaa    420
aagaagctac cgatcataca aaagatcatc atcatggata gcaagaccga ctaccagggc    480
ttccaaagca tgtacacctt cgtgacttcc catttgccac ccggcttcaa cgagtacgac    540
ttcgtgcccg agagcttcga ccgggacaaa accatcgccc tgatcatgaa cagtagtggc    600
agtaccggat tgcccaaggg cgtagcccta ccgcaccgca ccgcttgtgt ccgattcagt    660
catgcccgcg accccatctt cggcaaccag atcatccccg acaccgctat cctcagcgtg    720
gtgccatttc accacggctt cggcatgttc accacgctgg gctacttgat ctgcggcttt    780
cgggtcgtgc tcatgtaccg cttcgaggag gagctattct tgcgcagctt gcaagactat    840
aagattcaat tgcccctgct ggtgcccaca ctatttagct tcttcgctaa gagcactctc    900
atcgacaagt acgacctaag caacttgcac gagatcgcca cggcggggc gccgctcagc    960 aaggaggtag gtgaggccgt ggccaaacgc ttccacctac caggcatccg ccagggctac   1020
ggcctgacag aaacaaccag cgccattctg atcacccccg aaggggacga caagcctggc   1080
gcagtaggca aggtggtgcc cttcttcgag gctaaggtgg tggacttgga caccggtaag   1140
acactgggtg tgaaccagcg cggcgagctg tgcgtccgtg gccccatgat catgagcggc   1200
tacgttaaca accccgaggc tacaaacgct ctcatcgaca ggacggctg gctgcacagc   1260 ggcgacatcg cctactggga cgaggacgag cacttcttca tcgtggaccg gctgaagagc   1320
ctgatcaaat acaagggcta ccaggtagcc ccagccgaac tggagagcat cctgctgcaa   1380
caccccaaca tcttcgacgc cgggtcgcc ggcctgcccg acgacgatgc cggcgagctg   1440
cccgccgcag tcgtcgtgct ggaacacggt aaaaccatga ccgagaagga tatcgtggac   1500
tatgtggcca gccaggttac aaccgccaag aagctgcgcg gtggtgttgt gttcgtggac   1560
gaggtgccta aaggactgac cggcaagttg gacgcccgca agatccgcga gattctcatt   1620
```

```
aaggccaaga agggcggcaa gatcgccgtg                                       1650

<210> SEQ ID NO 9
<211> LENGTH: 678
<212> TYPE: DNA
<213> ORGANISM: Artificial Sequence
<220> FEATURE:
<223> OTHER INFORMATION: Synthetic

<400> SEQUENCE: 9
atggatagca ctgagaacgt catcaagccc ttcatgcgct tcaaggtgca catggagggc        60
tccgtgaacg gccacgagtt cgagatcgag ggcgtgggcg agggcaagcc ctacgagggc       120
acccagaccg ccaagctgca agtgaccaag ggcggccccc tgcccttcgc ctgggacatc       180
ctgtcccccc agttcttcta cggctccaag gcgtacatca agcaccccgc cgacatcccc       240
gactacctca gcagtccttc ccccgagggc ttcaagtggg agcgcgtgat gaacttcgag       300
gacggcggcg tggtgaccgt gacccaggac tcctccctgc aggacggcac cctcatctac       360
cacgtgaagt tcatcggcgt gaacttcccc tccgacggcc ccgtaatgca aagaagact        420 ctgggctggg agccctccac tgagcgcaac taccccgcg acggcgtgct gaagggcgag        480
aaccacatgg cgctgaagct gaagggcggc ggccactacc tgtgtgagtt caagtccatc       540
tacatggcca agaagcccgt gaagctgccc ggctaccact acgtggacta caagctcgac       600
atcacctccc acaacgagga ctacaccgtg gtggagcagt acgagcgcgc cgaggcccgc       660
caccacctgt tccagtaa                                                    678

<210> SEQ ID NO 10
<211> LENGTH: 2391
<212> TYPE: DNA
<213> ORGANISM: Artificial Sequence
<220> FEATURE:
<223> OTHER INFORMATION: Synthetic

<400> SEQUENCE: 10
atggaagatg ccaaaaacat taagaagggc ccagcgccat tctacccact cgaagacggg        60
accgccggcg agcagctgca caagccatg aagcgctacg ccctggtgcc cggcaccatc       120
gcctttaccg acgcacatat cgaggtggac attacctacg ccgagtactt cgagatgagc       180
gttcggctgg cagaagctat gaagcgctat gggctgaata caaaccatcg gatcgtggtg       240
tgcagcgaga atagcttgca gttcttcatg cccgtgttgg gtgccctgtt catcggtgtg       300
gctgtggccc cagctaacga catctacaac gagcgcgagc tgctgaacag catgggcatc       360
agccagccca ccgtcgtatt cgtgagcaag aaagggctgc aaaagatcct caacgtgcaa       420
aagaagctac cgatcatac aaagatcatc atcatggata gcaagaccga ctaccagggc       480
ttccaaagca tgtacacctt cgtgacttcc catttgccac ccggcttcaa cgagtacgac       540
ttcgtgcccg agagcttcga ccgggacaaa accatcgccc tgatcatgaa cagtagtggc       600
agtaccggat tgcccaaggg cgtagcccta ccgcaccgca ccgcttgtgt ccgattcagt       660
catgcccgcg accccatctt cggcaaccag atcatccccg acaccgctat cctcagcgtg       720
gtgccatttc accacggctt cggcatgttc accacgctgg ctacttgat ctgcggcttt       780 cgggtcgtgc tcatgtaccg cttcgaggag gagctattct tgcgcagctt gcaagactat       840
aagattcaat ctgcccctgct ggtgcccaca ctatttagct tcttcgctaa gagcactctc       900
atcgacaagt acgacctaag caacttgcac gagatcgcca cggcgggggc gccgctcagc       960
```
aaggaggtag gtgaggccgt ggccaaacgc ttccacctac caggcatccg ccagggctac    1020
ggcctgacag aaacaaccag cgccattctg atcaccccg aaggggacga caagcctggc    1080
gcagtaggca aggtggtgcc cttcttcgag gctaaggtgg tggacttgga caccggtaag    1140
acactgggtg tgaaccagcg cggcgagctg tgcgtccgtg gccccatgat catgagcggc    1200
tacgttaaca accccgaggc tacaaacgct ctcatcgaca aggacggctg gctgcacagc    1260
ggcgacatcg cctactggga cgaggacgag cacttcttca tcgtggaccg gctgaagagc    1320
ctgatcaaat acaagggcta ccaggtagcc ccagccgaac tggagagcat cctgctgcaa    1380 cacccaaca tcttcgacgc cggggtcgcc ggcctgcccg acgacgatgc cggcgagctg    1440
cccgccgcag tcgtcgtgct ggaacacggt aaaaccatga ccgagaagga gatcgtggac    1500
tatgtggcca gccaggttac aaccgccaag aagctgcgcg tggtgttgt gttcgtggac    1560 gaggtgccta aaggactgac cggcaagttg gacgcccgca agatccgcga gattctcatt    1620
aaggccaaga agggcggcaa gatcgccgtg ggaagcggag ctactaactt cagcctgctg    1680
aagcaggctg gagacgtgga ggagaaccct ggacctatgg atagcactga aacgtcatc    1740 aagcccttca tgcgcttcaa ggtgcacatg gagggctccg tgaacggcca cgagttcgag    1800
atcgagggcg tgggcgaggg caagcccctac gagggcaccc agaccgccaa gctgcaagtg    1860
accaagggcg gcccctgcc cttcgcctgg gacatcctgt ccccccagtt cttctacggc    1920
tccaaggcgt acatcaagca ccccgccgac atccccgact acctcaagca gtccttcccc    1980
gagggcttca gtgggagcg cgtgatgaac ttcgaggacg gcggcgtggt gaccgtgacc    2040
caggactcct ccctgcagga cggcaccctc atctaccacg tgaagttcat cggcgtgaac    2100
ttcccctccg acggccccgt aatgcagaag aagactctgg gctgggagcc ctccactgag    2160
cgcaactacc ccgcgacgg cgtgctgaag ggcgagaacc acatggcgct gaagctgaag    2220
ggcggcggcc actacctgtg tgagttcaag tccatctaca tggccaagaa gcccgtgaag    2280
ctgcccggct accactacgt ggactacaag ctcgacatca cctcccacaa cgaggactac    2340
accgtggtgg agcagtacga gcgcgccgag gcccgccacc acctgttcca g    2391

<210> SEQ ID NO 11
<211> LENGTH: 666
<212> TYPE: DNA
<213> ORGANISM: Artificial Sequence
<220> FEATURE:
<223> OTHER INFORMATION: Synthetic

<400> SEQUENCE: 11
atgcctgcca tgaagattga gtgccgcatc acgggaaccc tgaacggagt ggagtttgag     60
ctggtcggag gtggagaagg gactcctgag cagggacgta tgaccaacaa gatgaagtct    120
accaagggcg ccttgacctt ctcccccctac cttctctctc atgtcatggg atacgggttc    180
taccactttg gtacctatcc cagtgggtat gagaatccct tcctgcatgc catcaacaac    240 gggggtaca ccaacaccag gattgagaag tatgaggatg gaggagttct tcatgttagc    300
tttagctaca gatatgaagc aggcagggtg attgggatt tcaaggttgt cgggacagga    360
ttccctgagg acagtgtgat cttcaccgac aagatcatcc ggtccaatgc taccgtggag    420
cacttgcacc caatgggaga caacgttctt gtgggctcct tcgcgagaac ctttccctg    480 agggatggag gctactactc atttgtggtt gacagccaca tgcacttcaa gagtgccatc    540
cacccatcca tcctccagaa cggggggccc atgtttgcct tcaggagagt tgaggaactt    600
cactccaaca ctgaacttgg cattgtagag tatcaacatg ccttcaagac tcccatagca    660

| | |
|---|---|
| tttgct | 666 |

<210> SEQ ID NO 12
<211> LENGTH: 513
<212> TYPE: DNA
<213> ORGANISM: Artificial Sequence
<220> FEATURE:
<223> OTHER INFORMATION: Synthetic

<400> SEQUENCE: 12

| | |
|---|---|
| atggtcttca cactcgaaga tttcgttggg gactggcgac agacagccgg ctacaacctg | 60 |
| gaccaagtcc ttgaacaggg aggtgtgtcc agtttgtttc agaatctcgg ggtgtccgta | 120 |
| actccgatcc aaaggattgt cctgagcggt gaaaatgggc tgaagatcga catccatgtc | 180 |
| atcatcccgt atgaaggtct gagcggcgac caaatgggcc agatcgaaaa aatttttaag | 240 |
| gtggtgtacc ctgtggatga tcatcacttt aaggtgatcc tgcactatgg cacactggta | 300 |
| atcgacgggg ttacgccgaa catgatcgac tatttcggac ggccgtatga aggcatcgcc | 360 |
| gtgttcgacg gcaaaaagat cactgtaaca gggaccctgt ggaacggcaa caaaattatc | 420 |
| gacgagcgcc tgatcaaccc cgacggctcc ctgctgttcc gagtaaccat caacggagtg | 480 |
| accggctggc ggctgtgcga acgcattctg gcg | 513 |

<210> SEQ ID NO 13
<211> LENGTH: 57
<212> TYPE: DNA
<213> ORGANISM: Artificial Sequence
<220> FEATURE:
<223> OTHER INFORMATION: Synthetic

<400> SEQUENCE: 13

| | |
|---|---|
| gctactaact tcagcctgct gaagcaggct ggagacgtgg aggagaaccc tggacct | 57 |

<210> SEQ ID NO 14
<211> LENGTH: 1245
<212> TYPE: DNA
<213> ORGANISM: Artificial Sequence
<220> FEATURE:
<223> OTHER INFORMATION: Synthetic

<400> SEQUENCE: 14

| | |
|---|---|
| atgcctgcca tgaagattga gtgccgcatc acgggaaccc tgaacggagt ggagtttgag | 60 |
| ctggtcggag gtggagaagg gactcctgag cagggacgta tgaccaacaa gatgaagtct | 120 |
| accaagggcg ccttgacctt ctcccctac cttctctctc atgtcatggg atacgggttc | 180 |
| taccactttg gtacctatcc cagtgggtat gagaatccct tcctgcatgc catcaacaac | 240 |
| gggggtaca ccaacaccag gattgagaag tatgaggatg gaggagttct tcatgttagc | 300 |
| tttagctaca gatatgaagc aggcagggtg attgggggatt tcaaggttgt cgggacagga | 360 |
| ttccctgagg acagtgtgat cttcaccgac aagatcatcc ggtccaatgc taccgtggag | 420 |
| cacttgcacc caatgggaga caacgttctt gtgggctcct cgcgagaac cttttccctg | 480 |
| agggatggag gctactactc atttgtggtt gacagccaca tgcacttcaa gagtgccatc | 540 |
| cacccatcca tcctccagaa cggggggccc atgtttgcct tcaggagagt tgaggaactt | 600 |
| cactccaaca ctgaacttgg cattgtagag tatcaacatg ccttcaagac tcccatagca | 660 |
| tttgctggaa gcggagctac taacttcagc ctgctgaagc aggctggaga cgtggaggag | 720 |
| aaccctggac ctatggtctt cacactcgaa gatttcgttg gggactggcg acagacagcc | 780 |

| | |
|---|---|
| ggctacaacc tggaccaagt ccttgaacag ggaggtgtgt ccagtttgtt tcagaatctc | 840 |
| ggggtgtccg taactccgat ccaaaggatt gtcctgagcg gtgaaaatgg gctgaagatc | 900 |
| gacatccatg tcatcatccc gtatgaaggt ctgagcggcg accaaatggg ccagatcgaa | 960 |
| aaaatttta aggtggtgta ccctgtggat gatcatcact ttaaggtgat cctgcactat | 1020 |
| ggcacactgg taatcgacgg ggttacgccg aacatgatcg actatttcgg acggccgtat | 1080 |
| gaaggcatcg ccgtgttcga cggcaaaaag atcactgtaa cagggaccct gtggaacggc | 1140 |
| aacaaaatta tcgacgagcg cctgatcaac cccgacggct ccctgctgtt ccgagtaacc | 1200 |
| atcaacggag tgaccggctg gcggctgtgc gaacgcattc tggcg | 1245 |

<210> SEQ ID NO 15
<211> LENGTH: 9156
<212> TYPE: DNA
<213> ORGANISM: Artificial Sequence
<220> FEATURE:
<223> OTHER INFORMATION: Synthetic

<400> SEQUENCE: 15

| | |
|---|---|
| actcttcctt tttcaatatt attgaagcat ttatcagggt tattgtctca tgagcggata | 60 |
| catatttgaa tgtatttaga aaataaaca aatagggggt ccgcgcacat ttccccgaaa | 120 |
| agtgccacct aaattgtaag cgttaatatt ttgttaaaat tcgcgttaaa ttttgttaa | 180 |
| atcagctcat tttttaacca ataggccgaa atcggcaaaa tcccttataa atcaaaagaa | 240 |
| tagaccgaga tagggttgag tgttgttcca gtttggaaca agagtccact attaagaac | 300 |
| gtggactcca acgtcaaagg gcgaaaaacc gtctatcagg gcgatggccc actacgtgaa | 360 |
| ccatcaccct aatcaagttt tttggggtcg aggtgccgta aagcactaaa tcggaaccct | 420 |
| aaagggagcc cccgatttag agcttgacgg ggaaagccgg cgaacgtggc gagaaaggaa | 480 |
| gggaagaaag cgaaaggagc gggcgctagg gcgctggcaa gtgtagcggt cacgctgcgc | 540 |
| gtaaccacca cacccgccgc gcttaatgcg ccgctacagg gcgcgtccca ttcgccattc | 600 |
| aggctgcgca actgttggga agggcgatcg gtgcgggcct cttcgctatt acgccagctg | 660 |
| gcgaaagggg gatgtgctgc aaggcgatta agttgggtaa cgccagggtt ttcccagtca | 720 |
| cgacgttgta aaacgacggc cagtgagcgc gcctcgttca ttcacgtttt tgaacccgtg | 780 |
| gaggacgggc agactcgcgg tgcaaatgtg ttttacagcg tgatggagca gatgaagatg | 840 |
| ctcgacacgc tgcagaacac gcagctagat taaccctaga aagataatca tattgtgacg | 900 |
| tacgttaaag ataatcatgt gtaaaattga cgcatgtgtt ttatcggtct gtatatcgag | 960 |
| gtttatttat taatttgaat agatattaag ttttattata tttacactta catactaata | 1020 |
| ataaattcaa caaacaattt atttatgttt atttatttat taaaaaaaac aaaaactcaa | 1080 |
| aatttcttct ataaagtaac aaaactttta tgagggacag ccccccccca aagcccccag | 1140 |
| ggatgtaatt acgtccctcc cccgctaggg ggcagcagcg agccgcccgg ggctccgctc | 1200 |
| cggtccggcg ctccccccgc atcccgagcc ggcagcgtg cggggacagc ccgggcacgg | 1260 |
| ggaaggtggc acgggatcgc tttcctctga acgcttctcg ctgctctttg agcctgcaga | 1320 |
| cacctggggg gatacgggga aaaggcctcc acggccacta gtattatgcc cagtacatga | 1380 |
| ccttatggga ctttcctact tggcagtaca tctacgtatt agtcatcgct attaccatgg | 1440 |
| tgatgcggtt ttggcagtac atcaatgggc gtggatagcg gtttgactca cggggatttc | 1500 |
| caagtctcca ccccattgac gtcaatggga gtttgttttg gcaccaaaat caacgggact | 1560 |
| ttccaaaatg tcgtaacaac tccgccccat tgacgcaaat gggcggtagg cgtgtacggt | 1620 |

```
gggaggttta tataagcaga gctcgtttag tgaaccgtca gatcgcctgg agacgccatc    1680
cacgctgttt tgacctccat agaagattct agagccacca tggaaactga tacactcctg    1740
ctctgggttc tgctgctgtg ggttcctggc tctactggtg atgctagcga acagaaactc    1800
atctccgaag aagacctcaa cgcagtgggt caagacacac aagaagtcat cgtcgtgcca    1860
cattctctgc ccttcaaggt ggtggtgatc tctgctattc tcgcactcgt ggtgctcacc    1920
atcatctccc tgatcattct gatcatgctg tggcagaaga agcctcgcgg ttctggtgtg    1980
aaacagactt tgaattttga ccttctcaag ttggcgggag acgtcgagtc caaccctggg    2040
cccatggaag atgccaaaaa cattaagaag gcccagcgc cattctaccc actcgaagac    2100
gggaccgccg gcgagcagct gcacaaagcc atgaagcgct acgccctggt gcccggcacc    2160
atcgccttta ccgacgcaca tatcgagtg gacattacct acgccgagta cttcgagatg    2220
agcgttcggc tggcagaagc tatgaagcgc tatgggctga atacaaacca tcggatcgtg    2280
gtgtgcagcg agaatagctt gcagttcttc atgcccgtgt tgggtgccct gttcatcggt    2340
gtggctgtgg ccccagctaa cgacatctac aacgagcgcg agctgctgaa cagcatgggc    2400
atcagccagc ccaccgtcgt attcgtgagc aagaaagggc tgcaaaagat cctcaacgtg    2460
caaaagaagc taccgatcat acaaaagatc atcatcatgg atagcaagac cgactaccag    2520
ggcttccaaa gcatgtacac cttcgtgact tcccatttgc cacccggctt caacgagtac    2580
gacttcgtgc ccgagagctt cgaccgggac aaaaccatcg ccctgatcat gaacagtagt    2640
ggcagtaccg gattgcccaa gggcgtagcc taccgcacc gcaccgcttg tgtccgattc    2700
agtcatgccc gcgaccccat cttcggcaac cagatcatcc ccgacaccgc tatcctcagc    2760
gtggtgccat tcaccacgg cttcggcatg ttcaccacgc tgggctactt gatctgcggc    2820
tttcgggtcg tgctcatgta ccgcttcgag gaggagctat tcttgcgcag cttgcaagac    2880
tataagattc aatctgccct gctggtgccc acactattta gcttcttcgc taagagcact    2940
ctcatcgaca agtacgacct aagcaacttg cacgagatcg ccagcggcgg ggcgccgctc    3000
agcaaggagg taggtgaggc cgtggccaaa cgcttccacc taccaggcat ccgccagggc    3060
tacggcctga cagaaacaac cagcgccatt ctgatcaccc ccgaagggga cgacaagcct    3120
ggcgcagtag gcaaggtggt gcccttcttc gaggctaagg tggtggactt ggacaccggt    3180
aagacactgg gtgtgaacca gcgcggcgag ctgtgcgtcc gtggccccat gatcatgagc    3240
ggctacgtta acaaccccga ggctacaaac gctctcatcg acaaggacgg ctggctgcac    3300
agcggcgaca tcgcctactg ggacgaggac gagcacttct tcatcgtgga ccggctgaag    3360
agcctgatca aatacaaggg ctaccaggta gccccagccg aactggagag catcctgctg    3420
caacacccca acatcttcga cgccgggtc gccggcctgc ccgacgacga tgccggcgag    3480
ctgcccgccg cagtcgtcgt gctggaacac ggtaaaacca tgaccgagaa ggagatcgtg    3540
gactatgtgg ccagccaggt tacaaccgcc aagaagctgc gcggtggtgt tgtgttcgtg    3600
gacgaggtgc ctaaaggact gaccggcaag ttggacgccc gcaagatccg cgagattctc    3660
attaaggcca agaagggcgg caagatcgcc gtgtaatgat aacgcggccg cgaaggatct    3720
gcgatcgctc cggtgcccgt cagtgggcag agcgcacatc gcccacagtc cccgagaagt    3780
tggggggagg ggtcggcaat tgaacgggtg cctagagaag gtggcgcggg gtaaactggg    3840
aaagtgatgt cgtgtactgg ctccgccttt ttcccgaggg tggggagaa ccgtatataa    3900
gtgcagtagt cgccgtgaac gttctttttc gcaacgggtt tgccgccaga acacagctga    3960
```

-continued

```
agcttcgagg ggctcgcatc tctccttcac gcgcccgccg ccctacctga ggccgccatc    4020
cacgccggtt gagtcgcgtt ctgccgcctc ccgcctgtgg tgcctcctga actgcgtccg    4080
ccgtctaggt aagtttaaag ctcaggtcga gaccgggcct ttgtccggcg ctcccttgga    4140
gcctacctag actcagccgg ctctccacgc tttgcctgac cctgcttgct caactctacg    4200
tctttgtttc gttttctgtt ctgcgccgtt acagatccaa gctgtgaccg gcgcctacgc    4260
tagatggata gcactgagaa cgtcatcaag cccttcatgc gcttcaaggt gcacatggag    4320
ggctccgtga acggccacga gttcgagatc gagggcgtgg gcgagggcaa gccctacgag    4380
ggcacccaga ccgccaagct gcaagtgacc aagggcggcc ccctgccctt cgcctgggac    4440
atcctgtccc cccagttctt ctacggctcc aaggcgtaca tcaagcaccc cgccgacatc    4500
cccgactacc tcaagcagtc cttccccgag ggcttcaagt gggagcgcgt gatgaacttc    4560
gaggacggcg gcgtggtgac cgtgacccag gactcctccc tgcaggacgg caccctcatc    4620
taccacgtga agttcatcgg cgtgaacttc ccctccgacg gccccgtaat gcagaagaag    4680
actctgggct gggagccctc cactgagcgc aactaccccc gcgacggcgt gctgaagggc    4740
gagaaccaca tggcgctgaa ggtgaagggc ggcggccact acctgtgtga gttcaagtcc    4800
atctacatgg ccaagaagcc cgtgaagctg cccggctacc actacgtgga ctacaagctc    4860
gacatcacct cccacaacga ggactacacc gtggtggagc agtacgagcg cgccgaggcc    4920
cgccaccacc tgttccaggg aagcggagct actaacttca gcctgctgaa gcaggctgga    4980
gacgtggagg agaaccctgg acctatgacc gagtacaagc ccacggtgcg cctcgccacc    5040
cgcgacgacg tccccagggc cgtacgcacc ctcgccgccg cgttcgccga ctaccccgcc    5100
acgcgccaca ccgtcgatcc ggaccgccac atcgagcggg tcaccgagct gcaagaactc    5160
ttcctcacgc gcgtcgggct cgacatcggc aaggtgtggg tcgcggacga cggcgccgcg    5220
gtggcggtct ggaccacgcc ggagagcgtc gaagcggggg cggtgttcgc cgagatcggc    5280
ccgcgcatgc ccgagttgag cggttcccgg ctggccgcgc agcaacagat ggaaggcctc    5340
ctggcgccgc accggcccaa ggagcccgcg tggttcctgg ccaccgtcgg cgtctcgccc    5400
gaccaccagg gcaagggtct gggcagcgcc gtcgtgctcc ccgagtggga ggcggccgag    5460
cgcgccgggg tgcccgcctt cctggagacc tccgcgcccc gcaacctccc cttctacgag    5520
cggctcggct tcaccgtcac cgccgacgtc gaggtgcccg aaggaccgcg cacctggtgc    5580
atgacccgca agcccggtgc ctgagtcgac aatcaacctc tggattacaa aatttgtgaa    5640
agattgactg gtattcttaa ctatgttgct ccttttacgc tatgtggata cgctgcttta    5700
atgcctttgt atcatgcgtt aactaaactt gtttattgca gcttataatg gttacaaata    5760
aagcaatagc atcacaaatt tcacaaataa agcatttttt tcactgcatt ctagttgtgg    5820
tttgtccaaa ctcatcaatg tatcttatca tgtctggaat tgactcaaat gatgtcaatt    5880
agtctatcag aagctcatct ggtctccctt ccggggggaca agacatccct gtttaatatt    5940
taaacagcag tgttcccaaa ctgggttctt atatcccttg ctctggtcaa ccaggttgca    6000
gggtttcctg tcctcacagg aacgaagtcc ctaaagaaac agtggcagcc aggtttagcc    6060
ccggaattga ctggattcct ttttagggc ccattggtat ggcttttcc ccgtatcccc    6120 ccaggtgtct gcaggctcaa agagcagcga gaagcgttca gaggaaagcg atcccgtgcc    6180 accttcccg tgcccgggct gtccccgcac gctgccggct cggggatgcg gggggagcgc    6240
cggaccggag cggagccccg gcggctcgc tgctgccccc tagcggggga gggacgtaat    6300
tacatccctg ggggctttgg ggggggggctg tccctgatat ctataacaag aaaatatata    6360
```

```
tataataagt tatcacgtaa gtagaacatg aaataacaat ataattatcg tatgagttaa      6420
atcttaaaag tcacgtaaaa gataatcatg cgtcattttg actcacgcgg tcgttatagt      6480
tcaaaatcag tgacacttac cgcattgaca agcacgcctc acgggagctc caagcggcga      6540
ctgagatgtc ctaaatgcac agcgacggat tcgcgctatt tagaaagaga gagcaatatt      6600
tcaagaatgc atgcgtcaat tttacgcaga ctatctttct agggttaatc tagctgcatc      6660
aggatcatat cgtcgggtct ttttccggc tcagtcatcg cccaagctgg cgctatctgg       6720
gcatcgggga ggaagaagcc cgtgccttt cccgcgaggt tgaagcggca tggaaagagt       6780
ttgccgagga tgactgctgc tgcattgacg ttgagcgaaa acgcacgttt accatgatga      6840
ttcgggaagg tgtggccatg cacgccttta acggtgaact gttcgttcag gccacctggg      6900
ataccagttc gtcgcggctt ttccggacac agttccggat ggtcagcccg aagcgcatca      6960
gcaacccgaa caataccggc gacagccgga actgccgtgc cggtgtgcag attaatgaca      7020
gcggtgcggc gctgggatat tacgtcagcg aggacgggta tcctggctgg atgccgcaga      7080
aatggacatg gataccccgt gagttacccg gcgggcgcgc ttggcgtaat catggtcata      7140
gctgtttcct gtgtgaaatt gttatccgct cacaattcca cacaacatac gagccggaag      7200
cataaagtgt aaagcctggg gtgcctaatg agtgagctaa ctcacattaa ttgcgttgcg      7260
ctcactgccc gctttccagt cgggaaacct gtcgtgccag ctgcattaat gaatcggcca      7320
acgcgcgggg agaggcggtt tgcgtattgg gcgctcttcc gcttcctcgc tcactgactc      7380
gctgcgctcg tcgttcggc tgcggcgagc ggtatcagct cactcaaagg cggtaatacg       7440
gttatccaca gaatcagggg ataacgcagg aaagaacatg tgagcaaaag gccagcaaaa      7500
ggccaggaac cgtaaaaagg ccgcgttgct ggcgtttttc cataggctcc gcccccctga      7560
cgagcatcac aaaaatcgac gctcaagtca gaggtggcga aacccgacag gactataaag      7620
ataccaggcg tttccccctg gaagctccct cgtgcgctct cctgttccga cctgccgct      7680 taccggatac ctgtccgcct ttctcccttc gggaagcgtg gcgctttctc atagctcacg      7740
ctgtaggtat ctcagttcgg tgtaggtcgt tcgctccaag ctgggctgtg tgcacgaacc      7800
ccccgttcag cccgaccgct gcgccttatc cggtaactat cgtcttgagt ccaacccggt      7860
aagacacgac ttatcgccac tggcagcagc cactggtaac aggattagca gagcgaggta      7920
tgtaggcggt gctacagagt tcttgaagtg gtggcctaac tacggctaca ctagaaggac      7980
agtatttggt atctgcgctc tgctgaagcc agttaccttc ggaaaaagag ttggtagctc      8040
ttgatccggc aaacaaacca ccgctggtag cggtggtttt tttgtttgca agcagcagat      8100
tacgcgcaga aaaaaggat ctcaagaaga tcctttgatc ttttctacgg gtctgacgc        8160 tcagtggaac gaaaactcac gttaagggat tttggtcatg agattatcaa aaaggatctt     8220
cacctagatc cttttaaatt aaaaatgaag ttttaaatca atctaaagta tatatgagta     8280
aacttggtct gacagttacc aatgcttaat cagtgaggca cctatctcag cgatctgtct     8340
atttcgttca tccatagttg cctgactccc cgtcgtgtag ataactacga tacgggaggg     8400
cttaccatct ggccccagtg ctgcaatgat accgcgagac ccacgctcac cggctccaga     8460
tttatcagca ataaaccagc cagccggaag ggccgagcgc agaagtggtc ctgcaacttt     8520
atccgcctcc atccagtcta ttaattgttg ccgggaagct agagtaagta gttcgccagt     8580
taatagtttg cgcaacgttg ttgccattgc tacaggcatc gtggtgtcac gctcgtcgtt     8640
tggtatggct tcattcagct ccggttccca acgatcaagg cgagttacat gatcccccat     8700
```

| | |
|---|---|
| gttgtgcaaa aaagcggtta gctccttcgg tcctccgatc gttgtcagaa gtaagttggc | 8760 |
| cgcagtgtta tcactcatgg ttatggcagc actgcataat tctcttactg tcatgccatc | 8820 |
| cgtaagatgc ttttctgtga ctggtgagta ctcaaccaag tcattctgag aatagtgtat | 8880 |
| gcggcgaccg agttgctctt gcccggcgtc aatacgggat aataccgcgc cacatagcag | 8940 |
| aactttaaaa gtgctcatca ttggaaaacg ttcttcgggg cgaaaactct caaggatctt | 9000 |
| accgctgttg agatccagtt cgatgtaacc cactcgtgca cccaactgat cttcagcatc | 9060 |
| ttttactttc accagcgttt ctgggtgagc aaaaacagga aggcaaaatg ccgcaaaaaa | 9120 |
| gggaataagg gcgacacgga aatgttgaat actcat | 9156 |

<210> SEQ ID NO 16
<211> LENGTH: 13008
<212> TYPE: DNA
<213> ORGANISM: Artificial Sequence
<220> FEATURE:
<223> OTHER INFORMATION: Synthetic

<400> SEQUENCE: 16

| | |
|---|---|
| actcttcctt tttcaatatt attgaagcat ttatcagggt tattgtctca tgagcggata | 60 |
| catatttgaa tgtatttaga aaataaaca aataggggtt ccgcgcacat ttccccgaaa | 120 |
| agtgccacct aaattgtaag cgttaatatt ttgttaaaat tcgcgttaaa ttttttgttaa | 180 |
| atcagctcat ttttttaacca ataggccgaa atcggcaaaa tcccttataa atcaaaagaa | 240 |
| tagaccgaga tagggttgag tgttgttcca gtttggaaca agagtccact attaaagaac | 300 |
| gtggactcca acgtcaaagg gcgaaaaacc gtctatcagg gcgatggccc actacgtgaa | 360 |
| ccatcaccct aatcaagttt tttggggtcg aggtgccgta aagcactaaa tcggaaccct | 420 |
| aaagggagcc cccgatttag agcttgacgg ggaaagccgg cgaacgtggc gagaaaggaa | 480 |
| gggaagaaag cgaaaggagc gggcgctagg gcgctggcaa gtgtagcggt cacgctgcgc | 540 |
| gtaaccacca cacccgccgc gcttaatgcg ccgctacagg gcgcgtccca ttcgccattc | 600 |
| aggctgcgca actgttggga agggcgatcg gtgcgggcct cttcgctatt acgccagctg | 660 |
| gcgaaagggg gatgtgctgc aaggcgatta agttgggtaa cgccagggtt ttcccagtca | 720 |
| cgacgttgta aaacgacggc cagtgagcgc gcctcgttca ttcacgtttt tgaacccgtg | 780 |
| gaggacgggc agactcgcgg tgcaaatgtg ttttacagcg tgatggagca gatgaagatg | 840 |
| ctcgacacgc tgcagaacac gcagctagat taaccctaga aagataatca tattgtgacg | 900 |
| tacgttaaag ataatcatgt gtaaaattga cgcatgtgtt ttatcggtct gtatatcgag | 960 |
| gtttatttat taatttgaat agatattaag ttttattata tttacactta catactaata | 1020 |
| ataaattcaa caaacaattt atttatgttt atttatttat taaaaaaaac aaaaactcaa | 1080 |
| aatttcttct ataaagtaac aaaacttttta tgagggacag ccccccccca aagcccccag | 1140 |
| ggatgtaatt acgtccctcc cccgctaggg ggcagcagcg agccgccggg ggctccgctc | 1200 |
| cggtccggcg ctccccccgc atccccgagc cggcagcgtg cgggggacagc ccgggcacgg | 1260 |
| ggaaggtggc acgggatcgc tttcctctga acgcttctcg ctgctctttg agcctgcaga | 1320 |
| cacctggggg gatacgggga aaaggcctcc acgccacta gtattatgcc cagtacatga | 1380 |
| ccttatggga ctttcctact ggcagtaca tctacgtatt agtcatcgct attaccatgg | 1440 |
| tgatgcggtt ttggcagtac atcaatgggc gtggatagcg gtttgactca cggggatttc | 1500 |
| caagtctcca ccccattgac gtcaatggga gtttgttttg gcaccaaaat caacgggact | 1560 |
| ttccaaaatg tcgtaacaac tccgccccat tgacgcaaat gggcggtagg cgtgtacggt | 1620 |

```
gggaggttta tataagcaga gctcgtttag tgaaccgtca gatcgcctgg agacgccatc   1680
cacgctgttt tgacctccat agaagattct agagccacca tggaaactga tacactcctg   1740
ctctgggttc tgctgctgtg ggttcctggc tctactggtg attatccata cgatgttcca   1800
gattatgctg gatccatgtt tgtcttcctc gtcctcctgc ctctcgtttc ttctcagtgt   1860
gtgaacctca caactcgcac tcagctgcct cctgcttaca caaacagctt cactagaggc   1920
gtctactacc cagacaaggt cttcaggtcc tctgtcctgc actccaccca ggatctgttc   1980
ctcccattct ttagcaatgt cacatggttc catgctatcc atgtgagcgg aactaatggt   2040
acaaagaggt tcgacaaccc tgtgctccct ttcaatgatg gcgtctactt tgcctccaca   2100
gagaaatcta acatcattag aggttggatc ttcggcacaa ctctggacag caagacccag   2160
agcctcctga tcgtgaacaa cgctacaaat gtcgtcatca aggtgtgcga gtttcaattc   2220
tgtaatgatc ccttcctggg agtgtactac cacaagaaca caagtcttg atggagtcc   2280
gagttcagag tgtactcctc tgccaacaat tgtactttcg aatacgtgtc ccagcctttc   2340
ctcatggatc tggagggtaa acagggaaac ttcaagaacc tgagagagtt cgtgttcaag   2400
aacatcgacg gctacttcaa gatctacagc aaacacactc caatcaatct ggtgagggac   2460
ctccctcagg gtttctccgc tctggaacct ctcgtggatc tccctattgg catcaacatt   2520
actagatttc agaccctcct ggcactgcac cgctcttatc tgacaccagg cgactcttct   2580
agcggttgga ctgcaggtgc tgcagcctac tacgtggat acctccaacc tcgcaccttc   2640
ctgctgaagt acaacgagaa cggcactatc acagatgccg tggattgtgc actggaccct   2700
ctcagcgaga caaagtgtac actgaagagc tttactgtgg agaagggtat ctatcagacc   2760
tctaacttca gggttcagcc caccgagtct attgtgaggt tcccaaacat tactaacctc   2820
tgtcccttg gcgaggtctt caacgccaca agattcgctt ctgtgtatgc ttggaacaga   2880
aagaggattt ccaattgtgt tgccgactat tccgtcctct acaactccgc ttctttctct   2940
acattcaagt gctatggcgt gagccctacc aagctcaacg acctgtgctt tacaaatgtc   3000
tatgccgaca gcttcgtgat cagaggtgac gaggtcaggc agatcgctcc tggtcaaaca   3060
ggaaagattg ccgactacaa ctacaaactg ccagacgatt tcactggctg tgtgatcgcc   3120
tggaatagca caacctgga tagcaaagtt ggaggcaact acaactacct gtacagactg   3180
tttaggaaga gcaacctgaa gccatttgag agagacatta gcaccgaaat ctaccaagct   3240
ggcagcactc cctgtaatgg agttgagggc ttcaactgct acttccctct gcagtcttat   3300
ggcttccagc ccactaatgg cgttggctac caaccttaca gggtcgtggt cctcagcttc   3360
gagctgctgc acgctccagc taccgtctgt ggtcccaaga atctaccaa cctggtgaag   3420
aacaagtgtg ttaacttcaa cttcaacgga ctgaccggaa ccggagtgct gaccgagagc   3480
aacaagaagt tcctcccatt ccaacagttc ggaagagata tcgctgatac tacagacgct   3540
gtgagagatc cacagaccct ggagatcctg acatcacac cctgctcctt tggtggagtg   3600
tccgtgatta cacctggtac aaacacctct aaccaggtcg ctgtgctgta ccaggacgtt   3660
aactgcacag aagttcccgt tgctattcac gcagaccagc tgacaccaac ttggagggtc   3720
tactccactg gctccaacgt cttccaaacc agagctggat gcctcatcgg tgccgagcac   3780
gtcaacaaca gctacgaatg tgacatccca attggagcag gaatctgtgc ctcctatcag   3840
acacagacca actctcccag gagagctagg tctgttgcca gccagtccat catcgcttac   3900
accatgagcc tcggagcaga gaacagcgtg gcttacagca caattccat tgccatccca   3960
```

-continued

| | |
|---|---|
| accaacttca ccattagcgt tactaccgag attctgcctg ttagcatgac caagacttcc | 4020 |
| gtcgattgca ccatgtacat ttgtggtgat agcaccgagt gctctaatct gctgctccag | 4080 |
| tacggttcct tctgtaccca gctcaatagg gctctgacag gcatcgcagt ggaacaggac | 4140 |
| aagaacactc aagaagtgtt cgctcaggtg aagcaaatct acaagacacc tcccatcaag | 4200 |
| gactttggag gcttcaactt cagccagatc ctgcctgacc caagcaagcc atccaagcgc | 4260 |
| tccttcattg aggacctgct cttcaacaag gtgacactgg cagacgctgg cttcatcaag | 4320 |
| cagtacggag actgcctggg agatatcgca gctagggacc tgatttgtgc tcagaagttc | 4380 |
| aacggtctga ctgtgctgcc tcctctgctc accgacgaaa tgatcgctca gtacacaagc | 4440 |
| gcactgctcg ctggcaccat tacctctggc tggacattcg gagctggagc tgctctccag | 4500 |
| atcccttccg ccatgcagat ggcctacagg ttcaacggaa ttggcgttac tcagaatgtg | 4560 |
| ctgtatgaga atcagaaact gatcgccaac cagttcaact ccgctattgg aaagatccag | 4620 |
| gattccctct ccagcacagc ctctgctctg gaaagctcc aagatgttgt caaccagaac | 4680 |
| gctcaagctc tcaacaccct cgtgaagcag ctgtcctcta ctttggtgc catctccagc | 4740 |
| gtgctgaacg acattctgtc caggctcgac aaagtggaag ccgaggttca aatcgacagg | 4800 |
| ctcattactg gcagactcca gagcctgcaa acctacgtca cccagcagct gattagggca | 4860 |
| gcagagatca gggcttctgc taacctggct gctaccaaga tgtccgaatg cgtcctgggt | 4920 |
| cagtccaaga gggttgactt ctgtggtaag ggataccacc tgatgtcctt cccacagtcc | 4980 |
| gctccacacg gagtggtgtt tctccatgtc acttacgtgc ctgcccagga gaagaacttt | 5040 |
| accacagcac ctgctatctg tcacgacggt aaagcccatt tcccacgcga aggcgtcttc | 5100 |
| gtttccaacg gtacacactg gtttgtgact caaagaaact tctacgagcc tcagatcatc | 5160 |
| accactgaca acacattcgt ctctggcaat tgtgacgtcg tcatcggaat tgtgaacaat | 5220 |
| accgtgtacg atcctctgca gccagaactc gattctttca aggaggagct ggacaagtac | 5280 |
| ttcaagaacc acacctctcc cgatgtggac ctcggtgaca tttctggtat caacgcttct | 5340 |
| gtggtcaaca tccagaagga gatcgacagg ctcaacgagg ttgcaaagaa tctcaacgaa | 5400 |
| tccctcattg atctgcagga gctgggaaag tatgagcaat acatcaagtg gccttggtac | 5460 |
| atctggctgg gattcatcgc tggactcatc gctatcgtga tggtcactat catgctctgt | 5520 |
| tgcatgacct cttgttgtag ctgtctgaaa ggatgttgct cctgtggatc ttgttgtaag | 5580 |
| ttcgacgagg atgactccga acctgttctc aagggtgtca aactgcacta cactgctagc | 5640 |
| gaacagaaac tcatctccga agaagacctc aacgcagtgg gtcaagacac acaagaagtc | 5700 |
| atcgtcgtgc cacattctct gccccttcaag gtggtggtga tctctgctat tctcgcactc | 5760 |
| gtggtgctca ccatcatctc cctgatcatt ctgatcatgc tgtggcagaa gaagcctcgc | 5820 |
| ggttctggtg tgaaacagac tttgaatttt gaccttctca agttggcggg agacgtcgag | 5880 |
| tccaaccctg ggcccatgga agatgccaaa aacattaaga agggcccagc gccattctac | 5940 |
| ccactcgaag acgggaccgc cggcgagcag ctgcacaaag ccatgaagcg ctacgccctg | 6000 |
| gtgcccggca ccatcgcctt taccgacgca catatcgagg tggacattac ctacgccgag | 6060 |
| tacttcgaga tgagcgttcg gctggcagaa gctatgaagc gctatgggct gaatacaaac | 6120 |
| catcggatcg tggtgtgcag cgagaatagc ttgcagttct tcatgcccgt gttgggtgcc | 6180 |
| ctgttcatcg gtgtggctgt ggccccagct aacgacatct acaacgagcg cgagctgctg | 6240 |
| aacagcatgg gcatcagcca gcccaccgtc gtattcgtga gcaagaaggg gctgcaaaag | 6300 |
| atcctcaacg tgcaaaagaa gctaccgatc atacaaaaga tcatcatcat ggatagcaag | 6360 |

```
accgactacc agggcttcca aagcatgtac accttcgtga cttcccattt gccacccggc    6420
ttcaacgagt acgacttcgt gcccgagagc ttcgaccggg acaaaaccat cgccctgatc    6480
atgaacagta gtggcagtac cggattgccc aagggcgtag ccctaccgca ccgcaccgct    6540
tgtgtccgat tcagtcatgc ccgcgacccc atcttcggca accagatcat ccccgacacc    6600
gctatcctca gcgtggtgcc atttcaccac ggcttcggca tgttcaccac gctgggctac    6660
ttgatctgcg gctttcgggt cgtgctcatg taccgcttcg aggaggagct attcttgcgc    6720
agcttgcaag actataagat tcaatctgcc ctgctggtgc ccacactatt tagcttcttc    6780
gctaagagca ctctcatcga caagtacgac ctaagcaact tgcacgagat cgccagcggc    6840
ggggcgccgc tcagcaagga ggtaggtgag ccgtggcca aacgcttcca cctaccaggc     6900
atccgccagg gctacggcct gacagaaaca accagcgcca ttctgatcac ccccgaaggg    6960
gacgacaagc ctggcgcagt aggcaaggtg gtgcccttct tcgaggctaa ggtggtggac    7020
ttggacaccg gtaagacact gggtgtgaac cagcgcggcg agctgtgcgt ccgtggcccc    7080
atgatcatga gcggctacgt taacaacccc gaggctacaa acgctctcat cgacaaggac    7140
ggctggctgc acagcggcga catcgcctac tgggacgagg acgagcactt cttcatcgtg    7200
gaccggctga agagcctgat caaatacaag ggctaccagg tagccccagc cgaactggag    7260
agcatcctgc tgcaacaccc caacatcttc gacgccgggg tcgccggcct gcccgacgac    7320
gatgccggcg agctgcccgc cgcagtcgtc gtgctggaac acggtaaaac catgaccgag    7380
aaggagatcg tggactatgt ggccagccag gttacaaccg ccaagaagct gcgcggtggt    7440
gttgtgttcg tggacgaggt gcctaaagga ctgaccggca gttggacgc ccgcaagatc     7500 cgcgagattc tcattaaggc caagaagggc ggcaagatcg ccgtgggaag cggagctact    7560
aacttcagcc tgctgaagca ggctggagac gtggaggaga accctggacc tatggatagc    7620
actgagaacg tcatcaagcc cttcatgcgc ttcaaggtgc acatggaggg ctccgtgaac    7680
ggccacgagt tcgagatcga gggcgtgggc gagggcaagc cctacgaggg cacccagacc    7740
gccaagctgc aagtgaccaa gggcggcccc ctgcccttcg cctgggacat cctgtccccc    7800
cagttcttct acggctccaa ggcgtacatc aagcaccccg ccgacatccc cgactacctc    7860
aagcagtcct tccccgaggg cttcaagtgg gagcgcgtga tgaacttcga ggacggcggc    7920
gtggtgaccg tgacccagga ctcctccctg caggacggcc cctcatcta ccacgtgaag     7980 ttcatcggcg tgaacttccc ctccgacggc cccgtaatgc agaagaagac tctgggctgg    8040
gagccctcca ctgagcgcaa ctaccccgc gacggcgtgc tgaagggcga gaaccacatg     8100
gcgctgaagc tgaagggcgg cggccactac ctgtgtgagt tcaagtccat ctacatggcc    8160
aagaagcccg tgaagctgcc cggctaccac tacgtggact acaagctcga catcacctcc    8220
cacaacgagg actacaccgt ggtggagcag tacgagcgcg ccgaggcccg ccaccacctg    8280
ttccagtaat gataacgcgg ccgcgaagga tctgcgatcg ctccggtgcc cgtcagtggg    8340
cagagcgcac atcgcccaca gtccccgaga agttgggggg aggggtcggc aattgaacgg    8400
gtgcctagag aaggtggcgc ggggtaaact gggaaagtga tgtcgtgtac tggctccgcc    8460 ttttcccga gggtggggga gaaccgtata taagtgcagt agtcgccgtg aacgttcttt      8520
ttcgcaacgg gtttgccgcc agaacacagc tgaagcttcg aggggctcgc atctctcctt    8580
cacgcgcccg ccgccctacc tgaggccgcc atccacgccg gttgagtcgc gttctgccgc    8640
ctcccgcctg tggtgcctcc tgaactgcgt ccgccgtcta ggtaagttta agctcaggt     8700
```

```
cgagaccggg cctttgtccg gcgctccctt ggagcctacc tagactcagc cggctctcca    8760
cgctttgcct gaccctgctt gctcaactct acgtctttgt ttcgttttct gttctgcgcc    8820
gttacagatc caagctgtga ccggcgccta cgctagatga ccgagtacaa gcccacggtg    8880
cgcctcgcca cccgcgacga cgtccccagg gccgtacgca ccctcgccgc cgcgttcgcc    8940
gactaccccg ccacgcgcca caccgtcgat ccggaccgcc acatcgagcg ggtcaccgag    9000
ctgcaagaac tcttcctcac gcgcgtcggg ctcgacatcg gcaaggtgtg ggtcgcggac    9060
gacggcgccg cggtggcggt ctggaccacg ccggagagcg tcgaagcggg ggcggtgttc    9120
gccgagatcg gcccgcgcat ggccgagttg agcggttccc ggctggccgc gcagcaacag    9180
atggaaggcc tcctggcgcc gcaccggccc aaggagcccg cgtggttcct ggccaccgtc    9240
ggcgtctcgc ccgaccacca gggcaagggt ctgggcagcg ccgtcgtgct ccccggagtg    9300
gaggcggccg agcgcgccgg ggtgcccgcc ttcctggaga cctccgcgcc ccgcaacctc    9360
cccttctacg agcggctcgg cttcaccgtc accgccgacg tcgaggtgcc cgaaggaccg    9420
cgcacctggt gcatgacccg caagcccggt gcctgagtcg acaatcaacc tctggattac    9480
aaaatttgtg aaagattgac tggtattctt aactatgttg ctccttttac gctatgtgga    9540
tacgctgctt taatgccttt gtatcatgcg ttaactaaac ttgtttattg cagcttataa    9600
tggttacaaa taaagcaata gcatcacaaa tttcacaaat aaagcatttt tttcactgca    9660
ttctagttgt ggtttgtcca aactcatcaa tgtatcttat catgtctgga attgactcaa    9720
atgatgtcaa ttagtctatc agaagctcat ctggtctccc ttccggggga caagacatcc    9780
ctgtttaata tttaaacagc agtgttccca aactgggttc ttatatccct tgctctggtc    9840
aaccaggttg cagggtttcc tgtcctcaca ggaacgaagt ccctaaagaa acagtggcag    9900
ccaggtttag ccccggaatt gactggattc ctttttagg gcccattggt atggcttttt     9960
ccccgtatcc ccccaggtgt ctgcaggctc aaagagcagc gagaagcgtt cagaggaaag   10020
cgatcccgtg ccaccttccc cgtgcccggg ctgtccccgc acgctgccgg ctcggggatg   10080
cgggggagc gccggaccgg agcggagccc cgggcggctc gctgctgccc cctagcgggg   10140
gagggacgta attacatccc tgggggcttt gggggggggc tgtccctgat atctataaca   10200
agaaaatata tataataa gttatcacgt aagtagaaca tgaaataaca atataattat     10260
cgtatgagtt aaatcttaaa agtcacgtaa aagataatca tgcgtcattt tgactcacgc    10320
ggtcgttata gttcaaaatc agtgacactt accgcattga caagcacgcc tcacgggagc   10380
tccaagcggc gactgagatg tcctaaatgc acagcgacgg attcgcgcta tttagaaaga   10440
gagagcaata tttcaagaat gcatgcgtca attttacgca gactatcttt ctagggttaa   10500
tctagctgca tcaggatcat atcgtcgggt ctttttccg gctcagtcat cgcccaagct   10560
ggcgctatct gggcatcggg gaggaagaag cccgtgcctt ttcccgcgag gttgaagcgg   10620
catgaaaga gtttgccgag gatgactgct gctgcattga cgttgagcga aaacgcacgt   10680
ttaccatgat gattcgggaa ggtgtggcca tgcacgcctt taacggtgaa ctgttcgttc   10740
aggccacctg ggataccagt tcgtcgcggc ttttccggac acagttccgg atggtcagcc   10800
cgaagcgcat cagcaacccg aacaataccg gcgacagccg gaactgccgt gccggtgtgc   10860
agattaatga cagcggtgcg gcgctgggat tacgtcag cgaggacggg tatcctggct    10920
ggatgccgca gaaatggaca tggataccc gtgagttacc cggcgggcgc gcttggcgta   10980
atcatggtca tagctgtttc ctgtgtgaaa ttgttatccg ctcacaattc cacacaacat   11040
acgagccgga agcataaagt gtaaagcctg gggtgcctaa tgagtgagct aactcacatt   11100
```

```
aattgcgttg cgctcactgc ccgctttcca gtcgggaaac ctgtcgtgcc agctgcatta    11160
atgaatcggc caacgcgcgg ggagaggcgg tttgcgtatt gggcgctctt ccgcttcctc    11220
gctcactgac tcgctgcgct cggtcgttcg gctgcggcga gcggtatcag ctcactcaaa    11280
ggcggtaata cggttatcca cagaatcagg ggataacgca ggaaagaaca tgtgagcaaa    11340
aggccagcaa aaggccagga accgtaaaaa ggccgcgttg ctggcgtttt tccataggct    11400
ccgcccccct gacgagcatc acaaaaatcg acgctcaagt cagaggtggc gaaacccgac    11460
aggactataa agataccagg cgtttccccc tggaagctcc ctcgtgcgct ctcctgttcc    11520
gaccctgccg cttaccggat acctgtccgc ctttctccct tcgggaagcg tggcgctttc    11580
tcatagctca cgctgtaggt atctcagttc ggtgtaggtc gttcgctcca agctgggctg    11640
tgtgcacgaa ccccccgttc agcccgaccg ctgcgcctta tccggtaact atcgtcttga    11700
gtccaacccg gtaagacacg acttatcgcc actggcagca gccactggta acaggattag    11760
cagagcgagg tatgtaggcg gtgctacaga gttcttgaag tggtggccta actacggcta    11820
cactagaagg acagtatttg gtatctgcgc tctgctgaag ccagttacct tcggaaaaag    11880
agttggtagc tcttgatccg gcaaacaaac caccgctggt agcggtggtt tttttgtttg    11940
caagcagcag attacgcgca gaaaaaaagg atcctttga tcttttctac    12000 ggggtctgac gctcagtgga acgaaaactc acgttaaggg attttggtca tgagattatc    12060
aaaaaggatc ttcacctaga tccttttaaa ttaaaaatga agttttaaat caatctaaag    12120
tatatatgag taaacttggt ctgacagtta ccaatgctta atcagtgagg cacctatctc    12180
agcgatctgt ctatttcgtt catccatagt tgcctgactc cccgtcgtgt agataactac    12240
gatacgggag ggcttaccat ctggccccag tgctgcaatg ataccgcgag acccacgctc    12300
accggctcca gatttatcag caataaacca gccagccgga agggccgagc gcagaagtgg    12360
tcctgcaact ttatccgcct ccatccagtc tattaattgt tgccgggaag ctagagtaag    12420
tagttcgcca gttaatagtt tgcgcaacgt tgttgccatt gctacaggca tcgtggtgtc    12480
acgctcgtcg tttggtatgg cttcattcag ctccggttcc caacgatcaa ggcgagttac    12540
atgatccccc atgttgtgca aaaaagcggt tagctccttc ggtcctccga tcgttgtcag    12600
aagtaagttg gccgcagtgt tatcactcat ggttatggca gcactgcata attctcttac    12660
tgtcatgcca tccgtaagat gcttttctgt gactggtgag tactcaacca agtcattctg    12720
agaatagtgt atgcggcgac cgagttgctc ttgcccggcg tcaatacggg ataataccgc    12780
gccacatagc agaactttaa aagtgctcat cattggaaaa cgttcttcgg ggcgaaaact    12840
ctcaaggatc ttaccgctgt tgagatccag ttcgatgtaa cccactcgtg cacccaactg    12900
atcttcagca tcttttactt tcaccagcgt ttctgggtga gcaaaaacag gaaggcaaaa    12960
tgccgcaaaa aagggaataa gggcgacacg gaaatgttga atactcat                13008
```

<210> SEQ ID NO 17
<211> LENGTH: 12954
<212> TYPE: DNA
<213> ORGANISM: Artificial Sequence
<220> FEATURE:
<223> OTHER INFORMATION: Synthetic

<400> SEQUENCE: 17

```
actcttcctt tttcaatatt attgaagcat ttatcagggt tattgtctca tgagcggata       60
catatttgaa tgtatttaga aaaataaaca aataggggtt ccgcgcacat ttccccgaaa      120
```

```
agtgccacct aaattgtaag cgttaatatt ttgttaaaat tcgcgttaaa tttttgttaa      180
atcagctcat tttttaacca ataggccgaa atcggcaaaa tcccttataa atcaaaagaa      240
tagaccgaga tagggttgag tgttgttcca gtttggaaca agagtccact attaaagaac      300
gtggactcca acgtcaaagg gcgaaaaacc gtctatcagg gcgatggccc actacgtgaa      360
ccatcaccct aatcaagttt tttggggtcg aggtgccgta aagcactaaa tcggaacccct     420
aaagggagcc cccgatttag agcttgacgg ggaaagccgg cgaacgtggc gagaaaggaa      480
gggaagaaag cgaaaggagc gggcgctagg gcgctggcaa gtgtagcggt cacgctgcgc      540
gtaaccacca cacccgccgc gcttaatgcg ccgctacagg gcgcgtccca ttcgccattc      600
aggctgcgca actgttggga agggcgatcg gtgcgggcct cttcgctatt acgccagctg      660
gcgaagggg gatgtgctgc aaggcgatta agttgggtaa cgccagggtt ttcccagtca      720
cgacgttgta aaacgacggc cagtgagcgc gcctcgttca ttcacgtttt tgaacccgtg      780
gaggacgggc agactcgcgg tgcaaatgtg ttttacagcg tgatggagca gatgaagatg      840
ctcgacacgc tgcagaacac gcagctagat taaccctaga aagataatca tattgtgacg      900
tacgttaaag ataatcatgt gtaaaattga cgcatgtgtt ttatcggtct gtatatcgag      960
gtttatttat taatttgaat agatattaag ttttattata tttacactta catactaata     1020
ataaattcaa caaacaattt atttatgttt atttatttat taaaaaaaac aaaaactcaa     1080
aatttcttct ataaagtaac aaaacttttta tgagggacag ccccccccca aagcccccag     1140
ggatgtaatt acgtccctcc cccgctaggg ggcagcagcg agccgcccgg ggctccgctc     1200
cggtccggcg ctccccccgc atccccgagc cggcagcgtg cggggacagc ccgggcacgg     1260
ggaaggtggc acgggatcgc tttcctctga acgcttctcg ctgctctttg agcctgcaga     1320
cacctggggg gatacgggga aaaggcctcc acgccacta gtattatgcc cagtacatga     1380
ccttatggga ctttcctact tggcagtaca tctacgtatt agtcatcgct attaccatgg     1440
tgatgcggtt ttggcagtac atcaatgggc gtggatagcg gtttgactca cggggatttc     1500
caagtctcca ccccattgac gtcaatggga gtttgttttg gcaccaaaat caacgggact     1560
ttccaaaatg tcgtaacaac tccgccccat tgacgcaaat gggcggtagg cgtgtacggt     1620
gggaggttta taagcagag ctcgtttag tgaaccgtca gatcgcctgg agacgccatc      1680
cacgctgttt tgacctccat agaagattct agagccacca tggaaactga tacactcctg     1740
ctctgggttc tgctgctgtg ggttcctggc tctactggtg attatccata cgatgttcca     1800
gattatgctg gatccatgtt catcttttg ctgttcctga ctctgaccag tggtagtgat      1860
ctggatcgct gtaccacatt cgatgatgtg caggctccca actacacaca gcatacctcc     1920
agtatgagag gagtgtatta ccctgacgaa attttccgct ccgatacctt gtacctgaca     1980
caggacctct tcttgccttt ttattccaat gtcaccggct ttcatacgat caatcataca     2040
ttcgacaatc ctgtgattcc cttcaaggat ggcattttat tcgcagctac ggaaaagtct     2100
aacgtggtcc gcgggtgggt attcggaagc accatgaata taagtcaca gtctgttatc     2160
atcatcaata atagtactaa tgttgtaatc cgcgcttgca actttgaact gtgcgataat     2220
cccttcttcg cagtaagcaa gcccatgggg acacagactc acacgatgat ttttgacaat     2280
gccttcaatt gtacgtttga gtacatttct gatgccttca gcttggacgt gagcgagaaa     2340
tctggaaact tcaaacacct tcgcgagttc gtgtttaaaa acaaagacgg gttcttgtac     2400
gtatataagg gctatcagcc tattgacgta gttcgggact gccgagcgg gtttaatact     2460
ctcaaaccta tcttcaagct cccccctggga attaacataa ctaatttccg cgcaatcctg     2520
```

```
acggcattta gcccagcaca ggatacttgg ggaacctccg ccgcagccta cttcgtgggc    2580
tatctgaagc ctaccacctt catgctgaag tacgatgaga atggcacgat cactgatgct    2640
gttgactgtt cacagaaccc cctcgctgag ctgaagtgca gcgtgaagtc ctttgagatc    2700
gacaagggga tataccagac gagtaacttt cgcgtcgtcc cttccggtga tgttgtgcgc    2760
tttccgaata ttaccaatct gtcccgtttt ggagaggtct ttaacgctac aaagttcccc    2820
tctgtgtacg cttgggagag gaagaaaata tccaattgcg ttgctgacta ttccgtattg    2880
tataactcca ccttctttc aacttttaaa tgctatgggg tgtccgctac caaattgaac    2940
gatctgtgtt tttcaaacgt ttatgccgac tcttttgtag tgaaaggtga cgacgtgcgc    3000
caaatcgctc ctgggcaaac cggcgtcatc gctgattaca attacaagct ccctgatgac    3060
ttcatggggt gcgtgctcgc ttggaatacg cgaaatatag atgccacatc aaccgggaac    3120
tacaactaca aatatcgcta tttgcggcac ggaaaattgc gccccttcga acgggatata    3180
tctaacgtgc ccttcagccc ggatgggaaa ccgtgcactc cgcctgcact taactgttac    3240
tggcccctga acgactatgg cttttacaca actactggca tcggatatca gccctatagg    3300
gttgtagtgc tgagcttcga gctgctgaac gcccctgcta cggtgtgtgg acccaagctg    3360
agcacggatc tgatcaaaaa tcaatgcgtg aacttcaatt ttaacggcct tactggtacc    3420
ggcgtgctca caccatcaag caaacggttt caacccttc agcaattcgg aagagacgta    3480
agcgacttca cggattccgt cagagatcct aaaacaagcg agatactgga tatctcccct    3540
tgctccttcg gcggcgttag cgtgattaca cctggaacca atgcgagctc cgaagtagct    3600
gtgctctacc aggatgttaa ctgcacggac gtaagtaccg ccatccatgc cgaccaactc    3660
accccagctt ggaggatata ctctacgggg aacaatgtgt tccagacaca agcaggatgc    3720
ttgattggtg ctgagcacgt tgatacctct tatgaatgcg acatacccat aggggccggt    3780
atatgcgcct catatcatac cgtctccctg ctgcggtcca ccagtcagaa atcaatcgtt    3840
gcatacacca tgagcctggg cgcagactca tccattgcct atagcaataa tactatcgca    3900
atcccaacaa atttcagtat cagcataact accgaggtca tgccagtgtc aatggcaaaa    3960
acctctgttg actgcaacat gtacatctgt ggcgattcca cagagtgtgc taatttgctg    4020
ttgcaatacg ggtcttttg cacccagttg aacagggccc tgagcggaat cgcggccgag    4080
caggatagaa acacccgaga ggtcttcgcc caggtcaagc agatgtataa gactccaact    4140
ctgaaatact tcggcgggtt taactttct caaattctgc ccgatcctct gaaacccaca    4200
aagagatcat tcatcgaaga tctcctgttc aataaggtga ccctcgccga tgccggcttc    4260
atgaaacaat acggcgaatg tctgggggat atcaacgccc gcgacctgat ctgtgcccaa    4320
aagttcaatg gactgacagt gcttccccct ctgcttacgg atgacatgat tgctgcatac    4380
actgctgccc tcgtctctgg caccgccact gctgggtgga ccttcggcgc agggggcagcc    4440 ctgcagatcc ccttttgccat gcagatggct tacagattca atggtattgg cgtcacgcag    4500
aacgtcctct atgaaaaacca gaaacagatt gccaaccagt tcaataaagc gatcagtcaa    4560
attcaggaga gcctgactac caccagcact gctctgggaa agctccagga tgtggtcaat    4620
cagaatgccc aggccctcaa tactttggtg aaacaacttt ctagcaattt tggcgcaatt    4680
tcatctgttc ttaatgacat tctgtcaaga ctggacaagg tagaggctga ggttcaaata    4740
gataggctta ttcaggacg cctgcagagc ctgcagactt acgttacgca gcagctgatt    4800
agggcagccg agatccgcgc tagtgccaac ctggctgcga ctaaaatgtc cgagtgcgtc    4860
```

```
ttgggccaat ccaaacgcgt agacttttgc ggaaaagggt accatctgat gtcctttccc    4920
caggctgcgc ctcacggtgt tgtcttcctg cacgtgacct atgtgccctc ccaggaaaga    4980
aacttcacca ccgcacctgc catttgtcac gagggtaagg cttactttcc ccgcgagggt    5040
gtgtttgtat ttaatgggac tagctggttc atcacacagc gcaatttctt ctctccccag    5100
atcatcacaa ccgacaatac attcgtctca ggaaactgtg acgtggtgat tggaatcatc    5160
aacaataccg tgtacgaccc tcttcagccc gaactcgatt cattcaagga agaactcgac    5220
aagtacttta agaaccatac ttctcccgac gtggatctcg gggacatttc tggaataaat    5280
gctagtgtcg taaatattca gaaggagata gaccgcctga atgaagtcgc aaagaatctc    5340
aatgaaagcc tcatcgacct gcaagagctg gggaagtacg agcagtatat caaatggcca    5400
tggtacgtgt ggcttgggtt tatcgcaggc ctgatcgcta tagtgatggt gactatcctc    5460
ctgtgctgta tgacctcatg ttgttcctgt ctgaagggcg catgcagctg tgggtcttgt    5520
tgtaaatttg acgaagatga ttcagaaccc gttttgaagg gggtcaaatt gcactacacc    5580
gctagcgaac agaaactcat ctccgaagaa gacctcaacg cagtgggtca agacacacaa    5640
gaagtcatcg tcgtgccaca ttctctgccc ttcaaggtgg tggtgatctc tgctattctc    5700
gcactcgtgg tgctcaccat catctccctg atcattctga tcatgctgtg gcagaagaag    5760
cctcgcggtt ctggtgtgaa acagactttg aattttgacc ttctcaagtt ggcgggagac    5820
gtcgagtcca accctgggcc catggaagat gccaaaaaca ttaagaaggg cccagcgcca    5880
ttctacccac tcgaagacgg gaccgccggc gagcagctgc acaaagccat gaagcgctac    5940
gccctggtgc ccggcaccat cgcctttacc gacgcacata tcgaggtgga cattacctac    6000
gccgagtact tcgagatgag cgttcggctg gcagaagcta tgaagcgcta tgggctgaat    6060
acaaaccatc ggatcgtggt gtgcagcgag aatagcttgc agttcttcat gcccgtgttg    6120
ggtgccctgt tcatcggtgt ggctgtggcc ccagctaacg acatctacaa cgagcgcgag    6180
ctgctgaaca gcatgggcat cagccagccc accgtcgtat tcgtgagcaa gaaagggctg    6240
caaaagatcc tcaacgtgca aaagaagcta ccgatcatac aaaagatcat catcatggat    6300
agcaagaccg actaccaggg cttccaaagc atgtacacct tcgtgacttc ccatttgcca    6360
cccggcttca acgagtacga cttcgtgccc gagagcttcg accgggacaa aaccatcgcc    6420
ctgatcatga acagtagtgg cagtaccgga ttgcccaagg gcgtagccct accgcaccgc    6480
accgcttgtg tccgattcag tcatgcccgc gaccccatct tcggcaacca gatcatcccc    6540
gacaccgcta cctcagcgt ggtgccattt caccacggct tcggcatgtt caccacgctg    6600
ggctacttga tctgcggctt tcgggtcgtg ctcatgtacc gcttcgagga ggagctattc    6660
ttgcgcagct tgcaagacta taagattcaa tctgccctgc tggtgcccac actatttagc    6720
ttcttcgcta agagcactct catcgacaag tacgacctaa gcaacttgca cgagatcgcc    6780
agcggcgggg cgccgctcag caaggaggta ggtgaggccg tggccaaacg cttccacctc    6840
ccaggcatcc gccagggcta cggcctgaca gaaacaacca gcgccattct gatcaccccc    6900
gaaggggacg acaagcctgg cgcagtaggc aaggtggtgc ccttcttcga ggctaaggtg    6960
gtggacttgg acaccggtaa gacactgggt gtgaaccagc gcggcgagct gtgcgtccgt    7020
ggccccatga tcatgagcgg ctacgttaac aaccccgagg ctacaaacgc tctcatcgac    7080
aaggacggct ggctgcacag cggcgacatc gcctactggg acgaggacga gcacttcttc    7140
atcgtggacc ggctgaagag cctgatcaaa tacaagggct accaggtagc cccagccgaa    7200
ctggagagca tcctgctgca acaccccaac atcttcgacg ccggggtcgc cggcctgccc    7260
```

```
gacgacgatg ccggcgagct gcccgccgca gtcgtcgtgc tggaacacgg taaaaccatg   7320
accgagaagg agatcgtgga ctatgtggcc agccaggtta caaccgccaa gaagctgcgc   7380
ggtggtgttg tgttcgtgga cgaggtgcct aaaggactga ccggcaagtt ggacgcccgc   7440
aagatccgcg agattctcat taaggccaag aagggcggca agatcgccgt gggaagcgga   7500
gctactaact tcagcctgct gaagcaggct ggagacgtgg aggagaaccc tggacctatg   7560
gatagcactg agaacgtcat caagcccttc atgcgcttca aggtgcacat ggagggctcc   7620
gtgaacggcc acgagttcga gatcgagggc gtgggcgagg gcaagcccta cgagggcacc   7680
cagaccgcca agctgcaagt gaccaagggc ggcccctgc ccttcgcctg ggacatcctg   7740 tcccccccagt tcttctacgg ctccaaggcg tacatcaagc ccccgccga catccccgac   7800 tacctcaagc agtccttccc cgagggcttc aagtgggagc gcgtgatgaa cttcgaggac   7860
ggcggcgtgg tgaccgtgac ccaggactcc tccctgcagg acggcaccct catctaccac   7920
gtgaagttca tcggcgtgaa cttcccctcc gacggccccg taatgcagaa gaagactctg   7980
ggctgggagc cctccactga gcgcaactac ccccgcgacg gcgtgctgaa gggcgagaac   8040
cacatggcgc tgaagctgaa gggcggcggc cactacctgt gtgagttcaa gtccatctac   8100
atggccaaga agcccgtgaa gctgcccggc taccactacg tggactacaa gctcgacatc   8160
acctcccaca cgaggactac accgtggtg gagcagtacg agcgcgccga ggcccgccac   8220
cacctgttcc agtaatgata acgcggccgc gaaggatctg cgatcgctcc ggtgcccgtc   8280
agtgggcaga gcgcacatcg cccacagtcc ccgagaagtt ggggggaggg gtcggcaatt   8340
gaacgggtgc ctagagaagg tggcgcgggg taaactggga aagtgatgtc gtgtactggc   8400
tccgcctttt tcccgagggt gggggagaac cgtatataag tgcagtagtc gccgtgaacg   8460
ttctttttcg caacgggttt gccgccagaa cacagctgaa gcttcgaggg gctcgcatct   8520
ctccttcacg cgcccgccgc cctacctgag gccgccatcc acgccggttg agtcgcgttc   8580
tgccgcctcc cgcctgtggt gcctcctgaa ctgcgtccgc cgtctaggta agtttaaagc   8640
tcaggtcgag accgggcctt tgtccggcgc tcccttggag cctacctaga ctcagccggc   8700
tctccacgct ttgcctgacc ctgcttgctc aactctacgt ctttgtttcg ttttctgttc   8760
tgcgccgtta cagatccaag ctgtgaccgg cgcctacgct agatgaccga gtacaagccc   8820
acggtgcgcc tcgccacccg cgacgacgtc cccaggccg tacgcaccct cgccgccgcg   8880
ttcgccgact accccgccac gcgccacacc gtcgatccgg accgccacat cgagcgggtc   8940
accgagctgc aagaactctt cctcacgcgc gtcgggctcg acatcggcaa ggtgtgggtc   9000
gcggacgacg gcgccgcggt ggcggtctgg accacgccgg agagcgtcga agcggggcg   9060 gtgttcgccg agatcggccc cgcatggcc gagttgagcg gttcccggct ggccgcgcag   9120
caacagatgg aaggcctcct ggcgccgcac cggcccaagg agcccgcgtg gttcctggcc   9180
accgtcggcg tctcgcccga ccaccagggc aagggtctgg gcagcgccgt cgtgctcccc   9240
ggagtggagg cggccgagcg cgccggggtg cccgccttcc tggagacctc cgcgccccgc   9300
aacctcccct tctacgagcg gctcggcttc accgtcaccg ccgacgtcga ggtgcccgaa   9360
ggaccgcgca cctggtgcat gacccgcaag cccggtgcct gagtcgacaa tcaacctctg   9420
gattacaaaa tttgtgaaag attgactggt attcttaact atgttgctcc ttttacgcta   9480
tgtggatacg ctgctttaat gcctttgtat catgcgttaa ctaaacttgt ttattgcagc   9540
ttataatggt tacaaataaa gcaatagcat cacaaatttc acaaataaag catttttttc   9600
```

```
actgcattct agttgtggtt tgtccaaact catcaatgta tcttatcatg tctggaattg    9660
actcaaatga tgtcaattag tctatcagaa gctcatctgg tctcccttcc ggggacaag     9720 acatccctgt ttaatattta aacagcagtg ttcccaaact gggttcttat atcccttgct    9780
ctggtcaacc aggttgcagg gtttcctgtc ctcacaggaa cgaagtccct aaagaaacag    9840
tggcagccag gtttagcccc ggaattgact ggattccttt tttagggccc attggtatgg    9900 cttttttcccc gtatccccccc aggtgtctgc aggctcaaag agcagcgaga agcgttcaga  9960
ggaaagcgat cccgtgccac cttccccgtg cccgggctgt cccgcacgc tgccggctcg    10020 gggatgcggg gggagcgccg gaccggagcg gagccccggg cggctcgctg ctgccccta    10080 gcgggggagg gacgtaatta catccctggg ggctttgggg ggggctgtc cctgatatct    10140 ataacaagaa aatatatata taataagtta tcacgtaagt agaacatgaa ataacaatat   10200
aattatcgta tgagttaaat cttaaaagtc acgtaaaaga taatcatgcg tcattttgac   10260
tcacgcggtc gttatagttc aaaatcagtg acacttaccg cattgacaag cacgcctcac   10320
gggagctcca agcggcgact gagatgtcct aaatgcacag cgacggattc gcgctattta   10380
gaaagagaga gcaatatttc aagaatgcat gcgtcaattt tacgcagact atctttctag   10440
ggttaatcta gctgcatcag gatcatatcg tcgggtcttt tttccggctc agtcatcgcc   10500
caagctggcg ctatctgggc atcggggagg aagaagcccg tgccttttcc cgcgaggttg   10560
aagcggcatg gaaagagttt gccgaggatg actgctgctg cattgacgtt gagcgaaaac   10620
gcacgtttac catgatgatt cgggaaggtg tggccatgca cgcctttaac ggtgaactgt   10680
tcgttcaggc cacctgggat accagttcgt cgcggctttt ccggacacag ttccggatgg   10740
tcagcccgaa gcgcatcagc aacccgaaca ataccggcga cagccggaac tgccgtgccg   10800
gtgtgcagat taatgacagc ggtgcggcgc tgggatatta cgtcagcgag gacgggtatc   10860
ctggctggat gccgcagaaa tggacatgga taccccgtga gttacccggc gggcgcgctt   10920
ggcgtaatca tggtcatagc tgtttcctgt gtgaaattgt tatccgctca caattccaca   10980
caacatacga gccggaagca taaagtgtaa agcctggggt gcctaatgag tgagctaact   11040
cacattaatt gcgttgcgct cactgcccgc tttccagtcg ggaaacctgt cgtgccagct   11100
gcattaatga atcggccaac gcgcggggag aggcggtttg cgtattgggc gctcttccgc   11160
ttcctcgctc actgactcgc tgcgctcggt cgttcggctg cggcgagcgg tatcagctca   11220
ctcaaaggcg gtaatacggt tatccacaga atcagggggat aacgcaggaa agaacatgtg   11280
agcaaaaggc cagcaaaagg ccaggaaccg taaaaaggcc gcgttgctgg cgttttttcca   11340 taggctccgc ccccctgacg agcatcacaa aaatcgacgc tcaagtcaga ggtggcgaaa    11400
cccgacagga ctataaagat accaggcgtt tccccctgga agctccctcg tgcgctctcc    11460
tgttccgacc ctgccgctta ccggatacct gtccgccttt ctcccttcgg gaagcgtggc    11520
gctttctcat agctcacgct gtaggtatct cagttcggtg taggtcgttc gctccaagct    11580
gggctgtgtg cacgaacccc ccgttcagcc cgaccgctgc gccttatccg gtaactatcg    11640
tcttgagtcc aacccggtaa gacacgactt atcgccactg gcagcagcca ctggtaacag    11700
gattagcaga gcgaggtatg taggcggtgc tacagagttc ttgaagtggt ggcctaacta    11760
cggctacact agaaggacag tatttggtat ctgcgctctg ctgaagccag ttaccttcgg    11820
aaaaagagtt ggtagctctt gatccggcaa acaaaccacc gctggtagcg gtggtttttt    11880
tgtttgcaag cagcagatta cgcgcagaaa aaaaggatct caagaagatc ctttgatctt    11940
ttctacgggg tctgacgctc agtggaacga aaactcacgt taagggattt tggtcatgag   12000
```

```
attatcaaaa aggatcttca cctagatcct tttaaattaa aaatgaagtt ttaaatcaat    12060
ctaaagtata tatgagtaaa cttggtctga cagttaccaa tgcttaatca gtgaggcacc    12120
tatctcagcg atctgtctat ttcgttcatc catagttgcc tgactcccg tcgtgtagat     12180 aactacgata cgggagggct taccatctgg ccccagtgct gcaatgatac cgcgagaccc    12240
acgctcaccg gctccagatt tatcagcaat aaaccagcca gccggaaggg ccgagcgcag    12300
aagtggtcct gcaactttat ccgcctccat ccagtctatt aattgttgcc gggaagctag    12360
agtaagtagt tcgccagtta atagtttgcg caacgttgtt gccattgcta caggcatcgt    12420
ggtgtcacgc tcgtcgtttg gtatggcttc attcagctcc ggttcccaac gatcaaggcg    12480
agttacatga tcccccatgt tgtgcaaaaa agcggttagc tccttcggtc ctccgatcgt    12540
tgtcagaagt aagttggccg cagtgttatc actcatggtt atggcagcac tgcataattc    12600
tcttactgtc atgccatccg taagatgctt ttctgtgact ggtgagtact caaccaagtc    12660
attctgagaa tagtgtatgc ggcgaccgag ttgctcttgc ccggcgtcaa tacgggataa    12720
taccgcgcca catagcagaa ctttaaaagt gctcatcatt ggaaaacgtt cttcggggcg    12780
aaaactctca aggatcttac cgctgttgag atccagttcg atgtaaccca ctcgtgcacc    12840
caactgatct tcagcatctt ttactttcac cagcgtttct gggtgagcaa aaacaggaag    12900
gcaaaatgcc gcaaaaaagg gaataagggc gacacggaaa tgttgaatac tcat          12954

<210> SEQ ID NO 18
<211> LENGTH: 9886
<212> TYPE: DNA
<213> ORGANISM: Artificial Sequence
<220> FEATURE:
<223> OTHER INFORMATION: Synthetic

<400> SEQUENCE: 18
acgcgtgtag tcttatgcaa tactcttgta gtcttgcaac atggtaacga tgagttagca      60
acatgcctta caaggagaga aaaagcaccg tgcatgccga ttggtggaag taaggtggta     120
cgatcgtgcc ttattaggaa ggcaacagac gggtctgaca tggattggac gaaccactga     180
attgccgcat tgcagagata ttgtatttaa gtgcctagct cgatacaata aacgggtctc     240
tctggttaga ccagatctga gcctgggagc tctctggcta actagggaac ccactgctta     300
agcctcaata aagcttgcct tgagtgcttc aagtagtgtg tgcccgtctg ttgtgtgact     360
ctggtaacta gagatccctc agacccttt agtcagtgtg aaaatctct agcagtggcg       420 cccgaacagg gacctgaaag cgaaagggaa accagagctc tctcgacgca ggactcggct     480
tgctgaagcg cgcacggcaa gaggcgaggg gcggcgactg gtgagtacgc caaaaatttt     540
gactagcgga ggctagaagg agagagatgg gtgcgagagc gtcagtatta agcggggag      600 aattagatcg cgatgggaaa aaattcggtt aaggccaggg ggaaagaaaa aatataaatt     660
aaaacatata gtatgggcaa gcagggagct agaacgattc gcagttaatc ctggcctgtt     720
agaaacatca gaaggctgta gacaaatact gggacagcta caaccatccc ttcagacagg     780
atcagaagaa cttagatcat tatataatac agtagcaacc ctctattgtg tgcatcaaag     840
gatagagata aagacacca aggaagcttt agacaagata gaggaagagc aaaacaaaag     900
taagaccacc gcacagcaag cggccactga tcttcagacc tggaggagga gatatgaggg    960
acaattggag aagtgaatta tataaatata agtagtaaa aattgaacca ttaggagtag     1020
cacccaccaa ggcaaagaga agagtggtgc agagagaaaa aagagcagtg ggaataggag    1080
```

```
ctttgttcct tgggttcttg ggagcagcag gaagcactat gggcgcagcg tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg ggatttgggg   1320
gttgctctgg aaaactcatt tgcaccactg ctgtgccttg gaatgctagt tggagtaata   1380
aatctctgga acagatttgg aatcacacga cctggatgga gtgggacaga gaaattaaca   1440
attacacaag cttaatacac tccttaattg aagaatcgca aaaccagcaa gaaaagaatg   1500
aacaagaatt attggaatta gataaatggg caagtttgtg gaattggttt aacataacaa   1560
attggctgtg gtatataaaa ttattcataa tgatagtagg aggcttggta ggtttaagaa   1620 tagttttgc tgtactttct atagtgaata gagttaggca gggatattca ccattatcgt   1680
ttcagaccca cctcccaacc ccgaggggac ccgacaggcc cgaaggaata agaagaagaag   1740 gtggagagag agacagagac agatccattc gattagtgaa cggatctcga cggtatcggt   1800
taacttttaa agaaaaggg gggattgggg ggtacagtgc aggggaaaga atagtagaca   1860
taatagcaac agacatacaa actaaagaat tacaaaaaca aattacaaaa ttcaaaattt   1920
tatcgatgct agcggaggaa aaactgtttc atacagaagg cgtggaggaa aaactgtttc   1980
atacagaagg cgtggaggaa aaactgtttc atacagaagg cgtggaggaa aaactgtttc   2040
atacagaagg cgtggaggaa aaactgtttc atacagaagg cgtggaggaa aaactgtttc   2100
atacagaagg cgtagatcta gactctagag gtatataat ggaagctcga cttccagctt   2160
ggcattccgg tactgttggt aaaaagcttg gcaatccggt actgttggta aaggatccgc   2220
caccatgcct gccatgaaga ttgagtgccg catcacggga accctgaacg gagtggagtt   2280
tgagctggtc ggaggtggag aagggactcc tgagcaggga cgtatgacca acaagatgaa   2340
gtctaccaag ggcgccttga ccttctcccc ctaccttctc tctcatgtca tgggatacgg   2400
gttctaccac tttggtacct atcccagtgg gtatgagaat cccttcctgc atgccatcaa   2460
caacgggggg tacaccaaca ccaggattga gaagtatgag gatggaggag ttcttcatgt   2520
tagctttagc tacagatatg aagcaggcag ggtgattggg gatttcaagg ttgtcgggac   2580
aggattccct gaggacagtg tgatcttcac cgacaagatc atccggtcca atgctaccgt   2640
ggagcacttg cacccaatgg gagacaacgt tcttgtgggc tccttcgcga gaacctttc   2700 cctgagggat ggaggctact actcatttgt ggttgacagc cacatgcact tcaagagtgc   2760
catccaccca tccatcctcc agaacggggg gcccatgttt gccttcagga gagttgagga   2820
acttcactcc aacactgaac ttggcattgt agagtatcaa catgccttca gactcccat   2880 agcatttgct ggaagcggag ctactaactt cagcctgctg aagcaggctg agacgtgga   2940 ggagaaccct ggacctatgg tcttcacact cgaagatttc gttggggact ggcgacagac   3000
agccggctac aacctggacc aagtccttga cagggaggt gtgtccagtt tgtttcagaa   3060
tctcggggtg tccgtaactc cgatccaaag gattgtcctg agcggtgaaa atgggctgaa   3120
gatcgacatc catgtcatca tcccgtatga aggtctgagc ggcgaccaaa tgggccagat   3180
cgaaaaaatt tttaaggtgg tgtaccctgt ggatgatcat cactttaagg tgatcctgca   3240
ctatggcaca ctggtaatcg acggggttac gccgaacatg atcgactatt tcggacggcc   3300
gtatgaaggc atcgccgtgt tcgacggcaa aaagatcact gtaacaggga ccctgtggaa   3360
cggcaacaaa attatcgacg agcgcctgat caaccccgac ggctccctgc tgttccgagt   3420
aaccatcaac ggagtgaccg gctggcggct gtgcgaacgc attctggcgt aagcggccgc   3480
```

```
gaaggatctg cgatcgctcc ggtgcccgtc agtgggcaga gcgcacatcg cccacagtcc    3540
ccgagaagtt gggggagggg gtcggcaatt gaacgggtgc ctagagaagg tggcgcgggg    3600
taaactggga aagtgatgtc gtgtactggc tccgcctttt tcccgagggt gggggagaac    3660
cgtatataag tgcagtagtc gccgtgaacg ttcttttcg caacgggttt gccgccagaa     3720
cacagctgaa gcttcgaggg gctcgcatct ctccttcacg cgcccgccgc cctacctgag    3780
gccgccatcc acgccggttg agtcgcgttc tgccgcctcc cgcctgtggt gcctcctgaa    3840
ctgcgtccgc cgtctaggta agtttaaagc tcaggtcgag accgggcctt tgtccggcgc    3900
tcccttggag cctacctaga ctcagccggc tctccacgct ttgcctgacc ctgcttgctc    3960
aactctacgt ctttgtttcg ttttctgttc tgcgccgtta cagatccaag ctgtgaccgg    4020
cgcctactag tgccaccatg gactttcaag tgcagatctt cagctttctg ctgatctctg    4080
ctagtgtcat catgtctcaa gtgcaactgc aggaatctgg aggtggcctc gtgcaagctg    4140
gaggcagcct gaggctgagc tgtgctgcat ccggtcgcac ctttagcgag tatgcaatgg    4200
gttggtttcg ccaggcacca ggtaaggaga gggagtttgt ggcaaccatc tcctggtctg    4260
gtggctccac atactacaca gattccgtca agggaagatt cactatctcc agggacaacg    4320
caaagaacac agtgtatctg cagatgaata gcctcaagcc agatgacaca gccgtctact    4380
attgcgctgc agctggtctg ggcaccgtgg tgtccgaatg ggattacgac tacgattact    4440
ggggtcaagg cactcaggtg actgtgtcta gcggtagcga aatcgagcag aagctgattt    4500
ccgaagagga tctcaatgga gtgactgtca gcagcgctct gtctaactcc atcatgtact    4560
tctcacactt cgtgccagtg ttcctccctg ctaaacccac cacaactcca gcacctagac    4620
ctcccactcc agcaccaact attgcatccc agcctctctc cctcagacca gaagcatgca    4680
gacctgcagc aggtggagct gtgcacacaa gaggtctgga cccttcctgg gtcctcgtgg    4740
tggtgggtgg agtcctggca tgttacagcc tcctggtcac cgtggcattc atcatcttct    4800
gggtgagatc taagaggagc agactgctgc actctgatta catgaacatg acacccagaa    4860
gacctggtcc caccagaaag cactaccaac cctacgcacc accaagagac tttgctgcat    4920
acagaagtct cgagagggtc aagttctcaa ggagtgcaga tgctccagcc tatcaacagg    4980
gtcagaacca actgtacaac gagctgaatc tcggaagaag agaggagtac gatgtgctgg    5040
ataagagaag aggcagggac ccagagatgg gtgggaaacc cagaagaaag aatcctcaag    5100
agggactgta caatgagctg cagaaggata agatggctga ggcatactca gagatcggta    5160
tgaaggagga gaggagaaga ggcaaaggtc atgatggtct gtaccaaggt ctgtccacag    5220
caacaaagga tacatatgat gctctgcaca tgcaggcact cccaccacgg ggttccggag    5280
tgaaacagac tttgaacttt gaccttctca agttggctgg agacgtcgag tccaaccctg    5340
gtcccatgac cgagtacaag cccacggtgc gcctcgccac ccgcgacgac gtccccaggg    5400
ccgtacgcac cctcgccgcc gcgttcgccg actaccccgc cacgcgccac accgtcgatc    5460
cggaccgcca catcgagcgg gtcaccgagc tgcaagaact cttcctcacg cgcgtcgggc    5520
tcgacatcgg caaggtgtgg gtcgcggacg acggcgccgc ggtggcggtc tggaccacgc    5580
cggagagcgt cgaagcgggg gcggtgttcg ccgagatcgg cccgcgcatg gccgagttga    5640
gcggttcccg gctggccgcg cagcaacaga tggaaggcct cctggcgccg caccggccca    5700
aggagcccgc gtggttcctg gccaccgtcg gcgtctcgcc cgaccaccag ggcaagggtc    5760
tgggcagcgc cgtcgtgctc cccggagtgg aggcggccga gcgcgccggg gtgcccgcct    5820
```

```
tcctggagac ctccgcgccc cgcaacctcc ccttctacga gcggctcggc ttcaccgtca   5880
ccgccgacgt cgaggtgccc gaaggaccgc gcacctggtg catgacccgc aagcccggtg   5940
cctgattaat taagtcgaca atcaacctct ggattacaaa atttgtgaaa gattgactgg   6000
tattcttaac tatgttgctc cttttacgct atgtggatac gctgctttaa tgcctttgta   6060
tcatgctatt gcttccgta tggctttcat tttctcctcc ttgtataaat cctggttgct   6120
gtctctttat gaggagttgt ggcccgttgt caggcaacgt ggcgtggtgt gcactgtgtt   6180
tgctgacgca accccactg gttggggcat tgccaccacc tgtcagctcc tttccgggac   6240
tttcgctttc cccctcccta ttgccacggc ggaactcatc gccgcctgcc ttgcccgctg   6300
ctggacaggg gctcggctgt tgggcactga caattccgtg gtgttgtcgg ggaaatcatc   6360
gtcctttcct tggctgctcg cctgtgttgc cacctggatt ctgcgcggga cgtccttctg   6420
ctacgtccct tcggccctca atccagcgga ccttccttcc cgcggcctgc tgccggctct   6480
gcggcctctt ccgcgtcttc gccttcgccc tcagacgagt cggatctccc tttgggccgc   6540
ctccccgcct ggtacctta agaccaatga cttacaaggc agctgtagat cttagccact   6600
ttttaaaaga aaggggggga ctggaagggc taattcactc ccaacgaaga taagatctgc   6660
tttttgcttg tactgggtct ctctggttag accagatctg agcctgggag ctctctggct   6720
aactagggaa cccactgctt aagcctcaat aaagcttgcc ttgagtgctt caagtagtgt   6780
gtgcccgtct gttgtgtgac tctggtaact agagatccct cagaccctt tagtcagtgt   6840
ggaaaatctc tagcagtagt agttcatgtc atcttattat tcagtattta aacttgcaa   6900
agaaatgaat atcagagagt gagaggaact tgttattgc agcttataat ggttacaaat   6960
aaagcaatag catcacaaat ttcacaaata aagcattttt ttcactgcat tctagttgtg   7020
gtttgtccaa actcatcaat gtatcttatc atgtctggct ctagctatcc cgcccctaac   7080
tccgcccatc ccgcccctaa ctccgcccag ttccgcccat tctccgcccc atggctgact   7140
aattttttt atttatgcag aggccgaggc cgcctcggcc tctgagctat tccagaagta   7200
gtgaggaggc ttttttggag gcctagactt ttgcagagac ggcccaaatt cgtaatcatg   7260
gtcatagctg tttcctgtgt gaaattgtta tccgctcaca attccacaca acatacgagc   7320
cggaagcata aagtgtaaag cctggggtgc ctaatgagtg agctaactca cattaattgc   7380
gttgcgctca ctgcccgctt tccagtcggg aaacctgtcg tgccagctgc attaatgaat   7440
cggccaacgc gcgggagag gcggtttgcg tattgggcgc tcttccgctt cctcgctcac   7500
tgactcgctg cgctcggtcg ttcggctgcg gcgagcggta tcagctcact caaaggcggt   7560
aatacggtta tccacagaat caggggataa cgcaggaaag aacatgtgag caaaaggcca   7620
gcaaaaggcc aggaaccgta aaaaggccgc gttgctggcg tttttccata ggctccgccc   7680
ccctgacgag catcacaaaa atcgacgctc aagtcagagg tggcgaaacc cgacaggact   7740
ataaagatac caggcgtttc ccctggaag ctccctcgtg cgctctcctg ttccgaccct   7800
gccgcttacc ggatacctgt ccgcctttct cccttcggga agcgtggcgc tttctcatag   7860
ctcacgctgt aggtatctca gttcggtgta ggtcgttcgc tccaagctgg gctgtgtgca   7920
cgaacccccc gttcagcccg accgctgcgc cttatccggt aactatcgtc ttgagtccaa   7980
cccggtaaga cacgacttat cgccactggc agcagccact ggtaacagga ttagcagagc   8040
gaggtatgta ggcggtgcta cagagttctt gaagtggtgg cctaactacg gctacactag   8100
aaggacagta tttggtatct gcgctctgct gaagccagtt accttcggaa aaagagttgg   8160
tagctcttga tccggcaaac aaaccaccgc tggtagcggt ggtttttttg tttgcaagca   8220
```

| | |
|---|---|
| gcagattacg cgcagaaaaa aaggatctca agaagatcct ttgatctttt ctacggggtc | 8280 |
| tgacgctcag tggaacgaaa actcacgtta agggattttg gtcatgagat tatcaaaaag | 8340 |
| gatcttcacc tagatccttt taaattaaaa atgaagtttt aaatcaatct aaagtatata | 8400 |
| tgagtaaact tggtctgaca gttaccaatg cttaatcagt gaggcaccta tctcagcgat | 8460 |
| ctgtctattt cgttcatcca tagttgcctg actcccgtc gtgtagataa ctacgatacg | 8520 |
| ggagggctta ccatctggcc ccagtgctgc aatgataccg cgagacccac gctcaccggc | 8580 |
| tccagattta tcagcaataa accagccagc cggaagggcc gagcgcagaa gtggtcctgc | 8640 |
| aactttatcc gcctccatcc agtctattaa ttgttgccgg gaagctagag taagtagttc | 8700 |
| gccagttaat agtttgcgca acgttgttgc cattgctaca ggcatcgtgg tgtcacgctc | 8760 |
| gtcgtttggt atggcttcat tcagctccgg ttcccaacga tcaaggcgag ttacatgatc | 8820 |
| ccccatgttg tgcaaaaaag cggttagctc cttcggtcct ccgatcgttg tcagaagtaa | 8880 |
| gttggccgca gtgttatcac tcatggttat ggcagcactg cataattctc ttactgtcat | 8940 |
| gccatccgta agatgctttt ctgtgactgg tgagtactca accaagtcat tctgagaata | 9000 |
| gtgtatgcgg cgaccgagtt gctcttgccc ggcgtcaata cgggataata ccgcgccaca | 9060 |
| tagcagaact ttaaaagtgc tcatcattgg aaaacgttct cggggcgaa aactctcaag | 9120 |
| gatcttaccg ctgttgagat ccagttcgat gtaaccccact cgtgcaccca actgatcttc | 9180 |
| agcatctttt actttcacca gcgtttctgg gtgagcaaaa acaggaaggc aaaatgccgc | 9240 |
| aaaaaaggga ataagggcga cacggaaatg ttgaatactc atactcttcc ttttcaata | 9300 |
| ttattgaagc atttatcagg gttattgtct catgagcgga tacatatttg aatgtattta | 9360 |
| gaaaaataaa caaataggg ttccgcgcac atttccccga aaagtgccac ctgacgtcta | 9420 |
| agaaaccatt attatcatga cattaaccta taaaaatagg cgtatcacga ggccctttcg | 9480 |
| tctcgcgcgt ttcggtgatg acggtgaaaa cctctgacac atgcagctcc cggagacggt | 9540 |
| cacagcttgt ctgtaagcgg atgccgggag cagacaagcc cgtcagggcg cgtcagcggg | 9600 |
| tgttggcggg tgtcggggct ggcttaacta tgcggcatca gagcagattg tactgagagt | 9660 |
| gcaccatatg cggtgtgaaa taccgcacag atgcgtaagg agaaaatacc gcatcaggcg | 9720 |
| ccattcgcca ttcaggctgc gcaactgttg gaagggcga tcggtgcggg cctcttcgct | 9780 |
| attacgccag ctggcgaaag ggggatgtgc tgcaaggcga ttaagttggg taacgccagg | 9840 |
| gttttcccag tcacgacgtt gtaaaacgac ggccagtgcc aagctg | 9886 |

<210> SEQ ID NO 19
<211> LENGTH: 9241
<212> TYPE: DNA
<213> ORGANISM: Artificial Sequence
<220> FEATURE:
<223> OTHER INFORMATION: Synthetic

<400> SEQUENCE: 19

| | |
|---|---|
| acgcgtgtag tcttatgcaa tactcttgta gtcttgcaac atggtaacga tgagttagca | 60 |
| acatgcctta caaggagaga aaaagcaccg tgcatgccga ttggtggaag taaggtggta | 120 |
| cgatcgtgcc ttattaggaa ggcaacagac gggtctgaca tggattggac gaaccactga | 180 |
| attgccgcat tgcagagata ttgtatttaa gtgcctagct cgatacaata aacgggtctc | 240 |
| tctggttaga ccagatctga gcctgggagc tctctggcta actagggaac ccactgctta | 300 |
| agcctcaata aagcttgcct tgagtgcttc aagtagtgtg tgcccgtctg ttgtgtgact | 360 |

```
ctggtaacta gagatccctc agacccttt  agtcagtgtg aaaatctct  agcagtggcg    420 cccgaacagg gacctgaaag cgaaagggaa accagagctc tctcgacgca ggactcggct    480
tgctgaagcg cgcacggcaa gaggcgaggg cggcgactg  gtgagtacgc aaaaatttt     540 gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata agtagtaaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcg tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg aatgctagt  tggagtaata   1380 aatctctgga acagatttgg aatcacacga cctggatgga gtgggacaga gaaattaaca   1440
attacacaag cttaatacac tccttaattg aagaatcgca aaaccagcaa gaaaagaatg   1500
aacaagaatt attggaatta gataaatggg caagtttgtg gaattggttt aacataacaa   1560
attggctgtg gtatataaaa ttattcataa tgatagtagg aggcttggta ggtttaagaa   1620
tagtttttgc tgtactttct atagtgaata gagttaggca gggatattca ccattatcgt   1680
ttcagaccca cctcccaacc ccgaggggac ccgacaggcc cgaaggaata agaagaagaa   1740
gtggagagag agacagagac agatccattc gattagtgaa cggatctcga cggtatcggt   1800
taacttttaa aagaaaaggg gggattgggg ggtacagtgc aggggaaaga atagtagaca   1860
taatagcaac agacatacaa actaaagaat tacaaaaaca aattacaaaa ttcaaaattt   1920
tatcgatgct agcggaggaa aaactgtttc atacagaagg cgtggaggaa aaactgtttc   1980
atacagaagg cgtggaggaa aaactgtttc atacagaagg cgtggaggaa aaactgtttc   2040
atacagaagg cgtggaggaa aaactgtttc atacagaagg cgtggaggaa aaactgtttc   2100
atacagaagg cgtagatcta gactctagag ggtatataat ggaagctcga cttccagctt   2160
ggcattccgg tactgttggt aaaaagcttg gcaatccggt actgttggta aggatccgc    2220 caccatgaaa ctcgatatga ctggtgattg tactcctgtt ctggtgctga tggctgctgt   2280
gctcactgtt actggtgccg tccctgtggc cagactgcac ggagccctcc ctgacgctag   2340
aggatgccac atcgctcagt tcaagtctct ctctcctcag gaactccaag ccttcaagag   2400
agcaaaggat gctctggagg aaagcctgct gctgaaagac tgcagatgtc attccagact   2460
gtttcctaga acatgggacc tcaggcagct gcaggtcagg gagaggccaa tggctctgga   2520
ggctgagctg gcactcacac tcaaagtgct cgaagctacc gctgacaccg acccagccct   2580
cgttgatgtc ctcgatcagc ctctgcacac actgcaccac atcctctccc agttcagggc   2640
atgtatccag cctcagccta ctgcaggacc acgcactaga ggaagactcc atcactggct   2700
gtacaggctg caggaagcac caaagaaaga gagccctgga tgcctggaag cttccgtcac   2760
```

```
tttcaatctg ttcagactgc tgactaggga cctgaactgt gtcgcaagcg gtgatctgtg    2820
cgtgtaagcg gccgcgaagg atctgcgatc gctccggtgc ccgtcagtgg gcagagcgca    2880
catcgcccac agtccccgag aagttggggg gaggggtcgg caattgaacg ggtgcctaga    2940
gaaggtggcg cggggtaaac tgggaaagtg atgtcgtgta ctggctccgc cttttcccg     3000 agggtggggg agaaccgtat ataagtgcag tagtcgccgt gaacgttctt tttcgcaacg    3060
ggtttgccgc cagaacacag ctgaagcttc gaggggctcg catctctcct tcacgcgccc    3120
gccgccctac ctgaggccgc catccacgcc ggttgagtcg cgttctgccg cctcccgcct    3180
gtggtgcctc ctgaactgcg tccgccgtct aggtaagttt aaagctcagg tcgagaccgg    3240
gcctttgtcc ggcgctccct tggagcctac ctagactcag ccggctctcc acgctttgcc    3300
tgaccctgct tgctcaactc tacgtctttg tttcgttttc tgttctgcgc cgttacagat    3360
ccaagctgtg accggcgcct actagtgcca ccatggactt tcaagtgcag atcttcagct    3420
ttctgctgat ctctgctagt gtcatcatgt ctcaagtgca actgcaggaa tctggaggtg    3480
gcctcgtgca agctggaggc agcctgaggc tgagctgtgc tgcatccggt cgcacccttta   3540 gcgagtatgc aatgggttgg tttcgccagg caccaggtaa ggagagggag tttgtggcaa    3600
ccatctcctg gtctggtggc tccacatact acacagattc cgtcaaggga agattcacta    3660
tctccaggga caacgcaaag aacacagtgt atctgcagat gaatagcctc aagccagatg    3720
acacagccgt ctactattgc gctgcagctg gtctgggcac cgtggtgtcc gaatgggatt    3780
acgactacga ttactggggt caaggcactc aggtgactgt gtctagcggt agcgaaatcg    3840
agcagaagct gatttccgaa gaggatctca atggagtgac tgtcagcagc gctctgtcta    3900
actccatcat gtacttctca cacttcgtgc cagtgttcct ccctgctaaa cccaccacaa    3960
ctccagcacc tagacctccc actccagcac caactattgc atcccagcct ctctccctca    4020
gaccagaagc atgcagacct gcagcaggtg gagctgtgca cacaagaggt ctggacccct    4080
tctgggtcct cgtggtggtg ggtggagtcc tggcatgtta cagcctcctg gtcaccgtgg    4140
cattcatcat cttctgggtg agatctaaga ggagcagact gctgcactct gattacatga    4200
acatgacacc cagaagacct ggtcccacca gaaagcacta ccaaccctac gcaccaccaa    4260
gagactttgc tgcatacaga agtctcgaga gggtcaagtt ctcaaggagt gcagatgctc    4320
cagcctatca acagggtcag aaccaactgt acaacgagct gaatctcgga agaagagagg    4380
agtacgatgt gctggataag agaagaggca gggacccaga gatgggtggg aaacccagaa    4440
gaaagaatcc tcaagaggga ctgtacaatg agctgcagaa ggataagatg gctgaggcat    4500
actcagagat cggtatgaag ggagagagga gaagaggcaa aggtcatgat ggtctgtacc    4560
aaggtctgtc cacagcaaca aaggatacat atgatgctct gcacatgcag gcactcccac    4620
cacggggttc cggagtgaaa cagactttga actttgacct tctcaagttg gctggagacg    4680
tcgagtccaa ccctggtccc atgaccgagt acaagcccac ggtgcgcctc gccaccgcg    4740 acgacgtccc cagggccgta cgcaccctcg ccgccgcgtt cgccgactac cccgccacgc    4800
gccacaccgt cgatccggac cgccacatcg agcgggtcac cgagctgcaa gaactcttcc    4860
tcacgcgcgt cgggctcgac atcggcaagg tgtgggtcgc ggacgacggc gccgcggtgg    4920
cggtctggac cacgccggag agcgtcgaag cgggggcggt gttcgccgag atcggcccgc    4980
gcatggccga gttgagcggt tcccggctgg ccgcgcagca acagatggaa ggcctcctgg    5040
cgccgcaccg gcccaaggag cccgcgtggt tcctggccac cgtcggcgtc tcgcccgacc    5100
```

| | |
|---|---|
| accagggcaa gggtctgggc agcgccgtcg tgctccccgg agtggaggcg gccgagcgcg | 5160 |
| ccggggtgcc cgccttcctg gagacctccg cgccccgcaa cctcccct tc tacgagcggc | 5220 |
| tcggcttcac cgtcaccgcc gacgtcgagg tgcccgaagg accgcgcacc tggtgcatga | 5280 |
| cccgcaagcc cggtgcctga ttaattaagt cgacaatcaa cctctggatt acaaaatttg | 5340 |
| tgaaagattg actggtattc ttaactatgt tgctcctttt acgctatgtg gatacgctgc | 5400 |
| tttaatgcct ttgtatcatg ctattgcttc ccgtatggct ttcattttct cctccttgta | 5460 |
| taaatcctgg ttgctgtctc tttatgagga gttgtggccc gttgtcaggc aacgtggcgt | 5520 |
| ggtgtgcact gtgtttgctg acgcaacccc cactggttgg ggcattgcca ccacctgtca | 5580 |
| gctcctttcc gggactttcg ctttccccct cccta ttgcc acggcggaac tcatcgccgc | 5640 |
| ctgccttgcc cgctgctgga caggggctcg gctgttgggc actgacaatt ccgtggtgtt | 5700 |
| gtcggggaaa tcatcgtcct ttccttggct gctcgcctgt gttgccacct ggattctgcg | 5760 |
| cgggacgtcc ttctgctacg tcccttcggc cctcaatcca gcggaccttc cttcccgcgg | 5820 |
| cctgctgccg gctctgcggc ctcttccgcg tcttcgcctt cgcccagcga cgagtcggat | 5880 |
| ctccctttgg gccgcctccc cgcctggtac ctttaagacc aatgacttac aaggcagctg | 5940 |
| tagatcttag ccactttta aagaaaagg ggggactgga agggctaatt cactcccaac | 6000 |
| gaagataaga tctgcttttt gcttgtactg ggtctctctg gttagaccag atctgagcct | 6060 |
| gggagctctc tggctaacta gggaacccac tgcttaagcc tcaataaagc ttgccttgag | 6120 |
| tgcttcaagt agtgtgtgcc cgtctgttgt gtgactctgg taactagaga tccctcagac | 6180 |
| ccttttagtc agtgtggaaa atctctagca gtagtagttc atgtcatctt attattcagt | 6240 |
| atttataact tgcaaagaaa tgaatatcag agagtgagag gaacttgttt attgcagctt | 6300 |
| ataatggtta caaataaagc aatagcatca caaatttcac aaataaagca tttttttcac | 6360 |
| tgcattctag ttgtggtttg tccaaactca tcaatgtatc ttatcatgtc tggctctagc | 6420 |
| tatcccgccc ctaactccgc ccatcccgcc cctaactccg cccagttccg cccattctcc | 6480 |
| gccccatggc tgactaattt ttttta ttta tgcagaggcc gaggccgcct cggcctctga | 6540 |
| gctattccag aagtagtgag gaggcttttt tggaggccta acttttgca gagacggccc | 6600 |
| aaattcgtaa tcatggtcat agctgtttcc tgtgtgaaat tgttatccgc tcacaattcc | 6660 |
| acacaacata cgagccggaa gcataaagtg taaagcctgg ggtgcctaat gagtgagcta | 6720 |
| actcacatta attgcgttgc gctcactgcc cgctttccag tcgggaaacc tgtcgtgcca | 6780 |
| gctgcattaa tgaatcggcc aacgcgcggg gagaggcggt ttgcgtattg ggcgctcttc | 6840 |
| cgcttcctcg ctcactgact cgctgcgctc ggtcgttcgg ctgcggcgag cggtatcagc | 6900 |
| tcactcaaag gcggtaatac ggttatccac agaatcaggg gataacgcag gaaagaacat | 6960 |
| gtgagcaaaa ggccagcaaa aggccaggaa ccgtaaaaag gccgcgttgc tggcgttttt | 7020 |
| ccataggctc cgcccccctg acgagcatca caaaaatcga cgctcaagtc agaggtggcg | 7080 |
| aaacccgaca ggactataaa gataccaggc gtttccccct ggaagctccc tcgtgcgctc | 7140 |
| tcctgttccg accctgccgc ttaccggata cctgtccgcc tttctccctt cgggaagcgt | 7200 |
| ggcgctttct catagctcac gctgtaggta tctcagttcg gtgtaggtcg ttcgctccaa | 7260 |
| gctgggctgt gtgcacgaac ccccgttca gcccgaccgc tgcgccttat ccggtaacta | 7320 |
| tcgtcttgag tccaacccgg taagacacga cttatcgcca ctggcagcag ccactggtaa | 7380 |
| caggattagc agagcgaggt atgtaggcgg tgctacagag ttcttgaagt ggtggcctaa | 7440 |
| ctacggctac actagaagga cagtatttgg tatctgcgct ctgctgaagc cagttacctt | 7500 |

```
cggaaaaaga gttggtagct cttgatccgg caaacaaacc accgctggta gcggtggttt    7560
ttttgtttgc aagcagcaga ttacgcgcag aaaaaaagga tctcaagaag atcctttgat    7620
cttttctacg gggtctgacg ctcagtggaa cgaaaactca cgttaaggga ttttggtcat    7680
gagattatca aaaaggatct tcacctagat ccttttaaat taaaaatgaa gttttaaatc    7740
aatctaaagt atatatgagt aaacttggtc tgacagttac caatgcttaa tcagtgaggc    7800
acctatctca gcgatctgtc tatttcgttc atccatagtt gcctgactcc ccgtcgtgta    7860
gataactacg atacgggagg gcttaccatc tggccccagt gctgcaatga taccgcgaga    7920
cccacgctca ccggctccag atttatcagc aataaaccag ccagccggaa gggccgagcg    7980
cagaagtggt cctgcaactt tatccgcctc catccagtct attaattgtt gccgggaagc    8040
tagagtaagt agttcgccag ttaatagttt gcgcaacgtt gttgccattg ctacaggcat    8100
cgtggtgtca cgctcgtcgt ttggtatggc ttcattcagc tccggttccc aacgatcaag    8160
gcgagttaca tgatccccca tgttgtgcaa aaaagcggtt agctccttcg gtcctccgat    8220
cgttgtcaga agtaagttgg ccgcagtgtt atcactcatg gttatggcag cactgcataa    8280
ttctcttact gtcatgccat ccgtaagatg cttttctgtg actggtgagt actcaaccaa    8340
gtcattctga gaatagtgta tgcggcgacc gagttgctct tgcccggcgt caatacggga    8400
taataccgcg ccacatagca gaactttaaa agtgctcatc attggaaaac gttcttcggg    8460
gcgaaaactc tcaaggatct taccgctgtt gagatccagt tcgatgtaac ccactcgtgc    8520
acccaactga tcttcagcat cttttacttt caccagcgtt tctgggtgag caaaaacagg    8580
aaggcaaaat gccgcaaaaa agggaataag ggcgacacgg aaatgttgaa tactcatact    8640 cttcctttt caatattatt gaagcattta tcagggttat tgtctcatga gcggatacat    8700
atttgaatgt atttagaaaa ataaacaaat aggggttccg cgcacatttc cccgaaaagt    8760
gccacctgac gtctaagaaa ccattattat catgacatta acctataaaa ataggcgtat    8820
cacgaggccc tttcgtctcg cgcgtttcgg tgatgacggt gaaaacctct gacacatgca    8880
gctcccggag acggtcacag cttgtctgta agcggatgcc gggagcagac aagcccgtca    8940
gggcgcgtca gcgggtgttg gcgggtgtcg ggctggctt aactatgcgg catcagagca    9000
gattgtactg agagtgcacc atatgcggtg tgaaataccg cacagatgcg taaggagaaa    9060
ataccgcatc aggcgccatt cgccattcag gctgcgcaac tgttgggaag ggcgatcggt    9120
gcgggcctct tcgctattac gccagctggc gaaaggggga tgtgctgcaa ggcgattaag    9180
ttgggtaacg ccagggtttt cccagtcacg acgttgtaaa acgacggcca gtgccaagct    9240
g                                                                    9241
```

<210> SEQ ID NO 20
<211> LENGTH: 9241
<212> TYPE: DNA
<213> ORGANISM: Artificial Sequence
<220> FEATURE:
<223> OTHER INFORMATION: Synthetic

<400> SEQUENCE: 20

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
cgatcgtgcc ttattaggaa ggcaacagac gggtctgaca tggattggac gaaccactga    180
attgccgcat tgcagagata ttgtatttaa gtgcctagct cgatacaata aacgggtctc    240
```

```
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg aaaatctct  agcagtggcg    420
cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta agcggggag    600
aattagatcg cgatgggaaa aaattcggtt aaggccaggg ggaagaaaa  aatataaatt    660
aaaacatata gtatgggcaa gcaggagct  agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcg tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagatttgg aatcacacga cctggatgga gtgggacaga gaaattaaca   1440
attacacaag cttaatacac tccttaattg aagaatcgca aaaccagcaa gaaaagaatg   1500
aacaagaatt attggaatta gataaatggg caagtttgtg gaattggttt aacataacaa   1560
attggctgtg gtatataaaa ttattcataa tgatagtagg aggcttggta ggtttaagaa   1620
tagttttgc  tgtactttct atagtgaata gagttaggca gggatattca ccattatcgt   1680
ttcagaccca cctcccaacc ccgagggggac ccgacaggcc cgaaggaata gaagaagaag   1740
gtggagagag agacagagac agatccattc gattagtgaa cggatctcga cggtatcggt   1800
taactttta  aagaaaaggg gggattgggg ggtacagtgc aggggaaaga atagtagaca   1860
taatagcaac agacatacaa actaaagaat tacaaaaaca aattacaaaa ttcaaaattt   1920
tatcgatgct agcggaggaa aaactgtttc atacagaagg cgtggaggaa aaactgtttc   1980
atacagaagg cgtggaggaa aaactgtttc atacagaagg cgtggaggaa aaactgtttc   2040
atacagaagg cgtggaggaa aaactgtttc atacagaagg cgtggaggaa aaactgtttc   2100
atacagaagg cgtagatcta gactctagag ggtatataat ggaagctcga cttccagctt   2160
ggcattccgg tactgttggt aaaaagcttg gcaatccggt actgttggta aggatccgc    2220
caccatggct gcagcttgga cagttgttct cgttacactc gttctgggtc tggctgtggc   2280
tggtcctgtg cctacctcca aacctaccac aacaggtaag ggttgtcaca ttggacgctt   2340
caaatccctc agcccacagg agctggcctc cttcaagaaa gctagagatg ccctcgaaga   2400
gagcctgaaa ctcaagaact ggtcctgttc tagcccagtg ttcccaggaa actgggacct   2460
gaggctcctc caagttcgcg agaggccagt ggcactggag gcagagctgg ctctcactct   2520
caaagttctg gaggctgctg ctggaccagc tctggaagac gtgctcgacc agccactgca   2580
tactctgcac catatcctga gccaactgca ggcttgcatc cagccacagc ctacagcagg   2640
```

```
tcctagaccc agaggtcgcc tgcaccactg gctgcacagg ctccaagaag ctccaaagaa    2700
ggagtctgca ggttgcctgg aggccagcgt tacattcaat ctgttcagac tcctgactag    2760
ggatctgaag tacgtggcag acggtaatct gtgtctgcgc acctctactc atcccgagag    2820
cacttaagcg gccgcgaagg atctgcgatc gctccggtgc ccgtcagtgg gcagagcgca    2880
catcgcccac agtccccgag aagttggggg gaggggtcgg caattgaacg ggtgcctaga    2940
gaaggtggcg cggggtaaac tgggaaagtg atgtcgtgta ctggctccgc ctttttcccg    3000
agggtggggg agaaccgtat ataagtgcag tagtcgccgt gaacgttctt tttcgcaacg    3060
ggtttgccgc cagaacacag ctgaagcttc gaggggctcg catctctcct tcacgcgccc    3120
gccgccctac ctgaggccgc catccacgcc ggttgagtcg cgttctgccg cctcccgcct    3180
gtggtgcctc ctgaactgcg tccgccgtct aggtaagttt aaagctcagg tcgagaccgg    3240
gcctttgtcc ggcgctccct tggagcctac ctagactcag ccggctctcc acgctttgcc    3300
tgaccctgct tgctcaactc tacgtctttg tttcgttttc tgttctgcgc cgttacagat    3360
ccaagctgtg accggcgcct actagtgcca ccatggactt tcaagtgcag atcttcagct    3420
ttctgctgat ctctgctagt gtcatcatgt ctcaagtgca actgcaggaa tctggaggtg    3480
gcctcgtgca agctggaggc agcctgaggc tgagctgtgc tgcatccggt cgcacccttta   3540 gcgagtatgc aatgggttgg tttcgccagg caccaggtaa ggagagggag tttgtggcaa    3600
ccatctcctg gtctggtggc tccacatact acacagattc cgtcaaggga agattcacta    3660
tctccaggga caacgcaaag aacacagtgt atctgcagat gaatagcctc aagccagatg    3720
acacagccgt ctactattgc gctgcagctg gtctgggcac cgtggtgtcc gaatgggatt    3780
acgactacga ttactggggt caaggcactc aggtgactgt gtctagcggt agcgaaatcg    3840
agcagaagct gatttccgaa gaggatctca atggagtgac tgtcagcagc gctctgtcta    3900
actccatcat gtacttctca cacttcgtgc cagtgttcct ccctgctaaa cccaccacaa    3960
ctccagcacc tagacctccc actccagcac caactattgc atcccagcct ctctccctca    4020
gaccagaagc atgcagacct gcagcaggtg gagctgtgca cacaagaggt ctggacccctt   4080 tctgggtcct cgtggtggtg ggtggagtcc tggcatgtta cagcctcctg gtcaccgtgg    4140
cattcatcat cttctgggtg agatctaaga ggagcagact gctgcactct gattacatga    4200
acatgacacc cagaagacct ggtccaccca gaaagcacta ccaaccctac gcaccaccaa    4260
gagactttgc tgcatacaga agtctcgaga gggtcaagtt ctcaaggagt gcagatgctc    4320
cagcctatca acagggtcag aaccaactgt acaacgagct gaatctcgga agaagagagg    4380
agtacgatgt gctggataag agaagaggca gggacccaga gatgggtggg aaacccagaa    4440
gaaagaatcc tcaagaggga ctgtacaatg agctgcagaa ggataagatg gctgaggcat    4500
actcagagat cggtatgaag ggagagagga agagaggcaa aggtcatgat ggtctgtacc    4560
aaggtctgtc cacagcaaca aaggatacat atgatgctct gcacatgcag gcactcccac    4620
cacggggttc cggagtgaaa cagactttga actttgacct tctcaagttg gctggagacg    4680
tcgagtccaa ccctggtccc atgaccgagt acaagcccac ggtgcgcctc gccaccgcg    4740 acgacgtccc cagggccgta cgcacccctcg ccgccgcgtt cgccgactac cccgccacgc   4800
gccacaccgt cgatccggac cgccacatcg agcgggtcac cgagctgcaa gaactcttcc    4860
tcacgcgcgt cgggctcgac atcggcaagg tgtgggtcgc ggacgacggc gccgcggtgg    4920
cggtctggac cacgccggag agcgtcgaag cgggggcggt gttcgccgag atcggcccgc    4980
```

```
gcatggccga gttgagcggt tcccggctgg ccgcgcagca acagatggaa ggcctcctgg   5040
cgccgcaccg gcccaaggag cccgcgtggt tcctggccac cgtcggcgtc tcgcccgacc   5100
accagggcaa gggtctgggc agcgccgtcg tgctccccgg agtggaggcg gccgagcgcg   5160
ccggggtgcc cgccttcctg gagacctccg cgccccgcaa cctcccctcc tacgagcggc   5220
tcggcttcac cgtcaccgcc gacgtcgagg tgcccgaagg accgcgcacc tggtgcatga   5280
cccgcaagcc cggtgcctga ttaattaagt cgacaatcaa cctctggatt acaaaatttg   5340
tgaaagattg actggtattc ttaactatgt tgctcctttt acgctatgtg gatacgctgc   5400
tttaatgcct ttgtatcatg ctattgcttc ccgtatggct ttcattttct cctccttgta   5460
taaatcctgg ttgctgtctc tttatgagga gttgtggccc gttgtcaggc aacgtggcgt   5520
ggtgtgcact gtgtttgctg acgcaacccc cactggttgg ggcattgcca ccacctgtca   5580
gctcctttcc gggactttcg ctttccccct ccctattgcc acggcggaac tcatcgccgc   5640
ctgccttgcc cgctgctgga caggggctcg gctgttgggc actgacaatt ccgtggtgtt   5700
gtcggggaaa tcatcgtcct ttccttggct gctcgcctgt gttgccacct ggattctgcg   5760
cgggacgtcc ttctgctacg tccccttcggc cctcaatcca gcggaccttc cttcccgcgg   5820
cctgctgccg gctctgcggc ctcttccgcg tcttcgcctt cgccctcaga cgagtcggat   5880
ctccctttgg ccgcctccc cgcctggtac ctttaagacc aatgacttac aaggcagctg   5940
tagatcttag ccacttttta aagaaaagg ggggactgga agggctaatt cactcccaac   6000
gaagataaga tctgcttttt gcttgtactg ggtctctctg gttagaccag atctgagcct   6060
gggagctctc tggctaacta gggaacccac tgcttaagcc tcaataaagc ttgccttgag   6120
tgcttcaagt agtgtgtgcc cgtctgttgt gtgactctgg taactagaga tccctcagac   6180
ccttttagtc agtgtggaaa atctctagca gtagtagttc atgtcatctt attattcagt   6240
atttataact tgcaaagaaa tgaatatcag agagtgagag gaacttgttt attgcagctt   6300
ataatggtta caaataaagc aatagcatca caaatttcac aaataaagca tttttttcac   6360
tgcattctag ttgtggtttg tccaaactca tcaatgtatc ttatcatgtc tggctctagc   6420
tatcccgccc ctaactccgc ccatcccgcc cctaactccg cccagttccg ccattctcc   6480
gccccatggc tgactaattt tttttattta tgcagaggcc gaggccgcct cggcctctga   6540
gctattccag aagtagtgag gaggctttt tggaggccta cttttgca gagacggccc   6600
aaattcgtaa tcatggtcat agctgtttcc tgtgtgaaat tgttatccgc tcacaattcc   6660
acacaacata cgagccggaa gcataaagtg taaagcctgg ggtgcctaat gagtgagcta   6720
actcacatta attgcgttgc gctcactgcc cgctttccag tcgggaaacc tgtcgtgcca   6780
gctgcattaa tgaatcggcc aacgcgcggg gagaggcggt ttgcgtattg gcgctcttc   6840
cgcttcctcg ctcactgact cgctgcgctc ggtcgttcgg ctgcggcgag cggtatcagc   6900
tcactcaaag gcggtaatac ggttatccac agaatcaggg gataacgcag gaaagaacat   6960
gtgagcaaaa ggccagcaaa aggccaggaa ccgtaaaaag gccgcgttgc tggcgтттттt   7020
ccataggctc cgcccccctg acgagcatca aaaaatcga cgctcaagtc agaggtggcg   7080
aaacccgaca ggactataaa gataccaggc gtttccccct ggaagctccc tcgtgcgctc   7140
tcctgttccg accctgccgc ttaccggata cctgtccgcc tttctccctt cgggaagcgt   7200
ggcgctttct catagctcac gctgtaggta tctcagttcg gtgtaggtcg ttcgctccaa   7260
gctgggctgt gtgcacgaac cccccgttca gcccgaccgc tgcgccttat ccggtaacta   7320
tcgtcttgag tccaacccgg taagacacga cttatcgcca ctggcagcag ccactggtaa   7380
```

```
caggattagc agagcgaggt atgtaggcgg tgctacagag ttcttgaagt ggtggcctaa    7440
ctacggctac actagaagga cagtatttgg tatctgcgct ctgctgaagc cagttacctt    7500
cggaaaaaga gttggtagct cttgatccgg caaacaaacc accgctggta gcggtggttt    7560
ttttgtttgc aagcagcaga ttacgcgcag aaaaaaagga tctcaagaag atcctttgat    7620
cttttctacg gggtctgacg ctcagtggaa cgaaaactca cgttaaggga ttttggtcat    7680
gagattatca aaaaggatct tcacctagat ccttttaaat taaaaatgaa gttttaaatc    7740
aatctaaagt atatatgagt aaacttggtc tgacagttac caatgcttaa tcagtgaggc    7800
acctatctca gcgatctgtc tatttcgttc atccatagtt gcctgactcc ccgtcgtgta    7860
gataactacg atacgggagg gcttaccatc tggccccagt gctgcaatga taccgcgaga    7920
cccacgctca ccggctccag atttatcagc aataaaccag ccagccggaa gggccgagcg    7980
cagaagtggt cctgcaactt tatccgcctc catccagtct attaattgtt gccgggaagc    8040
tagagtaagt agttcgccag ttaatagttt gcgcaacgtt gttgccattg ctacaggcat    8100
cgtggtgtca cgctcgtcgt ttggtatggc ttcattcagc tccggttccc aacgatcaag    8160
gcgagttaca tgatccccca tgttgtgcaa aaaagcggtt agctccttcg gtcctccgat    8220
cgttgtcaga agtaagttgg ccgcagtgtt atcactcatg gttatggcag cactgcataa    8280
ttctcttact gtcatgccat ccgtaagatg cttttctgtg actggtgagt actcaaccaa    8340
gtcattctga atagtgtata tgcggcgacc gagttgctct tgcccggcgt caatacggga    8400
taataccgcg ccacatagca gaactttaaa agtgctcatc attggaaaac gttcttcggg    8460
gcgaaaactc tcaaggatct taccgctgtt gagatccagt tcgatgtaac ccactcgtgc    8520
acccaactga tcttcagcat cttttacttt caccagcgtt tctgggtgag caaaaacagg    8580
aaggcaaaat gccgcaaaaa agggaataag ggcgacacgg aaatgttgaa tactcatact    8640
cttccttttt caatattatt gaagcattta tcagggttat tgtctcatga gcggatacat    8700
atttgaatgt atttagaaaa ataaacaaat aggggttccg cgcacatttc cccgaaaagt    8760
gccacctgac gtctaagaaa ccattattat catgacatta acctataaaa ataggcgtat    8820
cacgaggccc tttcgtctcg cgcgtttcgg tgatgacggt gaaaacctct gacacatgca    8880
gctcccggag acggtcacag cttgtctgta agcggatgcc gggagcagac aagcccgtca    8940
gggcgcgtca gcgggtgttg gcgggtgtcg ggctggctt aactatgcgg catcagagca    9000
gattgtactg agagtgcacc atatgcggtg tgaaataccg cacagatgcg taaggagaaa    9060
ataccgcatc aggcgccatt cgccattcag gctgcgcaac tgttgggaag ggcgatcggt    9120
gcgggcctct tcgctattac gccagctggc gaaaggggga tgtgctgcaa ggcgattaag    9180
ttgggtaacg ccagggtttt cccagtcacg acgttgtaaa acgacggcca gtgccaagct    9240
g                                                                   9241
```

<210> SEQ ID NO 21
<211> LENGTH: 9139
<212> TYPE: DNA
<213> ORGANISM: Artificial Sequence
<220> FEATURE:
<223> OTHER INFORMATION: Synthetic

<400> SEQUENCE: 21

```
acgcgtgtag tcttatgcaa tactcttgta gtcttgcaac atggtaacga tgagttagca      60
acatgcctta caaggagaga aaaagcaccg tgcatgccga ttggtggaag taaggtggta     120
```

-continued

```
cgatcgtgcc ttattaggaa ggcaacagac gggtctgaca tggattggac gaaccactga      180
attgccgcat tgcagagata ttgtatttaa gtgcctagct cgatacaata aacgggtctc      240
tctggttaga ccagatctga gcctgggagc tctctggcta actagggaac ccactgctta      300
agcctcaata aagcttgcct tgagtgcttc aagtagtgtg tgcccgtctg ttgtgtgact      360
ctggtaacta gagatccctc agaccctttt agtcagtgtg aaaatctct agcagtggcg      420 cccgaacagg gacctgaaag cgaaagggaa accagagctc tctcgacgca ggactcggct      480
tgctgaagcg cgcacggcaa gaggcgaggg gcggcgactg gtgagtacgc caaaaatttt      540
gactagcgga ggctagaagg agagagatgg gtgcgagagc gtcagtatta gcgggggag       600 aattagatcg cgatgggaaa aaattcggtt aaggccaggg ggaaagaaaa aatataaatt      660
aaaacatata gtatgggcaa gcagggagct agaacgattc gcagttaatc ctggcctgtt      720
agaaacatca gaaggctgta gacaaatact gggacagcta caaccatccc ttcagacagg      780
atcagaagaa cttagatcat tatataatac agtagcaacc ctctattgtg tgcatcaaag      840
gatagagata aaagacacca aggaagcttt agacaagata gaggaagagc aaaacaaaag      900
taagaccacc gcacagcaag cggccactga tcttcagacc tggaggagga gatatgaggg      960
acaattggag aagtgaatta tataaatata aagtagtaaa aattgaacca ttaggagtag     1020
cacccaccaa ggcaaagaga agagtggtgc agagagaaaa aagagcagtg ggaataggag     1080 cttttgttcct tgggttcttg ggagcagcag gaagcactat gggcgcagcg tcaatgacgc     1140
tgacggtaca ggccagacaa ttattgtctg gtatagtgca gcagcagaac aatttgctga     1200
gggctattga ggcgcaacag catctgttgc aactcacagt ctggggcatc aagcagctcc     1260
aggcaagaat cctggctgtg gaaagatacc taaaggatca acagctcctg gggatttggg     1320
gttgctctgg aaaactcatt tgcaccactg ctgtgccttg gaatgctagt tggagtaata     1380
aatctctgga acagatttgg aatcacacga cctggatgga gtgggacaga gaaattaaca     1440
attacacaag cttaatacac tccttaattg aagaatcgca aaaccagcaa gaaaagaatg     1500
aacaagaatt attggaatta gataaatggg caagtttgtg gaattggttt aacataacaa     1560
attggctgtg gtatataaaa ttattcataa tgatagtagg aggcttggta ggtttaagaa     1620 tagttttgc tgtactttct atagtgaata gagttaggca gggatattca ccattatcgt      1680
ttcagaccca cctcccaacc ccgaggggac ccgacaggcc cgaaggaata agaagaagaag   1740 gtggagagag agacagagac agatccattc gattagtgaa cggatctcga cggtatcggt     1800
taacttttaa aagaaaaggg gggattgggg ggtacagtgc aggggaaaga atagtagaca     1860
taatagcaac agacatacaa actaaagaat tacaaaaaca aattacaaaa ttcaaaattt     1920
tatcgatgct agcggaggaa aaactgtttc atacagaagg cgtggaggaa aaactgtttc     1980
atacagaagg cgtggaggaa aaactgtttc atacagaagg cgtggaggaa aaactgtttc     2040
atacagaagg cgtggaggaa aaactgtttc atacagaagg cgtggaggaa aaactgtttc     2100
atacagaagg cgtagatcta gactctagag ggtatataat ggaagctcga cttccagctt     2160
ggcattccgg tactgttggt aaaaagcttg gcaatccggt actgttggta aaggatccgc     2220
caccatgtgt gatctgcctc agacccatag cctgggctcc agaagaaccc tgatgctgct     2280
ggctcaaatg agacgcattt ccctgttctc ctgtctgaag acagacacg actttggctt       2340 ccctcaagaa gagtttggaa accaattcca gaaggctgag acaatcccag tcctgcacga     2400
aatgatccaa caaatcttca atctgttctc caccaaggat tcctctgctg cttgggacga     2460
gacactcctc gacaagttct ataccgaact ctatcagcaa ctgaacgatc tcgaagcctg     2520
```

```
cgtgatccaa ggtgtgggtg tgaccgaaac tccactgatg aaggaagata gcatcctggc   2580
agtgaggaag tacttccaaa ggatcactct ctatctgaag gagaagaagt actctccatg   2640
cgcatgggaa gttgtgagag ctgagatcat gcgctctttc agcctgagca ccaacctcca   2700
ggaatccctc aggtctaaag agtaagcggc cgcgaaggat ctgcgatcgc tccggtgccc   2760
gtcagtgggc agagcgcaca tcgcccacag tccccgagaa gttgggggga gggtcggca   2820 attgaacggg tgcctagaga aggtggcgcg gggtaaactg ggaaagtgat gtcgtgtact   2880
ggctccgcct ttttcccgag ggtgggggag aaccgtatat aagtgcagta gtcgccgtga   2940
acgttctttt tcgcaacggg tttgccgcca gaacacagct gaagcttcga ggggctcgca   3000
tctctccttc acgcgcccgc cgccctacct gaggccgcca tccacgccgg ttgagtcgcg   3060
ttctgccgcc tcccgcctgt ggtgcctcct gaactgcgtc cgccgtctag gtaagtttaa   3120
agctcaggtc gagaccgggc ctttgtccgg cgctcccttg gagcctacct agactcagcc   3180
ggctctccac gctttgcctg accctgcttg ctcaactcta cgtctttgtt tcgttttctg   3240
ttctgcgccg ttacagatcc aagctgtgac cggcgcctac tagtgccacc atggactttc   3300
aagtgcagat cttcagcttt ctgctgatct ctgctagtgt catcatgtct caagtgcaac   3360
tgcaggaatc tggaggtggc ctcgtgcaag ctggaggcag cctgaggctg agctgtgctg   3420
catccggtcg cacctttagc gagtatgcaa tgggttggtt tcgccaggca ccaggtaagg   3480
agagggagtt tgtggcaacc atctcctggt ctggtggctc cacatactac acagattccg   3540
tcaagggaag attcactatc tccagggaca acgcaaagaa cacagtgtat ctgcagatga   3600
atagcctcaa gccagatgac acagccgtct actattgcgc tgcagctggt ctgggcaccg   3660
tggtgtccga atgggattac gactacgatt actgggtca aggcactcag gtgactgtgt   3720
ctagcggtag cgaaatcgag cagaagctga tttccgaaga ggatctcaat ggagtgactg   3780
tcagcagcgc tctgtctaac tccatcatgt acttctcaca cttcgtgcca gtgttcctcc   3840
ctgctaaacc caccacaact ccagcaccta gacctcccac tccagcacca actattgcat   3900
cccagcctct ctccctcaga ccagaagcat gcagacctgc agcaggtgga gctgtgcaca   3960
caagaggtct ggacccttc tgggtcctcg tggtggtggg tggagtcctg gcatgttaca   4020
gcctcctggt caccgtggca ttcatcatct tctgggtgag atctaagagg agcagactgc   4080
tgcactctga ttacatgaac atgacaccca gaagacctgg tccccaccaga aagcactacc   4140 aaccctacgc accaccaaga gactttgctg catacagaag tctcgagagg gtcaagttct   4200
caaggagtgc agatgctcca gcctatcaac agggtcagaa ccaactgtac aacgagctga   4260
atctcggaag aagagaggag tacgatgtgc tggataagag aagaggcagg gacccagaga   4320
tgggtgggaa acccagaaga aagaatcctc aagagggact gtacaatgag ctgcagaagg   4380
ataagatggc tgaggcatac tcagagatcg gtatgaaggg agagaggaga agaggcaaag   4440
gtcatgatgg tctgtaccaa ggtctgtcca cagcaacaaa ggatacatat gatgctctgc   4500
acatgcaggc actcccacca cggggttccg gagtgaaaca gactttgaac tttgaccttc   4560
tcaagttggc tggagacgtc gagtccaacc ctggtcccat gaccgagtac aagcccacgg   4620
tgcgcctcgc caccccgcgac gacgtcccca gggccgtacg caccctcgcc gccgcgttcg   4680
ccgactaccc cgccacgcgc cacaccgtcg atccggaccg ccacatcgag cgggtcaccg   4740
agctgcaaga actcttcctc acgcgcgtcg ggctcgacat cggcaaggtg tgggtcgcgg   4800
acgacggcgc cgcggtggcg gtctggacca cgccggagag cgtcgaagcg ggggcggtgt   4860
```

```
tcgccgagat cggcccgcgc atggccgagt tgagcggttc ccggctggcc gcgcagcaac      4920
agatggaagg cctcctggcg ccgcaccggc ccaaggagcc cgcgtggttc ctggccaccg      4980
tcggcgtctc gcccgaccac cagggcaagg gtctgggcag cgccgtcgtg ctccccggag      5040
tggaggcggc cgagcgcgcc ggggtgcccg ccttcctgga gacctccgcg ccccgcaacc      5100
tccccttcta cgagcggctc ggcttcaccg tcaccgccga cgtcgaggtg cccgaaggac      5160
cgcgcacctg gtgcatgacc cgcaagcccg gtgcctgatt aattaagtcg acaatcaacc      5220
tctggattac aaaatttgtg aaagattgac tggtattctt aactatgttg ctccttttac      5280
gctatgtgga tacgctgctt taatgccttt gtatcatgct attgcttccc gtatggcttt      5340
cattttctcc tccttgtata atcctggtt gctgtctctt tatgaggagt tgtggcccgt       5400
tgtcaggcaa cgtggcgtgg tgtgcactgt gtttgctgac gcaacccccca ctggttgggg    5460 cattgccacc acctgtcagc tcctttccgg gactttcgct ttccccctcc ctattgccac      5520
ggcggaactc atcgccgcct gccttgcccg ctgctggaca ggggctcggc tgttgggcac      5580
tgacaattcc gtggtgttgt cggggaaatc atcgtccttt ccttggctgc tcgcctgtgt      5640
tgccacctgg attctgcgcg ggacgtcctt ctgctacgtc ccttcggccc tcaatccagc      5700
ggaccttcct tcccgcggcc tgctgccggc tctgcgcct cttccgcgtc ttcgccttcg       5760
ccctcagacg agtcggatct ccctttgggc cgcctccccg cctggtacct ttaagaccaa      5820
tgacttacaa ggcagctgta gatcttagcc acttttaaaa agaaaagggg ggactggaag      5880
ggctaattca ctcccaacga agataagatc tgcttttgc ttgtactggg tctctctggt       5940
tagaccagat ctgagcctgg gagctctctg gctaactagg gaacccactg cttaagcctc      6000
aataaagctt gccttgagtg cttcaagtag tgtgtgcccg tctgttgtgt gactctggta      6060
actagagatc cctcagaccc ttttagtcag tgtggaaaat ctctagcagt agtagttcat      6120
gtcatcttat tattcagtat ttataacttg caaagaaatg aatatcagag agtgagagga      6180
acttgtttat tgcagcttat aatggttaca aataaagcaa tagcatcaca aatttcacaa      6240
ataaagcatt ttttcactg cattctagtt gtggtttgtc caaactcatc aatgtatctt       6300
atcatgtctg gctctagcta tcccgcccct aactccgccc atcccgcccc taactccgcc      6360
cagttccgcc cattctccgc cccatggctg actaattttt tttatttatg cagaggccga      6420
ggccgcctcg gcctctgagc tattccagaa gtagtgagga ggctttttg gaggcctaga      6480 cttttgcaga gacggcccaa attcgtaatc atggtcatag ctgtttcctg tgtgaaattg      6540
ttatccgctc acaattccac acaacatacg agccggaagc ataaagtgta aagcctgggg      6600
tgcctaatga gtgagctaac tcacattaat tgcgttgcgc tcactgcccg ctttccagtc      6660
gggaaacctg tcgtgccagc tgcattaatg aatcggccaa cgcgcgggga gaggcggttt      6720
gcgtattggg cgctcttccg cttcctcgct cactgactcg ctgcgctcgg tcgttcggct      6780
gcggcgagcg gtatcagctc actcaaaggc ggtaatacgg ttatccacag aatcaggga      6840 taacgcagga aagaacatgt gagcaaaagg ccagcaaaag gccaggaacc gtaaaaaggc      6900
cgcgttgctg gcgttttcc ataggctccg ccccctgac gagcatcaca aaaatcgacg       6960
ctcaagtcag aggtggcgaa acccgacagg actataaaga taccaggcgt ttccccctgg      7020
aagctccctc gtgcgctctc ctgttccgac cctgccgctt accggatacc tgtccgcctt      7080
tctcccttcg ggaagcgtgg cgcttttctca tagctcacgc tgtaggtatc tcagttcggt    7140
gtaggtcgtt cgctccaagc tgggctgtgt gcacgaaccc cccgttcagc ccgaccgctg     7200
cgccttatcc ggtaactatc gtcttgagtc caacccggta agacacgact tatcgccact      7260
```

-continued

```
ggcagcagcc actggtaaca ggattagcag agcgaggtat gtaggcggtg ctacagagtt    7320
cttgaagtgg tggcctaact acggctacac tagaaggaca gtatttggta tctgcgctct    7380
gctgaagcca gttaccttcg gaaaaagagt tggtagctct tgatccggca aacaaaccac    7440
cgctggtagc ggtggttttt ttgtttgcaa gcagcagatt acgcgcagaa aaaaggatc    7500 tcaagaagat cctttgatct tttctacggg gtctgacgct cagtggaacg aaaactcacg    7560
ttaagggatt ttggtcatga gattatcaaa aaggatcttc acctagatcc ttttaaatta    7620
aaaatgaagt tttaaatcaa tctaaagtat atatgagtaa acttggtctg acagttacca    7680
atgcttaatc agtgaggcac ctatctcagc gatctgtcta tttcgttcat ccatagttgc    7740
ctgactcccc gtcgtgtaga taactacgat acgggagggc ttaccatctg gccccagtgc    7800
tgcaatgata ccgcgagacc cacgctcacc ggctccagat ttatcagcaa taaaccagcc    7860
agccggaagg gccgagcgca gaagtggtcc tgcaacttta tccgcctcca tccagtctat    7920
taattgttgc cgggaagcta gagtaagtag ttcgccagtt aatagtttgc gcaacgttgt    7980
tgccattgct acaggcatcg tggtgtcacg ctcgtcgttt ggtatggctt cattcagctc    8040
cggttcccaa cgatcaaggc gagttacatg atcccccatg ttgtgcaaaa aagcggttag    8100
ctccttcggt cctccgatcg ttgtcagaag taagttggcc gcagtgttat cactcatggt    8160 tatgcagca ctgcataatt ctcttactgt catgccatcc gtaagatgct tttctgtgac    8220
tggtgagtac tcaaccaagt cattctgaga atagtgtatg cggcgaccga gttgctcttg    8280
cccggcgtca atacgggata ataccgcgcc acatagcaga actttaaaag tgctcatcat    8340
tggaaaacgt tcttcggggc gaaaactctc aaggatctta ccgctgttga tccagttc     8400 gatgtaaccc actcgtgcac ccaactgatc ttcagcatct tttactttca ccagcgtttc    8460
tgggtgagca aaaacaggaa ggcaaaatgc cgcaaaaaag gaataagggc gacacggaa    8520 atgttgaata ctcatactct tcctttttca atattattga agcatttatc agggttattg    8580
tctcatgagc ggatacatat ttgaatgtat ttagaaaaat aaacaaatag gggttccgcg    8640
cacatttccc cgaaaagtgc cacctgacgt ctaagaaacc attattatca tgacattaac    8700
ctataaaaat aggcgtatca cgaggccctt tcgtctcgcg cgtttcggtg atgacggtga    8760
aaacctctga cacatgcagc tcccggagac ggtcacagct tgtctgtaag cggatgccgg    8820
gagcagacaa gcccgtcagg gcgcgtcagc gggtgttggc gggtgtcggg gctggcttaa    8880
ctatgcggca tcagagcaga ttgtactgag agtgcaccat atgcggtgtg aaataccgca    8940
cagatgcgta aggagaaaat accgcatcag gcgccattcg ccattcaggc tgcgcaactg    9000
ttgggaaggg cgatcggtgc gggcctcttc gctattacgc cagctggcga aggggggatg    9060
tgctgcaagg cgattaagtt gggtaacgcc agggttttcc cagtcacgac gttgtaaaac    9120
gacggccagt gccaagctg                                                 9139
```

<210> SEQ ID NO 22
<211> LENGTH: 9202
<212> TYPE: DNA
<213> ORGANISM: Artificial Sequence
<220> FEATURE:
<223> OTHER INFORMATION: Synthetic

<400> SEQUENCE: 22

```
acgcgtgtag tcttatgcaa tactcttgta gtcttgcaac atggtaacga tgagttagca     60
acatgcctta caaggagaga aaaagcaccg tgcatgccga ttggtggaag taaggtggta    120
```

```
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg aaaatctct agcagtggcg    420 cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta gcgggggag    600 aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata agtagtaaa aattgaacca ttaggagtag   1020 caccccaccaa ggcaaagaga agagtggtgc agagagaaaa aagagcagtg gaataggag   1080 cttttgttcct tgggttcttg ggagcagcag gaagcactat gggcgcagcg tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagatttgg aatcacacga cctggatgga gtgggacaga gaaattaaca   1440
attacacaag cttaatacac tccttaattg aagaatcgca aaaccagcaa gaaaagaatg   1500
aacaagaatt attggaatta gataaatggg caagtttgtg gaattggttt aacataacaa   1560
attggctgtg gtatataaaa ttattcataa tgatagtagg aggcttggta ggtttaagaa   1620 tagttttttgc tgtactttct atagtgaata gagttaggca gggatattca ccattatcgt   1680
ttcagaccca cctcccaacc ccgagggac ccgacaggcc cgaaggaata agaagaagaag   1740 gtggagagag agacagagac agatccattc gattagtgaa cggatctcga cggtatcggt   1800
taacttttaa aagaaaaggg gggattgggg ggtacagtgc aggggaaaga atagtagaca   1860
taatagcaac agacatacaa actaaagaat tacaaaaaca aattacaaaa ttcaaaattt   1920
tatcgatgct agcggaggaa aaactgtttc atacagaagg cgtggaggaa aaactgtttc   1980
atacagaagg cgtggaggaa aaactgtttc atacagaagg cgtggaggaa aaactgtttc   2040
atacagaagg cgtggaggaa aaactgtttc atacagaagg cgtggaggaa aaactgtttc   2100
atacagaagg cgtagatcta gactctagag gtatataat ggaagctcga cttccagctt   2160
ggcattccgg tactgttggt aaaaagcttg gcaatccggt actgttggta aaggatccgc   2220
caccatgact aacaaatgtc tcctccagat tgcactgctg ctgtgtttct ctaccactgc   2280
tctctccatg agctacaacc tgctgggctt cctccaacgc tcctccaact ttcaatgtca   2340
gaaactcctg tggcagctga atggtcgcct cgaatactgc ctcaaggata ggatgaactt   2400
cgacatccct gaggaaatca aacagctcca gcaattccag aaggaagatg cagctctgac   2460
catctatgag atgctccaga acatcttcgc tatctttaga caagactcct ccagcacagg   2520
```

```
atggaatgag acaatcgttg agaacctgct cgctaacgtc taccatcaga tcaaccacct    2580
gaagaccgtg ctggaggaga agctggagaa ggaagacttt accagaggca agctgatgag    2640
cagcctgcac ctgaagaggt actacggcag aatcctgcac tatctgaagg ccaaggaata    2700
ctcccattgc gcatggacca ttgtcagagt ggagatcctc cgcaacttct acttcatcaa    2760
caggctgact ggctacctga gaaactaagc ggccgcgaag gatctgcgat cgctccggtg    2820
cccgtcagtg ggcagagcgc acatcgccca cagtccccga aagttgggg ggaggggtcg     2880
gcaattgaac gggtgcctag agaaggtggc gcggggtaaa ctgggaaagt gatgtcgtgt    2940
actggctccg cctttttccc gagggtgggg agaaccgta tataagtgca gtagtcgccg     3000
tgaacgttct ttttcgcaac gggtttgccg ccagaacaca gctgaagctt cgaggggctc    3060
gcatctctcc ttcacgcgcc cgccgcccta cctgaggccg ccatccacgc cggttgagtc    3120
gcgttctgcc gcctcccgcc tgtggtgcct cctgaactgc gtccgccgtc taggtaagtt    3180
taaagctcag gtcgagaccg gcctttgtc cggcgctccc ttggagccta cctagactca     3240
gccggctctc cacgctttgc ctgaccctgc ttgctcaact ctacgtcttt gtttcgtttt    3300
ctgttctgcg ccgttacaga tccaagctgt gaccggcgcc tactagtgcc accatggact    3360
ttcaagtgca gatcttcagc tttctgctga tctctgctag tgtcatcatg tctcaagtgc    3420
aactgcagga atctggaggt ggcctcgtgc aagctgagg cagcctgagg ctgagctgtg     3480
ctgcatccgg tcgcaccttt agcgagtatg caatgggttg gtttcgccag gcaccaggta    3540
aggagaggga gtttgtggca accatctcct ggtctggtgg ctccacatac tacacagatt    3600
ccgtcaaggg aagattcact atctccaggg acaacgcaaa gaacacagtg tatctgcaga    3660
tgaatagcct caagccagat gacacagccg tctactattg cgctgcagct ggtctgggca    3720
ccgtggtgtc cgaatgggat tacgactacg attactgggg tcaaggcact caggtgactg    3780
tgtctagcgg tagcgaaatc gagcagaagc tgatttccga agaggatctc aatggagtga    3840
ctgtcagcag cgctctgtct aactccatca tgtacttctc acacttcgtg ccagtgttcc    3900
tccctgctaa acccaccaca actccagcac ctagacctcc cactccagca ccaactattg    3960
catcccagcc tctctccctc agaccagaag catgcagacc tgcagcaggt ggagctgtgc    4020
acacaagagg tctggaccct ttctgggtcc tcgtggtggt gggtggagtc ctggcatgtt    4080
acagcctcct ggtcaccgtg gcattcatca tcttctgggt gagatctaag aggagcagac    4140
tgctgcactc tgattacatg aacatgacac cagaagacc tggtcccacc agaaagcact    4200
accaacccta cgcaccacca agagactttg ctgcatacag aagtctcgag agggtcaagt    4260
tctcaaggag tgcagatgct ccagcctatc aacagggtca gaaccaactg tacaacgagc    4320
tgaatctcgg aagaagagag gagtacgatg tgctggataa gaagagagc agggacccag    4380
agatgggtgg gaaacccaga agaagaatc ctcaagaggg actgtacaat gagctgcaga    4440
aggataagat ggctgaggca tactcagaga tcggtatgaa gggagagagg agaagaggca    4500
aaggtcatga tggtctgtac caaggtctgt ccacagcaac aaaggataca tatgatgctc    4560
tgcacatgca ggcactccca ccacggggtt ccggagtgaa acagactttg aactttgacc    4620
ttctcaagtt ggctggagac gtcgagtcca accctggtcc catgaccgag tacaagccca    4680
cggtgcgcct cgccacccgc gacgacgtcc cagggccgt acgcaccctc gccgccgcgt    4740
tcgccgacta ccccgccacg cgccacaccg tcgatccgga ccgccacatc gagcgggtca    4800
ccgagctgca agaactcttc ctcacgcgcg tcgggctcga catcggcaag gtgtgggtcg    4860
```

-continued

```
cggacgacgg cgccgcggtg gcggtctgga ccacgccgga gagcgtcgaa gcggggggcgg    4920
tgttcgccga gatcggcccg cgcatggccg agttgagcgg ttcccggctg gccgcgcagc    4980
aacagatgga aggcctcctg gcgccgcacc ggcccaagga gcccgcgtgg ttcctggcca    5040
ccgtcggcgt ctcgcccgac caccagggca agggtctggg cagcgccgtc gtgctccccg    5100
gagtggaggc ggccgagcgc gccggggtgc ccgccttcct ggagacctcc gcgccccgca    5160
acctcccctt ctacgagcgg ctcggcttca ccgtcaccgc cgacgtcgag gtgcccgaag    5220
gaccgcgcac ctggtgcatg acccgcaagc ccggtgcctg attaattaag tcgacaatca    5280
acctctggat tacaaaattt gtgaaagatt gactggtatt cttaactatg ttgctccttt    5340
tacgctatgt ggatacgctg ctttaatgcc tttgtatcat gctattgctt cccgtatggc    5400
tttcattttc tcctccttgt ataaatcctg gttgctgtct ctttatgagg agttgtggcc    5460
cgttgtcagg caacgtggcg tggtgtgcac tgtgtttgct gacgcaaccc ccactggttg    5520
gggcattgcc accacctgtc agctccttc cgggactttc gctttccccc tccctattgc    5580
cacggcggaa ctcatcgccg cctgccttgc ccgctgctgg acaggggctc ggctgttggg    5640
cactgacaat tccgtggtgt tgtcggggaa atcatcgtcc tttccttggc tgctcgcctg    5700
tgttgccacc tggattctgc gcgggacgtc cttctgctac gtcccttcgg ccctcaatcc    5760
agcggacctt ccttcccgcg gcctgctgcc ggctctgcgg cctcttccgc gtcttcgcct    5820
tcgccctcag acgagtcgga tctcccttg ggccgcctcc ccgcctggta cctttaagac    5880
caatgactta caaggcagct gtagatctta gccacttttt aaagaaaag ggggactgg    5940
aagggctaat tcactcccaa cgaagataag atctgctttt tgcttgtact gggtctctct    6000
ggttagacca gatctgagcc tgggagctct ctggctaact agggaaccca ctgcttaagc    6060
ctcaataaag cttgccttga gtgcttcaag tagtgtgtgc ccgtctgttg tgtgactctg    6120
gtaactagag atccctcaga cccttttagt cagtgtggaa aatctctagc agtagtagtt    6180
catgtcatct tattattcag tatttataac ttgcaaagaa atgaatatca gagagtgaga    6240
ggaacttgtt tattgcagct tataatggtt acaaataaag caatagcatc acaaatttca    6300
caaataaagc attttttttca ctgcattcta gttgtggttt gtccaaactc atcaatgtat    6360
cttatcatgt ctggctctag ctatcccgcc cctaactccg cccatcccgc ccctaactcc    6420
gcccagttcc gcccattctc cgccccatgg ctgactaatt ttttttattt atgcagaggc    6480
cgaggccgcc tcggcctctg agctattcca gaagtagtga ggaggctttt ttggaggcct    6540
agacttttgc agagacggcc caaattcgta atcatggtca tagctgtttc ctgtgtgaaa    6600
ttgttatccg ctcacaattc cacacaacat acgagccgga agcataaagt gtaaagcctg    6660
gggtgcctaa tgagtgagct aactcacatt aattgcgttg cgctcactgc ccgctttcca    6720
gtcgggaaac ctgtcgtgcc agctgcatta atgaatcggc caacgcgcgg ggagaggcgg    6780
tttgcgtatt gggcgctctt ccgcttcctc gctcactgac tcgctgcgct cggtcgttcg    6840
gctgcggcga gcggtatcag ctcactcaaa ggcggtaata cggttatcca cagaatcagg    6900
ggataacgca ggaaagaaca tgtgagcaaa aggccagcaa aaggccagga accgtaaaaa    6960
ggccgcgttg ctggcgtttt tccataggct ccgcccccct gacgagcatc acaaaaatcg    7020
acgctcaagt cagaggtggc gaaacccgac aggactataa agataccagg cgtttccccc    7080
tggaagctcc ctcgtgcgct ctcctgttcc gaccctgccg cttaccggat acctgtccgc    7140
ctttctccct tcgggaagcg tggcgctttc tcatagctca cgctgtaggt atctcagttc    7200
ggtgtaggtc gttcgctcca agctgggctg tgtgcacgaa ccccccgttc agcccgaccg    7260
```

```
ctgcgcctta tccggtaact atcgtcttga gtccaacccg gtaagacacg acttatcgcc    7320
actggcagca gccactggta acaggattag cagagcgagg tatgtaggcg gtgctacaga    7380
gttcttgaag tggtggccta actacggcta cactagaagg acagtatttg gtatctgcgc    7440
tctgctgaag ccagttacct tcggaaaaag agttggtagc tcttgatccg gcaaacaaac    7500
caccgctggt agcggtggtt tttttgtttg caagcagcag attacgcgca gaaaaaagg     7560
atctcaagaa gatcctttga tcttttctac ggggtctgac gctcagtgga acgaaaactc    7620
acgttaaggg attttggtca tgagattatc aaaaaggatc ttcacctaga tccttttaaa    7680
ttaaaaatga agttttaaat caatctaaag tatatatgag taaacttggt ctgacagtta    7740
ccaatgctta atcagtgagg cacctatctc agcgatctgt ctatttcgtt catccatagt    7800
tgcctgactc cccgtcgtgt agataactac gatacgggag ggcttaccat ctggccccag    7860
tgctgcaatg ataccgcgag acccacgctc accggctcca gatttatcag caataaacca    7920
gccagccgga agggccgagc gcagaagtgg tcctgcaact ttatccgcct ccatccagtc    7980
tattaattgt tgccgggaag ctagagtaag tagttcgcca gttaatagtt tgcgcaacgt    8040
tgttgccatt gctacaggca tcgtggtgtc acgctcgtcg tttggtatgg cttcattcag    8100
ctccggttcc caacgatcaa ggcgagttac atgatccccc atgttgtgca aaaaagcggt    8160
tagctccttc ggtcctccga tcgttgtcag aagtaagttg gccgcagtgt tatcactcat    8220
ggttatggca gcactgcata attctcttac tgtcatgcca tccgtaagat gcttttctgt    8280
gactggtgag tactcaacca agtcattctg agaatagtgt atgcggcgac cgagttgctc    8340
ttgcccggcg tcaatacggg ataataccgc gccacatagc agaactttaa aagtgctcat    8400
cattggaaaa cgttcttcgg ggcgaaaact ctcaaggatc ttaccgctgt tgagatccag    8460
ttcgatgtaa cccactcgtg cacccaactg atcttcagca tcttttactt tcaccagcgt    8520
ttctgggtga gcaaaaacag gaaggcaaaa tgccgcaaaa aagggaataa gggcgacacg    8580
gaaatgttga atactcatac tcttcctttt tcaatattat tgaagcattt atcagggtta    8640
ttgtctcatg agcggataca tatttgaatg tatttagaaa aataaacaaa taggggttcc    8700
gcgcacattt ccccgaaaag tgccacctga cgtctaagaa accattatta tcatgacatt    8760
aacctataaa aataggcgta tcacgaggcc ctttcgtctc gcgcgtttcg gtgatgacgg    8820
tgaaaacctc tgacacatgc agctcccgga cggtcaca gcttgtctgt aagcggatgc     8880
cgggagcaga caagcccgtc agggcgcgtc agcgggtgtt ggcgggtgtc ggggctggct    8940
taactatgcg gcatcagagc agattgtact gagagtgcac catatgcggt gtgaaatacc    9000
gcacagatgc gtaaggagaa ataccgcat caggcgccat cgccattca ggctgcgcaa      9060
ctgttgggaa gggcgatcgg tgcgggcctc ttcgctatta cgccagctgg cgaaggggg    9120
atgtgctgca aggcgattaa gttgggtaac gccagggttt tcccagtcac gacgttgtaa    9180
aacgacggcc agtgccaagc tg                                             9202

<210> SEQ ID NO 23
<211> LENGTH: 8060
<212> TYPE: DNA
<213> ORGANISM: Artificial Sequence
<220> FEATURE:
<223> OTHER INFORMATION: Synthetic

<400> SEQUENCE: 23
ggatcccctg aggggggccccc catgggctag aggatccggc ctcggcctct gcataaataa    60
```

```
aaaaaattag tcagccatga gcttggccca ttgcatacgt tgtatccata tcataatatg    120
tacatttata ttggctcatg tccaacatta ccgccatgtt gacattgatt attgactagt    180
tattaatagt aatcaattac ggggtcatta gttcatagcc catatatgga gttccgcgtt    240
acataactta cggtaaatgg cccgcctggc tgaccgccca acgaccccg cccattgacg    300 tcaataatga cgtatgttcc catagtaacg ccaataggga ctttccattg acgtcaatgg    360
gtggagtatt tacggtaaac tgcccacttg gcagtacatc aagtgtatca tatgccaagt    420
acgcccccta ttgacgtcaa tgacggtaaa tggcccgcct ggcattatgc ccagtacatg    480
accttatggg actttcctac ttggcagtac atctacgtat tagtcatcgc tattaccatg    540
gtgatgcggt tttggcagta catcaatggg cgtggatagc ggtttgactc acggggattt    600
ccaagtctcc accccattga cgtcaatggg agtttgtttt ggcaccaaaa tcaacgggac    660
tttccaaaat gtcgtaacaa ctccgcccca ttgacgcaaa tgggcggtag cgtgtacgg    720 tgggaggtct atataagcag agctcgttta gtgaaccgtc agatcgcctg gagacgccat    780
ccacgctgtt ttgacctcca tagaagacac cgggaccgat ccagcctccc ctcgaagctt    840
acatgtggta ccgagctcgg atcctgagaa cttcagggtg agtctatggg acccttgatg    900 ttttcttttcc ccttctttc tatggttaag ttcatgtcat aggaagggga gaagtaacag    960
ggtacacata ttgaccaaat cagggtaatt ttgcatttgt aattttaaaa aatgctttct   1020
tcttttaata tactttttg tttatcttat ttctaatact ttccctaatc tcttcttc     1080 agggcaataa tgatacaatg tatcatgcct ctttgcacca ttctaaagaa taacagtgat   1140
aatttctggg ttaaggcaat agcaatattt ctgcatataa atatttctgc atataaattg   1200
taactgatgt aagaggtttc atattgctaa tagcagctac aatccagcta ccattctgct   1260
tttattttat ggttgggata aggctggatt attctgagtc caagctaggc cttttgcta   1320 atcatgttca tacctcttat cttcctccca cagctcctgg caacgtgct ggtctgtgtg    1380 ctggcccatc actttggcaa agcacgtgag atctgaattc gctagccacc atgttcatct   1440
ttttgctgtt cctgactctg accagtggta gtgatctgga tcgctgtacc acattcgatg   1500
atgtgcaggc tcccaactac acacagcata cctccagtat gagaggagtg tattaccctg   1560
acgaaatttt ccgctccgat accttgtacc tgacacagga cctcttcttg ccttttatt    1620 ccaatgtcac cggcttttcat acgatcaatc atacattcga caatcctgtg attcccttca   1680
aggatggcat ttattcgca gctacggaaa agtctaacgt ggtccgcggg tgggtattcg    1740
gaagcaccat gaataataag tcacagtctg ttatcatcat caataatagt actaatgttg    1800
taatccgcgc ttgcaacttt gaactgtgcg ataatccctt cttcgcagta agcaagccca    1860
tggggacaca gactcacacg atgattttg acaatgcctt caattgtacg tttgagtaca   1920
tttctgatgc cttcagcttg gacgtgagcg agaaatctgg aaacttcaaa caccttcgcg   1980
agttcgtgtt taaaaacaaa gacgggttct tgtacgtata taagggctat cagcctattg    2040
acgtagttcg ggacttgccg agcggtttaa atactctcaa acctatcttc aagctccccc    2100
tgggaattaa cataactaat ttccgcgcaa tcctgacggc atttagccca gcacaggata   2160
cttggggaac ctccgccgca gcctacttcg tgggctatct gaagcctacc accttcatgc   2220
tgaagtacga tgagaatggc acgatcactg atgctgttga ctgttcacag aaccccctcg   2280
ctgagctgaa gtgcagcgtg aagtcctttg agatcgacaa ggggatatac cagacgagta   2340
actttcgcgt cgtcccttcc ggtgatgttg tgcgcttcc gaatattacc aatctgtgcc   2400
cgtttggaga ggtctttaac gctacaaagt tccctctgt gtacgcttgg gagaggaaga    2460
```

```
aaatatccaa ttgcgttgct gactattccg tattgtataa ctccaccttc tttttcaactt    2520 ttaaatgcta tggggtgtcc gctaccaaat tgaacgatct gtgtttttca aacgtttatg    2580
ccgactcttt tgtagtgaaa ggtgacgacg tgcgccaaat cgctcctggg caaaccggcg    2640
tcatcgctga ttacaattac aagctccctg atgacttcat ggggtgcgtg ctcgcttgga    2700
atacgcgaaa tatagatgcc acatcaaccg gaactacaa ctacaaatat cgctatttgc    2760
ggcacggaaa attgcgcccc ttcgaacggg atatatctaa cgtgcccttc agcccggatg    2820
ggaaaccgtg cactccgcct gcacttaact gttactggcc cctgaacgac tatggctttt    2880
acacaactac tggcatcgga tatcagccct atagggttgt agtgctgagc ttcgagctgc    2940
tgaacgcccc tgctacggtg tgtggaccca agctgagcac ggatctgatc aaaaatcaat    3000
gcgtgaactt caattttaac ggccttactg gtaccggcgt gctcacacca tcaagcaaac    3060
ggtttcaacc ctttcagcaa ttcggaagag acgtaagcga cttcacggat tccgtcagag    3120
atcctaaaac aagcgagata ctggatatct cccttgctc cttcggcggc gttagcgtga    3180
ttacacctgg aaccaatgcg agctccgaag tagctgtgct ctaccaggat gttaactgca    3240
cggacgtaag taccgccatc catgccgacc aactcacccc agcttggagg atatactcta    3300
cggggaacaa tgtgttccag acacaagcag gatgcttgat tggtgctgag cacgttgata    3360
cctcttatga atgcgacata cccataggg ccggtatatg cgcctcatat cataccgtct    3420
ccctgctgcg gtccaccagt cagaaatcaa tcgttgcata caccatgagc ctgggcgcag    3480
actcatccat tgcctatagc aataatacta tcgcaatccc aacaaatttc agtatcagca    3540
taactaccga ggtcatgcca gtgtcaatgg caaaaacctc tgttgactgc aacatgtaca    3600
tctgtggcga ttccacagag tgtgctaatt tgctgttgca atacgggtct ttttgcaccc    3660
agttgaacag ggccctgagc ggaatcgcgg ccgagcagga tagaaacacc cgagaggtct    3720
tcgcccaggt caagcagatg tataagactc caactctgaa atacttcggc gggtttaact    3780
tttctcaaat tctgcccgat cctctgaaac ccacaaagag atcattcatc gaagatctcc    3840
tgttcaataa ggtgaccctc gccgatgccg gcttcatgaa acaatacggc gaatgtctgg    3900
gggatatcaa cgcccgcgac ctgatctgtg cccaaaagtt caatggactg acagtgcttc    3960 ccctctgct tacggatgac atgattgctg catacactgc tgccctcgtc tctggcaccg    4020
ccactgctgg gtggaccttc ggcgcagggg cagccctgca gatcccccttt gccatgcaga    4080 tggcttacag attcaatggt attggcgtca cgcagaacgt cctctatgaa aaccagaaac    4140
agattgccaa ccagttcaat aaagcgatca gtcaaattca ggagagcctg actaccacca    4200
gcactgctct gggaaagctc caggatgtgg tcaatcagaa tgcccaggcc ctcaatactt    4260
tggtgaaaca actttctagc aattttggcg caatttcatc tgttcttaat gacattctgt    4320
caagactgga caaggtagag gctgaggttc aaatagatag gcttattaca ggacgcctgc    4380
agagcctgca gacttacgtt acgcagcagc tgattagggc agccgagatc cgcgctagtg    4440
ccaacctggc tgcgactaaa atgtccgagt gcgtcttggg ccaatccaaa cgcgtagact    4500
tttgcggaaa agggtaccat ctgatgtcct ttccccaggc tgcgcctcac ggtgttgtct    4560
tcctgcacgt gacctatgtg ccctcccagg aaagaaactt caccaccgca cctgccattt    4620
gtcacgaggg taaggcttac tttccccgcg agggtgtgtt tgtatttaat gggactagct    4680
ggttcatcac acagcgcaat ttcttctctc cccagatcat cacaaccgac aatacattcg    4740
tctcaggaaa ctgtgacgtg gtgattggaa tcatcaacaa taccgtgtac gaccctcttc    4800
```

```
agcccgaact cgattcattc aaggaagaac tcgacaagta ctttaagaac catacttctc    4860
ccgacgtgga tctcggggac atttctggaa taaatgctag tgtcgtaaat attcagaagg    4920
agatagaccg cctgaatgaa gtcgcaaaga atctcaatga aagcctcatc gacctgcaag    4980
agctggggaa gtacgagcag tatatcaaat ggccatggta cgtgtggctt gggtttatcg    5040
caggcctgat cgctatagtg atggtgacta tcctcctgtg ctgtatgacc tcatgttgtt    5100
cctgtctgaa gggcgcatgc agctgtgggt cttgttgtaa atttgacgaa gatgattcag    5160
aacccgtttt gaaggggggtc aaattgcact acacctaact cgagaaatcc tgcacaacag    5220
attcttcatg tttggaccaa atcaacttgt gataccatgc tcaaagaggc ctcaattata    5280
tttgagtttt taattttat gaaaaaaaaa aaaaaaacg gaattcaccc caccagtgca    5340
ggctgcctat cagaaagtgg tggctggtgt ggctaatgcc ctggcccaca agtatcacta    5400
agctcgcttt cttgctgtcc aatttctatt aaaggttcct tgttcccta agtccaacta    5460 ctaaactggg ggatattatg aagggccttg agcatctgga ttctgcctaa taaaaaacat    5520
ttattttcat tgcaatgatg tatttaaatt atttctgaat attttactaa aaagggaatg    5580
tgggaggtca gtgcatttaa aacataaaga aatgaagagc tagttcaaac cttgggaaaa    5640
tacactatat cttaaactcc atgaaagaag gtgaggctgc aaacagctaa tgcacattgg    5700
caacagcccc tgatgcctat gccttattca tccctcagaa aaggattcaa gtagaggctt    5760
gatttggagg ttaaagtttt gctatgctgt attttacatt acttattgtt ttagctgtcc    5820
tcatgaatgt cttttcacta cccatttgct tatcctgcat ctctcagcct tgactccact    5880
cagttctctt gcttagagat accaccttt ccctgaagtg ttccttccat gttttacggc    5940
gagatggttt ctcctcgcct ggccactcag ccttagttgt ctctgttgtc ttatagaggt    6000
ctacttgaag aaggaaaaac aggggcatg gtttgactgt cctgtgagcc cttcttccct    6060
gcctccccca ctcacagtga cccggaatcc ctcgacatgg cagtctagca ctagtgcggc    6120
cgcagatctg cttcctcgct cactgactcg ctgcgctcgg tcgttcggct gcggcgagcg    6180
gtatcagctc actcaaaggc ggtaatacgg ttatccacag aatcagggga taacgcagga    6240
aagaacatgt gagcaaaagg ccagcaaaag gccaggaacc gtaaaaaggc cgcgttgctg    6300 gcgttttttcc ataggctccg ccccccctgac gagcatcaca aaaatcgacg ctcaagtcag    6360
aggtggcgaa acccgacagg actataaaga taccaggcgt ttccccctgg aagctccctc    6420
gtgcgctctc ctgttccgac cctgccgctt accggatacc tgtccgcctt tctcccttcg    6480
ggaagcgtgg cgctttctca tagctcacgc tgtaggtatc tcagttcggt gtaggtcgtt    6540
cgctccaagc tgggctgtgt gcacgaaccc cccgttcagc ccgaccgctg cgccttatcc    6600
ggtaactatc gtcttgagtc aacccggta agacacgact tatcgccact ggcagcagcc    6660
actggtaaca ggattagcag agcgaggtat gtaggcggtg ctacagagtt cttgaagtgg    6720
tggcctaact acggctacac tagaagaaca gtatttggta tctgcgctct gctgaagcca    6780
gttaccttcg gaaaaagagt tggtagctct tgatccggca acaaaccac cgctggtagc    6840 ggtggttttt ttgtttgcaa gcagcagatt acgcgcagaa aaaaggatc tcaagaagat    6900 cctttgatct tttctacggg gtctgacgct cagtggaacg aaaactcacg ttaagggatt    6960
ttggtcatga gattatcaaa aaggatcttc acctagatcc ttttaaatta aaatgaagt    7020 tttaaatcaa tctaaagtat atatgagtaa acttggtctg acagttacca atgcttaatc    7080
agtgaggcac ctatctcagc gatctgtcta tttcgttcat ccatagttgc ctgactcccc    7140
gtcgtgtaga taactacgat acgggagggc ttaccatctg gccccagtgc tgcaatgata    7200
```

-continued

| | |
|---|---|
| ccgcgagacc cacgctcacc ggctccagat ttatcagcaa taaaccagcc agccggaagg | 7260 |
| gccgagcgca gaagtggtcc tgcaacttta tccgcctcca tccagtctat taattgttgc | 7320 |
| cgggaagcta gagtaagtag ttcgccagtt aatagtttgc gcaacgttgt tgccattgct | 7380 |
| acaggcatcg tggtgtcacg ctcgtcgttt ggtatggctt cattcagctc cggttcccaa | 7440 |
| cgatcaaggc gagttacatg atcccccatg ttgtgcaaaa aagcggttag ctccttcggt | 7500 |
| cctccgatcg ttgtcagaag taagttggcc gcagtgttat cactcatggt tatggcagca | 7560 |
| ctgcataatt ctcttactgt catgccatcc gtaagatgct tttctgtgac tggtgagtac | 7620 |
| tcaaccaagt cattctgaga atagtgtatg cggcgaccga gttgctcttg cccggcgtca | 7680 |
| atacgggata taccgcgcc acatagcaga actttaaaag tgctcatcat tggaaaacgt | 7740 |
| tcttcggggc gaaaactctc aaggatctta ccgctgttga gatccagttc gatgtaaccc | 7800 |
| actcgtgcac ccaactgatc ttcagcatct tttactttca ccagcgtttc tgggtgagca | 7860 |
| aaaacaggaa ggcaaaatgc cgcaaaaaag gaataaggg cgacacggaa atgttgaata | 7920 |
| ctcatactct tcctttttca atattattga agcatttatc agggttattg tctcatgagc | 7980 |
| ggatacatat ttgaatgtat ttagaaaaat aaacaaatag gggttccgcg cacatttccc | 8040 |
| cgaaaagtgc cacctgacgt | 8060 |

<210> SEQ ID NO 24
<211> LENGTH: 8306
<212> TYPE: DNA
<213> ORGANISM: Artificial Sequence
<220> FEATURE:
<223> OTHER INFORMATION: Synthetic

<400> SEQUENCE: 24

| | |
|---|---|
| acgcgtgtag tcttatgcaa tactcttgta gtcttgcaac atggtaacga tgagttagca | 60 |
| acatgcctta caaggagaga aaaagcaccg tgcatgccga ttggtggaag taaggtggta | 120 |
| cgatcgtgcc ttattaggaa ggcaacagac gggtctgaca tggattggac gaaccactga | 180 |
| attgccgcat tgcagagata ttgtatttaa gtgcctagct cgatacaata aacgggtctc | 240 |
| tctggttaga ccagatctga gcctgggagc tctctggcta actagggaac ccactgctta | 300 |
| agcctcaata aagcttgcct tgagtgcttc aagtagtgtg tgcccgtctg ttgtgtgact | 360 |
| ctggtaacta gagatccctc agacccttt agtcagtgtg gaaaatctct agcagtggcg | 420 |
| cccgaacagg gacctgaaag cgaaagggaa accagagctc tctcgacgca ggactcggct | 480 |
| tgctgaagcg cgcacggcaa gaggcgaggg gcggcgactg gtgagtacgc caaaaatttt | 540 |
| gactagcgga ggctagaagg agagagatgg gtgcgagagc gtcagtatta agcggggggag | 600 |
| aattagatcg cgatgggaaa aaattcggtt aaggccaggg ggaaagaaaa aatataaatt | 660 |
| aaaacatata gtatgggcaa gcagggagct agaacgattc gcagttaatc ctggcctgtt | 720 |
| agaaacatca gaaggctgta gacaaatact gggacagcta caaccatccc ttcagacagg | 780 |
| atcagaagaa cttagatcat tatataatac agtagcaacc ctctattgtg tgcatcaaag | 840 |
| gatagagata aaagacacca aggaagcttt agacaagata gaggaagagc aaaacaaaag | 900 |
| taagaccacc gcacagcaag cggccactga tcttcagacc tggaggagga gatatgaggg | 960 |
| acaattggag aagtgaatta tataaatata agtagtaaa aattgaacca ttaggagtag | 1020 |
| cacccaccaa ggcaaagaga agagtggtgc agagagaaaa aagagcagtg gaataggag | 1080 |
| ctttgttcct tgggttcttg ggagcagcag gaagcactat gggcgcagcg tcaatgacgc | 1140 |

```
tgacggtaca ggccagacaa ttattgtctg gtatagtgca gcagcagaac aatttgctga    1200
gggctattga ggcgcaacag catctgttgc aactcacagt ctggggcatc aagcagctcc    1260
aggcaagaat cctggctgtg aaagatacc taaaggatca acagctcctg gggatttggg     1320
gttgctctgg aaaactcatt tgcaccactg ctgtgccttg aatgctagt tggagtaata     1380 aatctctgga acagatttgg aatcacacga cctggatgga gtgggacaga gaaattaaca    1440
attacacaag cttaatacac tccttaattg aagaatcgca aaaccagcaa gaaaagaatg    1500
aacaagaatt attggaatta gataaatggg caagtttgtg gaattggttt aacataacaa    1560
attggctgtg gtatataaaa ttattcataa tgatagtagg aggcttggta ggtttaagaa    1620
tagtttttgc tgtactttct atagtgaata gagttaggca gggatattca ccattatcgt    1680
ttcagaccca cctcccaacc ccgagggac ccgacaggcc cgaaggaata aagaagaag     1740 gtggagagag agacagagac agatccattc gattagtgaa cggatctcga cggtatcggt    1800
taacttttaa aagaaaaggg gggattgggg ggtacagtgc aggggaaaga atagtagaca    1860
taatagcaac agacatacaa actaaagaat tacaaaaaca aattacaaaa ttcaaaattt    1920
tatcgatgct agcgggcaga gcgcacatcg cccacagtcc ccgagaagtt ggggggaggg    1980
gtcggcaatt gaacgggtgc ctagagaagg tggcgcgggg taaactggga aagtgatgtc    2040
gtgtactggc tccgcctttt tcccgagggt gggggagaac cgtatataag tgcagtagtc    2100
gccgtgaacg ttctttttcg caacgggttt ccgccagaa cacagctgaa gcttcgaggg     2160
gctcgcatct ctccttcacg cgcccgccgc cctacctgag gccgccatcc acgccggttg    2220
agtcgcgttc tgccgcctcc cgcctgtggt gcctcctgaa ctgcgtccgc cgtctaggta    2280
agtttaaagc tcaggtcgag accgggcctt tgtccggcgc tcccttggag cctacctaga    2340
ctcagccggc tctccacgct ttgcctgacc ctgcttgctc aactctacgt ctttgtttcg    2400
ttttctgttc tgcgccgtta cagatccaag ctgtgaccgg cgcctactag tgccaccatg    2460
gactttcaag tgcagatctt cagctttctg ctgatctctg ctagtgtcat catgtctcaa    2520
gtgcaactgc aggaatctgg aggtggcctc gtgcaagctg gaggcagcct gaggctgagc    2580
tgtgctgcat ccggtcgcac cttagcgag tatgcaatgg gttggtttcg ccaggcacca    2640
ggtaaggaga gggagtttgt ggcaaccatc tcctggtctg gtggctccac atactacaca    2700
gattccgtca agggaagatt cactatctcc agggacaacg caaagaacac agtgtatctg    2760
cagatgaata gcctcaagcc agatgacaca gccgtctact attgcgctgc agctggtctg    2820
ggcaccgttg tgtccgaatg ggattacgac tacgattact ggggtcaagg cactcaggtg    2880
actgtgtcta gcggtagcga aatcgagcag aagctgattt ccgaagagga tctcaatgga    2940
gtgactgtca gcagcgctct gtctaactcc atcatgtact ctcacacttt cgtgccagtg    3000
ttcctccctg ctaaacccac cacaactcca gcacctagac ctcccactcc agcaccaact    3060
attgcatccc agcctctctc cctcagacca gaagcatgca gacctgcagc aggtggagct    3120
gtgcacacaa gaggtctgga ccctttctgg gtcctcgtgg tggtgggtgg agtcctggca    3180
tgttacagcc tcctggtcac cgtggcattc atcatcttct gggtgagatc taagaggagc    3240
agactgctgc actctgatta catgaacatg acacccagaa gacctggtcc caccagaaag    3300
cactaccaac cctacgcacc accaagagac tttgctgcat acagaagtct cgagagggtc    3360
aagttctcaa ggagtgcaga tgctccagcc tatcaacagg gtcagaacca actgtacaac    3420
gagctgaatc tcggaagaag agaggagtac gatgtgctgg ataagagaag aggcagggac    3480
ccagagatgg gtgggaaacc cagaagaaag aatcctcaag agggactgta caatgagctg    3540
```

```
cagaaggata agatggctga ggcatactca gagatcggta tgaagggaga gaggagaaga    3600
ggcaaaggtc atgatggtct gtaccaaggt ctgtccacag caacaaagga tacatatgat    3660
gctctgcaca tgcaggcact cccaccacgg ggttccggag tgaaacagac tttgaacttt    3720
gaccttctca agttggctgg agacgtcgag tccaaccctg gtcccatgac cgagtacaag    3780
cccacggtgc gcctcgccac ccgcgacgac gtccccaggg ccgtacgcac cctcgccgcc    3840
gcgttcgccg actacccgc cacgcgccac accgtcgatc cggaccgcca catcgagcgg     3900
gtcaccgagc tgcaagaact cttcctcacg cgcgtcgggc tcgacatcgg caaggtgtgg    3960
gtcgcggacg acgcgccgc ggtggcggtc tggaccacgc cggagagcgt cgaagcgggg     4020
gcggtgttcg ccgagatcgg cccgcgcatg gccgagttga gcggttcccg gctggccgcg    4080
cagcaacaga tggaaggcct cctggcgccg caccggccca aggagcccgc gtggttcctg    4140
gccaccgtcg gcgtctcgcc cgaccaccag ggcaagggtc tgggcagcgc cgtcgtgctc    4200
cccggagtgg aggcggccga gcgcgccggg gtgcccgcct tcctggagac ctccgcgccc    4260
cgcaacctcc ccttctacga gcggctcggc ttcaccgtca ccgccgacgt cgaggtgccc    4320
gaaggaccgc gcacctggtg catgacccgc aagcccggtg cctgattaat taagtcgaca    4380
atcaacctct ggattacaaa atttgtgaaa gattgactgg tattcttaac tatgttgctc    4440
cttttacgct atgtggatac gctgctttaa tgcctttgta tcatgctatt gcttcccgta    4500
tggctttcat tttctcctcc ttgtataaat cctggttgct gtctctttat gaggagttgt    4560
ggcccgttgt caggcaacgt ggcgtggtgt gcactgtgtt tgctgacgca acccccactg    4620
gttgggcat tgccaccacc tgtcagctcc tttccgggac tttcgctttc ccctcccta     4680
ttgccacggc ggaactcatc gccgcctgcc ttgcccgctg ctggacaggg gctcggctgt    4740
tgggcactga caattccgtg gtgttgtcgg ggaaatcatc gtcctttcct ggctgctcg    4800
cctgtgttgc cacctggatt ctgcgcggga cgtccttctg ctacgtccct tcggccctca    4860
atccagcgga ccttccttcc cgcggcctgc tgccggctct gcggcctctt ccgcgtcttc    4920
gccttcgccc tcagacgagt cggatctccc tttgggccgc ctccccgcct ggtaccttta   4980
agaccaatga cttacaaggc agctgtagat cttagccact ttttaaaaga aaaggggga    5040
ctggaagggc taattcactc ccaacgaaga taagatctgc tttttgcttg tactgggtct    5100
ctctggttag accagatctg agcctgggag ctctctggct aactaggaa cccactgctt     5160
aagcctcaat aaagcttgcc ttgagtgctt caagtagtgt gtgcccgtct gttgtgtgac    5220
tctggtaact agagatccct cagacccttt tagtcagtgt ggaaaatctc tagcagtagt    5280
agttcatgtc atcttattat tcagtattta taacttgcaa agaaatgaat atcagagagt    5340
gagaggaact tgtttattgc agcttataat ggttacaaat aaagcaatag catcacaaat    5400
ttcacaaata aagcattttt ttcactgcat tctagttgtg gtttgtccaa actcatcaat    5460
gtatcttatc atgtctggct ctagctatcc cgccctaac tccgcccatc ccgcccctaa    5520
ctccgcccag ttccgcccat tctccgcccc atggctgact aatttttttt atttatgcag    5580
aggccgaggc cgcctcggcc tctgagctat tccagaagta gtgaggaggc ttttttggag    5640
gcctagactt ttgcagagac ggcccaaatt cgtaatcatg gtcatagctg tttcctgtgt    5700
gaaattgtta tccgctcaca attccacaca acatacgagc cggaagcata aagtgtaaag    5760
cctggggtgc ctaatgagtg agctaactca cattaattgc gttgcgctca ctgcccgctt    5820
tccagtcggg aaacctgtcg tgccagctgc attaatgaat cggccaacgc gcggggagag    5880
```

-continued

```
gcggtttgcg tattgggcgc tcttccgctt cctcgctcac tgactcgctg cgctcggtcg   5940
ttcggctgcg gcgagcggta tcagctcact caaaggcggt aatacggtta tccacagaat   6000
caggggataa cgcaggaaag aacatgtgag caaaaggcca gcaaaaggcc aggaaccgta   6060
aaaaggccgc gttgctggcg ttttccata ggctccgccc ccctgacgag catcacaaaa    6120
atcgacgctc aagtcagagg tggcgaaacc cgacaggact ataaagatac caggcgtttc   6180
cccctggaag ctccctcgtg cgctctcctg ttccgaccct gccgcttacc ggatacctgt   6240
ccgcctttct cccttcggga agcgtggcgc tttctcatag ctcacgctgt aggtatctca   6300
gttcggtgta ggtcgttcgc tccaagctgg gctgtgtgca cgaaccccccc gttcagcccg   6360
accgctgcgc cttatccggt aactatcgtc ttgagtccaa cccggtaaga cacgacttat   6420
cgccactggc agcagccact ggtaacagga ttagcagagc gaggtatgta ggcggtgcta   6480
cagagttctt gaagtggtgg cctaactacg gctacactag aaggacagta tttggtatct   6540
gcgctctgct gaagccagtt accttcggaa aaagagttgg tagctcttga tccggcaaac   6600
aaaccaccgc tggtagcggt ggtttttttg tttgcaagca gcagattacg cgcagaaaaa   6660
aaggatctca agaagatcct ttgatctttt ctacggggtc tgacgctcag tggaacgaaa   6720
actcacgtta agggattttg gtcatgagat tatcaaaaag gatcttcacc tagatccttt   6780
taaattaaaa atgaagtttt aaatcaatct aaagtatata tgagtaaact tggtctgaca   6840
gttaccaatg cttaatcagt gaggcaccta tctcagcgat ctgtctattt cgttcatcca   6900
tagttgcctg actccccgtc gtgtagataa ctacgatacg ggagggctta ccatctggcc   6960
ccagtgctgc aatgataccg cgagacccac gctcaccggc tccagattta tcagcaataa   7020
accagccagc cggaagggcc gagcgcagaa gtggtcctgc aactttatcc gcctccatcc   7080
agtctattaa ttgttgccgg gaagctagag taagtagttc gccagttaat agtttgcgca   7140
acgttgttgc cattgctaca ggcatcgtgg tgtcacgctc gtcgtttggt atggcttcat   7200
tcagctccgt tcccaacga tcaaggcgag ttacatgatc ccccatgttg tgcaaaaaag    7260
cggttagctc cttcggtcct ccgatcgttg tcagaagtaa gttggccgca gtgttatcac   7320
tcatggttat ggcagcactg cataattctc ttactgtcat gccatccgta agatgctttt   7380
ctgtgactgg tgagtactca accaagtcat tctgagaata gtgtatgcgg cgaccgagtt   7440
gctcttgccc ggcgtcaata cgggataata ccgcgccaca tagcagaact ttaaaagtgc   7500
tcatcattgg aaaacgttct cggggcgaaa actctcaag gatcttaccg ctgttgagat    7560
ccagttcgat gtaacccact cgtgcaccca actgatcttc agcatctttt actttcacca   7620
gcgtttctgg gtgagcaaaa acaggaaggc aaaatgccgc aaaaaaggga ataagggcga   7680
cacggaaatg ttgaatactc atactcttcc ttttcaata ttattgaagc atttatcagg    7740
gttattgtct catgagcgga tacatatttg aatgtattta gaaaaataaa caaatagggg   7800
ttccgcgcac atttccccga aaagtgccac ctgacgtcta agaaaccatt attatcatga   7860
cattaaccta taaaaatagg cgtatcacga ggccctttcg tctcgcgcgt ttcggtgatg   7920
acggtgaaaa cctctgacac atgcagctcc cggagacggt cacagcttgt ctgtaagcgg   7980
atgccgggag cagacaagcc cgtcaggcg cgtcagcggg tgttggcggg tgtcggggct     8040
ggcttaacta tgcggcatca gagcagattg tactgagagt gcaccatatg cggtgtgaaa   8100
taccgcacag atgcgtaagg agaaaatacc gcatcaggcg ccattcgcca ttcaggctgc   8160
gcaactgttg ggaagggcga tcggtgcggg cctcttcgct attacgccag ctggcgaaag   8220
ggggatgtgc tgcaaggcga ttaagttggg taacgccagg gttttcccag tcacgacgtt   8280
```

```
gtaaaacgac ggccagtgcc aagctg                                        8306
```

<210> SEQ ID NO 25
<211> LENGTH: 354
<212> TYPE: DNA
<213> ORGANISM: Artificial Sequence
<220> FEATURE:
<223> OTHER INFORMATION: Synthetic

<400> SEQUENCE: 25

```
caagtgcaac tggtggaaac tggtggtgga ctggttcagc caggtggaag cctgagactc      60
tcctgtgcag caagcggttt caccttctct tctgtctaca tgaactgggt caggcaagct     120
cctggcaaag gacccgaatg ggtgtccagg atttctccca actccggtaa catcggctac     180
acagatagcg tcaagggtag gtttactatc tccagagata cgccaagaa taccctctac      240
ctgcaaatga caacctgaa gcctgaggat acagccctct actattgcgc aatcggactc      300
aacctgtcta gctcctctgt cagaggtcag ggtacccaag tcactgtgtc cagc            354
```

<210> SEQ ID NO 26
<211> LENGTH: 381
<212> TYPE: DNA
<213> ORGANISM: Artificial Sequence
<220> FEATURE:
<223> OTHER INFORMATION: Synthetic

<400> SEQUENCE: 26

```
caagttcaac tggttcaatc cggagcagaa gtgaagaagc ctggtgcaag cgtgaaagtg      60
agctgcaagg catctggcta cccattcact agctacggta tctcctgggt gagacaagca     120
cctggtcaag gactcgaatg gatgggctgg atctctacct acaatggaaa caccaactat     180
gcccagaagt tccagggtag agttacaatg actacagata ctagcactac cacaggctac     240
atggaactca ggaggctcag gtctgacgac acagctgtct actattgtgc acgcgactac     300
actagaggag cttggtttgg tgagagcctc attggtggct tcgacaattg gggtcagggt     360
actctggtca ccgtctccag c                                              381
```

<210> SEQ ID NO 27
<211> LENGTH: 381
<212> TYPE: DNA
<213> ORGANISM: Artificial Sequence
<220> FEATURE:
<223> OTHER INFORMATION: Synthetic

<400> SEQUENCE: 27

```
caagcacagc tcgtggagtc tggaggtgct ctggtgcaac tggtaggag cctcagactc       60
tcctgtgctg cttccggatt cacattcaga aactacgcaa tgcactgggt caggcaagct     120
ccagctacag gtctgcagtg gctggctgtg attaccagcg atggcaggaa caagttctat     180
gccgactctg tgaaaggcag gttcactatc tctcgcgaag acagcaagaa taccctgtat     240
ctgcaaatgg attctctcag aggtgaagat acagctgtgt actattgcgt cacacagagg     300
gataactcta gggactactt tcctcattac tttcatgaca tggacgtttg gggtcagggc     360
accaccgttg ctgtgtcctc t                                              381
```

<210> SEQ ID NO 28
<211> LENGTH: 354
<212> TYPE: DNA
<213> ORGANISM: Artificial Sequence
<220> FEATURE:

<223> OTHER INFORMATION: Synthetic

<400> SEQUENCE: 28

| | | | | | |
|---|---|---|---|---|---|
| caagtgcaac | tccaacaaag | cggagctgaa | gtgaagaaac | ctggttcctc | cgtgaaagtc | 60 |
| tcttgtaagg | cttctggagg | tacattcagc | tcttacacca | tcagctgggt | gaggcaagct | 120 |
| cctggccaag | gtctggagtg | gatgggaggc | atcactccta | tcctgggaat | cgcaaactac | 180 |
| gcacagaagt | tcagggtag | ggtgactatc | accactgatg | aaagcacctc | taccgcttac | 240 |
| atggagctgt | ccagcctgag | gtccgaggac | actgccgtgt | actattgcgc | aagagatact | 300 |
| gtgatgggag | gcatggacgt | gtggggacaa | ggtactactg | ttaccgtttc | cagc | 354 |

<210> SEQ ID NO 29
<211> LENGTH: 357
<212> TYPE: DNA
<213> ORGANISM: Artificial Sequence
<220> FEATURE:
<223> OTHER INFORMATION: Synthetic

<400> SEQUENCE: 29

| | | | | | |
|---|---|---|---|---|---|
| cagatgcaac | tggtccaaag | cggtactgag | gtgaagaagc | caggagagtc | cctgaagatt | 60 |
| tcctgcaagg | gctctggata | cggtttcatc | acctactgga | tcggatgggt | gaggcaaatg | 120 |
| ccaggtaaag | gactggaatg | gatgggaatc | atctaccctg | cgacagcga | gacaagatac | 180 |
| tctccttcct | tccagggaca | ggtgaccatc | tctgcagaca | agagcatcaa | cacagcttat | 240 |
| ctgcagtggt | ctagcctcaa | agcctccgat | acagccatct | actattgtgc | tggtggttct | 300 |
| ggcatctcca | ctccaatgga | cgtgtgggga | caaggtacta | ctgttaccgt | ttccagc | 357 |

<210> SEQ ID NO 30
<211> LENGTH: 1932
<212> TYPE: DNA
<213> ORGANISM: Artificial Sequence
<220> FEATURE:
<223> OTHER INFORMATION: Synthetic

<400> SEQUENCE: 30

| | | | | | |
|---|---|---|---|---|---|
| atcccactgg | gtgttataca | caattccact | ctccaggttt | ccgatgtgga | caaactggtc | 60 |
| tgtagggaca | agctgagtag | caccaaccag | ctgaggagcg | ttggcctcaa | cctggagggc | 120 |
| aacggagtgg | ccactgatgt | gccttccgct | accaaacggt | ggggtttccg | gtcaggtgtc | 180 |
| ccacccaagg | tcgttaacta | tgaagctggc | gagtgggctg | agaactgtta | caatctggag | 240 |
| atcaagaagc | ccgatgggag | tgaatgcctg | cctgctgctc | cagacggcat | tcggggtttc | 300 |
| ccacggtgtc | ggtacgtgca | taagtgagc | ggcactgggc | catgtgcagg | tgactttgct | 360 |
| tttcataagg | agggtgcctt | cttcctgtat | gatagactgg | cctcaacagt | gatctatagg | 420 |
| ggaaccactt | ttgcagaagg | ggtggtgcc | tttctgattc | tgccacaggc | taagaaagat | 480 |
| ttctttttcct | cccatcccct | cagagaaccc | gttaacgcta | cagaggaccc | ctcctcagga | 540 |
| tactattcaa | caacaatacg | ctaccaggca | actgggttcg | aactaatga | aaccgagtac | 600 |
| ctgttcgagg | tcgataatct | gacatacgtg | cagctcgaaa | gtcggttcac | tccccagttt | 660 |
| ctcctccagc | tgaacgagac | tatctacaca | tccgggaaaa | ggtcaaatac | tactggcaag | 720 |
| ctcatctgga | aggtgaaccc | cgagatcgat | accaccatag | gagagtgggc | cttttgggaa | 780 |
| accaagaaga | acctcactcg | gaaaatccgg | tccgaggagc | tgtcctttac | cgtcgttagc | 840 |
| aatggtgcta | gaacatctc | cggtcaatct | cctgcacgga | catctagcga | tccaggcacc | 900 |
| aacactacaa | cagaggacca | taagatcatg | gcaagtgaaa | actcaagtgc | aatggtccag | 960 |

```
gttcatagcc aaggaaggga ggctgctgtg tcacatctga caaccctcgc caccatttca    1020
acttcacctc agagtctgac aacaaagcca ggccctgaca attcaacaca caacacaccc    1080
gtgtacaagc tggacatcag tgaggcaacc caggtggagc agcaccatcg cagaaccgac    1140
aacgacagca ctgccagcga tacccettca gccaccaccg cagctggccc tcccaaagcc    1200
gaaaacacca acaccagcaa atctaccgac ttcctggacc cagcaaccac aacctcacct    1260
caaaaccaca gcgagactgc cggtaacaat aacacacacc accaagacac cggagaggaa    1320
agcgcttcca gcggtaaaact gggactgata acaaacacca tcgcaggagt cgctgggctg    1380
atcacaggag gtcgcagaac acggagggaa gctatagtga atgcacagcc caagtgcaat    1440
cctaacctgc attactggac cactcaagac gagggagccg ctatcggcct cgcctggatt    1500
ccttacttcg gtcccgcagc tgaggggata tacatcgagg ggctcatgca caaccaggac    1560
ggcctcattt gtggcctcag acagctggcc aatgagacta cccaggccct gcaactgttt    1620
ctgagagcta ctacagaact ccgcactttc tccattctga atcgcaaagc catcgacttc    1680
ctgctgcaac gctggggagg gacatgtcat atcctgggtc cagactgctg tatcgaaccc    1740
cacgactgga ccaagaacat aaccgacaag attgaccaaa tcatccacga ctttgtggac    1800
aaaactctcc ccgatcaagg ggacaacgat aactggtgga ccggatggag gcaatggatt    1860
cccgctggta tcggcgtgac cggagtgatc attgccgtta tagccctgtt ttgcatctgt    1920
aagttcgtgt tt                                                       1932

<210> SEQ ID NO 31
<211> LENGTH: 768
<212> TYPE: DNA
<213> ORGANISM: Artificial Sequence
<220> FEATURE:
<223> OTHER INFORMATION: Synthetic

<400> SEQUENCE: 31
gaagtgcagc tcgtggaatc tggaggagga ctggttaagc ctggtggatc tctcagactc      60
tcctgcgctg cttctggatt cacattctct aacgcttgga tgtcttgggt caggcaggca     120
cctggcaagg gtctggaatg ggttggaaga atcaaatcca agactgatgg tgcaccatt      180 gactacgcag ctcctgtcaa gggcagattc actatctcta gggatgatag caagaacact     240
gtctacctcc agatgacatc cctgaagaca gaagatacag ccgtgtacta ctgtaccaca     300
tacaccgagg atatgaggta cttcgactgg ctgctgagag gtggagagac tttcgactac     360
tggggtcaag gaactctggt gacagttagc agcggaggtg gaggcagtgg aggtggtgga     420
tctggaggag gagggtctga tatcaggctc acacaatctc cttcttctct ctccgcatcc     480
gttggcgatc gcgtgaccat tacatgcagg gcttctcact acatctccac ataacctgaac     540 tggtatcagc agaaacctgg caaagctcca aagctgctca tctatgcagc ttctaacctg     600
caatctggag tcccttccag attctctggc tctggattcg aactgatttt ctccctcact     660
atcagcagcc tccagcctga ggatttcgct acatatcatt gccagcaaag ctactccact     720
ccaggcaggt atactttcgg tcaaggaaca aaagtcgaga tcaaaagg                  768

<210> SEQ ID NO 32
<211> LENGTH: 1989
<212> TYPE: DNA
<213> ORGANISM: Artificial Sequence
<220> FEATURE:
<223> OTHER INFORMATION: Synthetic
```

<400> SEQUENCE: 32

```
ctgcctatcc tcgaaatcgc aagcaacaac caaccacaga atgttgattc cgtgtgcagc      60
ggtacactcc agaagactga ggatgttcac ctcatgggtt tcactctctc tggccagaag     120
gtggcagact ctcctctgga ggcttctaag agatgggcat tcaggactgg tgtgccacct     180
aagaatgttg agtataccga aggtgaggag gccaagacat gctacaacat ctccgtgacc     240
gacccatctg gaaagtccct cctgctggac cctcccacta acatcagaga ctacccaaag     300
tgcaagacca tccaccacat ccagggtcag aatccacatg cccagggtat cgctctgcat     360
ctgtggggag ccttctttct ctacgaccgc atcgcttcca ccacaatgta cagaggtaag     420
gtctttaccg agggtaacat cgctgcaatg attgtgaaca agaccgtgca caagatgatc     480
ttctctcgcc agggacaggg ctatcgccca atgaatctga cttccacaaa caagtattgg     540
accagcagca acggaaccca gaccaatgat actggctgtt tcggagcact ccaggaatac     600
aactccacca agaatcagac ctgcgctcct tctaagatcc caccaccact cccaactgca     660
agacctgaaa tcaagctcac aagcacacct accgatgcca ccaaactcaa caccacagat     720
ccatcttctg acgacgaaga cctcgctaca agcggttctg gctccggtga gagggaacct     780
cacacaacca gcgacgcagt gaccaaacag ggactctcta gcactatgcc acccacacca     840
agccctcaac ctagcactcc tcagcaggga ggaaacaata ctaaccactc tcaagatgca     900
gttactgaac tggataagaa caacacaact gctcaaccct ctatgcctcc tcataacact     960
accactatca gcacaaacaa cacatccaaa cacaacttct ctaccctctc cgcacctctg    1020
cagaatacca ccaacgacaa cacccagagc actatcacag agaacgaaca gacctccgct    1080
ccatccatta ctaccctgcc acctacaggc aatcccacaa cagctaagtc caccagctct    1140
aagaagggac cagccacaac cgctcccaat actacaaatg agcacttcac atctcctcca    1200
cctactccat cctctacagc tcagcacctc gtctacttta ggaggaagag gtccatcctg    1260
tggagggaag gcgatatgtt ccctttcctg gatggcctca tcaacgctcc cattgacttt    1320
gatccagtgc caaacactaa gactatcttt gacgaatcct cttcttccgg agccagcgca    1380
gaagaggacc agcacgcttc tcccaacatt tccctgacac tcagctactt tccaaacatc    1440
aacgagaata ctgcctattc tggagagaat gagaacgact gtgatgctga actgcgcatc    1500
tggtccgttc aggaggatga tctggcagca ggactctctt ggattccctt cttcggacct    1560
ggtatcgagg gtctgtatac tgcagtcctc atcaagaacc agaacaacct cgtttgcagg    1620
ctgaggagac tggcaaacca gactgccaaa tccctggaac tgctgctgag gtcactacc     1680
gaggagagaa cctttagcct gatcaatagg cacgcaatcg acttcctcct gaccaggtgg    1740
ggcggaactt gtaaagtgct gggtccgac tgctgtatcg gcatcgagga tctgtccaag     1800
aacatttccg aacaaatcga ccagatcaag aaggatgagc agaaggaagg tacaggttgg    1860
ggtctgggtg gaaagtggtg gacctccgat tggggagtgc tgacaaacct cggcattctc    1920
ctgctgctgt ccatcgcagt gctcatcgca ctctcttgta tctgcaggat cttcactaag    1980
tacattgga                                                           1989
```

<210> SEQ ID NO 33
<211> LENGTH: 744
<212> TYPE: DNA
<213> ORGANISM: Artificial Sequence
<220> FEATURE:
<223> OTHER INFORMATION: Synthetic

<400> SEQUENCE: 33

| | |
|---|---|
| caactgcaac tccaagaatc tggtcctggt ctggtcaagc cttctgaaac cctgtctctg | 60 |
| acatgcaccg tctctggtgg ctccatttcc tcttctagct actattgggg atggatcagg | 120 |
| cagccaccag gaaagggact cgaatggatc ggaagcgtct actactctgg aggtgcttcc | 180 |
| tacaatcctt ctctcaagtc cagagccacc atctccgttg atacatctaa gaatcagttc | 240 |
| agcctcaatc tggactccgt cagcgcagca gacacagcca tctactactg tgcctccatc | 300 |
| tacggtagcg gtacattcta ctactacttc tacatggatg tgtggggtaa gggtagcacc | 360 |
| gtcaccgtgt ccagcggagg tggaggcagt ggaggtggtg atctggagg aggagggtct | 420 |
| gatatccaaa tgactcaatc tccatcttcc ctgtctgctt ccgtcggtga cagagttacc | 480 |
| atcacatgcc aggccagcca ggttatcagc aactacctga actggtatca gcagaagcct | 540 |
| ggaaaggctc ccaagctgct gatctatgat acatctaatc tcaagactgg tgtgccttcc | 600 |
| aggttctccg gtagcggatc tggcacagac ttcacattca ccatctcctc cctgcagcct | 660 |
| gaggacatcg caacctacta ctgtcagcaa tacgagaatc tgcagttcac cttcggacca | 720 |
| ggaacaaagg tggacatcaa gaga | 744 |

<210> SEQ ID NO 34
<211> LENGTH: 1212
<212> TYPE: DNA
<213> ORGANISM: Artificial Sequence
<220> FEATURE:
<223> OTHER INFORMATION: Synthetic

<400> SEQUENCE: 34

| | |
|---|---|
| ccttatctgg ctcattgtcc tgattgtgga gagggtcatt cttgtcatag cccagtcgct | 60 |
| ctggagagaa tcaggaatga ggcaacagat ggtactctga agattcaggt gtctctccag | 120 |
| atcggcatca agactgacga ctcccatgac tggaccaaac tcaggtacat ggataaccac | 180 |
| atgcctgcag atgctgaaag agctggcctg tttgtcagga cctccgctcc ctgtacaatc | 240 |
| actggcacta tgggtcattt catcctggct cgctgcccta agggtgaaac tctgacagtg | 300 |
| ggctttaccg actctcgcaa gatttcccac agctgtaccc acccattcca ccatgatcca | 360 |
| ccagttatcg gtagagagaa gtttcattct aggccacaac acggcaaaga actgccatgc | 420 |
| agcacatacg ttcagtccac cgcagccact actgaggaaa tcgaggtcca catgcctccc | 480 |
| gacacacctg acaggaccct gatgtcccaa caaagcggta acgtgaagat cacagtgaat | 540 |
| ggccaaactg tgcgctacaa gtgtaactgt ggtggtagca cgaaggact cactaccacc | 600 |
| gacaaagtta tcaacaactg caaagttgat cagtgtcacg cagccgtcac taaccacaag | 660 |
| aaatggcagt acaatagccc actcgtgccc agaaacgcag agctgggaga tcgcaagggc | 720 |
| aagatccaca tccctttccc tctggctaat gtgacatgca gggttccaaa ggcacgcaat | 780 |
| cctacagtga cctatggcaa gaaccaggtc atcatgctcc tctaccctga tcatcccacc | 840 |
| ctcctgagct accgcaacat gggtgaagaa ccaaactatc aggaagagtg ggtcatgcac | 900 |
| aagaaggaag ttgtgctgac cgtgcctact gaaggtctgg aagtgacttg ggaaacaac | 960 |
| gagccctaca gtattggcc acagctctcc acaaatggca ctgcccacgg tcacccacac | 1020 |
| gagatcatcc tgtactacta cgaactctac ccaaccatga ccgtcgttgt ggtcagcgtc | 1080 |
| gccaccttca tcctgctgag catggtcggt atggcagctg gtatgtgcat gtgcgctcgc | 1140 |
| agacgctgta tcactccata cgagctgact ccaggtgcca ctgtgccatt cctcctctcc | 1200 |
| ctgatttgtt gc | 1212 |

<210> SEQ ID NO 35
<211> LENGTH: 720
<212> TYPE: DNA
<213> ORGANISM: Artificial Sequence
<220> FEATURE:
<223> OTHER INFORMATION: Synthetic

<400> SEQUENCE: 35

```
caagtgcaac tgcaacagcc aggagctgaa ctggttagac ctggaagctc cgtgaaactg      60
tcttgcaaag caagcggtta cacattcacc agcaagtgga tgcactgggt gaaacaaagg     120
ccaatccaag gactggagtg gatcggcaac attgatccct ctgacagcga aacacactac     180
aaccagaagt tcaaggacaa ggccactctg accgtggaca agtcttcttc tactgcctac     240
atgcagctct ccagcctcac tagcgaggac tccgctgtct actactgcgc aagaggcgtt     300
accagaggct acttcgacgt gtggggtaca ggtacaactg tgacagttag cagcggaggt     360
ggaggcagtg gaggtggtgg atctggagga ggagggtctc agatcgttct gactcaatct     420
ccagccatca tgtccgcatc tccaggagag aaggtgacca tgacctgctc tgcttccagc     480
tccgtgacct acatgtattg gtatcagcag aagccaggct ctagcccaag gctgctcatc     540
tacgatactt ccaacctcgc cagcggagtg ccagtgcgct ctccggatc tggatctgga     600
acctcttact ccctcactat ctccaggatg gaggcagagg atgcagctac ttactactgc     660
cagcagagga ccaactatcc tctgactttc ggtgctggca ccaagctgga gctgaaaagg     720
```

<210> SEQ ID NO 36
<211> LENGTH: 1560
<212> TYPE: DNA
<213> ORGANISM: Artificial Sequence
<220> FEATURE:
<223> OTHER INFORMATION: Synthetic

<400> SEQUENCE: 36

```
atcctgcact atgagaaact gtctaagatt gggctcgtga agggtgtcac aaggaagtat      60
aagataaagt ccaaccctct caccaaggac atcgtgatca agatgatccc caacgtttca     120
aacatgagcc agtgtaccgg atctgtcatg gagaactata agacacggct gaacggcatt     180
ctgacaccta ttaagggagc tctcgaaatc tacaagaaca cactcatga cctggtgggt     240
gacgtgagac tcgctggcgt tatcatggcc ggcgttgcta tcggaattgc caccgcagcc     300
cagatcactg ccggagttgc tctgtatgaa gctatgaaga atgctgataa catcaacaag     360
ctcaaatctt ccattgagtc tactaatgag gcagtggtta aactgcaaga aactgcagag     420
aagaccgtgt atgttctgac agccctccaa gactacataa acacaaacct ggtgcccacc     480
atcgacaaga tttcatgtaa gcaaacagag ctgagcctgg acctggcct ctccaaatac     540
ctgtctgacc tgctgtttgt cttcgggccc aacctgcagg acccagtcag caacagcatg     600
accatccagg caatctcaca ggccttcgga ggcaactatg agactctgct gagaactctg     660
ggctatgcta cagaggattt tgatgatctg ctggagtccg actccatcac tggacagatc     720
atctatgtcg atctctcaag ctactacatc atcgtgcggg tgtacttccc aatcctgacc     780
gaaatccagc aagcatacat ccaggagctg ctccctgtgt ccttcaacaa tgacaatagt     840
gagtggatct ctatcgtccc caacttcatt ctggtgcgca acactgat ctccaatata     900
gagattggat tctgtctcat taccaagagg agcgtgatct gcaatcagga ttatgccacc     960
ccaatgacca caatatgag agaatgtctg acaggcagca ccgagaagtg tcccaggaa    1020
ctggttgtca gcagtcatgt gccaaggttt gccctgagca acggtgttct gtttgctaac    1080
```

| | |
|---|---|
| tgcattagcg tgacttgtca atgccagaca accggaagag ccatctcaca gtctggcgag | 1140 |
| cagaccctcc tgatgattga caatactaca tgcccaactg ctgtcctggg caacgtcata | 1200 |
| atatccctgg gcaagtatct gggtagcgtg aactacaata gcgaagggat tgccatcgga | 1260 |
| ccacctgttt tcaccgataa ggtggacatt tctagccaga tcagctccat gaatcaaagt | 1320 |
| ctgcagcagt ccaaagacta catcaaggaa gcccaacgcc tgctggatac cgtcaatccc | 1380 |
| tccctgatca gtatgctgag catgattatc ctgtatgtcc tgtccatcgc cagcctgtgt | 1440 |
| atcggactca tcaccttcat ttccttcatt attgtcgaaa agaagagaaa cacctatagt | 1500 |
| agactggagg atagacgcgt gaggcctaca agttctggcg atctctatta cattggaacc | 1560 |

<210> SEQ ID NO 37
<211> LENGTH: 723
<212> TYPE: DNA
<213> ORGANISM: Artificial Sequence
<220> FEATURE:
<223> OTHER INFORMATION: Synthetic

<400> SEQUENCE: 37

| | |
|---|---|
| gaagtgcagc tcgtggaatc tggaggagga ctggttaagc ctggtggatc tctcaagctg | 60 |
| tcttgtgcag catctggctt tacattcagc tcctacgata tgtcttgggt caggcagaca | 120 |
| cccgagaaac gcctcgaatg ggtggctatg atctcctccg gtggctctta ctcctactat | 180 |
| cccgacagcg tgaagggcag gtttaccatc agcagagaca atgccaagaa cactctgtat | 240 |
| ctgcagatgt cctccctgcg ctctgaggat acagcaatgt actactgtgc taggcaaggt | 300 |
| gactacgcat ggtttgccta ttggggacag ggaacactgg tcacagtgtc tgctggaggt | 360 |
| ggaggcagtg gaggtggtgg atctggagga ggagggtctg atatccaaat gacacaatct | 420 |
| ccagcttctc aatccgcttc tctgggtgag tccgtcacaa tcacttgtct ggcctctcaa | 480 |
| actatcggca cctggctggc ttggtatcag cagaagccag gcaaatctcc acagctcctg | 540 |
| atctatgctg caacctccct ggctgatggc gtgcccagca gattctctgg cagcggttct | 600 |
| ggaactaagt tctctttcaa gatcagctcc ctccaggcag aggacttcgt gtcctactat | 660 |
| tgtcaacagt tctactctac accattcaca ttcggaggag gtacaaagct ggagatcaaa | 720 |
| agg | 723 |

<210> SEQ ID NO 38
<211> LENGTH: 1503
<212> TYPE: DNA
<213> ORGANISM: Artificial Sequence
<220> FEATURE:
<223> OTHER INFORMATION: Synthetic

<400> SEQUENCE: 38

| | |
|---|---|
| ttcaactgcc tcggtatgag caacagggac ttcctggaag gagtgagcgg tgctacatgg | 60 |
| gtggatctgg tgctcgaagg cgactcttgc gttaccatca tgtccaagga caaaccaacc | 120 |
| attgatgtga agatgatgaa catggaagca gctaacctgg cagaagtccg ctcctattgc | 180 |
| tacctggcta ctgttagcga cctctctact aaggctgctt gtccaactat gggtgaagct | 240 |
| cacaacgaca gagggctga tcctgccttt gtctgtaggc agggtgtggt ggacagaggt | 300 |
| tggggtaatg gttgtggcct gttcggtaag gctccatcg acacctgcgc taagttcgct | 360 |
| tgtagcacaa aggccatcgg taggactatc ctgaaagaga acatcaagta cgaggtggct | 420 |
| atcttcgtgc atggacctac aacagttgaa tctcacggca actacagcac ccaggctgga | 480 |

-continued

```
gcaacacaag caggcagatt cagcatcaca ccagctgcac ctagctacac cctcaagctc      540
ggtgaatacg gtgaagtcac agttgactgc gagcccagat ccggtatcga cacaaatgcc      600
tactacgtta tgactgtcgg aactaagaca ttcctggtcc acagggaatg gttcatggac      660
ctgaatctcc cttggtctag cgcaggcagc acagtctgga gaaacagaga gactctgatg      720
gagttcgagg aaccacacgc aaccaaacag tccgtcattg ccctgggatc tcaggagggt      780
gctctgcacc aagctctggc tggtgccatt cctgtggagt ttagctctaa caccgtgaag      840
ctgaccagcg gtcatctgaa atgcagggtt aagatggaga agctgcaact caagggaact      900
acttacggag tgtgtagcaa ggcattcaag tttctgggaa ctcctgcaga tacaggacat      960
ggtacagtcg tgctcgaact gcagtacact ggcactgatg gtccctgcaa agtgccaatc     1020
agcagcgtcg cttctctgaa cgacctgact cccgtgggta gactggtgac cgtgaatcct     1080
ttcgtctctg tggccacagc taacgcaaag gttctgattg aactggagcc tcccttcgga     1140
gacagctaca ttgttgtcgg aagaggtgag cagcagatca accaccactg gcacaagagc     1200
ggaagcagca tcggcaaggc attcactaca acactcaaag gtgcacaaag actggctgct     1260
ctcggtgata ctgcctggga tttcggtagc gttggaggcg tcttcacatc tgttggcaag     1320
gcagttcacc aggtcttcgg tggtgctttc aggtccctgt tcggaggcat gagctggatt     1380
actcagggac tgctgggtgc tctgctcctc tggatgggca tcaacgcaag agatagatcc     1440
atcgcactga catttctcgc tgtgggaggc gttctcctct cctgtccgt caatgttcat      1500
gct                                                                   1503
```

<210> SEQ ID NO 39
<211> LENGTH: 726
<212> TYPE: DNA
<213> ORGANISM: Artificial Sequence
<220> FEATURE:
<223> OTHER INFORMATION: Synthetic

<400> SEQUENCE: 39

```
caagtgcaac tgcaacaatc tggtagcgaa ctcatgaaac ctggtgcctc cgtccagatc       60
agctgcaaag caacaggtta cactttctct gactactgga tcgagtgggt gaagcaaaga      120
cctggacatg gactcgaatg gatcggtgac attctgtgcg gaaccggaag gactcgctac      180
aacgagaagc tgaaggcaat ggcaaccttc accgcagata cttccagcaa caccgctttc      240
atgcaactgt ccagcctgac aagcgaggac tctgctgtct actattgcgc aaggtctgca      300
tcctatggcg actacgctga ttactggggt cacggtacaa ccctgactgt cagcagcgga      360
ggtggaggca gtggaggtgg tggatctgga ggaggagggt ctgatatcgt gatgactcaa      420
tcccacaagt tcatgtctac ctccgtcggt gacagggtgt ctatcacttg caaggcatcc      480
caggacgtct ctactgctgt ggcctggtat caacagaagc tggccagag ccctaaactc       540
ctgatcagct gggcttctac taggcacaca ggcgttccag atcgctttac tggctctgga      600
tctggaactg attacaccct gactatcagc agcgtgcagg ctgaggatct ggctctctac      660
tactgtcaac agcattacac cacaccactg accttcggag ctggaactaa gctggaactg      720
aagagg                                                                726
```

<210> SEQ ID NO 40
<211> LENGTH: 9859
<212> TYPE: DNA
<213> ORGANISM: Artificial Sequence
<220> FEATURE:
<223> OTHER INFORMATION: Synthetic

<400> SEQUENCE: 40

```
acgcgtgtag tcttatgcaa tactcttgta gtcttgcaac atggtaacga tgagttagca      60
acatgcctta caaggagaga aaaagcaccg tgcatgccga ttggtggaag taaggtggta     120
cgatcgtgcc ttattaggaa ggcaacagac gggtctgaca tggattggac gaaccactga     180
attgccgcat tgcagagata ttgtatttaa gtgcctagct cgatacaata acgggtctc      240
tctggttaga ccagatctga gcctgggagc tctctggcta actagggaac ccactgctta     300
agcctcaata aagcttgcct tgagtgcttc aagtagtgtg tgcccgtctg ttgtgtgact     360
ctggtaacta gagatccctc agaccctttt agtcagtgtg gaaaatctct agcagtggcg     420
cccgaacagg gacctgaaag cgaaagggaa accagagctc tctcgacgca ggactcggct     480
tgctgaagcg cgcacggcaa gaggcgaggg cggcgactg tgagtacgc caaaaatttt      540
gactagcgga ggctagaagg agagagatgg gtgcgagagc gtcagtatta agcggggag      600
aattagatcg cgatgggaaa aaattcggtt aaggccaggg ggaaagaaaa aatataaatt     660
aaaacatata gtatgggcaa gcagggagct agaacgattc gcagttaatc ctggcctgtt     720
agaaacatca gaaggctgta gacaaatact gggacagcta caaccatccc ttcagacagg     780
atcagaagaa cttagatcat tatataatac agtagcaacc ctctattgtg tgcatcaaag     840
gatagagata aagacacca aggaagcttt agacaagata gaggaagagc aaaacaaaag      900
taagaccacc gcacagcaag cggccactga tcttcagacc tggaggagga gatatgaggg     960
acaattggag aagtgaatta tataaatata agtagtaaa aattgaacca ttaggagtag     1020
cacccaccaa ggcaaagaga agagtggtgc agagagaaaa aagagcagtg ggaataggag    1080
ctttgttcct tgggttcttg ggagcagcag gaagcactat gggcgcagcg tcaatgacgc    1140
tgacggtaca ggccagacaa ttattgtctg gtatagtgca gcagcagaac aatttgctga    1200
gggctattga ggcgcaacag catctgttgc aactcacagt ctgggggcatc aagcagctcc    1260
aggcaagaat cctggctgtg gaaagatacc taaaggatca acagctcctg gggatttggg    1320
gttgctctgg aaaactcatt tgcaccactg ctgtgccttg gaatgctagt tggagtaata    1380
aatctctgga acagatttgg aatcacacga cctggatgga gtgggacaga gaattaaca    1440
attacacaag cttaatacac tccttaattg aagaatcgca aaaccagcaa gaaaagaatg    1500
aacaagaatt attggaatta gataaatggg caagtttgtg gaattggttt aacataacaa    1560
attggctgtg gtatataaaa ttattcataa tgatagtagg aggcttggta ggtttaagaa    1620
tagttttgc tgtactttct atagtgaata gagttaggca gggatattca ccattatcgt    1680
ttcagaccca cctcccaacc ccgagggac ccgacaggcc cgaaggaata gaagaagaag    1740
gtggagagag agacagagac agatccattc gattagtgaa cggatctcga cggtatcgt     1800
taacttttaa aagaaaggg gggattgggg ggtacagtgc aggggaaaga atagtagaca    1860
taatagcaac agacatacaa actaaagaat tacaaaaaca aattacaaaa ttcaaaattt    1920
tatcgatgct agcggaggaa aaactgtttc atacagaagg cgtggaggaa aaactgtttc    1980
atacagaagg cgtggaggaa aaactgtttc atacagaagg cgtggaggaa aaactgtttc    2040
atacagaagg cgtggaggaa aaactgtttc atacagaagg cgtggaggaa aaactgtttc    2100
atacagaagg cgtagatcta gactctagag ggtatataat ggaagctcga cttccagctt    2160
ggcattccgg tactgttggt aaaaagcttg gcaatccggt actgttggta aaggatccgc    2220
caccatgcct gccatgaaga ttgagtgccg catcacggga accctgaacg gagtggagtt    2280
```

-continued

```
tgagctggtc ggaggtggag aagggactcc tgagcaggga cgtatgacca acaagatgaa    2340
gtctaccaag ggcgccttga ccttctcccc ctaccttctc tctcatgtca tgggatacgg    2400
gttctaccac tttggtacct atcccagtgg gtatgagaat cccttcctgc atgccatcaa    2460
caacgggggg tacaccaaca ccaggattga aagtatgag gatggaggag ttcttcatgt    2520
tagctttagc tacagatatg aagcaggcag ggtgattggg gatttcaagg ttgtcgggac    2580
aggattccct gaggacagtg tgatcttcac cgacaagatc atccggtcca atgctaccgt    2640
ggagcacttg cacccaatgg gagacaacgt tcttgtgggc tccttcgcga aaccttttc    2700
cctgagggat ggaggctact actcatttgt ggttgacagc cacatgcact caagagtgc    2760
catccaccca tccatcctcc agaacggggg gcccatgttt gccttcagga gagttgagga    2820
acttcactcc aacactgaac ttggcattgt agagtatcaa catgccttca agactcccat    2880
agcatttgct ggaagcggag ctactaactt cagcctgctg aagcaggctg agacgtgga    2940
ggagaaccct ggacctatgg tcttcacact cgaagatttc gttggggact ggcgacagac    3000
agccggctac aacctggacc aagtccttga acagggaggt gtgtccagtt tgtttcagaa    3060
tctcgggggtg tccgtaactc cgatccaaag gattgtcctg agcggtgaaa atgggctgaa    3120
gatcgacatc catgtcatca tcccgtatga aggtctgagc ggcgaccaaa tgggccagat    3180
cgaaaaaatt tttaaggtgg tgtaccctgt ggatgatcat cactttaagg tgatcctgca    3240
ctatggcaca ctggtaatcg acggggttac gccgaacatg atcgactatt tcggacggcc    3300
gtatgaaggc atcgccgtgt tcgacggcaa aaagatcact gtaacaggga ccctgtggaa    3360
cggcaacaaa attatcgacg agcgcctgat caaccccgac ggctccctgc tgttccgagt    3420
aaccatcaac ggagtgaccg gctggcggct gtgcgaacgc attctggcgt aagcggccgc    3480
gaaggatctg cgatcgctcc ggtgcccgtc agtgggcaga gcgcacatcg cccacagtcc    3540
ccgagaagtt gggggggaggg gtcggcaatt gaacgggtgc ctagagaagg tggcgcgggg    3600
taaactggga aagtgatgtc gtgtactggc tccgcctttt tcccgagggt gggggagaac    3660
cgtatataag tgcagtagtc gccgtgaacg ttcttttttcg caacgggttt gccgccagaa    3720
cacagctgaa gcttcgaggg gctcgcatct ctccttcacg cgcccgccgc cctacctgag    3780
gccgccatcc acgccggttg agtcgcgttc tgccgcctcc cgcctgtggt gcctcctgaa    3840
ctgcgtccgc cgtctaggta agtttaaagc tcaggtcgag accgggccctt tgtccggcgc    3900
tcccttggag cctacctaga ctcagccggc tctccacgct ttgcctgacc ctgcttgctc    3960
aactctacgt ctttgtttcg ttttctgttc tgcgccgtta cagatccaag ctgtgaccgg    4020
cgcctactag tgccaccatg gactttcaag tgcagatctt cagctttctg ctgatctctg    4080
ctagtgtcat catgtctcaa gtgcaactgg tggaaactgg tggtggactg gttcagccag    4140
gtggaagcct gagactctcc tgtgcagcaa gcggtttcac cttctcttct gtctacatga    4200
actgggtcag gcaagctcct ggcaaaggac ccgaatgggt gtccaggatt tctcccaact    4260
ccggtaacat cggctacaca gatagcgtca agggtaggtt tactatctcc agagataacg    4320
ccaagaatac cctctacctg caaatgaaca acctgaagcc tgaggataca gccctctact    4380
attgcgcaat cggactcaac ctgtctagct cctctgtcag aggtcagggt acccaagtca    4440
ctgtgtccag cgaaatcgag cagaagctga tttccgaaga ggatctcaat ggagtgactg    4500
tcagcagcgc tctgtctaac tccatcatgt acttctcaca cttcgtgcca gtgttcctcc    4560
ctgctaaacc caccacaact ccagcaccta gacctcccac tccagcacca actattgcat    4620
cccagcctct ctccctcaga ccagaagcat gcagacctgc agcaggtgga gctgtgcaca    4680
```

```
caagaggtct ggacccttc tgggtcctcg tggtggtggg tggagtcctg gcatgttaca    4740
gcctcctggt caccgtggca ttcatcatct tctgggtgag atctaagagg agcagactgc    4800
tgcactctga ttacatgaac atgacaccca gaagacctgg tcccaccaga aagcactacc    4860
aaccctacgc accaccaaga gactttgctg catacagaag tctcgagagg gtcaagttct    4920
caaggagtgc agatgctcca gcctatcaac agggtcagaa ccaactgtac aacgagctga    4980
atctcggaag aagagaggag tacgatgtgc tggataagag aagaggcagg gacccagaga    5040
tgggtgggaa acccagaaga aagaatcctc aagagggact gtacaatgag ctgcagaagg    5100
ataagatggc tgaggcatac tcagagatcg gtatgaaggg agagaggaga agaggcaaag    5160
gtcatgatgg tctgtaccaa ggtctgtcca cagcaacaaa ggatacatat gatgctctgc    5220
acatgcagga ctcccacca cggggttccg gagtgaaaca gactttgaac tttgaccttc    5280
tcaagttggc tggagacgtc gagtccaacc ctggtcccat gaccgagtac aagcccacgg    5340
tgcgcctcgc cacccgcgac gacgtcccca gggccgtacg caccctcgcc gccgcgttcg    5400
ccgactaccc cgccacgcgc cacaccgtcg atccggaccg ccacatcgag cgggtcaccg    5460
agctgcaaga actcttcctc acgcgcgtcg ggctcgacat cggcaaggtg tgggtcgcgg    5520
acgacggcgc cgcggtggcg gtctggacca cgccggagag cgtcgaagcg ggggcggtgt    5580
tcgccgagat cggcccgcgc atggccgagt tgagcggttc ccggctggcc gcgcagcaac    5640
agatggaagg cctcctggcg ccgcaccggc ccaaggagcc cgcgtggttc ctggccaccg    5700
tcggcgtctc gcccgaccac cagggcaagg gtctgggcag cgccgtcgtg ctccccggag    5760
tggaggcggc cgagcgcgcc ggggtgcccg ccttcctgga gacctccgcg ccccgcaacc    5820
tccccttcta cgagcggctc ggcttcaccg tcaccgccga cgtcgaggtg cccgaaggac    5880
cgcgcacctg gtgcatgacc cgcaagcccg gtgcctgatt aattaagtcg acaatcaacc    5940
tctggattac aaaatttgtg aaagattgac tggtattctt aactatgttg ctccttttac    6000
gctatgtgga tacgctgctt taatgccttt gtatcatgct attgcttccc gtatggcttt    6060
cattttctcc tccttgtata aatcctggtt gctgtctctt tatgaggagt tgtggcccgt    6120
tgtcaggcaa cgtggcgtgg tgtgcactgt gtttgctgac gcaaccccca ctggttgggg    6180
cattgccacc acctgtcagc tcctttccgg gactttcgct ttcccctcc ctattgccac    6240
ggcggaactc atcgccgcct gccttgcccg ctgctggaca ggggctcggc tgttgggcac    6300
tgacaattcc gtggtgttgt cggggaaatc atcgtccttt ccttggctgc tcgcctgtgt    6360
tgccacctgg attctgcgcg gacgtcctt ctgctacgtc ccttcggccc tcaatccagc    6420
ggaccttcct tcccgcggcc tgctgccggc tctgcggcct cttccgcgtc ttcgccttcg    6480
ccctcagacg agtcggatct ccttttgggc cgcctcccg cctggtacct ttaagaccaa    6540
tgacttacaa ggcagctgta gatcttagcc acttttaaa agaaagggg ggactggaag    6600
ggctaattca ctcccaacga agataagatc tgcttttgc ttgtactggg tctctctggt    6660
tagaccagat ctgagcctgg gagctctctg gctaactagg gaacccactg cttaagcctc    6720
aataaagctt gccttgagtg cttcaagtag tgtgtgcccg tctgttgtgt gactctggta    6780
actagagatc cctcagaccc ttttagtcag tgtggaaaat ctctagcagt agtagttcat    6840
gtcatcttat tattcagtat ttataacttg caaagaaatg aatatcagag agtgagagga    6900
acttgtttat tgcagcttat aatggttaca aataaagcaa tagcatcaca atttcacaa    6960
ataaagcatt ttttcactg cattctagtt gtggtttgtc caaactcatc aatgtatctt    7020
```

```
atcatgtctg gctctagcta tcccgcccct aactccgccc atcccgcccc taactccgcc   7080
cagttccgcc cattctccgc cccatggctg actaattttt tttatttatg cagaggccga   7140
ggccgcctcg gcctctgagc tattccagaa gtagtgagga ggctttttttg gaggcctaga  7200 cttttgcaga gacggcccaa attcgtaatc atggtcatag ctgtttcctg tgtgaaattg   7260
ttatccgctc acaattccac acaacatacg agccggaagc ataaagtgta aagcctgggg   7320
tgcctaatga gtgagctaac tcacattaat tgcgttgcgc tcactgcccg ctttccagtc   7380
gggaaacctg tcgtgccagc tgcattaatg aatcggccaa cgcgcgggga gaggcggttt   7440
gcgtattggg cgctcttccg cttcctcgct cactgactcg ctgcgctcgg tcgttcggct   7500
gcggcgagcg gtatcagctc actcaaaggc ggtaatacgg ttatccacag aatcagggga   7560
taacgcagga aagaacatgt gagcaaaagg ccagcaaaag gccaggaacc gtaaaaaggc   7620
cgcgttgctg gcgttttttcc ataggctccg ccccccctgac gagcatcaca aaaatcgacg  7680
ctcaagtcag aggtggcgaa acccgacagg actataaaga taccaggcgt ttccccctgg   7740
aagctccctc gtgcgctctc ctgttccgac cctgccgctt accggatacc tgtccgcctt   7800
tctcccttcg ggaagcgtgg cgctttctca tagctcacgc tgtaggtatc tcagttcggt   7860
gtaggtcgtt cgctccaagc tgggctgtgt gcacgaaccc cccgttcagc ccgaccgctg   7920
cgccttatcc ggtaactatc gtcttgagtc aacccggta agacacgact tatcgccact   7980
ggcagcagcc actggtaaca ggattagcag agcgaggtat gtaggcggtg ctacagagtt   8040
cttgaagtgg tggcctaact acggctacac tagaaggaca gtatttggta tctgcgctct   8100
gctgaagcca gttaccttcg gaaaaagagt tggtagctct tgatccggca acaaaccac   8160 cgctggtagc ggtggttttt ttgtttgcaa gcagcagatt acgcgcagaa aaaaaggatc   8220
tcaagaagat cctttgatct tttctacggg gtctgacgct cagtggaacg aaaactcacg   8280
ttaagggatt ttggtcatga gattatcaaa aaggatcttc acctagatcc ttttaaatta   8340
aaaatgaagt tttaaatcaa tctaaagtat atatgagtaa acttggtctg acagttacca   8400
atgcttaatc agtgaggcac ctatctcagc gatctgtcta tttcgttcat ccatagttgc   8460
ctgactcccc gtcgtgtaga taactacgat acgggagggc ttaccatctg gccccagtgc   8520
tgcaatgata ccgcgagacc cacgctcacc ggctccagat ttatcagcaa taaaccagcc   8580
agccggaagg gccgagcgca gaagtggtcc tgcaacttta tccgcctcca tccagtctat   8640
taattgttgc cgggaagcta gagtaagtag ttcgccagtt aatagtttgc gcaacgttgt   8700
tgccattgct acaggcatcg tggtgtcacg ctcgtcgttt ggtatggctt cattcagctc   8760
cggttcccaa cgatcaaggc gagttacatg atccccccatg ttgtgcaaaa aagcggttag   8820
ctccttcggt cctccgatcg ttgtcagaag taagttggcc gcagtgttat cactcatggt   8880
tatggcagca ctgcataatt ctcttactgt catgccatcc gtaagatgct tttctgtgac   8940
tggtgagtac tcaaccaagt cattctgaga atagtgtatg cggcgaccga gttgctcttg   9000
cccggcgtca atacgggata ataccgcgcc acatagcaga actttaaaag tgctcatcat   9060
tggaaaacgt tcttcggggc gaaaactctc aaggatctta ccgctgttga tccagttc    9120 gatgtaaccc actcgtgcac ccaactgatc ttcagcatct tttactttca ccagcgtttc   9180
tgggtgagca aaaacaggaa ggcaaaatgc cgcaaaaaag gaataagggc gacacggaa    9240 atgttgaata ctcatactct tcctttttca atattattga agcatttatc agggttattg   9300
tctcatgagc ggatacatat ttgaatgtat ttagaaaaat aaacaaatag gggttccgcg   9360
cacatttccc cgaaaagtgc cacctgacgt ctaagaaacc attattatca tgacattaac   9420
```

-continued

```
ctataaaaat aggcgtatca cgaggcccct tcgtctcgcg cgtttcggtg atgacggtga    9480
aaacctctga cacatgcagc tcccggagac ggtcacagct tgtctgtaag cggatgccgg    9540
gagcagacaa gcccgtcagg gcgcgtcagc gggtgttggc gggtgtcggg gctggcttaa    9600
ctatgcggca tcagagcaga ttgtactgag agtgcaccat atgcggtgtg aaataccgca    9660
cagatgcgta aggagaaaat accgcatcag gcgccattcg ccattcaggc tgcgcaactg    9720
ttgggaaggg cgatcggtgc gggcctcttc gctattacgc cagctggcga aggggggatg    9780
tgctgcaagg cgattaagtt gggtaacgcc agggttttcc cagtcacgac gttgtaaaac    9840
gacggccagt gccaagctg                                                 9859
```

<210> SEQ ID NO 41
<211> LENGTH: 10252
<212> TYPE: DNA
<213> ORGANISM: Artificial Sequence
<220> FEATURE:
<223> OTHER INFORMATION: Synthetic

<400> SEQUENCE: 41

```
acgcgtgtag tcttatgcaa tactcttgta gtcttgcaac atggtaacga tgagttagca      60
acatgcctta caaggagaga aaaagcaccg tgcatgccga ttggtggaag taaggtggta     120
cgatcgtgcc ttattaggaa ggcaacagac gggtctgaca tggattggac gaaccactga     180
attgccgcat tgcagagata ttgtatttaa gtgcctagct cgatacaata aacgggtctc     240
tctggttaga ccagatctga gcctgggagc tctctggcta actagggaac ccactgctta     300
agcctcaata aagcttgcct tgagtgcttc aagtagtgtg tgcccgtctg ttgtgtgact     360
ctggtaacta gagatccctc agacccttttt agtcagtgtg gaaaatctct agcagtggcg     420
cccgaacagg gacctgaaag cgaaagggaa accagagctc tctcgacgca ggactcggct     480
tgctgaagcg cgcacggcaa gaggcgaggg cggcgactg tgagtacgc caaaattt       540 gactagcgga ggctagaagg agagagatgg gtgcgagagc gtcagtatta agcgggggag     600
aattagatcg cgatgggaaa aaattcggtt aaggccaggg ggaaagaaaa aatataaatt     660
aaaacatata gtatgggcaa gcaggagct agaacgattc gcagttaatc ctggcctgtt     720
agaaacatca gaaggctgta gacaaatact gggacagcta caaccatccc ttcagacagg     780
atcagaagaa cttagatcat tatataatac agtagcaacc ctctattgtg tgcatcaaag     840
gatagagata aaagacacca aggaagcttt agacaagata gaggaagagc aaaacaaaag     900
taagaccacc gcacagcaag cggccactga tcttcagacc tggaggagga gatatgaggg     960
acaattggag aagtgaatta tataaatata agtagtaaa aattgaacca ttaggagtag    1020
cacccaccaa ggcaaagaga agagtggtgc agagagaaaa aagagcagtg ggaataggag    1080 cttttgttcct tgggttcttg ggagcagcag gaagcactat gggcgcagcg tcaatgacgc    1140
tgacggtaca ggccagacaa ttattgtctg gtatagtgca gcagcagaac aatttgctga    1200
gggctattga ggcgcaacag catctgttgc aactcacagt ctggggcatc aagcagctcc    1260
aggcaagaat cctggctgtg gaaagatacc taaaggatca acagctcctg gggatttggg    1320
gttgctctgg aaaactcatt tgcaccactg ctgtgccttg gaatgctagt tggagtaata    1380
aatctctgga acagatttgg aatcacacga cctggatgga gtgggacaga gaattaaca    1440 attacacaag cttaatacac tccttaattg aagaatcgca aaaccagcaa gaaaagaatg    1500
aacaagaatt attggaatta gataaatggg caagtttgtg gaattggttt aacataacaa    1560
```

```
attggctgtg gtatataaaa ttattcataa tgatagtagg aggcttggta ggtttaagaa   1620
tagtttttgc tgtactttct atagtgaata gagttaggca gggatattca ccattatcgt   1680
ttcagaccca cctcccaacc ccgaggggac ccgacaggcc cgaaggaata aagaagaag    1740 gtggagagag agacagagac agatccattc gattagtgaa cggatctcga cggtatcggt   1800
taacttttaa aagaaaaggg gggattgggg ggtacagtgc aggggaaaga atagtagaca   1860
taatagcaac agacatacaa actaaagaat tacaaaaaca aattacaaaa ttcaaaattt   1920
tatcgatgct agcggaggaa aaactgtttc atacagaagg cgtggaggaa aaactgtttc   1980
atacagaagg cgtggaggaa aaactgtttc atacagaagg cgtggaggaa aaactgtttc   2040
atacagaagg cgtggaggaa aaactgtttc atacagaagg cgtggaggaa aaactgtttc   2100
atacagaagg cgtagatcta gactctagag ggtatataat ggaagctcga cttccagctt   2160
ggcattccgg tactgttggt aaaaagcttg gcaatccggt actgttggta aaggatccgc   2220
caccatgcct gccatgaaga ttgagtgccg catcacggga accctgaacg gagtggagtt   2280
tgagctggtc ggaggtggag aagggactcc tgagcaggga cgtatgacca acaagatgaa   2340
gtctaccaag ggcgccttga ccttctcccc ctaccttctc tctcatgtca tgggatacgg   2400
gttctaccac tttggtacct atcccagtgg gtatgagaat cccttcctgc atgccatcaa   2460 caacggggggg tacaccaaca ccaggattga aagtatgag atggaggag ttcttcatgt    2520 tagctttagc tacagatatg aagcaggcag ggtgattggg gatttcaagg ttgtcgggac   2580
aggattccct gaggacagtg tgatcttcac cgacaagatc atccggtcca atgctaccgt   2640
ggagcacttg cacccaatgg gagacaacgt tcttgtgggc ccttcgcga gaaccttttc    2700 cctgagggat ggaggctact actcatttgt ggttgacagc cacatgcact tcaagagtgc   2760
catccaccca tccatcctcc agaacgggg gcccatgttt gccttcagga gagttgagga    2820
acttcactcc aacactgaac ttggcattgt agagtatcaa catgccttca agactcccat   2880
agcatttgct ggaagcggag ctactaactt cagcctgctg aagcaggctg agacgtgga    2940 ggagaaccct ggacctatgg tcttcacact cgaagatttc gttggggact ggcgacagac   3000
agccggctac aacctggacc aagtccttga acagggaggt gtgtccagtt tgtttcagaa   3060
tctcggggtg tccgtaactc cgatccaaag gattgtcctg agcggtgaaa atgggctgaa   3120
gatcgacatc catgtcatca tcccgtatga aggtctgagc ggcgaccaaa tgggccagat   3180
cgaaaaaatt tttaaggtgg tgtaccctgt ggatgatcat cactttaagg tgatcctgca   3240
ctatggcaca ctggtaatcg acggggttac gccgaacatg atcgactatt tcggacggcc   3300
gtatgaaggc atcgccgtgt tcgacggcaa aaagatcact gtaacaggga ccctgtggaa   3360
cggcaacaaa attatcgacg agcgcctgat caaccccgac ggctccctgc tgttccgagt   3420
aaccatcaac ggagtgaccg gctggcggct gtgcgaacgc attctggcgt aagcggccgc   3480
gaaggatctg cgatcgctcc ggtgcccgtc agtgggcaga gcgcacatcg cccacagtcc   3540
ccgagaagtt ggggggaggg gtcggcaatt gaacgggtgc ctagaaaagg tggcgcgggg   3600
taaactggga aagtgatgtc gtgtactggc tccgcctttt tcccgagggt gggggagaac   3660
cgtatataag tgcagtagtc gccgtgaacg ttcttttttcg caacgggttt gccgccagaa   3720
cacagctgaa gcttcgaggg gctcgcatct ctccttcacg cgcccgccgc cctacctgag   3780
gccgccatcc acgccggttg agtcgcgttc tgccgcctcc cgcctgtggt gcctcctgaa   3840
ctgcgtccgc cgtctaggta agtttaaagc tcaggtcgag accgggcctt tgtccggcgc   3900
tcccttggag cctacctaga ctcagccggc tctccacgct ttgcctgacc ctgcttgctc   3960
```

```
aactctacgt ctttgtttcg ttttctgttc tgcgccgtta cagatccaag ctgtgaccgg   4020
cgcctactag tgccaccatg gactttcaag tgcagatctt cagctttctg ctgatctctg   4080
ctagtgtcat catgtctcaa gttcaactgg ttcaatccgg agcagaagtg aagaagcctg   4140
gtgcaagcgt gaaagtgagc tgcaaggcat ctggctaccc attcactagc tacggtatct   4200
cctgggtgag acaagcacct ggtcaaggac tcgaatggat gggctggatc tctacctaca   4260
atggaaacac caactatgcc cagaagttcc agggtagagt tacaatgact acagatacta   4320
gcactaccac aggctacatg gaactcagga ggctcaggtc tgacgacaca gctgtctact   4380
attgtgcacg cgactacact agaggagctt ggtttggtga gagcctcatt ggtggcttcg   4440
acaattgggg tcagggtact ctggtcaccg tctccagcgg aggtggaggc agtggaggtg   4500
gtggatctgg aggaggaggg tctgagattg ttctgactca atctcctggt actctgtctc   4560
tgagcccagg tgagagagca accctgtctt gtagagcatc ccagactgtc tctagcacat   4620
ccctcgcatg gtatcagcag aaaccaggtc aagcacccag gctcctcatc tatggtgctt   4680
ctagcagggc aactggaatc cctgatcgct tctctggatc tggcagcgga actgatttca   4740
ctctgaccat ctctcgcctg gaacccgagg actttgccgt gtactattgt cagcagcacg   4800
atacttctct gacattcggt ggaggtacaa aggtggagat caaggaaatc gagcagaagc   4860
tgatttccga agaggatctc aatggagtga ctgtcagcag cgctctgtct aactccatca   4920
tgtacttctc acacttcgtg ccagtgttcc tccctgctaa acccaccaca actccagcac   4980
ctagacctcc cactccagca ccaactattg catcccagcc tctctccctc agaccagaag   5040
catgcagacc tgcagcaggt ggagctgtgc acacaagagg tctggaccct ttctgggtcc   5100
tcgtggtggt gggtggagtc ctggcatgtt acagcctcct ggtcaccgtg cattcatca   5160 tcttctgggt gagatctaag aggagcagac tgctgcactc tgattacatg aacatgacac   5220
ccagaagacc tggtcccacc agaaagcact accaacccta cgcaccacca agagactttg   5280
ctgcatacag aagtctcgag agggtcaagt tctcaaggag tgcagatgct ccagcctatc   5340
aacagggtca gaaccaactg tacaacgagc tgaatctcgg aagaagagag gagtacgatg   5400
tgctggataa gagaagaggc agggacccag agatgggtgg gaaacccaga agaagaatc   5460 ctcaagaggg actgtacaat gagctgcaga aggataagat ggctgaggca tactcagaga   5520
tcggtatgaa gggagagagg agaagaggca aggtcatga tggtctgtac aaggtctgt    5580 ccacagcaac aaaggataca tatgatgctc tgcacatgca ggcactccca ccacggggtt   5640
ccggagtgaa acagactttg aactttgacc ttctcaagtt ggctggagac gtcgagtcca   5700
accctggtcc catgaccgag tacaagccca cggtgcgcct cgccaccgc gacgacgtcc    5760 ccagggccgt acgcacctc gccgcgcgt tcgccgacta ccccgccacg cgccacaccg    5820
tcgatccgga ccgccacatc gagcgggtca ccgagctgca agaactcttc ctcacgcgcg   5880
tcgggctcga catcggcaag gtgtgggtcg cggacgacgg cgccgcggtg gcggtctgga   5940
ccacgccgga gagcgtcgaa gcggggcgg tgttcgccga atcggcccg cgcatggccg    6000 agttgagcgg ttcccggctg gccgcgcagc aacagatgga aggcctcctg gcgccgcacc   6060
ggcccaagga gcccgcgtgg ttcctggcca ccgtcggcgt ctcgcccgac caccagggca   6120
agggtctggg cagcgccgtc gtgctccccg gagtggaggc ggccgagcgc gccggggtgc   6180
ccgccttcct ggagacctcc gcgccccgca acctccccct ctacgagcgg ctcggcttca   6240
ccgtcaccgc cgacgtcgag gtgcccgaag gaccgcgcac ctggtgcatg acccgcaagc   6300
```

```
ccggtgcctg attaattaag tcgacaatca acctctggat tacaaaattt gtgaaagatt    6360
gactggtatt cttaactatg ttgctccttt tacgctatgt ggatacgctg ctttaatgcc    6420
tttgtatcat gctattgctt cccgtatggc tttcattttc tcctccttgt ataaatcctg    6480
gttgctgtct ctttatgagg agttgtggcc cgttgtcagg caacgtggcg tggtgtgcac    6540
tgtgtttgct gacgcaaccc ccactggttg gggcattgcc accacctgtc agctcctttc    6600
cgggactttc gctttccccc tccctattgc cacggcggaa ctcatcgccg cctgccttgc    6660
ccgctgctgg acaggggctc ggctgttggg cactgacaat tccgtggtgt tgtcggggaa    6720
atcatcgtcc tttccttggc tgctcgcctg tgttgccacc tggattctgc gcggacgtc     6780 cttctgctac gtcccttcgg ccctcaatcc agcggacctt ccttcccgcg gcctgctgcc    6840
ggctctgcgg cctcttccgc gtcttcgcct tcgccctcag acgagtcgga tctccctttg    6900
ggccgcctcc ccgcctggta cctttaagac caatgactta caaggcagct gtagatctta    6960 gccactttt aaaagaaaag gggggactgg aagggctaat tcactcccaa cgaagataag    7020
atctgctttt tgcttgtact gggtctctct ggttagacca gatctgagcc tgggagctct    7080
ctggctaact agggaaccca ctgcttaagc ctcaataaag cttgccttga gtgcttcaag    7140
tagtgtgtgc ccgtctgttg tgtgactctg gtaactagag atccctcaga ccctttagt    7200 cagtgtggaa aatctctagc agtagtagtt catgtcatct tattattcag tatttataac    7260
ttgcaaagaa atgaatatca gagagtgaga ggaacttgtt tattgcagct tataatggtt    7320
acaaataaag caatagcatc acaaatttca caaataaagc attttttca ctgcattcta    7380 gttgtggttt gtccaaactc atcaatgtat cttatcatgt ctggctctag ctatcccgcc    7440
cctaactccg cccatcccgc cctaactccg gccagttcc gcccattctc cgccccatgg    7500
ctgactaatt tttttattt atgcagaggc cgaggccgcc tcggcctctg agctattcca    7560
gaagtagtga ggaggctttt ttggaggcct agactttgc agagacggcc caaattcgta    7620
atcatggtca tagctgtttc ctgtgtgaaa ttgttatccg ctcacaattc cacacaacat    7680
acgagccgga agcataaagt gtaaagcctg gggtgcctaa tgagtgagct aactcacatt    7740
aattgcgttg cgctcactgc ccgctttcca gtcgggaaac ctgtcgtgcc agctgcatta    7800
atgaatcggc caacgcgcgg ggagaggcgg tttgcgtatt gggcgctctt ccgcttcctc    7860
gctcactgac tcgctgcgct cggtcgttcg gctgcggcga gcggtatcag ctcactcaaa    7920
ggcggtaata cggttatcca cagaatcagg ggataacgca ggaaagaaca tgtgagcaaa    7980
aggccagcaa aaggccagga accgtaaaaa ggccgcgttg ctggcgtttt tccataggct    8040
ccgcccccct gacgagcatc acaaaaatcg acgctcaagt cagaggtggc gaaacccgac    8100
aggactataa agataccagg cgtttccccc tggaagctcc ctcgtgcgct ctcctgttcc    8160
gaccctgccg cttaccggat acctgtccgc ctttctccct tcgggaagcg tggcgctttc    8220
tcatagctca cgctgtaggt atctcagttc ggtgtaggtc gttcgctcca agctgggctg    8280
tgtgcacgaa ccccccgttc agcccgaccg ctgcgcctta tccggtaact atcgtcttga    8340
gtccaacccg gtaagacacg acttatcgcc actggcagca gccactggta acaggattag    8400
cagagcgagg tatgtaggcg gtgctacaga gttcttgaag tggtggccta actacggcta    8460
cactagaagg acagtatttg gtatctgcgc tctgctgaag ccagttacct tcggaaaaag    8520
agttggtagc tcttgatccg gcaaacaaac caccgctggt agcggtggtt ttttgtttg    8580 caagcagcag attacgcgca gaaaaaaagg atctcaagaa gatcctttga tcttttctac    8640
ggggtctgac gctcagtgga acgaaaactc acgttaaggg attttggtca tgagattatc    8700
```

```
aaaaaggatc ttcacctaga tcctttttaaa ttaaaaatga agtttttaaat caatctaaag    8760 tatatatgag taaacttggt ctgacagtta ccaatgctta atcagtgagg cacctatctc    8820
agcgatctgt ctatttcgtt catccatagt tgcctgactc cccgtcgtgt agataactac    8880
gatacgggag ggcttaccat ctggccccag tgctgcaatg ataccgcgag acccacgctc    8940
accggctcca gatttatcag caataaacca gccagccgga agggccgagc gcagaagtgg    9000
tcctgcaact ttatccgcct ccatccagtc tattaattgt tgccgggaag ctagagtaag    9060
tagttcgcca gttaatagtt tgcgcaacgt tgttgccatt gctacaggca tcgtggtgtc    9120
acgctcgtcg tttggtatgg cttcattcag ctccggttcc caacgatcaa ggcgagttac    9180
atgatccccc atgttgtgca aaaaagcggt tagctccttc ggtcctccga tcgttgtcag    9240
aagtaagttg gccgcagtgt tatcactcat ggttatggca gcactgcata attctcttac    9300
tgtcatgcca tccgtaagat gcttttctgt gactggtgag tactcaacca agtcattctg    9360
agaatagtgt atgcggcgac cgagttgctc ttgcccggcg tcaatacggg ataataccgc    9420
gccacatagc agaactttaa aagtgctcat cattggaaaa cgttcttcgg ggcgaaaact    9480
ctcaaggatc ttaccgctgt tgagatccag ttcgatgtaa cccactcgtg cacccaactg    9540
atcttcagca tcttttactt tcaccagcgt ttctgggtga gcaaaaacag gaaggcaaaa    9600
tgccgcaaaa aagggaataa gggcgacacg gaaatgttga atactcatac tcttcctttt    9660
tcaatattat tgaagcattt atcagggtta ttgtctcatg agcggataca tatttgaatg    9720
tatttagaaa aataaacaaa tagggggttcc gcgcacattt ccccgaaaag tgccacctga    9780
cgtctaagaa accattatta tcatgacatt aacctataaa aataggcgta tcacgaggcc    9840
ctttcgtctc gcgcgtttcg gtgatgacgg tgaaaacctc tgacacatgc agctcccgga    9900
gacggtcaca gcttgtctgt aagcggatgc cgggagcaga caagcccgtc agggcgcgtc    9960
agcgggtgtt ggcgggtgtc ggggctggct taactatgcg gcatcagagc agattgtact   10020
gagagtgcac catatgcggt gtgaaatacc gcacagatgc gtaaggagaa aataccgcat   10080
caggcgccat tcgccattca ggctgcgcaa ctgttgggaa gggcgatcgg tgcgggcctc   10140
ttcgctatta cgccagctgg cgaaaggggg atgtgctgca aggcgattaa gttgggtaac   10200
gccagggttt tcccagtcac gacgttgtaa aacgacggcc agtgccaagc tg          10252
```

<210> SEQ ID NO 42
<211> LENGTH: 10270
<212> TYPE: DNA
<213> ORGANISM: Artificial Sequence
<220> FEATURE:
<223> OTHER INFORMATION: Synthetic

<400> SEQUENCE: 42

```
acgcgtgtag tcttatgcaa tactcttgta gtcttgcaac atggtaacga tgagttagca      60
acatgcctta caaggagaga aaaagcaccg tgcatgccga ttggtggaag taaggtggta     120
cgatcgtgcc ttattaggaa ggcaacagac gggtctgaca tggattggac gaaccactga     180
attgccgcat tgcagagata ttgtatttaa gtgcctagct cgatacaata aacgggtctc     240
tctggttaga ccagatctga gcctgggagc tctctggcta actagggaac ccactgctta     300
agcctcaata aagcttgcct tgagtgcttc aagtagtgtg tgcccgtctg ttgtgtgact     360
ctggtaacta gagatccctc agacccttttt agtcagtgtg gaaaatctct agcagtggcg     420
cccgaacagg gacctgaaag cgaaagggaa accagagctc tctcgacgca ggactcggct     480
```

```
tgctgaagcg cgcacggcaa gaggcgaggg gcggcgactg gtgagtacgc caaaaatttt    540
gactagcgga ggctagaagg agagagatgg gtgcgagagc gtcagtatta agcgggggag    600
aattagatcg cgatgggaaa aaattcggtt aaggccaggg ggaaagaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata aagtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcg tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca acagctcctg gggatttggg   1320
gttgctctgg aaaactcatt tgcaccactg ctgtgccttg gaatgctagt tggagtaata   1380
aatctctgga acagatttgg aatcacacga cctggatgga gtgggacaga gaaattaaca   1440
attacacaag cttaatacac tccttaattg aagaatcgca aaaccagcaa gaaaagaatg   1500
aacaagaatt attggaatta gataaatggg caagtttgtg gaattggttt aacataacaa   1560
attggctgtg gtatataaaa ttattcataa tgatagtagg aggcttggta ggtttaagaa   1620
tagttttgc tgtactttct atagtgaata gagttaggca gggatattca ccattatcgt   1680
ttcagaccca cctcccaacc ccgaggggac ccgacaggcc cgaaggaata gaagaagaag   1740
gtggagagag agacagagac agatccattc gattagtgaa cggatctcga cggtatcggt   1800
taactttta aagaaaaggg gggattgggg ggtacagtgc aggggaaaga atagtagaca   1860
taatagcaac agacatacaa actaaagaat tacaaaaaca aattacaaaa ttcaaaattt   1920
tatcgatgct agcggaggaa aaactgtttc atacagaagg cgtggaggaa aaactgtttc   1980
atacagaagg cgtggaggaa aaactgtttc atacagaagg cgtggaggaa aaactgtttc   2040
atacagaagg cgtggaggaa aaactgtttc atacagaagg cgtggaggaa aaactgtttc   2100
atacagaagg cgtagatcta gactctagag ggtatataat ggaagctcga cttccagctt   2160
ggcattccgg tactgttggt aaaaagcttg gcaatccggt actgttggta aaggatccgc   2220
caccatgcct gccatgaaga ttgagtgccg catcacggga accctgaacg gagtggagtt   2280
tgagctggtc ggaggtggag aagggactcc tgagcaggga cgtatgacca acaagatgaa   2340
gtctaccaag ggcgccttga ccttctcccc ctaccttctc tctcatgtca tgggatacgg   2400
gttctaccac tttggtacct atcccagtgg gtatgagaat cccttcctgc atgccatcaa   2460
caacgggggg tacaccaaca ccaggattga gaagtatgag gatggaggag ttcttcatgt   2520
tagctttagc tacagatatg aagcaggcag ggtgattggg gatttcaagg ttgtcgggac   2580
aggattccct gaggacagtg tgatcttcac cgacaagatc atccggtcca atgctaccgt   2640
ggagcacttg cacccaatgg gagacaacgt tcttgtgggc tccttcgcga gaacctttc   2700
cctgagggat ggaggctact actcatttgt ggttgacagc cacatgcact tcaagagtgc   2760
catccaccca tccatcctcc agaacggggg gcccatgttt gccttcagga gagttggagga   2820
acttcactcc aacactgaac ttggcattgt agagtatcaa catgccttca gactcccat    2880
```

```
agcatttgct ggaagcggag ctactaactt cagcctgctg aagcaggctg gagacgtgga   2940
ggagaaccct ggacctatgg tcttcacact cgaagatttc gttggggact ggcgacagac   3000
agccggctac aacctggacc aagtccttga acagggaggt gtgtccagtt tgtttcagaa   3060
tctcggggtg tccgtaactc cgatccaaag gattgtcctg agcggtgaaa atgggctgaa   3120
gatcgacatc catgtcatca tcccgtatga aggtctgagc ggcgaccaaa tgggccagat   3180
cgaaaaaatt tttaaggtgg tgtaccctgt ggatgatcat cactttaagg tgatcctgca   3240
ctatggcaca ctggtaatcg acggggttac gccgaacatg atcgactatt cggacggcc   3300
gtatgaaggc atcgccgtgt tcgacggcaa aaagatcact gtaacaggga ccctgtggaa   3360
cggcaacaaa attatcgacg agcgcctgat caaccccgac ggctccctgc tgttccgagt   3420
aaccatcaac ggagtgaccg gctggcggct gtgcgaacgc attctggcgt aagcggccgc   3480
gaaggatctg cgatcgctcc ggtgcccgtc agtgggcaga gcgcacatcg cccacagtcc   3540
ccgagaagtt gggggagggt gtcggcaatt gaacgggtgc ctagagaagg tggcgcgggg   3600
taaactggga aagtgatgtc gtgtactggc tccgcctttt tcccgagggt ggggagaac   3660
cgtatataag tgcagtagtc gccgtgaacg ttcttttttcg caacgggttt gccgccagaa   3720
cacagctgaa gcttcgaggg gctcgcatct ctccttcacg cgcccgccgc cctacctgag   3780
gccgccatcc acgccggttg agtgcgcgttc tgccgcctcc cgcctgtggt gcctcctgaa   3840
ctgcgtccgc cgtctaggta agtttaaagc tcaggtcgag accgggcctt tgtccggcgc   3900
tcccttggag cctacctaga ctcagccggc tctccacgct ttgcctgacc ctgcttgctc   3960
aactctacgt cttttgtttcg ttttctgttc tgcgccgtta cagatccaag ctgtgaccgg   4020
cgcctactag tgccaccatg gactttcaag tgcagatctt cagctttctg ctgatctctg   4080
ctagtgtcat catgtctcaa gcacagctcg tggagtctgg aggtgctctg gtgcaacctg   4140
gtaggagcct cagactctcc tgtgctgctt ccggattcac attcagaaac tacgcaatgc   4200
actgggtcag gcaagctcca gctacaggtc tgcagtggct ggctgtgatt accagcgatg   4260
gcaggaacaa gttctatgcc gactctgtga aaggcaggtt cactatctct cgcgaagaca   4320
gcaagaatac cctgtatctg caaatggatt ctctcagagg tgaagataca gctgtgtact   4380
attgcgtcac acagagggat aactctaggg actactttcc tcattacttt catgacatgg   4440
acgtttgggg tcagggcacc accgttgctg tgtcctctgg aggtggaggc agtggaggtg   4500
gtggatctgg aggaggaggg tctgatgttg ttctcactca atctcctctg tctctcccag   4560
ttactctggg tcagccagcc tccattagct gtaggtcttc ccagtctctc gtgtactccg   4620
atggcgacac atacctcaac tggtttcaac agaggccagg acagtctccc agacgcctga   4680
tctaccaggt ttccaacaga gattctgcgc tgcctgaccg cttctctgga gcggatctg   4740
gcaccgactt caccctcaag atcagcagag ttgaagccga agacgttggt gtttactact   4800
gtatgcaggg atctcattgg ccaccaacct tcggtcaggg aactaaggtg gaaatcaaga   4860
gggaaatcga gcagaagctg atttccgaag aggatctcaa tggagtgact gtcagcagcg   4920
ctctgtctaa ctccatcatg tacttctcac acttcgtgcc agtgttcctc cctgctaaac   4980
ccaccacaac tccagcacct agacctccca ctccagcacc aactattgca tcccagcctc   5040
tctcccctcag accagaagca tgcagacctg cagcaggtgg agctgtgcac acaagaggtc   5100
tggacccttt ctgggtcctc gtggtggtgg gtggagtcct ggcatgttac agcctcctgg   5160
tcaccgtggc attcatcatc ttctgggtga gatctaagag gagcagactg ctgcactctg   5220
```

```
attacatgaa catgacaccc agaagacctg gtcccaccag aaagcactac caaccctacg    5280
caccaccaag agactttgct gcatacagaa gtctcgagag ggtcaagttc tcaaggagtg    5340
cagatgctcc agcctatcaa cagggtcaga accaactgta caacgagctg aatctcggaa    5400
gaagagagga gtacgatgtg ctggataaga gaagaggcag ggaccagag atgggtggga     5460
aacccagaag aaagaatcct caagagggac tgtacaatga gctgcagaag gataagatgg    5520
ctgaggcata ctcagagatc ggtatgaagg gagagaggag aagaggcaaa ggtcatgatg    5580
gtctgtacca aggtctgtcc acagcaacaa aggatacata tgatgctctg cacatgcagg    5640
cactcccacc acggggttcc ggagtgaaac agactttgaa cttttgacctt ctcaagttgg   5700
ctggagacgt cgagtccaac cctggtccca tgaccgagta caagcccacg gtgcgcctcg    5760
ccacccgcga cgacgtcccc agggccgtac gcaccctcgc cgccgcgttc gccgactacc    5820
cgccacgcgc ccacaccgtc gatccggacc gccacatcga gcgggtcacc gagctgcaag    5880
aactcttcct cacgcgcgtc gggctcgaca tcggcaaggt gtgggtcgcg gacgacggcg    5940
ccgcggtggc ggtctggacc acgccggaga gcgtcgaagc gggggcggtg ttcgccgaga    6000
tcggcccgcg catggccgag ttgagcggtt cccggctggc cgcgcagcaa cagatggaag    6060
gcctcctggc gccgcaccgg cccaaggagc ccgcgtggtt cctggccacc gtcggcgtct    6120
cgcccgacca ccagggcaag ggtctgggca gcgccgtcgt gctccccgga gtggaggcgg    6180
ccgagcgcgc cggggtgccc gccttcctgg agacctccgc gccccgcaac ctccccttct    6240
acgagcggct cggcttcacc gtcaccgccg acgtcgaggt gcccgaagga ccgcgcacct    6300
ggtgcatgac ccgcaagccc ggtgcctgat aattaagtc gacaatcaac ctctggatta    6360
caaaatttgt gaaagattga ctggtattct taactatgtt gctccttta cgctatgtgg    6420
atacgctgct ttaatgcctt tgtatcatgc tattgcttcc cgtatggctt tcattttctc   6480
ctccttgtat aaatcctggt tgctgtctct ttatgaggag ttgtggcccg ttgtcaggca    6540
acgtggcgtg gtgtgcactg tgtttgctga cgcaaccccc actggttggg gcattgccac    6600
cacctgtcag ctcctttccg ggactttcgc tttccccctc cctattgcca cggcggaact    6660
catcgccgcc tgccttgccc gctgctggac agggctcgg ctgttgggca ctgacaattc     6720
cgtggtgttg tcggggaaat catcgtcctt ccttggctg ctcgcctgtg ttgccacctg     6780
gattctgcgc gggacgtcct tctgctacgt cccttcggcc ctcaatccag cggaccttcc    6840
ttcccgcggc ctgctgccgg ctctgcggcc tcttccgcgt cttcgccttc gccctcagac    6900
gagtcggatc tccctttggg ccgcctcccc gcctggtacc tttaagacca atgacttaca    6960
aggcagctgt agatcttagc cactttttaa agaaaaggg gggactggaa gggctaattc     7020
actcccaacg aagataagat ctgctttttg cttgtactgg gtctctctgg ttagaccaga    7080
tctgagcctg ggagctctct ggctaactag ggaacccact gcttaagcct caataaagct    7140
tgccttgagt gcttcaagta gtgtgtgccc gtctgttgtg tgactctggt aactagagat    7200
ccctcagacc cttttagtca gtgtggaaaa tctctagcag tagtagttca tgtcatctta    7260
ttattcagta tttataactt gcaaagaaat gaatatcaga gagtgagagg aacttgttta    7320
ttgcagctta taatggttac aaataaagca atagcatcac aaatttcaca aataaagcat    7380
ttttttcact gcattctagt tgtggtttgt ccaaactcat caatgtatct tatcatgtct    7440
ggctctagct atcccgcccc taactccgcc catcccgccc ctaactccgc ccagttccgc    7500
ccattctccg ccccatggct gactaatttt ttttatttat gcagaggccg aggccgcctc    7560
ggcctctgag ctattccaga agtagtgagg aggcttttt ggaggcctag acttttgcag    7620
```

```
agacggccca aattcgtaat catggtcata gctgtttcct gtgtgaaatt gttatccgct    7680
cacaattcca cacaacatac gagccggaag cataaagtgt aaagcctggg gtgcctaatg    7740
agtgagctaa ctcacattaa ttgcgttgcg ctcactgccc gctttccagt cgggaaacct    7800
gtcgtgccag ctgcattaat gaatcggcca acgcgcgggg agaggcggtt tgcgtattgg    7860
gcgctcttcc gcttcctcgc tcactgactc gctgcgctcg gtcgttcggc tgcggcgagc    7920
ggtatcagct cactcaaagg cggtaatacg gttatccaca gaatcagggg ataacgcagg    7980
aaagaacatg tgagcaaaag gccagcaaaa ggccaggaac cgtaaaaagg ccgcgttgct    8040
ggcgtttttc cataggctcc gcccccctga cgagcatcac aaaaatcgac gctcaagtca    8100
gaggtggcga acccgacag gactataaag ataccaggcg tttccccctg gaagctccct    8160
cgtgcgctct cctgttccga ccctgccgct taccggatac ctgtccgcct ttctcccttc    8220
gggaagcgtg gcgctttctc atagctcacg ctgtaggtat ctcagttcgg tgtaggtcgt    8280
tcgctccaag ctgggctgtg tgcacgaacc ccccgttcag cccgaccgct gcgccttatc    8340
cggtaactat cgtcttgagt ccaacccggt aagacacgac ttatcgccac tggcagcagc    8400
cactggtaac aggattagca gagcgaggta tgtaggcggt gctacagagt tcttgaagtg    8460
gtggcctaac tacggctaca ctagaaggac agtatttggt atctgcgctc tgctgaagcc    8520
agttaccttc ggaaaaagag ttggtagctc ttgatccggc aaacaaacca ccgctggtag    8580
cggtggtttt tttgtttgca agcagcagat tacgcgcaga aaaaaggat ctcaagaaga    8640 tcctttgatc ttttctacgg ggtctgacgc tcagtggaac gaaaactcac gttaagggat    8700
tttggtcatg agattatcaa aaaggatctt cacctagatc cttttaaatt aaaaatgaag    8760
ttttaaatca atctaaagta tatatgagta aacttggtct gacagttacc aatgcttaat    8820
cagtgaggca cctatctcag cgatctgtct atttcgttca tccatagttg cctgactccc    8880
cgtcgtgtag ataactacga tacgggaggg cttaccatct ggccccagtg ctgcaatgat    8940
accgcgagac ccacgctcac cggctccaga tttatcagca ataaaccagc cagccggaag    9000
ggccgagcgc agaagtggtc ctgcaacttt atccgcctcc atccagtcta ttaattgttg    9060
ccgggaagct agagtaagta gttcgccagt taatagtttg cgcaacgttg ttgccattgc    9120
tacaggcatc gtggtgtcac gctcgtcgtt tggtatggct tcattcagct ccggttccca    9180
acgatcaagg cgagttacat gatccccat gttgtgcaaa aaagcggtta gctccttcgg    9240
tcctccgatc gttgtcagaa gtaagttggc cgcagtgtta tcactcatgg ttatggcagc    9300
actgcataat tctcttactg tcatgccatc cgtaagatgc ttttctgtga ctggtgagta    9360
ctcaaccaag tcattctgag aatagtgtat gcggcgaccg agttgctctt gcccggcgtc    9420
aatacgggat aataccgcgc cacatagcag aactttaaaa gtgctcatca ttggaaaacg    9480
ttcttcgggg cgaaaactct caaggatctt accgctgttg agatccagtt cgatgtaacc    9540
cactcgtgca cccaactgat cttcagcatc ttttactttc accagcgttt ctgggtgagc    9600
aaaaacagga aggcaaaatg ccgcaaaaaa gggaataagg gcgacacgga atgttgaat    9660 actcatactc ttcctttttc aatattattg aagcatttat cagggttatt gtctcatgag    9720
cggatacata tttgaatgta tttagaaaaa taaacaaata ggggttccgc gcacatttcc    9780
ccgaaaagtg ccacctgacg tctaagaaac cattattatc atgacattaa cctataaaaa    9840
taggcgtatc acgaggccct ttcgtctcgc gcgtttcggt gatgacggtg aaaacctctg    9900
acacatgcag ctcccggaga cggtcacagc ttgtctgtaa gcggatgccg ggagcagaca    9960
```

| | | | | |
|---|---|---|---|---|
| agcccgtcag | ggcgcgtcag | cgggtgttgg | cgggtgtcgg | ggctggctta actatgcggc 10020 |
| atcagagcag | attgtactga | gagtgcacca | tatgcggtgt | gaaataccgc acagatgcgt 10080 |
| aaggagaaaa | taccgcatca | ggcgccattc | gccattcagg | ctgcgcaact gttgggaagg 10140 |
| gcgatcggtg | cgggcctctt | cgctattacg | ccagctggcg | aaaggggat gtgctgcaag 10200 |
| gcgattaagt | tgggtaacgc | cagggttttc | ccagtcacga | cgttgtaaaa cgacggccag 10260 |
| tgccaagctg | | | | 10270 |

<210> SEQ ID NO 43
<211> LENGTH: 10231
<212> TYPE: DNA
<213> ORGANISM: Artificial Sequence
<220> FEATURE:
<223> OTHER INFORMATION: Synthetic

<400> SEQUENCE: 43

| | | | | |
|---|---|---|---|---|
| acgcgtgtag | tcttatgcaa | tactcttgta | gtcttgcaac | atggtaacga tgagttagca 60 |
| acatgcctta | caaggagaga | aaaagcaccg | tgcatgccga | ttggtggaag taaggtggta 120 |
| cgatcgtgcc | ttattaggaa | ggcaacagac | gggtctgaca | tggattggac gaaccactga 180 |
| attgccgcat | tgcagagata | ttgtatttaa | gtgcctagct | cgatacaata aacgggtctc 240 |
| tctggttaga | ccagatctga | gcctgggagc | tctctggcta | actagggaac ccactgctta 300 |
| agcctcaata | aagcttgcct | tgagtgcttc | aagtagtgtg | tgcccgtctg ttgtgtgact 360 |
| ctggtaacta | gagatccctc | agaccctttt | agtcagtgtg | gaaaatctct agcagtggcg 420 |
| cccgaacagg | gacctgaaag | cgaaagggaa | accagagctc | tctcgacgca ggactcggct 480 |
| tgctgaagcg | cgcacggcaa | gaggcgaggg | gcggcgactg | gtgagtacgc caaaaatttt 540 |
| gactagcgga | ggctagaagg | agagagatgg | gtgcgagagc | gtcagtatta agcggggag 600 |
| aattagatcg | cgatgggaaa | aaattcggtt | aaggccaggg | ggaaagaaaa aatataaatt 660 |
| aaaacatata | gtatgggcaa | gcaggagct | agaacgattc | gcagttaatc ctggcctgtt 720 |
| agaaacatca | gaaggctgta | gacaaatact | gggacagcta | caaccatccc ttcagacagg 780 |
| atcagaagaa | cttagatcat | tatataatac | agtagcaacc | ctctattgtg tgcatcaaag 840 |
| gatagagata | aaagacacca | aggaagcttt | agacaagata | gaggaagagc aaaacaaaag 900 |
| taagaccacc | gcacagcaag | cggccactga | tcttcagacc | tggaggagga gatatgaggg 960 |
| acaattggag | aagtgaatta | tataaatata | aagtagtaaa | aattgaacca ttaggagtag 1020 |
| cacccaccaa | ggcaaagaga | agagtggtgc | agagagaaaa | aagagcagtg ggaataggag 1080 |
| ctttgttcct | tgggttcttg | ggagcagcag | gaagcactat | gggcgcagcg tcaatgacgc 1140 |
| tgacggtaca | ggccagacaa | ttattgtctg | gtatagtgca | gcagcagaac aatttgctga 1200 |
| gggctattga | ggcgcaacag | catctgttgc | aactcacagt | ctggggcatc aagcagctcc 1260 |
| aggcaagaat | cctggctgtg | gaaagatacc | taaaggatca | acagctcctg ggatttgg 1320 |
| gttgctctgg | aaaactcatt | tgcaccactg | ctgtgccttg | gaatgctagt tggagtaata 1380 |
| aatctctgga | acagatttgg | aatcacacga | cctggatgga | gtgggacaga gaattaaca 1440 |
| attacacaag | cttaatacac | tccttaattg | aagaatcgca | aaaccagcaa gaaaagaatg 1500 |
| aacaagaatt | attggaatta | gataaatggg | caagtttgtg | gaattggttt aacataacaa 1560 |
| attggctgtg | gtatataaaa | ttattcataa | tgatagtagg | aggcttggta ggtttaagaa 1620 |
| tagttttgc | tgtactttct | atagtgaata | gagttaggca | gggatattca ccattatcgt 1680 |
| ttcagaccca | cctcccaacc | ccgaggggac | ccgacaggcc | cgaaggaata agaagaag 1740 |

```
gtggagagag agacagagac agatccattc gattagtgaa cggatctcga cggtatcggt    1800
taacttttaa aagaaaaggg gggattgggg ggtacagtgc aggggaaaga atagtagaca    1860
taatagcaac agacatacaa actaaagaat tacaaaaaca aattacaaaa ttcaaaattt    1920
tatcgatgct agcggaggaa aaactgtttc atacagaagg cgtggaggaa aaactgtttc    1980
atacagaagg cgtggaggaa aaactgtttc atacagaagg cgtggaggaa aaactgtttc    2040
atacagaagg cgtggaggaa aaactgtttc atacagaagg cgtggaggaa aaactgtttc    2100
atacagaagg cgtagatcta gactctagag ggtatataat ggaagctcga cttccagctt    2160
ggcattccgg tactgttggt aaaaagcttg gcaatccggt actgttggta aaggatccgc    2220
caccatgcct gccatgaaga ttgagtgccg catcacggga accctgaacg gagtggagtt    2280
tgagctggtc ggaggtggag aagggactcc tgagcaggga cgtatgacca acaagatgaa    2340
gtctaccaag ggcgccttga ccttctcccc ctaccttctc tctcatgtca tgggatacgg    2400
gttctaccac tttggtacct atcccagtgg gtatgagaat cccttcctgc atgccatcaa    2460 caacggggg tacaccaaca ccaggattga aagtatgag gatggaggag ttcttcatgt    2520
tagctttagc tacagatatg aagcaggcag ggtgattggg gatttcaagg ttgtcgggac    2580
aggattccct gaggacagtg tgatcttcac cgacaagatc atccggtcca atgctaccgt    2640
ggagcacttg cacccaatgg gagacaacgt tcttgtgggc tccttcgcga gaaccttttc    2700
cctgagggat ggaggctact actcatttgt ggttgacagc cacatgcact tcaagagtgc    2760
catccaccca tccatcctcc agaacggggg gcccatgttt gccttcagga gagttgagga    2820
acttcactcc aacactgaac ttggcattgt agagtatcaa catgccttca agactcccat    2880
agcatttgct ggaagcggag ctactaactt cagcctgctg aagcaggctg agacgtgga    2940 ggagaaccct ggacctatgg tcttcacact cgaagatttc gttggggact ggcgacagac    3000
agccggctac aacctggacc aagtccttga acagggaggt gtgtccagtt tgtttcagaa    3060
tctcggggtg tccgtaactc cgatccaaag gattgtcctg agcggtgaaa atgggctgaa    3120
gatcgacatc catgtcatca tcccgtatga aggtctgagc ggcgaccaaa tgggccagat    3180
cgaaaaaatt tttaaggtgg tgtaccctgt ggatgatcat cactttaagg tgatcctgca    3240
ctatggcaca ctggtaatcg acggggttac gccgaacatg atcgactatt tcggacggcc    3300
gtatgaaggc atcgccgtgt tcgacggcaa aaagatcact gtaacaggga ccctgtggaa    3360
cggcaacaaa attatcgacg agcgcctgat caaccccgac ggctccctgc tgttccgagt    3420
aaccatcaac ggagtgaccg gctggcggct gtgcgaacgc attctggcgt aagcggccgc    3480
gaaggatctg cgatcgctcc ggtgcccgtc agtgggcaga gcgcacatcg cccacagtcc    3540
ccgagaagtt ggggggaggg gtcggcaatt gaacgggtgc ctagaaaagg tggcgcgggg    3600
taaactggga aagtgatgtc gtgtactggc tccgcctttt tcccgagggt gggggagaac    3660
cgtatataag tgcagtagtc gccgtgaacg ttcttttttcg caacgggttt gccgccagaa    3720
cacagctgaa gcttcgaggg gctcgcatct ctccttcacg cgcccgccgc cctacctgag    3780
gccgccatcc acgccggttg agtcgcgttc tgccgcctcc cgcctgtggt gcctcctgaa    3840
ctgcgtccgc cgtctaggta agtttaaagc tcaggtcgag accgggcctt tgtccggcgc    3900
tcccttggag cctacctaga ctcagccggc tctccacgct ttgcctgacc ctgcttgctc    3960
aactctacgt ctttgtttcg ttttctgttc tgcgccgtta cagatccaag ctgtgaccgg    4020
cgcctactag tgccaccatg gactttcaag tgcagatctt cagcttttg ctgatctctg    4080
```

```
ctagtgtcat catgtctcaa gtgcaactcc aacaaagcgg agctgaagtg aagaaacctg    4140
gttcctccgt gaaagtctct tgtaaggctt ctggaggtac attcagctct tacaccatca    4200
gctgggtgag gcaagctcct ggccaaggtc tggagtggat gggaggcatc actcctatcc    4260
tgggaatcgc aaactacgca cagaagtttc agggtagggt gactatcacc actgatgaaa    4320
gcacctctac cgcttacatg gagctgtcca gcctgaggtc cgaggacact gccgtgtact    4380
attgcgcaag agatactgtg atgggaggca tggacgtgtg gggacaaggt actactgtta    4440
ccgtttccag cggaggtgga ggcagtggag gtggtggatc tggaggagga gggtcttctt    4500
atgaactgac tcaacctcct tctgtttctg ttgcacctgg caagaccgct aggattacat    4560
gcggaggcaa caacatcggt agcaaatccg tgcattggta tcaacagaaa cctggccagg    4620
cacctgttct ggtcgtgtac gacgattccg atagaccttc cggtattccc gaacgcttct    4680
ccggatctaa ctctggcaac acagctacac tcaccattag cagagtcgag gctggcgatg    4740
aggctgatta ctattgtcag gtctgggatt cttccagcga ctacgtgttt ggtacaggaa    4800
caaaggtgac tgtcctcggt caggaaatcg agcagaagct gatttccgaa gaggatctca    4860
atggagtgac tgtcagcagc gctctgtcta actccatcat gtacttctca cacttcgtgc    4920
cagtgttcct ccctgctaaa cccaccacaa ctccagcacc tagacctccc actccagcac    4980
caactattgc atcccagcct ctctccctca gaccagaagc atgcagacct gcagcaggtg    5040
gagctgtgca cacaagaggt ctggacccaa tctgggtcct cgtggtggtg ggtggagtcc    5100
tggcatgtta cagcctcctg gtcaccgtgg cattcatcat cttctgggtg agatctaaga    5160
ggagcagact gctgcactct gattacatga acatgacacc cagaagacct ggtcccacca    5220
gaaagcacta ccaaccctac gcaccaccaa gagactttgc tgcatacaga agtctcgaga    5280
gggtcaagtt ctcaaggagt gcagatgctc cagcctatca acagggtcag aaccaactgt    5340
acaacgagct gaatctcgga agaagagagg agtacgatgt gctggataag agaagaggca    5400
gggacccaga gatgggtggg aaacccagaa gaaagaatcc tcaagaggga ctgtacaatg    5460
agctgcagaa ggataagatg gctgaggcat actcagagat cggtatgaag ggagagagga    5520
gaagaggcaa aggtcatgat ggtctgtacc aaggtctgtc cacagcaaca aaggatacat    5580
atgatgctct gcacatgcag gcactcccac cacggggttc cggagtgaaa cagactttga    5640
actttgacct tctcaagttg gctggagacg tcgagtccaa ccctggtccc atgaccgagt    5700
acaagcccac ggtgcgcctc gccacccgcg acgacgtccc cagggccgta cgcacccctcg    5760
ccgccgcgtt cgccgactac cccgccacgc gccacaccgt cgatccggac cgccacatcg    5820
agcgggtcac cgagctgcaa gaactcttcc tcacgcgcgt cgggctcgac atcggcaagg    5880
tgtgggtcgc ggacgacggc gccgcggtgg cggtctggac cacgccggag agcgtcgaag    5940
cgggggcggt gttcgccgag atcggcccgc gcatggccga gttgagcggt tcccggctgg    6000
ccgcgcagca acagatggaa ggcctcctgg cgccgcaccg gcccaaggag cccgcgtggt    6060
tcctggccac cgtcggcgtc tcgcccgacc accaggcaa gggtctgggc agcgccgtcg    6120
tgctccccgg agtggaggcg gccgagcgcg ccggggtgcc cgccttcctg gagacctccg    6180
cgccccgcaa cctcccttc tacgagcggc tcggcttcac cgtcaccgcc gacgtcgagg    6240
tgcccgaagg accgcgcacc tggtgcatga cccgcaagcc cggtgcctga ttaattaagt    6300
cgacaatcaa cctctggatt acaaaatttg tgaaagattg actggtattc ttaactatgt    6360
tgctcctttt acgctatgtg gatacgctgc tttaatgcct ttgtatcatg ctattgcttc    6420
ccgtatggct ttcattttct cctccttgta taaatcctgg ttgctgtctc tttatgagga    6480
```

```
gttgtggccc gttgtcaggc aacgtggcgt ggtgtgcact gtgtttgctg acgcaacccc    6540
cactggttgg ggcattgcca ccacctgtca gctcctttcc gggactttcg ctttcccccct   6600 ccctattgcc acggcggaac tcatcgccgc ctgccttgcc cgctgctgga cagggcctcg    6660
gctgttgggc actgacaatt ccgtggtgtt gtcgggaaaa tcatcgtcct ttccttggct    6720
gctcgcctgt gttgccacct ggattctgcg cgggacgtcc ttctgctacg tcccttcggc    6780
cctcaatcca gcggaccttc cttcccgcgg cctgctgccg gtctgcggc ctcttccgcg     6840 tcttcgcctt cgccctcaga cgagtcggat ctccctttgg gccgcctccc cgcctggtac    6900 cttaagacc aatgacttac aaggcagctg tagatcttag ccactttta aagaaaagg      6960 ggggactgga agggctaatt cactcccaac gaagataaga tctgcttttt gcttgtactg    7020
ggtctctctg gttagaccag atctgagcct gggagctctc tggctaacta gggaacccac    7080
tgcttaagcc tcaataaagc ttgccttgag tgcttcaagt agtgtgtgcc cgtctgttgt    7140
gtgactctgg taactagaga tccctcagac ccttttagtc agtgtggaaa atctctagca    7200
gtagtagttc atgtcatctt attattcagt atttataact tgcaaagaaa tgaatatcag    7260
agagtgagag gaacttgttt attgcagctt ataatggtta caaataaagc aatagcatca    7320
caaatttcac aaataaagca ttttttttcac tgcattctag ttgtggttg tccaaactca    7380 tcaatgtatc ttatcatgtc tggctctagc tatcccgccc ctaactccgc ccatcccgcc    7440
cctaactccg cccagttccg cccattctcc gccccatggc tgactaattt tttttattta    7500
tgcagaggcc gaggccgcct cggcctctga gctattccag aagtagtgag gaggcttttt    7560
tggaggccta gacttttgca gagacggccc aaattcgtaa tcatggtcat agctgtttcc    7620
tgtgtgaaat tgttatccgc tcacaattcc acacaacata cgagccggaa gcataaagtg    7680
taaagcctgg ggtgcctaat gagtgagcta actcacatta attgcgttgc gctcactgcc    7740
cgctttccag tcgggaaacc tgtcgtgcca gctgcattaa tgaatcggcc aacgcgcggg    7800
gagaggcggt ttgcgtattg ggcgctcttc cgcttcctcg ctcactgact cgctgcgctc    7860
ggtcgttcgg ctgcggcgag cggtatcagc tcactcaaag gcggtaatac ggttatccac    7920
agaatcaggg gataacgcag gaaagaacat gtgagcaaaa ggccagcaaa aggccaggaa    7980
ccgtaaaaag gccgcgttgc tggcgttttt ccataggctc cgcccccctg acgagcatca    8040
caaaaatcga cgctcaagtc agaggtggcg aaacccgaca ggactataaa gataccaggc    8100
gtttccccct ggaagctccc tcgtgcgctc tcctgttccg accctgccgc ttaccggata    8160
cctgtccgcc tttctccctt cgggaagcgt ggcgctttct catagctcac gctgtaggta    8220
tctcagttcg gtgtaggtcg ttcgctccaa gctgggctgt gtgcacgaac ccccgttca    8280 gcccgaccgc tgcgccttat ccggtaacta tcgtcttgag tccaacccgg taagacacga    8340
cttatcgcca ctggcagcag ccactggtaa caggattagc agagcgaggt atgtaggcgg    8400
tgctacagag ttcttgaagt ggtggcctaa ctacggctac actagaagga cagtatttgg    8460
tatctgcgct ctgctgaagc cagttacctt cggaaaaaga gttggtagct cttgatccgg    8520
caaacaaacc accgctggta gcggtggttt ttttgtttgc aagcagcaga ttacgcgcag    8580
aaaaaaagga tctcaagaag atcctttgat cttttctacg gggtctgacg ctcagtggaa    8640
cgaaaactca cgttaaggga ttttggtcat gagattatca aaaaggatct tcacctagat    8700
ccttttaaat taaaaatgaa gttttaaatc aatctaaagt atatatgagt aaacttggtc    8760
tgacagttac caatgcttaa tcagtgaggc acctatctca gcgatctgtc tatttcgttc    8820
```

| | |
|---|---|
| atccatagtt gcctgactcc ccgtcgtgta gataactacg atacgggagg gcttaccatc | 8880 |
| tggccccagt gctgcaatga taccgcgaga cccacgctca ccggctccag atttatcagc | 8940 |
| aataaaccag ccagccggaa gggccgagcg cagaagtggt cctgcaactt tatccgcctc | 9000 |
| catccagtct attaattgtt gccgggaagc tagagtaagt agttcgccag ttaatagttt | 9060 |
| gcgcaacgtt gttgccattg ctacaggcat cgtggtgtca cgctcgtcgt ttggtatggc | 9120 |
| ttcattcagc tccggttccc aacgatcaag gcgagttaca tgatccccca tgttgtgcaa | 9180 |
| aaaagcggtt agctccttcg gtcctccgat cgttgtcaga agtaagttgg ccgcagtgtt | 9240 |
| atcactcatg gttatggcag cactgcataa ttctcttact gtcatgccat ccgtaagatg | 9300 |
| cttttctgtg actggtgagt actcaaccaa gtcattctga aatagtgta tgcggcgacc | 9360 |
| gagttgctct tgcccggcgt caatacggga taataccgcg ccacatagca gaactttaaa | 9420 |
| agtgctcatc attggaaaac gttcttcggg gcgaaaactc tcaaggatct taccgctgtt | 9480 |
| gagatccagt tcgatgtaac ccactcgtgc acccaactga tcttcagcat ctttactttt | 9540 |
| caccagcgtt tctgggtgag caaaaacagg aaggcaaaat gccgcaaaaa agggaataag | 9600 |
| ggcgacacgg aaatgttgaa tactcatact cttcctttt caatattatt gaagcattta | 9660 |
| tcagggttat tgtctcatga gcggatacat atttgaatgt atttagaaaa ataaacaaat | 9720 |
| aggggttccg cgcacatttc cccgaaaagt gccacctgac gtctaagaaa ccattattat | 9780 |
| catgacatta acctataaaa ataggcgtat cacgaggccc tttcgtctcg cgcgtttcgg | 9840 |
| tgatgacggt gaaaacctct gacacatgca gctcccggag acggtcacag cttgtctgta | 9900 |
| agcggatgcc gggagcagac aagcccgtca gggcgcgtca gcgggtgttg gcgggtgtcg | 9960 |
| gggctggctt aactatgcgg catcagagca gattgtactg agagtgcacc atatgcggtg | 10020 |
| tgaaataccg cacagatgcg taaggagaaa ataccgcatc aggcgccatt cgccattcag | 10080 |
| gctgcgcaac tgttgggaag ggcgatcggt gcgggcctct tcgctattac gccagctggc | 10140 |
| gaaaggggga tgtgctgcaa ggcgattaag ttgggtaacg ccagggtttt cccagtcacg | 10200 |
| acgttgtaaa acgacggcca gtgccaagct g | 10231 |

<210> SEQ ID NO 44
<211> LENGTH: 10249
<212> TYPE: DNA
<213> ORGANISM: Artificial Sequence
<220> FEATURE:
<223> OTHER INFORMATION: Synthetic

<400> SEQUENCE: 44

| | |
|---|---|
| acgcgtgtag tcttatgcaa tactcttgta gtcttgcaac atggtaacga tgagttagca | 60 |
| acatgcctta caaggagaga aaagcaccg tgcatgccga ttggtggaag taaggtggta | 120 |
| cgatcgtgcc ttattaggaa ggcaacagac gggtctgaca tggattggac gaaccactga | 180 |
| attgccgcat tgcagagata ttgtatttaa gtgcctagct cgatacaata aacgggtctc | 240 |
| tctggttaga ccagatctga gcctgggagc tctctggcta actagggaac ccactgctta | 300 |
| agcctcaata aagcttgcct tgagtgcttc aagtagtgtg tgcccgtctg ttgtgtgact | 360 |
| ctggtaacta gagatccctc agacccttt agtcagtgtg aaaatctct agcagtggcg | 420 |
| cccgaacagg gacctgaaag cgaaagggaa accagagctc tctcgacgca ggactcggct | 480 |
| tgctgaagcg cgcacggcaa gaggcgaggg gcggcgactg gtgagtacgc caaaaatttt | 540 |
| gactagcgga ggctagaagg agagagatgg gtgcgagagc gtcagtatta gcggggggag | 600 |
| aattagatcg cgatgggaaa aaattcggtt aaggccaggg ggaaagaaaa aatataaatt | 660 |

```
aaaacatata gtatgggcaa gcagggagct agaacgattc gcagttaatc ctggcctgtt     720
agaaacatca gaaggctgta gacaaatact gggacagcta caaccatccc ttcagacagg     780
atcagaagaa cttagatcat tatataatac agtagcaacc ctctattgtg tgcatcaaag     840
gatagagata aaagacacca aggaagcttt agacaagata gaggaagagc aaaacaaaag     900
taagaccacc gcacagcaag cggccactga tcttcagacc tggaggagga gatatgaggg     960
acaattggag aagtgaatta tataaatata agtagtaaaa attgaaccca ttaggagtag    1020
cacccaccaa ggcaaagaga agagtggtgc agagagaaaa aagagcagtg ggaataggag    1080
ctttgttcct tgggttcttg ggagcagcag gaagcactat gggcgcagcg tcaatgacgc    1140
tgacggtaca ggccagacaa ttattgtctg gtatagtgca gcagcagaac aatttgctga    1200
gggctattga ggcgcaacag catctgttgc aactcacagt ctggggcatc aagcagctcc    1260
aggcaagaat cctggctgtg gaaagatacc taaaggatca acagctcctg ggatttggg     1320
gttgctctgg aaaactcatt tgcaccactg ctgtgccttg gaatgctagt tggagtaata    1380
aatctctgga acagatttgg aatcacacga cctggatgga gtgggacaga gaaattaaca    1440
attacacaag cttaatacac tccttaattg aagaatcgca aaaccagcaa gaaaagaatg    1500
aacaagaatt attggaatta gataaatggg caagtttgtg gaattggttt aacataacaa    1560
attggctgtg gtatataaaa ttattcataa tgatagtagg aggcttggta ggtttaagaa    1620
tagttttgc tgtactttct atagtgaata gagttaggca gggatattca ccattatcgt     1680
ttcagaccca cctcccaacc ccgaggggac ccgacaggcc cgaaggaata agaagaagaa    1740
gtggagagag agacagagac agatccattc gattagtgaa cggatctcga cggtatcggt    1800
taacttttaa aagaaaaggg gggattgggg ggtacagtgc aggggaaaga atagtagaca    1860
taatagcaac agacatacaa actaaagaat tacaaaaaca aattacaaaa ttcaaaattt    1920
tatcgatgct agcggaggaa aaactgtttc atacagaagg cgtggaggaa aaactgtttc    1980
atacagaagg cgtggaggaa aaactgtttc atacagaagg cgtggaggaa aaactgtttc    2040
atacagaagg cgtggaggaa aaactgtttc atacagaagg cgtggaggaa aaactgtttc    2100
atacagaagg cgtagatcta gactctagag gtatataat ggaagctcga cttccagctt     2160
ggcattccgg tactgttggt aaaaagcttg gcaatccggt actgttggta aaggatccgc    2220
caccatgcct gccatgaaga ttgagtgccg catcacggga accctgaacg gagtggagtt    2280
tgagctggtc ggaggtggag aagggactcc tgagcaggga cgtatgacca acaagatgaa    2340
gtctaccaag ggcgccttga ccttctcccc ctaccttctc tctcatgtca tgggatacgg    2400
gttctaccac tttggtacct atcccagtgg gtatgagaat cccttcctgc atgccatcaa    2460
caacggggg tacaccaaca ccaggattga aagtatgag gatggaggag ttcttcatgt      2520
tagctttagc tacagatatg aagcaggcag ggtgattggg gatttcaagg ttgtcgggac    2580
aggattccct gaggacagtg tgatcttcac cgacaagatc atccggtcca atgctaccgt    2640
ggagcacttg cacccaatgg gagacaacgt tcttgtgggc tccttcgcga gaaccttttc    2700
cctgagggat ggaggctact actcatttgt ggttgacagc cacatgcact tcaagagtgc    2760
catccacca tccatcctcc agaacggggg gcccatgttt gccttcagga gagttgagga   2820
acttcactcc aacactgaac ttggcattgt agagtatcaa catgccttca gactcccat     2880
agcatttgct ggaagcggag ctactaactt cagcctgctg aagcaggctg agacgtgga    2940
ggagaaccct ggacctatgg tcttcacact cgaagatttc gttggggact ggcgacagac    3000
```

```
agccggctac aacctggacc aagtccttga acagggaggt gtgtccagtt tgtttcagaa    3060
tctcggggtg tccgtaactc cgatccaaag gattgtcctg agcggtgaaa atgggctgaa    3120
gatcgacatc catgtcatca tcccgtatga aggtctgagc ggcgaccaaa tgggccagat    3180
cgaaaaaatt tttaaggtgg tgtaccctgt ggatgatcat cactttaagg tgatcctgca    3240
ctatggcaca ctggtaatcg acggggttac gccgaacatg atcgactatt cggacggcc    3300
gtatgaaggc atcgccgtgt tcgacggcaa aaagatcact gtaacaggga ccctgtggaa    3360
cggcaacaaa attatcgacg agcgcctgat caaccccgac ggctccctgc tgttccgagt    3420
aaccatcaac ggagtgaccg gctggcggct gtgcgaacgc attctggcgt aagcggccgc    3480
gaaggatctg cgatcgctcc ggtgcccgtc agtgggcaga gcgcacatcg cccacagtcc    3540
ccgagaagtt ggggggaggg gtcggcaatt aacgggtgc ctagagaagg tggcgcgggg    3600
taaactggga aagtgatgtc gtgtactggc tccgcctttt tcccgagggt ggggagaac    3660
cgtatataag tgcagtagtc gccgtgaacg ttcttttcg caacgggttt gccgccagaa    3720
cacagctgaa gcttcgaggg gctcgcatct ctccttcacg cgcccgccgc cctacctgag    3780
gccgccatcc acgccggttg agtcgcgttc tgccgcctcc cgcctgtggt gcctcctgaa    3840
ctgcgtccgc cgtctaggta agtttaaagc tcaggtcgag accgggcctt tgtccggcgc    3900
tcccttggag cctacctaga ctcagccggc tctccacgct ttgcctgacc ctgcttgctc    3960
aactctacgt ctttgtttcg ttttctgttc tgcgccgtta cagatccaag ctgtgaccgg    4020
cgcctactag tgccaccatg gactttcaag tgcagatctt cagctttctg ctgatctctg    4080
ctagtgtcat catgtctcag atgcaactgg tccaaagcgg tactgaggtg aagaagccag    4140
gagagtccct gaagatttcc tgcaagggct ctggatacgg tttcatcacc tactggatcg    4200
gatgggtgag gcaaatgcca ggtaaaggac tggaatggat gggaatcatc taccctggcg    4260
acagcgagac aagatactct ccttccttcc agggacaggt gaccatctct gcagacaaga    4320
gcatcaacac agcttatctg cagtggtcta gcctcaaagc ctccgataca gccatctact    4380
attgtgctgg tggttctggc atctccactc caatggacgt gtggggacaa ggtactactg    4440
ttaccgtttc cagcggaggt ggaggcagtg gaggtggtgg atctggagga ggagggtctg    4500
atatccaact cactcagtct cccgattctc tggctgtttc tctgggtgag agggcaacca    4560
tcaactgtaa gtcctcccaa tccgttctgt actcctccat caacaagaac tatctggctt    4620
ggtatcaaca gaagcctggc cagcctccca agctgctgat ctactgggct tctaccaggg    4680
agtctggcgt ccctgaccgc ttcagcggat ctggatctgg tacagacttt accctgacta    4740
tctcctccct gcaagcagag gatgtcgctg tctactattg ccaacagtac tactccactc    4800
cctatacttt cggacaagga actaaggtgg agatcaagag agaaatcgag cagaagctga    4860
tttccgaaga ggatctcaat ggagtgactg tcagcagcgc tctgtctaac tccatcatgt    4920
acttctcaca cttcgtgcca gtgttcctcc ctgctaaacc caccacaact ccagcaccta    4980
gacctcccac tccagcacca actattgcat cccagcctct ctccctcaga ccagaagcat    5040
gcagacctgc agcaggtgga gctgtgcaca agagggtct ggaccctttc tgggtcctcg    5100
tggtggtggg tggagtcctg gcatgttaca gcctcctggt caccgtggca ttcatcatct    5160
tctgggtgag atctaagagg agcagactgc tgcactctga ttacatgaac atgacaccca    5220
gaagacctgg tcccaccaga aagcactacc aaccctacgc accaccaaga gactttgctg    5280
catacagaag tctcgagagg gtcaagttct caaggagtgc agatgctcca gcctatcaac    5340
agggtcagaa ccaactgtac aacgagctga atctcggaag aagagaggag tacgatgtgc    5400
```

```
tggataagag aagaggcagg gacccagaga tgggtgggaa acccagaaga aagaatcctc    5460
aagagggact gtacaatgag ctgcagaagg ataagatggc tgaggcatac tcagagatcg    5520
gtatgaaggg agagaggaga agaggcaaag gtcatgatgg tctgtaccaa ggtctgtcca    5580
cagcaacaaa ggatacatat gatgctctgc acatgcaggc actcccacca cggggttccg    5640
gagtgaaaca gactttgaac tttgaccttc tcaagttggc tggagacgtc gagtccaacc    5700
ctggtcccat gaccgagtac aagcccacgg tgcgcctcgc cacccgcgac gacgtcccca    5760
gggccgtacg caccctcgcc gccgcgttcg ccgactaccc cgccacgcgc cacaccgtcg    5820
atccggaccg ccacatcgag cgggtcaccg agctgcaaga actcttcctc acgcgcgtcg    5880
ggctcgacat cggcaaggtg tgggtcgcgg acgacggcgc cgcggtggcg gtctggacca    5940
cgccggagag cgtcgaagcg ggggcggtgt tcgccgagat cggcccgcgc atggccgagt    6000
tgagcggttc ccggctggcc gcgcagcaac agatggaagg cctcctggcg ccgcaccggc    6060
ccaaggagcc cgcgtggttc ctggccaccg tcggcgtctc gcccgaccac cagggcaagg    6120
gtctgggcag cgccgtcgtg ctccccggag tggaggcggc cgagcgcgcc ggggtgcccg    6180
ccttcctgga gacctccgcg ccccgcaacc tccccttcta cgagcggctc ggcttcaccg    6240
tcaccgccga cgtcgaggtg cccgaaggac gcgcacctg gtgcatgacc cgcaagcccg    6300
gtgcctgatt aattaagtcg acaatcaacc tctggattac aaaatttgtg aaagattgac    6360
tggtattctt aactatgttg ctccttttac gctatgtgga tacgctgctt taatgccttt    6420
gtatcatgct attgcttccc gtatggcttt cattttctcc tccttgtata atcctggtt    6480 gctgtctctt tatgaggagt tgtggcccgt tgtcaggcaa cgtggcgtgg tgtgcactgt    6540
gtttgctgac gcaaccccca ctggttgggg cattgccacc acctgtcagc tcctttccgg    6600
gactttcgct ttccccctcc ctattgccac ggcggaactc atcgccgcct gccttgcccg    6660
ctgctggaca ggggctcggc tgttgggcac tgacaattcc gtggtgttgt cggggaaatc    6720
atcgtccttt ccttggctgc tcgcctgtgt tgccacctgg attctgcgcg gacgtcctt    6780 ctgctacgtc ccttcggccc tcaatccagc ggaccttcct tcccgcggcc tgctgccggc    6840
tctgcggcct cttccgcgtc ttcgccttcg ccctcagacg agtcggatct ccctttgggc    6900 cgcctcccccg cctggtacct ttaagaccaa tgacttacaa ggcagctgta gatcttagcc    6960 acttttaaa agaaaagggg ggactggaag ggctaattca ctcccaacga agataagatc    7020 tgcttttttgc ttgtactggg tctctctggt tagaccagat ctgagcctgg gagctctctg    7080
gctaactagg gaacccactg cttaagcctc aataaagctt gccttgagtg cttcaagtag    7140
tgtgtgcccg tctgttgtgt gactctggta actagagatc cctcagaccc ttttagtcag    7200
tgtggaaaat ctctagcagt agtagttcat gtcatcttat tattcagtat ttataacttg    7260
caaagaaatg aatatcagag agtgagagga acttgtttat tgcagcttat aatggttaca    7320
aataaagcaa tagcatcaca aatttcacaa ataaagcatt ttttttcactg cattctagtt    7380 gtggtttgtc caaactcatc aatgtatctt atcatgtctg gctctagcta tcccgcccct    7440
aactccgccc atcccgcccc taactccgcc cagttccgcc cattctccgc cccatggctg    7500 actaatttttt tttatttatg cagaggccga ggccgcctcg gcctctgagc tattccagaa    7560
gtagtgagga ggcttttttg gaggcctaga cttttgcaga cggcccaa attcgtaatc    7620 atggtcatag ctgtttcctg tgtgaaattg ttatccgctc acaattccac acaacatacg    7680
agccggaagc ataaagtgta aagcctgggg tgcctaatga gtgagctaac tcacattaat    7740
```

```
tgcgttgcgc tcactgcccg ctttccagtc gggaaacctg tcgtgccagc tgcattaatg    7800
aatcggccaa cgcgcgggga gaggcggttt gcgtattggg cgctcttccg cttcctcgct    7860
cactgactcg ctgcgctcgg tcgttcggct gcggcgagcg gtatcagctc actcaaaggc    7920
ggtaatacgg ttatccacag aatcagggga taacgcagga agaacatgt gagcaaaagg     7980
ccagcaaaag gccaggaacc gtaaaaaggc cgcgttgctg gcgtttttcc ataggctccg    8040
cccccctgac gagcatcaca aaaatcgacg ctcaagtcag aggtggcgaa acccgacagg    8100
actataaaga taccaggcgt ttccccctgg aagctccctc gtgcgctctc ctgttccgac    8160
cctgccgctt accggatacc tgtccgcctt tctcccttcg ggaagcgtgg cgctttctca    8220
tagctcacgc tgtaggtatc tcagttcggt gtaggtcgtt cgctccaagc tgggctgtgt    8280
gcacgaaccc cccgttcagc ccgaccgctg cgccttatcc ggtaactatc gtcttgagtc    8340
caacccggta agacacgact tatcgccact ggcagcagcc actggtaaca ggattagcag    8400
agcgaggtat gtaggcggtg ctacagagtt cttgaagtgg tggcctaact acggctacac    8460
tagaaggaca gtatttggta tctgcgctct gctgaagcca gttaccttcg gaaaaagagt    8520
tggtagctct tgatccggca aacaaaccac cgctggtagc ggtggttttt ttgtttgcaa    8580
gcagcagatt acgcgcagaa aaaaaggatc tcaagaagat cctttgatct tttctacggg    8640
gtctgacgct cagtggaacg aaaactcacg ttaagggatt ttggtcatga gattatcaaa    8700
aaggatcttc acctagatcc ttttaaatta aaaatgaagt tttaaatcaa tctaaagtat    8760
atatgagtaa acttggtctg acagttacca atgcttaatc agtgaggcac ctatctcagc    8820
gatctgtcta tttcgttcat ccatagttgc ctgactcccc gtcgtgtaga taactacgat    8880
acgggagggc ttaccatctg gccccagtgc tgcaatgata ccgcgagacc cacgctcacc    8940
ggctccagat ttatcagcaa taaaccagcc agccggaagg gccgagcgca gaagtggtcc    9000
tgcaacttta tccgcctcca tccagtctat taattgttgc cgggaagcta gagtaagtag    9060
ttcgccagtt aatagtttgc gcaacgttgt tgccattgct acaggcatcg tggtgtcacg    9120
ctcgtcgttt ggtatggctt cattcagctc cggttcccaa cgatcaaggc gagttacatg    9180
atcccccatg ttgtgcaaaa aagcggttag ctccttcggt cctccgatcg ttgtcagaag    9240
taagttggcc gcagtgttat cactcatggt tatggcagca ctgcataatt ctcttactgt    9300
catgccatcc gtaagatgct tttctgtgac tggtgagtac tcaaccaagt cattctgaga    9360
atagtgtatg cggcgaccga gttgctcttg cccggcgtca atacgggata ataccgcgcc    9420
acatagcaga actttaaaag tgctcatcat tggaaaacgt tcttcggggc gaaaactctc    9480
aaggatctta ccgctgttga gatccagttc gatgtaaccc actcgtgcac ccaactgatc    9540
ttcagcatct tttactttca ccagcgtttc tgggtgagca aaaacaggaa ggcaaaatgc    9600
cgcaaaaaag ggaataaggg cgacacggaa atgttgaata ctcatactct tccttttca    9660
atattattga agcatttatc agggttattg tctcatgagc ggatacatat ttgaatgtat    9720
ttagaaaaat aaacaaatag gggttccgcg cacatttccc cgaaaagtgc cacctgacgt    9780
ctaagaaacc attattatca tgacattaac ctataaaaat aggcgtatca cgaggccctt    9840
tcgtctcgcg cgtttcggtg atgacggtga aaacctctga cacatgcagc tcccggagac    9900
ggtcacagct tgtctgtaag cggatgccgg gagcagacaa gcccgtcagg gcgcgtcagc    9960
gggtgttggc gggtgtcggg gctggcttaa ctatgcggca tcagagcaga ttgtactgag   10020
agtgcaccat atgcggtgtg aaataccgca cagatgcgta aggagaaaat accgcatcag   10080
gcgccattcg ccattcaggc tgcgcaactg ttgggaaggg cgatcggtgc gggcctcttc   10140
```

-continued

```
gctattacgc cagctggcga aaggggatg tgctgcaagg cgattaagtt gggtaacgcc      10200
agggttttcc cagtcacgac gttgtaaaac gacggccagt gccaagctg                10249
```

<210> SEQ ID NO 45
<211> LENGTH: 10935
<212> TYPE: DNA
<213> ORGANISM: Artificial Sequence
<220> FEATURE:
<223> OTHER INFORMATION: Synthetic

<400> SEQUENCE: 45

```
actcttcctt tttcaatatt attgaagcat ttatcagggt tattgtctca tgagcggata      60
catatttgaa tgtatttaga aaataaaca ataggggtt ccgcgcacat ttccccgaaa      120
agtgccacct aaattgtaag cgttaatatt ttgttaaaat tcgcgttaaa ttttgttaa      180 atcagctcat ttttaacca ataggccgaa atcggcaaaa tcccttataa atcaaaagaa      240
tagaccgaga tagggttgag tgttgttcca gtttggaaca agagtccact attaaagaac      300
gtggactcca acgtcaaagg gcgaaaaacc gtctatcagg gcgatggccc actacgtgaa      360
ccatcaccct aatcaagttt ttgggtcg aggtgccgta aagcactaaa tcggaaccct      420
aaagggagcc cccgatttag agcttgacgg ggaaagccgg cgaacgtggc gagaaaggaa      480
gggaagaaag cgaaaggagc gggcgctagg gcgctggcaa gtgtagcggt cacgctgcgc      540
gtaaccacca cacccgccgc gcttaatgcg ccgctacagg gcgcgtccca ttcgccattc      600
aggctgcgca actgttggga agggcgatcg gtgcgggcct cttcgctatt acgccagctg      660
gcgaaagggg gatgtgctgc aaggcgatta agttgggtaa cgccagggtt ttcccagtca      720
cgacgttgta aaacgacggc cagtgagcgc gcctcgttca ttcacgtttt tgaacccgtg      780
gaggacgggc agactcgcgg tgcaaatgtg ttttacagcg tgatggagca gatgaagatg      840
ctcgacacgc tgcagaacac gcagctagat taaccctaga aagataatca tattgtgacg      900
tacgttaaag ataatcatgt gtaaaattga cgcatgtgtt ttatcggtct gtatatcgag      960
gtttatttat taatttgaat agatattaag ttttattata tttacactta catactaata      1020
ataaattcaa caaacaattt atttatgttt atttatttat taaaaaaac aaaaactcaa      1080 aatttcttct ataaagtaac aaaactttta tgagggacag ccccccccca aagcccccag      1140
ggatgtaatt acgtccctcc cccgctaggg ggcagcagcg agccgcccgg ggctccgctc      1200
cggtccggcg ctcccccgc atccccgagc cggcagcgtg cggggacagc ccgggcacgg      1260
ggaaggtggc acgggatcgc tttcctctga acgcttctcg ctgctctttg agcctgcaga      1320
cacctggggg gatacgggga aaaggcctcc acggccacta gtattatgcc cagtacatga      1380
ccttatggga ctttcctact tggcagtaca tctacgtatt agtcatcgct attaccatgg      1440
tgatgcggtt ttggcagtac atcaatgggc gtggatagcg gtttgactca cggggatttc      1500
caagtctcca ccccattgac gtcaatggga gtttgttttg gcaccaaaat caacgggact      1560
ttccaaaatg tcgtaacaac tccgccccat tgacgcaaat gggcggtagg cgtgtacggt      1620
gggaggttta taagcagagc tcgttttag tgaaccgtca gatcgcctgg agacgccatc      1680
cacgctgttt tgacctccat agaagattct agagccacca tggaaactga tacactcctg      1740
ctctgggttc tgctgctgtg ggttcctggc tctactggtg attatccata cgatgttcca      1800
gattatgctg gatccatccc actgggtgtt atacacaatt ccactctcca ggtttccgat      1860
gtggacaaac tggtctgtag ggacaagctg agtagcacca accagctgag gagcgttggc      1920
```

```
ctcaacctgg agggcaacgg agtggccact gatgtgcctt ccgctaccaa acggtgggt      1980
ttccggtcag gtgtcccacc caaggtcgtt aactatgaag ctggcgagtg ggctgagaac      2040
tgttacaatc tggagatcaa gaagcccgat gggagtgaat gcctgcctgc tgctccagac      2100
ggcattcggg gtttcccacg gtgtcggtac gtgcataaag tgagcggcac tgggccatgt      2160
gcaggtgact ttgcttttca taaggagggt gccttcttcc tgtatgatag actggcctca      2220
acagtgatct ataggggaac cacttttgca gaaggggtgg tggcctttct gattctgcca      2280
caggctaaga aagatttctt ttcctcccat cccctcagag aacccgttaa cgctacagag      2340
gacccctcct caggatacta ttcaacaaca atacgctacc aggcaactgg gttcggaact      2400
aatgaaaccg agtacctgtt cgaggtcgat aatctgacat acgtgcagct cgaaagtcgg      2460
ttcactcccc agtttctcct ccagctgaac gagactatct acacatccgg aaaaggtca      2520
aatactactg gcaagctcat ctggaaggtg aaccccgaga tcgataccac cataggagag      2580
tgggcctttt gggaaaccaa gaagaacctc actcggaaaa tccggtccga ggagctgtcc      2640
tttaccgtcg ttagcaatgg tgctaagaac atctccggtc aatctcctgc acggacatct      2700
agcgatccag gcaccaacac tacaacagag gaccataaga tcatggcaag tgaaaactca      2760
agtgcaatgg tccaggttca tagccaagga agggaggctg ctgtgtcaca tctgacaacc      2820
ctcgccacca tttcaacttc acctcagagt ctgacaacaa agccaggccc tgacaattca      2880
acacacaaca cacccgtgta caagctggac atcagtgagg caacccaggt ggagcagcac      2940
catcgcagaa ccgacaacga cagcactgcc agcgataccc cttcagccac caccgcagct      3000
ggccctccca aagccgaaaa caccaacacc agcaaatcta ccgacttcct ggacccagca      3060
accacaaccct cacctcaaaa ccacagcgag actgccggta acaataacac acaccaccaa      3120
gacaccggag aggaaagcgc ttccagcggt aaactgggac tgataacaaa caccatcgca      3180
ggagtcgctg ggctgatcac aggaggtcgc agaacacgga gggaagctat agtgaatgca      3240
cagcccaagt gcaatcctaa cctgcattac tggaccactc aagacgaggg agccgctatc      3300
ggcctcgcct ggattcctta cttcggtccc gcagctgagg ggatatacat cgaggggctc      3360
atgcacaacc aggacggcct catttgtggc ctcagacagc tggccaatga gactacccag      3420
gccctgcaac tgtttctgag agctactaca gaactccgca cttttctccat tctgaatcgc      3480
aaagccatcg acttcctgct gcaacgctgg ggagggacat gtcatatcct gggtccagac      3540
tgctgtatcg aaccccacga ctggaccaag aacataaccg acaagattga ccaaatcatc      3600
cacgactttg tggacaaaac tctccccgat caagggacaa cgataactg gtggaccgga      3660
tggaggcaat ggattcccgc tggtatcggc gtgaccggag tgatcattgc cgttatagcc      3720
ctgtttttgca tctgtaagtt cgtgtttggt tctggtgtga acagactttt gaattttgac      3780
cttctcaagt tggcgggaga cgtcgagtcc aaccctgggc ccatggaaga tgccaaaaac      3840
attaagaagg gcccagcgcc attctaccca ctcgaagacg ggaccgccgg cgagcagctg      3900
cacaaagcca tgaagcgcta cgccctggtg cccggcacca tcgcctttac cgacgcacat      3960
atcgaggtgg acattaccta cgccgagtac ttcgagatga cgttcggct ggcagaagct      4020
atgaagcgct atgggctgaa tacaaaccat cggatcgtgg tgtgcagcga aatagcttg      4080
cagttcttca tgcccgtgtt gggtgccctg ttcatcggtg tggctgtggc cccagctaac      4140
gacatctaca cgagcgcga gctgctgaac agcatgggca tcagccagcc caccgtcgta      4200
ttcgtgagca agaagggct gcaaaagatc ctcaacgtgc aaaagaagct accgatcata      4260
caaaagatca tcatcatgga tagcaagacc gactaccagg gcttccaaag catgtacacc      4320
```

```
ttcgtgactt cccatttgcc acccggcttc aacgagtacg acttcgtgcc cgagagcttc    4380
gaccgggaca aaaccatcgc cctgatcatg aacagtagtg gcagtaccgg attgcccaag    4440
ggcgtagccc taccgcaccg caccgcttgt gtccgattca gtcatgcccg cgaccccatc    4500
ttcggcaacc agatcatccc cgacaccgct atcctcagcg tggtgccatt tcaccacggc    4560
ttcggcatgt tcaccacgct gggctacttg atctgcggct tcgggtcgt gctcatgtac    4620 cgcttcgagg aggagctatt cttgcgcagc ttgcaagact ataagattca atctgccctg    4680
ctggtgccca cactatttag cttcttcgct aagagcactc tcatcgacaa gtacgaccta    4740
agcaacttgc acgagatcgc cagcggcggg gcgccgctca gcaaggaggt aggtgaggcc    4800
gtggccaaac gcttccacct accaggcatc cgccagggct acggcctgac agaaacaacc    4860
agcgccattc tgatcacccc cgaaggggac gacaagcctg cgcagtagg caaggtggtg     4920 cccttcttcg aggctaaggt ggtggacttg gacaccggta agacactggg tgtgaaccag    4980
cgcggcgagc tgtgcgtccg tggccccatg atcatgagcg gctacgttaa caaccccgag    5040
gctacaaacg ctctcatcga caaggacggc tggctgcaca gcggcgacat cgcctactgg    5100
gacgaggacg agcacttctt catcgtggac cggctgaaga gcctgatcaa atacaagggc    5160
taccaggtag ccccagccga actggagagc atcctgctgc aacaccccaa catcttcgac    5220 gccgggtcg ccggcctgcc cgacgacgat gccggcgagc tgcccgccgc agtcgtcgtg     5280
ctggaacacg gtaaaaccat gaccgagaag gagatcgtgg actatgtggc cagccaggtt    5340
acaaccgcca agaagctgcg cggtggtgtt gtgttcgtgg acgaggtgcc taaaggactg    5400
accggcaagt tggacgcccg caagatccgc gagattctca ttaaggccaa gaagggcggc    5460
aagatcgccg tgggaagcgg agctactaac ttcagcctgc tgaagcaggc tggagacgtg    5520
gaggagaacc ctggacctat ggatagcact gagaacgtca tcaagccctt catgcgcttc    5580
aaggtgcaca tggagggctc cgtgaacggc cacgagttcg agatcgaggg cgtgggcgag    5640
ggcaagccct acgagggcac ccagaccgcc aagctgcaag tgaccaaggg cggccccctg    5700
cccttcgcct gggacatcct gtccccccag ttcttctacg gctccaaggc gtacatcaag    5760 cacccgccg acatccccga ctacctcaag cagtccttcc ccgagggctt caagtgggag    5820
cgcgtgatga acttcgagga cggcggcgtg gtgaccgtga cccaggactc ctccctgcag    5880
gacggcaccc tcatctacca cgtgaagttc atcggcgtga cttcccctc cgacggcccc    5940 gtaatgcaga agaagactct gggctgggag ccctccactg agcgcaacta ccccgcgac    6000 ggcgtgctga agggcgagaa ccacatggcg ctgaagctga agggcggcgg ccactacctg    6060
tgtgagttca gtccatcta catggccaag aagcccgtga agctgcccgg ctaccactac    6120
gtggactaca agctcgacat cacctcccac aacgaggact acaccgtggt ggagcagtac    6180
gagcgcgccg aggcccgcca ccacctgttc cagtaatgat aacgcggccg cgaaggatct    6240
gcgatcgctc cggtgcccgt cagtgggcag agcgcacatc gcccacagtc cccgagaagt    6300 tgggggagg ggtcggcaat tgaacgggtg cctagagaag gtggcgcggg gtaaactggg     6360
aaagtgatgt cgtgtactgg ctccgccttt ttcccgaggg tggggagaa ccgtatataa     6420 gtgcagtagt cgccgtgaac gttctttttc gcaacgggtt tgccgccaga acacagctga    6480
agcttcgagg ggctcgcatc tctccttcac gcgcccgccg ccctacctga ggccgccatc    6540
cacgccggtt gagtcgcgtt ctgccgcctc ccgcctgtgg tgcctcctga actgcgtccg    6600
ccgtctaggt aagtttaaag ctcaggtcga gaccgggcct ttgtccggcg ctcccttgga    6660
```

```
gcctacctag actcagccgg ctctccacgc tttgcctgac cctgcttgct caactctacg    6720
tctttgtttc gttttctgtt ctgcgccgtt acagatccaa gctgtgaccg gcgcctacgc    6780
tagatgaccg agtacaagcc cacggtgcgc ctcgccaccc gcgacgacgt ccccagggcc    6840
gtacgcaccc tcgccgccgc gttcgccgac taccccgcca cgcgcacac  cgtcgatccg    6900
gaccgccaca tcgagcgggt caccgagctg caagaactct tcctcacgcg cgtcgggctc    6960
gacatcggca aggtgtgggt cgcggacgac ggcgccgcgg tggcggtctg gaccacgccg    7020
gagagcgtcg aagcggggc  ggtgttcgcc gagatcggcc gcgcatggc  cgagttgagc    7080
ggttcccggc tggccgcgca gcaacagatg gaaggcctcc tggcgccgca ccggcccaag    7140
gagcccgcgt ggttcctggc caccgtcggc gtctcgcccg accaccaggg caagggtctg    7200
ggcagcgccg tcgtgctccc cggagtggag gcggccgagc gcgccggggt gcccgccttc    7260
ctggagacct ccgcgccccg caacctcccc ttctacgagc ggctcggctt caccgtcacc    7320
gccgacgtcg aggtgcccga aggaccgcgc acctggtgca tgacccgcaa gcccggtgcc    7380
tgagtcgaca atcaacctct ggattacaaa atttgtgaaa gattgactgg tattcttaac    7440
tatgttgctc cttttacgct atgtggatac gctgctttaa tgcctttgta tcatgcgtta    7500
actaaacttg tttattgcag cttataatgg ttacaaaata agcaatagca tcacaaattt    7560
cacaaataaa gcatttttt  cactgcattc tagttgtggt ttgtccaaac tcatcaatgt    7620
atcttatcat gtctggaatt gactcaaatg atgtcaatta gtctatcaga agctcatctg    7680
gtctcccttc cgggggacaa gacatccctg tttaatattt aaacagcagt gttcccaaac    7740
tgggttctta tatcccttgc tctggtcaac caggttgcag ggtttcctgt cctcacagga    7800
acgaagtccc taaagaaaca gtggcagcca ggtttagccc cggaattgac tggattcctt    7860
ttttagggcc cattggtatg gcttttccc  cgtatccccc caggtgtctg caggctcaaa    7920
gagcagcgag aagcgttcag aggaaagcga tcccgtgcca ccttccccgt gcccgggctg    7980
tccccgcacg ctgccggctc ggggatgcgg ggggagcgcc ggaccggagc ggagccccgg    8040
gcggctcgct gctgcccct  agcggggag  ggacgtaatt acatccctgg gggctttggg    8100
ggggggctgt ccctgatatc tataacaaga aaatatatat ataataagtt atcacgtaag    8160
tagaacatga ataacaata  taattatcgt atgagttaaa tcttaaaagt cacgtaaaag    8220
ataatcatgc gtcattttga ctcacgcggt cgttatagtt caaaatcagt gacacttacc    8280
gcattgacaa gcacgcctca cgggagctcc aagcggcgac tgagatgtcc taaatgcaca    8340
gcgacggatt cgcgctattt agaaagagag agcaatattt caagaatgca tgcgtcaatt    8400
ttacgcagac tatctttcta gggttaatct agctgcatca ggatcatatc gtcgggtctt    8460
ttttccggct cagtcatcgc ccaagctggc gctatctggg catcggggag gaagaagccc    8520
gtgccttttc ccgcgaggtt gaagcggcat ggaaagagtt gccgaggat  gactgctgct    8580
gcattgacgt tgagcgaaaa cgcacgttta ccatgatgat tcgggaaggt gtggccatgc    8640
acgcctttaa cggtgaactg ttcgttcagg ccacctggga taccagttcg tcgcggcttt    8700
tccggacaca gttccggatg gtcagcccga gcgcatcag  caacccgaac aataccggcg    8760
acagccggaa ctgccgtgcc ggtgtgcaga ttaatgacag cggtgcggcg ctgggatatt    8820
acgtcagcga ggacgggtat cctggctgga tgccgcagaa atggacatgg ataccccgtg    8880
agttacccgg cgggcgcgct tggcgtaatc atggtcatag ctgtttcctg tgtgaaattg    8940
ttatccgctc acaattccac acaacatacg agccggaagc ataaagtgta aagcctgggg    9000
tgcctaatga gtgagctaac tcacattaat tgcgttgcgc tcactgcccg ctttccagtc    9060
```

```
gggaaacctg tcgtgccagc tgcattaatg aatcggccaa cgcgcgggga gaggcggttt    9120
gcgtattggg cgctcttccg cttcctcgct cactgactcg ctgcgctcgg tcgttcggct    9180
gcggcgagcg gtatcagctc actcaaaggc ggtaatacgg ttatccacag aatcagggga    9240
taacgcagga aagaacatgt gagcaaaagg ccagcaaaag gccaggaacc gtaaaaaggc    9300
cgcgttgctg gcgtttttcc ataggctccg ccccccctgac gagcatcaca aaaatcgacg    9360
ctcaagtcag aggtggcgaa acccgacagg actataaaga taccaggcgt ttccccctgg    9420
aagctccctc gtgcgctctc ctgttccgac cctgccgctt accggatacc tgtccgcctt    9480
tctcccttcg ggaagcgtgg cgctttctca tagctcacgc tgtaggtatc tcagttcggt    9540
gtaggtcgtt cgctccaagc tgggctgtgt gcacgaaccc cccgttcagc ccgaccgctg    9600
cgccttatcc ggtaactatc gtcttgagtc caacccggta agacacgact tatcgccact    9660
ggcagcagcc actggtaaca ggattagcag agcgaggtat gtaggcggtg ctacagagtt    9720
cttgaagtgg tggcctaact acggctacac tagaaggaca gtatttggta tctgcgctct    9780
gctgaagcca gttaccttcg gaaaaagagt tggtagctct tgatccggca aacaaaccac    9840
cgctggtagc ggtggttttt tgtttgcaa gcagcagatt acgcgcagaa aaaaaggatc    9900
tcaagaagat cctttgatct tttctacggg gtctgacgct cagtggaacg aaaactcacg    9960
ttaagggatt ttggtcatga gattatcaaa aaggatcttc acctagatcc ttttaaatta   10020
aaaatgaagt tttaaatcaa tctaaagtat atatgagtaa acttggtctg acagttacca   10080
atgcttaatc agtgaggcac ctatctcagc gatctgtcta tttcgttcat ccatagttgc   10140
ctgactcccc gtcgtgtaga taactacgat acgggagggc ttaccatctg gccccagtgc   10200
tgcaatgata ccgcgagacc cacgctcacc ggctccagat ttatcagcaa taaaccagcc   10260
agccggaagg gccgagcgca gaagtggtcc tgcaacttta tccgcctcca tccagtctat   10320
taattgttgc cgggaagcta gagtaagtag ttcgccagtt aatagtttgc gcaacgttgt   10380
tgccattgct acaggcatcg tggtgtcacg ctcgtcgttt ggtatggctt cattcagctc   10440
cggttcccaa cgatcaaggc gagttacatg atcccccatg ttgtgcaaaa aagcggttag   10500
ctccttcggt cctccgatcg ttgtcagaag taagttggcc gcagtgttat cactcatggt   10560
tatggcagca ctgcataatt ctcttactgt catgccatcc gtaagatgct tttctgtgac   10620
tggtgagtac tcaaccaagt cattctgaga atagtgtatg cggcgaccga gttgctcttg   10680
cccggcgtca atacgggata ataccgcgcc acatagcaga actttaaaag tgctcatcat   10740
tggaaaacgt tcttcgggc gaaaactctc aaggatctta ccgctgttga tccagttc     10800 gatgtaaccc actcgtgcac ccaactgatc ttcagcatct tttactttca ccagcgtttc   10860
tgggtgagca aaaacaggaa ggcaaaatgc cgcaaaaaag gaataagggc gacacggaa    10920 atgttgaata ctcat                                                   10935
```

<210> SEQ ID NO 46
<211> LENGTH: 10273
<212> TYPE: DNA
<213> ORGANISM: Artificial Sequence
<220> FEATURE:
<223> OTHER INFORMATION: Synthetic

<400> SEQUENCE: 46

```
acgcgtgtag tcttatgcaa tactcttgta gtcttgcaac atggtaacga tgagttagca      60
acatgcctta caaggagaga aaaagcaccg tgcatgccga ttggtggaag taaggtggta     120
```

```
cgatcgtgcc ttattaggaa ggcaacagac gggtctgaca tggattggac gaaccactga    180
attgccgcat tgcagagata ttgtatttaa gtgcctagct cgatacaata aacgggtctc    240
tctggttaga ccagatctga gcctgggagc tctctggcta actagggaac ccactgctta    300
agcctcaata aagcttgcct tgagtgcttc aagtagtgtg tgcccgtctg ttgtgtgact    360
ctggtaacta gagatccctc agaccctttt agtcagtgtg aaaatctct agcagtggcg     420 cccgaacagg gacctgaaag cgaaagggaa accagagctc tctcgacgca ggactcggct    480
tgctgaagcg cgcacggcaa gaggcgaggg gcggcgactg gtgagtacgc caaaaatttt    540
gactagcgga ggctagaagg agagagatgg gtgcgagagc gtcagtatta gcgggggag     600 aattagatcg cgatgggaaa aaattcggtt aaggccaggg ggaagaaaaa aatataaatt    660
aaaacatata gtatgggcaa gcagggagct agaacgattc gcagttaatc ctggcctgtt    720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag    900
taagaccacc gcacagcaag cggccactga tcttcagacc tggaggagga gatatgaggg    960
acaattggag aagtgaatta tataaatata agtagtaaaa aattgaacca ttaggagtag    1020
cacccaccaa ggcaaagaga agagtggtgc agagagaaaa aagagcagtg gaataggag    1080 ctttgttcct tgggttcttg ggagcagcag gaagcactat gggcgcagcg tcaatgacgc    1140
tgacggtaca ggccagacaa ttattgtctg gtatagtgca gcagcagaac aatttgctga    1200
gggctattga ggcgcaacag catctgttgc aactcacagt ctggggcatc aagcagctcc    1260
aggcaagaat cctggctgtg gaaagatacc taaaggatca acagctcctg gggatttggg    1320
gttgctctgg aaaactcatt tgcaccactg ctgtgccttg gaatgctagt tggagtaata    1380
aatctctgga acagatttgg aatcacacga cctggatgga gtgggacaga gaaattaaca    1440
attacacaag cttaatacac tccttaattg aagaatcgca aaaccagcaa gaaaagaatg    1500
aacaagaatt attggaatta gataaatggg caagtttgtg gaattggttt aacataacaa    1560
attggctgtg gtatataaaa ttattcataa tgatagtagg aggcttggta ggtttaagaa    1620 tagttttgc tgtactttct atagtgaata gagttaggca gggatattca ccattatcgt    1680
ttcagaccca cctcccaacc ccgaggggac ccgacaggcc cgaaggaata agaagaagaag   1740 gtggagagag agacagagac agatccattc gattagtgaa cggatctcga cggtatcggt    1800 taactttaa aagaaagggg gggattgggg ggtacagtgc aggggaaaga atagtagaca     1860
taatagcaac agacatacaa actaaagaat tacaaaaaca aattacaaaa ttcaaaattt    1920
tatcgatgct agcggaggaa aaactgtttc atacagaagg cgtggaggaa aaactgtttc    1980
atacagaagg cgtggaggaa aaactgtttc atacagaagg cgtggaggaa aaactgtttc    2040
atacagaagg cgtggaggaa aaactgtttc atacagaagg cgtggaggaa aaactgtttc    2100
atacagaagg cgtagatcta gactctagag ggtatataat ggaagctcga cttccagctt    2160
ggcattccgg tactgttggt aaaaagcttg gcaatccggt actgttggta aggatccgc     2220 caccatgcct gccatgaaga ttgagtgccg catcacggga accctgaacg gagtggagtt    2280
tgagctggtc ggaggtggag aagggactcc tgagcaggga cgtatgacca acaagatgaa    2340
gtctaccaag ggcgccttga ccttctcccc ctaccttctc tctcatgtca tgggatacgg    2400
gttctaccac tttggtacct atcccagtgg gtatgagaat cccttcctgc atgccatcaa    2460
caacgggggg tacaccaaca ccaggattga gaagtatgag gatggaggag ttcttcatgt    2520
```

```
tagctttagc tacagatatg aagcaggcag ggtgattggg gatttcaagg ttgtcgggac    2580
aggattccct gaggacagtg tgatcttcac cgacaagatc atccggtcca atgctaccgt    2640
ggagcacttg cacccaatgg gagacaacgt tcttgtgggc tccttcgcga gaaccttttc    2700
cctgagggat ggaggctact actcatttgt ggttgacagc cacatgcact tcaagagtgc    2760
catccaccca tccatcctcc agaacggggg gcccatgttt gccttcagga gagttgagga    2820
acttcactcc aacactgaac ttggcattgt agagtatcaa catgccttca agactcccat    2880
agcatttgct ggaagcggag ctactaactt cagcctgctg aagcaggctg agacgtgga    2940 ggagaaccct ggacctatgg tcttcacact cgaagatttc gttggggact ggcgacagac    3000
agccggctac aacctggacc aagtccttga cagggaggt gtgtccagtt tgtttcagaa    3060 tctcgggggtg tccgtaactc cgatccaaag gattgtcctg agcggtgaaa atgggctgaa    3120
gatcgacatc catgtcatca tcccgtatga aggtctgagc ggcgaccaaa tgggccagat    3180
cgaaaaaatt tttaaggtgg tgtaccctgt ggatgatcat cactttaagg tgatcctgca    3240
ctatggcaca ctggtaatcg acggggttac gccgaacatg atcgactatt cggacggcc    3300 gtatgaaggc atcgccgtgt tcgacggcaa aaagatcact gtaacaggga ccctgtggaa    3360
cggcaacaaa attatcgacg agcgcctgat caaccccgac ggctccctgc tgttccgagt    3420
aaccatcaac ggagtgaccg gctggcggct gtgcgaacgc attctggcgt aagcggccgc    3480
gaaggatctg cgatcgctcc ggtgcccgtc agtgggcaga gcgcacatcg cccacagtcc    3540
ccgagaagtt gggggagggg tcggcaatt gaacgggtgc ctagagaagg tggcgcgggg    3600
taaactggga aagtgatgtc gtgtactggc tccgcctttt tcccgagggt gggggagaac    3660
cgtatataag tgcagtagtc gccgtgaacg ttctttttcg caacgggttt gccgccagaa    3720
cacagctgaa gcttcgaggg gctcgcatct ctccttcacg cgcccgccgc cctacctgag    3780
gccgccatcc acgccggttg agtcgcgttc tgccgcctcc cgcctgtggt gcctcctgaa    3840
ctgcgtccgc cgtctaggta agtttaaagc tcaggtcgag accgggcctt tgtccggcgc    3900
tcccttggag cctacctaga ctcagccggc tctccacgct ttgcctgacc ctgcttgctc    3960
aactctacgt cttttgtttcg ttttctgttc tgcgccgtta cagatccaag ctgtgaccgg    4020
cgcctactag tgccaccatg gactttcaag tgcagatctt cagctttctg ctgatctctg    4080
ctagtgtcat catgtctgaa gtgcagctcg tggaatctgg aggaggactg gttaagcctg    4140
gtggatctct cagactctcc tgcgctgctt ctggattcac attctctaac gcttggatgt    4200
cttgggtcag gcaggcacct ggcaagggtc tggaatgggt tggaagaatc aaatccaaga    4260
ctgatggtgg caccattgac tacgcagctc ctgtcaaggg cagattcact atctctaggg    4320
atgatagcaa gaacactgtc tacctccaga tgacatccct gaagacagaa gatacagccg    4380
tgtactactg taccacatac accgaggata tgaggtactt cgactggctg ctgagaggtg    4440
gagagacttt cgactactgg ggtcaaggaa ctctggtgac agttagcagc ggaggtggag    4500
gcagtggagg tggtggatct ggaggaggag ggtctgatat caggctcaca caatctcctt    4560
cttctctctc cgcatccgtt ggcgatcgcg tgaccattac atgcagggct tctcactaca    4620
tctccacata cctgaactgg tatcagcaga aacctggcaa agctccaaag ctgctcatct    4680
atgcagcttc taacctgcaa tctggagtcc cttccagatt ctctggctct ggattcggaa    4740
ctgatttctc cctcactatc agcagcctcc agcctgagga tttcgctaca tatcattgcc    4800
agcaaagcta ctccactcca ggcaggtata ctttcggtca aggaacaaaa gtcgagatca    4860
```

```
aaagggaaat cgagcagaag ctgatttccg aagaggatct caatggagtg actgtcagca    4920
gcgctctgtc taactccatc atgtacttct cacacttcgt gccagtgttc ctccctgcta    4980
aacccaccac aactccagca cctagacctc ccactccagc accaactatt gcatcccagc    5040
ctctctccct cagaccagaa gcatgcagac ctgcagcagg tggagctgtg cacacaagag    5100
gtctggaccc tttctgggtc ctcgtggtgg tgggtggagt cctggcatgt tacagcctcc    5160
tggtcaccgt ggcattcatc atcttctggg tgagatctaa gaggagcaga ctgctgcact    5220
ctgattacat gaacatgaca cccagaagac ctggtcccac cagaaagcac taccaaccct    5280
acgcaccacc aagagacttt gctgcataca gaagtctcga gagggtcaag ttctcaagga    5340
gtgcagatgc tccagcctat caacagggtc agaaccaact gtacaacgag ctgaatctcg    5400
gaagaagaga ggagtacgat gtgctggata agagaagagg cagggaccca gagatgggtg    5460
ggaaacccag aagaaagaat cctcaagagg gactgtacaa tgagctgcag aaggataaga    5520
tggctgaggc atactcagag atcggtatga agggagagag gagaagaggc aaaggtcatg    5580
atggtctgta ccaaggtctg tccacagcaa caaaggatac atatgatgct ctgcacatgc    5640
aggcactccc accacggggt tccggagtga acagactttt gaactttgac cttctcaagt    5700
tggctggaga cgtcgagtcc aaccctggtc ccatgaccga gtacaagccc acggtgcgcc    5760
tcgccacccg cgacgacgtc cccgggccg tacgcaccct cgccgccgcg ttcgccgact    5820
acccccgccac gcgccacacc gtcgatccgg accgccacat cgagcgggtc accgagctgc    5880
aagaactctt cctcacgcgc gtcgggctcg acatcggcaa ggtgtgggtc gcggacgacg    5940
gcgccgcggt ggcggtctgg accacgccgg agagcgtcga agcgggggcg gtgttcgccg    6000
agatcggccc gcgcatggcc gagttgagcg gttcccggct ggccgcgcag caacagatgg    6060
aaggcctcct ggcgccgcac cggcccaagg agcccgcgtg gttcctggcc accgtcggcg    6120
tctcgcccga ccaccagggc aagggtctgg gcagcgccgt cgtgctcccc ggagtggagg    6180
cggccgagcg cgccggggtg cccgccttcc tggagacctc cgcgccccgc aacctcccct    6240
tctacgagcg gctcggcttc accgtcaccg ccgacgtcga ggtgcccgaa ggaccgcgca    6300
cctggtgcat gacccgcaag cccggtgcct gattaattaa gtcgacaatc aacctctgga    6360
ttacaaaatt tgtgaaagat tgactggtat tcttaactat gttgctcctt ttacgctatg    6420
tggatacgct gctttaatgc cttttgtatca tgctattgct tcccgtatgg ctttcatttt    6480
ctcctccttg tataaatcct ggttgctgtc tctttatgag gagttgtggc ccgttgtcag    6540
gcaacgtggc gtggtgtgca ctgtgtttgc tgacgcaacc cccactggtt ggggcattgc    6600
caccacctgt cagctccttt ccgggacttt cgctttcccc ctccctattg ccacggcgga    6660
actcatcgcc gcctgccttg cccgctgctg gacaggggct cggctgttgg gcactgacaa    6720
ttccgtggtg ttgtcgggga aatcatcgtc ctttccttgg ctgctcgcct gtgttgccac    6780
ctggattctg cgcgggacgt ccttctgcta cgtcccttcg ccctcaatc cagcggacct    6840
tccttcccgc ggcctgctgc cggctctgcg gcctcttccg cgtcttcgcc ttcgccctca    6900
gacgagtcgg atctcccttt gggccgcctc cccgcctggt acctttaaga ccaatgactt    6960
acaaggcagc tgtagatctt agccactttt taaaagaaaa ggggggactg aagggctaa     7020
ttcactccca acgaagataa gatctgcttt ttgcttgtac tgggtctctc tggttagacc    7080
agatctgagc ctgggagctc tctggctaac tagggaaccc actgcttaag cctcaataaa    7140
gcttgccttg agtgcttcaa gtagtgtgtg cccgtctgtt gtgtgactct ggtaactaga    7200
gatccctcag acccttttag tcagtgtgga aaatctctag cagtagtagt tcatgtcatc    7260
```

| | |
|---|---|
| ttattattca gtatttataa cttgcaaaga aatgaatatc agagagtgag aggaacttgt | 7320 |
| ttattgcagc ttataatggt tacaaataaa gcaatagcat cacaaatttc acaaataaag | 7380 |
| catttttttc actgcattct agttgtggtt tgtccaaact catcaatgta tcttatcatg | 7440 |
| tctggctcta gctatcccgc ccctaactcc gcccatcccg cccctaactc cgcccagttc | 7500 |
| cgcccattct ccgccccatg gctgactaat ttttttatt tatgcagagg ccgaggccgc | 7560 |
| ctcggcctct gagctattcc agaagtagtg aggaggcttt tttggaggcc tagacttttg | 7620 |
| cagagacggc ccaaattcgt aatcatggtc atagctgttt cctgtgtgaa attgttatcc | 7680 |
| gctcacaatt ccacacaaca tacgagccgg aagcataaag tgtaaagcct ggggtgccta | 7740 |
| atgagtgagc taactcacat taattgcgtt gcgctcactg cccgctttcc agtcgggaaa | 7800 |
| cctgtcgtgc cagctgcatt aatgaatcgg ccaacgcgcg gggagaggcg gtttgcgtat | 7860 |
| tgggcgctct tccgcttcct cgctcactga ctcgctgcgc tcggtcgttc ggctgcggcg | 7920 |
| agcggtatca gctcactcaa aggcggtaat acggttatcc acagaatcag gggataacgc | 7980 |
| aggaaagaac atgtgagcaa aaggccagca aaaggccagg aaccgtaaaa aggccgcgtt | 8040 |
| gctggcgttt ttccataggc tccgcccccc tgacgagcat cacaaaaatc gacgctcaag | 8100 |
| tcagaggtgg cgaaacccga caggactata aagataccag gcgtttcccc ctggaagctc | 8160 |
| cctcgtgcgc tctcctgttc cgaccctgcc gcttaccgga tacctgtccg cctttctccc | 8220 |
| ttcgggaagc gtggcgcttt ctcatagctc acgctgtagg tatctcagtt cggtgtaggt | 8280 |
| cgttcgctcc aagctgggct gtgtgcacga accccccgtt cagcccgacc gctgcgcctt | 8340 |
| atccggtaac tatcgtcttg agtccaaccc ggtaagacac gacttatcgc cactggcagc | 8400 |
| agccactggt aacaggatta gcagagcgag gtatgtaggc ggtgctacag agttcttgaa | 8460 |
| gtggtggcct aactacggct acactagaag gacagtattt ggtatctgcg ctctgctgaa | 8520 |
| gccagttacc ttcggaaaaa gagttggtag ctcttgatcc ggcaaacaaa ccaccgctgg | 8580 |
| tagcggtggt ttttttgttt gcaagcagca gattacgcgc agaaaaaaag gatctcaaga | 8640 |
| agatcctttg atcttttcta cggggtctga cgctcagtgg aacgaaaact cacgttaagg | 8700 |
| gattttggtc atgagattat caaaaaggat cttcacctag atccttttaa attaaaaatg | 8760 |
| aagttttaaa tcaatctaaa gtatatatga gtaaacttgg tctgacagtt accaatgctt | 8820 |
| aatcagtgag gcacctatct cagcgatctg tctatttcgt tcatccatag ttgcctgact | 8880 |
| ccccgtcgtg tagataacta cgatacggga gggcttacca tctggcccca gtgctgcaat | 8940 |
| gataccgcga gacccacgct caccggctcc agatttatca gcaataaacc agccagccgg | 9000 |
| aagggccgag cgcagaagtg gtcctgcaac tttatccgcc tccatccagt ctattaattg | 9060 |
| ttgccgggaa gctagagtaa gtagttcgcc agttaatagt ttgcgcaacg ttgttgccat | 9120 |
| tgctacaggc atcgtggtgt cacgctcgtc gtttggtatg gcttcattca gctccggttc | 9180 |
| ccaacgatca aggcgagtta catgatcccc catgttgtgc aaaaaagcgg ttagctcctt | 9240 |
| cggtcctccg atcgttgtca gaagtaagtt ggccgcagtg ttatcactca tggttatggc | 9300 |
| agcactgcat aattctctta ctgtcatgcc atccgtaaga tgcttttctg tgactggtga | 9360 |
| gtactcaacc aagtcattct gagaatagtg tatgcggcga ccgagttgct cttgcccggc | 9420 |
| gtcaatacgg gataataccg cgccacatag cagaacttta aaagtgctca tcattggaaa | 9480 |
| acgttcttcg gggcgaaaac tctcaaggat cttaccgctg ttgagatcca gttcgatgta | 9540 |
| acccactcgt gcacccaact gatcttcagc atcttttact ttcaccagcg tttctgggtg | 9600 |

| | |
|---|---|
| agcaaaaaca ggaaggcaaa atgccgcaaa aagggaata agggcgacac ggaaatgttg | 9660 |
| aatactcata ctcttccttt ttcaatatta ttgaagcatt tatcagggtt attgtctcat | 9720 |
| gagcggatac atatttgaat gtatttagaa aaataaacaa ataggggttc cgcgcacatt | 9780 |
| tccccgaaaa gtgccacctg acgtctaaga aaccattatt atcatgacat taacctataa | 9840 |
| aaataggcgt atcacgaggc cctttcgtct cgcgcgtttc ggtgatgacg gtgaaaacct | 9900 |
| ctgacacatg cagctcccgg agacggtcac agcttgtctg taagcggatg ccgggagcag | 9960 |
| acaagcccgt cagggcgcgt cagcgggtgt tggcgggtgt cggggctggc ttaactatgc | 10020 |
| ggcatcagag cagattgtac tgagagtgca ccatatgcgg tgtgaaatac cgcacagatg | 10080 |
| cgtaaggaga aaataccgca tcaggcgcca ttcgccattc aggctgcgca actgttggga | 10140 |
| agggcgatcg gtgcgggcct cttcgctatt acgccagctg gcgaaagggg gatgtgctgc | 10200 |
| aaggcgatta agttgggtaa cgccagggtt ttcccagtca cgacgttgta aaacgacggc | 10260 |
| cagtgccaag ctg | 10273 |

<210> SEQ ID NO 47
<211> LENGTH: 10992
<212> TYPE: DNA
<213> ORGANISM: Artificial Sequence
<220> FEATURE:
<223> OTHER INFORMATION: Synthetic

<400> SEQUENCE: 47

| | |
|---|---|
| actcttcctt tttcaatatt attgaagcat ttatcagggt tattgtctca tgagcggata | 60 |
| catatttgaa tgtatttaga aaaataaaca ataggggttc cgcgcacatt tccccgaaaa | 120 |
| agtgccacct aaattgtaag cgttaatatt ttgttaaaat tcgcgttaaa ttttttgttaa | 180 |
| atcagctcat tttttaacca ataggccgaa atcggcaaaa tcccttataa atcaaaagaa | 240 |
| tagaccgaga tagggttgag tgttgttcca gtttggaaca agagtccact attaaagaac | 300 |
| gtggactcca acgtcaaagg gcgaaaaacc gtctatcagg gcgatggccc actacgtgaa | 360 |
| ccatcaccct aatcaagttt tttggggtcg aggtgccgta aagcactaaa tcggaaccct | 420 |
| aaagggagcc cccgatttag agcttgacgg ggaaagccgg cgaacgtggc gagaaaggaa | 480 |
| gggaagaaag cgaaaggagc gggcgctagg gcgctggcaa gtgtagcggt cacgctgcgc | 540 |
| gtaaccacca cacccgccgc gcttaatgcg ccgctacagg gcgcgtccca ttcgccattc | 600 |
| aggctgcgca actgttggga agggcgatcg gtgcgggcct cttcgctatt acgccagctg | 660 |
| gcgaaagggg gatgtgctgc aaggcgatta agttgggtaa cgccagggtt ttcccagtca | 720 |
| cgacgttgta aaacgacggc cagtgagcgc gcctcgttca ttcacgtttt tgaacccgtg | 780 |
| gaggacgggc agactcgcgg tgcaaatgtg ttttacagcg tgatggagca gatgaagatg | 840 |
| ctcgacacgc tgcagaacac gcagctagat taaccctaga aagataatca tattgtgacg | 900 |
| tacgttaaag ataatcatgt gtaaaattga cgcatgtgtt ttatcggtct gtatatcgag | 960 |
| gtttatttat taatttgaat agatattaag ttttattata tttacactta catactaata | 1020 |
| ataaattcaa caaacaattt atttatgttt atttatttat taaaaaaaac aaaaactcaa | 1080 |
| aatttcttct ataaagtaac aaaacttttta tgagggacag cccccccca aagccccag | 1140 |
| ggatgtaatt acgtccctcc cccgctaggg ggcagcagcg agccgcccgg ggctccgctc | 1200 |
| cggtccggcg ctccccccgc atcccgagcc cggcagcgtg cggggacagc ccgggcacgg | 1260 |
| ggaaggtggc acgggatcgc tttcctctga acgcttctcg ctgctctttg agcctgcaga | 1320 |
| cacctggggg gatacgggga aaaggcctcc acggccacta gtattatgcc cagtacatga | 1380 |

-continued

```
ccttatggga ctttcctact tggcagtaca tctacgtatt agtcatcgct attaccatgg   1440
tgatgcggtt ttggcagtac atcaatgggc gtggatagcg gtttgactca cggggatttc   1500
caagtctcca ccccattgac gtcaatggga gtttgttttg gcaccaaaat caacgggact   1560
ttccaaaatg tcgtaacaac tccgccccat tgacgcaaat gggcggtagg cgtgtacggt   1620
gggaggttta tataagcaga gctcgtttag tgaaccgtca gatcgcctgg agacgccatc   1680
cacgctgttt tgacctccat agaagattct agagccacca tggaaactga tacactcctg   1740
ctctgggttc tgctgctgtg ggttcctggc tctactggtg attatccata cgatgttcca   1800
gattatgctg gatccctgcc tatcctcgaa atcgcaagca caaccaacc acagaatgtt   1860 gattccgtgt gcagcggtac actccagaag actgaggatg ttcacctcat gggtttcact   1920
ctctctggcc agaaggtggc agactctcct ctggaggctt ctaagagatg gcattcagg   1980 actggtgtgc cacctaagaa tgttgagtat accgaaggtg aggaggccaa gacatgctac   2040
aacatctccg tgaccgaccc atctggaaag tccctcctgc tggaccctcc cactaacatc   2100
agagactacc caaagtgcaa gaccatccac cacatccagg gtcagaatcc acatgcccag   2160
ggtatcgctc tgcatctgtg gggagccttc tttctctacg accgcatcgc ttccaccaca   2220
atgtacagag gtaaggtctt taccgagggt aacatcgctg caatgattgt gaacaagacc   2280
gtgcacaaga tgatcttctc tcgccaggga cagggctatc gccacatgaa tctgacttcc   2340
acaaacaagt attggaccag cagcaacgga acccagacca atgatactgg ctgtttcgga   2400
gcactccagg aatacaactc caccaagaat cagacctgcg ctccttctaa gatcccacca   2460
ccactcccaa ctgcaagacc tgaaatcaag ctcacaagca cacctaccga tgccaccaaa   2520
ctcaacacca cagatccatc ttctgacgac gaagacctcg ctacaagcgg ttctggctcc   2580
ggtgagaggg aacctcacac aaccagcgac gcagtgacca acagggact ctctagcact   2640 atgccaccca caccaagccc tcaacctagc actcctcagc agggaggaaa caatactaac   2700
cactctcaag atgcagttac tgaactggat aagaacaaca caactgctca accctctatg   2760
cctcctcata acactaccac tatcagcaca aacaacacat ccaaacacaa cttctctacc   2820
ctctccgcac ctctgcagaa taccaccaac gacaacaccc agagcactat cacagagaac   2880
gaacagacct ccgctccatc cattactacc ctgccaccta caggcaatcc cacaacagct   2940
aagtccacca gctctaagaa gggaccagcc acaaccgctc caatactac aaatgagcac   3000 ttcacatctc ctccacctac tccatcctct acagctcagc acctcgtcta ctttaggagg   3060
aagaggtcca tcctgtggag ggaaggcgat atgttcccct tcctggatgg cctcatcaac   3120
gctcccattg actttgatcc agtgccaaac actaagacta tctttgacga atcctcttct   3180
tccggagcca gcgcagaaga ggaccagcac gcttctccca catttccct gacactcagc   3240 tactttccaa acatcaacga gaatactgcc tattctggag agaatgagaa cgactgtgat   3300
gctgaactgc gcatctggtc cgttcaggag gatgatctgg cagcaggact ctcttggatt   3360
cccttcttcg gacctggtat cgagggtctg tatactgcag tcctcatcaa gaaccagaac   3420
aacctcgttt gcaggctgag gagactggca accagactg ccaaatccct ggaactgctg   3480
ctgagggtca ctaccgagga gagaaccttt agcctgatca ataggcacgc aatcgacttc   3540
ctcctgacca ggtggggcgg aacttgtaaa gtgctgggtc cagactgctg tatcggcatc   3600
gaggatctgt ccaagaacat ttccgaacaa atcgaccaga tcaagaagga tgagcagaag   3660
gaaggtacag gttgggtct gggtggaaag tggtggacct ccgattgggg agtgctgaca   3720
```

```
aacctcggca ttctcctgct gctgtccatc gcagtgctca tcgcactctc ttgtatctgc   3780
aggatcttca ctaagtacat tggaggttct ggtgtgaaac agactttgaa ttttgacctt   3840
ctcaagttgg cgggagacgt cgagtccaac cctgggccca tggaagatgc caaaaacatt   3900
aagaagggcc cagcgccatt ctacccactc gaagacggga ccgccggcga gcagctgcac   3960
aaagccatga agcgctacgc cctggtgccc ggcaccatcg cctttaccga cgcacatatc   4020
gaggtggaca ttacctacgc cgagtacttc gagatgagcg ttcggctggc agaagctatg   4080
aagcgctatg ggctgaatac aaaccatcgg atcgtggtgt gcagcgagaa tagcttgcag   4140
ttcttcatgc ccgtgttggg tgccctgttc atcggtgtgg ctgtggcccc agctaacgac   4200
atctacaacg agcgcgagct gctgaacagc atgggcatca gccagcccac cgtcgtattc   4260
gtgagcaaga aagggctgca aaagatcctc aacgtgcaaa agaagctacc gatcatacaa   4320
aagatcatca tcatggatag caagaccgac taccagggct tccaaagcat gtacaccttc   4380
gtgacttccc catttgccac cggcttcaac gagtacgact tcgtgcccga gagcttcgac   4440
cgggacaaaa ccatcgccct gatcatgaac agtagtggca gtaccggatt gcccaagggc   4500
gtagccctac cgcaccgcac cgcttgtgtc cgattcagtc atgcccgcga ccccatcttc   4560
ggcaaccaga tcatccccga caccgctatc ctcagcgtgg tgccatttca ccacggcttc   4620
ggcatgttca ccacgctggg ctacttgatc tgcggctttc gggtcgtgct catgtaccgc   4680
ttcgaggagg agctattctt gcgcagcttg caagactata agattcaatc tgccctgctg   4740
gtgcccacac tatttagctt cttcgctaag agcactctca tcgacaagta cgacctaagc   4800
aacttgcacg agatcgccag cggcggggcg ccgctcagca aggaggtagg tgaggccgtg   4860
gccaaacgct tccacctacc aggcatccgc cagggctacg gcctgacaga aacaaccagc   4920
gccattctga tcacccccga aggggacgac aagcctggcg cagtaggcaa ggtggtgccc   4980
ttcttcgagg ctaaggtggt ggacttggac accggtaaga cactgggtgt gaaccagcgc   5040
ggcgagctgt gcgtccgtgg ccccatgatc atgagcggct acgttaacaa ccccgaggct   5100
acaaacgctc tcatcgacaa ggacggctgg ctgcacagcg gcgacatcgc ctactgggac   5160
gaggacgagc acttcttcat cgtggaccgg ctgaagagcc tgatcaaata caagggctac   5220
caggtagccc cagccgaact ggagagcatc ctgctgcaac accccaacat cttcgacgcc   5280
ggggtcgccg gcctgcccga cgacgatgcc ggcgagctgc ccgccgcagt cgtcgtgctg   5340
gaacacggta aaaccatgac cgagaaggag atcgtggact atgtggccag ccaggttaca   5400
accgccaaga gctgcgcggc tggtgttgtg ttcgtggacg aggtgcctaa aggactgacc   5460
ggcaagttgg acgcccgcaa gatccgcgag attctcatta aggccaagaa gggcggcaag   5520
atcgccgtgg gaagcggagc tactaacttc agcctgctga gcaggctgga gacgtggag   5580
gagaaccctg gacctatgga tagcactgag aacgtcatca gcccttcat gcgcttcaag   5640
gtgcacatgg agggctccgt gaacggccac gagttcgaga tcgagggcgt gggcgagggc   5700
aagccctacg agggcaccca gaccgccaag ctgcaagtga ccaagggcgg ccccctgccc   5760
ttcgcctggg acatcctgtc cccccagttc ttctacggct ccaaggcgta catcaagcac   5820
cccgccgaca tccccgacta cctcaagcag tccttcccg agggcttcaa gtgggagcgc   5880
gtgatgaact tcgaggacgg cggcgtggtg accgtgaccc aggactcctc cctgcaggac   5940
ggcacccctca tctaccacgt gaagttcatc ggcgtgaact tcccctccga cggccccgta   6000
atgcagaaga gactctgggg ctgggagccc tccactgagc gcaactaccc ccgcgacggc   6060
gtgctgaagg gcgagaacca catggcgctg aagctgaagg gcggcggcca ctacctgtgt   6120
```

```
gagttcaagt ccatctacat ggccaagaag cccgtgaagc tgcccggcta ccactacgtg   6180
gactacaagc tcgacatcac ctcccacaac gaggactaca ccgtggtgga gcagtacgag   6240
cgcgccgagg cccgccacca cctgttccag taatgataac gcggccgcga aggatctgcg   6300
atcgctccgg tgcccgtcag tgggcagagc gcacatcgcc cacagtcccc gagaagttgg   6360
ggggaggggt cggcaattga acgggtgcct agagaaggtg gcgcggggta aactgggaaa   6420
gtgatgtcgt gtactggctc cgcctttttc ccgagggtgg gggagaaccg tatataagtg   6480
cagtagtcgc cgtgaacgtt cttttttcgca acgggtttgc cgccagaaca cagctgaagc   6540 ttcgagggge tcgcatctct ccttcacgcg cccgccgccc tacctgaggc cgccatccac   6600
gccggttgag tcgcgttctg ccgcctcccg cctgtggtgc ctcctgaact gcgtccgccg   6660
tctaggtaag tttaaagctc aggtcgagac cgggcctttg tccggcgctc ccttggagcc   6720
tacctagact cagccggctc tccacgcttt gcctgaccct gcttgctcaa ctctacgtct   6780
ttgtttcgtt ttctgttctg cgccgttaca gatccaagct gtgaccggcg cctacgctag   6840
atgaccgagt acaagcccac ggtgcgcctc gccacccgcg acgacgtccc cagggccgta   6900
cgcaccctcg ccgccgcgtt cgccgactac cccgccacgc gccacaccgt cgatccggac   6960
cgccacatcg agcgggtcac cgagctgcaa gaactcttcc tcacgcgcgt cgggctcgac   7020
atcggcaagg tgtgggtcgc ggacgacggc gccgcggtgg cggtctggac cacgccggag   7080
agcgtcgaag cgggggcggt gttcgccgag atcggcccgc gcatggccga gttgagcggt   7140
tcccggctgg ccgcgcagca acagatggaa ggcctcctgg cgccgcaccg gcccaaggag   7200
cccgcgtggt tcctggccac cgtcggcgtc tcgcccgacc accagggcaa gggtctgggc   7260
agcgccgtcg tgctccccgg agtggaggcg gccgagcgcg ccggggtgcc cgccttcctg   7320
gagacctccg cgccccgcaa cctcccttc tacgagcggc tcggcttcac cgtcaccgcc   7380
gacgtcgagg tgcccgaagg accgcgcacc tggtgcatga cccgcaagcc cggtgcctga   7440
gtcgacaatc aacctctgga ttacaaaatt tgtgaaagat tgactggtat tcttaactat   7500
gttgctcctt ttacgctatg tggatacgct gctttaatgc ctttgtatca tgcgttaact   7560
aaacttgttt attgcagctt ataatggtta caaataaagc aatagcatca caaatttcac   7620
aaataaagca ttttttttcac tgcattctag ttgtggtttg tccaaactca tcaatgtatc   7680
ttatcatgtc tggaattgac tcaaatgatg tcaattagtc tatcagaagc tcatctggtc   7740
tcccttccgg gggacaagac atccctgttt aatatttaaa cagcagtgtt cccaaactgg   7800
gttcttatat cccttgctct ggtcaaccag gttgcagggt ttcctgtcct cacaggaacg   7860
aagtccctaa agaaacagtg gcagccaggt ttagccccgg aattgactgg attccttttt   7920
tagggcccat tggtatggct ttttccccgt atccccccag gtgtctgcag gctcaaagag   7980
cagcgagaag cgttcagagg aaagcgatcc cgtgccacct tccccgtgcc cgggctgtcc   8040
ccgcacgctg ccggctcggg gatgcggggg gagcgccgga ccgagcggaa gccccgggcg   8100
gctcgctgct gccccctagc gggggaggga cgtaattaca tccctggggg ctttgggggg   8160
gggctgtccc tgatatctat aacaagaaaa tatatatata ataagttatc acgtaagtag   8220
aacatgaaat aacaatataa ttatcgtatg agttaaatct taaagtcac gtaaaagata   8280 atcatgcgtc attttgactc acgcggtcgt tatagttcaa aatcagtgac acttaccgca   8340
ttgacaagca cgcctcacgg gagctccaag cggcgactga gatgtcctaa atgcacagcg   8400
acggattcgc gctatttaga aagagagagc aatatttcaa gaatgcatgc gtcaatttta   8460
```

```
cgcagactat ctttctaggg ttaatctagc tgcatcagga tcatatcgtc gggtcttttt    8520
tccggctcag tcatcgccca agctggcgct atctgggcat cggggaggaa gaagcccgtg    8580
cctttcccg cgaggttgaa gcggcatgga aagagtttgc cgaggatgac tgctgctgca    8640
ttgacgttga gcgaaaacgc acgtttacca tgatgattcg ggaaggtgtg gccatgcacg    8700
cctttaacgg tgaactgttc gttcaggcca cctgggatac cagttcgtcg cggcttttcc    8760
ggacacagtt ccgatggtc agcccgaagc gcatcagcaa cccgaacaat accggcgaca    8820
gccggaactg ccgtgccggt gtgcagatta atgacagcgg tgcggcgctg ggatattacg    8880
tcagcgagga cgggtatcct ggctggatgc cgcagaaatg gacatggata ccccgtgagt    8940
tacccggcgg gcgcgcttgg cgtaatcatg gtcatagctg tttcctgtgt gaaattgtta    9000
tccgctcaca attccacaca acatacgagc cggaagcata aagtgtaaag cctggggtgc    9060
ctaatgagtg agctaactca cattaattgc gttgcgctca ctgcccgctt tccagtcggg    9120
aaacctgtcg tgccagctgc attaatgaat cggccaacgc gcgggagag gcggtttgcg    9180
tattgggcgc tcttccgctt cctcgctcac tgactcgctg cgctcggtcg ttcggctgcg    9240
gcgagcggta tcagctcact caaaggcggt aatacggtta ccacagaat caggggataa    9300
cgcaggaaag aacatgtgag caaaaggcca gcaaaaggcc aggaaccgta aaaaggccgc    9360
gttgctggcg ttttccata ggctccgccc ccctgacgag catcacaaaa atcgacgctc    9420
aagtcagagg tggcgaaacc cgacaggact ataaagatac caggcgtttc ccctggaag    9480
ctccctcgtg cgctctcctg ttccgaccct gccgcttacc ggatacctgt ccgcctttct    9540
cccttcggga agcgtggcgc tttctcatag ctcacgctgt aggtatctca gttcggtgta    9600
ggtcgttcgc tccaagctgg gctgtgtgca cgaacccccc gttcagcccg accgctgcgc    9660
cttatccggt aactatcgtc ttgagtccaa cccggtaaga cacgacttat cgccactggc    9720
agcagccact ggtaacagga ttagcagagc gaggtatgta ggcggtgcta cagagttctt    9780
gaagtggtgg cctaactacg gctacactag aaggacagta tttggtatct gcgctctgct    9840
gaagccagtt accttcggaa aaagagttgg tagctcttga tccggcaaac aaaccaccgc    9900
tggtagcggt ggtttttttg tttgcaagca gcagattacg cgcagaaaaa aaggatctca    9960
agaagatcct ttgatctttt ctacggggtc tgacgctcag tggaacgaaa actcacgtta   10020
agggattttg gtcatgagat tatcaaaaag gatcttcacc tagatccttt taaattaaaa   10080
atgaagtttt aaatcaatct aaagtatata tgagtaaact tggtctgaca gttaccaatg   10140
cttaatcagt gaggcaccta tctcagcgat ctgtctattt cgttcatcca tagttgcctg   10200
actccccgtc gtgtagataa ctacgatacg ggagggctta ccatctggcc ccagtgctgc   10260
aatgataccg cgagacccac gctcaccggc tccagattta tcagcaataa accagccagc   10320
cggaagggcc gagcgcagaa gtggtcctgc aactttatcc gcctccatcc agtctattaa   10380
ttgttgccgg gaagctagag taagtagttc gccagttaat agtttgcgca acgttgttgc   10440
cattgctaca ggcatcgtgg tgtcacgctc gtcgtttggt atggcttcat tcagctccgg   10500
ttcccaacga tcaaggcgag ttacatgatc ccccatgttg tgcaaaaaag cggttagctc   10560
cttcggtcct ccgatcgttg tcagaagtaa gttggccgca gtgttatcac tcatggttat   10620
ggcagcactg cataattctc ttactgtcat gccatccgta agatgctttt ctgtgactgg   10680
tgagtactca accaagtcat tctgagaata gtgtatgcgg cgaccgagtt gctcttgccc   10740
ggcgtcaata cgggataata ccgcgccaca tagcagaact ttaaaagtgc tcatcattgg   10800
aaaacgttct tcggggcgaa aactctcaag gatcttaccg ctgttgagat ccagttcgat   10860
```

```
gtaacccact cgtgcaccca actgatcttc agcatctttt actttcacca gcgtttctgg    10920
gtgagcaaaa acaggaaggc aaaatgccgc aaaaaaggga ataagggcga cacggaaatg    10980
ttgaatactc at                                                        10992
```

<210> SEQ ID NO 48
<211> LENGTH: 10249
<212> TYPE: DNA
<213> ORGANISM: Artificial Sequence
<220> FEATURE:
<223> OTHER INFORMATION: Synthetic

<400> SEQUENCE: 48

```
acgcgtgtag tcttatgcaa tactcttgta gtcttgcaac atggtaacga tgagttagca      60
acatgcctta caaggagaga aaaagcaccg tgcatgccga ttggtggaag taaggtggta     120
cgatcgtgcc ttattaggaa ggcaacagac gggtctgaca tggattggac gaaccactga     180
attgccgcat tgcagagata ttgtatttaa gtgcctagct cgatacaata aacgggtctc     240
tctggttaga ccagatctga gcctgggagc tctctggcta actagggaac ccactgctta     300
agcctcaata aagcttgcct tgagtgcttc aagtagtgtg tgcccgtctg ttgtgtgact     360
ctggtaacta gagatccctc agaccctttt agtcagtgtg gaaaatctct agcagtggcg     420
cccgaacagg gacctgaaag cgaaagggaa accagagctc tctcgacgca ggactcggct     480
tgctgaagcg cgcacggcaa gaggcgaggg gcggcgactg gtgagtacgc caaaaatttt     540
gactagcgga ggctagaagg agagagatgg gtgcgagagc gtcagtatta agcggggag     600 aattagatcg cgatgggaaa aaattcggtt aaggccaggg ggaaagaaaa aatataaatt     660
aaaacatata gtatgggcaa gcagggagct agaacgattc gcagttaatc ctggcctgtt     720
agaaacatca gaaggctgta gacaaatact gggacagcta caaccatccc ttcagacagg     780
atcagaagaa cttagatcat tatataatac agtagcaacc ctctattgtg tgcatcaaag     840
gatagagata aaagacacca aggaagcttt agacaagata gaggaagagc aaaacaaaag     900
taagaccacc gcacagcaag cggccactga tcttcagacc tggaggagga gatatgaggg     960
acaattggag aagtgaatta tataaatata agtagtaaa aattgaacca ttaggagtag    1020
cacccaccaa ggcaaagaga agagtggtgc agagagaaaa aagagcagtg gaataggag    1080 ctttgttcct tgggttcttg ggagcagcag gaagcactat gggcgcagcg tcaatgacgc    1140
tgacggtaca ggccagacaa ttattgtctg gtatagtgca gcagcagaac aatttgctga    1200
gggctattga ggcgcaacag catctgttgc aactcacagt ctggggcatc aagcagctcc    1260
aggcaagaat cctggctgtg gaaagatacc taaaggatca acagctcctg gggatttggg    1320
gttgctctgg aaaactcatt tgcaccactg ctgtgccttg gaatgctagt tggagtaata    1380
aatctctgga acagatttgg aatcacacga cctggatgga gtgggacaga gaaattaaca    1440
attacacaag cttaatacac tccttaattg aagaatcgca aaaccagcaa gaaaagaatg    1500
aacaagaatt attggaatta gataaatggg caagtttgtg gaattggttt aacataacaa    1560
attggctgtg gtatataaaa ttattcataa tgatagtagg aggcttggta ggtttaagaa    1620 tagttttgc tgtactttct atagtgaata gagttaggca gggatattca ccattatcgt    1680
ttcagaccca cctcccaacc ccgagggac ccgacaggcc cgaaggaata agaagaag    1740 gtggagagag agacagagac agatccattc gattagtgaa cggatctcga cggtatcggt    1800
taacttttaa aagaaaaggg gggattgggg ggtacagtgc aggggaaaga atagtagaca    1860
```

| | |
|---|---|
| taatagcaac agacatacaa actaaagaat tacaaaaaca aattacaaaa ttcaaaattt | 1920 |
| tatcgatgct agcggaggaa aaactgtttc atacagaagg cgtggaggaa aaactgtttc | 1980 |
| atacagaagg cgtggaggaa aaactgtttc atacagaagg cgtggaggaa aaactgtttc | 2040 |
| atacagaagg cgtggaggaa aaactgtttc atacagaagg cgtggaggaa aaactgtttc | 2100 |
| atacagaagg cgtagatcta gactctagag gtatataat ggaagctcga cttccagctt | 2160 |
| ggcattccgg tactgttggt aaaaagcttg gcaatccggt actgttggta aaggatccgc | 2220 |
| caccatgcct gccatgaaga ttgagtgccg catcacggga accctgaacg gagtggagtt | 2280 |
| tgagctggtc ggaggtggag aagggactcc tgagcaggga cgtatgacca acaagatgaa | 2340 |
| gtctaccaag ggcgccttga ccttctcccc ctaccttctc tctcatgtca tgggatacgg | 2400 |
| gttctaccac tttggtacct atcccagtgg gtatgagaat cccttcctgc atgccatcaa | 2460 |
| caacgggggg tacaccaaca ccaggattga gaagtatgag gatggaggag ttcttcatgt | 2520 |
| tagctttagc tacagatatg aagcaggcag ggtgattggg gatttcaagg ttgtcgggac | 2580 |
| aggattccct gaggacagtg tgatcttcac cgacaagatc atccggtcca atgctaccgt | 2640 |
| ggagcacttg cacccaatgg gagacaacgt tcttgtgggc tccttcgcga gaaccttttc | 2700 |
| cctgagggat ggaggctact actcatttgt ggttgacagc cacatgcact tcaagagtgc | 2760 |
| catccaccca tccatcctcc agaacggggg gcccatgttt gccttcagga gagttgagga | 2820 |
| acttcactcc aacactgaac ttggcattgt agagtatcaa catgccttca agactcccat | 2880 |
| agcatttgct ggaagcggag ctactaactt cagcctgctg aagcaggctg agacgtgga | 2940 |
| ggagaaccct ggacctatgg tcttcacact cgaagatttc gttggggact ggcgacagac | 3000 |
| agccggctac aacctggacc aagtccttga acagggaggt gtgtccagtt tgtttcagaa | 3060 |
| tctcggggtg tccgtaactc cgatccaaag gattgtcctg agcggtgaaa atgggctgaa | 3120 |
| gatcgacatc catgtcatca tcccgtatga aggtctgagc ggcgaccaaa tgggccagat | 3180 |
| cgaaaaaatt tttaaggtgg tgtaccctgt ggatgatcat cacttaagg tgatcctgca | 3240 |
| ctatggcaca ctggtaatcg acggggttac gccgaacatg atcgactatt cggacggcc | 3300 |
| gtatgaaggc atcgccgtgt tcgacggcaa aaagatcact gtaacaggga ccctgtggaa | 3360 |
| cggcaacaaa attatcgacg agcgcctgat caaccccgac ggctccctgc tgttccgagt | 3420 |
| aaccatcaac ggagtgaccg gctggcggct gtgcgaacgc attctggcgt aagcggccgc | 3480 |
| gaaggatctg cgatcgctcc ggtgcccgtc agtgggcaga gcgcacatcg cccacagtcc | 3540 |
| ccgagaagtt ggggggaggg gtcggcaatt gaacgggtgc ctagagaagg tggcgcgggg | 3600 |
| taaactggga aagtgatgtc gtgtactggc tccgcctttt tcccgagggt ggggagaac | 3660 |
| cgtatataag tgcagtagtc gccgtgaacg ttcttttcg caacgggttt gccgccagaa | 3720 |
| cacagctgaa gcttcgaggg gctcgcatct ctccttcacg cgcccgccgc cctacctgag | 3780 |
| gccgccatcc acgccggttg agtcgcgttc tgccgcctcc cgcctgtggt gcctcctgaa | 3840 |
| ctgcgtccgc cgtctaggta agtttaaagc tcaggtcgag accgggcctt tgtccggcgc | 3900 |
| tcccttggag cctacctaga ctcagccggc tctccacgct tgcctgacc ctgcttgctc | 3960 |
| aactctacgt ctttgtttcg ttttctgttc tgcgccgtta cagatccaag ctgtgaccgg | 4020 |
| cgcctactag tgccaccatg gactttcaag tgcagatctt cagctttctg ctgatctctg | 4080 |
| ctagtgtcat catgtctcaa ctgcaactcc aagaatctgg tcctggtctg gtcaagcctt | 4140 |
| ctgaaaccct gtctctgaca tgcaccgtct ctggtggctc catttcctct tctagctact | 4200 |
| attggggatg gatcaggcag ccaccaggaa agggactcga atggatcgga agcgtctact | 4260 |

```
actctggagg tgcttcctac aatccttctc tcaagtccag agccaccatc tccgttgata    4320
catctaagaa tcagttcagc ctcaatctgg actccgtcag cgcagcagac acagccatct    4380
actactgtgc ctccatctac ggtagcggta cattctacta ctacttctac atggatgtgt    4440
ggggtaaggg tagcaccgtc accgtgtcca gcggaggtgg aggcagtgga ggtggtggat    4500
ctggaggagg agggtctgat atccaaatga ctcaatctcc atcttccctg tctgcttccg    4560
tcggtgacag agttaccatc acatgccagg ccagccaggt tatcagcaac tacctgaact    4620
ggtatcagca gaagcctgga aaggctccca agctgctgat ctatgataca tctaatctca    4680
agactggtgt gccttccagg ttctccggta gcggatctgg cacagacttc acattcacca    4740
tctcctccct gcagcctgag gacatcgcaa cctactactg tcagcaatac gagaatctgc    4800
agttcacctt cggaccagga acaaaggtgg acatcaagag agaaatcgag cagaagctga    4860
tttccgaaga ggatctcaat ggagtgactg tcagcagcgc tctgtctaac tccatcatgt    4920
acttctcaca cttcgtgcca gtgttcctcc ctgctaaacc caccacaact ccagcaccta    4980
gacctcccac tccagcacca actattgcat cccagcctct ctccctcaga ccagaagcat    5040
gcagacctgc agcaggtgga gctgtgcaca caagaggtct ggacccttt ctgggtcctcg    5100
tggtggtggg tggagtcctg gcatgttaca gcctcctggt caccgtggca ttcatcatct    5160
tctgggtgag atctaagagg agcagactgc tgcactctga ttacatgaac atgacaccca    5220
gaagacctgg tcccaccaga aagcactacc aaccctacgc accaccaaga gactttgctg    5280
catacagaag tctcgagagg gtcaagttct caaggagtgc agatgctcca gcctatcaac    5340
agggtcagaa ccaactgtac aacgagctga atctcggaag aagagaggag tacgatgtgc    5400
tggataagag aagaggcagg gacccagaga tgggtgggaa acccagaaga aagaatcctc    5460
aagagggact gtacaatgag ctgcagaagg ataagatggc tgaggcatac tcagagatcg    5520
gtatgaaggg agagaggaga agaggcaaag gtcatgatgg tctgtaccaa ggtctgtcca    5580
cagcaacaaa ggatacatat gatgctctgc acatgcaggc actcccacca cggggttccg    5640
gagtgaaaca gactttgaac tttgaccttc tcaagttggc tggagacgtc gagtccaacc    5700
ctggtcccat gaccgagtac aagcccacgg tgcgcctcgc cacccgcgac gacgtcccca    5760
gggccgtacg caccctcgcc gccgcgttcg ccgactaccc cgccacgcgc acaccgtcg    5820
atccggaccg ccacatcgag cgggtcaccg agctgcaaga actcttcctc acgcgcgtcg    5880
ggctcgacat cggcaaggtg tgggtcgcgg acgacggcgc gcggtggcg gtctggacca    5940
cgccggagag cgtcgaagcg ggggcggtgt tcgccgagat cggcccgcgc atggccgagt    6000
tgagcggttc ccggctggcc gcgcagcaac agatggaagg cctcctggcg ccgcaccggc    6060
ccaaggagcc cgcgtggttc ctggccaccg tcggcgtctc gcccgaccac cagggcaagg    6120
gtctgggcag cgccgtcgtg ctccccggag tggaggcggc cgagcgcgcc ggggtgcccg    6180
ccttcctgga gacctccgcg ccccgcaacc tccccttcta cgagcggctc ggcttcaccg    6240
tcaccgccga cgtcgaggtg cccgaaggac gcgcacctg tgcatgacc cgcaagcccg    6300
gtgcctgatt aattaagtcg acaatcaacc tctggattac aaaatttgtg aaagattgac    6360
tggtattctt aactatgttg ctcctttac gctatgtgga tacgctgctt taatgccttt    6420
gtatcatgct attgcttccc gtatggcttt cattttctcc tccttgtata atcctggtt    6480
gctgtctctt tatgaggagt tgtggcccgt tgtcaggcaa cgtggcgtgg tgtgcactgt    6540
gtttgctgac gcaacccca ctggttgggg cattgccacc acctgtcagc tcctttccgg    6600
```

```
gactttcgct ttccccctcc ctattgccac ggcggaactc atcgccgcct gccttgcccg   6660
ctgctggaca ggggctcggc tgttgggcac tgacaattcc gtggtgttgt cggggaaatc   6720
atcgtccttt ccttggctgc tcgcctgtgt tgccacctgg attctgcgcg gacgtccttt   6780
ctgctacgtc ccttcggccc tcaatccagc ggaccttcct tcccgcggcc tgctgccggc   6840
tctgcggcct cttccgcgtc ttcgccttcg ccctcagacg agtcggatct ccctttgggc   6900
cgcctccccg cctggtacct ttaagaccaa tgacttacaa ggcagctgta gatcttagcc   6960
actttttaaa agaaaagggg ggactggaag ggctaattca ctcccaacga agataagatc   7020 tgcttttttgc ttgtactggg tctctctggt tagaccagat ctgagcctgg gagctctctg   7080
gctaactagg gaacccactg cttaagcctc aataaagctt gccttgagtg cttcaagtag   7140
tgtgtgcccg tctgttgtgt gactctggta actagagatc cctcagaccc ttttagtcag   7200
tgtggaaaat ctctagcagt agtagttcat gtcatcttat tattcagtat ttataacttg   7260
caaagaaatg aatatcagag agtgagagga acttgtttat tgcagcttat aatggttaca   7320
aataaagcaa tagcatcaca aatttcacaa ataaagcatt ttttcactg cattctagtt   7380 gtggtttgtc caaactcatc aatgtatctt atcatgtctg gctctagcta tcccgcccct   7440
aactccgccc atcccgcccc taactccgcc cagttccgcc cattctccgc cccatggctg   7500
actaattttt tttatttatg cagaggccga ggccgcctcg gcctctgagc tattccagaa   7560
gtagtgagga ggcttttttg gaggcctaga cttttgcaga gacggcccaa attcgtaatc   7620
atggtcatag ctgtttcctg tgtgaaattg ttatccgctc acaattccac acaacatacg   7680
agccggaagc ataaagtgta aagcctgggg tgcctaatga gtgagctaac tcacattaat   7740
tgcgttgcgc tcactgcccg ctttccagtc gggaaacctg tcgtgccagc tgcattaatg   7800
aatcggccaa cgcgcgggga gaggcggttt gcgtattggg cgctcttccg cttcctcgct   7860
cactgactcg ctgcgctcgg tcgttcggct gcggcgagcg gtatcagctc actcaaaggc   7920
ggtaatacgg ttatccacag aatcagggga taacgcagga agaacatgt gagcaaaagg   7980 ccagcaaaag gccaggaacc gtaaaaaggc cgcgttgctg gcgtttttcc ataggctccg   8040 ccccctgac gagcatcaca aaaatcgacg ctcaagtcag aggtggcgaa acccgacagg   8100
actataaaga taccaggcgt ttccccctgg aagctccctc gtgcgctctc ctgttccgac   8160
cctgccgctt accggatacc tgtccgcctt tctcccttcg ggaagcgtgg cgctttctca   8220
tagctcacgc tgtaggtatc tcagttcggt gtaggtcgtt cgctccaagc tgggctgtgt   8280
gcacgaaccc cccgttcagc ccgaccgctg cgccttatcc ggtaactatc gtcttgagtc   8340
caacccggta agacacgact tatcgccact ggcagcagcc actggtaaca ggattagcag   8400
agcgaggtat gtaggcggtg ctacagagtt cttgaagtgg tggcctaact acggctacac   8460
tagaaggaca gtatttggta tctgcgctct gctgaagcca gttaccttcg gaaaaagagt   8520
tggtagctct tgatccggca aacaaaccac cgctggtagc ggtggttttt ttgtttgcaa   8580
gcagcagatt acgcgcagaa aaaaggatc tcaagaagat cctttgatct tttctacggg   8640
gtctgacgct cagtggaacg aaaactcacg ttaagggatt ttggtcatga gattatcaaa   8700
aaggatcttc acctagatcc ttttaaatta aaaatgaagt tttaaatcaa tctaaagtat   8760
atatgagtaa acttggtctg acagttacca atgcttaatc agtgaggcac ctatctcagc   8820
gatctgtcta tttcgttcat ccatagttgc ctgactcccc gtcgtgtaga taactacgat   8880
acgggagggc ttaccatctg gccccagtgc tgcaatgata ccgcgagacc cacgctcacc   8940
ggctccagat ttatcagcaa taaaccagcc agccggaagg gccgagcgca gaagtggtcc   9000
```

```
tgcaacttta tccgcctcca tccagtctat taattgttgc cgggaagcta gagtaagtag    9060
ttcgccagtt aatagtttgc gcaacgttgt tgccattgct acaggcatcg tggtgtcacg    9120
ctcgtcgttt ggtatggctt cattcagctc cggttcccaa cgatcaaggc gagttacatg    9180
atcccccatg ttgtgcaaaa aagcggttag ctccttcggt cctccgatcg ttgtcagaag    9240
taagttggcc gcagtgttat cactcatggt tatggcagca ctgcataatt ctcttactgt    9300
catgccatcc gtaagatgct tttctgtgac tggtgagtac tcaaccaagt cattctgaga    9360
atagtgtatg cggcgaccga gttgctcttg cccggcgtca atacgggata taccgcgcc    9420 acatagcaga actttaaaag tgctcatcat tggaaaacgt tcttcgggc gaaaactctc    9480 aaggatctta ccgctgttga gatccagttc gatgtaaccc actcgtgcac ccaactgatc    9540
ttcagcatct tttactttca ccagcgtttc tgggtgagca aaaacaggaa ggcaaaatgc    9600
cgcaaaaaag ggaataaggg cgacacggaa atgttgaata ctcatactct tcctttttca    9660
atattattga agcatttatc agggttattg tctcatgagc ggatacatat ttgaatgtat    9720
ttagaaaaat aaacaaatag gggttccgcg cacatttccc cgaaaagtgc cacctgacgt    9780
ctaagaaacc attattatca tgacattaac ctataaaaat aggcgtatca cgaggccctt    9840
tcgtctcgcg cgtttcggtg atgacggtga aacctctga cacatgcagc tcccggagac    9900
ggtcacagct tgtctgtaag cggatgccgg gagcagacaa gcccgtcagg gcgcgtcagc    9960
gggtgttggc gggtgtcggg gctggcttaa ctatgcggca tcagagcaga ttgtactgag   10020
agtgcaccat atgcggtgtg aaataccgca cagatgcgta aggagaaaat accgcatcag   10080
gcgccattcg ccattcaggc tgcgcaactg ttgggaaggg cgatcggtgc gggcctcttc   10140
gctattacgc cagctggcga aaggggatg tgctgcaagg cgattaagtt gggtaacgcc   10200
agggttttcc cagtcacgac gttgtaaaac gacggccagt gccaagctg              10249
```

<210> SEQ ID NO 49
<211> LENGTH: 10215
<212> TYPE: DNA
<213> ORGANISM: Artificial Sequence
<220> FEATURE:
<223> OTHER INFORMATION: Synthetic

<400> SEQUENCE: 49

```
actcttcctt tttcaatatt attgaagcat ttatcagggt tattgtctca tgagcggata     60
catatttgaa tgtatttaga aaataaaca aatagggggtt ccgcgcacat ttccccgaaa    120
agtgccacct aaattgtaag cgttaatatt ttgttaaaat tcgcgttaaa tttttgttaa    180
atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttggggtcg aggtgccgta agcactaaa tcggaaccct    420 aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaggggg gatgtgctgc aaggcgatta agttgggtaa cgccagggtt tcccagtca    720 cgacgttgta aaacgacggc cagtgagcgc gcctcgttca ttcacgtttt tgaacccgtg    780
```

```
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgt gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaac aaaaactcaa   1080
aatttcttct ataaagtaac aaaacttttta tgagggacag ccccccccca aagccccccag  1140 ggatgtaatt acgtccctcc cccgctaggg ggcagcagcg agccgcccgg ggctccgctc   1200
cggtccggcg ctcccccgc atccccgagc cggcagcgtg cggggacagc ccgggcacgg    1260
ggaaggtggc acgggatcgc tttcctctga acgcttctcg ctgctctttg agcctgcaga   1320
cacctggggg gatacgggga aaaggcctcc acggccacta gtattatgcc cagtacatga    1380
ccttatggga ctttcctact tggcagtaca tctacgtatt agtcatcgct attaccatgg   1440
tgatgcggtt ttggcagtac atcaatgggc gtggatagcg gtttgactca cggggatttc   1500
caagtctcca ccccattgac gtcaatggga gtttgttttg gcaccaaaat caacgggact   1560
ttccaaaatg tcgtaacaac tccgccccat tgacgcaaat gggcggtagg cgtgtacggt   1620
gggaggttta tataagcaga gctcgtttag tgaaccgtca gatcgcctgg agacgccatc   1680
cacgctgttt tgacctccat agaagattct agagccacca tggaaactga tacactcctg   1740
ctctgggttc tgctgctgtg ggttcctggc tctactggtg attatccata cgatgttcca   1800
gattatgctg gatccccctta tctggctcat tgtcctgatt gtggagaggg tcattcttgt   1860
catagcccag tcgctctgga gagaatcagg aatgaggcaa cagatggtac tctgaagatt   1920
caggtgtctc tccagatcgg catcaagact gacgactccc atgactggac caaactcagg   1980
tacatggata accacatgcc tgcagatgct gaaagagctg gcctgtttgt caggacctcc   2040
gctccctgta caatcactgg cactatgggt catttcatcc tggctcgctg ccctaagggt   2100
gaaactctga cagtgggctt taccgactct cgcaagattt cccacagctg tacccaccca   2160
ttccaccatg atccaccagt tatcggtaga gagaagtttc attctaggcc acaacacggc   2220
aaagaactgc catgcagcac atacgttcag tccaccgcag ccactactga ggaaatcgag   2280
gtccacatgc ctcccgacac acctgacagg accctgatgt cccaacaaag cggtaacgtg   2340
aagatcacag tgaatggcca aactgtgcgc tacaagtgta actgtggtgg tagcaacgaa   2400
ggactcacta ccaccgacaa agttatcaac aactgcaaag ttgatcagtg tcacgcagcc   2460
gtcactaacc acaagaaatg gcagtacaat agcccactcg tgcccagaaa cgcagagctg   2520
ggagatcgca agggcaagat ccacatccct ttccctctgg ctaatgtgac atgcagggtt   2580
ccaaaggcac gcaatcctac agtgacctat ggcaagaacc aggtcatcat gctcctctac   2640
cctgatcatc ccaccctcct gagctaccgc aacatgggtg aagaaccaaa ctatcaggaa   2700
gagtgggtca tgcacaagaa ggaagttgtg ctgaccgtgc ctactgaagg tctggaagtg   2760
acttggggaa acaacgagcc ctacaagtat tggccacagc tctccacaaa tggcactgcc   2820
cacggtcacc cacacgagat catcctgtac tactacgaac tctacccaac catgaccgtc   2880
gttgtggtca gcgtcgccac cttcatcctg ctgagcatgg tcggtatggc agctggtatg   2940
tgcatgtgcg ctcgcagacg ctgtatcact ccatacgagc tgactccagg tgccactgtg   3000
ccattcctcc tctccctgat tgttgcggt tctggtgtga acagactttt gaattttgac   3060
cttctcaagt tggcgggaga cgtcgagtcc aaccctgggc ccatggaaga tgccaaaaac   3120
attaagaagg gcccagcgcc attctaccca ctcgaagacg ggaccgccgg cgagcagctg   3180
```

-continued

```
cacaaagcca tgaagcgcta cgccctggtg cccggcacca tcgcctttac cgacgcacat   3240
atcgaggtgg acattaccta cgccgagtac ttcgagatga gcgttcggct ggcagaagct   3300
atgaagcgct atgggctgaa tacaaaccat cggatcgtgg tgtgcagcga gaatagcttg   3360
cagttcttca tgcccgtgtt gggtgccctg ttcatcggtg tggctgtggc cccagctaac   3420
gacatctaca acgagcgcga gctgctgaac agcatgggca tcagccagcc caccgtcgta   3480
ttcgtgagca agaaagggct gcaaaagatc ctcaacgtgc aaaagaagct accgatcata   3540
caaaagatca tcatcatgga tagcaagacc gactaccagg gcttccaaag catgtacacc   3600
ttcgtgactt cccatttgcc acccggcttc aacgagtacg acttcgtgcc cgagagcttc   3660
gaccgggaca aaaccatcgc cctgatcatg aacagtagtg gcagtaccgg attgcccaag   3720
ggcgtagccc taccgcaccg caccgcttgt gtccgattca gtcatgcccg cgaccccatc   3780
ttcggcaacc agatcatccc cgacaccgct atcctcagcg tggtgccatt tcaccacggc   3840
ttcggcatgt tcaccacgct gggctacttg atctgcggct ttcgggtcgt gctcatgtac   3900
cgcttcgagg aggagctatt cttgcgcagc ttgcaagact ataagattca atctgccctg   3960
ctggtgccca cactatttag cttcttcgct aagagcactc tcatcgacaa gtacgaccta   4020
agcaacttgc acgagatcgc cagcggcggg gcgccgctca gcaaggaggt aggtgaggcc   4080
gtggccaaac gcttccacct accaggcatc cgccagggct acggcctgac agaaacaacc   4140
agcgccattc tgatcacccc cgaaggggac gacaagcctg gcgcagtagg caaggtggtg   4200
cccttcttcg aggctaaggt ggtggacttg acaccggta agacactggg tgtgaaccag   4260
cgcggcgagc tgtgcgtccg tggccccatg atcatgagcg gctacgttaa caaccccgag   4320
gctacaaacg ctctcatcga caaggacggc tggctgcaca gcggcgacat cgcctactgg   4380
gacgaggacg agcacttctt catcgtggac cggctgaaga gcctgatcaa atacaagggc   4440
taccaggtag ccccagccga actggagagc atcctgctgc aacaccccaa catcttcgac   4500
gccggggtcg ccggcctgcc cgacgacgat gccggcgagc tgcccgccgc agtcgtcgtg   4560
ctggaacacg gtaaaaccat gaccgagaag gagatcgtgg actatgtggc cagccaggtt   4620
acaaccgcca agaagctgcg cggtggtgtt gtgttcgtgg acgaggtgcc taaaggactg   4680
accggcaagt tggacgcccg caagatccgc gagattctca ttaaggccaa gaagggcggc   4740
aagatcgccg tgggaagcgg agctactaac ttcagcctgc tgaagcaggc tggagacgtg   4800
gaggagaacc ctggacctat ggatagcact gagaacgtca tcaagcccct catgcgcttc   4860
aaggtgcaca tggagggctc cgtgaacggc cacgagttcg agatcgaggg cgtgggcgag   4920
ggcaagccct acgagggcac ccagaccgcc aagctgcaag tgaccaaggg cggcccectg   4980 cccttcgcct gggacatcct gtcccccag ttcttctacg gctccaaggc gtacatcaag   5040
caccccgccg acatccccga ctacctcaag cagtccttcc ccgagggctt caagtgggag   5100
cgcgtgatga cttcgagga cggcggcgtg gtgaccgtga cccaggactc ctccctgcag   5160
gacggcaccc tcatctacca cgtgaagttc atcggcgtga acttcccctc cgacggcccc   5220
gtaatgcaga gaagactct gggctgggag ccctccactg agcgcaacta ccccgcgac   5280 ggcgtgctga agggcgagaa ccacatggcg ctgaagctga agggcggcgg ccactacctg   5340
tgtgagttca gtccatctca catggccaag aagcccgtga gctgcccgg ctaccactac   5400 gtggactaca gctcgacat caccteccac aacgaggact acaccgtggt ggagcagtac   5460
gagcgcgccg aggcccgcca ccacctgttc cagtaatgat aacgcggccg cgaaggatct   5520
```

```
gcgatcgctc cggtgcccgt cagtgggcag agcgcacatc gcccacagtc cccgagaagt   5580
tgggggagg ggtcggcaat tgaacgggtg cctagagaag gtggcgcggg gtaaactggg    5640
aaagtgatgt cgtgtactgg ctccgccttt ttcccgaggg tgggggagaa ccgtatataa   5700
gtgcagtagt cgccgtgaac gttcttttc gcaacgggtt tgccgccaga acacagctga    5760
agcttcgagg ggctcgcatc tctccttcac gcgcccgccg ccctacctga ggccgccatc   5820
cacgccggtt gagtcgcgtt ctgccgcctc ccgcctgtgg tgcctcctga actgcgtccg   5880
ccgtctaggt aagtttaaag ctcaggtcga gaccgggcct ttgtccggcg ctcccttgga   5940
gcctacctag actcagccgg ctctccacgc tttgcctgac cctgcttgct caactctacg   6000
tctttgtttc gttttctgtt ctgcgccgtt acagatccaa gctgtgaccg gcgcctacgc   6060
tagatgaccg agtacaagcc cacggtgcgc ctcgccaccc gcgacgacgt ccccagggcc   6120
gtacgcaccc tcgccgccgc gttcgccgac taccccgcca cgcgccacac cgtcgatccg   6180
gaccgccaca tcgagcgggt caccgagctg caagaactct tcctcacgcg cgtcgggctc   6240
gacatcggca aggtgtgggt cgcggacgac ggcgccgcgg tggcggtctg gaccacgccc   6300
gagagcgtcg aagcgggggc ggtgttcgcc gagatcggcc cgcgcatggc cgagttgagc   6360
ggttcccggc tggccgcgca gcaacagatg gaaggcctcc tggcgccgca ccggcccaag   6420
gagcccgcgt ggttcctggc caccgtcggc gtctcgcccg accaccaggg caagggtctg   6480
ggcagcgccg tcgtgctccc cggagtggag gcggccgagc gcgccggggt gcccgccttc   6540
ctggagacct ccgcgccccg caacctcccc ttctacgagc ggctcggctt caccgtcacc   6600
gccgacgtcg aggtgcccga aggaccgcgc acctggtgca tgacccgcaa gcccggtgcc   6660
tgagtcgaca atcaacctct ggattacaaa atttgtgaaa gattgactgg tattcttaac   6720
tatgttgctc cttttacgct atgtggatac gctgctttaa tgcctttgta tcatgcgtta   6780
actaaacttg tttattgcag cttataatgg ttacaaataa agcaatagca tcacaaattt   6840
cacaaataaa gcattttttt cactgcattc tagttgtggt ttgtccaaac tcatcaatgt   6900
atcttatcat gtctggaatt gactcaaatg atgtcaatta gtctatcaga agctcatctg   6960
gtctcccttc cggggacaa gacatccctg tttaatattt aaacagcagt gttcccaaac    7020
tgggttctta tatcccttgc tctggtcaac caggttgcag ggtttcctgt cctcacagga   7080
acgaagtccc taaagaaaca gtggcagcca ggtttagccc cggaattgac tggattcctt   7140
ttttagggcc cattggtatg gcttttttcc cgtatccccc caggtgtctg caggctcaaa   7200
gagcagcgag aagcgttcag aggaaagcga tcccgtgcca ccttcccgt gcccgggctg    7260
tccccgcacg ctgccggctc ggggatgcgg ggggagcgcc ggaccggagc ggagccccgg   7320
gcggctcgct gctgccccct agcggggag ggacgtaatt acatccctgg ggctttggg     7380
gggggctgt ccctgatatc tataacaaga aatatatat ataataagtt atcacgtaag     7440
tagaacatga ataacaata taattatcgt atgagttaaa tcttaaagt cacgtaaaag     7500
ataatcatgc gtcattttga ctcacgcggt cgttatagtt caaaatcagt gacacttacc   7560
gcattgacaa gcacgcctca cgggagctcc aagcggcgac tgagatgtcc taaatgcaca   7620
gcgacggatt cgcgctattt agaaagagag agcaatattt caagaatgca tgcgtcaatt   7680
ttacgcagac tatctttcta gggttaatct agctgcatca ggatcatatc gtcgggtctt   7740
ttttccggct cagtcatcgc ccaagctggc gctatctggg catcggggag gaagaagccc   7800
gtgccttttc ccgcgaggtt gaagcggcat ggaaagagtt tgccgaggat gactgctgct   7860
gcattgacgt tgagcgaaaa cgcacgttta ccatgatgat tcgggaaggt gtggccatgc   7920
```

```
acgcctttaa cggtgaactg ttcgttcagg ccacctggga taccagttcg tcgcggcttt    7980
tccggacaca gttccggatg gtcagcccga agcgcatcag caacccgaac aataccggcg    8040
acagccggaa ctgccgtgcc ggtgtgcaga ttaatgacag cggtgcggcg ctgggatatt    8100
acgtcagcga ggacgggtat cctggctgga tgccgcagaa atggacatgg ataccccgtg    8160
agttacccgg cgggcgcgct tggcgtaatc atggtcatag ctgtttcctg tgtgaaattg    8220
ttatccgctc acaattccac acaacatacg agccggaagc ataaagtgta aagcctgggg    8280
tgcctaatga gtgagctaac tcacattaat tgcgttgcgc tcactgcccg ctttccagtc    8340
gggaaacctg tcgtgccagc tgcattaatg aatcggccaa cgcgcgggga gaggcggttt    8400
gcgtattggg cgctcttccg cttcctcgct cactgactcg ctgcgctcgg tcgttcggct    8460
gcggcgagcg gtatcagctc actcaaaggc ggtaatacgg ttatccacag aatcagggga    8520
taacgcagga agaacatgt gagcaaaagg ccagcaaaag gccaggaacc gtaaaaaggc    8580
cgcgttgctg gcgtttttcc ataggctccg ccccctgac gagcatcaca aaatcgacg    8640 ctcaagtcag aggtggcgaa acccgacagg actataaaga taccaggcgt ttccccctgg    8700
aagctccctc gtgcgctctc ctgttccgac cctgccgctt accggatacc tgtccgcctt    8760
tctcccttcg ggaagcgtgg cgctttctca tagctcacgc tgtaggtatc tcagttcggt    8820
gtaggtcgtt cgctccaagc tgggctgtgt gcacgaaccc cccgttcagc ccgaccgctg    8880
cgccttatcc ggtaactatc gtcttgagtc caacccggta agacacgact tatcgccact    8940
ggcagcagcc actggtaaca ggattagcag agcgaggtat gtaggcggtg ctacagagtt    9000
cttgaagtgg tggcctaact acggctacac tagaaggaca gtatttggta tctgcgctct    9060
gctgaagcca gttaccttcg gaaaaagagt tggtagctct tgatccggca acaaaccac    9120 cgctggtagc ggtggttttt ttgtttgcaa gcagcagatt acgcgcagaa aaaaaggatc    9180
tcaagaagat cctttgatct tttctacggg gtctgacgct cagtggaacg aaaactcacg    9240
ttaagggatt ttggtcatga gattatcaaa aaggatcttc acctagatcc ttttaaatta    9300
aaaatgaagt tttaaatcaa tctaaagtat atatgagtaa acttggtctg acagttacca    9360
atgcttaatc agtgaggcac ctatctcagc gatctgtcta tttcgttcat ccatagttgc    9420
ctgactcccc gtcgtgtaga taactacgat acgggagggc ttaccatctg gccccagtgc    9480
tgcaatgata ccgcgagacc cacgctcacc ggctccagat ttatcagcaa taaaccagcc    9540
agccggaagg gccgagcgca gaagtggtcc tgcaacttta tccgcctcca tccagtctat    9600
taattgttgc cgggaagcta gagtaagtag ttcgccagtt aatagtttgc gcaacgttgt    9660
tgccattgct acaggcatcg tggtgtcacg ctcgtcgttt ggtatggctt cattcagctc    9720
cggttcccaa cgatcaaggc gagttacatg atcccccatg ttgtgcaaaa aagcggttag    9780
ctccttcggt cctccgatcg ttgtcagaag taagttggcc gcagtgttat cactcatggt    9840
tatggcagca ctgcataatt ctcttactgt catgccatcc gtaagatgct tttctgtgac    9900
tggtgagtac tcaaccaagt cattctgaga atagtgtatg cggcgaccga gttgctcttg    9960
cccggcgtca atacgggata ataccgcgcc acatagcaga actttaaaag tgctcatcat   10020
tggaaaacgt tcttcggggc gaaaactctc aaggatctta ccgctgttga tccagttc    10080 gatgtaaccc actcgtgcac ccaactgatc ttcagcatct tttacttca ccagcgtttc   10140 tgggtgagca aaaacaggaa ggcaaaatgc cgcaaaaaag ggaataaggg cgacacggaa   10200
atgttgaata ctcat                                                    10215
```

<210> SEQ ID NO 50
<211> LENGTH: 10225
<212> TYPE: DNA
<213> ORGANISM: Artificial Sequence
<220> FEATURE:
<223> OTHER INFORMATION: Synthetic

<400> SEQUENCE: 50

| | | | | | |
|---|---|---|---|---|---|
| acgcgtgtag | tcttatgcaa | tactcttgta | gtcttgcaac | atggtaacga | tgagttagca | 60 |
| acatgcctta | caaggagaga | aaaagcaccg | tgcatgccga | ttggtggaag | taaggtggta | 120 |
| cgatcgtgcc | ttattaggaa | ggcaacagac | gggtctgaca | tggattggac | gaaccactga | 180 |
| attgccgcat | tgcagagata | ttgtatttaa | gtgcctagct | cgatacaata | aacgggtctc | 240 |
| tctggttaga | ccagatctga | gcctgggagc | tctctggcta | actagggaac | ccactgctta | 300 |
| agcctcaata | aagcttgcct | tgagtgcttc | aagtagtgtg | tgcccgtctg | ttgtgtgact | 360 |
| ctggtaacta | gagatccctc | agaccctttt | agtcagtgtg | gaaaatctct | agcagtggcg | 420 |
| cccgaacagg | gacctgaaag | cgaaagggaa | accagagctc | tctcgacgca | ggactcggct | 480 |
| tgctgaagcg | cgcacggcaa | gaggcgaggg | gcggcgactg | gtgagtacgc | caaaaatttt | 540 |
| gactagcgga | ggctagaagg | agagagatgg | gtgcgagagc | gtcagtatta | agcggggag | 600 |
| aattagatcg | cgatgggaaa | aaattcggtt | aaggccaggg | ggaaagaaaa | aatataaatt | 660 |
| aaaacatata | gtatgggcaa | gcaggagct | agaacgattc | gcagttaatc | ctggcctgtt | 720 |
| agaaacatca | gaaggctgta | gacaaatact | gggacagcta | caaccatccc | ttcagacagg | 780 |
| atcagaagaa | cttagatcat | tatataatac | agtagcaacc | ctctattgtg | tgcatcaaag | 840 |
| gatagagata | aaagacacca | aggaagcttt | agacaagata | gaggaagagc | aaaacaaaag | 900 |
| taagaccacc | gcacagcaag | cggccactga | tcttcagacc | tggaggagga | gatatgaggg | 960 |
| acaattggag | aagtgaatta | tataaatata | aagtagtaaa | aattgaacca | ttaggagtag | 1020 |
| cacccaccaa | ggcaaagaga | agagtggtgc | agagagaaaa | aagagcagtg | ggaataggag | 1080 |
| ctttgttcct | tgggttcttg | ggagcagcag | gaagcactat | gggcgcagcg | tcaatgacgc | 1140 |
| tgacggtaca | ggccagacaa | ttattgtctg | gtatagtgca | gcagcagaac | aatttgctga | 1200 |
| gggctattga | ggcgcaacag | catctgttgc | aactcacagt | ctggggcatc | aagcagctcc | 1260 |
| aggcaagaat | cctggctgtg | gaaagatacc | taaaggatca | acagctcctg | ggatttggg | 1320 |
| gttgctctgg | aaaactcatt | tgcaccactg | ctgtgccttg | gaatgctagt | tggagtaata | 1380 |
| aatctctgga | acagatttgg | aatcacacga | cctggatgga | gtgggacaga | gaaattaaca | 1440 |
| attacacaag | cttaatacac | tccttaattg | aagaatcgca | aaaccagcaa | gaaaagaatg | 1500 |
| aacaagaatt | attggaatta | gataaatggg | caagtttgtg | gaattggttt | aacataacaa | 1560 |
| attggctgtg | gtatataaaa | ttattcataa | tgatagtagg | aggcttggta | ggtttaagaa | 1620 |
| tagttttgc | tgtactttct | atagtgaata | gagttaggca | gggatattca | ccattatcgt | 1680 |
| ttcagaccca | cctcccaacc | ccgaggggac | ccgacaggcc | cgaaggaata | gaagaagaag | 1740 |
| gtggagagag | agacagagac | agatccattc | gattagtgaa | cggatctcga | cggtatcgt | 1800 |
| taacttttaa | aagaaaaggg | gggattgggg | ggtacagtgc | aggggaaaga | atagtagaca | 1860 |
| taatagcaac | agacatacaa | actaaagaat | tacaaaaaca | aattacaaaa | ttcaaaattt | 1920 |
| tatcgatgct | agcggaggaa | aaactgtttc | atacagaagg | cgtggaggaa | aaactgtttc | 1980 |
| atacagaagg | cgtggaggaa | aaactgtttc | atacagaagg | cgtggaggaa | aaactgtttc | 2040 |
| atacagaagg | cgtggaggaa | aaactgtttc | atacagaagg | cgtggaggaa | aaactgtttc | 2100 |

```
atacagaagg cgtagatcta gactctagag ggtatataat ggaagctcga cttccagctt   2160
ggcattccgg tactgttggt aaaaagcttg gcaatccggt actgttggta aaggatccgc   2220
caccatgcct gccatgaaga ttgagtgccg catcacggga accctgaacg gagtggagtt   2280
tgagctggtc ggaggtggag aagggactcc tgagcaggga cgtatgacca acaagatgaa   2340
gtctaccaag ggcgccttga ccttctcccc ctaccttctc tctcatgtca tgggatacgg   2400
gttctaccac tttggtacct atcccagtgg gtatgagaat cccttcctgc atgccatcaa   2460
caacgggggg tacaccaaca ccaggattga aagtatgag gatggaggag ttcttcatgt    2520
tagctttagc tacagatatg aagcaggcag ggtgattggg gatttcaagg ttgtcgggac   2580
aggattccct gaggacagtg tgatcttcac cgacaagatc atccggtcca atgctaccgt   2640
ggagcacttg cacccaatgg gagacaacgt tcttgtgggc tccttcgcga aaccttttc    2700 cctgagggat ggaggctact actcatttgt ggttgacagc cacatgcact tcaagagtgc   2760
catccaccca tccatcctcc agaacggggg gcccatgttt gccttcagga gagttgagga   2820
acttcactcc aacactgaac ttggcattgt agagtatcaa catgccttca agactcccat   2880
agcatttgct ggaagcggag ctactaactt cagcctgctg aagcaggctg agacgtggaa   2940
ggagaaccct ggacctatgg tcttcacact cgaagattc gttggggact ggcgacagac    3000
agccggctac aacctggacc aagtccttga acagggaggt gtgtccagtt tgtttcagaa   3060
tctcggggtg tccgtaactc cgatccaaag gattgtcctg agcggtgaaa atgggctgaa   3120
gatcgacatc catgtcatca tcccgtatga aggtctgagc ggcgaccaaa tgggccagat   3180
cgaaaaaatt tttaaggtgg tgtaccctgt ggatgatcat cactttaagg tgatcctgca   3240
ctatggcaca ctggtaatcg acggggttac gccgaacatg atcgactatt tcggacggcc   3300
gtatgaaggc atcgccgtgt tcgacggcaa aaagatcact gtaacaggga ccctgtggaa   3360
cggcaacaaa attatcgacg agcgcctgat caaccccgac ggctccctgc tgttccgagt   3420
aaccatcaac ggagtgaccg gctggcggct gtgcgaacgc attctggcgt aagcggccgc   3480
gaaggatctg cgatcgctcc ggtgcccgtc agtgggcaga gcgcacatcg cccacagtcc   3540
ccgagaagtt ggggggaggg gtcggcaatt gaacgggtgc ctagagaagg tggcgcgggg   3600
taaactggga aagtgatgtc gtgtactggc tccgcctttt tcccgagggt gggggagaac   3660
cgtatataag tgcagtagtc gccgtgaacg ttctttttcg caacgggttt gccgccagaa   3720
cacagctgaa gcttcgaggg gctcgcatct ctccttcacg cgcccgccgc cctacctgag   3780
gccgccatcc acgccggttg agtcgcgttc tgccgcctcc cgctgtggt gcctcctgaa     3840 ctgcgtccgc cgtctaggta agtttaaagc tcaggtcgag accgggcctt tgtccggcgc   3900
tcccttggag cctacctaga ctcagccggc tctccacgct tgcctgacc ctgcttgctc     3960 aactctacgt ctttgtttcg ttttctgttc tgcgccgtta cagatccaag ctgtgaccgg   4020
cgcctactag tgccaccatg gactttcaag tgcagatctt cagctttctg ctgatctctg   4080
ctagtgtcat catgtctcaa gtgcaactgc aacagccagg agctgaactg gttagacctg   4140
gaagctccgt gaaactgtct tgcaaagcaa gcggttacac attcaccagc aagtggatgc   4200
actgggtgaa acaaaggcca atccaaggac tggagtggat cggcaacatt gatcctctg    4260 acagcgaaac acactacaac cagaagttca aggacaaggc cactctgacc gtggacaagt   4320
cttcttctac tgcctacatg cagctctcca gcctcactag cgaggactcc gctgtctact   4380
actgcgcaag aggcgttacc agaggctact tcgacgtgtg gggtacaggt acaactgtga   4440
```

-continued

```
cagttagcag cggaggtgga ggcagtggag gtggtggatc tggaggagga gggtctcaga    4500
tcgttctgac tcaatctcca gccatcatgt ccgcatctcc aggagagaag gtgaccatga    4560
cctgctctgc ttccagctcc gtgacctaca tgtattggta tcagcagaag ccaggctcta    4620
gcccaaggct gctcatctac gatacttcca acctcgccag cggagtgcca gtgcgcttct    4680
ccggatctgg atctggaacc tcttactccc tcactatctc caggatggag gcagaggatg    4740
cagctactta ctactgccag cagaggacca actatcctct gactttcggt gctggcacca    4800
agctggagct gaaaagggaa atcgagcaga agctgatttc cgaagaggat ctcaatggag    4860
tgactgtcag cagcgctctg tctaactcca tcatgtactt ctcacacttc gtgccagtgt    4920
tcctccctgc taaacccacc acaactccag cacctagacc tcccactcca gcaccaacta    4980
ttgcatccca gcctctctcc ctcagaccag aagcatgcag acctgcagca ggtgagctg    5040 tgcacacaag aggtctggac cctttctggg tcctcgtggt ggtgggtgga gtcctggcat    5100
gttacagcct cctggtcacc gtggcattca tcatcttctg ggtgagatct aagaggagca    5160
gactgctgca ctctgattac atgaacatga cacccagaaa acctggtccc accagaaagc    5220
actaccaacc ctacgcacca ccaagagact ttgctgcata cagaagtctc gagagggtca    5280
agttctcaag gagtgcagat gctccagcct atcaacaggg tcagaaccaa ctgtacaacg    5340
agctgaatct cggaagaaga gaggagtacg atgtgctgga taagagaaga ggcagggacc    5400
cagagatggg tgggaaaccc agaagaaaga tcctcaaga gggactgtac aatgagctgc    5460
agaaggataa gatggctgag gcatactcag agatcggtat gaagggagag aggagaagag    5520
gcaaaggtca tgatggtctg taccaaggtc tgtccacagc aacaaaggat acatatgatg    5580
ctctgcacat gcaggcactc ccaccacggg gttccggagt gaaacagact ttgaactttg    5640
accttctcaa gttggctgga gacgtcgagt ccaaccctgg tcccatgacc gagtacaagc    5700
ccacggtgcg cctcgccacc cgcgacgacg tccccagggc cgtacgcacc ctcgccgccg    5760
cgttccgcga ctaccccgcc acgcgccaca ccgtcgatcc ggaccgccac atcgagcggg    5820
tcaccgagct gcaagaactc ttcctcacgc gcgtcgggct cgacatcggc aaggtgtggg    5880
tcgcggacga cggcgccgcg gtggcggtct ggaccacgcc ggagagcgtc gaagcggggg    5940
cggtgttcgc cgagatcggc ccgcgcatgg ccgagttgag cggttcccgg ctggccgcgc    6000
agcaacagat ggaaggcctc ctggcgccgc accggcccaa ggagcccgcg tggttcctgg    6060
ccaccgtcgg cgtctcgccc gaccaccagg gcaagggtct gggcagcgcc gtcgtgctcc    6120
ccggagtgga ggcggccgag cgcgccgggg tgcccgcctt cctggagacc tccgcgcccc    6180
gcaacctccc cttctacgag cggctcggct tcaccgtcac cgccgacgtc gaggtgcccg    6240
aaggaccgcg cacctggtgc atgacccgca agccggtgc ctgattaatt aagtcgacaa    6300
tcaacctctg gattacaaaa tttgtgaaag attgactggt attcttaact atgttgctcc    6360
ttttacgcta tgtggatacg ctgctttaat gcctttgtat catgctattg cttcccgtat    6420
ggctttcatt ttctcctcct tgtataaatc ctggttgctg tctctttatg aggagttgtg    6480
gcccgttgtc aggcaacgtg gcgtggtgtg cactgtgttt gctgacgcaa cccccactgg    6540
ttggggcatt gccaccacct gtcagctcct tccgggact ttcgctttcc cctcccctat    6600
tgccacggcg gaactcatcg ccgcctgcct tgcccgctgc tggacagggg ctcggctgtt    6660
gggcactgac aattccgtgg tgttgtcggg gaaatcatcg tcctttcctt ggctgctcgc    6720
ctgtgttgcc acctggattc tgcgcgggac gtccttctgc tacgtccctt cggccctcaa    6780
tccagcggac cttccttccc gcggcctgct gccggctctg cggcctcttc cgcgtcttcg    6840
```

```
ccttcgccct cagacgagtc ggatctccct ttgggccgcc tccccgcctg gtacctttaa    6900
gaccaatgac ttacaaggca gctgtagatc ttagccactt tttaaaagaa aagggggggac   6960
tggaagggct aattcactcc caacgaagat aagatctgct ttttgcttgt actgggtctc    7020
tctggttaga ccagatctga gcctgggagc tctctggcta actagggaac ccactgctta    7080
agcctcaata aagcttgcct tgagtgcttc aagtagtgtg tgcccgtctg ttgtgtgact    7140
ctggtaacta gagatccctc agacccttt agtcagtgtg gaaaatctct agcagtagta     7200
gttcatgtca tcttattatt cagtatttat aacttgcaaa gaaatgaata tcagagagtg    7260
agaggaactt gtttattgca gcttataatg gttacaaata aagcaatagc atcacaaatt    7320
tcacaaataa agcattttt tcactgcatt ctagttgtgg tttgtccaaa ctcatcaatg     7380
tatcttatca tgtctggctc tagctatccc gccctaact ccgccatcc cgccctaac       7440
tccgcccagt tccgcccatt ctccgcccca tggctgacta attttttta tttatgcaga     7500
ggccgaggcc gcctcggcct ctgagctatt ccagaagtag tgaggaggct ttttggagg     7560
cctagacttt tgcagagacg gcccaaattc gtaatcatgg tcatagctgt ttcctgtgtg   7620
aaattgttat ccgctcacaa ttccacacaa catacgagcc ggaagcataa agtgtaaagc    7680
ctggggtgcc taatgagtga gctaactcac attaattgcg ttgcgctcac tgcccgcttt   7740
ccagtcggga aacctgtcgt gccagctgca ttaatgaatc ggccaacgcg cggggagagg    7800
cggtttgcgt attgggcgct cttccgcttc ctcgctcact gactcgctgc gctcggtcgt    7860
tcggctgcgg cgagcggtat cagctcactc aaaggcggta atacggttat ccacagaatc    7920
aggggataac gcaggaaaga acatgtgagc aaaaggccag caaaaggcca ggaaccgtaa    7980
aaaggccgcg ttgctggcgt ttttccatag gctccgcccc cctgacgagc atcacaaaaa    8040
tcgacgctca agtcagaggt ggcgaaaccc gacaggacta taaagatacc aggcgtttcc    8100
ccctggaagc tccctcgtgc gctctcctgt tccgaccctg ccgcttaccg gatacctgtc    8160
cgcctttctc ccttcgggaa gcgtggcgct ttctcatagc tcacgctgta ggtatctcag    8220
ttcggtgtag gtcgttcgct ccaagctggg ctgtgtgcac gaaccccccg ttcagcccga    8280
ccgctgcgcc ttatccggta actatcgtct tgagtccaac ccggtaagac acgacttatc    8340
gccactggca gcagccactg gtaacaggat tagcagagcg aggtatgtag gcggtgctac    8400
agagttcttg aagtggtggc ctaactacgg ctacactaga aggacagtat ttggtatctg    8460
cgctctgctg aagccagtta ccttcggaaa aagagttggt agctcttgat ccggcaaaca    8520
aaccaccgct ggtagcggtg gtttttttgt ttgcaagcag cagattacgc gcagaaaaaa    8580
aggatctcaa gaagatcctt tgatcttttc tacggggtct gacgctcagt ggaacgaaaa    8640
ctcacgttaa gggattttgg tcatgagatt atcaaaaagg atcttcacct agatcctttt    8700
aaattaaaaa tgaagtttta aatcaatcta agtatatat gagtaaactt ggtctgacag     8760
ttaccaatgc ttaatcagtg aggcaccta t ctcagcgatc tgtctatttc gttcatccat   8820
agttgcctga ctccccgtcg tgtagataac tacgatacgg gagggcttac catctggccc    8880
cagtgctgca atgataccgc gagacccacg ctcaccggct ccagatttat cagcaataaa    8940
ccagccagcc ggaagggccg agcgcagaag tggtcctgca actttatccg cctccatcca    9000
gtctattaat tgttgccggg aagctagagt aagtagttcg ccagttaata gtttgcgcaa    9060
cgttgttgcc attgctacag gcatcgtggt gtcacgctcg tcgtttggta tggcttcatt    9120
cagctccggt tcccaacgat caaggcgagt tacatgatcc cccatgttgt gcaaaaaagc    9180
```

```
ggttagctcc ttcggtcctc cgatcgttgt cagaagtaag ttggccgcag tgttatcact    9240
catggttatg gcagcactgc ataattctct tactgtcatg ccatccgtaa gatgcttttc    9300
tgtgactggt gagtactcaa ccaagtcatt ctgagaatag tgtatgcggc gaccgagttg    9360
ctcttgcccg cgtcaatac gggataatac cgcgccacat agcagaactt taaaagtgct    9420
catcattgga aaacgttctt cggggcgaaa actctcaagg atcttaccgc tgttgagatc    9480
cagttcgatg taacccactc gtgcacccaa ctgatcttca gcatctttta ctttcaccag    9540
cgtttctggg tgagcaaaaa caggaaggca aaatgccgca aaaagggaa taagggcgac    9600 acggaaatgt tgaatactca tactcttcct ttttcaatat tattgaagca tttatcaggg    9660
ttattgtctc atgagcggat acatatttga atgtatttag aaaaataaac aaataggggt    9720
tccgcgcaca tttccccgaa aagtgccacc tgacgtctaa gaaaccatta ttatcatgac    9780
attaacctat aaaaataggc gtatcacgag gccctttcgt ctcgcgcgtt tcggtgatga    9840
cggtgaaaac ctctgacaca tgcagctccc ggagacggtc acagcttgtc tgtaagcgga    9900
tgccgggagc agacaagccc gtcagggcgc gtcagcgggt gttggcgggt gtcggggctg    9960
gcttaactat gcggcatcag agcagattgt actgagagtg caccatatgc ggtgtgaaat   10020
accgcacaga tgcgtaagga gaaaataccg catcaggcgc cattcgccat tcaggctgcg   10080
caactgttgg aagggcgat cggtgcgggc ctcttcgcta ttacgccagc tggcgaaagg   10140
gggatgtgct gcaaggcgat taagttgggt aacgccaggg ttttcccagt cacgacgttg   10200
taaaacgacg gccagtgcca agctg                                         10225
```

<210> SEQ ID NO 51
<211> LENGTH: 10749
<212> TYPE: DNA
<213> ORGANISM: Artificial Sequence
<220> FEATURE:
<223> OTHER INFORMATION: Synthetic

<400> SEQUENCE: 51

```
actcttcctt tttcaatatt attgaagcat ttatcagggt tattgtctca tgagcggata      60
catatttgaa tgtatttaga aaaataaaca aataggggtt ccgcgcacat ttccccgaaa     120
agtgccacct aaattgtaag cgttaatatt ttgttaaaat tcgcgttaaa ttttttgttaa    180 atcagctcat tttttaacca ataggccgaa atcggcaaaa tcccttataa atcaaaagaa    240
tagaccgaga tagggttgag tgttgttcca gtttggaaca agagtccact attaaagaac    300
gtggactcca acgtcaaagg gcgaaaaacc gtctatcagg gcgatggccc actacgtgaa    360
ccatcaccct aatcaagttt tttggggtcg aggtgccgta aagcactaaa tcggaaccct    420
aaagggagcc cccgatttag agcttgacgg ggaaagccgg cgaacgtggc gagaaaggaa    480
gggaagaaag cgaaaggagc gggcgctagg gcgctggcaa gtgtagcggt cacgctgcgc    540
gtaaccacca cacccgccgc gcttaatgcg ccgctacagg gcgcgtccca ttcgccattc    600
aggctgcgca actgttggga agggcgatcg gtgcgggcct cttcgctatt acgccagctg    660
gcgaaagggg gatgtgctgc aaggcgatta agttgggtaa cgccagggtt tcccagtca    720 cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgt gtaaaattga cgcatgtgtt ttatcggtct gtatatcgag    960
gtttatttat taatttgaat agatattaag ttttattata tttacactta catactaata   1020
```

```
ataaattcaa caaacaattt atttatgttt atttatttat taaaaaaaac aaaaactcaa      1080
aatttcttct ataaagtaac aaaactttta tgagggacag ccccccccca aagcccccag      1140
ggatgtaatt acgtccctcc cccgctaggg ggcagcagcg agccgcccgg ggctccgctc      1200
cggtccggcg ctccccccgc atccccgagc cggcagcgtg cggggacagc ccgggcacgg      1260
ggaaggtggc acgggatcgc tttcctctga acgcttctcg ctgctctttg agcctgcaga      1320
cacctggggg gatacgggga aaaggcctcc acggccacta gtattatgcc cagtacatga      1380
ccttatggga ctttcctact tggcagtaca tctacgtatt agtcatcgct attaccatgg      1440
tgatgcggtt ttggcagtac atcaatgggc gtggatagcg gtttgactca cggggatttc      1500
caagtctcca ccccattgac gtcaatggga gtttgttttg gcaccaaaat caacgggact      1560
ttccaaaatg tcgtaacaac tccgccccat tgacgcaaat gggcggtagg cgtgtacggt      1620
gggaggttta taagcaga gctcgtttag tgaaccgtca gatcgcctgg agacgccatc       1680
cacgctgttt tgacctccat agaagattct agagccacca tggaaactga tacactcctg      1740
ctctgggttc tgctgctgtg ggttcctggc tctactggtg attatccata cgatgttcca      1800
gattatgctg gatccatcct gcactatgag aaactgtcta agattgggct cgtgaagggt      1860
gtcacaagga agtataagat aaagtccaac cctctcacca aggacatcgt gatcaagatg      1920
atccccaacg tttcaaacat gagccagtgt accggatctg tcatggagaa ctataagaca      1980
cggctgaacg gcattctgac acctattaag ggagctctcg aaatctacaa gaacaacact      2040
catgacctgg tgggtgacgt gagactcgct ggcgttatca tggccggcgt tgctatcgga      2100
attgccaccg cagcccagat cactgccgga gttgctctgt atgaagctat gaagaatgct      2160
gataacatca acaagctcaa atcttccatt gagtctacta atgaggcagt ggttaaactg      2220
caagaaactg cagagaagac cgtgtatgtt ctgacagccc tccaagacta cataaacaca      2280
aacctggtgc ccaccatcga caagatttca tgtaagcaaa cagagctgag cctggacctg      2340
gccctctcca aatacctgtc tgacctgctg tttgtcttcg ggcccaacct gcaggaccca      2400
gtcagcaaca gcatgaccat ccaggcaatc tcacaggcct tcggaggcaa ctatgagact      2460
ctgctgagaa ctctgggcta tgctacagag gattttgatg atctgctgga gtccgactcc      2520
atcactggac agatcatcta tgtcgatctc tcaagctact acatcatcgt gcgggtgtac      2580
ttcccaatcc tgaccgaaat ccagcaagca tacatccagg agctgctccc tgtgtccttc      2640
aacaatgaca atagtgagtg gatctctatc gtccccaact tcattctggt gcgcaacaca      2700
ctgatctcca atatagagat tggattctgt ctcattacca agaggagcgt gatctgcaat      2760
caggattatg ccaccccaat gaccaacaat atgagagaat gtctgacagg cagcaccgag      2820
aagtgtccca gggaactggt tgtcagcagt catgtgccaa ggtttgccct gagcaacggt      2880
gttctgtttg ctaactgcat tagcgtgact tgtcaatgcc agacaaccgg aagagccatc      2940
tcacagtctg gcgagcagac cctcctgatg attgacaata ctacatgccc aactgctgtc      3000
ctgggcaacg tcataatatc cctgggcaag tatctgggta gcgtgaacta caatagcgaa      3060
gggattgcca tcggaccacc tgttttcacc gataaggtgg acatttctag ccagatcagc      3120
tccatgaatc aaagtctgca gcagtccaaa gactacatca aggaagccca acgcctgctg      3180
gataccgtca atcctccct gatcagtatg ctgagcatga ttatcctgta tgtcctgtcc      3240
atcgccagcc tgtgtatcgg actcatcacc ttcatttcct tcattattgt cgaaaagaag      3300
agaaacacct atagtagact ggaggataga cgcgtgaggc ctacaagttc tggcgatctc      3360
```

```
tattacattg gaaccgctag cgaacagaaa ctcatctccg aagaagacct caacgcagtg    3420
ggtcaagaca cacaagaagt catcgtcgtg ccacattctc tgcccttcaa ggtggtggtg    3480
atctctgcta ttctcgcact cgtggtgctc accatcatct ccctgatcat tctgatcatg    3540
ctgtggcaga agaagcctcg cggttctggt gtgaaacaga cttttgaattt tgaccttctc    3600 aagttggcgg agacgtcga gtccaaccct gggcccatgg aagatgccaa aaacattaag    3660
aagggcccag cgccattcta cccactcgaa gacgggaccg ccggcgagca gctgcacaaa    3720
gccatgaagc gctacgccct ggtgcccggc accatcgcct ttaccgacgc acatatcgag    3780
gtggacatta cctacgccga gtacttcgag atgagcgttc ggctggcaga agctatgaag    3840
cgctatgggc tgaatacaaa ccatcggatc gtggtgtgca gcgagaatag cttgcagttc    3900
ttcatgcccg tgttgggtgc cctgttcatc ggtgtggctg tggccccagc taacgacatc    3960
tacaacgagc gcgagctgct gaacagcatg ggcatcagcc agcccaccgt cgtattcgtg    4020
agcaagaaag gctgcaaaa gatcctcaac gtgcaaaaga gctaccgat catacaaaag    4080 atcatcatca tggatagcaa gaccgactac cagggcttcc aaagcatgta caccttcgtg    4140
acttcccatt tgccacccgg cttcaacgag tacgacttcg tgcccgagag cttcgaccgg    4200
gacaaaacca tcgccctgat catgaacagt agtggcagta ccggattgcc caagggcgta    4260
gccctaccgc accgcaccgc ttgtgtccga ttcagtcatg cccgcgaccc catcttcggc    4320
aaccagatca tccccgacac cgctatcctc agcgtggtgc catttcacca cggcttcggc    4380
atgttcacca cgctgggcta cttgatctgc ggctttcggg tcgtgctcat gtaccgcttc    4440
gaggaggagc tattcttgcg cagcttgcaa gactataaga ttcaatctgc cctgctggtg    4500
cccacactat ttagcttctt cgctaagagc actctcatcg acaagtacga cctaagcaac    4560
ttgcacgaga tcgccagcgg cggggcgccg ctcagcaagg aggtaggtga ggccgtggcc    4620
aaacgcttcc acctaccagg catccgccag ggctacggcc tgacagaaac aaccagcgcc    4680
attctgatca cccccgaagg ggacgacaag cctggcgcag taggcaaggt ggtgcccttc    4740
ttcgaggcta aggtggtgga cttggacacc ggtaagacac tgggtgtgaa ccagcgcggc    4800
gagctgtgcg tccgtggccc catgatcatg agcggctacg ttaacaaccc cgaggctaca    4860
aacgctctca tcgacaagga cggctggctg cacagcggcg acatcgccta ctgggacgag    4920
gacgagcact tcttcatcgt ggaccggctg aagagcctga tcaaatacaa gggctaccag    4980
gtagccccag ccgaactgga gagcatcctg ctgcaacacc ccaacatctt cgacgccggg    5040
gtcgccggcc tgcccgacga cgatgccggc gagctgcccg ccgcagtcgt cgtgctggaa    5100
cacggtaaaa ccatgaccga aaggagatc gtggactatg tggccagcca ggttacaacc    5160
gccaagaagc tgcgcggtgg tgttgtgttc gtggacgagg tgcctaaagg actgaccggc    5220
aagttggacg cccgcaagat ccgcgagatt ctcattaagg ccaagaaggg cggcaagatc    5280
gccgtgggaa gcggagctac taacttcagc ctgctgaagc aggctggaga cgtggaggag    5340
aaccctggac ctatggatag cactgagaac gtcatcaagc ccttcatgcg cttcaaggtg    5400
cacatggagg gctccgtgaa cggccacgag ttcgagatcg agggcgtggg cgagggcaag    5460
ccctacgagg gcacccagac cgccaagctg caagtgacca agggcggccc cctgcccttc    5520
gcctgggaca tcctgtcccc ccagttcttc tacggctcca aggcgtacat caagcacccc    5580
gccgacatcc ccgactacct caagcagtcc ttccccgagg gcttcaagtg ggagcgcgtg    5640
atgaacttcg aggacggcgg cgtggtgacc gtgacccagg actcctccct gcaggacggc    5700
accctcatct accacgtgaa gttcatcggc gtgaacttcc cctccgacgg ccccgtaatg    5760
```

```
cagaagaaga ctctgggctg ggagccctcc actgagcgca actaccccg cgacggcgtg    5820 ctgaagggcg agaaccacat ggcgctgaag ctgaagggcg gcggccacta cctgtgtgag    5880
ttcaagtcca tctacatggc caagaagccc gtgaagctgc ccggctacca ctacgtggac    5940
tacaagctcg acatcacctc ccacaacgag gactacaccg tggtggagca gtacgagcgc    6000
gccgaggccc gccaccacct gttccagtaa tgataacgcg gccgcgaagg atctgcgatc    6060
gctccggtgc ccgtcagtgg gcagagcgca catcgcccac agtccccgag aagttggggg    6120
gaggggtcgg caattgaacg ggtgcctaga aaggtggcg cggggtaaac tgggaaagtg    6180
atgtcgtgta ctggctccgc ctttttcccg agggtggggg agaaccgtat ataagtgcag    6240
tagtcgccgt gaacgttctt tttcgcaacg ggtttgccgc cagaacacag ctgaagcttc    6300
gaggggctcg catctctcct tcacgcgccc gccgccctac ctgaggccgc catccacgcc    6360
ggttgagtcg cgttctgccg cctcccgcct gtggtgcctc ctgaactgcg tccgccgtct    6420
aggtaagttt aaagctcagg tcgagaccgg gcctttgtcc ggcgctccct ggagcctac    6480 ctagactcag ccggctctcc acgctttgcc tgaccctgct tgctcaactc tacgtctttg    6540
tttcgttttc tgttctgcgc cgttacagat ccaagctgtg accggcgcct acgctagatg    6600
accgagtaca agcccacggt gcgcctcgcc acccgcgacg acgtccccag ggccgtacgc    6660
accctcgccg ccgcgttcgc cgactacccc gccacgcgcc acaccgtcga tccggaccgc    6720
cacatcgagc gggtcaccga gctgcaagaa ctcttcctca cgcgcgtcgg gctcgacatc    6780
ggcaaggtgt gggtcgcgga cgacggcgcc gcggtggcgg tctggaccac gccggagagc    6840
gtcgaagcgg gggcggtgtt cgccgagatc ggcccgcgca tggccgagtt gagcggttcc    6900
cggctggccg cgcagcaaca gatggaaggc ctcctggcgc cgcaccggcc caaggagccc    6960
gcgtggttcc tggccaccgt cggcgtctcg cccgaccacc agggcaaggg tctgggcagc    7020
gccgtcgtgc tccccggagt ggaggcggcc gagcgcgccg gggtgcccgc cttcctggag    7080
acctccgcgc cccgcaacct ccccttctac gagcggctcg gcttcaccgt caccgccgac    7140
gtcgaggtgc ccgaaggacc gcgcacctgg tgcatgaccc gcaagcccgg tgcctgagtc    7200
gacaatcaac ctctggatta caaaatttgt gaaagattga ctggtattct taactatgtt    7260
gctcctttta cgctatgtgg atacgctgct ttaatgcctt tgtatcatgc gttaactaaa    7320
cttgtttatt gcagcttata atggttacaa ataaagcaat agcatcacaa atttcacaaa    7380
taaagcattt ttttcactgc attctagttg tggtttgtcc aaactcatca atgtatctta    7440
tcatgtctgg aattgactca atgatgtca attagtctat cagaagctca tctggtctcc    7500
cttccggggg acaagacatc cctgtttaat atttaaacag cagtgttccc aaactgggtt    7560
cttatatccc ttgctctggt caaccaggtt gcagggtttc ctgtcctcac aggaacgaag    7620
tccctaaaga aacagtggca gccaggttta gccccggaat tgactggatt cctttttttag    7680 ggcccattgg tatggctttt tcccgtatc ccccaggtg tctgcaggct caaagagcag    7740
cgagaagcgt tcagaggaaa gcgatcccgt gccaccttcc ccgtgcccgg gctgtccccg    7800
cacgctgccg gctcggggat gcgggggag cgccggaccg gagcggagcc ccgggcggct    7860
cgctgctgcc ccctagcggg ggaggacgt aattacatcc ctgggggctt ggggggggg    7920 ctgtccctga tatctataac aagaaaatat atatataata agttatcacg taagtagaac    7980
atgaaataac aatataatta tcgtatgagt taaatcttaa aagtcacgta aaagataatc    8040
atgcgtcatt ttgactcacg cggtcgttat agttcaaaat cagtgacact taccgcattg    8100
```

```
acaagcacgc ctcacgggag ctccaagcgg cgactgagat gtcctaaatg cacagcgacg    8160
gattcgcgct atttagaaag agagagcaat atttcaagaa tgcatgcgtc aattttacgc    8220
agactatctt tctagggtta atctagctgc atcaggatca tatcgtcggg tcttttttcc    8280
ggctcagtca tcgcccaagc tggcgctatc tgggcatcgg ggaggaagaa gcccgtgcct    8340
tttccgcgcga ggttgaagcg gcatggaaag agtttgccga ggatgactgc tgctgcattg    8400
acgttgagcg aaaacgcacg tttaccatga tgattcggga aggtgtggcc atgcacgcct    8460
ttaacggtga actgttcgtt caggccacct gggataccag ttcgtcgcgg cttttccgga    8520
cacagttccg gatggtcagc ccgaagcgca tcagcaaccc gaacaatacc ggcgacagcc    8580
ggaactgccg tgccggtgtg cagattaatg acagcggtgc ggcgctggga tattacgtca    8640
gcgaggacgg gtatcctggc tggatgccgc agaaatggac atggataccc cgtgagttac    8700
ccggcgggcg cgcttggcgt aatcatggtc atagctgttt cctgtgtgaa attgttatcc    8760
gctcacaatt ccacacaaca tacgagccgg aagcataaag tgtaaagcct ggggtgccta    8820
atgagtgagc taactcacat taattgcgtt gcgctcactg cccgctttcc agtcgggaaa    8880
cctgtcgtgc cagctgcatt aatgaatcgg ccaacgcgcg gggagaggcg gtttgcgtat    8940
tgggcgctct tccgcttcct cgctcactga ctcgctgcgc tcggtcgttc ggctgcggcg    9000
agcggtatca gctcactcaa aggcggtaat acggttatcc acagaatcag gggataacgc    9060
aggaaagaac atgtgagcaa aaggccagca aaaggccagg aaccgtaaaa aggccgcgtt    9120
gctggcgttt ttccataggc tccgcccccc tgacgagcat cacaaaaatc gacgctcaag    9180
tcagaggtgg cgaaacccga caggactata aagataccag gcgtttcccc ctggaagctc    9240
cctcgtgcgc tctcctgttc cgaccctgcc gcttaccgga tacctgtccg cctttctccc    9300
ttcgggaagc gtggcgcttt ctcatagctc acgctgtagg tatctcagtt cggtgtaggt    9360
cgttcgctcc aagctgggct gtgtgcacga accccccgtt cagcccgacc gctgcgcctt    9420
atccggtaac tatcgtcttg agtccaaccc ggtaagacac gacttatcgc cactggcagc    9480
agccactggt aacaggatta gcagagcgag gtatgtaggc ggtgctacag agttcttgaa    9540
gtggtggcct aactacggct acactagaag gacagtattt ggtatctgcg ctctgctgaa    9600
gccagttacc ttcggaaaaa gagttggtag ctcttgatcc ggcaaacaaa ccaccgctgg    9660
tagcggtggt ttttttgttt gcaagcagca gattacgcgc agaaaaaaag gatctcaaga    9720
agatcctttg atcttttcta cggggtctga cgctcagtgg aacgaaaact cacgttaagg    9780
gattttggtc atgagattat caaaaaggat cttcacctag atccttttaa attaaaaatg    9840
aagttttaaa tcaatctaaa gtatatatga gtaaacttgg tctgacagtt accaatgctt    9900
aatcagtgag gcacctatct cagcgatctg tctatttcgt tcatccatag ttgcctgact    9960
ccccgtcgtg tagataacta cgatacggga gggcttacca tctggcccca gtgctgcaat    10020
gataccgcga gacccacgct caccggctcc agatttatca gcaataaacc agccagccgg    10080
aagggccgag cgcagaagtg gtcctgcaac tttatccgcc tccatccagt ctattaattg    10140
ttgccgggaa gctagagtaa gtagttcgcc agttaatagt ttgcgcaacg ttgttgccat    10200
tgctacaggc atcgtggtgt cacgctcgtc gtttggtatg gcttcattca gctccggttc    10260
ccaacgatca aggcgagtta catgatcccc catgttgtgc aaaaaagcgg ttagctcctt    10320
cggtcctccg atcgttgtca gaagtaagtt ggccgcagtg ttatcactca tggttatggc    10380
agcactgcat aattctctta ctgtcatgcc atccgtaaga tgcttttctg tgactggtga    10440
gtactcaacc aagtcattct gagaatagtg tatgcggcga ccgagttgct cttgcccggc    10500
```

```
gtcaatacgg gataataccg cgccacatag cagaacttta aaagtgctca tcattggaaa    10560
acgttcttcg gggcgaaaac tctcaaggat cttaccgctg ttgagatcca gttcgatgta    10620
acccactcgt gcacccaact gatcttcagc atcttttact ttcaccagcg tttctgggtg    10680
agcaaaaaca ggaaggcaaa atgccgcaaa aagggaata agggcgacac ggaaatgttg    10740
aatactcat                                                           10749
```

<210> SEQ ID NO 52
<211> LENGTH: 10228
<212> TYPE: DNA
<213> ORGANISM: Artificial Sequence
<220> FEATURE:
<223> OTHER INFORMATION: Synthetic

<400> SEQUENCE: 52

```
acgcgtgtag tcttatgcaa tactcttgta gtcttgcaac atggtaacga tgagttagca      60
acatgcctta caaggagaga aaaagcaccg tgcatgccga ttggtggaag taaggtggta     120
cgatcgtgcc ttattaggaa ggcaacagac gggtctgaca tggattggac gaaccactga     180
attgccgcat tgcagagata ttgtatttaa gtgcctagct cgatacaata aacgggtctc     240
tctggttaga ccagatctga gcctgggagc tctctggcta actagggaac ccactgctta     300
agcctcaata aagcttgcct tgagtgcttc aagtagtgtg tgcccgtctg ttgtgtgact     360
ctggtaacta gagatccctc agacccttt agtcagtgtg gaaaatctct agcagtggcg     420
cccgaacagg gacctgaaag cgaaagggaa accagagctc tctcgacgca ggactcggct     480
tgctgaagcg cgcacggcaa gaggcgaggg gcggcgactg gtgagtacgc caaaaatttt     540
gactagcgga ggctagaagg agagagatgg gtgcgagagc gtcagtatta gcgggggag     600 aattagatcg cgatgggaaa aaattcggtt aaggccaggg ggaaagaaaa aatataaatt     660
aaaacatata gtatgggcaa gcaggagct agaacgattc gcagttaatc ctggcctgtt     720
agaaacatca gaaggctgta gacaaatact gggacagcta caaccatccc ttcagacagg     780
atcagaagaa cttagatcat tatataatac agtagcaacc ctctattgtg tgcatcaaag     840
gatagagata aaagacacca aggaagcttt agacaagata gaggaagagc aaaacaaaag     900
taagaccacc gcacagcaag cggccactga tcttcagacc tggaggagga gatatgaggg     960
acaattggag aagtgaatta tataaatata agtagtaaa aattgaacca ttaggagtag    1020 caccccaccaa ggcaaagaga agagtggtgc agagagaaaa aagagcagtg gaataggag    1080 ctttgttcct tgggttcttg ggagcagcag gaagcactat gggcgcagcg tcaatgacgc    1140
tgacggtaca ggccagacaa ttattgtctg gtatagtgca gcagcagaac aatttgctga    1200
gggctattga ggcgcaacag catctgttgc aactcacagt ctggggcatc aagcagctcc    1260
aggcaagaat cctggctgtg aaagatacc taaaggatca acagctcctg gggatttggg    1320
gttgctctgg aaaactcatt tgcaccactg ctgtgccttg aatgctagt tggagtaata    1380 aatctctgga acagatttgg aatcacacga cctggatgga gtgggacaga gaaattaaca    1440
attacacaag cttaatacac tccttaattg aagaatcgca aaaccagcaa gaaaagaatg    1500
aacaagaatt attggaatta gataaatggg caagtttgtg gaattggttt aacataacaa    1560
attggctgtg gtatataaaa ttattcataa tgatagtagg aggcttggta ggtttaagaa    1620
tagtttttgc tgtactttct atagtgaata gagttaggca gggatattca ccattatcgt    1680
ttcagaccca cctcccaacc ccgaggggac ccgacaggcc cgaaggaata agaagaagaag   1740
```

-continued

```
gtggagagag agacagagac agatccattc gattagtgaa cggatctcga cggtatcggt      1800
taacttttaa aagaaaaggg gggattgggg ggtacagtgc aggggaaaga atagtagaca      1860
taatagcaac agacatacaa actaaagaat tacaaaaaca aattacaaaa ttcaaaattt      1920
tatcgatgct agcggaggaa aaactgtttc atacagaagg cgtggaggaa aaactgtttc      1980
atacagaagg cgtggaggaa aaactgtttc atacagaagg cgtggaggaa aaactgtttc      2040
atacagaagg cgtggaggaa aaactgtttc atacagaagg cgtggaggaa aaactgtttc      2100
atacagaagg cgtagatcta gactctagag gtatataat ggaagctcga cttccagctt      2160
ggcattccgg tactgttggt aaaaagcttg gcaatccggt actgttggta aaggatccgc      2220
caccatgcct gccatgaaga ttgagtgccg catcacggga accctgaacg gagtggagtt      2280
tgagctggtc ggaggtggag aagggactcc tgagcaggga cgtatgacca acaagatgaa      2340
gtctaccaag ggcgccttga ccttctcccc ctaccttctc tctcatgtca tgggatacgg      2400
gttctaccac tttggtacct atcccagtgg gtatgagaat cccttcctgc atgccatcaa      2460
caacgggggg tacaccaaca ccaggattga gaagtatgag gatggaggag ttcttcatgt      2520
tagctttagc tacagatatg aagcaggcag ggtgattggg gatttcaagg ttgtcgggac      2580
aggattccct gaggacagtg tgatcttcac cgacaagatc atccggtcca atgctaccgt      2640
ggagcacttg cacccaatgg gagacaacgt tcttgtgggc tccttcgcga gaacctttc      2700 cctgagggat ggaggctact actcatttgt ggttgacagc cacatgcact tcaagagtgc      2760
catccaccca tccatcctcc agaacggggg gcccatgttt gccttcagga gagttgagga      2820
acttcactcc aacactgaac ttggcattgt agagtatcaa catgccttca agactcccat      2880
agcatttgct ggaagcggag ctactaactt cagcctgctg aagcaggctg agacgtgga      2940 ggagaaccct ggacctatgg tcttcacact cgaagatttc gttggggact ggcgacagac      3000
agccggctac aacctggacc aagtccttga acagggaggt gtgtccagtt tgtttcagaa      3060
tctcggggtg tccgtaactc cgatccaaag gattgtcctg agcggtgaaa atgggctgaa      3120
gatcgacatc catgtcatca tcccgtatga aggtctgagc ggcgaccaaa tgggccagat      3180
cgaaaaaatt tttaaggtgg tgtaccctgt ggatgatcat cactttaagg tgatcctgca      3240
ctatggcaca ctggtaatcg acgggggtac gccgaacatg atcgactatt tcggacggcc      3300
gtatgaaggc atcgccgtgt tcgacggcaa aaagatcact gtaacaggga ccctgtggaa      3360
cggcaacaaa attatcgacg agcgcctgat caaccccgac ggctccctgc tgttccgagt      3420
aaccatcaac ggagtgaccg gctggcggct gtgcgaacgc attctggcgt aagcggccgc      3480
gaaggatctg cgatcgctcc ggtgcccgtc agtgggcaga gcgcacatcg cccacagtcc      3540
ccgagaagtt gggggggaggg gtcggcaatt gaacgggtgc ctagagaagg tggcgcgggg      3600
taaactggga aagtgatgtc gtgtactggc tccgcctttt tcccgagggt ggggagaac      3660 cgtatataag tgcagtagtc gccgtgaacg ttctttttcg caacgggttt gccgccagaa      3720
cacagctgaa gcttcgaggg gctcgcatct ctccttcacg cgcccgccgc cctacctgag      3780
gccgccatcc acgccggttg agtcgcgttc tgccgcctcc cgcctgtggt gcctcctgaa      3840
ctgcgtccgc cgtctaggta gtttaaagc tcaggtcgag accgggcctt gtcggcgc      3900 tcccttggag cctacctaga ctcagccggc tctccacgct tgcctgacc ctgcttgctc      3960 aactctacgt ctttgtttcg ttttctgttc tgcgccgtta cagatccaag ctgtgaccgg      4020
cgcctactag tgccaccatg gactttcaag tgcagatctt cagcttctg ctgatctctg      4080 ctagtgtcat catgtctgaa gtgcagctcg tggaatctgg aggaggactg gttaagcctg      4140
```

```
gtggatctct caagctgtct tgtgcagcat ctggctttac attcagctcc tacgatatgt   4200
cttgggtcag gcagacaccc gagaaacgcc tcgaatgggt ggctatgatc tcctccggtg   4260
gctcttactc ctactatccc gacagcgtga agggcaggtt taccatcagc agagacaatg   4320
ccaagaacac tctgtatctg cagatgtcct ccctgcgctc tgaggataca gcaatgtact   4380
actgtgctag gcaaggtgac tacgcatggt ttgcctattg gggacaggga acactggtca   4440
cagtgtctgc tggaggtgga ggcagtggag gtggtggatc tggaggagga gggtctgata   4500
tccaaatgac acaatctcca gcttctcaat ccgcttctct gggtgagtcc gtcacaatca   4560
cttgtctggc ctctcaaact atcggcacct ggctggcttg gtatcagcag aagccaggca   4620
aatctccaca gctcctgatc tatgctgcaa cctccctggc tgatggcgtg cccagcagat   4680
tctctggcag cggttctgga actaagttct cttttcaagat cagctccctc caggcagagg   4740
acttcgtgtc ctactattgt caacagttct actctacacc attcacattc ggaggaggta   4800
caaagctgga gatcaaaagg gaaatcgagc agaagctgat ttccgaagag gatctcaatg   4860
gagtgactgt cagcagcgct ctgtctaact ccatcatgta cttctcacac ttcgtgccag   4920
tgttcctccc tgctaaaccc accacaactc cagcacctag acctcccact ccagcaccaa   4980
ctattgcatc ccagcctctc tccctcagac cagaagcatg cagacctgca gcaggtggag   5040
ctgtgcacac aagaggtctg gacccttct gggtcctcgt ggtggtgggt ggagtcctgg   5100
catgttacag cctcctggtc accgtggcat tcatcatctt ctgggtgaga tctaagagga   5160
gcagactgct gcactctgat tacatgaaca tgacacccag aagacctggt cccaccagaa   5220
agcactacca accctacgca ccaccaagag actttgctgc atacagaagt ctcgagaggg   5280
tcaagttctc aaggagtgca gatgctccag cctatcaaca gggtcagaac caactgtaca   5340
acgagctgaa tctcggaaga agagaggagt acgatgtgct ggataagaga gaggcagggg   5400
acccagagat gggtgggaaa cccagaagaa agaatcctca agagggactg tacaatgagc   5460
tgcagaagga taagatggct gaggcatact cagagatcgg tatgaaggga gagaggagaa   5520
gaggcaaagg tcatgatggt ctgtaccaag gtctgtccac agcaacaaag gatacatatg   5580
atgctctgca catgcaggca ctcccaccac gggttccgg agtgaaacag actttgaact   5640
ttgaccttct caagttggct ggagacgtcg agtccaaccc tggtcccatg accgagtaca   5700
agcccacggt gcgcctcgcc acccgcgacg acgtccccag ggccgtacgc accctcgccg   5760
ccgcgttcgc cgactacccc gccacgcgcc acaccgtcga tccggaccgc cacatcgagc   5820
gggtcaccga gctgcaagaa ctcttcctca cgcgcgtcgg gctcgacatc ggcaaggtgt   5880
gggtcgcgga cgacggcgcc gcggtggcgg tctggaccac gccggagagc gtcgaagcgg   5940
gggcggtgtt cgccgagatc ggcccgcgca tggccgagtt gagcggttcc cggctggccg   6000
cgcagcaaca gatggaaggc ctcctggcgc cgcaccggcc caaggagccc gcgtggttcc   6060
tggccaccgt cggcgtctcg cccgaccacc agggcaaggg tctgggcagc gccgtcgtgc   6120
tccccggagt ggaggcggcc gagcgcgccg gggtgcccgc cttcctggag acctccgcgc   6180
cccgcaacct ccccttctac gagcggctcg gcttcaccgt caccgccgac gtcgaggtgc   6240
ccgaaggacc gcgcacctgg tgcatgaccc gcaagcccgg tgcctgatta attaagtcga   6300
caatcaacct ctggattaca aaatttgtga aagattgact ggtattctta actatgttgc   6360
tccttttacg ctatgtggat acgctgcttt aatgcctttg tatcatgcta ttgcttcccg   6420
tatggctttc attttctcct ccttgtataa atcctggttg ctgtctcttt atgaggagtt   6480
```

```
gtggcccgtt gtcaggcaac gtggcgtggt gtgcactgtg tttgctgacg caaccccac    6540 tggttgggc  attgccacca cctgtcagct cctttccggg actttcgctt tccccctccc   6600
tattgccacg gcggaactca tcgccgcctg ccttgcccgc tgctggacag gggctcggct   6660
gttgggcact gacaattccg tggtgttgtc ggggaaatca tcgtcctttc cttggctgct   6720
cgcctgtgtt gccacctgga ttctgcgcgg gacgtccttc tgctacgtcc cttcggccct   6780
caatccagcg gaccttcctt cccgcggcct gctgccggct ctgcggcctc ttccgcgtct   6840
tcgccttcgc cctcagacga gtcggatctc cctttgggcc gcctcccgc  ctggtacctt   6900 taagaccaat gacttacaag gcagctgtag atcttagcca cttttaaaa  gaaaaggggg   6960 gactggaagg gctaattcac tcccaacgaa gataagatct gcttttgct  tgtactgggt   7020 ctctctggtt agaccagatc tgagcctggg agctctctgg ctaactaggg aacccactgc   7080
ttaagcctca ataaagcttg ccttgagtgc ttcaagtagt gtgtgcccgt ctgttgtgtg   7140
actctggtaa ctagagatcc ctcagaccct tttagtcagt gtggaaaatc tctagcagta   7200
gtagttcatg tcatcttatt attcagtatt tataacttgc aaagaaatga atatcagaga   7260
gtgagaggaa cttgtttatt gcagcttata atggttacaa ataaagcaat agcatcacaa   7320
atttcacaaa taaagcattt ttttcactgc attctagttg tggtttgtcc aaactcatca   7380
atgtatctta tcatgtctgg ctctagctat cccgccccta actccgccca tcccgcccct   7440
aactccgccc agttccgccc attctccgcc ccatggctga ctaatttttt ttatttatgc   7500
agaggccgag gccgcctcgg cctctgagct attccagaag tagtgaggag ctttttttgg   7560
aggcctagac ttttgcagag acggcccaaa ttcgtaatca tggtcatagc tgtttcctgt   7620
gtgaaattgt tatccgctca caattccaca acatacga   gccggaagca taaagtgtaa   7680
agcctggggt gcctaatgag tgagctaact cacattaatt gcgttgcgct cactgcccgc   7740
tttccagtcg ggaaacctgt cgtgccagct gcattaatga atcggccaac gcgcggggag   7800
aggcggtttg cgtattgggc gctcttccgc ttcctcgctc actgactcgc tgcgctcggt   7860
cgttcggctg cggcgagcgg tatcagctca ctcaaaggcg gtaatacggt tatccacaga   7920 atcagggat  aacgcaggaa agaacatgtg agcaaaaggc cagcaaaagg ccaggaaccg   7980
taaaaaggcc gcgttgctgg cgttttcca  taggctccgc cccctgacg  agcatcacaa   8040 aaatcgacgc tcaagtcaga ggtggcgaaa cccgacagga ctataaagat accaggcgtt   8100
tccccctgga agctccctcg tgcgctctcc tgttccgacc ctgccgctta ccggatacct   8160
gtccgccttt ctcccttcgg gaagcgtggc gctttctcat agctcacgct gtaggtatct   8220
cagttcggtg taggtcgttc gctccaagct gggctgtgtg cacgaacccc ccgttcagcc   8280
cgaccgctgc gccttatccg gtaactatcg tcttgagtcc aacccggtaa gacacgactt   8340
atcgccactg gcagcagcca ctggtaacag gattagcaga gcgaggtatg taggcggtgc   8400
tacagagttc ttgaagtggt ggcctaacta cggctacact agaaggacag tatttggtat   8460
ctgcgctctg ctgaagccag ttaccttcgg aaaaagagtt ggtagctctt gatccggcaa   8520
acaaaccacc gctggtagcg gtggtttttt tgtttgcaag cagcagatta cgcgcagaaa   8580
aaaaggatct caagaagatc ctttgatctt ttctacgggg tctgacgctc agtggaacga   8640
aaactcacgt taagggattt tggtcatgag attatcaaaa aggatcttca cctagatcct   8700
tttaaattaa aaatgaagtt ttaaatcaat ctaaagtata tatgagtaaa cttggtctga   8760
cagttaccaa tgcttaatca gtgaggcacc tatctcagcg atctgtctat ttcgttcatc   8820
catagttgcc tgactccccg tcgtgtagat aactacgata cgggagggct taccatctgg   8880
```

| | | | | | |
|---|---|---|---|---|---|
| ccccagtgct | gcaatgatac | cgcgagaccc | acgctcaccg | gctccagatt | tatcagcaat | 8940 |
| aaaccagcca | gccggaaggg | ccgagcgcag | aagtggtcct | gcaactttat | ccgcctccat | 9000 |
| ccagtctatt | aattgttgcc | gggaagctag | agtaagtagt | tcgccagtta | atagtttgcg | 9060 |
| caacgttgtt | gccattgcta | caggcatcgt | ggtgtcacgc | tcgtcgtttg | gtatggcttc | 9120 |
| attcagctcc | ggttcccaac | gatcaaggcg | agttacatga | tcccccatgt | tgtgcaaaaa | 9180 |
| agcggttagc | tccttcggtc | ctccgatcgt | tgtcagaagt | aagttggccg | cagtgttatc | 9240 |
| actcatggtt | atggcagcac | tgcataattc | tcttactgtc | atgccatccg | taagatgctt | 9300 |
| ttctgtgact | ggtgagtact | caaccaagtc | attctgagaa | tagtgtatgc | ggcgaccgag | 9360 |
| ttgctcttgc | ccggcgtcaa | tacgggataa | taccgcgcca | catagcagaa | ctttaaaagt | 9420 |
| gctcatcatt | ggaaaacgtt | cttcggggcg | aaaactctca | aggatcttac | cgctgttgag | 9480 |
| atccagttcg | atgtaaccca | ctcgtgcacc | caactgatct | tcagcatctt | ttactttcac | 9540 |
| cagcgtttct | gggtgagcaa | aaacaggaag | gcaaaatgcc | gcaaaaaagg | gaataagggc | 9600 |
| gacacggaaa | tgttgaatac | tcatactctt | ccttttcaa | tattattgaa | gcatttatca | 9660 |
| gggttattgt | ctcatgagcg | gatacatatt | tgaatgtatt | tagaaaaata | aacaaatagg | 9720 |
| ggttccgcgc | acatttcccc | gaaaagtgcc | acctgacgtc | taagaaacca | ttattatcat | 9780 |
| gacattaacc | tataaaaata | ggcgtatcac | gaggcccttt | cgtctcgcgc | gtttcggtga | 9840 |
| tgacggtgaa | aacctctgac | acatgcagct | cccggagacg | gtcacagctt | gtctgtaagc | 9900 |
| ggatgccggg | agcagacaag | cccgtcaggg | cgcgtcagcg | ggtgttggcg | ggtgtcgggg | 9960 |
| ctggcttaac | tatgcggcat | cagagcagat | tgtactgaga | gtgcaccata | tgcggtgtga | 10020 |
| aataccgcac | agatgcgtaa | ggagaaaata | ccgcatcagg | cgccattcgc | cattcaggct | 10080 |
| gcgcaactgt | tgggaagggc | gatcggtgcg | ggcctcttcg | ctattacgcc | agctggcgaa | 10140 |
| agggggatgt | gctgcaaggc | gattaagttg | ggtaacgcca | gggttttccc | agtcacgacg | 10200 |
| ttgtaaaacg | acggccagtg | ccaagctg | | | | 10228 |

<210> SEQ ID NO 53
<211> LENGTH: 10509
<212> TYPE: DNA
<213> ORGANISM: Artificial Sequence
<220> FEATURE:
<223> OTHER INFORMATION: Synthetic

<400> SEQUENCE: 53

| | | | | | |
|---|---|---|---|---|---|
| actcttcctt | tttcaatatt | attgaagcat | ttatcagggt | tattgtctca | tgagcggata | 60 |
| catatttgaa | tgtatttaga | aaaataaaca | ataggggtt | ccgcgcacat | ttccccgaaa | 120 |
| agtgccacct | aaattgtaag | cgttaatatt | ttgttaaaat | tcgcgttaaa | tttttgttaa | 180 |
| atcagctcat | tttttaacca | ataggccgaa | atcggcaaaa | tcccttataa | atcaaaagaa | 240 |
| tagaccgaga | tagggttgag | tgttgttcca | gtttggaaca | agagtccact | attaaagaac | 300 |
| gtggactcca | acgtcaaagg | gcgaaaaacc | gtctatcagg | gcgatggccc | actacgtgaa | 360 |
| ccatcaccct | aatcaagttt | tttggggtcg | aggtgccgta | aagcactaaa | tcggaaccct | 420 |
| aaagggagcc | cccgatttag | agcttgacgg | ggaaagccgg | cgaacgtggc | gagaaaggaa | 480 |
| gggaagaaag | cgaaaggagc | gggcgctagg | gcgctggcaa | gtgtagcggt | cacgctgcgc | 540 |
| gtaaccacca | cacccgccgc | gcttaatgcg | ccgctacagg | gcgcgtccca | ttcgccattc | 600 |
| aggctgcgca | actgttggga | agggcgatcg | gtgcgggcct | cttcgctatt | acgccagctg | 660 |

```
gcgaaagggg gatgtgctgc aaggcgatta agttgggtaa cgccagggtt ttcccagtca    720
cgacgttgta aaacgacggc cagtgagcgc gcctcgttca ttcacgtttt tgaacccgtg    780
gaggacgggc agactcgcgg tgcaaatgtg ttttacagcg tgatggagca gatgaagatg    840
ctcgacacgc tgcagaacac gcagctagat taaccctaga aagataatca tattgtgacg    900
tacgttaaag ataatcatgt gtaaaattga cgcatgtgtt ttatcggtct gtatatcgag    960
gtttatttat taatttgaat agatattaag ttttattata tttacactta catactaata   1020
ataaattcaa caaacaattt atttatgttt atttatttat taaaaaaaac aaaaactcaa   1080
aatttcttct ataaagtaac aaaactttta tgagggacag ccccccccca aagcccccag   1140
ggatgtaatt acgtccctcc cccgctaggg ggcagcagcg agccgcccgg ggctccgctc   1200
cggtccggcg ctccccccgc atccccgagc cggcagcgtg cggggacagc ccgggcacgg   1260
ggaaggtggc acgggatcgc tttcctctga acgcttctcg ctgctctttg agcctgcaga   1320
cacctggggg gatacgggga aaaggcctcc acggccacta gtattatgcc cagtacatga   1380
ccttatggga ctttcctact tggcagtaca tctacgtatt agtcatcgct attaccatgg   1440
tgatgcggtt ttggcagtac atcaatgggc gtggatagcg gtttgactca cggggatttc   1500
caagtctcca ccccattgac gtcaatggga gtttgttttg gcaccaaaat caacgggact   1560
ttccaaaatg tcgtaacaac tccgccccat tgacgcaaat gggcggtagg cgtgtacggt   1620
gggaggttta taagcaga gctcgtttag tgaaccgtca gatcgcctgg agacgccatc   1680
cacgctgttt tgacctccat agaagattct agagccacca tggaaactga tacactcctg   1740
ctctgggttc tgctgctgtg ggttcctggc tctactggtg attatccata cgatgttcca   1800
gattatgctg gatccttcaa ctgcctcggt atgagcaaca gggacttcct ggaaggagtg   1860
agcggtgcta catgggtgga tctggtgctc gaaggcgact cttgcgttac catcatgtcc   1920
aaggacaaac caaccattga tgtgaagatg atgaacatgg aagcagctaa cctggcagaa   1980
gtccgctcct attgctacct ggctactgtt agcgacctct ctactaaggc tgcttgtcca   2040
actatgggtg aagctcacaa cgacaagagg gctgatcctg cctttgtctg taggcagggt   2100
gtggtggaca gaggttgggg taatggttgt ggcctgttcg gtaagggctc catcgacacc   2160
tgcgctaagt tcgcttgtag cacaaaggcc atcggtagga ctatcctgaa agagaacatc   2220
aagtacgagg tggctatctt cgtgcatgga cctacaacag ttgaatctca cggcaactac   2280
agcacccagg ctggagcaac acaagcaggc agattcagca tcacaccagc tgcacctagc   2340
tacaccctca agctcggtga atacggtgaa gtcacagttg actgcgagcc cagatccggt   2400
atcgacacaa atgcctacta cgttatgact gtcggaacta agacattcct ggtccacagg   2460
gaatggttca tggacctgaa tctcccttgg tctagcgcag gcagcacagt ctggagaaac   2520
agagagactc tgatggagtt cgaggaacca cacgcaacca acagtccgt cattgccctg   2580
ggatctcagg agggtgctct gcaccaagct ctggctggtg ccattcctgt ggagtttagc   2640
tctaacaccg tgaagctgac cagcggtcat ctgaaatgca gggttaagat ggagaagctg   2700
caactcaagg gaactactta cggagtgtgt agcaaggcat tcaagtttct gggaactcct   2760
gcagatacag acatggtac agtcgtgctc gaactgcagt acactggcac tgatggtccc   2820
tgcaaagtgc caatcagcag cgtcgcttct ctgaacgacc tgactcccgt gggtagactg   2880
gtgaccgtga atccttccgt ctctgtggcc acagctaacg caaaggttct gattgaactg   2940
gagcctccct tcggagacag ctacattgtt gtcggaagag gtgagcagca gatcaaccac   3000
cactggcaca agagcggaag cagcatcggc aaggcattca ctacaacact caaaggtgca   3060
```

```
caaagactgg ctgctctcgg tgatactgcc tgggatttcg gtagcgttgg aggcgtcttc    3120
acatctgttg gcaaggcagt tcaccaggtc ttcggtggtg ctttcaggtc cctgttcgga    3180
ggcatgagct ggattactca gggactgctg ggtgctctgc tcctctggat gggcatcaac    3240
gcaagagata gatccatcgc actgacattt ctcgctgtgg gaggcgttct cctcttcctg    3300
tccgtcaatg ttcatgctag cggttctggt gtgaaacaga ctttgaattt tgaccttctc    3360
aagttggcgg gagacgtcga gtccaaccct gggcccatgg aagatgccaa aacattaag    3420 aagggcccag cgccattcta cccactcgaa gacgggaccg ccggcgagca gctgcacaaa    3480
gccatgaagc gctacgccct ggtgcccggc accatcgcct ttaccgacgc acatatcgag    3540
gtggacatta cctacgccga gtacttcgag atgagcgttc ggctggcaga agctatgaag    3600
cgctatgggc tgaatacaaa ccatcggatc gtggtgtgca gcgagaatag cttgcagttc    3660
ttcatgcccg tgttgggtgc cctgttcatc ggtgtggctg tggccccagc taacgacatc    3720
tacaacgagc gcgagctgct gaacagcatg ggcatcagcc agcccaccgt cgtattcgtg    3780
agcaagaaag ggctgcaaaa gatcctcaac gtgcaaaaga agctaccgat catacaaaag    3840
atcatcatca tggatagcaa gaccgactac cagggcttcc aaaagcatgta caccttcgtg    3900 acttcccatt tgccacccgg cttcaacgag tacgacttcg tgcccgagag cttcgaccgg    3960
gacaaaacca tcgccctgat catgaacagt agtggcagta ccggattgcc caagggcgta    4020
gccctaccgc accgcaccgc ttgtgtccga ttcagtcatg cccgcgaccc catcttcggc    4080
aaccagatca tccccgacac cgctatcctc agcgtggtgc catttcacca cggcttcggc    4140
atgttcacca cgctgggcta cttgatctgc ggctttcggg tcgtgctcat gtaccgcttc    4200
gaggaggagc tattcttgcg cagcttgcaa gactataaga ttcaatctgc cctgctggtg    4260
cccacactat ttagcttctt cgctaagagc actctcatcg acaagtacga cctaagcaac    4320
ttgcacgaga tcgccagcgg cggggcgccg ctcagcaagg aggtaggtga ggccgtggcc    4380
aaacgcttcc acctaccagg catccgccag ggctacggcc tgacagaaac aaccagcgcc    4440
attctgatca cccccgaagg ggacgacaag cctggcgcag taggcaaggt ggtgcccttc    4500
ttcgaggcta aggtggtgga cttggacacc ggtaagacac tgggtgtgaa ccagcgcggc    4560
gagctgtgcg tccgtggccc catgatcatg agcggctacg ttaacaaccc cgaggctaca    4620
aacgctctca tcgacaagga cggctggctg cacagcggcg acatcgccta ctgggacgag    4680
gacgagcact tcttcatcgt ggaccggctg aagagcctga tcaaatacaa gggctaccag    4740
gtagccccag ccgaactgga gagcatcctg ctgcaacacc ccaacatctt cgacgccggg    4800
gtcgccggcc tgcccgacga cgatgccggc gagctgcccg ccgcagtcgt cgtgctggaa    4860
cacggtaaaa ccatgaccga aaggagatc gtggactatg tggccagcca ggttacaacc    4920
gccaagaagc tgcgcggtgg tgttgtgttc gtggacgagg tgcctaaagg actgaccggc    4980
aagttggacg cccgcaagat ccgcgagatt ctcattaagg ccaagaaggg cggcaagatc    5040
gccgtgggaa gcggagctac taacttcagc ctgctgaagc aggctggaga cgtggaggag    5100
aaccctggac ctatggatag cactgagaac gtcatcaagc ccttcatgcg cttcaaggtg    5160
cacatggagg gctccgtgaa cggccacgag ttcgagatca agggcgtggg cgagggcaag    5220
ccctacgagg gcacccagac cgccaagctg caagtgacca agggcggccc cctgcccttc    5280
gcctgggaca tcctgtcccc ccagttcttc tacggctcca aggcgtacat caagcacccc    5340
gccgacatcc ccgactacct caagcagtcc ttccccgagg gcttcaagtg ggagcgcgtg    5400
```

```
atgaacttcg aggacggcgg cgtggtgacc gtgacccagg actcctccct gcaggacggc    5460
accctcatct accacgtgaa gttcatcggc gtgaacttcc cctccgacgg ccccgtaatg    5520
cagaagaaga ctctgggctg ggagccctcc actgagcgca actaccccg cgacggcgtg     5580
ctgaagggcg agaaccacat ggcgctgaag ctgaagggcg gcggccacta cctgtgtgag    5640
ttcaagtcca tctacatggc caagaagccc gtgaagctgc ccggctacca ctacgtggac    5700
tacaagctcg acatcacctc ccacaacgag gactacaccg tggtggagca gtacgagcgc    5760
gccgaggccc gccaccacct gttccagtaa tgataacgcg gccgcgaagg atctgcgatc    5820
gctccggtgc ccgtcagtgg gcagagcgca catcgcccac agtccccgag aagttgggggg   5880
gaggggtcgg caattgaacg ggtgcctaga gaaggtggcg cggggtaaac tgggaaagtg    5940
atgtcgtgta ctggctccgc cttttttccg agggtggggg agaaccgtat ataagtgcag    6000
tagtcgccgt gaacgttctt tttcgcaacg ggtttgccgc cagaacacag ctgaagcttc    6060
gaggggctcg catctctcct tcacgcgccc gccgccctac ctgaggccgc catccacgcc    6120
ggttgagtcg cgttctgccg cctcccgcct gtggtgcctc ctgaactgcg tccgccgtct    6180
aggtaagttt aaagctcagg tcgagaccgg gcctttgtcc ggcgctccct tggagcctac    6240
ctagactcag ccggctctcc acgctttgcc tgacccttgct tgctcaactc tacgtctttg   6300
tttcgttttc tgttctgcgc cgttacagat ccaagctgtg accggcgcct acgctagatg    6360
accgagtaca agcccacggt gcgcctcgcc acccgcgacg acgtccccag ggccgtacgc    6420
accctcgccg ccgcgttcgc cgactacccc gccacgcgcc acaccgtcga tccggaccgc    6480
cacatcgagc gggtcaccga gctgcaagaa ctcttcctca cgcgcgtcgg gctcgacatc    6540
ggcaaggtgt gggtcgcgga cgacggcgcc gcggtggcgg tctggaccac gccggagagc    6600
gtcgaagcgg gggcggtgtt cgccgagatc ggcccgcgca tggccgagtt gagcggttcc    6660
cggctggccg cgcagcaaca gatggaaggc ctcctggcgc cgcaccggcc caaggagccc    6720
gcgtggttcc tggccaccgt cggcgtctcg cccgaccacc agggcaaggg tctgggcagc    6780
gccgtcgtgc tccccggagt ggaggcggcc gagcgcgccg gggtgcccgc cttcctggag    6840
acctccgcgc cccgcaacct ccccttctac gagcggctcg gcttcaccgt caccgccgac    6900
gtcgaggtgc ccgaaggacc gcgcacctgg tgcatgaccc gcaagcccgg tgcctgagtc    6960
gacaatcaac ctctggatta caaaatttgt gaaagattga ctggtattct taactatgtt    7020
gctcctttta cgctatgtgg atacgctgct ttaatgcctt tgtatcatgc gttaactaaa    7080
cttgtttatt gcagcttata atggttacaa ataaagcaat agcatcacaa atttcacaaa    7140
taaagcattt ttttcactgc attctagttg tggtttgtcc aaactcatca atgtatctta    7200
tcatgtctgg aattgactca aatgatgtca attagtctat cagaagctca tctggtctcc    7260
cttccggggg acaagacatc cctgtttaat atttaaacag cagtgttccc aaactgggtt    7320
cttatatccc ttgctctggt caaccaggtt gcagggtttc ctgtcctcac aggaacgaag    7380
tccctaaaga aacagtggca gccaggttta gccccggaat tgactggatt ccttttttag    7440
ggcccattgg tatggctttt tcccccgtatc cccccaggtg tctgcaggct caaagagcag    7500
cgagaagcgt tcagaggaaa gcgatcccgt gccaccttcc ccgtgcccgg gctgtccccg    7560
cacgctgccg gctcggggat gcggggggag cgccggaccg gagcggagcc ccgggcggct    7620
cgctgctgcc ccctagcggg ggagggacgt aattacatcc ctgggggctt gggggggggg    7680
ctgtccctga tatctataac aagaaaatat atatataata agttatcacg taagtagaac    7740
atgaaataac aatataatta tcgtatgagt taaatcttaa aagtcacgta aaagataatc    7800
```

```
atgcgtcatt ttgactcacg cggtcgttat agttcaaaat cagtgacact taccgcattg    7860
acaagcacgc ctcacgggag ctccaagcgg cgactgagat gtcctaaatg cacagcgacg    7920
gattcgcgct atttagaaag agagagcaat atttcaagaa tgcatgcgtc aattttacgc    7980
agactatctt tctagggtta atctagctgc atcaggatca tatcgtcggg tcttttttcc    8040
ggctcagtca tcgcccaagc tggcgctatc tgggcatcgg ggaggaagaa gcccgtgcct    8100
tttcccgcga ggttgaagcg gcatggaaag agtttgccga ggatgactgc tgctgcattg    8160
acgttgagcg aaaacgcacg tttaccatga tgattcggga aggtgtggcc atgcacgcct    8220
ttaacggtga actgttcgtt caggccacct gggataccag ttcgtcgcgg cttttccgga    8280
cacagttccg gatggtcagc ccgaagcgca tcagcaaccc gaacaatacc ggcgacagcc    8340
ggaactgccg tgccggtgtg cagattaatg acagcggtgc ggcgctggga tattacgtca    8400
gcgaggacgg gtatcctggc tggatgccgc agaaatggac atggataccc cgtgagttac    8460
ccggcgggcg cgcttggcgt aatcatggtc atagctgttt cctgtgtgaa attgttatcc    8520
gctcacaatt ccacacaaca tacgagccgg aagcataaag tgtaaagcct ggggtgccta    8580
atgagtgagc taactcacat taattgcgtt gcgctcactg cccgctttcc agtcgggaaa    8640
cctgtcgtgc cagctgcatt aatgaatcgg ccaacgcgcg gggagaggcg gtttgcgtat    8700
tgggcgctct tccgcttcct cgctcactga ctcgctgcgc tcggtcgttc ggctgcggcg    8760
agcggtatca gctcactcaa aggcggtaat acggttatcc acagaatcag gggataacgc    8820
aggaaagaac atgtgagcaa aaggccagca aaaggccagg aaccgtaaaa aggccgcgtt    8880
gctggcgttt ttccataggc tccgcccccc tgacgagcat cacaaaaatc gacgctcaag    8940
tcagaggtgg cgaaacccga caggactata aagataccag gcgtttcccc ctggaagctc    9000
cctcgtgcgc tctcctgttc cgaccctgcc gcttaccgga tacctgtccg cctttctccc    9060
ttcgggaagc gtggcgcttt ctcatagctc acgctgtagg tatctcagtt cggtgtaggt    9120
cgttcgctcc aagctgggct gtgtgcacga accccccgtt cagcccgacc gctgcgcctt    9180
atccggtaac tatcgtcttg agtccaaccc ggtaagacac gacttatcgc cactggcagc    9240
agccactggt aacaggatta gcagagcgag gtatgtaggc ggtgctacag agttcttgaa    9300
gtggtggcct aactacggct acactagaag gacagtattt ggtatctgcg ctctgctgaa    9360
gccagttacc ttcggaaaaa gagttggtag ctcttgatcc ggcaaacaaa ccaccgctgg    9420
tagcggtggt ttttttgttt gcaagcagca gattacgcgc agaaaaaaag gatctcaaga    9480
agatcctttg atcttttcta cggggtctga cgctcagtgg aacgaaaact cacgttaagg    9540
gattttggtc atgagattat caaaaaggat cttcacctag atccttttaa attaaaaatg    9600
aagttttaaa tcaatctaaa gtatatatga gtaaacttgg tctgacagtt accaatgctt    9660
aatcagtgag gcacctatct cagcgatctg tctatttcgt tcatccatag ttgcctgact    9720
ccccgtcgtg tagataacta cgatacggga gggcttacca tctggcccca gtgctgcaat    9780
gataccgcga gacccacgct caccggctcc agatttatca gcaataaacc agccagccgg    9840
aagggccgag cgcagaagtg gtcctgcaac tttatccgcc tccatccagt ctattaattg    9900
ttgccgggaa gctagagtaa gtagttcgcc agttaatagt ttgcgcaacg ttgttgccat    9960
tgctacaggc atcgtggtgt cacgctcgtc gtttggtatg gcttcattca gctccggttc   10020
ccaacgatca aggcgagtta catgatcccc catgttgtgc aaaaaagcgg ttagctcctt   10080
cggtcctccg atcgttgtca gaagtaagtt ggccgcagtg ttatcactca tggttatggc   10140
```

```
agcactgcat aattctctta ctgtcatgcc atccgtaaga tgcttttctg tgactggtga    10200
gtactcaacc aagtcattct gagaatagtg tatgcggcga ccgagttgct cttgcccggc    10260
gtcaatacgg gataataccg cgccacatag cagaacttta aaagtgctca tcattggaaa    10320
acgttcttcg gggcgaaaac tctcaaggat cttaccgctg ttgagatcca gttcgatgta    10380
acccactcgt gcacccaact gatcttcagc atctttact ttcaccagcg tttctgggtg     10440
agcaaaaaca ggaaggcaaa atgccgcaaa aagggaata agggcgacac ggaaatgttg      10500
aatactcat                                                             10509

<210> SEQ ID NO 54
<211> LENGTH: 10231
<212> TYPE: DNA
<213> ORGANISM: Artificial Sequence
<220> FEATURE:
<223> OTHER INFORMATION: Synthetic

<400> SEQUENCE: 54
acgcgtgtag tcttatgcaa tactcttgta gtcttgcaac atggtaacga tgagttagca      60
acatgcctta caaggagaga aaaagcaccg tgcatgccga ttggtggaag taaggtggta     120
cgatcgtgcc ttattaggaa ggcaacagac gggtctgaca tggattggac gaaccactga     180
attgccgcat tgcagagata ttgtatttaa gtgcctagct cgatacaata acgggtctc      240
tctggttaga ccagatctga gcctgggagc tctctggcta actagggaac ccactgctta     300
agcctcaata aagcttgcct tgagtgcttc aagtagtgtg tgcccgtctg ttgtgtgact     360
ctggtaacta gagatccctc agacccttt agtcagtgtg aaaatctct agcagtggcg      420
cccgaacagg gacctgaaag cgaaagggaa accagagctc tctcgacgca ggactcggct     480
tgctgaagcg cgcacggcaa gaggcgaggg cggcgactg tgagtacgc caaaattt         540
gactagcgga ggctagaagg agagagatgg gtgcgagagc gtcagtatta gcgggggag      600
aattagatcg cgatgggaaa aaattcggtt aaggccaggg ggaagaaaa aatataaatt      660
aaaacatata gtatgggcaa gcagggagct agaacgattc gcagttaatc ctggcctgtt     720
agaaacatca gaaggctgta gacaaatact gggacagcta caaccatccc ttcagacagg    780
atcagaagaa cttagatcat tatataatac agtagcaacc ctctattgtg tgcatcaaag    840
gatagagata aaagacacca aggaagcttt agacaagata gaggaagagc aaaacaaaag   900
taagaccacc gcacagcaag cggccactga tcttcagacc tggaggagga gatatgaggg   960
acaattggag aagtgaatta tataaatata agtagtaaa aattgaacca ttaggagtag   1020
cacccaccaa ggcaaagaga agagtggtgc agagagaaaa aagagcagtg ggaataggag   1080
ctttgttcct tgggttcttg ggagcagcag gaagcactat gggcgcagcg tcaatgacgc   1140
tgacggtaca ggccagacaa ttattgtctg gtatagtgca gcagcagaac aatttgctga   1200
gggctattga ggcgcaacag catctgttgc aactcacagt ctggggcatc aagcagctcc   1260
aggcaagaat cctggctgtg gaaagatacc taaaggatca cagctcctg gggatttggg    1320
gttgctctgg aaaactcatt tgcaccactg ctgtgccttg gaatgctagt tggagtaata   1380
aatctctgga acagatttgg aatcacacga cctggatgga gtgggacaga gaaattaaca   1440
attacacaag cttaatacac tccttaattg aagaatcgca aaaccagcaa gaaaagaatg   1500
aacaagaatt attggaatta gataaatggg caagtttgtg gaattggttt aacataacaa   1560
attggctgtg gtatataaaa ttattcataa tgatagtagg aggcttggta ggtttaagaa   1620
tagttttgc tgtactttct atagtgaata gagttaggca gggatattca ccattatcgt   1680
```

```
ttcagaccca cctcccaacc ccgaggggac ccgacaggcc cgaaggaata gaagaagaag    1740
gtggagagag agacagagac agatccattc gattagtgaa cggatctcga cggtatcggt    1800
taacttttaa aagaaaaggg gggattgggg ggtacagtgc aggggaaaga atagtagaca    1860
taatagcaac agacatacaa actaaagaat tacaaaaaca aattacaaaa ttcaaaattt    1920
tatcgatgct agcggaggaa aaactgtttc atacagaagg cgtggaggaa aaactgtttc    1980
atacagaagg cgtggaggaa aaactgtttc atacagaagg cgtggaggaa aaactgtttc    2040
atacagaagg cgtggaggaa aaactgtttc atacagaagg cgtggaggaa aaactgtttc    2100
atacagaagg cgtagatcta gactctagag ggtatataat ggaagctcga cttccagctt    2160
ggcattccgg tactgttggt aaaaagcttg gcaatccggt actgttggta aaggatccgc    2220
caccatgcct gccatgaaga ttgagtgccg catcacggga accctgaacg gagtggagtt    2280
tgagctggtc ggaggtggag aagggactcc tgagcaggga cgtatgacca acaagatgaa    2340
gtctaccaag ggcgccttga ccttctcccc ctaccttctc tctcatgtca tgggatacgg    2400
gttctaccac tttggtacct atcccagtgg gtatgagaat cccttcctgc atgccatcaa    2460
caacgggggg tacaccaaca ccaggattga gaagtatgag gatggaggag ttcttcatgt    2520
tagctttagc tacagatatg aagcaggcag ggtgattggg gatttcaagg ttgtcgggac    2580
aggattccct gaggacagtg tgatcttcac cgacaagatc atccggtcca atgctaccgt    2640
ggagcacttg cacccaatgg gagacaacgt tcttgtgggc tccttcgcga gaacctttc    2700 cctgagggat ggaggctact actcatttgt ggttgacagc cacatgcact tcaagagtgc    2760
catccaccca tccatcctcc agaacggggg gcccatgttt gccttcagga gagttgagga    2820
acttcactcc aacactgaac ttggcattgt agagtatcaa catgccttca agactcccat    2880
agcatttgct ggaagcggag ctactaactt cagcctgctg aagcaggctg agacgtgga    2940 ggagaaccct ggacctatgg tcttcacact cgaagatttc gttggggact ggcgacagac    3000
agccggctac aacctggacc aagtccttga acagggaggt gtgtccagtt tgtttcagaa    3060
tctcggggtg tccgtaactc cgatccaaag gattgtcctg agcggtgaaa atgggctgaa    3120
gatcgacatc catgtcatca tcccgtatga aggtctgagc ggcgaccaaa tgggccagat    3180
cgaaaaaatt tttaaggtgg tgtaccctgt ggatgatcat cactttaagg tgatcctgca    3240
ctatggcaca ctggtaatcg acgggggtac gccgaacatg atcgactatt tcggacggcc    3300
gtatgaaggc atcgccgtgt tcgacggcaa aaagatcact gtaacaggga ccctgtggaa    3360
cggcaacaaa attatcgacg agcgcctgat caaccccgac ggctccctgc tgttccgagt    3420
aaccatcaac ggagtgaccg gctggcggct gtgcgaacgc attctggcgt aagcggccgc    3480
gaaggatctg cgatcgctcc ggtgcccgtc agtgggcaga gcgcacatcg cccacagtcc    3540
ccgagaagtt ggggggaggg gtcggcaatt gaacgggtgc ctagagaagg tggcgcgggg    3600
taaactggga aagtgatgtc gtgtactggc tccgcctttt tcccgagggt gggggagaac    3660
cgtatataag tgcagtagtc gccgtgaacg ttcttttcg caacgggttt ccgccagaa     3720 cacagctgaa gcttcgaggg gctcgcatct ctccttcacg cgcccgccgc cctacctgag    3780
gccgccatcc acgccggttg agtcgcgttc tgccgcctcc cgcctgtggt gcctcctgaa    3840
ctgcgtccgc cgtctaggta agtttaaagc tcaggtcgag accgggcctt tgtccggcgc    3900
tcccttggag cctacctaga ctcagccggc tctccacgct ttgcctgacc ctgcttgctc    3960
aactctacgt ctttgtttcg ttttctgttc tgcgccgtta cagatccaag ctgtgaccgg    4020
```

```
cgcctactag tgccaccatg actttcaag tgcagatctt cagctttctg ctgatctctg    4080
ctagtgtcat catgtctcaa gtgcaactgc aacaatctgg tagcgaactc atgaaacctg    4140
gtgcctccgt ccagatcagc tgcaaagcaa caggttacac tttctctgac tactggatcg    4200
agtgggtgaa gcaaagacct ggacatggac tcgaatggat cggtgacatt ctgtgcggaa    4260
ccggaaggac tcgctacaac gagaagctga aggcaatggc aaccttcacc gcagatactt    4320
ccagcaacac cgctttcatg caactgtcca gcctgacaag cgaggactct gctgtctact    4380
attgcgcaag gtctgcatcc tatggcgact acgctgatta ctggggtcac ggtacaaccc    4440
tgactgtcag cagcggaggt ggaggcagtg gaggtggtgg atctggagga ggagggtctg    4500
atatcgtgat gactcaatcc cacaagttca tgtctaccct cgtcggtgac agggtgtcta    4560
tcacttgcaa ggcatcccag gacgtctcta ctgctgtggc ctggtatcaa cagaagcctg    4620
gccagagccc taaactcctg atcagctggg cttctactag gcacacaggc gttccagatc    4680
gctttactgg ctctggatct ggaactgatt acaccctgac tatcagcagc gtgcaggctg    4740
aggatctggc tctctactac tgtcaacagc attacaccac accactgacc ttcggagctg    4800
gaactaagct ggaactgaag agggaaatcg agcagaagct gatttccgaa gaggatctca    4860
atggagtgac tgtcagcagc gctctgtcta actccatcat gtacttctca cacttcgtgc    4920
cagtgttcct ccctgctaaa cccaccacaa ctccagcacc tagacctccc actccagcac    4980
caactattgc atcccagcct ctctccctca gaccagaagc atgcagacct gcagcaggtg    5040
gagctgtgca cacaagaggt ctggacccct tctgggtcct cgtggtggtg ggtggagtcc    5100
tggcatgtta cagcctcctg gtcaccgtgg cattcatcat cttctgggtg agatctaaga    5160
ggagcagact gctgcactct gattacatga acatgacacc cagaagacct ggtcccacca    5220
gaaagcacta ccaaccctac gcaccaccaa gagactttgc tgcatacaga agtctcgaga    5280
gggtcaagtt ctcaaggagt gcagatgctc cagcctatca acagggtcag aaccaactgt    5340
acaacgagct gaatctcgga agaagagagg agtacgatgt gctggataag agaagaggca    5400
gggacccaga gatgggtggg aaacccagaa gaagaatcc tcaagaggga ctgtacaatg    5460
agctgcagaa ggataagatg gctgaggcat actcagagat cggtatgaag ggagagagga    5520
gaagaggcaa aggtcatgat ggtctgtacc aaggtctgtc cacagcaaca aaggatacat    5580
atgatgctct gcacatgcag gcactcccac cacgggttc cggagtgaaa cagactttga    5640
actttgacct tctcaagttg gctggagacg tcgagtccaa ccctggtccc atgaccgagt    5700
acaagcccac ggtgcgcctc gccacccgcg acgacgtccc cagggccgta cgcacccctcg    5760 ccgccgcgtt cgccgactac cccgccacgc gccacaccgt cgatccggac cgccacatcg    5820
agcgggtcac cgagctgcaa gaactcttcc tcacgcgcgt cgggctcgac atcggcaagg    5880
tgtgggtcgc ggacgacggc gccgcggtgg cggtctggac cacgccggag agcgtcgaag    5940
cgggggcggt gttcgccgag atcgcccgc gcatggccga ttgagcggt tccggctgg    6000 ccgcgcagca acagatggaa ggcctcctgg cgccgcaccg gcccaaggag cccgcgtggt    6060
tcctggccac cgtcggcgtc tcgcccgacc accagggcaa gggtctgggc agcgccgtcg    6120
tgctccccgg agtggaggcg gccgagcgcg ccggggtgcc cgccttcctg gagacctccg    6180
cgccccgcaa cctcccttc tacgagcggc tcggcttcac cgtcaccgcc gacgtcgagg    6240
tgcccgaagg accgcgcacc tggtgcatga cccgcaagcc cggtgcctga ttaattaagt    6300
cgacaatcaa cctctggatt acaaaatttg tgaaagattg actggtattc ttaactatgt    6360
tgctcctttt acgctatgtg gatacgctgc tttaatgcct ttgtatcatg ctattgcttc    6420
```

```
ccgtatggct tcattttct cctccttgta taaatcctgg ttgctgtctc tttatgagga   6480
gttgtggccc gttgtcaggc aacgtggcgt ggtgtgcact gtgtttgctg acgcaacccc   6540
cactggttgg ggcattgcca ccacctgtca gctccttcc gggactttcg ctttcccct    6600 ccctattgcc acggcggaac tcatcgccgc ctgccttgcc cgctgctgga caggggctcg   6660
gctgttgggc actgacaatt ccgtggtgtt gtcggggaaa tcatcgtcct tccttggct   6720 gctcgcctgt gttgccacct ggattctgcg cgggacgtcc ttctgctacg tcccttcggc   6780
cctcaatcca gcggaccttc cttcccgcgg cctgctgccg gctctgcggc tcttccgcg    6840 tcttcgcctt cgccctcaga cgagtcggat ctcccttggg gccgcctccc cgcctggtac   6900
ctttaagacc aatgacttac aaggcagctg tagatcttag ccacttttta aagaaaagg    6960 ggggactgga agggctaatt cactcccaac gaagataaga tctgcttttt gcttgtactg   7020
ggtctctctg gttagaccag atctgagcct gggagctctc tggctaacta gggaacccac   7080
tgcttaagcc tcaataaagc ttgccttgag tgcttcaagt agtgtgtgcc cgtctgttgt   7140
gtgactctgg taactagaga tccctcagac ccttttagtc agtgtggaaa atctctagca   7200
gtagtagttc atgtcatctt attattcagt atttataact tgcaaagaaa tgaatatcag   7260
agagtgagag gaacttgttt attgcagctt ataatggtta caaataaagc aatagcatca   7320
caaatttcac aaataaagca ttttttttcac tgcattctag ttgtggtttg tccaaactca   7380
tcaatgtatc ttatcatgtc tggctctagc tatcccgccc ctaactccgc ccatcccgcc   7440
cctaactccg cccagttccg cccattctcc gccccatggc tgactaattt ttttttattta   7500 tgcagaggcc gaggccgcct cggcctctga gctattccag aagtagtgag gaggcttttt   7560
tggaggccta acttttgca gagacggccc aaattcgtaa tcatggtcat agctgtttcc   7620
tgtgtgaaat tgttatccgc tcacaattcc acacaacata cgagccggaa gcataaagtg   7680
taaagcctgg ggtgcctaat gagtgagcta actcacatta ttgcgttgc gctcactgcc   7740 cgctttccag tcgggaaacc tgtcgtgcca gctgcattaa tgaatcggcc aacgcgcggg   7800
gagaggcggt ttgcgtattg ggcgctcttc cgcttcctcg ctcactgact cgctgcgctc   7860
ggtcgttcgg ctgcggcgag cggtatcagc tcactcaaag gcggtaatac ggttatccac   7920
agaatcaggg gataacgcag gaaagaacat gtgagcaaaa ggccagcaaa aggccaggaa   7980
ccgtaaaaag gccgcgttgc tggcgttttt ccataggctc cgcccccctg acgagcatca   8040
caaaaatcga cgctcaagtc agaggtggcg aaacccgaca ggactataaa gataccaggc   8100
gtttccccct ggaagctccc tcgtgcgctc tcctgttccg accctgccgc ttaccggata   8160
cctgtccgcc tttctccctt cgggaagcgt ggcgctttct catagctcac gctgtaggta   8220
tctcagttcg gtgtaggtcg ttcgctccaa gctgggctgt gtgcacgaac cccccgttca   8280
gcccgaccgc tgcgccttat ccggtaacta tcgtcttgag tccaacccgg taagacacga   8340
cttatcgcca ctggcagcag ccactggtaa caggattagc agagcgaggt atgtaggcgg   8400
tgctacagag ttcttgaagt ggtggcctaa ctacggctac actagaagga cagtatttgg   8460
tatctgcgct ctgctgaagc cagttacctt cggaaaaaga gttggtagct cttgatccgg   8520
caaacaaacc accgctggta gcggtggttt ttttgtttgc aagcagcaga ttacgcgcag   8580
aaaaaaagga tctcaagaag atcctttgat cttttctacg gggtctgacg ctcagtggaa   8640
cgaaaactca cgttaaggga ttttggtcat gagattatca aaaaggatct tcacctagat   8700 cctttttaaat taaaaatgaa gttttaaatc aatctaaagt atatatgagt aaacttggtc   8760
```

```
tgacagttac caatgcttaa tcagtgaggc acctatctca gcgatctgtc tatttcgttc    8820
atccatagtt gcctgactcc ccgtcgtgta gataactacg atacgggagg gcttaccatc    8880
tggccccagt gctgcaatga taccgcgaga cccacgctca ccggctccag atttatcagc    8940
aataaaccag ccagccggaa gggccgagcg cagaagtggt cctgcaactt tatccgcctc    9000
catccagtct attaattgtt gccgggaagc tagagtaagt agttcgccag ttaatagttt    9060
gcgcaacgtt gttgccattg ctacaggcat cgtggtgtca cgctcgtcgt ttggtatggc    9120
ttcattcagc tccggttccc aacgatcaag gcgagttaca tgatccccca tgttgtgcaa    9180
aaaagcggtt agctccttcg gtcctccgat cgttgtcaga agtaagttgg ccgcagtgtt    9240
atcactcatg gttatggcag cactgcataa ttctcttact gtcatgccat ccgtaagatg    9300
cttttctgtg actggtgagt actcaaccaa gtcattctga aatagtgta tgcggcgacc     9360 gagttgctct tgcccggcgt caatacggga taataccgcg ccacatagca gaactttaaa    9420
agtgctcatc attggaaaac gttcttcggg gcgaaaactc tcaaggatct taccgctgtt    9480
gagatccagt tcgatgtaac ccactcgtgc acccaactga tcttcagcat cttttacttt    9540
caccagcgtt tctgggtgag caaaaacagg aaggcaaaat gccgcaaaaa agggaataag    9600
ggcgacacgg aaatgttgaa tactcatact cttcctttt caatattatt gaagcattta    9660
tcagggttat tgtctcatga gcggatacat atttgaatgt atttagaaaa ataaacaaat    9720
aggggttccg cgcacatttc cccgaaaagt gccacctgac gtctaagaaa ccattattat    9780
catgacatta acctataaaa ataggcgtat cacgaggccc tttcgtctcg cgcgtttcgg    9840
tgatgacggt gaaaacctct gacacatgca gctcccggag acggtcacag cttgtctgta    9900
agcggatgcc gggagcagac aagcccgtca gggcgcgtca gcgggtgttg gcgggtgtcg    9960
gggctggctt aactatgcgg catcagagca gattgtactg agagtgcacc atatgcggtg   10020
tgaaataccg cacagatgcg taaggagaaa ataccgcatc aggcgccatt cgccattcag   10080
gctgcgcaac tgttgggaag ggcgatcggt gcgggcctct tcgctattac gccagctggc   10140
gaaaggggga tgtgctgcaa ggcgattaag ttgggtaacg ccagggtttt cccagtcacg   10200
acgttgtaaa acgacggcca gtgccaagct g                                  10231

<210> SEQ ID NO 55
<211> LENGTH: 348
<212> TYPE: DNA
<213> ORGANISM: Artificial Sequence
<220> FEATURE:
<223> OTHER INFORMATION: Synthetic

<400> SEQUENCE: 55
gacaacaagt tcaacaaaga gcagcagaac gccttctacg agatcctcca cctgcccaac     60
ctgaatgagg agcagaggaa cgctttcatt cagtctctca agacgaccc ttctcaaagc    120 gctaatctgc tggcagaagc taagaagctc aatgacgctc aggctcctaa agtcgataac    180
aagttcaaca agaacagca gaatgccttc tacgagattc tgcacctgcc aaatctgaac    240
gaagagcaac gcaatgcctt catccaatcc ctgaaggacg atccatccca gtctgcaaac    300
ctgctggctg aggctaagaa actgaatgat gcacaagctc ctaaagtg               348

<210> SEQ ID NO 56
<211> LENGTH: 9853
<212> TYPE: DNA
<213> ORGANISM: Artificial Sequence
<220> FEATURE:
<223> OTHER INFORMATION: Synthetic
```

<400> SEQUENCE: 56

```
acgcgtgtag tcttatgcaa tactcttgta gtcttgcaac atggtaacga tgagttagca      60
acatgcctta caaggagaga aaaagcaccg tgcatgccga ttggtggaag taaggtggta     120
cgatcgtgcc ttattaggaa ggcaacagac gggtctgaca tggattggac gaaccactga     180
attgccgcat tgcagagata ttgtatttaa gtgcctagct cgatacaata aacgggtctc     240
tctggttaga ccagatctga gcctgggagc tctctggcta actagggaac ccactgctta     300
agcctcaata aagcttgcct tgagtgcttc aagtagtgtg tgcccgtctg ttgtgtgact     360
ctggtaacta gagatccctc agaccctttt agtcagtgtg gaaaatctct agcagtggcg     420
cccgaacagg gacctgaaag cgaaagggaa accagagctc tctcgacgca ggactcggct     480
tgctgaagcg cgcacggcaa gaggcgaggg cggcgactg tgagtacgc caaaattttt     540
gactagcgga ggctagaagg agagagatgg gtgcgagagc gtcagtatta agcgggggag     600
aattagatcg cgatgggaaa aaattcggtt aaggccaggg ggaagaaaaa aatataaatt     660
aaaacatata gtatgggcaa gcagggagct agaacgattc gcagttaatc ctggcctgtt     720
agaaacatca gaaggctgta gacaaatact gggacagcta caaccatccc ttcagacagg     780
atcagaagaa cttagatcat tatataatac agtagcaacc ctctattgtg tgcatcaaag     840
gatagagata aaagacacca aggaagcttt agacaagata gaggaagagc aaaacaaaag     900
taagaccacc gcacagcaag cggccactga tcttcagacc tggaggagga gatatgaggg     960
acaattggag aagtgaatta tataaatata agtagtaaa aattgaacca ttaggagtag    1020
cacccaccaa ggcaaagaga agagtggtgc agagagaaaa aagagcagtg ggaataggag    1080
ctttgttcct tgggttcttg ggagcagcag gaagcactat gggcgcagcg tcaatgacgc    1140
tgacggtaca ggccagacaa ttattgtctg gtatagtgca gcagcagaac aatttgctga    1200
gggctattga ggcgcaacag catctgttgc aactcacagt ctggggcatc aagcagctcc    1260
aggcaagaat cctggctgtg gaaagatacc taaaggatca acagctcctg gggatttggg    1320
gttgctctgg aaaactcatt tgcaccactg ctgtgccttg gaatgctagt tggagtaata    1380
aatctctgga acagatttgg aatcacacga cctggatgga gtgggacaga gaaattaaca    1440
attacacaag cttaatacac tccttaattg aagaatcgca aaaccagcaa gaaaagaatg    1500
aacaagaatt attggaatta gataaatggg caagtttgtg gaattggttt aacataacaa    1560
attggctgtg gtatataaaa ttattcataa tgatagtagg aggcttggta ggtttaagaa    1620
tagtttttgc tgtactttct atagtgaata gagttaggca gggatattca ccattatcgt    1680
ttcagaccca cctcccaacc ccgagggac ccgacaggcc cgaaggaata gaagaagaag    1740
gtggagagag agacagagac agatccattc gattagtgaa cggatctcga cggtatcggt    1800
taactttaa aagaaaggg gggattgggg ggtacagtgc aggggaaaga atagtagaca    1860
taatagcaac agacatacaa actaaagaat tacaaaaaca aattacaaaa ttcaaaattt    1920
tatcgatgct agcggaggaa aaactgtttc atacagaagg cgtggaggaa aaactgtttc    1980
atacagaagg cgtggaggaa aaactgtttc atacagaagg cgtggaggaa aaactgtttc    2040
atacagaagg cgtggaggaa aaactgtttc atacagaagg cgtggaggaa aaactgtttc    2100
atacagaagg cgtagatcta gactctagag gtatataat ggaagctcga cttccagctt    2160
ggcattccgg tactgttggt aaaaagcttg gcaatccggt actgttggta aaggatccgc    2220
caccatgcct gccatgaaga ttgagtgccg catcacggga accctgaacg gagtggagtt    2280
```

-continued

```
tgagctggtc ggaggtggag aagggactcc tgagcaggga cgtatgacca acaagatgaa    2340
gtctaccaag ggcgccttga ccttctcccc ctaccttctc tctcatgtca tgggatacgg    2400
gttctaccac tttggtacct atcccagtgg gtatgagaat cccttcctgc atgccatcaa    2460
caacgggggg tacaccaaca ccaggattga aagtatgag gatggaggag ttcttcatgt     2520
tagctttagc tacagatatg aagcaggcag ggtgattggg gatttcaagg ttgtcgggac    2580
aggattccct gaggacagtg tgatcttcac cgacaagatc atccggtcca atgctaccgt    2640
ggagcacttg cacccaatgg gagacaacgt tcttgtgggc tccttcgcga gaaccttttc    2700
cctgagggat ggaggctact actcatttgt ggttgacagc cacatgcact tcaagagtgc    2760
catccaccca tccatcctcc agaacggggg gcccatgttt gccttcagga gagttgagga    2820
acttcactcc aacactgaac ttggcattgt agagtatcaa catgccttca agactcccat    2880
agcatttgct ggaagcggag ctactaactt cagcctgctg aagcaggctg agacgtgga    2940
ggagaaccct ggacctatgg tcttcacact cgaagatttc gttggggact ggcgacagac    3000
agccggctac aacctggacc aagtccttga acagggaggt gtgtccagtt tgtttcagaa    3060
tctcggggtg tccgtaactc cgatccaaag gattgtcctg agcggtgaaa atgggctgaa    3120
gatcgacatc catgtcatca tcccgtatga aggtctgagc ggcgaccaaa tgggccagat    3180
cgaaaaaatt tttaaggtgg tgtaccctgt ggatgatcat cactttaagg tgatcctgca    3240
ctatggcaca ctggtaatcg acggggttac gccgaacatg atcgactatt cggacggcc    3300
gtatgaaggc atcgccgtgt cgacggcaa aaagatcact gtaacaggga ccctgtggaa    3360
cggcaacaaa attatcgacg agcgcctgat caaccccgac ggctccctgc tgttccgagt    3420
aaccatcaac ggagtgaccg gctggcggct gtgcgaacgc attctggcgt aagcggccgc    3480
gaaggatctg cgatcgctcc ggtgcccgtc agtgggcaga gcgcacatcg cccacagtcc    3540
ccgagaagtt gggggaggg gtcggcaatt gaacgggtgc ctagagaagg tggcgcgggg    3600
taaactggga aagtgatgtc gtgtactggc tccgcctttt tcccgagggt gggggagaac    3660
cgtatataag tgcagtagtc gccgtgaacg ttcttttcg caacgggttt gccgccagaa     3720
cacagctgaa gcttcgaggg gctcgcatct ctccttcacg cgcccgccgc cctacctgag    3780
gccgccatcc acgccggttg agtcgcgttc tgccgcctcc cgcctgtggt gcctcctgaa    3840
ctgcgtccgc cgtctaggta agtttaaagc tcaggtcgag accgggcctt tgtccggcgc    3900
tcccttggag cctacctaga ctcagccggc tctccacgct ttgcctgacc ctgcttgctc    3960
aactctacgt ctttgtttcg ttttctgttc tgcgccgtta cagatccaag ctgtgaccgg    4020
cgcctactag tgccaccatg gactttcaag tgcagatctt cagctttctg ctgatctctg    4080
ctagtgtcat catgtctgac aacaagttca caaagagca gcagaacgcc ttctacgaga    4140
tcctccacct gcccaacctg aatgaggagc agaggaacgc tttcattcag tctctcaaag    4200
acgaccttc tcaaagcgct aatctgctgg cagaagctaa gaagctcaat gacgctcagg    4260
ctcctaaagt cgataacaag ttcaacaaag aacagcagaa tgccttctac gagattctgc    4320
acctgccaaa tctgaacgaa gagcaacgca tgccttcat ccaatccctg aaggacgatc    4380
catcccagtc tgcaaacctg ctggctgagg ctaagaaact gaatgatgca caagctccta    4440
aagtggaaat cgagcagaag ctgatttccg aagaggatct caatggagtg actgtcagca    4500
gcgctctgtc taactccatc atgtacttct cacacttcgt gccagtgttc ctccctgcta    4560
aacccaccac aactccagca cctagacctc ccactccagc accaactatt gcatcccagc    4620
ctctctccct cagaccagaa gcatgcagac ctgcagcagg tggagctgtg cacacaagag    4680
```

```
gtctggaccc tttctgggtc ctcgtggtgg tgggtggagt cctggcatgt tacagcctcc   4740
tggtcaccgt ggcattcatc atcttctggg tgagatctaa gaggagcaga ctgctgcact   4800
ctgattacat gaacatgaca cccagaagac ctggtcccac cagaaagcac taccaaccct   4860
acgcaccacc aagagacttt gctgcataca gaagtctcga gagggtcaag ttctcaagga   4920
gtgcagatgc tccagcctat caacagggtc agaaccaact gtacaacgag ctgaatctcg   4980
gaagaagaga ggagtacgat gtgctggata agaagagagg cagggaccca gagatgggtg   5040
ggaaacccag aagaaagaat cctcaagagg gactgtacaa tgagctgcag aaggataaga   5100
tggctgaggc atactcagag atcggtatga agggagagag gagaagaggc aaaggtcatg   5160
atggtctgta ccaaggtctg tccacagcaa caaaggatac atatgatgct ctgcacatgc   5220
aggcactccc accacggggt tccggagtga acagactttt gaactttgac cttctcaagt   5280
tggctggaga cgtcgagtcc aaccctggtc ccatgaccga gtacaagccc acggtgcgcc   5340
tcgccacccg cgacgacgtc cccagggccg tacgcaccct cgccgccgcg ttcgccgact   5400
accccgccac gcgccacacc gtcgatccgg accgccacat cgagcgggtc accgagctgc   5460
aagaactctt cctcacgcgc gtcgggctcg acatcggcaa ggtgtgggtc gcggacgacg   5520
gcgccgcggt ggcggtctgg accacgccgg agagcgtcga agcgggggcg gtgttcgccg   5580
agatcggccc gcgcatggcc gagttgagcg gttcccggct ggccgcgcag caacagatgg   5640
aaggcctcct ggcgccgcac cggcccaagg agcccgcgtg gttcctggcc accgtcggcg   5700
tctcgcccga ccaccagggc aagggtctgg gcagcgccgt cgtgctcccc ggagtggagg   5760
cggccgagcg cgccggggtg cccgccttcc tggagacctc cgcgccccgc aacctcccct   5820
tctacgagcg gctcggcttc accgtcaccg ccgacgtcga ggtgcccgaa ggaccgcgca   5880
cctggtgcat gacccgcaag cccggtgcct gattaattaa gtcgacaatc aacctctgga   5940
ttacaaaatt tgtgaaagat tgactggtat tcttaactat gttgctcctt ttacgctatg   6000
tggatacgct gctttaatgc ctttgtatca tgctattgct tcccgtatgg ctttcatttt   6060
ctcctccttg tataaatcct ggttgctgtc tctttatgag gagttgtggc ccgttgtcag   6120
gcaacgtggc gtggtgtgca ctgtgtttgc tgacgcaacc cccactggtt ggggcattgc   6180
caccacctgt cagctccttt ccgggacttt cgctttcccc ctccctattg ccacggcgga   6240
actcatcgcc gcctgccttg cccgctgctg gacagggggct cggctgttgg gcactgacaa   6300
ttccgtggtg ttgtcgggga atcatcgtc ctttccttgg ctgctcgcct gtgttgccac   6360
ctggattctg cgcgggacgt ccttctgcta cgtcccttcg ccctcaatc cagcggacct   6420 tccttcccgc ggcctgctgc cggctctgcg gcctcttccg cgtcttcgcc ttcgccctca   6480
gacgagtcgg atctcccttt gggccgcctc cccgcctggt acctttaaga ccaatgactt   6540
acaaggcagc tgtagatctt agccactttt taaaagaaaa ggggggactg aagggctaa    6600 ttcactccca acgaagataa gatctgcttt ttgcttgtac tgggtctctc tggttagacc   6660
agatctgagc ctgggagctc tctggctaac tagggaaccc actgcttaag cctcaataaa   6720
gcttgccttg agtgcttcaa gtagtgtgtg cccgtctgtt gtgtgactct ggtaactaga   6780
gatccctcag acccttttag tcagtgtgga aatctctag cagtagtagt tcatgtcatc    6840
ttattattca gtatttataa cttgcaaaga atgaatatc agagagtgag aggaacttgt    6900
ttattgcagc ttataatggt tacaaataaa gcaatagcat cacaaatttc acaaataaag   6960 cattttttc actgcattct agttgtggtt tgtccaaact catcaatgta tcttatcatg   7020
```

```
tctggctcta gctatcccgc ccctaactcc gcccatcccg cccctaactc cgcccagttc    7080
cgcccattct ccgccccatg gctgactaat ttttttatt tatgcagagg ccgaggccgc    7140
ctcggcctct gagctattcc agaagtagtg aggaggcttt tttggaggcc tagacttttg    7200
cagagacggc ccaaattcgt aatcatggtc atagctgttt cctgtgtgaa attgttatcc    7260
gctcacaatt ccacacaaca tacgagccgg aagcataaag tgtaaagcct ggggtgccta    7320
atgagtgagc taactcacat taattgcgtt gcgctcactg cccgctttcc agtcgggaaa    7380
cctgtcgtgc cagctgcatt aatgaatcgg ccaacgcgcg gggagaggcg gtttgcgtat    7440
tgggcgctct tccgcttcct cgctcactga ctcgctgcgc tcggtcgttc ggctgcggcg    7500
agcggtatca gctcactcaa aggcggtaat acggttatcc acagaatcag gggataacgc    7560
aggaaagaac atgtgagcaa aaggccagca aaaggccagg aaccgtaaaa aggccgcgtt    7620
gctggcgttt ttccataggc tccgcccccc tgacgagcat cacaaaaatc gacgctcaag    7680
tcagaggtgg cgaaacccga caggactata aagataccag gcgtttcccc ctggaagctc    7740
cctcgtgcgc tctcctgttc cgaccctgcc gcttaccgga tacctgtccg cctttctccc    7800
ttcgggaagc gtggcgcttt ctcatagctc acgctgtagg tatctcagtt cggtgtaggt    7860
cgttcgctcc aagctgggct gtgtgcacga accccccgtt cagcccgacc gctgcgcctt    7920
atccggtaac tatcgtcttg agtccaaccc ggtaagacac gacttatcgc cactggcagc    7980
agccactggt aacaggatta gcagagcgag gtatgtaggc ggtgctacag agttcttgaa    8040
gtggtggcct aactacggct acactagaag gacagtattt ggtatctgcg ctctgctgaa    8100
gccagttacc ttcggaaaaa gagttggtag ctcttgatcc ggcaaacaaa ccaccgctgg    8160
tagcggtggt ttttttgttt gcaagcagca gattacgcgc agaaaaaaag gatctcaaga    8220
agatcctttg atcttttcta cggggtctga cgctcagtgg aacgaaaact cacgttaagg    8280
gattttggtc atgagattat caaaaaggat cttcacctag atcctttta attaaaaatg    8340 aagttttaaa tcaatctaaa gtatatatga gtaaacttgg tctgacagtt accaatgctt    8400
aatcagtgag gcacctatct cagcgatctg tctatttcgt tcatccatag ttgcctgact    8460
ccccgtcgtg tagataacta cgatacggga gggcttacca tctggcccca gtgctgcaat    8520
gataccgcga gacccacgct caccggctcc agatttatca gcaataaacc agccagccgg    8580
aagggccgag cgcagaagtg gtcctgcaac tttatccgcc tccatccagt ctattaattg    8640
ttgccgggaa gctagagtaa gtagttcgcc agttaatagt ttgcgcaacg ttgttgccat    8700
tgctacaggc atcgtggtgt cacgctcgtc gtttggtatg gcttcattca gctccggttc    8760
ccaacgatca aggcgagtta catgatcccc catgttgtgc aaaaaagcgg ttagctcctt    8820
cggtcctccg atcgttgtca gaagtaagtt ggccgcagtg ttatcactca tggttatggc    8880
agcactgcat aattctctta ctgtcatgcc atccgtaaga tgcttttctg tgactggtga    8940
gtactcaacc aagtcattct gagaatagtg tatgcggcga ccgagttgct cttgcccggc    9000
gtcaatacgg gataataccg cgccacatag cagaacttta aaagtgctca tcattggaaa    9060
acgttcttcg gggcgaaaac tctcaaggat cttaccgctg ttgagatcca gttcgatgta    9120
acccactcgt gcacccaact gatcttcagc atcttttact ttcaccagcg tttctgggtg    9180
agcaaaaaca ggaaggcaaa atgccgcaaa aagggaata agggcgacac ggaaatgttg    9240
aatactcata ctcttccttt ttcaatatta ttgaagcatt tatcagggtt attgtctcat    9300
gagcggatac atatttgaat gtatttagaa aaataaacaa ataggggttc cgcgcacatt    9360
tccccgaaaa gtgccacctg acgtctaaga aaccattatt atcatgacat taacctataa    9420
```

-continued

```
aaataggcgt atcacgaggc cctttcgtct cgcgcgtttc ggtgatgacg gtgaaaacct   9480
ctgacacatg cagctcccgg agacggtcac agcttgtctg taagcggatg ccgggagcag   9540
acaagcccgt cagggcgcgt cagcgggtgt tggcgggtgt cggggctggc ttaactatgc   9600
ggcatcagag cagattgtac tgagagtgca ccatatgcgg tgtgaaatac cgcacagatg   9660
cgtaaggaga aaataccgca tcaggcgcca ttcgccattc aggctgcgca actgttggga   9720
agggcgatcg gtgcgggcct cttcgctatt acgccagctg gcgaaagggg gatgtgctgc   9780
aaggcgatta agttgggtaa cgccagggtt ttcccagtca cgacgttgta aaacgacggc   9840
cagtgccaag ctg                                                      9853
```

GENETICALLY ENGINEERED CORONAVIRUS-SPECIFIC EFFECTOR CELLS FOR IN SITU SYNTHESIS OF ANTIVIRAL PROTEINS

GOVERNMENT RIGHTS

This invention was made with Government support under contract no. D19AP00024 awarded by the Defense Advanced Research Projects Agency and with Government support under grant number 1DP2EB024245-01 awarded by National Institutes of Health, under contract no. DP2EB0242454 awarded by the National Institute of Biomedical Imaging and Bioengineering of the National Institutes of Health and under grant number 7R21CA193064-02 awarded by the National Institutes of Health. The government has certain rights to this invention.

INCORPORATION-BY-REFERENCE OF MATERIAL SUBMITTED ELECTRONICALLY

Incorporated by reference in its entirety is a computer-readable nucleotide sequence listing, an ASCII text file which is 382 kb in size, submitted concurrently herewith, and identified as follows: "S1647137102_SequenceListing_ST25" and created on Jan. 26, 2022.

BACKGROUND

Vaccination is an effective approach for preventing epidemic outbreaks. However, the process to develop vaccines is lengthy and resource-intensive, requiring antigen identification and determining safe and effective administration. Accordingly, there is an unmet need for a platform treatment that can be rapidly deployed in the event of an outbreak or biological attack, such as with Severe Acute Respiratory Syndrome Coronavirus 2 (SARS-CoV-2).

SUMMARY

The present invention is directed to overcoming the above-mentioned challenges and others related to therapeutics for treating viruses, such as involving a genetically engineered effector cell line which can be activated in situ to cause synthesis of an antiviral protein against a SARS-CoV-2 infection.

A genetically engineered effector cell comprising an exogenous polynucleotide sequence that includes, in operative association: a receptor element that encodes a chimeric antigen receptor (CAR) comprising an extracellular antigen binding domain operably linked to a transmembrane domain, and an intracellular signaling domain, wherein the extracellular antigen binding domain recognizes an antigen on a surface of a SARS-CoV-2-infected cell; an actuator element that encodes a transcription factor binding site that upregulates synthesis of an antiviral protein in response to the antigen binding domain of the CAR binding to the antigen of the SARS-CoV-2-infected cell; and an effector element that encodes the antiviral protein, wherein, in response to the antigen binding domain of the CAR binding to the antigen of the SARS-CoV-2-infected cell, the genetically engineered effector cell is configured to activate and, to synthesize and secrete the antiviral protein.

In some aspects, the genetically engineered effector cell is configured to synthesize and secrete an amount of the antiviral protein as a function of an amount of the SARS-CoV-2-infected cell present in a sample or in situ.

In some aspects, the amount of the antiviral protein is proportional to the amount of SARS-COV-2-infected cell present in situ.

In some aspects, the effector element further encodes a signal peptide upstream of the antiviral protein, the signal peptide being non-native to the antiviral protein.

In some aspects, the antiviral protein is selected from the group consisting of: a Type-1 interferon (IFN), a Type-3 IFN, and a combination thereof.

In some aspects, the activation of the genetically engineered effector cell is configured to regulate stimulation of cytokines in a host.

In some aspects, the genetically engineered effector cell comprises a T-cell, a natural killer cell, a pluripotent stem cell, a multipotent stem cell, an epithelial cell, or a K562 cell.

In some aspects, the antigen on the surface of the SARS-COV-2-infected cell comprises the spike glycoprotein or envelope glycoprotein of SARS-COV-2.

In some aspects, intracellular signaling domain includes one or more of: an intracellular signaling portion of a CD28, an intracellular signaling portion of a 4-1BB, and an intracellular signaling portion of a CD3 zeta.

In some aspects, the transcription factor binding site is selected from the group consisting of: a nuclear factor of activated T-cell (NFAT) response element, a serum response element (SRE), and a cyclic AMP response element (CRE).

Various aspects are directed to a population of genetically engineered effector cells, each of the genetically engineered effector cells of the population comprising an exogenous polynucleotide sequence that includes an actuator element, an effector element, and a receptor element, wherein: the receptor element encodes a CAR comprising an extracellular antigen binding domain operably linked to a transmembrane domain, and an intracellular signaling domain, wherein the extracellular antigen binding domain recognizes an antigen on a surface of a SARS-COV-2-infected cell; the actuator element encodes a transcription factor binding site that upregulates synthesis of an antiviral protein in response to the antigen binding domain of the CAR binding to the antigen of the SARS-COV-2-infected cell; and the effector element encodes the antiviral protein, wherein, in response to the antigen binding domain of the CAR binding to the antigen of the SARS-COV-2-infected cell, the population of genetically engineered effector cells are configured to activate and, in response, to synthesize and secrete a calibrated amount of the antiviral protein based on a presence of the SARS-COV-2-infected cell.

In some aspects, the antiviral protein includes a first antiviral protein and a second antiviral protein, and a first subset of the population includes the effector element that encodes the first antiviral protein and a second subset of the population includes the effector element that encodes the second antiviral protein or the effector element include the first antiviral protein bound to the second antiviral protein by a 2A linker peptide.

In some aspects, wherein the first antiviral protein includes a Type-1 interferon (IFN) and the second antiviral protein includes a Type-3 IFN.

In some aspects, the antigen includes the spike glycoprotein of SARS-COV-2 and the antiviral protein is configured to cause action on the SARS-COV-2-infected cell to treat or prevent a coronavirus infection.

In some aspects, the calibrated amount of the antiviral protein is a function of an amount of the SARS-COV-2-infected cell present in a plurality of cells or in a sample.

Various aspects are directed to a method comprising contacting a plurality of cells with a volume of a genetically engineered effector cell, wherein the genetically engineered effector cell comprises a polynucleotide sequence that includes: a receptor element that encodes a CAR comprising an extracellular antigen binding domain operably linked to a transmembrane domain, and an intracellular signaling domain, wherein the extracellular antigen binding domain recognizes an antigen on a surface of a SARS-COV-2-infected cell from the plurality of cells; an actuator element that encodes a transcription factor binding site; and an effector element that encodes an antiviral protein. The method further includes, in response to contacting the plurality of cells with the volume of the genetically engineered effector cell and a presence of the SARS-CoV-2-infected cell within the plurality of cells, causing binding of the antigen binding domain to the antigen of the SARS-CoV-2-infected cell; and in response to the antigen binding domain of the CAR binding to the antigen of the SARS-COV-2-infected cell, initiating expression of the antiviral protein by the actuator element to synthesize the antiviral protein, and secreting the antiviral protein by a signal peptide.

In some aspects, the method further includes detecting expression of the antiviral protein, wherein detectable expression of the antiviral protein indicates the presence of the SARS-COV-2-infected cell.

In some aspects, the method further includes, in response to the antigen binding domain of the CAR binding to the antigen of the SARS-COV-2-infected cell, activating the effector cell and, in response, synthesizing and secreting a calibrated amount of the antiviral protein based on the presence of the SARS-COV-2-infected cell.

In some aspects, the calibrated amount of the antiviral protein is proportional to an amount of the SARS-COV-2-infected cell present within the plurality of cells.

In some aspects, the antiviral protein includes an IFN, and the method further includes neutralizing the SARS-COV-2-infected cell by the IFN.

BRIEF DESCRIPTION OF THE DRAWINGS

The patent application file contains at least one drawing executed in color. Copies of this patent application publication with color drawings will be provided by the Office upon request and payment of the necessary fee.

Various example embodiments can be more completely understood in consideration of the following detailed description in connection with the accompanying drawings, in which:

FIGS. 10A-10D illustrate plots characterizing therapeutic activity of example genetically engineered effector cells, in accordance with the present disclosure.

FIGS. 19A-19F show example data results of implementing an example diagnostic cell with infectious SARS-CoV-2 virus particles, in accordance with the present disclosure.

DETAILED DESCRIPTION

Figure 1:
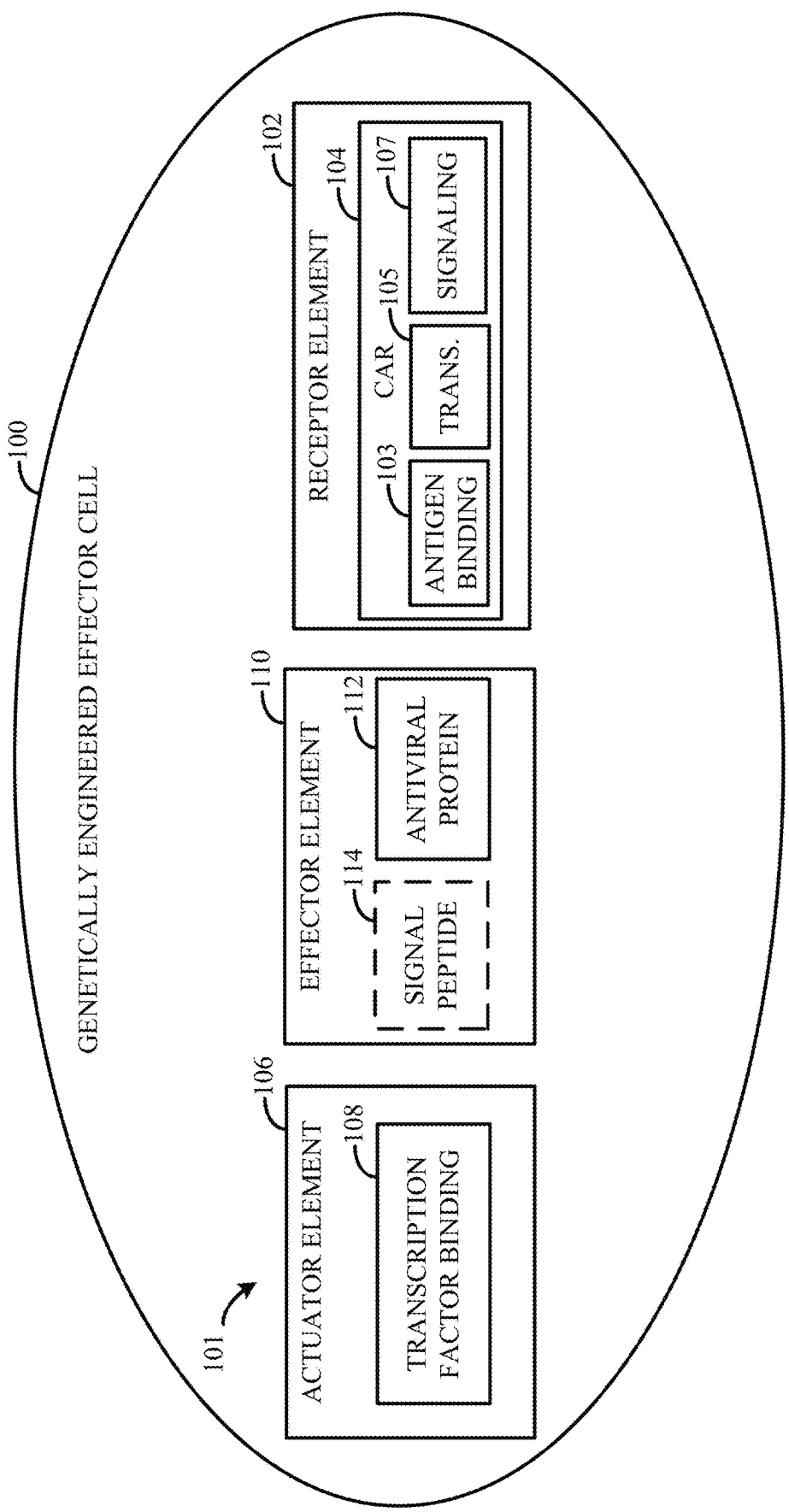
FIG. 1 illustrates an example of a genetically engineered effector cell that is specific to SARS-CoV-2, in accordance with the present disclosure.

In the following detailed description, reference is made to the accompanying drawings which form a part hereof, and in which is shown by way of illustration specific examples in which the disclosure can be practiced. It is to be understood that other examples can be utilized, and various changes may be made without departing from the scope of the disclosure. The following detailed description, therefore, is not to be taken in a limiting sense, and the scope of the disclosure is defined by the appended claims. It is to be understood that features of the various examples described herein may be combined, in part or whole, with each other, unless specifically noted otherwise.

In some embodiments, a cell can be engineered to express genetic elements including transmembrane receptor(s) that autonomously regulate the intracellular transcriptional machinery. The genetic elements of the cell can be modular and/or a cell can include multiple genetic elements to yield an engineered effector cell having the capacity to serve as a vector for a variety of in vitro, ex vivo, and in vivo applications. Such cells can be modular in that parts can be conserved, and parts can be changed for different applications. The genetically engineered effectors cells can be used for therapeutics and treatment methods that self-regulate the therapeutic response upon stimulation by the disease cells and that are applicable to a variety of cell-based diseases, including cancers, emerging pathogens, and others that evade the immune system or involve its malfunction. In other examples, the genetically engineered effector cells can be used in diagnostics, such as antigen or serology test for different pathogens or molecules. Multiple types of such genetically engineered cells provide a robust, reproducible cellular system to therapeutically target complex diseases in vivo. In various embodiments, the cell-based platform is useful for neutralizing viral threats and/or detecting infections or immunity. For example, in the wake of growing number of virus pandemics, the disclosed cell-based platform can be activated to produce antiviral proteins upon interaction with virally infected target cells, such SARS-CoV-2-infected cells.

COVID-19 morbidities and mortalities have continued to devastate global economies. Vaccines and other control measures have helped reduce its new infections, but there is few or no clinically approved therapies to treat the disease. Expression of both innate Type-I and Type-III interferons (IFNs) results in an anti-viral state within a host (e.g., a subject) to clear off the infection. However, a diminished IFN response in COVID-19 infections, that leads to progression of severe clinical symptoms, has been reported. In addition, although use of exogenous IFNs has shown therapeutic benefits, excessive or delayed induction have also been linked to poor clinical outcomes.

Embodiments of the present disclosure include cells and cell lines that are genetically engineered with chimeric antigen receptors (CARs) to specifically detect (e.g., bind) antigens expressed on the surface of SARs-CoV-2 infected cells. In response to the CAR binding to the antigens of SARs-CoV-2 infected cells, antiviral proteins (AVP) can be expressed. This AVP-producing cell is specific and its expression of the AVP is directly proportional to the number of SARs-CoV-2 infected cells. The cells are transformed into an in vivo living vector (antigen specific biofactory) for synthesizing AVPs (e.g. Type-I or Type-III IFNs) in situ upon interacting with infected target cells, and their activity is proportional to the disease burden. More particularly, upon binding to an infected target cell, the effector cell synthesizes and delivers therapeutic IFNs with spatiotemporal resolution, allowing release of calibrated amounts and only when needed in COVID-19 patients. This controlled release reduces the current adverse events with COVID-19 therapies by providing a living vector as a drug-delivery system for patients.

Type-I and Type-III IFN response, mediated through pattern recognition receptors in host cells, offers the first line of defense against viruses and acts by autocrine/paracrine signaling to induce hundreds of antiviral IFN-stimulated genes (ISGs). The diminished IFN response in case of SARS-CoV-2 has also been implicated for the progression of COVID-19 to different severity levels. While both Type-I and Type-III IFNs generate similar ISGs expression profiles, the timing of their expression during the course of infection differs, and the proportion of their expression to the viral burden determines the severity of the disease. For example, the Type-I IFNs response, which is suppressed by SARS-CoV, is short-lived and occurs during early stages of the infection to serve as a prophylaxis, and Type-III IFNs prevent the progression of disease to severe stages by exerting a long-lasting, non-inflammatory therapeutic response that helps clear systemic infection. Systemically delivered exogenous Type-I IFN has shown therapeutic benefits when infused before the peak viral load. Its use after the infection has however been correlated with the progression of disease to severe stages. Total immunity is additive of Type-I and Type-III IFNs and the challenge is to develop a system that tightly regulates IFN synthesis to autonomously limit their expression with spatiotemporal resolution.

In various embodiments, the genetically engineered effector cell is modular and SARS-CoV-2 antigen-specific. Antigen-specificity can be used to diminish IFN response. Further, the artificial cell-signaling pathway of such genetically engineered effector cells can introduce the capability to serve as vector by producing calibrated amounts of AVPs and inducting intended autocrine and paracrine signaling, upon the genetically engineered effector cell engaging the target antigen. The genetically engineered effector cell can allow for focused synthesis of the biologics at the target site and/or extend treatment duration for better patient outcome by limiting systemic toxicity.

Various embodiments demonstrate the successful implementation of the artificial cell-signaling pathway in a cell line. In some experimental embodiments, the cell line was transformed into a vector for engaging antigen-presenting SARS-CoV-2-infected cells and to trigger the synthesis of calibrated amounts of AVPs in situ, herein sometimes referred to as "effector proteins".

As used herein, a "genetically engineered effector cell" includes and/or refers to a cell that is genetically engineered or modified to comprise a (i) receptor element, (ii) actuator element, and (iii) effector element, each of which can be modular. As used herein, the terms "modular" and "modularity" include and/or refer to the versatility associated with recombinant sequence domains and the resulting recombinant polypeptides when assembled in various combinations for introduction into an engineered effector cell. The genetically engineered effects cells can be modified for different functionalities by changing portions of the effector element and/or receptor element to develop cell with the different functionalities and for different implementations, such as therapeutic cells, diagnostics cells, and/or reporter cells, as further described herein.

As used herein, "receptor element" includes and/or refers to a polynucleotide sequence encoding a transmembrane receptor, such as a CAR, capable of a specific interaction with a target cell, such as a SARS-CoV-2-infected cell, a genetically engineered target cell that expresses an antigen specific to SARS-CoV-2, a virion or SARs-CoV-2 virus particle or virus-like particle (e.g., natural or genetically engineered), an antibody associated with SARs-CoV-2, and/or other molecules. Depending on the particular application, the receptor element can be reprogrammed by exchanging the single chain variable fragment (scFV) portion of CAR for an extracellular antigen binding domain specific for a different disease-associated antigen or general for an antibody or other molecule (e.g., cytokines, chemokines, proteins). Other receptor elements that can be used include, without limitation, CARs having specificity for antigens associated with autoimmune disorders, CARs having specificity for antigens associated with other viruses or pathogens and/or antibodies.

As used herein, "actuator element" includes and/or refers to a polynucleotide sequence encoding a transcription factor binding site that initiates transcription and translation events downstream of a triggering signal (e.g., binding of the receptor element to a target antigen). In general, the underlying molecular mechanism of the actuator element is based on the intracellular calcium $[Ca^{2+}]_i$ dynamics, a mechanism used by almost all types of cells to regulate their functions. Exemplary response elements include, without limitation, NFAT ("nuclear factor of activated T cells") response element (NFAT-RE), serum response element (SRE), and cyclic AMP response element (CRE).

As used herein, "effector element" includes and/or refers to a polynucleotide sequence encoding an effector protein, and in some instances, an effector protein operably linked to a signal peptide. Example effector proteins include an AVP and a detectable reporter protein. The polynucleotide sequence encoding the effector protein can be, for example, a sequence derived from a human gene, a sequence derived from a gene of a non-human species, a recombinant sequence, a sequence encoding a detectable reporter molecule, a sequence encoding a detectable imaging molecule, a sequence encoding a therapeutic molecule, and the like.

The genetically engineered effector cell into which the receptor element, the actuator element, and the effector element are introduced can be any cell type including human cells or non-human cells (e.g., mammal, reptiles, plants, among others). In this manner, the genetically modified cellular "source" of the modular elements provides a cellular chassis or frame providing, among other things, transcriptional and translational machinery for expression and presentation of the receptor element, the actuator element, and the effector element. In some embodiments, the effector cells can be from a source (e.g., a first human), modified, and administered to an organism that is different than the source (e.g., the host which is a second human). In other embodiments, the cells can be from the source (e.g., a first human), modified, and administered back to the source (e.g., the source is the host).

FIG. 1 illustrates an example of a genetically engineered ES effector cell that is specific to SARS-CoV-2, in accordance with the present disclosure. The genetically engineered effector cell 100, herein generally referred to as "an effector cell" can be modular in that genetic elements 102, 106, 110 can be adjusted for different target cells and to synthesize different effector proteins.

The effector cell 100 comprises an exogenous polynucleotide sequence 101 that includes, in operative association, a receptor element 102, an actuator element 106, and an effector element 110. A variety of different types of cells can be genetically modified to form the effector cell 100. Example cells include T-cell, a natural killer cell, a pluripotent stem cell, a multipotent stem cell, an epithelial cell, or a K562 cell. The cell modified to generate the effector cell 100 can include a living cell from an organism, such as a basic membrane-bound unit that contains structural and functional elements. In some embodiments, the exogenous polynucleotide sequence 101 is selected from SEQ ID NOs: 18-22 and 24. In some embodiments, the exogenous polynucleotide sequence 101 includes SEQ ID NO: 18 or SEQ ID NO: 24. However, embodiments are not so limited and the exogenous polynucleotide sequence 101 can include other sequences, such as a sequence with at least 80 percent (%), 85%, 90%, 95%, or 99% sequence identity to one of the sequences set forth in SEQ ID NOs: 18-22 and 24, among others.

The receptor element 102 encodes a CAR 104. A CAR is sometimes called a "chimeric receptor", a "T-body", or a "chimeric immune receptor (CAR)." As used herein, a CAR includes and/or refers to an artificially constructed hybrid protein or polypeptide comprising extracellular antigen binding domain(s) 103 of an antibody (e.g., scFv, VHH) operably linked to a transmembrane domain 105 and at least one intracellular signally domain 107. For example, the CAR 104 includes an extracellular antigen binding domain 103 operably linked to the transmembrane domain 105, and the intracellular signaling domain 107. The CAR 104 can be designed to identify an antigen on a surface of a SARS-CoV-2-infected cell, such as a target cell of a host. The CAR 104 can mobilize internal $Ca^{+2}$ stores for intracellular $Ca^{+2}$ release in response to antigen binding. For example, the extracellular antigen binding domain 103 of the CAR 104 can recognize a surface antigen on a surface of a target cell, such as diseased cells of a host. In some embodiments, the extracellular antigen binding domain 103 includes SEQ ID NO: 3. In other embodiments, the extracellular antigen binding domain 103 includes any of SEQ ID NOs: 3 and 25-29. However, embodiments are not so limited and the extracellular antigen binding domain 103 can include other sequences, such as a sequence with at least 80%, 85%, 90%, 95%, or 99% sequence identity to one of the sequences set forth in SEQ ID NOs: 3 and 25-29, among other sequences.

As used herein, the extracellular antigen binding domain 103 includes and/or refers to a polynucleotide sequence that is complementary to a target, such as an antigen of the SARS-CoV-2-infected cell. The extracellular antigen binding domain 103 can bind to the surface antigen of the SARS-CoV-2-infected cell, as described above. In some embodiments, the antigen can include the spike glycoprotein (Sgp) or the envelope glycoprotein (Egp) of SARS-CoV-2. In some embodiments, the antigen includes any of SEQ ID NOs: 1-2, or antigens with at least 80%, 85%, 90%, 95%, or 99% sequence identity to one of the sequences set forth in SEQ ID NOs: 1-2, among other sequences.

The transmembrane domain 105 includes and/or refers to a polynucleotide sequence encoding a transmembrane segment of a transmembrane protein, e.g., a type of membrane protein that spans the membrane of a cell, such as the membrane of the cell 100. The transmembrane domain 105 can be derived from a natural polypeptide, or can be artificially designed. A transmembrane domain 105 derived from a natural polypeptide can be obtained from any membrane-binding or transmembrane protein. For example, a transmembrane domain of a T-cell receptor α or β chain, a CD3ζ chain, CD28, CD3ε, CD45, CD4, CD5, CD8, CD9, CD16, CD22, CD33, CD37, CD64, CD80, CD86, CD134, CD137, ICOS, CD154, or a GITR can be used.

The intracellular signaling domain 107 includes and/or refers to a polynucleotide sequence encoding any oligopeptide or polypeptide known to function as a domain that transmits a signal to cause activation or inhibition of a biological process in a cell. Example intracellular signaling domains include an intracellular signaling portion of a CD28, an intercellular signaling portion of a 4-1BB, and an intracellular signal portion of a CD3-zeta. In some embodiments, the intracellular signaling domain 107 includes the intracellular signaling portion of CD28, the intercellular signaling portion of 4-1BB, and the intracellular signal portion of CD3-zeta. However, embodiments are not so limited and can include other types and combinations of intracellular signaling domains. For example, the intracellular signaling domain 107 can include encode any molecule that can transmit a signal into a cell when the extracellular antigen binding domain 103 present within the same molecule binds to (interacts with) the antigen.

Generally, the antigen binding domain 103 of a CAR 104 has specificity for a particular antigen expressed on the surface of a target cell of interest, a SARS-CoV-2-infected cell. As described above, the extracellular binding domain 103 is capable of binding to an antigen includes any oligopeptide or polypeptide that can bind to the antigen, and includes, for example, an antigen-binding domain of an antibody and a ligand-binding domain of a receptor. The extracellular antigen binding domain 103 binds to and interacts with the antigen present on a cell surface of the SARS-CoV-2-infected cell, and thereby imparts specificity to an effector cell 100 expressing the CAR 104. In some embodiments, the receptor element 102 encodes a CAR 104 comprising an extracellular antigen binding domain 103 having specificity for the Sgp or Egp associated with SARS-CoV-2.

The actuator element 106 encodes a transcription factor binding site 108. The transcription factor binding site 108 includes and/or refers to binding site for a protein that upregulates synthesis of the AVP 112 in response to the extracellular antigen binding domain 103 of the CAR 104 binding to the antigen of the SARS-CoV-2-infected cell. The transcription factor binding site 108 can bind to transcription factors as triggered by [$Ca^{2+}$], which as described above, are caused to release in response to the antigen binding. In some embodiments, the transcription factor binding site 108 is selected from a nuclear factor of activated T-cell (NFAT) response element, a serum response element (SRE), and a cyclic AMP response element (CRE). The actuator element 106 can thereby include a sequence for binding the factors triggered by [$Ca^{2+}$], and can trigger amplified synthesis of the AVP 112 (and/or another type of protein) in response to [$Ca^{2+}$]$_i$ rise.

In some embodiments, the actuator element 106 encodes a NFAT transcription factor binding site for a transcription factor protein. In some embodiments, the actuator element 106 encodes a set of NFAT transcription factor binding sites, such as at least two transcription factor binding sites, three transcription factor binding sites, or six transcription factor binding sites (e.g., six NFAT-RE, among other amounts. NFAT transcription factor family consists of five members NFATc1, NFATc2, NFATc3, NFATc4, and NFAT5. See Sharma S et al. (2011) PNAS, 108(28); Hogan P G et al. (2010) Ann Rev Immunol, 28; Rao A, Hogan P G (2009) Immunol Rev, 231(1); Rao A (2009) Nat Immunol, 10(1), M. R. Müller and A. Rao, Nature Reviews Immunology, 2010, 10, 645-656; M. Oh-Hora and A. Rao, Curr. Opin. Immunol., 2008, 20, 250-258. Crabtree & Olson E N (April 2002), Cell 109 Suppl (2): S67-79, which are each hereby incorporated herein in their entireties for their teaching. NFATc1 through NFATc4 are regulated by calcium signaling. Calcium signaling is critical to NFAT activation because calmodulin, a well-known calcium sensor protein, activates the serine/threonine phosphatase calcineurin. The underlying molecular mechanism of this strategy is based on intracellular $Ca^{+2}$ ([$Ca^{2+}$]$_i$) dynamics (as further shown by FIG. 2). The [$Ca^{2+}$]$_i$ dynamics are common to almost all cell types, and the approach is thus broadly applicable. The [$Ca^{2+}$]$_i$ rise from CAR-mediated stimulation of cells leads to dephosphorylation of the nuclear factor of an activated effector cell 100 (through $Ca^{+2}$/calmodulin-dependent serine phosphatase calcineurin), which then translocated to the nucleus and interact with the NFAT-RE to upregulate expression of the AVP 112. In parallel, the NFAT-RE also performs its natural function of inducing Interleukin-2 in the activated effector cell 100 that regulates clonal expansion proportional to the disease burden.

The effector element 110 encodes the AVP 112, and in some instances, encodes the AVP 112 operably linked to a signal peptide 114. As further illustrated herein, in some embodiments, the signal peptide 114 is upstream of the AVP 112 (or other protein). The signal peptide 114 can be non-native to the AVP 112. For example, the AVP 112 can be unable to secrete into the extracellular environment without the addition of the signal peptide 114. However, embodiments are not so limited and in some embodiments, the AVP 112 includes a native signal peptide. For example, the AVP 112 can (natively) include the signal peptide 114. In other embodiments, the native signal peptide of the effector protein 112 can be removed and a non-native signal peptide 114 can be added. In some embodiments, the AVP 112 can be encoded by and/or include SEQ ID NO: 4, SEQ ID NO: 5, SEQ ID NO: 6 or SEQ ID NO: 7. As such, in some embodiments, the effector element 110 can include one or more of SEQ ID NO: 4, SEQ ID NO: 5, SEQ ID NO: 6, and SEQ ID NO: 7. However, embodiments are not so limited and the effector element 110 can include other sequences, such as a sequence with at least 80%, 85%, 90%, 95%, or 99% sequence identity to one or more of the sequences set forth in SEQ ID NOs: 4-7, among other sequences.

As used herein, the terms "secretor", "secretory peptide and "signal peptide" are used interchangeable and include and/or refer to a peptide that assists or directs the synthesized AVP 112 into the extracellular environment (e.g., assists with translocating the effector element 110). The signal peptide 114 can be operably linked or fused to the AVP 112 for release into the extracellular environment. In this manner, the signal peptide 114 can direct movement of the AVP 112 outside of the effector cell 100. A signal peptide 114 is particularly advantageous when included in the effector cell 100 expressing an AVP 112 that is unable to and/or minimally able to translocate natively, where the AVP 112 can remain inside the effector cell 100 in the absence of the signal peptide 114 and/or can translocate at a rate below a threshold. Generally, signal peptides are located at the N-terminus of nascent secreted proteins and characteristically have three domains: (1) a basic domain at the N-terminus, (2) a central hydrophobic core, and (3) a carboxy-terminal cleavage region. Any signal peptide can be used. For example, the signal peptide 114 can be the signal peptide of Interleukin-6 or Interleukin-2.

In various embodiments, in response to the extracellular antigen binding domain 103 of the CAR 104 binding to the antigen of the target cell (e.g., a target host cell), the effector cell 100 is configured to activate, and to synthesize and secrete the AVP 112. For example, the effector cell 100 can synthesize and secrete an amount of the AVP 112 as a function of an amount of the SARS-CoV-2-infected cell and/or an amount of other antigen-presenting cells in the environment (e.g., the extracellular environment), such as secreting an amount of the AVP 112 in the environment that is proportional to the number of SARS-CoV-2-infected cells present in the environment (e.g., in a sample or in situ).

The AVP 112 can include a variety of different types of proteins, which can be used to provide treatment for SARS-CoV-2 or to prevent infection. An AVP protein includes and/or refers to a protein that provides a therapeutic effect to a host from a viral infection. Example antiviral proteins include IFN, such as a Type-I IFN and/or Type-III IFN, Molnupiravir, Ivermectin, Nitazoxanide, Hydroxychloroquine, Chloroquine, and Azithromycin, among others. In some embodiments, the AVP 112 can stimulate production of other therapeutic proteins in the host. For example, the activation of the effector cell 100 can regulate stimulation of cytokines and/or other proteins in the host.

Different parts of the genetic elements 102, 106, 110 of the effector cell 100 can be modular and other parts can be conserved (e.g., may not change for different implementations). For example, in some embodiments, the intracellular signaling domain 107, the actuator element 106, and the optional signal peptide 114 are constant domains, and the extracellular antigen binding domain 103 and the AVP 112 are variable domains. As an example, the extracellular antigen binding domain 103 can be changed for different targets and/or the AVP 112 can be changed to cause in situ synthesis of different proteins, while the intracellular signaling domain 107, the actuator element 106, and the signal peptide 114 remain the same for the different implementations. Keeping parts conserved can reduce production time. However, embodiments are not so limited, and any part of the effector cell 100 can be modified.

In some embodiments, the effector cell 100 can include multiple (e.g., two or more) of some or all of the genetic elements 102, 106, 110. For example, the effector cell 100 can include multiple receptor elements 102, multiple actuator elements 106, and/or multiple effector elements 110. In some embodiments, multiplicity takes the form of providing multiple genetically engineered effector cells (e.g., a plurality of cells) modified as described herein to a host to provide more than one therapeutic task for treating or preventing SARS-CoV-2 and/or for other purposes.

In some embodiments, the effector element 110 can encode multiple effector proteins, such as at least two AVPs, an AVP and a detectable reporter protein, or at least two detectable reporter proteins, among other types of effector protein combinations. For example, two effector proteins can be encoded linked together by a 2A linker peptide. A 2A linker peptide, as used herein, includes and/or refers to a peptide which induces ribosomal skipping during translation of a protein complex (e.g., encoding of two proteins or peptides linked by the 2A linker peptide) in a cell, such that the protein complex is translated into two proteins that independently fold. Example 2A linker peptides include F2A, P2A, E2A, and T2A, among others. Such peptides are generally 18-22 amino acids long, and derived from viruses.

In some embodiments, the actuator element 106 is connected to and/or associated with the effector element 110. In some embodiments, the exogenous polynucleotide sequence 101 includes the actuator element 106 connected to the effector element 110 connected to the receptor element 102, which are all formed on a single plasmid vector. For example, the exogenous polynucleotide sequence 101 can include the actuator element 106 connected to and upstream from the effector element 110, and the effector element 110 connected to and upstream or downstream from the receptor element 102, wherein the signal peptide 114 is upstream from the AVP 112. In other embodiments, the receptor element 102 can be on a different plasmid vector than the actuator element 106 and the effector element 110.

Figure 2:
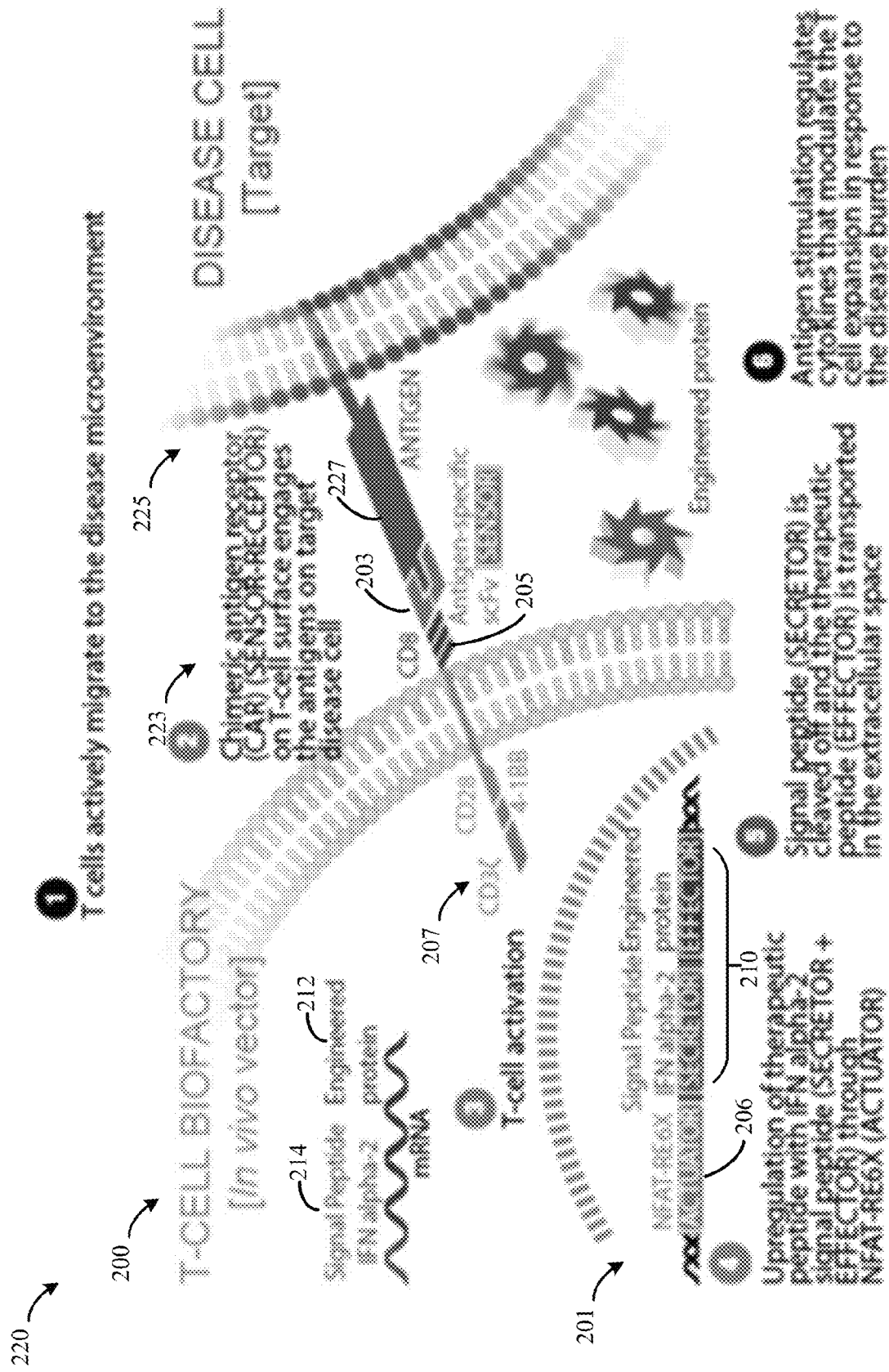
FIG. 2 illustrates an example of a genetically engineered effector cell and a sequence of events triggered when in a diseased environment, in accordance with the present disclosure.

FIG. 2 illustrates an example of a genetically engineered effector cell and a sequence of events triggered when in a diseased environment, in accordance with the present disclosure. The genetically engineered effector cell 200, herein generally referred to as the "effector cell 200" for ease of reference, can be used as or act as a living vector to synthesize the AVP 212 using the artificial cell-signaling pathway and/or to trigger a sequence of events 220. The effector cell 200 synthesizes the engineered AVP 212 in situ upon interacting with the antigen-presenting target cell 225, as shown at 222.

As previously described, the effector cell 200 can comprise a polynucleotide sequence 201 including the receptor element encoding the extracellular antigen binding domain 203, transmembrane domain 205, and the intracellular signaling domain 207, the actuator element 206 encoding the transcription factor binding site (e.g., NFAT), and the effector element 210 encoding the AVP 212 and, optionally, the signal peptide 214. The polynucleotide sequence 201 can comprise a single plasmid (e.g., a single construct including each of) comprising three constant domains (e.g., the actuator element 206, the signal peptide 214, and portions of the receptor element, such as the transmembrane domain 205 and the intracellular signaling domain 207), and two variable domains (e.g., the antigen binding domain 203 (labeled as the "sensor") and AVP 212) arranged in cis. In other embodiments, the polynucleotide sequence 201 can comprise multiple plasmids such as a first plasmid comprising the actuator element 206 and the effector element 210, and a second plasmid comprising the receptor element.

The constant domains can be configured to provide functionality to the effector cell 200. The constant domains form part of the intracellular signaling pathway and include a transmembrane molecule (e.g., transmembrane domain 205) that mobilizes the calcium-dependent transcriptional machinery (e.g., actuator element 206) to upregulate the effector transgene (e.g., AVP 212) fused to the signal peptide 214 that assists in transporting the effector transgene into the extracellular space 223. In various embodiments, the AVP 212 can include a native signal peptide, which forms part of the AVP 212.

The variable domains can be responsible for the applicability of the effector cell 200 to different diseases, target cells, therapy, and/or other applications. For example, the variable domains can impart specificity to the effector cell 200 against particular diseases. The variable domains can include a variable heavy-light (VH-VL) chain (e.g., the antigen binding domain 203, labeled as the "sensor") to identify the antigen biomarker on the target cell (e.g., labeled "diseased cell") independent of the peptide-major histocompatibility complex, and the effector transgene (e.g., AVP 212). The variable domains are modular. For example, the antigen binding domain 203 can be exchanged or revised to reprogram the effector cell 200 to target biomarkers specific to different cell-based diseases. As another example, the AVP 212 can be exchanged or revised with different therapeutic transgenes, such as for neutralizing the pathology that activated the effector cell 200 and essentially creating an off-shelf living vector, which is enhanced further by the innate cytolytic activity of effector cells.

In some embodiments, the receptor element encodes a CAR. Characteristics of CARs include their ability to redirect T-cell specificity and reactivity toward a selected target in a non-MHC-restricted manner, exploiting the antigen-binding properties of monoclonal antibodies. The non-MHC-restricted antigen recognition gives effector cells expressing CARs the ability to recognize antigen independent of antigen processing. Referring to FIG. 2, expression of a transmembrane CAR enables an effector cell 200 to sense and bind to the target antigen 227 expressed on the surface of target cell 225, such as SARS-CoV-2 infected cells. Binding of the CAR and target surface antigen 227 on the target cell 225 activates the effector cell 200, which triggers an activation cascade leading to the expression of the AVP 212. For example, expression of the AVP 212, or other effector protein is autonomously expressed as part of the effector cell 200 activation cascade in response to binding of the transmembrane receptor to the antigen 227 presented on the target cell 225.

More particularly, the effector cell 200 expressing a CAR can bind to a SARS-CoV-2 specific antigen via the CAR, and in response a signal is transmitted into the effector cell 200, and as a result, the effector cell 200 is activated. The activation of the effector cell 200 expressing the CAR is varied depending on the kind of target cell and an intracellular domain of the CAR, and can be confirmed based on, for example, release of a cytokine, improvement of a cell proliferation rate, change in a cell surface molecule, or the like as an index. For example, release of a cytotoxic cytokine (e.g., tumor necrosis factor, a lymphotoxin, etc.) from the activated effector cell 200 causes destruction of a target cell 225 expressing an antigen 227. In addition, release of a cytokine or change in a cell surface molecule stimulates other immune cells, for example, a B cell, a dendritic cell, a natural killer cell, and a macrophage.

As shown by FIG. 2, an example sequence of events 220 triggered by or related to the effector cell 200 includes (1) the effector cell 200 actively migrating to the diseased environment, (2) the CAR on the effector cell 200 surface engaging the antigen 227 of the target cell 225 that comprises a SARS-CoV-2-infected cell, (3) the effector cell activation, (4) upregulation of the AVP 212 with the signal peptide 214 through the NFAT, (5) signal peptide 214 is cleaved off and AVP 212 is transported into the extracellular space 223, and (6) antigen stimulation regulates cytokines that modulate cell expansion in response to the disease burden.

Figure 3:
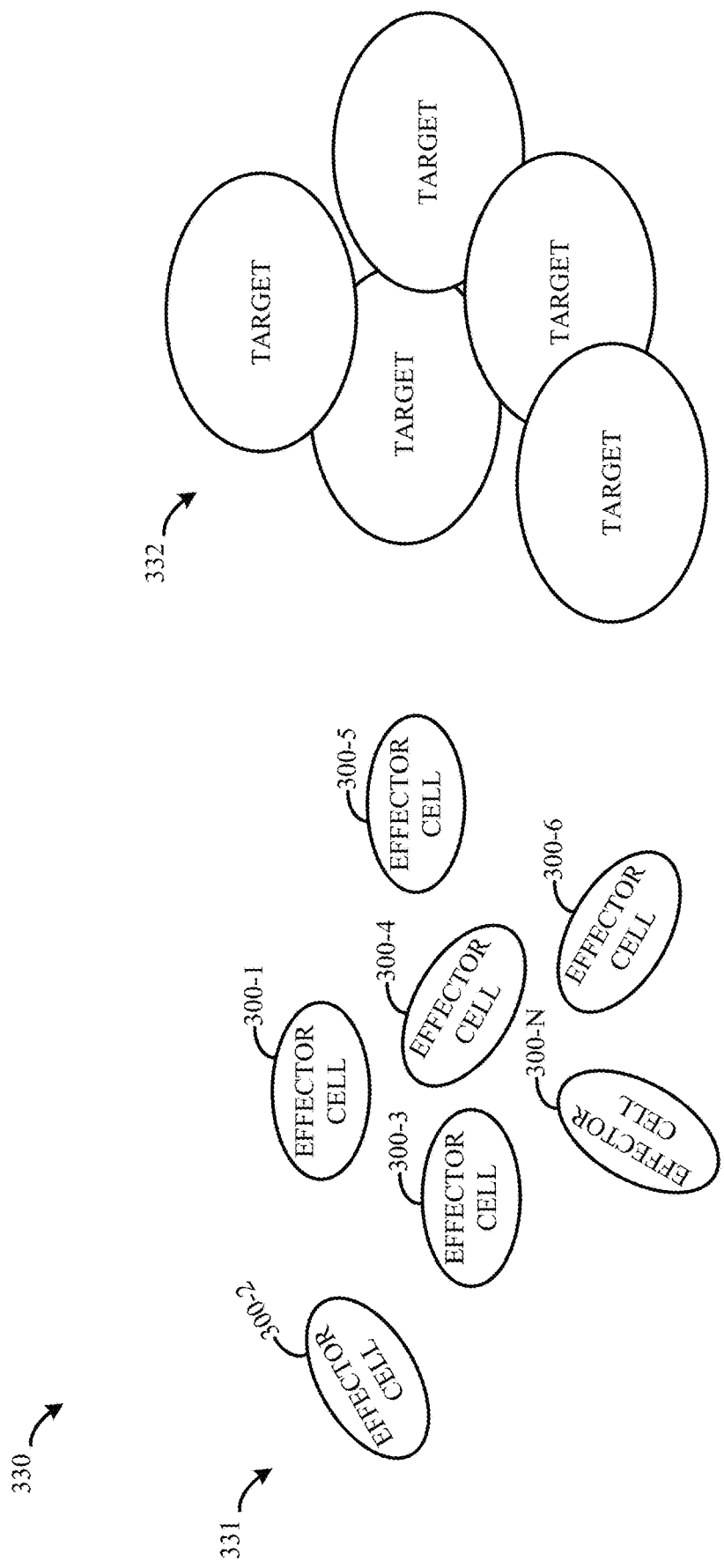
FIG. 3 illustrates an example of a population of genetically engineered effector cells in a diseased environment, in accordance with the present disclosure.

FIG. 3 illustrates an example of a population of genetically engineered effector cells in a diseased environment, in accordance with the present disclosure. The population 331 can include a plurality of genetically engineered effector cells 300-1, 300-2, 300-3, 300-4, 300-5, 300-6, 300-N (herein generally referend to as "the effector cells 300" for ease of references). Each of the effector cells 300 can include at least substantially the same components and features as the effector cell 100 of FIG. 1, the details of which are not repeated for ease of reference.

In the example illustrated by FIG. 3, the environment is an extracellular space 330 that includes (a presence of) target cell(s) 332, such that the space 330 can be referred to as a diseased environment. The population 331 of effector cells 300 can bind to the antigens of the target cell(s) 332 via the antigen binding domain of the CAR. In response to the binding, the effector cells 300 can activate and, in response, synthesize and secrete a calibrated amount of the effector protein based on a presence of the target cell(s) 332. For example, the calibrated amount of the effector protein is a function of an amount of the target cell 332 present in a plurality of (host) cells, such as in an extracellular space 330 or in a sample. As previously described, the calibrated amount of the effector protein can be proportional to the amount of the target cell 332. Although the extracellular space 330 illustrates effector cells 300 and the target cells 332, the extracellular space 330 and the plurality of (host) cells can further include other normal and/or diseased cells, among other non-cellular components.

In some embodiments, the target cell(s) 332 include SARS-CoV-2-infected cells and the effector protein includes an AVP. In such embodiments, the antigen can include the Sgp or the Egp of SARS-CoV-2 and the AVP may cause action on the SARs-CoV-2 to treat or prevent an infection. More particularly, the AVP may co-opt other surrounding cells to produced IFN stimulated genes (ISGs), many of which are antiviral. The effector cells 300 may generate a calibrated amount of AVP, where the calibrated amount of the AVP is a function of an amount of the SARS-COV-2-infected cell (or other antigen-presenting cells) present in a plurality of cells or in a sample.

In some embodiments, different effector cells of the population 331 can encode different AVPs and/or can encode for multiple AVPs or other effector proteins. For example, a first subset of the population 331 of effector cells 300 can include the effector element that encodes a first AVP and a second subset of the population 331 of effector cells 300 can include the effector element that encodes the second AVP. In other embodiments, each of the effector cells 300 or a sub-portion thereof can include effector elements that encode the first AVP bound to the second AVP by a 2A linker peptide. In some embodiments, the first and second AVPs include Type-I IFN and Type-III IFN, however, embodiments are not so limited.

Figure 4:
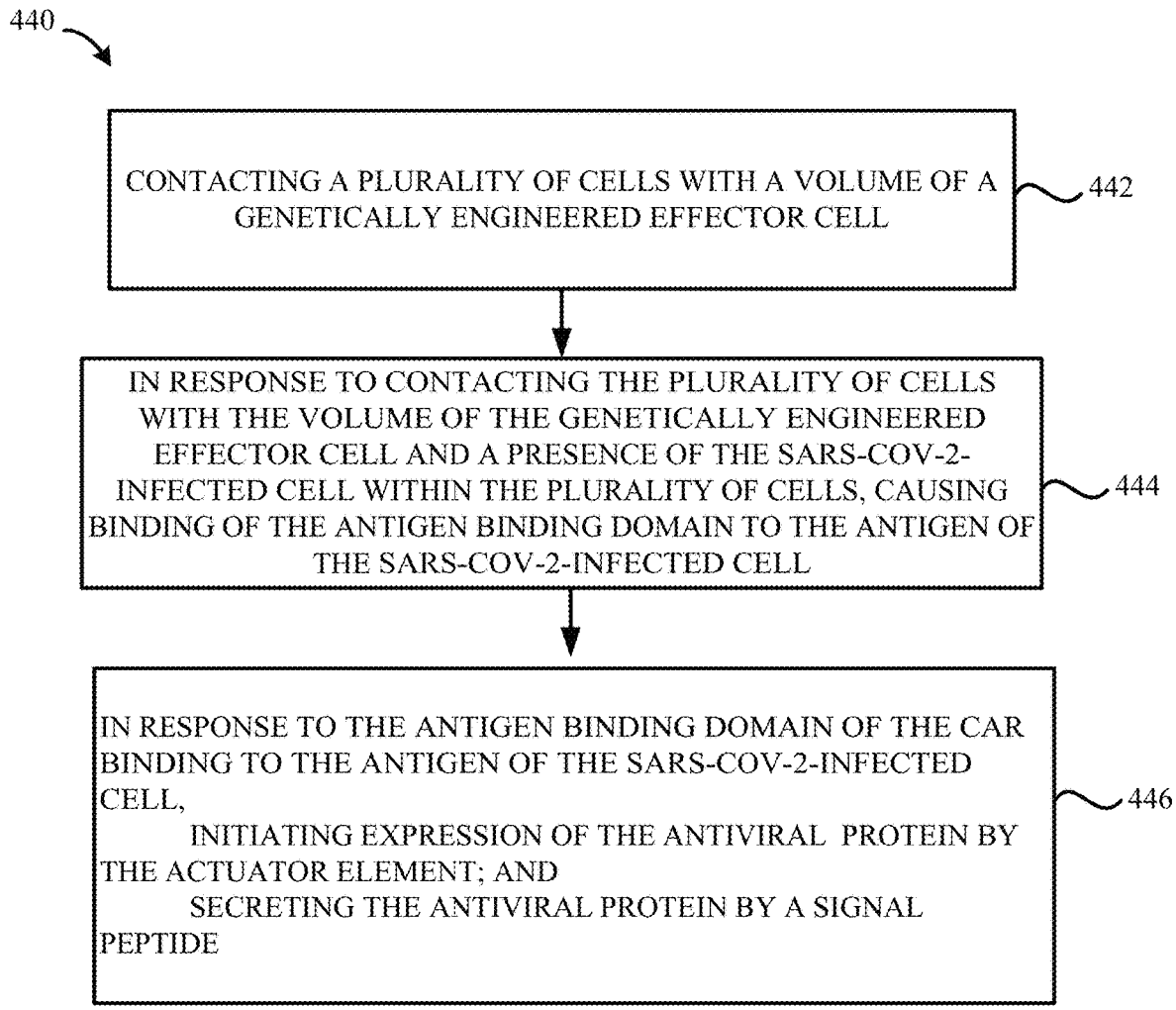
FIG. 4 illustrates an example method of contacting a plurality of cells with a volume of a genetically engineered effector cell, in accordance with the present disclosure.

FIG. 4 illustrates an example method of contacting a plurality of cells with a volume of a genetically engineered effector cell, in accordance with the present disclosure. The method 440 can be implemented using the effector cell 100 illustrated by FIG. 1 and/or the population 331 of effector cells 300 illustrated by FIG. 3.

At 442, the method 440 includes contacting a plurality of cells with a volume of a genetically engineered effector cell. The cells can be contacted by contacting a sample with or administering the volume of the genetically engineered effector cell to a host, such as a patient. The genetically engineered effector cell can include at least some of substantially the same components and features as previously described by the effector cell 100 of FIG. 1, the details of which are not repeated for ease of reference.

At 444, in response to contacting the plurality of cells with the genetically engineered effector cell and a presence of the SARS-CoV-2-infected cell within the plurality of cells, the method 440 includes causing binding of the antigen binding domain to an antigen on a surface of the SARS-CoV-2-infected cell. The plurality of cells, including the infected cell, can include cells of a host (e.g., host cells and target host cells).

At 446, in response to the antigen binding domain (of the CAR) binding to the antigen of the SARS-CoV-2-infected cell, the method 440 includes initiating expression of (e.g., transcription and translation of) the AVP by the actuator element to synthesize the AVP, and secreting the AVP by a signal peptide. The signal peptide can be native to the AVP or can be non-native and is encoded by the effector element. In some embodiments, the method 440 can further include, in response to the antigen binding domain of the CAR binding to the antigen of the SARS-CoV-2-infected cell, activating the effector cell and, in response, synthesizing and secreting a calibrated amount of the AVP based on the presence of the SARS-CoV-2-infected cell. As previously described, the calibrated amount of the AVP can be a function of (e.g., is proportional to) an amount of the SARS-CoV-2-infected cell present within the plurality of cells in the environment.

In some embodiments, the method 440 further includes detecting expression of the AVP. Detectable expression of the AVP can indicate the presence of the target cell. In some embodiments, as described above, the AVP can be bound to a detectable reporter protein by a 2A linker peptide.

The AVP can act directly on the target cell, such as killing the target cell, or indirectly by co-opting other therapeutic proteins or cells in the body. As previously described, the AVP can include an IFN and/or a set of AVPs or other effector proteins.

Various experiments, as further described below, were directed to developing a cell-based therapeutic that induces the desired IFN response found to be a critical contributor to severe COVID-19. Example results can include assessing the production of two different IFNs (Type-I IFN-β1a and Type-III IFN-λ2) from two effector cell, determining the protection offered to the SARS-CoV-2 infected host cells, and demonstrating the upregulation of antiviral ISGs in response to these IFNs. The results indicate that the effector cell has specificity toward SARS-CoV-2 and SARS-CoV-1, and it can also be activated by the infectious SARS-CoV-2 virion particles to produce a desired effector protein. This effector cell technology can be applied beyond SARS-CoV-2. The engineered effector can be genetically reprogrammed to target other pathogenic viruses and regulate the production of desired therapeutic peptides. The effector cell utilizes the synthetic pathway that bypasses the natural pathway of using pattern recognition receptors to trigger IFN signaling and is often compromised in the pathogenic viral infections. The approach represents a substantive departure from the status quo and offers and effective means to keep future pandemics in check.

Like other pathogenic viruses, SARS-CoV-2 virus evades the innate immune response of a host, which is critical in the establishment of an early antiviral defense. It has been reported that SARS-CoV-2 virus causes a delayed IFN response thereby contributing to the severity of COVID-19. As such, recombinant IFN proteins, with broad antiviral activity, have been applied in the management of COVID-19 and other viral infections. Several studies have demonstrated that recombinant IFNs can reduce viral replication in vitro and improve clinical outcomes in animal studies. Clinical trials for both Type-I and Type-III IFNs have also been undertaken in COVID-19 patients to show their safety and efficacy. However, due to the increased hyperinflammation caused by infusion of exogenous IFNs, most of these clinical studies underlines dose, timing, and disease stage as critical for a better clinical outcome. The effector cell is designed to mitigate these concerns and make the IFNs available with spatiotemporal resolution. The effector cell activates only when it engages with infected cells and synthesizes IFNs proportional to the infection burden. This active regulation of therapeutics with localized precision can reduce the inefficacies due to the suboptimal levels of IFNs or adverse events caused by its excess, both of which have been reported for systemic infusions.

In example embodiments, exogenous IFN treatments can be beneficial for COVID-19 patients. Experiments show that delivery of IFNs through the effector cell is protective at the cellular levels when administered at the right time and with right amounts. The effector cell presents a unique route of administering calibrated amounts of IFNs with localized precision and therefore extends the possibility of avoiding undesired side effects in COVID-19 patients. This cell-based intervention circumvents the ex vivo production of clinical-grade IFNs and its platform nature further adds to its impact and can be redirected to target other pathogens and immunological diseases, e.g., cancers, autoimmune disorders. Integration of next generation safety and kill switches to ensure efficient and quick removal of the infused T-cells is crucial for the safe translation and application in clinics.

IFNs clear most viruses and once approved through the regulatory agencies, the treatment can be deployed quickly in case of an outbreak. The deployment of a pre-approved intervention thus offers to boost public's confidence in health policies. While systemic infusion of IFNs has shown clinical benefit against many viruses, unregulated delivery causes inflammation, tissue damage, and multiorgan failure. Effector cells can address the challenge of regulating the bioavailability of antiviral IFNs by engineering a T-cell line for synthesizing calibrated amounts of the desired IFNs with spatiotemporal resolution and making it safe for use by rendering it non-proliferative. The IFN-producing effector cell offers to be an antiviral intervention that can be deployed against many emerging pathogens by making a change of exchanging the binding portion of the receptor element to redirect specificity against the envelop protein or other antigens of the new pathogens.

Various embodiments are directed to a pharmaceutical composition comprising a genetically engineered effector cell and a pharmaceutically acceptable carrier or excipient, such as the effector cell 100 of FIG. 1 and/or the population 331 of effector cells 300 of FIG. 3.

For example, an effector cell composition, such as a pharmaceutical composition, can comprises a plurality of the genetically engineered effector cells described herein and an acceptable carrier, diluents, or excipient (e.g., a pharmaceutically acceptable carrier, diluent, excipient or a combination thereof). The means of making such a composition have been described in the art (see, for instance, Remington's Pharmaceutical Sciences, 16th Ed., Mack, ed. (1980)). Preferably, the composition is prepared to facilitate the administration of the cells into a living organism. In some embodiments, the pharmaceutical composition comprises a plurality of genetically engineered effector cells as described herein and, for example, a balanced salt solution, preferably Hanks' balanced salt solution, or normal saline.

Examples are not limited to effector cells which are used for therapeutics. In some examples, the effector cell can include an effector element that encodes a detectable reporter protein, which can be used for diagnostics. For example, the effector cell can be used to diagnose a current infection, and can be referred to as a diagnostic cell. In some embodiments, the effector cell can be used to test for an antibody response, such as testing for past infections or immunity, and can be referred to as a reporter cell.

Figure 5A:
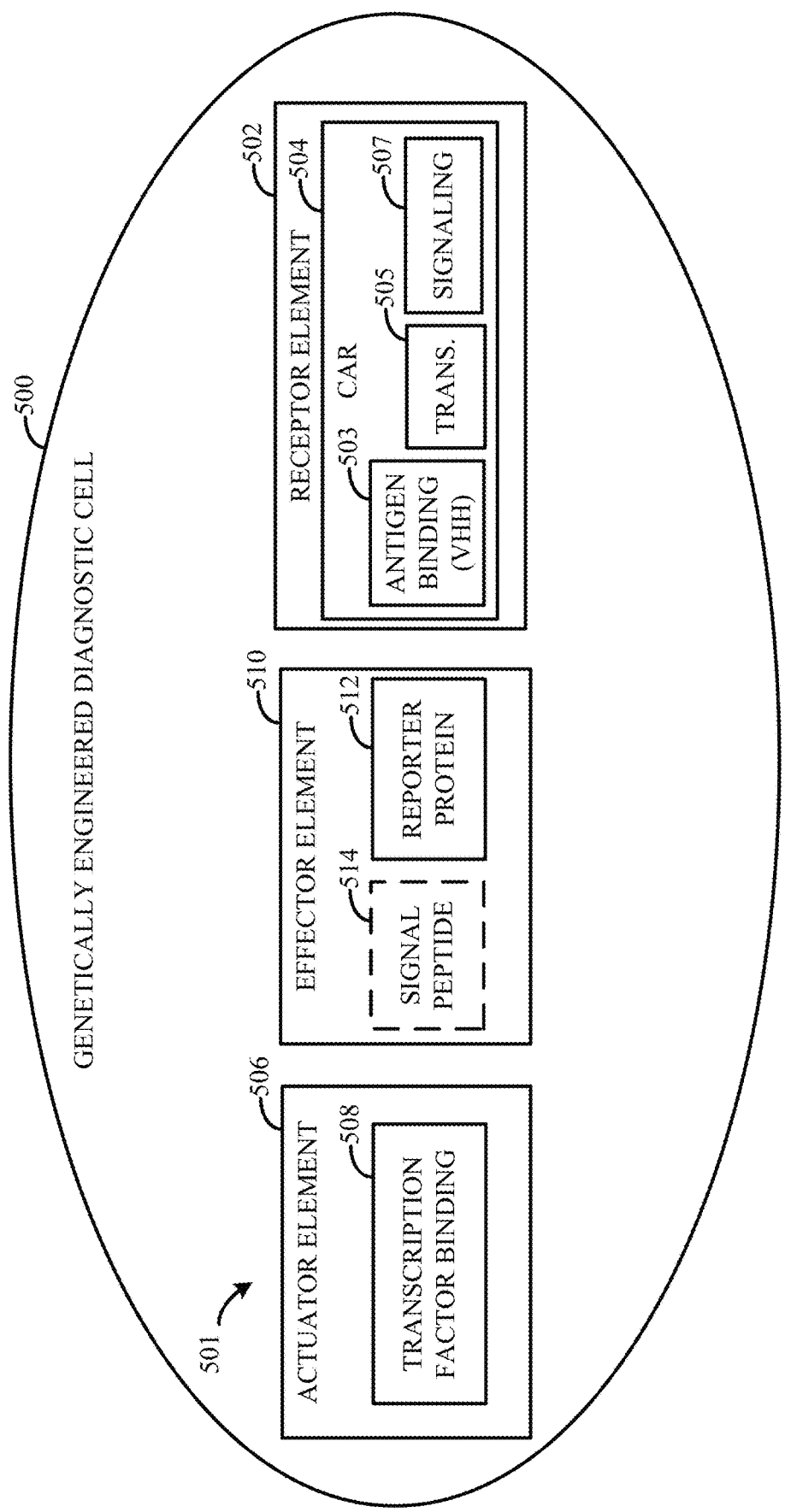
FIGS. 5A-5C illustrate an example of a genetically engineered diagnostic cell and a sequence of events triggered for providing an antigen test, in accordance with the present disclosure.
Figure 5B:
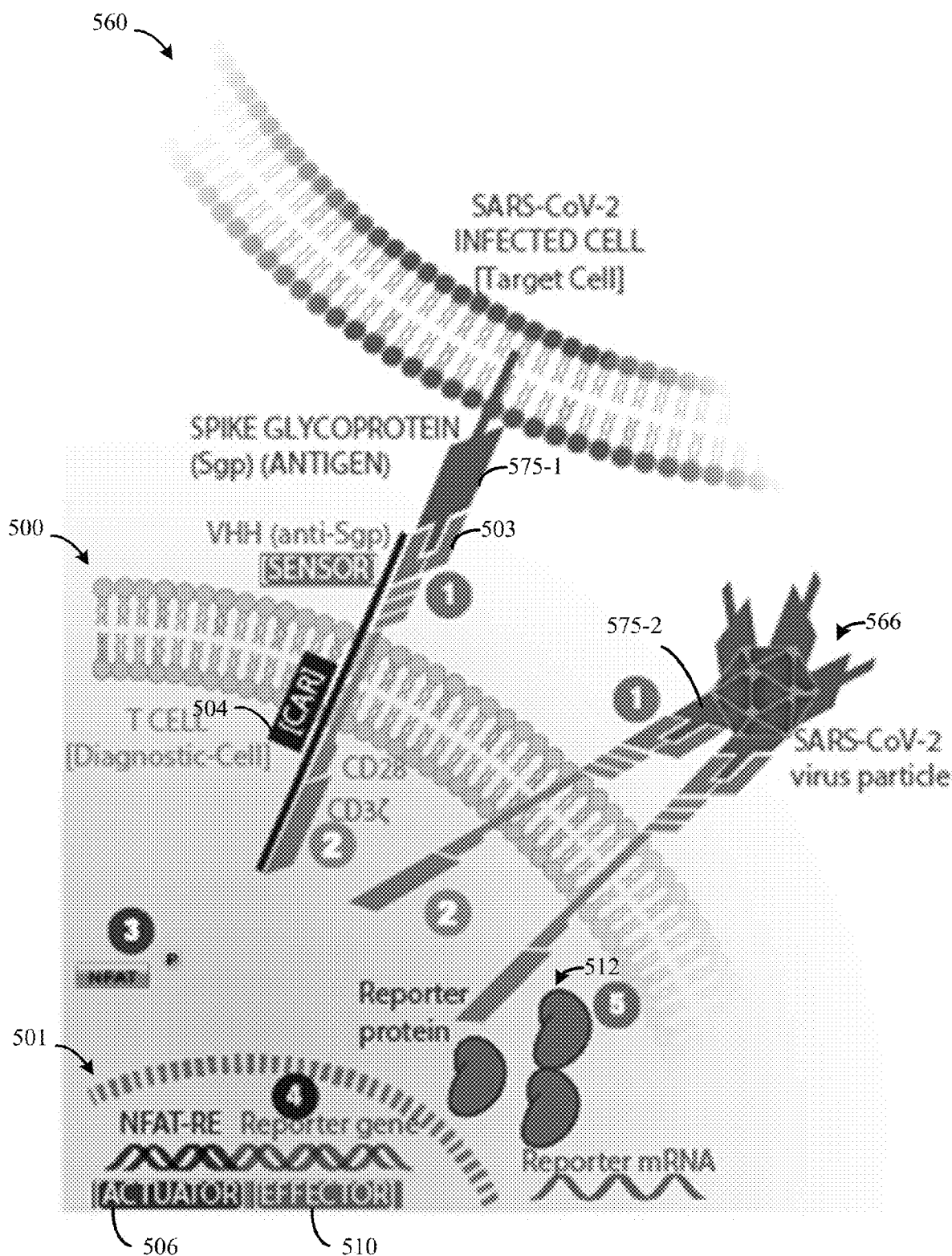
Figure 5C:
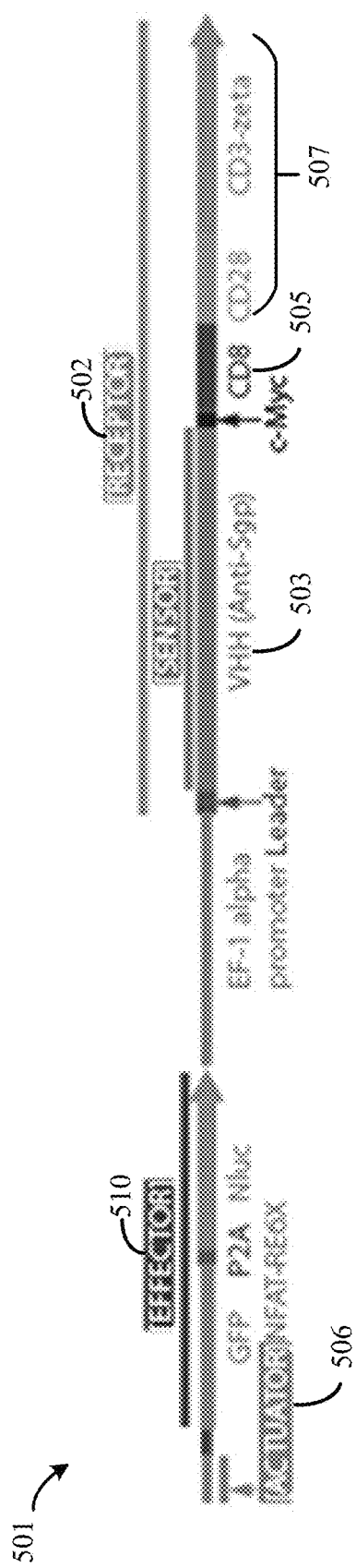

FIGS. 5A-5C illustrate an example of a genetically engineered diagnostic cell and a sequence of events triggered for providing an antigen test, in accordance with the present disclosure. For ease of reference, the genetically engineered diagnostic cell 500 is generally referred as "the diagnostic cell 500."

In various embodiments, the diagnostic cell 500 can be used to perform an antigen test to diagnose an infection for SARS-CoV-2. Asymptomatic viral transmission may be responsible for a viral spread that escapes clinical surveillance strategies, posing an obstacle to controlling outbreaks. Aggressive triaging, rapid contact tracing, and testing/retesting of hosts suspected of having the infection are the cornerstones of successful pandemic mitigation. The diagnostic cell 500 can use virus-specific molecular signatures to diagnose hosts with active infections and can be used in both clinically symptomatic and asymptomatic stages. While the various embodiments describe use for SARS-CoV-2, the diagnostic cell 500 can be modified to be specific for other virus.

As shown by FIGS. 5A-5C, the diagnostic cell 500 can include at least some of substantially the same components and features as the effector cell 100 of FIG. 1, with the receptor element encoding a different extracellular antigen binding domain and the effector element encoding different proteins. For example, the diagnostic cell 500 comprises an exogenous polynucleotide sequence 501 that includes, in operative association, a receptor element 502, an actuator element 506, and an effector element 510. A variety of different types of cells can be genetically modified to form the diagnostic cell 500 (e.g., T-cells, NK cells, etc.). In some embodiments, the exogenous polynucleotide sequence 501 is selected from any of SEQ ID NOs: 18, 40-44, 46, 48, 50, 52, and 54. However, embodiments are not so limited and the exogenous polynucleotide sequence 501 can include other sequences, such as a sequence with at least 80%, 85%, 90%, 95%, or 99% sequence identity to one of the sequences set forth in SEQ ID NOs: 18, 40-44, 46, 48, 50, 52, and 54, among others.

The receptor element 502 encodes a CAR 504. The CAR can include an extracellular binding that includes a single-domain heavy chain (VHH) region of an antibody specific to an antigen of SARS-CoV-2, such as the Sgp. However, embodiments are not so limited, and in some embodiments, a variable-heavy light (VH-VL) portion of the scFv of antibody specific to a SARS-CoV-2 antigen can be used. The extracellular antigen binding domain 503 can recognize Sgp 575-1, 575-2, or other antigen(s), on a surface of a target cell, such as a SARS-CoV-2 infected cell 560 or a SARS-CoV-2 virus particle 566. In some embodiments, the extracellular antigen binding domain 503 is selected from SEQ ID NOs: 3 and 25-29 (e.g., for SARs-Cov-1 and/or SARs-Cov-2), SEQ ID NO: 31 (e.g., for Ebola), SEQ ID NO: 33 (e.g., for Marburg), SEQ ID NO: 35 (e.g., for Chikungunya), SEQ ID NO: 37 (e.g., for Nipah), and SEQ ID NO: 39 (e.g., for West Nile), among combinations thereof. In some embodiments, the extracellular antigen binding domain 503 is selected from SEQ ID NOs: 3 and 25-29. However, embodiments are not so limited and the extracellular antigen binding domain 503 can include other sequences, such as a sequence with at least 80%, 85%, 90%, 95%, or 99% sequence identity to one or more of the sequences set forth in SEQ ID NOs: 3 and 25-29, among others.

The extracellular antigen binding domain 503 can bind to an antigen, such as any of SEQ ID NOs: 1-2 (e.g., for SARs-Cov-1 and/or SARs-Cov-2), SEQ ID NO: 30 (e.g., for Ebola), SEQ ID NO: 32 (e.g., for Marburg), SEQ ID NO: 34 (e.g., for Chikungunya), SEQ ID NO: 36 (e.g., for Nipah), and SEQ ID NO: 38 (e.g., for West Nile), among combinations thereof. However, embodiments are not so limited and can include a variety of different antigens.

As previously described, the extracellular antigen binding domain 503 is operably linked to the transmembrane domain 505 and the intracellular signaling domain 507. The transmembrane domain 505 and the intracellular signaling domain 507 can include at least some of substantially the same components and features as the transmembrane domain 105 and the intracellular signaling domain 107 of FIG. 1, the common features and attributes not being repeated for ease of reference.

The actuator element 506 can include at least some of substantially the same components and features as the actuator element 106 of FIG. 1, the common features and attributes not being repeated for ease of reference. For example, the actuator element 506 can encode a transcription factor binding site 508, such as a NFAT transcription factor binding site for a transcription factor protein and/or a set of NFAT-REs.

The effector element 510 of the diagnostic cell 500 encodes a detectable reporter protein 512. For example, and as further illustrated by FIG. 5C, the effector element 510 can encode two detectable reporter proteins which are linked by a 2A linker peptide. In some embodiments, the detectable reporter protein(s) can have a native signal peptide. In other embodiments, the non-native signal peptide 514 can be added to the effector element 510, as previously described, or may otherwise not be required. In some embodiments, the detectable reporter protein 512 can be encoded by and/or include any of SEQ ID NOs: 8-14, and combinations thereof. As such, in some embodiments, the effector element 510 can include one or more of SEQ ID NO: 8, SEQ ID NO: 9, SEQ ID NO: 10, SEQ ID NO: 11, SEQ ID NO: 12, SEQ ID NO: 13, and SEQ ID NO: 14. However, embodiments are not so limited and the effector element 510 can include other sequences, such as a sequence with at least 80%, 85%, 90%, 95%, or 99% sequence identity to one or more of the sequences set forth in SEQ ID NOs: 8-14, among others.

As used herein, a detectable reporter protein includes and/or refers to a protein that is detectable upon expression, such as a protein that provides an optical, electrical, and/or other type of detectable signal. Example detectable reporter peptides include luciferase or a bioluminescent variant thereof, Green Fluorescent Protein (GFP) or a fluorescent variant thereof, and lacZ or a colorimetric variant thereof.

In various embodiments, and as shown by FIG. 5B, in response to the extracellular antigen binding domain 503 of the CAR 504 binding to the antigen 575-1, 575-2 of the target cell (e.g., a SARS-CoV-2 infected cell 560 or a SARS-CoV-2 virus particle 566), the diagnostic cell 500 is configured to activate, and to synthesize and secrete the detectable reporter protein 512. For example, the diagnostic cell 500 can synthesize and secrete an amount of the detectable reporter protein 512 as a function of an amount of the SARS-CoV-2-infected cell 560 and/or SARS-CoV-2 virus particle 566 in the environment (e.g., the extracellular environment), such as in a sample or in situ. In some embodiments, a nasal or saliva sample can be taken from a host (e.g., a subject) and used to detect for infection.

The detectable reporter protein 512 is detectable and can be used to diagnose a host for a currently occurring SARS-CoV-2 infection, such as for performing an antigen test. Additionally, the amount (e.g., intensity) of the detectable reporter protein 512 can be used to assess the disease burden, as the amount is proportional to the amount of antigens present in the environment.

Although the above described use for SARS-CoV-2, embodiments are not so limited and can include additional antigen tests performed as a panel.

FIG. 5C illustrates an example polynucleotide sequence 501 of the diagnostic cell of FIG. 5A. As shown, the polynucleotide sequence 501 encodes an actuator element 506 connected to and upstream from an effector element 510 that encodes at least one detectable reporter protein (e.g., GFP linked to Nluc by a P2A linker peptide). The polynucleotide sequence 501 further includes a receptor element 502 that encodes an antigen binding domain 503 (e.g., the VHH that is specific to Sgp) operably linked to the transmembrane domain 505 and the intracellular signaling domain 507. In various embodiments, the receptor element 502 may be encoded on a separate plasmid vector from the actuator element 506 and the effector element 510.

FIGS. 6A-6D illustrate an example of a genetically engineered reporter cell and a sequence of events triggered for providing a serology test, in accordance with the present disclosure. For ease of reference, the genetically engineered reporter cell 600 is generally referred as "the reporter cell 600."

As shown by FIGS. 6A-6D, the reporter cell 600 can include at least some of substantially the same components and features as the effector cell 100 of FIG. 1, with the receptor element encoding a different extracellular binding domain and the effector element encoding different proteins. The effector cell 600 comprises an exogenous polynucleotide sequence 601 that includes, in operative association, a receptor element 602, an actuator element 606, and an effector element 610. A variety of different types of cells can be genetically modified to form the effector cell 600. In some embodiments, the exogenous polynucleotide sequence 601 can include SEQ ID NO: 56, however examples are not so limited. However, embodiments are not so limited and the exogenous polynucleotide sequence 601 can include other sequences, such as a sequence with at least 80%, 85%, 90%, 95%, or 99% sequence identity to SEQ ID NO: 56, among other sequences.

Figure 6A:
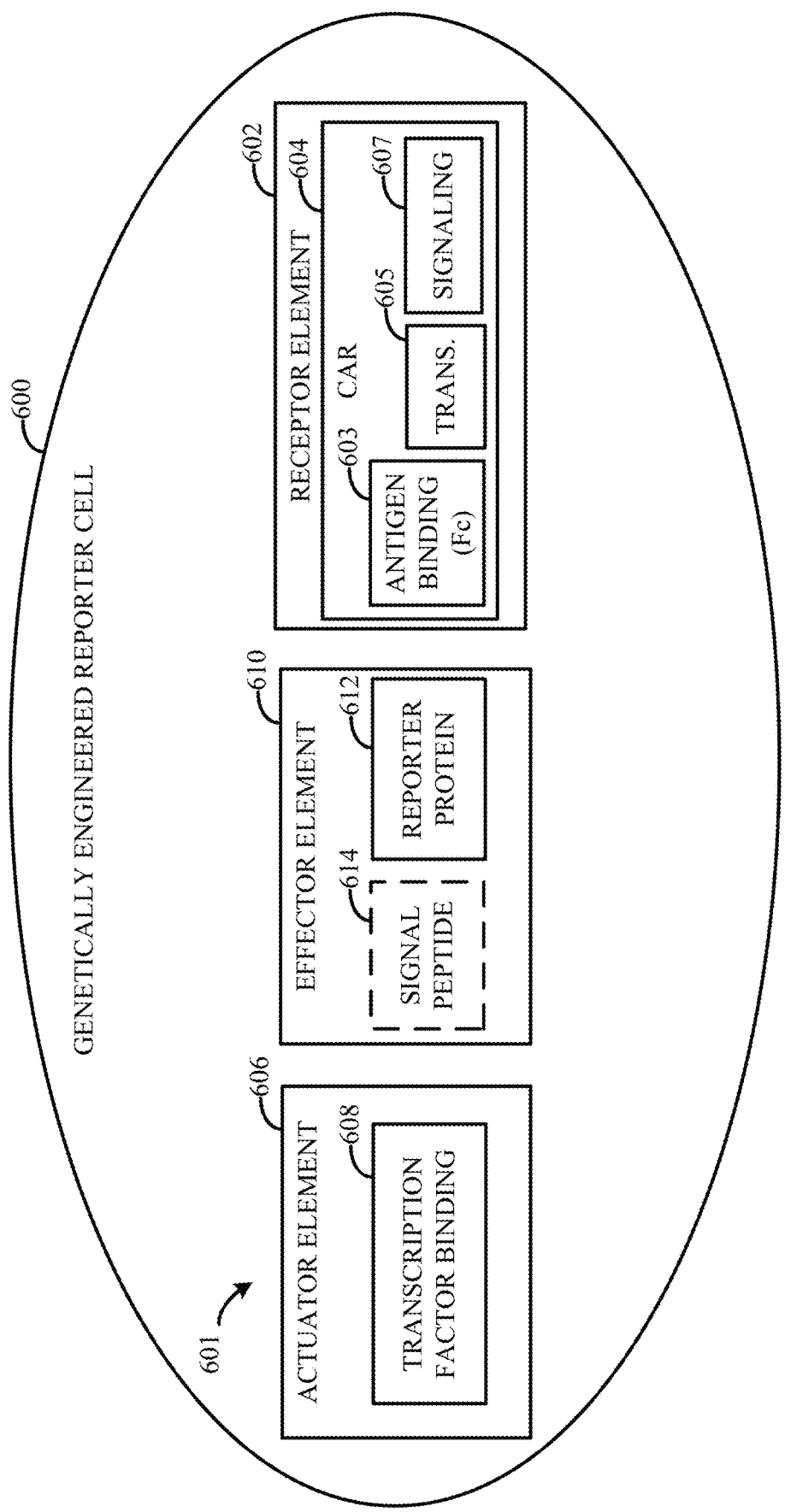
FIGS. 6A-6D illustrate an example of a genetically engineered reporter cell and a sequence of events triggered for providing a serology test, in accordance with the present disclosure.
Figure 6B:
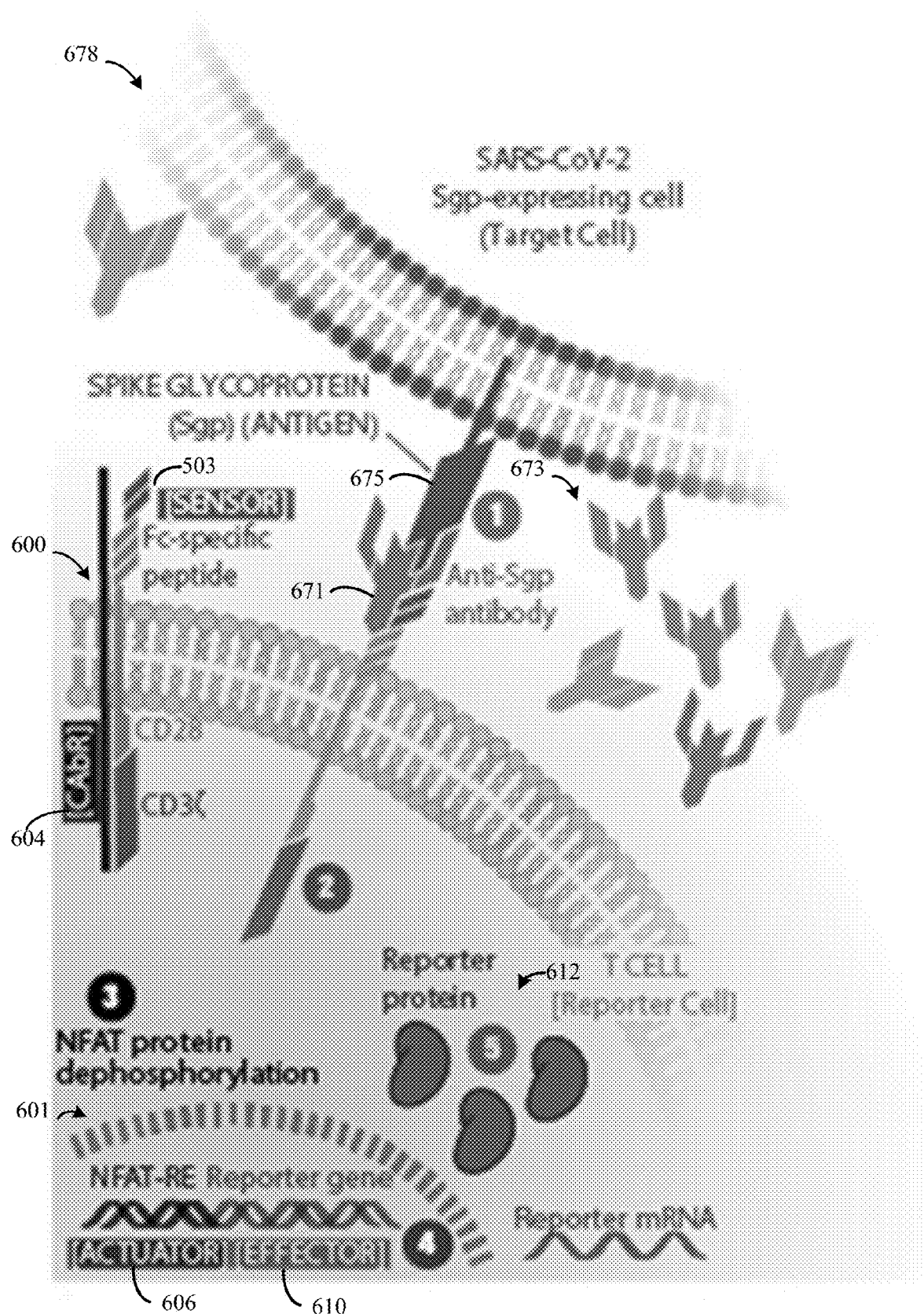
Figure 6C:
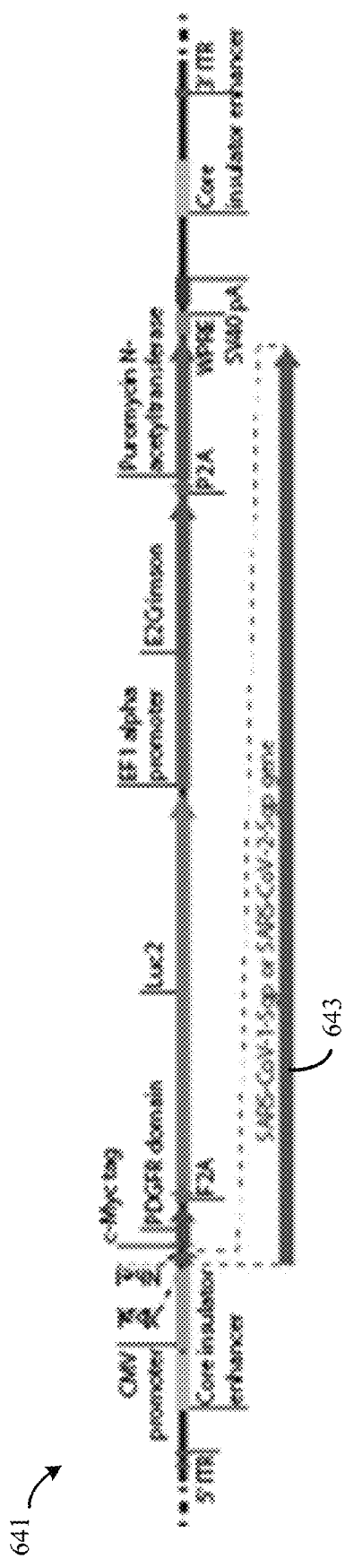
Figure 6D:
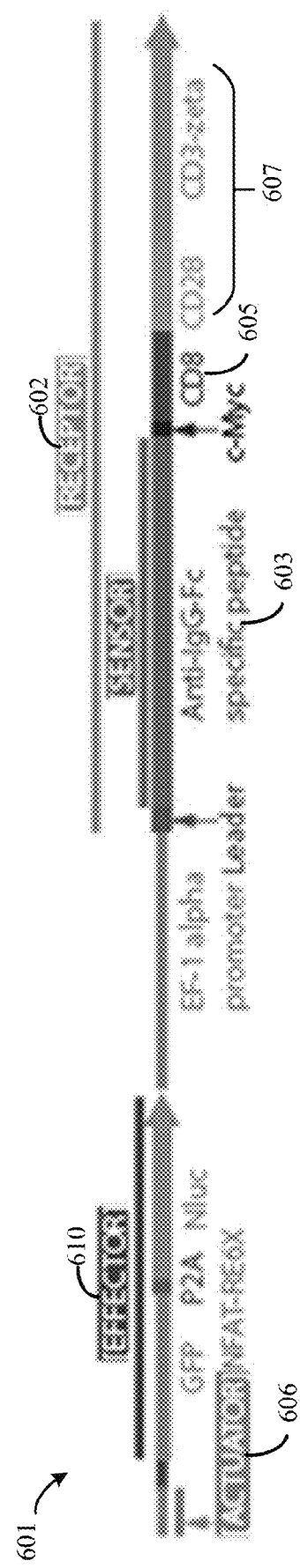
Figures 7A, 7B:
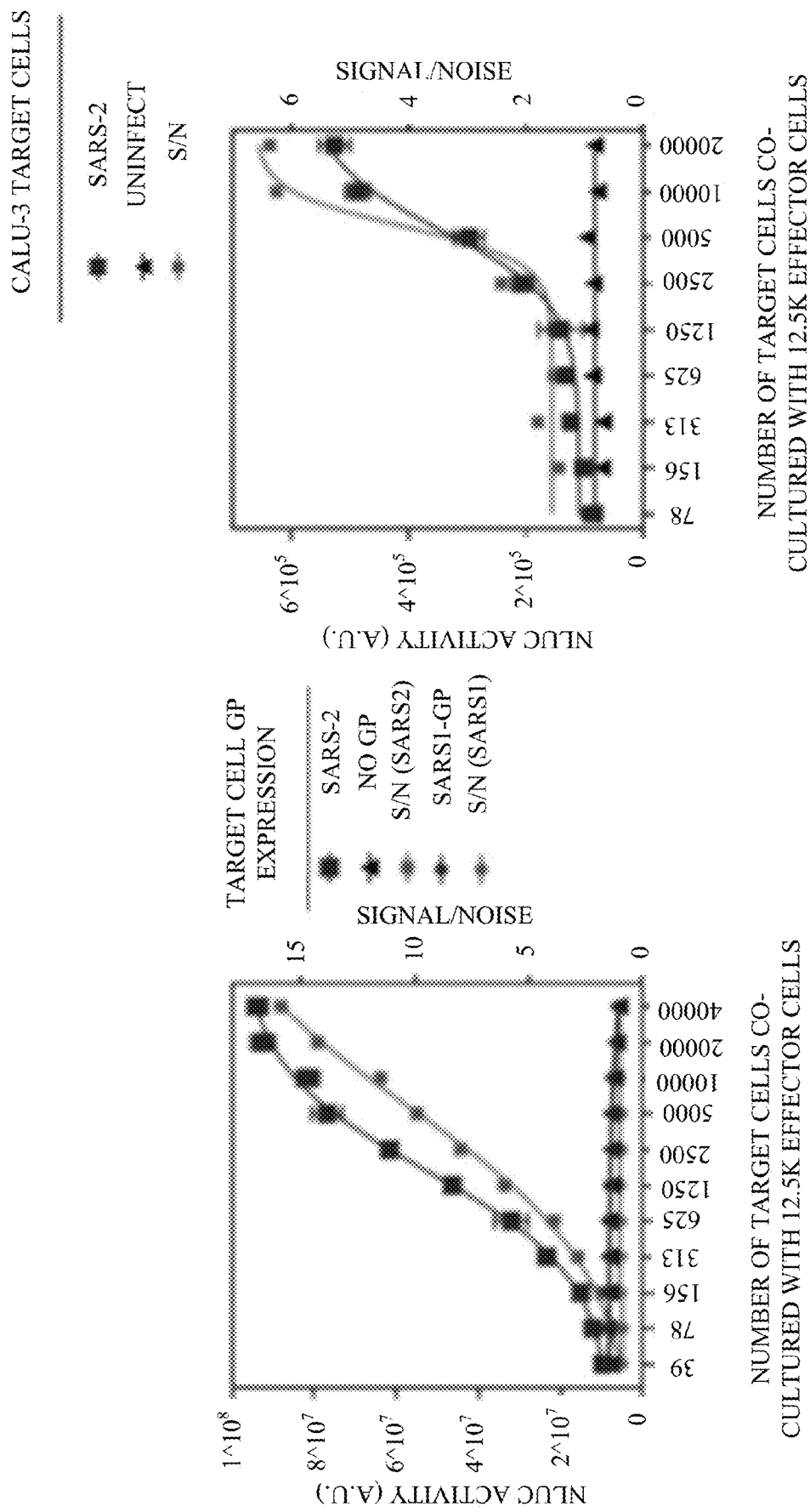
FIGS. 7A-7F illustrate plots characterizing genetically engineered effector cell function with specificity against SARS-CoV-2 antigens, in accordance with the present disclosure.
Figure 7D:
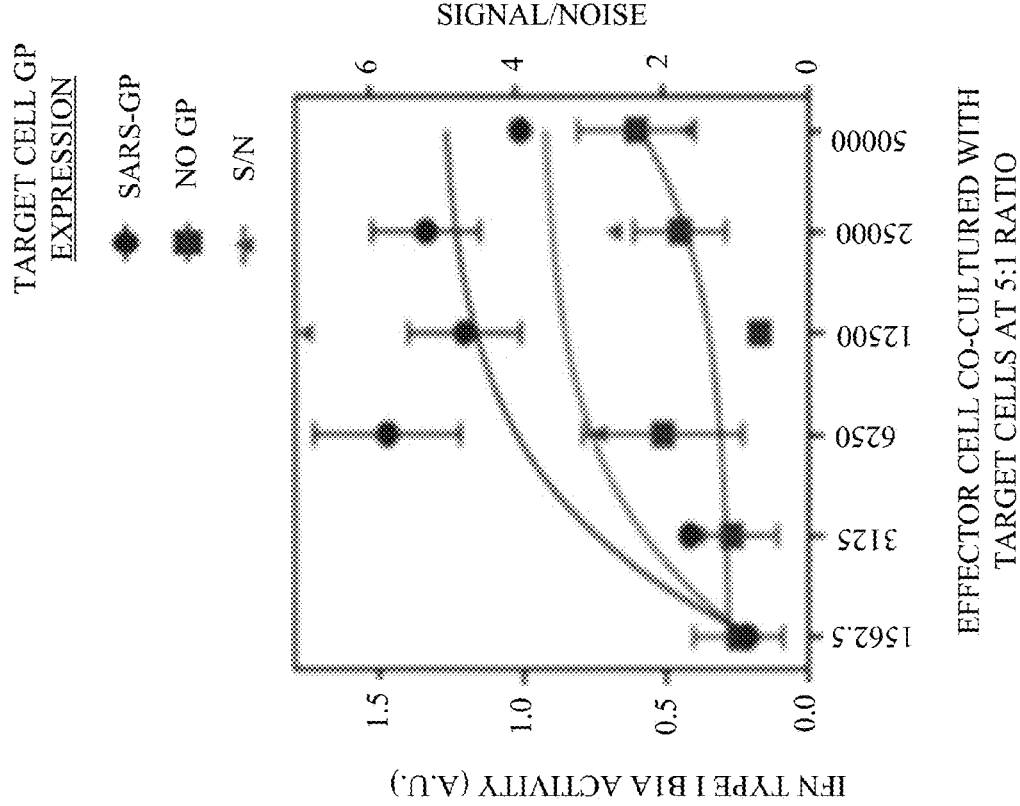
Figure 7C:
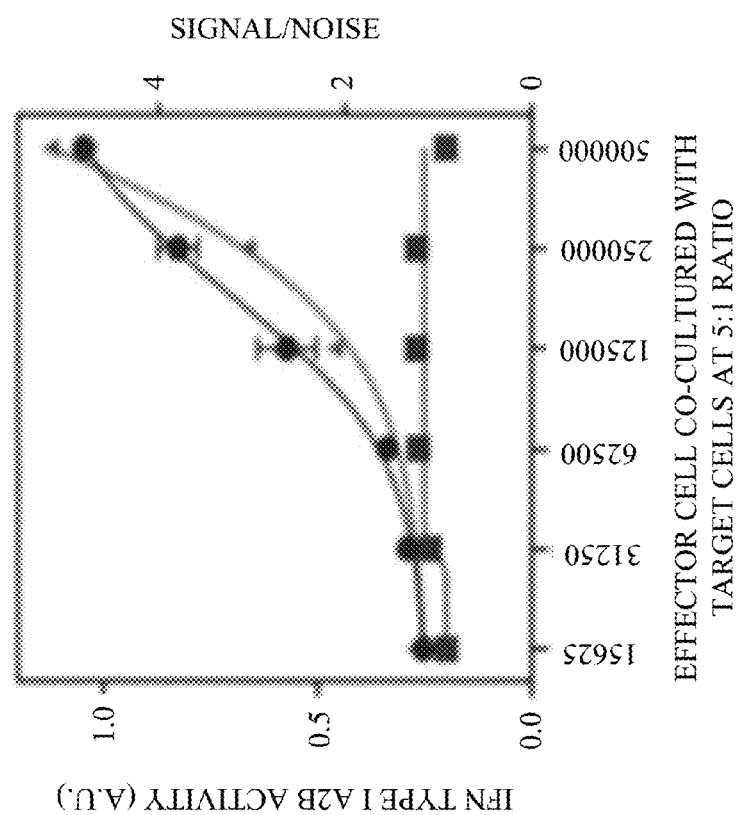
Figure 7F:
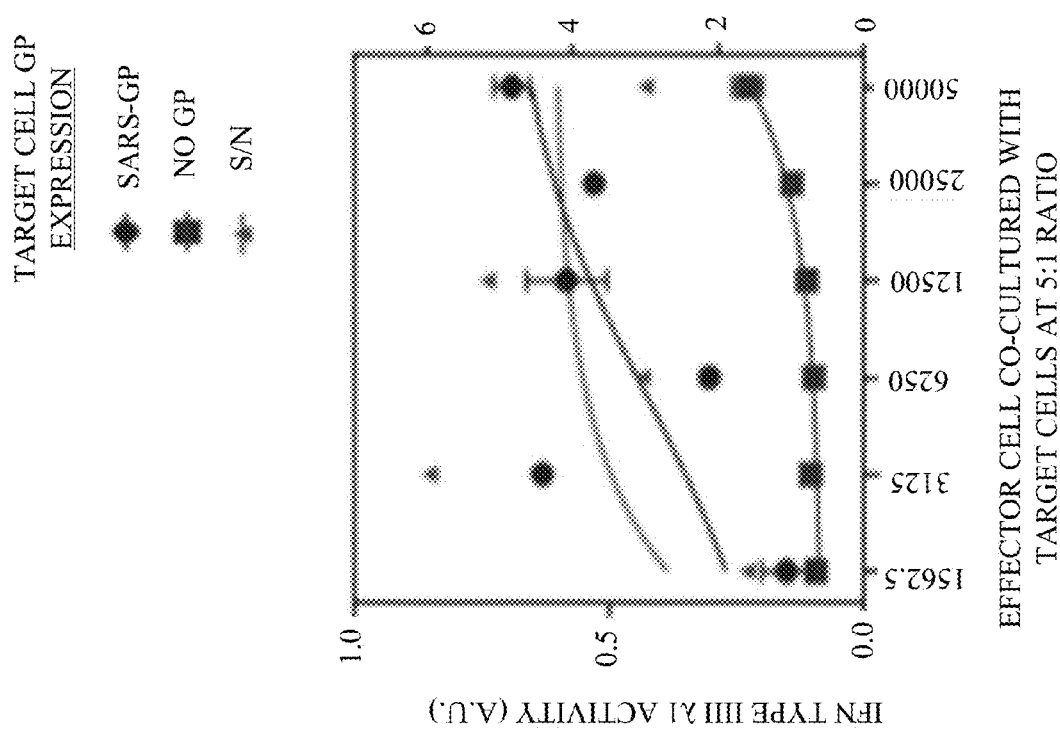
Figure 7E:
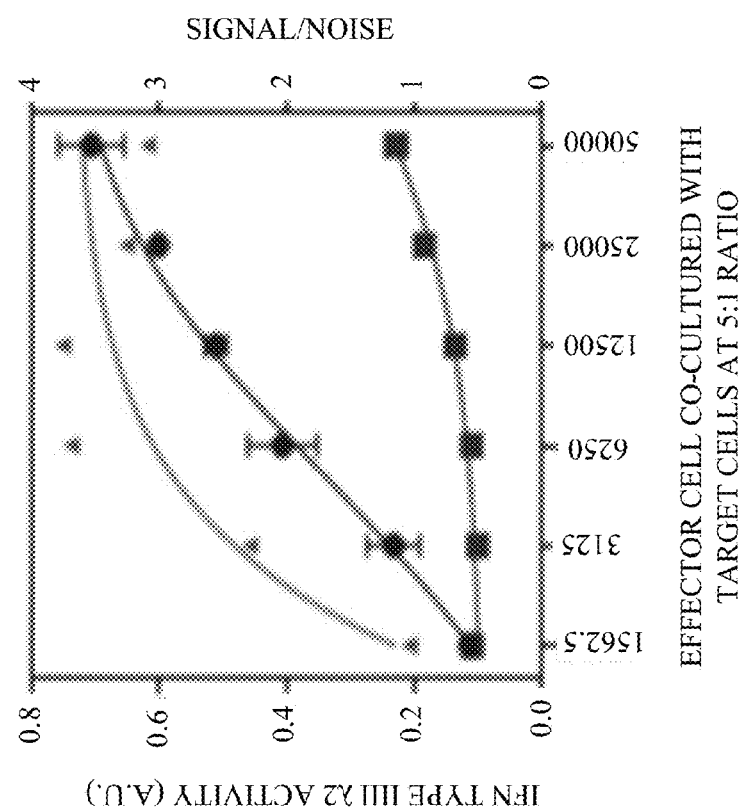

As shown by FIGS. 6B-6D, two different cells types can be generated. The first includes the reporter cell 600, which is a type of effector cell. A target cell 678 can additionally be generated, which can be a cell that is modified to express or present a target antigen 675 and is herein referred to as a "genetically engineered target cell" or an "antigen-presenting target cell". In some embodiments, the target cells 678 can be referred to as pseudo-infected cells, in that the cells are modified to present or express the antigen 675 but are not infectious. In some embodiments, genetically engineered antigen-presenting virus-like particles or virions are generated, which are modified to present or express the antigen 675 but are not infectious and can be referred to as pseudo-virus-like particles. However, embodiments are not limited to detecting antibodies associated with a virus, and in some embodiments, the target cells 678 can include a target antigen 675 which is specific to other types of molecules, such as cytokines, chemokines, and/or proteins. In such embodiments, the target antigen 675 on the target cells 678 (as well as the antigen binding domain of the reporter cell 600) can include peptides or scFvs that are specific to a segment (e.g., epitope) on the molecule to be detected. The cells can be modified to form target cells 678 using an exogenous polynucleotide sequence 641 that encodes an antigen 643.

In some embodiments, the target cells 678 can include antigens 678 such as any of SEQ ID NOs: 1-2 (e.g., for SARs-Cov-1 and/or SARs-Cov-2), SEQ ID NO: 30 (e.g., for Ebola), SEQ ID NO: 32 (e.g., for Marburg), SEQ ID NO: 34 (e.g., for Chikungunya), SEQ ID NO: 36 (e.g., for Nipah), and SEQ ID NO: 38 (e.g., for West Nile), among combinations thereof. In some embodiments, the target cells 678 can be encoded and/or formed using any of SEQ ID NOs: 16-17 and 23 (e.g., for SARs-Cov-1 and/or SARs-Cov-2), SEQ ID NO: 45 (e.g., for Ebola), SEQ ID NO: 47 (e.g., for Marburg), SEQ ID NO: 49 (e.g., for Chikungunya), SEQ ID NO: 51 (e.g., for Nipah), and SEQ ID NO: 53 (e.g., for West Nile), among others. However, embodiments are not so limited and the target cells 678 and/or antigens 678 of the target cells 678 can include other sequences, such as a sequence with at least 80%, 85%, 90%, 95%, or 99% sequence identity to one or more of the sequences set forth in SEQ ID NOs: 1-2, 16-17, 23, 30, 32, 34, 36, 38, 45, 47, 49, 51, and 53, among other sequences.

The receptor element 602 encodes a CAR 604. The CAR can include an extracellular antigen binding domain 603 that includes an anti-IgG-Fc specific peptide. The extracellular antigen binding domain 603 can recognize any IgG antibody 673, and is not specific to a target antibody 671. As such, the reporter cell 600 can be used to test for antibodies specific to different pathogens by generating different target cells 678 which present the target antigen 675. While other antibodies 673 can bind to the binding domain 603, the environment can be controlled to only include target cells 678 expressing the target antigen 675, and not include other antigens or targets. As such, the reporter cell 600 is only activated in response to the presence of IgG antibodies specific to the target antigen 675, e.g., Sgp. As described above, embodiments are not limited to testing or detecting antibodies and/or antibodies specific to pathogens. In some embodiments, the extracellular antigen binding domain 603 can include a peptide or ScFv that recognizes and/or is specific to a segment (e.g., epitope) on another type of molecule to be detected, such as cytokines, chemokines, proteins, among other molecules. In such embodiments, the extracellular antigen binding domain 603 and the antigen of the target cells 678 can be specific to two different and unique segments, e.g., epitopes, of the molecule to be detected. In some embodiments, the extracellular antigen binding domain 603 can include SEQ ID NO: 55. However, embodiments are not so limited and the extracellular antigen binding domain 603 can include other sequences, such as a sequence with at least 80%, 85%, 90%, 95%, or 99% sequence identity to SEQ ID NO: 55, among other sequences.

As previously described, the extracellular antigen binding domain 603 operably linked to the transmembrane domain 605 and the intracellular signaling domain 607. The transmembrane domain 605 and the intracellular signaling domain 607 can include at least some of substantially the same components and features as the transmembrane domain 105 and the intracellular signaling domain 107 of FIG. 1, the common components and features not being repeated for ease of reference.

The actuator element 606 can include at least some of substantially the same components and features as the actuator element 106 of FIG. 1, the common components and features not being repeated for ease of reference. For example, the actuator element 606 can encode a transcription factor binding site 608, such as a NFAT transcription factor binding site for a transcription factor protein and/or a set of NFAT-REs.

The effector element 610 of the reporter cell 600 encodes a detectable reporter protein. For example, and as further illustrated by FIG. 6D, the effector element 610 can encode two detectable reporter proteins which are linked by a 2A linker peptide, as previously described by FIG. 5B. In some examples, the effector element can optionally encode a signal peptide 614. In some embodiments, the detectable reporter protein 600 can be encoded by and/or include any of SEQ ID NOs: 8-14, and combinations thereof. As such, in some embodiments, the effector element 610 can include one or more of SEQ ID NO: 8, SEQ ID NO: 9, SEQ ID NO: 10, SEQ ID NO: 11, SEQ ID NO: 12, SEQ ID NO: 13, and SEQ ID NO: 14. However, embodiments are not so limited and the effector element 610 can include other sequences, such as a sequence with at least 80%, 85%, 90%, 95%, or 99% sequence identity to one or more of the sequences set forth in SEQ ID NOs: 8-14, among other sequences.

In various embodiments, as shown by FIG. 6B, in response to the extracellular antigen binding domain 603 of the CAR 604 binding to the target antibody 671, e.g., the anti-Sgp antibody, and the target antibody 671 binding to the antigen-presenting target cell 678, e.g., SARS-CoV-2 Sgp-expressing cell, the reporter cell 600 is configured to activate, and to synthesize and secrete the detectable reporter protein 612. For example, the reporter cell 600 can synthesize and secrete an amount of the detectable reporter protein 612 as a function of an amount of the target antibody 671 present in the environment, such as in a sample or in situ.

The detectable reporter protein 612 is detectable and used to assess for immune response to the pathogen or other purposes, such as for performing a serology test. For example, blood (among other types of samples, such as nasal samples) can be taken from a host and used to perform the test. Additionally, the amount (e.g., intensity) of the detectable reporter protein 612 can be used to assess immune response, as the amount can be proportional to the amount of antibody present in the environment.

Although the above described use for SARS-CoV-2, embodiments are not so limited and can include additional antigen and/or serology tests performed as a panel. In other embodiments, the target molecule detected can include a molecule other than an antibody, as described above.

FIG. 6C illustrates an example polynucleotide sequence 641 used to generate an antigen-expressing modified cell as shown by FIG. 6A. As shown, the polynucleotide sequence 641 encodes the antigen 643, such as the SARS-CoV-1 Sgp or the SARS-CoV-2 Sgp.

FIG. 6D illustrates an example polynucleotide sequence 601 of the reporter cell of FIG. 6A. As shown, the polynucleotide sequence 601 encodes an actuator element 606 connected and upstream from an effector element 610 that encodes at least one detectable reporter protein (e.g., GFP linked to Nluc by a P2A linker peptide). The polynucleotide sequence 601 further includes a receptor element 602 that encodes a binding domain 603 (e.g., the Anti-IgG-Fc specific peptide) operably linked to the transmembrane domain 605 and the intracellular signaling domain 607. In various embodiments, the receptor element 602 may be encoded on a separate plasmid vector from the actuator element 606 and the effector element 610.

Some embodiments are directed to methods of forming the genetically engineered effector cells, such as genetically engineering or modifying an effector cell to include the components and features as described by the effector cell 100 of FIG. 1, diagnostic cell 500 of FIG. 5A, and/or reporter cell 600 of FIG. 6A.

The genetically engineered effector cells and cell compositions provided herein have properties advantageous for use in a variety of in vitro, ex vivo, and in vivo applications. For example, in vitro uses of the effector cells and cell compositions provided herein include, without limitation, detecting target cells on the basis of antigens expressed on the surface of the target cells. The target cell can be a cell infected by a pathogen such as a virus or bacterium, a cell type associated with an immune response to a pathogen (e.g., antibody). Also, the target (host) cell can be a cell type associated with any other pathology for which the affected (host) cell having aberrant expression of a cell surface antigen relative to an unaffected (host) cell. Methods for using the genetically engineered effector cells or cell compositions for in vitro target cell detection are described above and further below. In various embodiments, multiple effector cells that are targeted to different pathogens or different immune responses to the different pathogens can be used to form panel antigen test or panel serology tests for the different pathogens. For example, a single antigen test can be used to test for SARS-CoV-2, the flu, and various common cold strains.

Ex vivo uses of the genetically engineered effector cells and cell compositions provided herein include, without limitation, early disease detection and companion diagnostic or therapeutic applications for the disease target cells identified on the basis of antigens expressed on the surface of the disease target cells. For example, the cells can be used for ex vivo applications in companion diagnostics for cancer immunotherapy. By way of example, the effector cell engineered with NFAT_RE6X with Nluc-2A-GFP can be engineered to express different types of CARs. The expression of Nluc when CAR engages its target antigen versus the non-specific Nluc expression can inform on the comparative and quantitative robustness of each CAR for its efficiency to cause the intended on-target effect versus unintended off-target effects. Methods for using the genetically engineered effector cells or cell compositions in ex vivo therapeutic applications are described further below.

In vivo applications of the genetically engineered effector cells and cell compositions provided herein include, without limitation, in vivo methods for localized therapy at a disease site (e.g., targeted therapy for ovarian cancer) or site of pathogen infection (e.g., targeted therapy for cells infected by SARs-Cov-2, dengue virus, Zika virus, West Nile virus, yellow fever, HIV, or a hepatitis virus (e.g., HepB, HepC)).

Various embodiments are directed to a panel of different types of genetically engineered effector cells, such as a plurality of effector cells engineered with different effector proteins and/or extracellular antigen binding domains (among other differences), and which are used to simultaneously target different cells and/or secrete different effector proteins.

In some embodiments, a method of detecting a target cell comprises (a) contacting a genetically engineered effector cell to a cell population, and (b) detecting expression of the effector protein, wherein detectable expression of the effector protein indicates the presence of the target cell of interest. In some embodiments, the effector cell includes a NFAT-RE and a reporter protein, and in the presence of the target cell in the contacted cell population, the genetically engineered effector cell binds to a surface molecular antigen on the target cell and activates the NFAT-RE; and (b) detecting expression of the reporter protein, wherein detectable expression of the reporter protein indicates the presence of the target cell.

In embodiments, the detected target cell is a virus-infected host cell such as, for example, a SARS-CoV-2-infected cell. In some such embodiments, the surface molecular antigen expressed on the virus-infected cell can be a SARS-CoV-2 virus-specific Egp or Sgp. For example, the antigen-recognizing portion of the CAR is modified or exchanged to quantitatively assess different viral pathogens such as SARS-CoV-2, dengue virus (DENV), West Nile (WNV), and Yellow Fever (YFV). In some embodiments, the methods harness the translational machinery of the infected host cell to process viral RNA into a virus-specific antigen that is detectable by the genetically engineered effector cell.

Some embodiments are directed to methods of treating or preventing a disease using genetically engineered effector cells expressing a CAR as a therapeutic agent. For example, provided herein are methods comprising administering a genetically engineered effector cell expressing the CAR as an active therapeutic agent. The disease against which the effector cell expressing the CAR is administered is not particularly limited as long as the disease shows sensitivity to the effector cell. In some embodiments, a genetically engineered effector cell expressing the CAR binds to an antigen expressed on the surface of a target cell that targeted to be decreased or eliminated for treatment of the aforementioned diseases, that is, a viral antigen for effector, is administered to treat or prevent such diseases. The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, methods described herein can provide any amount of any level of treatment or prevention of SARS-CoV-2 in a mammal. Furthermore, the treatment or prevention provided by example methods can include treatment or prevention of one or more conditions or symptoms of the virus, e.g., SARS-CoV-2, being treated or prevented. Also, for purposes herein, "prevention" can encompass delaying the onset of the disease, or a symptom or condition thereof.

In some embodiments, genetically engineered effector cells are administered to a host (e.g., subject) in need thereof as a composition comprising the genetically engineered effector cells and a suitable carrier, diluent, or excipient as described herein. Any appropriate method of providing modified CAR-expressing cells to a host can be used for methods described herein. In some embodiments, methods for providing effector cells to a host can be adapted from clinical protocols for cellular and adoptive immunotherapy for infusion of donor-derived immune cells into a human host. In some embodiments, an adapted clinical protocol suitable for methods provided herein comprises obtaining effector cells from a host, genetically engineering (e.g., modifying) effector cells to express a CAR and NFAT-RE regulated AVP transgene as described herein, and infusing the genetically engineered effector cells back into the host. A host, as used herein, includes and/or refers to any organism, such as a human, an animal (e.g., mammal, reptile, bird), insect, plant, among others, and which can be a subject of a study or test and/or a patient. A "subject" is sometimes interchangeably used with "host". Host cells include cells obtained from the host.

Administration of the genetically engineered effector cells provided herein can be administered by any appropriate route, including, without limitation, administration intravenously, intratumorally, intramuscularly, subcutaneously, intraperitoneally, intra-arterially, or into an afferent lymph vessel, by parenteral administration, for example, by injection or infusion. In some embodiments, where genetically engineered effector cells or populations of such effector cells are administered, the effector cells can be cells that are allogeneic or autologous to the host, such as a mammal. Preferably, the effector cells are autologous to the host.

In some embodiments, the genetically engineered effector cells comprise a CAR that detects an antigen on a pathogen-infected cell (e.g., SARS-CoV-2) or an antibody triggered in response to prior infection, and a NFAT response element to induce expression of a reporter polypeptide. Such embodiments can be used for transfusion medicine to detect the presence of emerging pathogens and/or to identify and track natural immunity.

As used herein, a target cell (sometimes herein interchangeably referred to as a "target cell of a host", "target cell of interest", "a diseased cell", or "a target disease cell") includes and/or refers to a cell of interest associated with a living organism (e.g., a biological component of interest) or a modified live cell in a test environment (e.g., genetically modified test cells or other antigen-present cells in solution). An antigen of the target cell includes and/or refers to a structure (e.g., binding site) of the target cell which the antigen binding domain of the receptor element can bind to (e.g., has an affinity for). The effector cell can be from a variety of different type of cells, such as human and non-human cells, and sometimes herein referred to as "the source". As used herein, the terms "genetically modified" and "genetically engineered" are used interchangeably and include and/or refer to a prokaryotic or eukaryotic cell that includes an exogenous polynucleotide, regardless of the method used for insertion. In some embodiments, the effector cell is modified to comprise a non-naturally occurring nucleic acid molecule that is created or modified by the hand of man (e.g., using recombinant deoxyribonucleic acid (DNA) technology) or is derived from such a molecule (e.g., by transcription, translation, etc.). An effector cell that contains an exogenous, recombinant, synthetic, and/or otherwise modified polynucleotide is considered to be a genetically engineered effector cell.

"Nucleic acid", as used herein, includes and/or refers to a "polynucleotide," "oligonucleotide," and "nucleic acid molecule," and generally means a polymer of DNA or ribonucleic acid (RNA), which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions. In some embodiments, the nucleic acid can encode additional amino acid sequences that do not affect the function of the CAR and polynucleotide and which may or may not be translated upon expression of the nucleic acid by a host cell.

Nucleic acids can be obtained using any suitable method, including those described by Maniatis et al., Molecular Cloning: A Laboratory Manual, Cold Spring Harbor, N.Y., pp. 280-281 (1982) and/or U.S. Patent Application Publication No. US2002/0190663, each of which are herein fully incorporated in their entireties for their teachings. Nucleic acids obtained from biological samples typically are fragmented to produce suitable fragments for analysis.

Nucleic acids and/or other moieties can be isolated. As used herein, "isolated" includes and/or refers to separate from at least some of the components with which it is usually associated whether it is derived from a naturally occurring source or made synthetically, in whole or in part. Nucleic acids and/or other moieties of the invention can be purified. As used herein, "purified" includes and/or refers s separate from the majority of other compounds or entities. A compound or moiety can be partially purified or substantially purified. Purity can be denoted by a weight by weight measure and can be determined using a variety of analytical techniques such as but not limited to mass spectrometry, HPLC, etc.

EXPERIMENTAL EMBODIMENTS

A number of experimental embodiments were conducted to generate genetically engineered effector cells including therapeutic cells, diagnostic cells, and reporter cells, and to characterize the effector cell functionality. Example constructs used to generate genetically engineered cells include the nucleotide sequences set forth in SEQ ID NOs: 1-56. SEQ ID NOs: 1-56 are each synthetic DNA.

In various embodiments, immune cells are modified to form effector cells that, upon engaging the antigen-presenting target cells (e.g., natural or genetically modified), produce non-endogenous proteins for exerting a target effect locally. In some embodiments, two different types of T-cells are modified to form effector cells that synthesize anti-viral Type-1 (IFN-α2b, IFN-β1a) and Type-III (IFN-λ2; IFN-λ1), which are sometimes herein referred to as "T-cell Biofactories" or "cell biofactory". Prophylactic and therapeutic effects of the IFN produced from the T-cell Biofactory were determined on SARS-CoV-2 infected cells. The ISGs activated in the host cells were investigate, when exposed to the Type-I or Type-III IFN producing T-cell Biofactory. The radiation dose (γ-radiation) used to render the T-cell Biofactory non-proliferative was identified, while conserving the cell-based IFN production, to mitigate potential oncogenesis risks. This ensures safe administration of the T-cell Biofactory that can have translational implications and can be made available in compliance with cGMP for Phase I/II clinical trials.

FIGS. 7A-7F illustrate plots characterizing genetically engineered effector cells function with specificity against SARS-CoV-2 antigens, in accordance with the present disclosure.

An effector cell was engineered to target viral infection to develop cell-based delivery of AVO therapeutics. A fast-growing cell line, Jurkat E6-1, was modified to include a receptor element, an actuator element, and an effector element. The receptor elements encoded a CAR with specificity to the Sgp of SARS-CoV-2, sometime referred to as "Sgp-CAR". The Sgp-CAR triggers the downstream pathway, e.g., activates the actuator element encoding a NFAT-RE to synthesize an AVP of IFN encoded by the effector element. Different effector cells, sometimes referred to as cell biofactories, were developed that encoded Type-I IFN and Type-III IFN. Target cells were artificially prepared to express the Sgp from SARS-CoV-1 and SARS-CoV-2, which can be referred to as genetically modified target cells. The genetically modified target cells were co-cultured with the Spg-specific effector cell, which resulted in production of Type-I IFN or Type-III IFN upon engaging with the genetically modified target cells. IFN-sensitive reporter cells (Type-I, Type-III) were used to assess the output of the Sgp-specific effector cell in the context of efficacy and off-target activity. Validations were further conducting using target cells with infectious SARS-COV-2 virus particles in BSL3.

FIG. 7A illustrates the results of co-culturing anti-SARS-CoV-2 effector cells with HEK cell lines that model viral infection through expression of viral-specific Sgp and FIG. 7B illustrates the results of results of co-culturing anti-SARS-CoV-2 effector cells with SARS-CoV-2 infected Calu-3 cells, activates nLuciferase reporter expression, as shown by the plot of FIG. 7B. Activation of the effector cell is mediated through the Sgp that is specific for the virus and is proportional to mock or live viral load. Further engineering of the virus-specific effector cell replaced nLuciferase reporter with Type-I IFN (as shown by FIGS. 7C and 7D) and Type-III IFN (as shown by FIGS. 7E and 7F). Coculture of IFN-effector cell with modeled or artificial SARS-CoV-2-infected target cells induces interferon secretion proportional to the number of effector cells.

The modified effector cell can serve as a therapeutic to treat severe cases and a prophylactic to prevent the progression of mild/moderate cases to severe cases of SARS-CoV-2 and related diseases. Such effector cell can be used as a readily-available stockpile of broad-spectrum antiviral cells that, in event of an epidemic of bioweapon attach, can be rapidly deployed and activated using extracorporeal devices without the need for developing vaccines specific for each viral pathogen.

As may be appreciated, embodiments were not limited to SARS-CoV-2. Different effector cells, diagnostic cells, and reporter cells were generated to assess different viruses and other pathogens.

FIG. 8 illustrates plots characterizing genetically engineered effector cell function with specificity against different pathogens, in accordance with the present disclosure. For example, effector cells which produce IFNs were generated that were specific to different pathogens including SARS-CoV-2, SARS-CoV-1, Ebola, Marburg, West Nile, Chikungunya, and Nipah.

Various embodiments were directed to assessing the artificial cell-signaling pathway, which comprises three constant domains (portions of the receptor element (e.g., transmembrane domain, and intracellular signaling domain), actuator element, signal peptide) and two variable domains (the CAR of the receptor element, effector element) domains arranged in cis, was used to generate the effector cell from T-cells that produces Type-I or Type-III IFNs upon detecting the Sgp as an antigenic biomarker on the surface of host cells infected with SARS-associated coronaviruses, which can be referred to as target cells. The constant domains provide functionality to the effector cell and include a transmembrane molecule that mobilizes the T-cell activation machinery actuator element to express the desired transgene. To assist the secretion of IFNs, the natural signal peptide of the two IFNs was used. Variable domains, which can be exchanged to reprogram the specificity of the effector cell against different disease indications, include an antigen-binding camelid-derived single domain heavy chain (VHH-72; PDB: 6WAQ) as the binding domain of the CAR which has specificity towards SARS-CoV-1 Sgp and cross-reactivity with SARS-CoV-2 Sgp (See FIGS. 10A-10B). To reprogram the effector cell for desired specificity, the VHH-72 sequence can be replaced by an appropriate VHH or variable heavy-light [VH-VL] portion of the scFv. Upon engaging the Sgp, the Sgp-specific effector cell mobilizes the transcriptional machinery of the T-cell to synthesize Type-I (IFN-α2b; IFN-β1a) or Type-III (IFN-λ2; IFN-λ1) IFNs (e.g., the effector proteins) that exert prophylactic or therapeutic effects.

Referring back to FIG. 2, FIG. 2 shows an example schematic of the Sgp-specific effector cell 200 and the potential to identify the SARS-CoV-2-specific Sgp independent of presentation in the peptide-major histocompatibility complex (pMHC). The SARS-CoV-2-specific function of the Sgp-specific effector cell was initially assessed using an genetically engineered target cell that is artificially or pseudo-infected, which is prepared by engineering HEK293T/17 cell line to stably express the Sgp from SARS-CoV-2 (SARS-CoV-2-Sgp-cell) while the non-engineered parental cell line was used as the uninfected negative control. Two classes of the Sgp-specific effector cells were prepared that produced different effector proteins (i) Type-I (IFN-α2b; IFN-β1a), and (ii) Type-III (IFN-λ2; IFN-λ1). Comparison of the two Type-I IFNs (IFN-α2b; IFN-β1a) and two Type-III IFNs (IFN-λ2; IFN-λ1) in context of effector protein production is further illustrated by FIGS. 13A-13D. Based on this comparison, IFN-β1a and IFN-λ1 were used to represent Type-I and Type-III IFNs, respectively. An initial dose assessment of the gamma radiation that does not substantially degrade the artificial cell-signaling pathway but renders the effector cell non-proliferative and non-oncogenic was determined to be at least 20 Gy (FIG. 14A-14B).

Figure 9B:
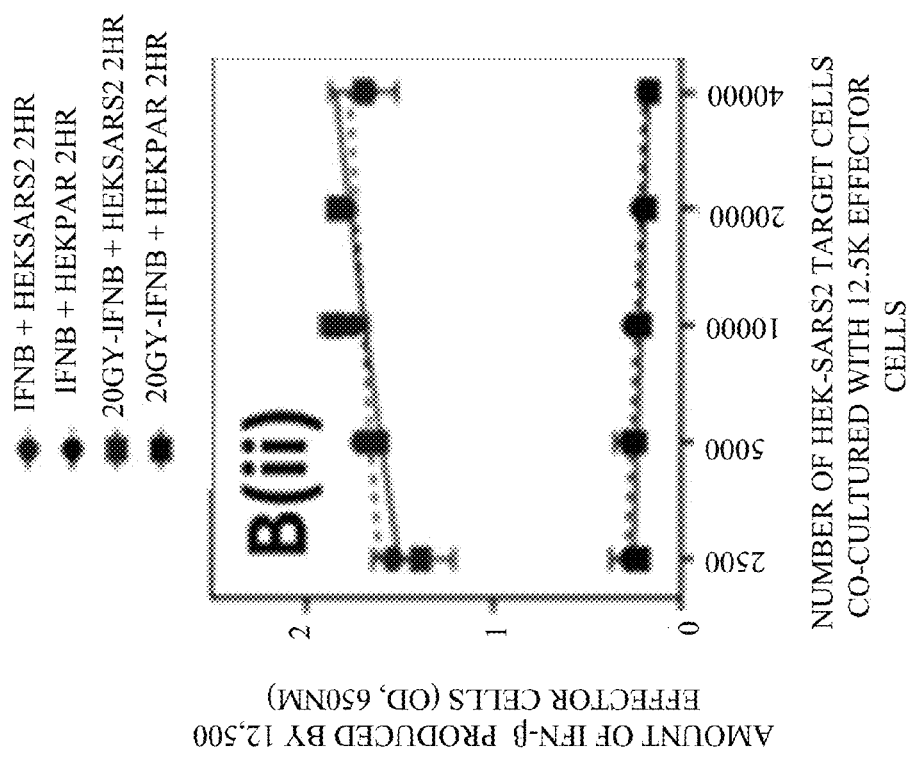
FIGS. 9A-9D illustrate plots characterizing genetically engineered effector cell function, in accordance with the present disclosure.
Figure 9A:
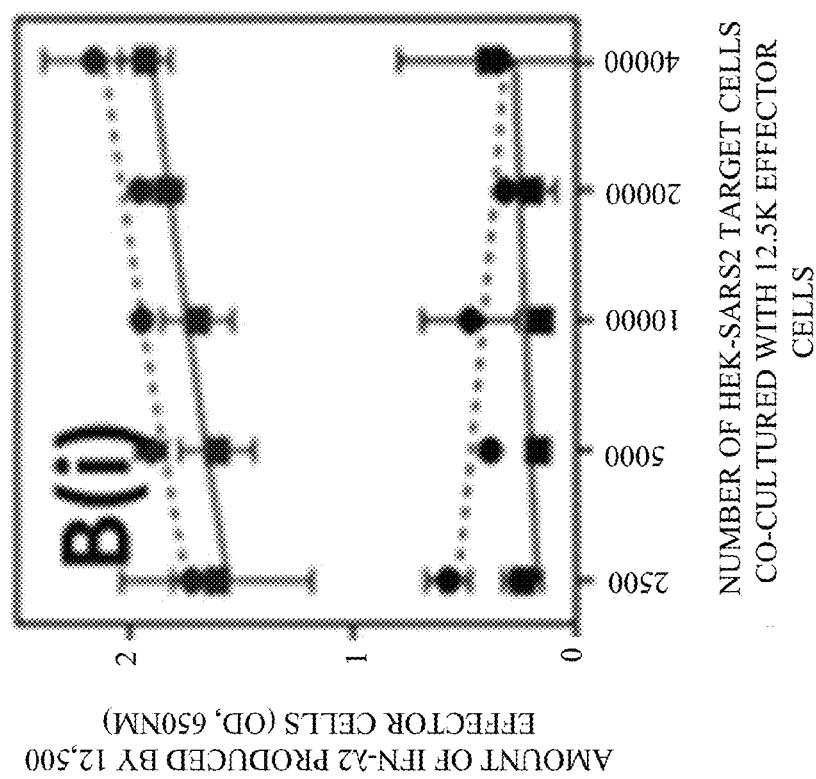
Figure 9D:
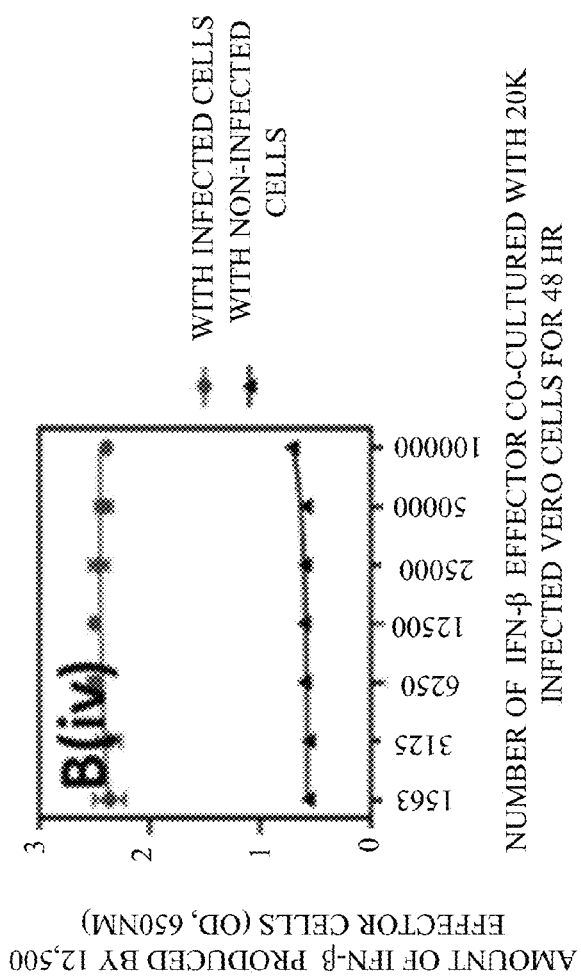
Figure 9C:
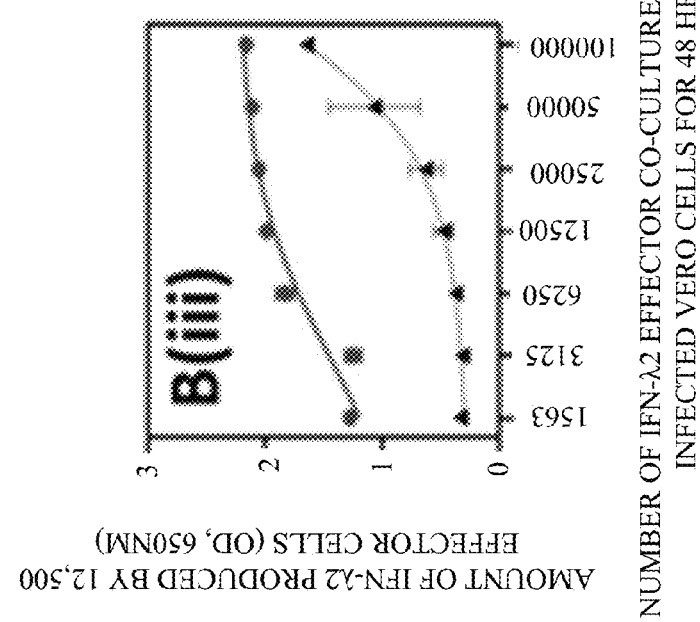

FIGS. 9A-9D illustrate plots characterizing genetically engineered effector cell function, in accordance with the present disclosure. FIGS. 9A-9D illustrate the expression of Type-I and Type-III IFNs in irradiated and non-irradiated effector cells is proportional to the number of target SARS-CoV-2-Sgp cells (e.g., artificial infected cells). FIGS. 9A and 9B show IFN-λ2 and IFN-β production when the effector cell is activated by pseudo-infected cells respectively and the effector cell production is proportional to the target cell count (data collected with effector cell=12,500, 24 hours; Solid lines=Irradiated cells at 20 G and Dotted lines=Non-irradiated cells). FIGS. 9C and 9D show for IFN-λ2 and IFN-β in-situ production respectively by the effector cell when stimulated by SARS-CoV-2-infected Vero-E6 cells, and effector proteins production is proportional to the number of effector cell count (data collected with Vero-E6 cells=20,000; MOI=0.05; 48 hours). IFN expression for all observations was measured using n=3, error bars indicate ±1 standard deviation (SD), and can also be considered as one half-width of a 68% confidence interval for the mean.

More particularly, FIGS. 9A-9B demonstrate the expression of Type-I IFNs (IFN-β1a) and Type-III IFNs (IFN-λ2) by the effector cells formed using T-cells respectively and compares it with the IFNs produced from the two T-cell types irradiated at 20 Gy. The effector protein (IFNs) expression was proportionate to target cell count and was observed at all effector cell to target cell (E:T) ratios. The expression was significantly elevated ($p<0.00001$ at all E:T) when stimulated by the target SARS-CoV-2-Sgp-cell compared to when stimulated by the non-engineered negative control cells. Similar results were observed when the two types of T-cell-based effector cells were irradiated with 20 Gy ($p<0.0006$ at all E:T). To validate the observations from effector cells formed using T-cells with genetically modified target cell, e.g., an artificial or pseudo-infected SARS-CoV-2-Sgp-cell, the target SARS-CoV-2-Sgp-cell was exchanged with the Vero-E6 host cells infected with competent SARS-CoV-2 virus (Isolate: Hong Kong/VM20001061/2020) in BSL3 containment facility. The results presented in FIGS. 9C-9D demonstrate the Type-I IFN (IFN-β1a) and Type-III IFN (IFN-λ2) expression by the respective Sgp-specific effector cell, which was significantly higher when compared the IFN expression from the Sgp-specific effector cell stimulated by uninfected Vero-E6 cells ($p<0.0002$ for IFN-β1a and $p<0.0099$ for IFN-λ2 at all E:T ratios). FIGS. 15A-15D depict similar observations from the different Sgp-specific effector cells upon engaging the genetically modified target cell, a pseudo-infected cell-based model of presenting SARS-CoV-1-specific Sgp (SARS-CoV-1-Sgp-cell).

FIGS. 10A-10D illustrate plots characterizing therapeutic activity of example genetically engineered effector cells, in accordance with the present disclosure. Various experiments were directed to assessing the effects of the Type-I IFNs (IFN-β1a) and Type-III IFNs (IFN-λ2) effector cells. To simulate the role of timing in infection, the relative protection offered by the two IFNs before and after the viral challenge was investigated, e.g., their prophylactic and therapeutic effects. Toward this goal, either i) Vero-E6-Luc2$^+$ host cells were pretreated with the supernatants from the respective effector cells (IFN-β1a or IFN-λ2) before infecting them with SARS-CoV-2, e.g., prophylaxis effect, or ii) co-cultured the two effectors cells with previously infected Vero-E6-Luc2$^+$ host cells, e.g., therapeutic effect. The protection offered by the two effector cells was determined by assessing the live host cells. Protective effects from the other effector cells (type-I IFN-α2b and type-III IFN-λ1) were also measured and are reported in FIGS. 16A-14D.

Figures 10A, 10B:
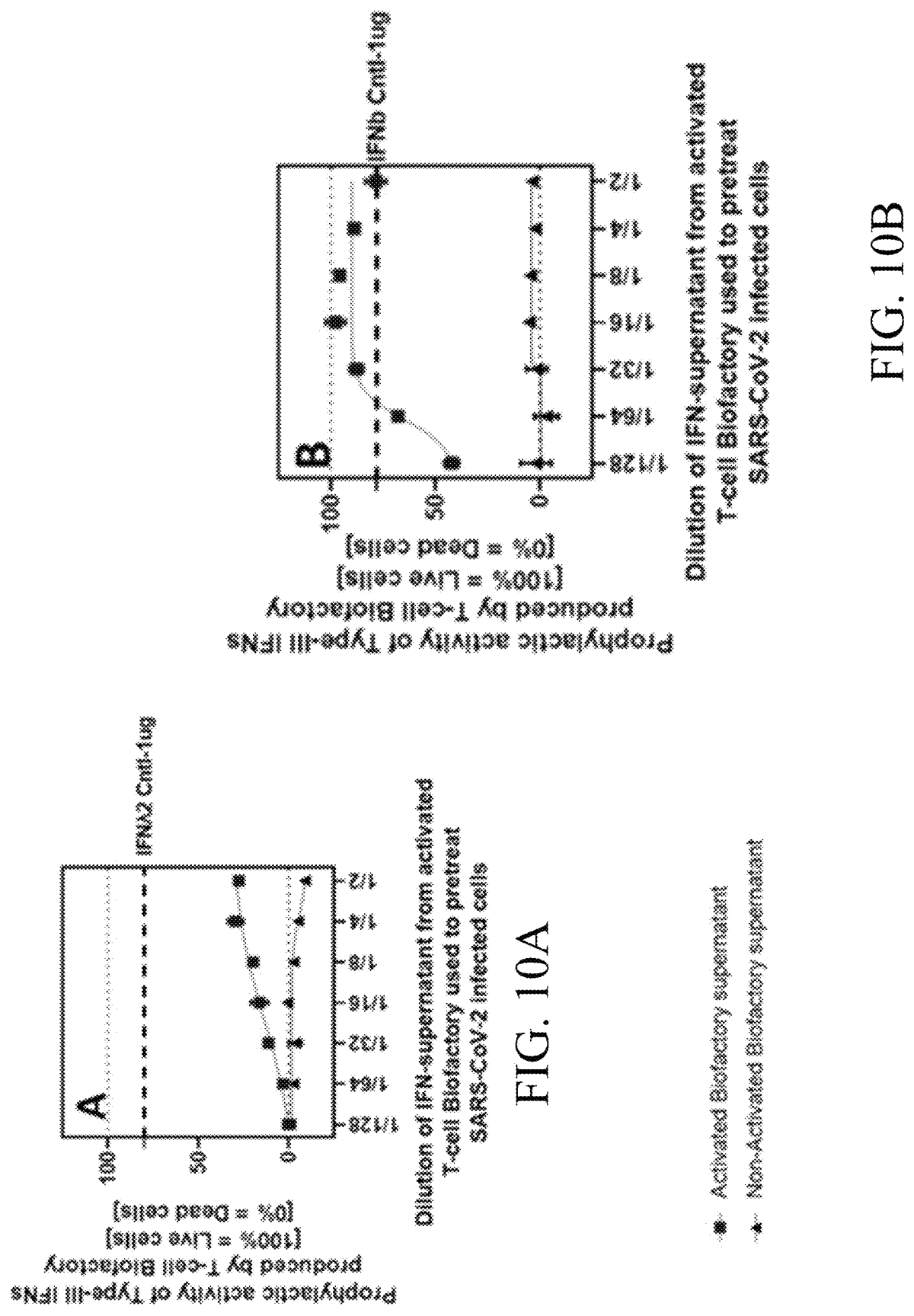
Figure 10C:
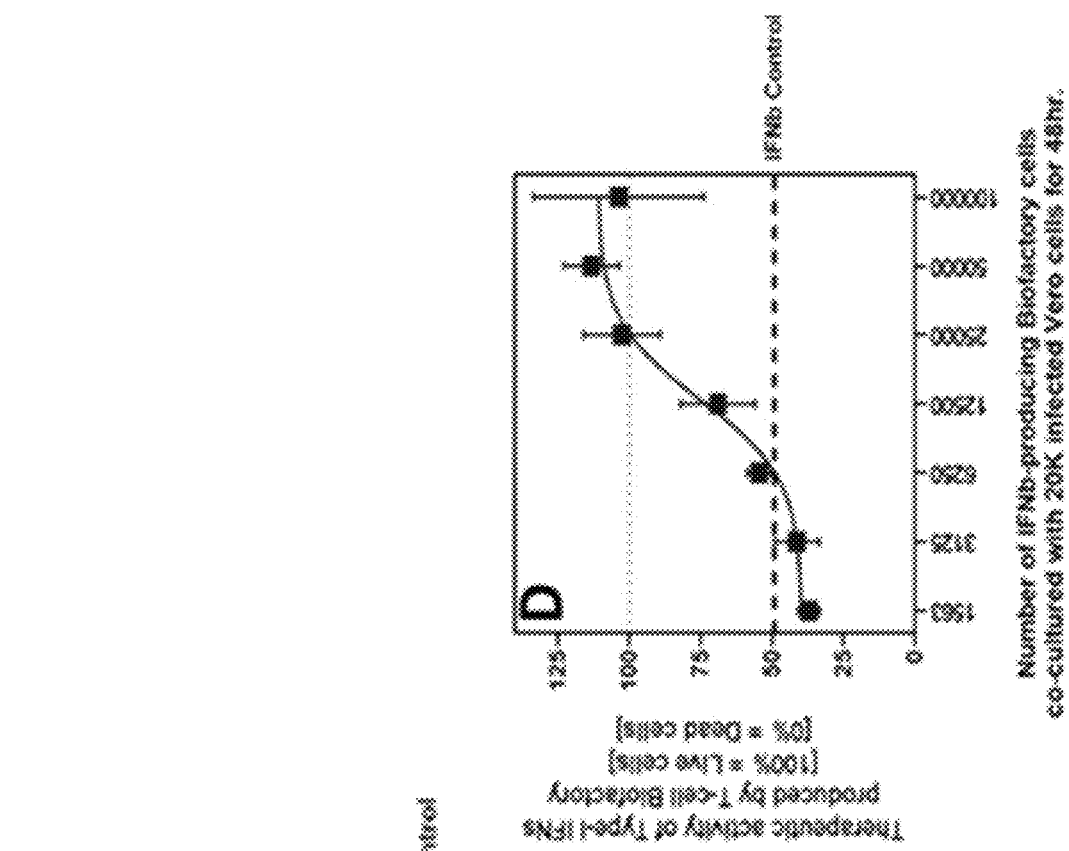
Figure 10D:
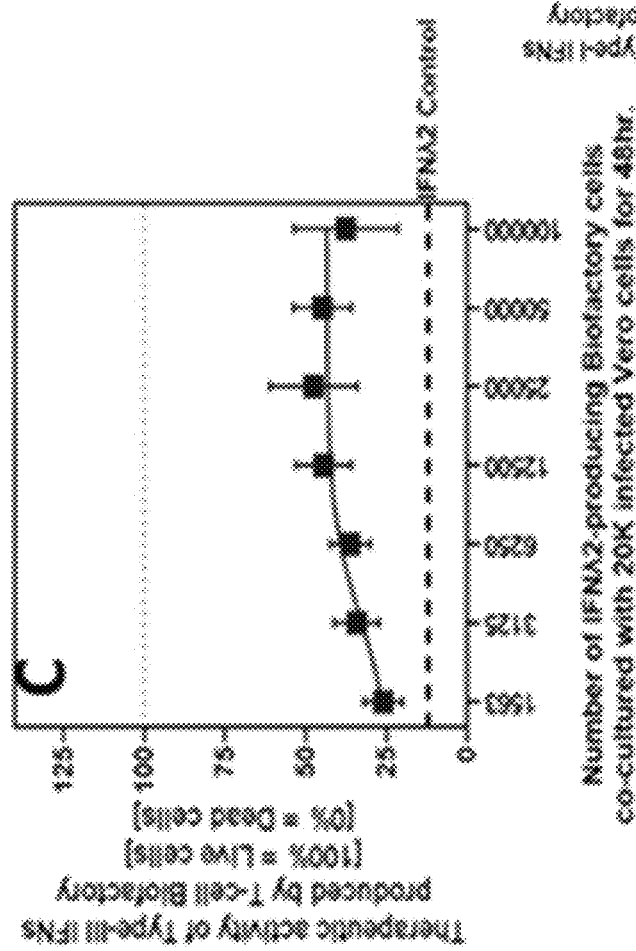

The IFN producing effector cell can be used as prophylaxis or therapeutic to protect the SARS-CoV-2 infected Vero-E6 cell population. The effect is proportional to the amount of Type-I and Type-III IFNs produced by the effector cell. Activity of the IFN-λ2-T-cell effector cell is shown by FIGS. 10A and 10C. Activity of the IFN-β-T-cell effector cell is shown by FIGS. 10B and 10D. Tge data was collected with Vero-E6 cells=20,000; MOI=0.05; 48 hr. 1 μg of recombinant human IFN was used as control in all experiments (dashed black line). Red dotted line=100% viability; Black dotted line=0% viability. All observations were measured using n=3, error bars indicate ±1 SD and can also be considered as one half-width of a 68% confidence interval for the mean.

Figure 8:
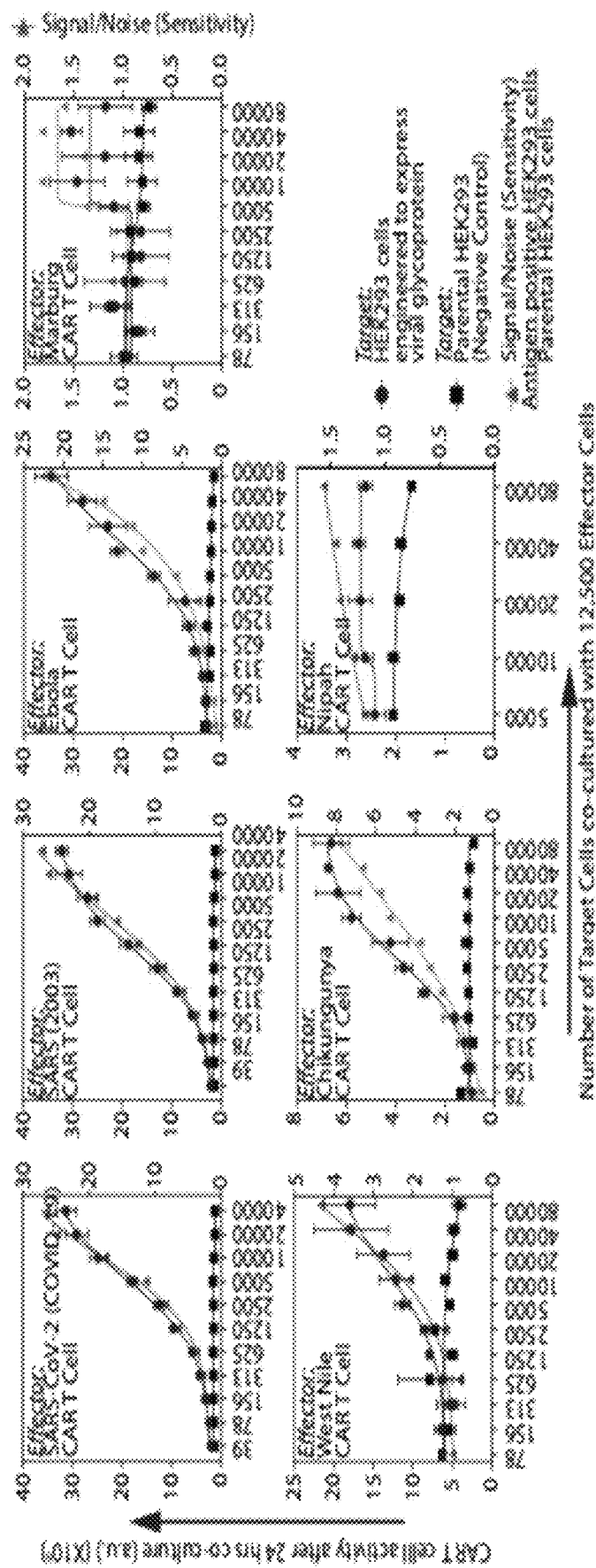
FIG. 8 illustrates plots characterizing genetically engineered effector cell function with specificity against different pathogens, in accordance with the present disclosure.

Data in FIGS. 10A-10B illustrate the prophylactic activity of Type-I IFNs (IFN-β1a) and Type-III IFNs (IFN-λ2) produced by respective activated T-cell based effector cells, when compared to the non-activated effector cells. Although Type-III IFNs show reduced protection of host cells (FIG. 10A), cell viability was significantly higher at all concentrations above 0.587 ng/mL, e.g., diluted less than 1/32 ($p<0.002$), compared to the negative control. Similarly, improved protection was observed by Type-I IFNs when present more than 0.009 ng/mL ($p<0.001$) (FIG. 10B), compared to the negative control. Results presented in FIGS. 8C-8D demonstrate the therapeutic activity of Type-I IFN (IFN-β1a) and Type-III IFN (IFN-λ2) T-cell-based effector cell when co-cultured with infected host cells. The protection offered by the two effector cells (or amount of IFNs) as a therapeutic for infected host cells was proportional to their number (see FIG. 10C for IFN-λ2; and FIG. 10D for IFN-β1a). This prophylactic and therapeutic activity of IFNs confirm that the SARS-CoV-2 virus is susceptible to IFN treatment and demonstrates the potency of the IFNs produced by the respective effector cell types in reducing viral replication.

Figure 11:
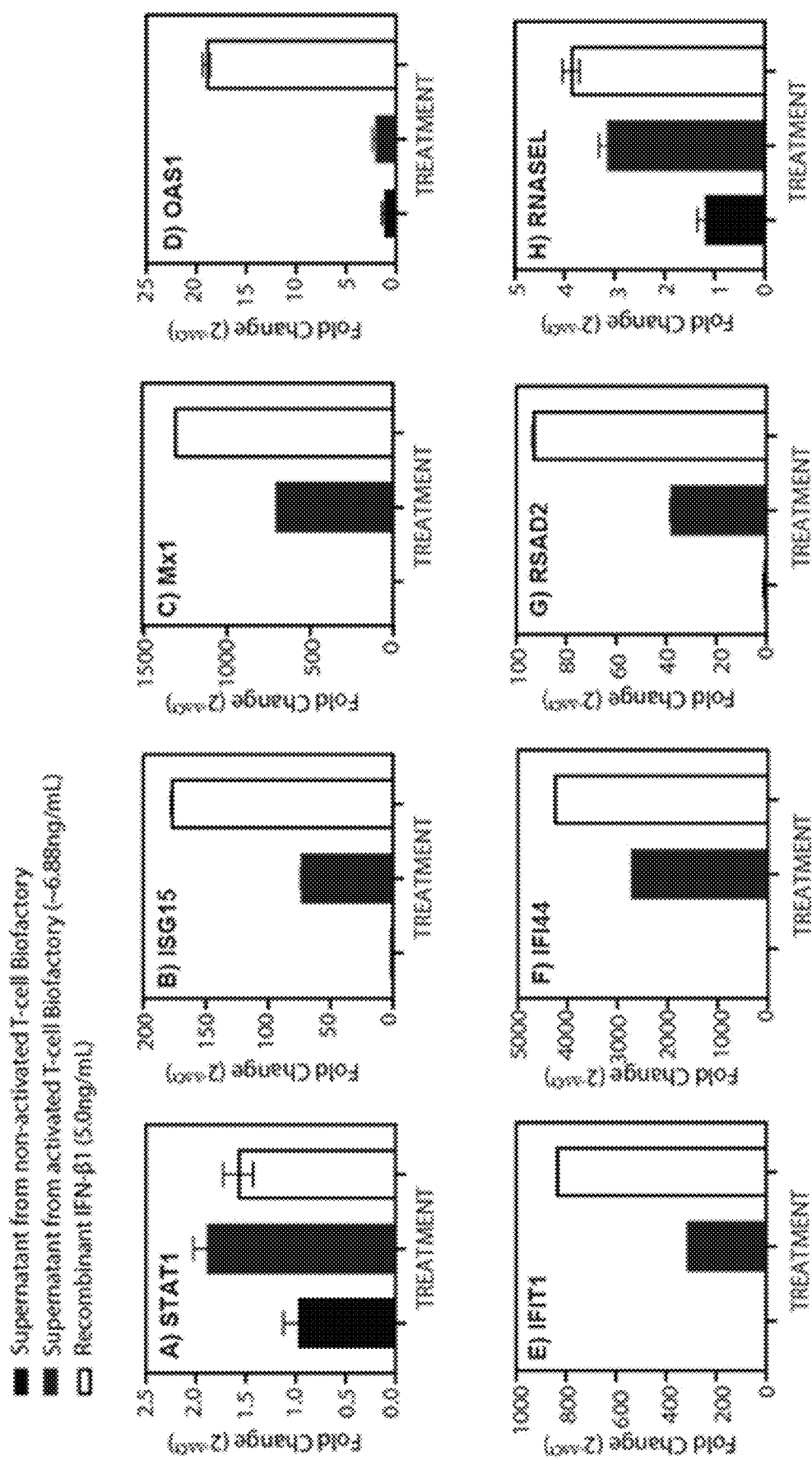
FIG. 11 illustrates plots characterizing IFN signaling of example genetically engineered effector cells, in accordance with the present disclosure.

FIG. 11 illustrates plots characterizing IFN signaling of example genetically engineered effector cells, in accordance with the present disclosure. FIG. 11 demonstrates the expression profiles of representative IFN-stimulated genes (ISGs) induced by IFN-β1a from the activated effector cells. Many ISGs control viral spread by directly targeting pathways and functions critical to the viral replication cycle. Expression of Mx1 can inhibit viral entry; ISG15, OAS-RNASEL and IFIT proteins are all reported as inhibitors of viral replication and translation; while upregulation of RSAD2 inhibits viral budding/egress. The induction of ISGs and their downstream production of antiviral effects in the treated host cells was assessed. Both Type-I and Type-III IFNs induced ISG transcription through the Janus Kinase-Signal Transducers and Activators of Transcription (JAK-STAT) signaling pathway, and their expression from the activated effector cells explains the antiviral effects of IFNs observed in FIGS. 10A-10D. The results demonstrate that transcription of most antiviral effector genes (or ISGs) was significantly upregulated in infected Vero-E6 cells treated with supernatants from the activated IFN-β1 producing effector cell, compared to the negative controls, e.g., infected cells treated with supernatants from the unstimulated IFN-β1 producing effector cell (FIG. 11). Similar expression profiles were observed when the supernatant from IFN-β1 producing effector cells were used to treat Calu-3 human epithelial cells (FIG. 17).

FIG. 11 shows the IFN signaling in Vero-E6 cells treated with type-I IFN-β1 from activated effector cells. Vero E6 cells were incubated with the indicated amounts of Type-I IFN supernatants from activated effector cells for 24 hours and then analyzed for expression of ISGs. Error bars represent standard error means (SEM) from three biological replicates.

FIGS. 12A-12B illustrate plots characterizing activation and growth of example genetically engineered effector cells, in accordance with the present disclosure. More particular, FIGS. 12A-12B show specificity of the VHH-72 effector to SARS-CoV-1 and SARS-CoV-2. FIG. 12A shows that the Nluc protein expression is proportional to the number of SARS-CoV-2-Sgp-cells or SARS-CoV-1-Sgp-cell target cells (effector cell=12,500, 24 hour). FIG. 12B shows the Nluc activity in the VHH-72 effector cell (50,000) increased with respect to the number of SARS-CoV-1 pseudovirus particles present in solution. Nluc expression for all observations was measured using n=4, error bars indicate ±1 SD, and can also be considered as one half-width of a 68% confidence interval for the mean.

FIGS. 13A-13D illustrate plots characterizing activation of example genetically engineered effector cells by SARS-CoV-2-infected cells, in accordance with the present disclosure. More particularly, FIGS. 13A-13D show IFN production in the Sgp-specific effector cells. FIGS. 13A and 13B respectively illustrate IFN-λ1 and IFN-α production when the effector cell is activated by pseudo-infected cells and its production is proportional to the target cell count (data collected with effector cell=12,500, 24 hours; Solid lines=Irradiated cells at 20 G and Dotted lines=Non-irradiated cells); while C) and D) show for IFN-λ1 and IFN-α in-situ production by the effector cell when stimulated by SARS-CoV-2-infected Vero-E6 cells, and production is proportional to the number of effector cell count (data collected with Vero-E6 cells=20,000; MOI=0.05; 48 hours). IFN expression for all observations was measured using n=3, error bars indicate ±1 SD, and can also be considered as one half-width of a 68% confidence interval for the mean.

FIGS. 14A-14B illustrate plot characterizing activation and growth curves of example genetically engineered effector cells, in accordance with the present disclosure. FIGS. 14A-14B more particularly show an activation and growth curve of the irradiated Sgp-specific effector cells. FIG. 14A shows the Nluc protein expression in the effector cell is proportional to the number of target cells. Nluc activity for all observations was measured using n=4, error bars indicate ±1 SD and can also be considered as one half-width of a 68% confidence interval for that mean (blue line=SARS-CoV-2-Sgp-cell targets; black line=non-engineered targets; solid line=Irradiated effector cell; dotted line=Non-irradiated effector cell; effector cell=12,500). FIG. 14B shows the growth kinetics of the irradiated effector cell, at different radiation doses, versus the non-irradiated effector cell.

FIGS. 15A-15D illustrate plots characterizing prophylactic and therapeutic activating of example genetically engineered effector cells, in accordance with the present disclosure. More particularly, FIGS. 15A-15D illustrated VHH-72 effector cell activation by target SARS-CoV-1-Sgp-cell. Expression of Type-I and T-III Interferons (IFNs) in the VHH-72 effector cell is proportional to the effector cell count, IFN-λ2 (as shown by FIG. 15A), IFN-λ1 (as shown by FIG. 15B), IFN-α (as shown by FIG. 15C), and IFN-β (as shown by FIG. 15D) (data collected at 24 hours). IFN expression for all observations was measured using n=3, error bars indicate ±1 SD and can also be considered as one half-width of a 68% confidence interval for the mean.

FIGS. 16A-16D illustrate plot characterizing activation of example genetically engineered effector cells, in accordance with the present disclosure. Prophylactic and therapeutic activity of IFNs produced by the Sgp-specific effector cell are illustrated by FIGS. 16A-16D. The viability of SARS-CoV-2 infected Vero-E6 cells is proportional to the amount of Type-I and Type-III IFNs produced by the effector cell. FIGS. 16A and 16C show activity of the IFN-λ1-effector cell, and FIGS. 16B and 16D show activity of the IFN-α-effector cell (data collected with Vero-E6 cells=20,000; MOI=0.05; 48 hour). 1 μg of recombinant human IFN was used as a control in all experiments (dashed black line). Red dotted line=100% viability; black dotted line=0% viability. All observations were measured using n=3, error bars indicate ±1 SD and can also be considered as one half-width of a 68% confidence interval for that mean.

FIG. 17 illustrates plots characterizing IFN signaling of example genetically engineered effector cells in response to SARS-CoV-2-infected cells, in accordance with the present disclosure. More particularly, FIG. 17 shows IFN signaling in Calu-3 cells treated with Type-I IFNs from activated effector cells. Calu-3 cells were incubated with the indicated amounts of Type-I IFN supernatants from activated effector cells for 24 hours and then analyzed for expression of ISGs. Error bars represent SEM from three biological replicates.

Synthesis and Experimental Information for Effector Cell Specific to Sgp (1) Materials and reagents. Engineered Jurkat E6-1 (ATCC, Cat #TIB-152) cell lines were maintained in complete RPMI media (RPMI1640 [Corning, Cat #10-040-CV], 10% were heat-inactivated fetal bovine serum or FBS [Sigma-Aldrich, Cat #F2442-500ML] and 1× Penicillin-Streptomycin solution [Corning, Cat #30-002-Cl]). Parental and Engineered Vero-E6 cells (ATCC, Cat #CRL-1586) were cultured in complete EMEM (EMEM growth media [Corning, Cat #10-009-CV] supplemented with 10% heat-inactivated FBS and 1× Penicillin-Streptomycin solution).

Parental and Engineered HEK293T/17 cells (ATCC, Cat #CRL-11268) were cultured in complete DMEM (DMEM growth media [Corning, Cat #10-013-CV] supplemented with 10% FBS and 1× Penicillin-Streptomycin solution). All cells were expanded, and liquid nitrogen stocks were maintained using freezing media (50% FBS, 40% growth media and 10% Dimethyl sulfoxide). Plasmids encoding different genetic payloads (transfer plasmids) were designed in SnapGene software (GSL Biotech LLC) and sub-cloned into lentivirus vector plasmid (System Biosciences, Cat #CD510B-1) or PiggyBac Transposon vector plasmid (System Biosciences, Cat #PB510B-1). Plasmids encoding 2nd generation packaging plasmids (psPAX2—Cat #12260, pMD2.G—Cat #12259) were obtained from Addgene. pAdvantage was obtained from Promega (Cat #E1711). PiggyBac Transposase sequence was provided by the Johns Hopkins University School of Medicine [Doherty, J. E. et al. Hyperactive piggyBac gene transfer in human cells and in vivo. Human Gene Therapy 23, 311-320 (2012).] An insert for "EF1alpha promoter—i7pB transgene—bGH poly(A) signal" was chemically synthesized and assembled using overlapping PCR products into pUC19 (GenBank: L09137, New England Biolabs, #N3041). All plasmid preparation services (chemical synthesis of DNA insert sequences, subcloning into respective vector backbones, and the amplification) were obtained from Epoch Life Science, Inc. (Missouri City, Tex.). For lentivirus production, Transporter 5™ reagent (Polysciences, Inc, Cat #26008-5) was used to transfect parental HEK293T/17 cells. The collected lentivirus was transduced into Jurkat cells using Polybrene (Abm®, Cat #G062). TransIT®-2020 transfection reagent (Mirus #MIR5400) was used to transfect PiggyBac Transposon system plasmids into parental HEK293T/17 cells to engineer stable antigen-presenting cells (APCs) or pseudo-infected host target cells. Puromycin dihydrochloride (ThermoFisher Scientific, Cat #A1113803) was used for selecting stable cells. Phosphate buffered saline (PBS) without $Ca^{+2}$ and $Mg^{+2}$ (Corning, Cat #21-040-CV) was used to wash cells. The SARS-CoV-2 virus culture (BEI Resources, NIH; Hong Kong/VM20001061/2020 [Cat #NR-52282]) was provided SRI International. Viability of Vero-E6-Luc2$^+$ cells was assessed using either CellTiter-Glo™ Luminescent Cell Viability Assay Kit (Promega, Cat #PR-G7570) or One-Glo™ assay (Promega, Cat #E6110) for Luc2 activity. HEK-Blue IFN-α/β cells (InvivoGen, Cat #hkb-ifnab) or HEK-Blue IFN-λ cells (InvivoGen, Cat #hkb-ifnl) were used to quantify the amount of IFNs produced by the T-cell Biofactory, following manufacturer's instructions. Recombinant human interferon proteins from R&D systems (IFN-β [Cat #8499-IF-010/CF], [Cat #1598-IL-025/CF], IFN-λ2 [Cat #8417-IL-025/CF]) and IFN-α2b from Invivogen [Cat #rcyc-hifna2b] were used as controls. For RNA preparations, Direct-zol RNA Mini-Prep Kit (Zymo Research, Cat #11-331) and reverse transcription by SuperScript III RT (Invitrogen, Cat #18080044) were used following the manufacturers' instructions. TaqMan Universal PCR Master Mix (Applied Biosystems, Cat #4305719) was used for gene expression qPCR.

(2) Lentivirus production. Lentivirus particles were prepared by packaging the transfer plasmid using $2^{nd}$ generation lentivirus system as detailed previously by Radhakrishnan H, et al. (2020); Lentivirus Manufacturing Process for Primary T-cell Biofactory Production. Advanced Biosystems, 1900288, which is hereby incorporated herein in its entirety for its teaching.

(3) Generation of the Sgp-specific effector cell (T-cell Biofactory). The Jurkat E6-1 suspension cell line was engineered with lentivirus particles carrying the genetic payload (FIG. 2) with a VHH-72 (PDB: 6WAQ) CAR or sensor domain, as detailed previously by Radhakrishnan H, et al. (2020), entitled "Lentivirus Manufacturing Process for Primary T-cell Biofactory Production. Advanced Biosystems", 1900288, which is hereby incorporated herein in its entirety for its teaching. The cells were treated with lentivirus in the presence of 8 μg/mL Polybrene. After 48 hours, the engineered effector cells were placed in selection using 0.5 μg/mL of Puromycin dihydrochloride. The unmodified parental cell line was also placed under selection as a positive control for cell killing by Puromycin. Following selection, cells were expanded as required for different assays and frozen using freezing media. For irradiation, the Sgp-specific effector cell was exposed to 20 Gy (or as indicated) using a 137Cs γ-emitting irradiator, Mark I-68A (JL Shepherd and Associates) at a dose rate of 222 mGy/min. The control cells were treated similarly except for the irradiation.

(4) Generation of genetically modified target cells (SARS-CoV-2-Sgp-cell and Vero-E6-Luc2$^+$). Parental HEK293T/17 were engineered to stably express Sgp (SARS-CoV-2-Sgp-cell) while parental Vero-E6 cells were engineered to express intracellular Luc2 reporter protein (Vero-E6-Luc2$^+$), using the PiggyBac Transposon system as previously described by Repellin C E, et al. (2020); Engineered Ovarian Cancer Cell Lines for Validation of CAR T-cell Function. Advanced Biosystems, 1900224. The plasmids were designed with the PiggyBac transposon vector backbone for cell surface expression of Sgp from SARS-CoV-2 (GenBank: QHD43416.1) and for expression of Luc2 Reporter transgene (GenBank: AY738222.1) respectively. A monolayer of HEK293T/17 or Vero-E6 cells were transfected with the transposon plasmid (carrying the gene of interest) and transposase plasmid, in a ratio of 2.5:1, respectively, using TransIT®-2020 transfection reagent. After 48 hours of transfection, the transfected cells were placed under selection using 0.5 μg/mL (or 3 ug/mL for Vero-E6-Luc2$^+$) of Puromycin dihydrochloride. The unmodified parental cell lines were placed under selection as a positive control for cell killing by the antibiotics. The generated stable cell lines were expanded as required for different assays.

(5) Co-culture of Sgp-specific effector cell (T-cell Biofactory) with target SARS-CoV-2-Sgp-cell (genetically modified target cell). Target SARS-CoV-2-Sgp-cell or non-engineered cells were co-cultured at different effector cell to target cell (E:T) ratios with the Sgp-specific effector cell in 100 μL of complete RPMI media in a single well of a 96-well plate. After the specified amount of time in co-culture, the original amount of IFNs produced by the effector cell was assessed using the HEK-Blue IFN-α/β or IFN-λ reporter assays, following the manufacturer's protocol. Similar co-culture procedures were used when testing the irradiated Sgp-specific effector cells.

(6) Determining the prophylactic effect of IFNs produced by the Sgp-specific effector cells. $2\times10^5$ of target SARS-CoV-2-Sgp-cell or non-engineered cells were co-cultured with $1\times10^6$ of the Sgp-specific effector cells (effector cell to target cell ratio, E:T=5:1) in 0.5 mL of complete RPMI media in a single well of a 24-well plate. After the specified amount of time in co-culture, supernatants with IFNs were collected and serially diluted in complete EMEM media. 100 μL of serially diluted IFN-supernatants (2-fold) was then used to pre-treat a monolayer of Vero-E6-Luc2$^+$ cells for 24 hours (20,000 cells/well, triplicates) in a 96-well plate; recombinant human IFNs (1 μg/mL) were included as controls. The pre-treated cells were then infected with SARS-CoV-2 virus culture at a multiplicity of infection (MOI) of 0.05 for 48 hours. Cell viability was determined using CellTiter-Glo™ Luminescent Cell Viability Assay Kit following the manufacturer's instructions. The enzyme substrate (Nluc substrate or Luc2 substrate) was diluted in the cell lysis buffer provided with the Nano-Glo® or One-Glo® assay and added to the co-cultures in a 96-well plate for assessing enzyme (Nluc or Luc2) activity. Following a brief incubation period (3 minutes for Nluc or 10 minutes for Luc2), bioluminescence was read on a microplate reader (Perkin Elmer, EnVision™ Multilabel Plate Reader Model: 2104-0010A). The original amount of IFNs produced by each effector cell was assessed using the HEK-Blue IFN-α/β or IFN-λ reporter assays as described below. ATP activity was normalized, where 100%=No IFN or virus treatment used and 0%=only virus infection.

(7) Determining the therapeutic effect of IFNs produced by the Sgp-specific effector cell. A monolayer of Vero-E6-Luc2$^+$ (20,000/well in a 96-well plate) were infected with SARS-CoV-2 virus culture at an MOI of 0.05 and incubated for 2 hours to allow virus attachment. After 2 hours, the virus inoculum was removed, and 150 μL of serially diluted IFN-producing effector cell (2-fold) was immediately added to the wells (triplicates). Recombinant human IFNs (1 μg/mL) and Non-infected Vero-E6-Luc2$^+$ cells were used as controls. After 48 hours of co-culture, 50 μL of supernatant was removed from each well to quantify the amount of IFNs produced by the effector cell at each E:T ratio, using the HEK-Blue IFN-α/β or IFN-λ reporter assays. Then, Vero-E6-Luc2$^+$ cell viability was determined by assessing Luc2 activity using the One-Glo® assay kit, following the manufacturer's instructions. The Luc2 enzyme substrate was diluted in the cell lysis buffer provided and added to the cells in 96-well plate for assessing Luc2 enzyme activity. Following a 10-minute incubation, bioluminescence was read on a microplate reader. Luc2 activity was normalized, where 100%=No IFN or virus treatment used and 0%=only virus infection.

(8) HEK-Blue IFN-α/β and IFN-λ reporter assays. Following the manufacturer's instructions, 150 μl of growth media containing 50,000 HEK-Blue IFN-α/β and HEK-Blue IFN-λ reporter cells were mixed with 50 μL of supernatant from the activated IFN-producing effector cell and plated in a single well of a 96-well plate. Serial dilutions of Type-I or Type-III IFNs in complete DMEM were added in parallel to generate a standard curve. After 24 hours of incubation, 20 μL of HEK-Blue IFN-α/β (or HEK-Blue IFN-2) supernatants were added to 180 μL of Quanti-blue substrate (InvivoGen) and incubated at 37° C. for 2 hours. Absorbance was measured at 650 nm using an Envision microplate reader (Perkin-Elmer). The standard curves were used to estimate the IFN concentrations produced by the Sgp-specific effector cell.

(9) Quantification of IFN-stimulated gene (ISG) mRNA expression. IFN-β1a supernatants from stimulated effector cell (diluted at ¼ dilution or ~6.88 ng/mL) were used to treat a monolayer of 2×10$^5$ Vero-E6 (or Calu-3) cells (in triplicate) for 24 hr (5 ng/mL of recombinant IFN-β1a was used as control). 300 uL of TRIzol was used to lyse cells and then RNA purifications were performed using Direct-zol RNA Miniprep kit following manufacturer's instructions. Purified RNA was reverse transcribed into cDNA using the SuperScript™ III Reverse Transcriptase. The cDNAs were analyzed by qPCR using TaqMan Universal PCR Master Mix and TaqMan gene expression assays. The following TaqMan primer/probe sets were used to assess type-I IFN signaling: GAPDH (Hs02786624_g1), 18S (Hs99999901_s1), ACTB (Hs03023880_g1) IFIT1 (Hs03027069_s1), IFI44 (Hs00951348_m1), STAT1 (Hs00234829_m1), ISG15 (Hs01921425_s1), OAS1 (Hs05048921_s1), RNASEL (Hs05030865_s1), RSAD2 (Hs04967697_s1), and MX1 (Hs00895608_m1). All qPCR was performed in 384-well plates and run on a ViiA7 real time PCR system (Cat #4453545). ISG expression was calculated using the ΔΔCT method[43] by normalizing the threshold cycle (Ct) values to reference genes (GAPDH, 18S and ACTB), and expressions are represented as fold changes over untreated cell samples. Error bars represent standard error means (SEM) from the three biological replicates.

(10) Experimental designs and statistical analysis. The experimental design for each panel in the figures is described below. GraphPad Prism 9.2.0 (GraphPad Software, Inc) was used to conduct all statistical analyses.

(i) FIG. 9A and FIG. 9B are directed to IFN production by the irradiated and non-irradiated effector cells when activated by pseudo-infected target cells. The IFN production in the Sgp-specific effector cells when stimulated by the target (SARS-CoV-2-Sgp-cell) or non-target (non-engineered) cells was fitted using the equation Y=a+b*X; where Y is the IFN amount produced, X is the $\log_{10}$ (target cell count), a is the Y-intercept and b is the slope of the fitted curve.

(ii) FIG. 9C and FIG. 9D are directed to IFN production by the effector cell when activated by virally infected target cells. The IFN production in the Sgp-specific effector cell when stimulated by the infected target or non-infected target cells was fitted using the using a four-parameter logistic model, IFN=IFN$_{min}$+{[[IFN$_{max}$−IFN$_{min}$}/[[1+10^[b*($\log_{10}$[Effector-Cell$_{50}$]−X)]}; where X is the $\log_{10}$ of the effector cell (T-cell Biofactory) count, IFN$_{max}$ is an estimated parameter defining a upper asymptote for IFN production, IFN$_{min}$ is an estimated parameter defining a lower asymptote for IFN production, b is a "Hill" parameter defining the slope at the inflection point of the fitted curve, and Effector-Cell$_{50}$ is an estimated parameter representing the X value corresponding to (IFN$_{max}$−IFN$_{min}$)/2.

(iii) FIG. 10A and FIG. 10B are directed to demonstrating the prophylactic activity of IFNs produced by the effector cell. Comparison of all data points was calculated by the false discovery rate (FDR) multiple comparison approach, using the two-stage step-up procedure of Benjamini, Krieger, and Yekutieli with FDR=1%. There was no adjustment for multiple comparisons. The error bars extend 1 SD above and below the mean and can also be considered as one half-width of an 68% confidence interval for that mean. The ATP activity was normalized and fitted using a four-parameter logistic model ATP=ATP$_{min}$+{[[ATP$_{max}$−ATP$_{min}$}/[[1+10^[b*($\log_{10}$[Dilution$_{50}$]−X)]}; where X is the $\log_{10}$ of the IFN-dilution, ATP$_{max}$ is an estimated parameter defining a upper asymptote for ATP activity, ATP$_{min}$ is an estimated parameter defining a lower asymptote for ATP activity, b is a "Hill" parameter defining the slope at the inflection point of the fitted curve, and Dilution$_{50}$ is an estimated parameter representing the X value corresponding (ATP$_{max}$−ATP$_{min}$)/2.

(iv) FIG. 10C and FIG. 10D are directed to demonstrating the therapeutic activity of IFNs produced by the effector cells. Comparison of all data points was calculated by the false discovery rate (FDR) multiple comparison approach, using the two-stage step-up procedure of Benjamini, Krieger, and Yekutieli with FDR=1%. There was no adjustment for multiple comparisons. The error bars extend 1 SD above and below the mean and can also be considered as one half-width of a 68% confidence interval for that mean. The Luc2 activity when the effector cell was co-cultured with infected or non-infected Vero-E6-Luc2+ target cells was fitted using a four-parameter logistic model, Luc2=Luc2min+{[[Luc2max−Luc2min]/[[1+10^[b*(log 10[η(E:T)$_{50}$]−X)]}; where X is the log 10 of the number of Effector-Cells (T-cell Biofactory), Luc2max is an estimated parameter defining an upper asymptote for the Luc2 activity, Luc2min is an estimated parameter defining a lower asymptote for the Luc2 activity, b is a "Hill" parameter defining the slope at the inflection point of the fitted curve. A parameter for defining the antiviral efficiency of the produced IFNs, η(E:T)$_{50}$, was determined as the E:T at which Luc2 activity in infected or non-infected target cells was 50% of the difference between the maximum and minimum values of their respective normalized Luc2 activities, when co-cultured with the effector cell, e.g., the η(E:T)$_{50}$ is an estimated E:T value corresponding to (Luc2max−Luc2min)/2.

(v) FIG. 11 shows IFN signaling in Vero-E6 cells treated with type-I IFNs from activated effector cells. Differential gene expression was calculated using the ΔΔCT method by normalizing the sample Ct values to mean Ct values of 3 reference genes, and expressions are represented as fold changes over untreated cell samples. Error bars represent SEM from the three biological replicates.

Figure 12A:
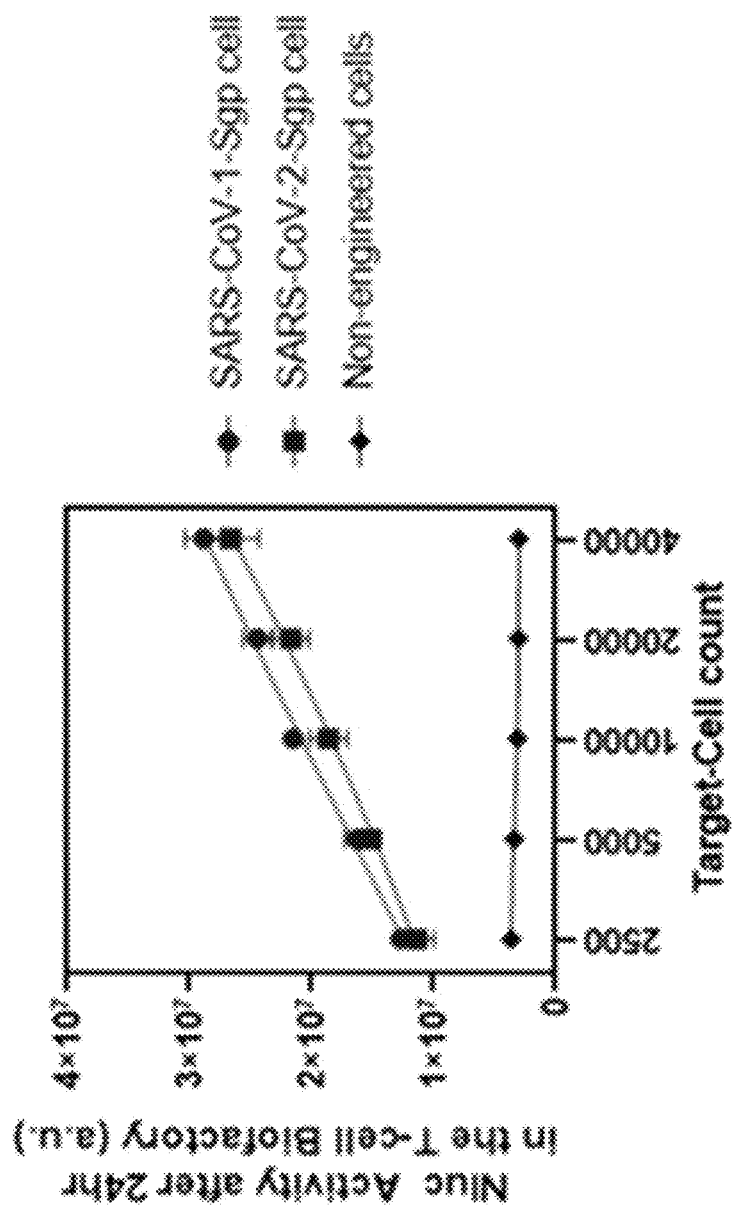
FIGS. 12A-12B illustrate plots characterizing activation and growth of example genetically engineered effector cells, in accordance with the present disclosure.
Figure 12B:
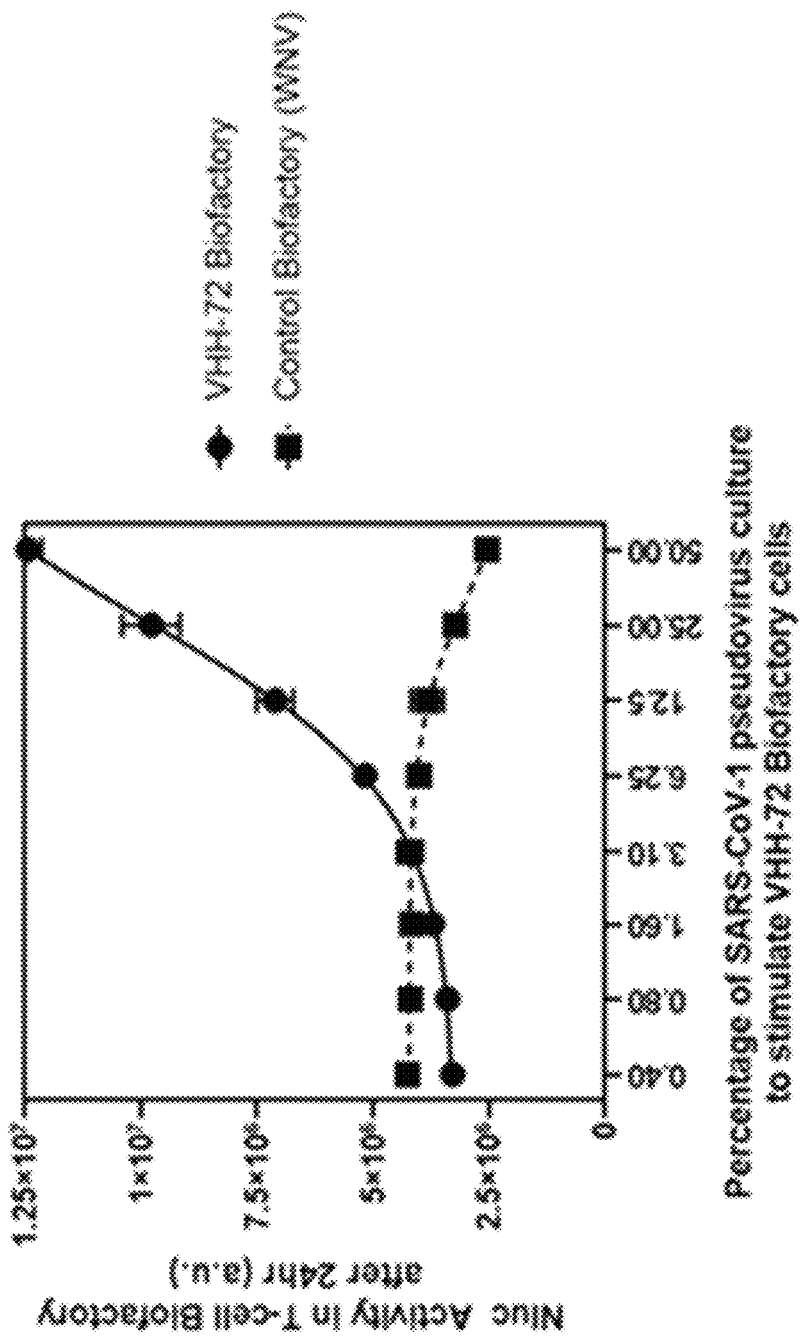

(vi) FIGS. 12A-12B show Sgp-specific effector cell specificity to SARS-CoV-2 and SARS-CoV-1 infections. The Nluc reporter activity in the Sgp-specific effector cell when stimulated by genetically modified target cells (SARS-CoV-2-Sgp-cell and SARS-CoV-1-Sgp-cell) or non-target (non-engineered) cells was fitted using a four-parameter logistic model Nluc=Nluc$_{min}$+{[[Nluc$_{max}$−Nluc$_{min}$]/[[1+10^[b*(log$_{10}$[Target$_{50}$]−X)]}; where X is the log$_{10}$ of the target cell count, Nluc$_{max}$ is an estimated parameter defining a upper asymptote for Nluc activity, Nluc$_{min}$ is an estimated parameter defining a lower asymptote for Nluc activity, b is a "Hill" parameter defining the slope at the inflection point of the fitted curve, and Target$_{50}$ is an estimated parameter representing the X value corresponding (Nluc$_{max}$−Nluc$_{min}$)/2.

Figures 13A, 13B:
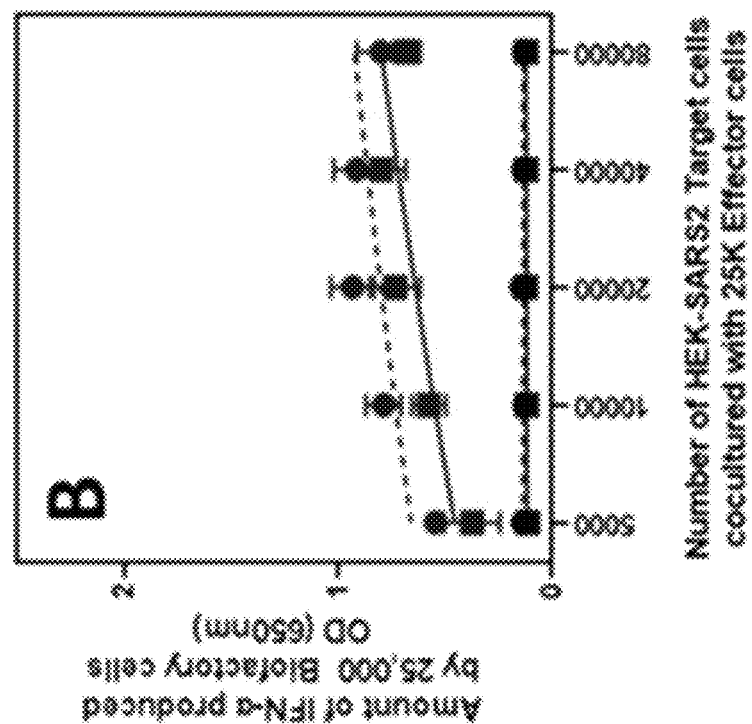
FIGS. 13A-13D illustrate plots characterizing activation of example genetically engineered effector cells by SARS-CoV-2-infected cells, in accordance with the present disclosure.
Figures 14A, 14B:
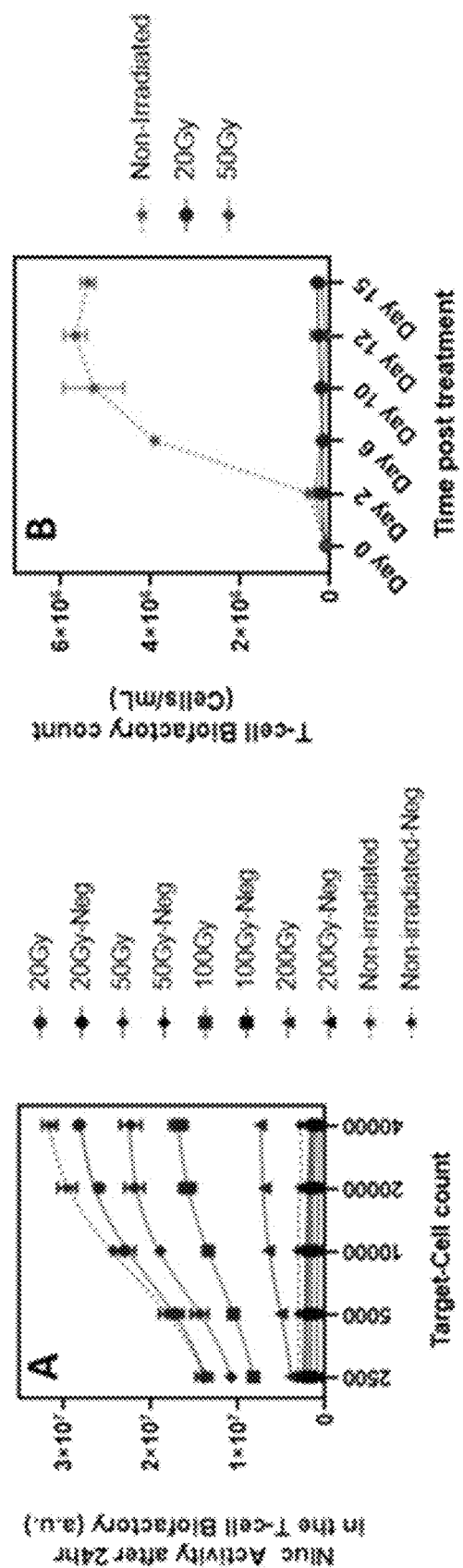
FIGS. 14A-14B illustrate plots characterizing activation and growth curves of example genetically engineered effector cells, in accordance with the present disclosure.
Figures 15A, 15B:
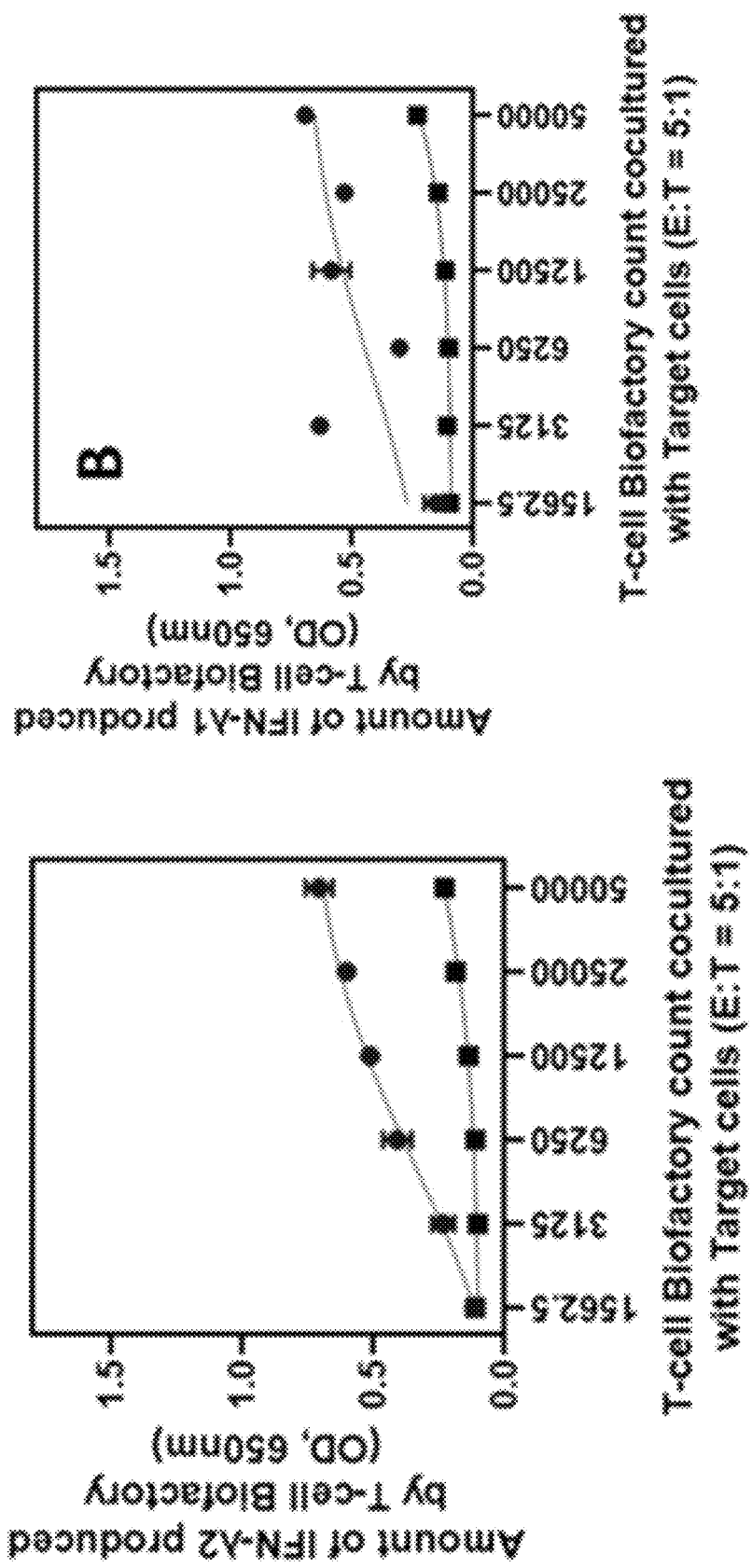
FIGS. 15A-15D illustrate plots characterizing prophylactic and therapeutic activating of example genetically engineered effector cells, in accordance with the present disclosure.
Figure 15D:
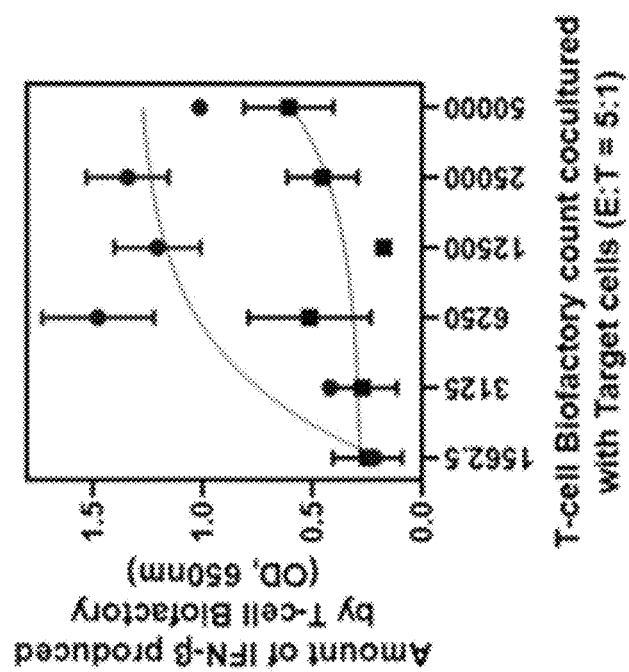
Figure 15C:
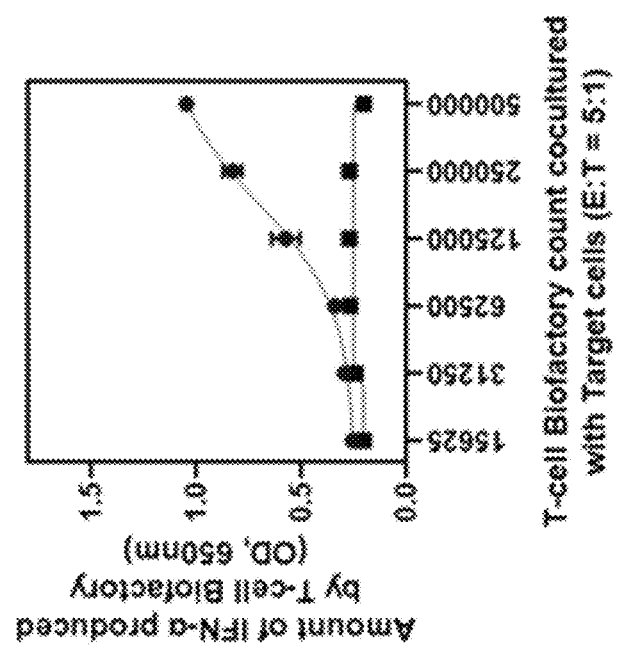

(vii) FIG. 13A and FIG. 13B show IFN production by the irradiated and non-irradiated effector cells when activated by genetically modified target cell, e.g., pseudo-infected target cells. The IFN production in the Sgp-specific effector cell when stimulated by the target (SARS-CoV-2-Sgp-cell) or non-target (non-engineered) cells was fitted using the equation Y=a+b*X; where Y is the IFN amount produced, X is the Log$_{10}$ (target cell count), a is the Y-intercept and b is the slope of the fitted curve.

Figures 13C, 13D:
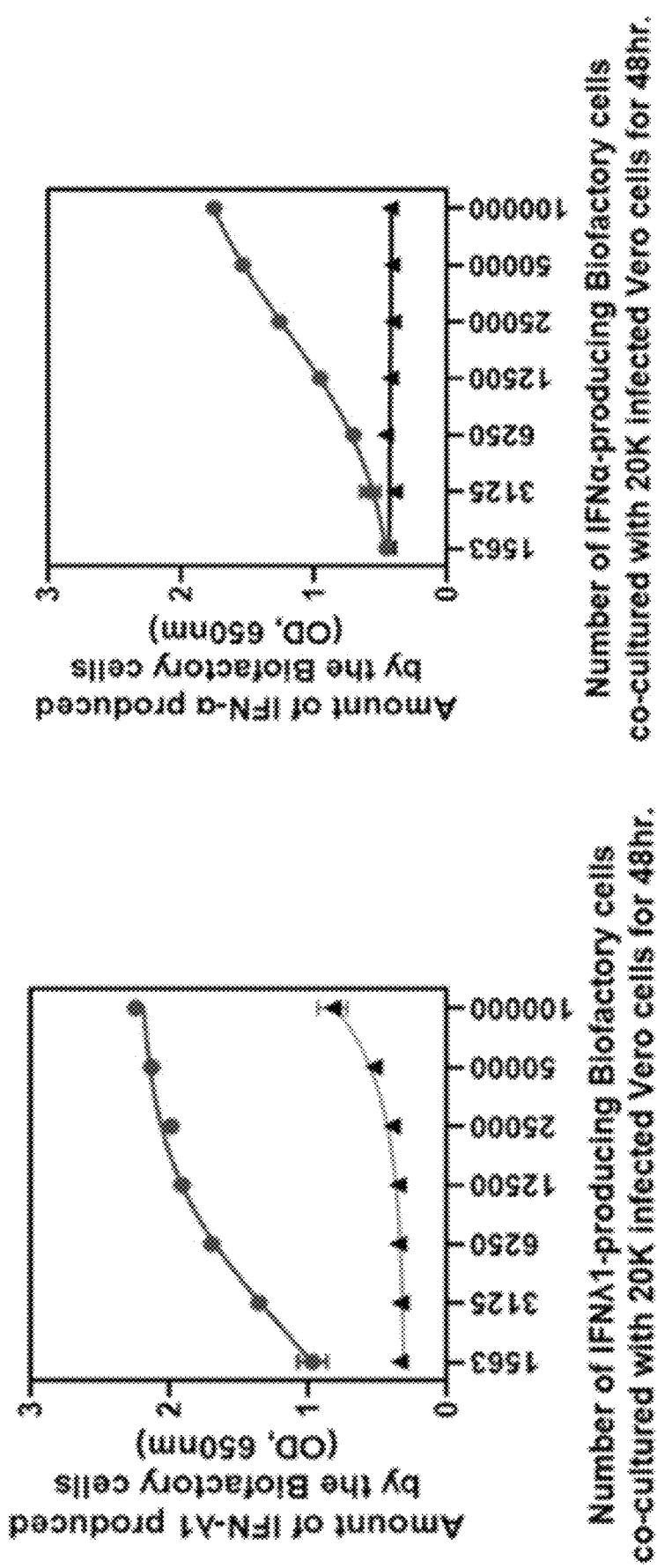

(viii) FIG. 13C and FIG. 13D show IFN production by the effector cell when activated by virally infected target cells. The IFN production in the Sgp-specific effector cell when stimulated by the infected target or non-infected target cells was fitted using the using a four-parameter logistic model, IFN=IFN$_{min}$+{[[IFN$_{max}$−IFN$_{min}$]/[[1+10^[b*(log$_{10}$[effector cell$_{50}$]−X)]}; where X is the log$_{10}$ of the effector cell (T-cell Biofactory) count, IFN$_{max}$ is an estimated parameter defining a upper asymptote for IFN production, IFN$_{min}$ is an estimated parameter defining a lower asymptote for IFN production, b is a "Hill" parameter defining the slope at the inflection point of the fitted curve, and effector cell$_{50}$ is an estimated parameter representing the X value corresponding to (IFN$_{max}$−IFN$_{min}$)/2.

(ix) FIG. 14A shows Nluc activity in irradiated effector cell is proportional to the number of target cell. The Nluc activity in the irradiated or non-irradiated effector cells stimulated by the target (SARS-CoV-2-Sgp-cell) or non-target (non-engineered) cells was fitted using a four-parameter logistic model Nluc=Nluc$_{min}$+{[[Nluc$_{max}$−Nluc$_{min}$]/ [[[1+10^[b*(log$_{10}$[infected-Target$_{50}$]−X)]}; where X is the log$_{10}$ of the infected target cell count, Nluc$_{max}$ is an estimated parameter defining a upper asymptote for Nluc activity, Nluc$_{min}$ is an estimated parameter defining a lower asymptote for Nluc activity, b is a "Hill" parameter defining the slope at the inflection point of the fitted curve, and infected-Target$_{50}$ is an estimated parameter representing the X value corresponding (Nluc$_{max}$−Nluc$_{min}$)/2. Multiple t-test comparisons were calculated by the false discovery rate (FDR), using the two-stage step-up procedure of Benjamini, Krieger, and Yekutieli with FDR=1%. There was no adjustment for multiple comparisons. The error bars extend 1 SD above and below the mean and can also be considered as one half-width of a 68% confidence interval for that mean.

(x) FIG. 14B shows growth kinetics of the effector cell. Line graph showing effector cell counts per mL over time (in days).

(xi) FIGS. 15A-15D show IFN production by effector cell activated by SARS-CoV-1 genetically modified target cell, e.g., pseudo-infected target cells. The IFN production in the Sgp-specific effector cell when stimulated by SARS-CoV-1 pseudo-infected or non-engineered target cells was fitted using the using a four-parameter logistic model, IFN=IFN$_{min}$+{[[IFN$_{max}$−IFN$_{min}$]/[[1+10^[b*(log$_{10}$[Effector-Cell$_{50}$]−X)]}; where X is the log$_{10}$ of the effector cell (T-cell Biofactory) count, IFN$_{max}$ is an estimated parameter defining a upper asymptote for IFN production, IFN$_{min}$ is an estimated parameter defining a lower asymptote for IFN production, b is a "Hill" parameter defining the slope at the inflection point of the fitted curve, and effector-cell$_{50}$ is an estimated parameter representing the X value corresponding to (IFN$_{max}$−IFN$_{min}$)/2.

Figures 16A, 16B:
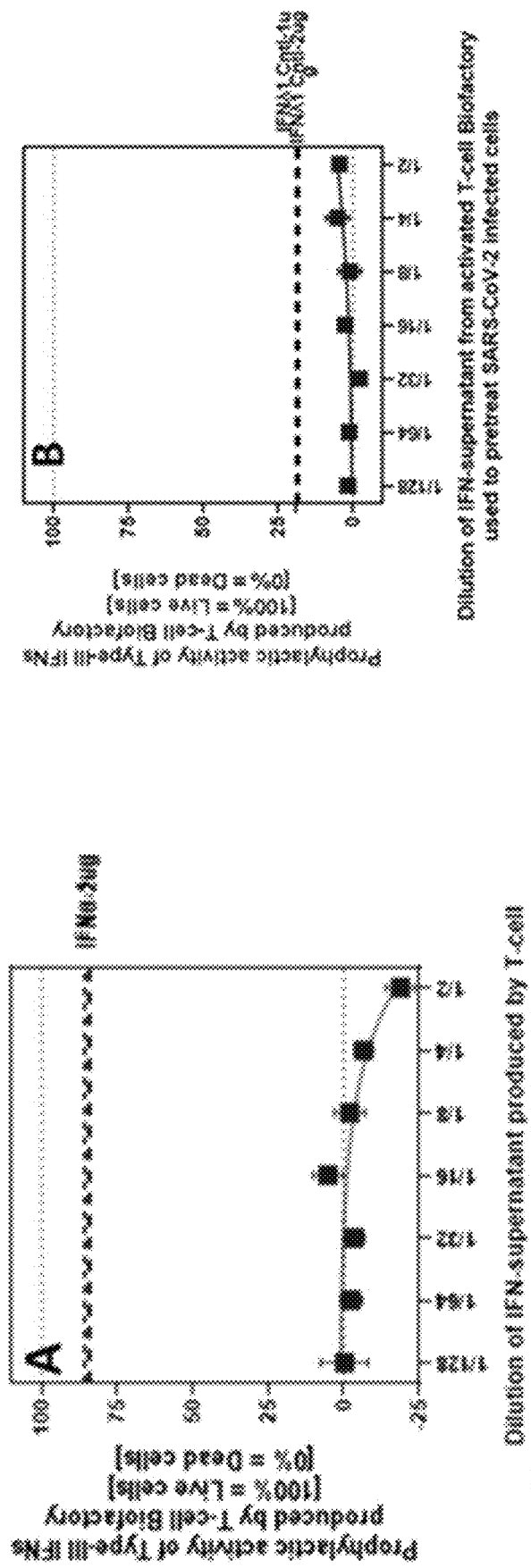
FIGS. 16A-16D illustrate plots characterizing activation of example genetically engineered effector cells, in accordance with the present disclosure.

(xii) FIGS. 16A-16B show prophylactic activity of IFNs produced by the effector cell. Comparison of all data points was calculated by the false discovery rate (FDR) multiple comparison approach, using the two-stage step-up procedure of Benjamini, Krieger, and Yekutieli with FDR=1%. There was no adjustment for multiple comparisons. The error bars extend 1 SD above and below the mean and can also be considered as one half-width of a 68% confidence interval for that mean. The ATP activity was normalized and fitted using a four-parameter logistic model ATP=ATP$_{min}$+{[[ATP$_{max}$−ATP$_{min}$]/[[1+10^[b*(log$_{10}$[Dilution$_{50}$]−X)]}; where X is the log$_{10}$ of the IFN-dilution, ATP$_{max}$ is an estimated parameter defining a upper asymptote for ATP activity, ATP$_{min}$ is an estimated parameter defining a lower asymptote for ATP activity, b is a "Hill" parameter defining the slope at the inflection point of the fitted curve, and Dilution$_{50}$ is an estimated parameter representing the X value corresponding (ATP$_{max}$−ATP$_{min}$)/2.

Figure 16D:
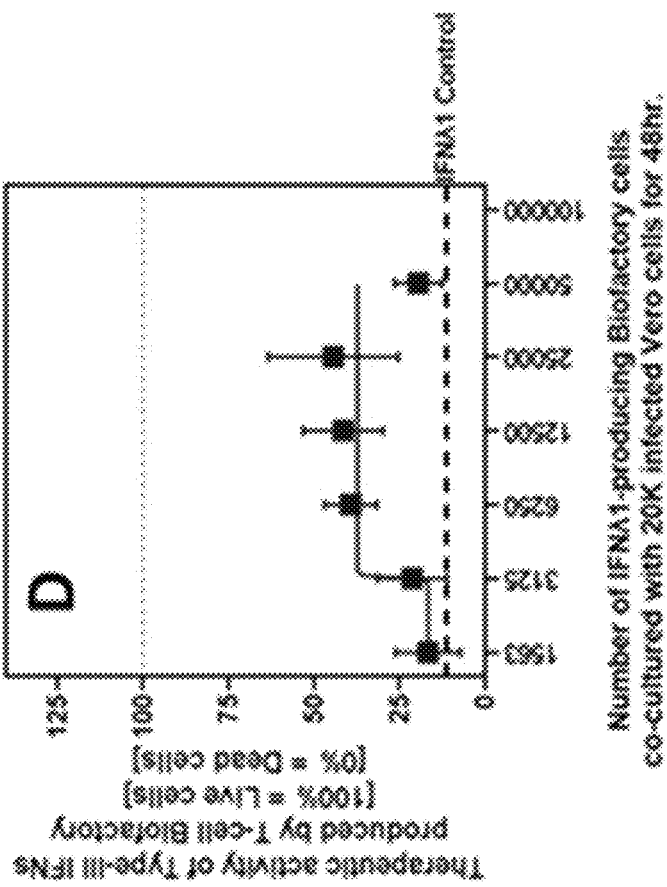
Figure 16C:
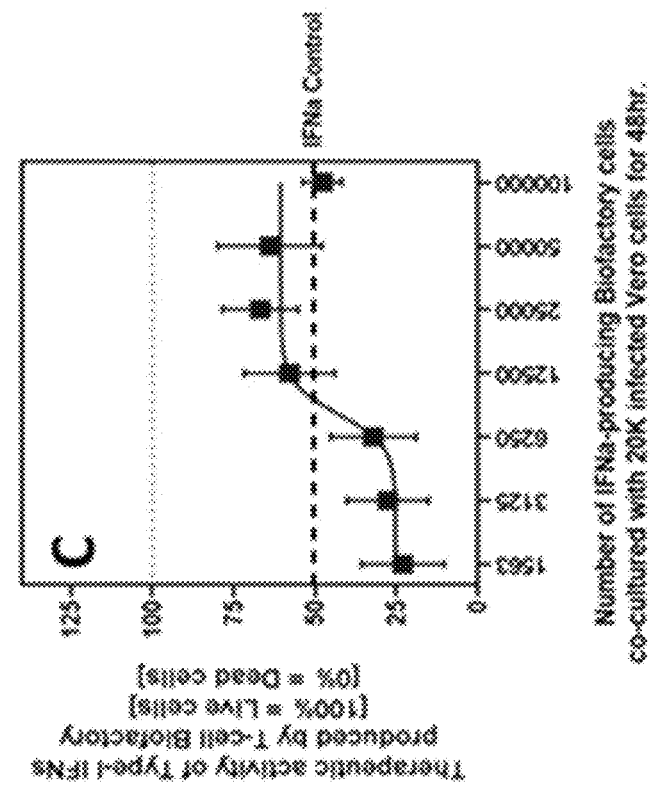

(xiii) FIGS. 16C-16D show therapeutic activity of IFNs produced by the effector cells. Comparison of all data points was calculated by the false discovery rate (FDR) multiple comparison approach, using the two-stage step-up procedure of Benjamini, Krieger, and Yekutieli with FDR=1%. There was no adjustment for multiple comparisons. The error bars extend 1 SD above and below the mean and can also be considered as one half-width of a 68% confidence interval for the mean. The Luc2 activity when the effector cell was co-cultured with infected or non-infected Vero-E6-Luc2+ target cells was fitted using a four-parameter logistic model, Luc2=Luc2min+{[[Luc2max−Luc2min]/[[1+10^[b*(log 10[η(E:T)$_{50}$]−X)]}; where X is the log 10 of the number of effector cells (T-cell Biofactory), Luc2max is an estimated parameter defining an upper asymptote for the Luc2 activity, Luc2min is an estimated parameter defining a lower asymptote for the Luc2 activity, b is a "Hill" parameter defining the slope at the inflection point of the fitted curve. A parameter for defining the antiviral efficiency of the produced IFNs, $\eta(E:T)_{50}$, was determined as the E:T at which Luc2 activity in infected or non-infected target cells was 50% of the difference between the maximum and minimum values of their respective normalized Luc2 activities, when co-cultured with the effector cell; e.g., the $\eta(E:T)_{50}$ is an estimated E:T value corresponding to (Luc2max−Luc2min)/2.

Figure 17:
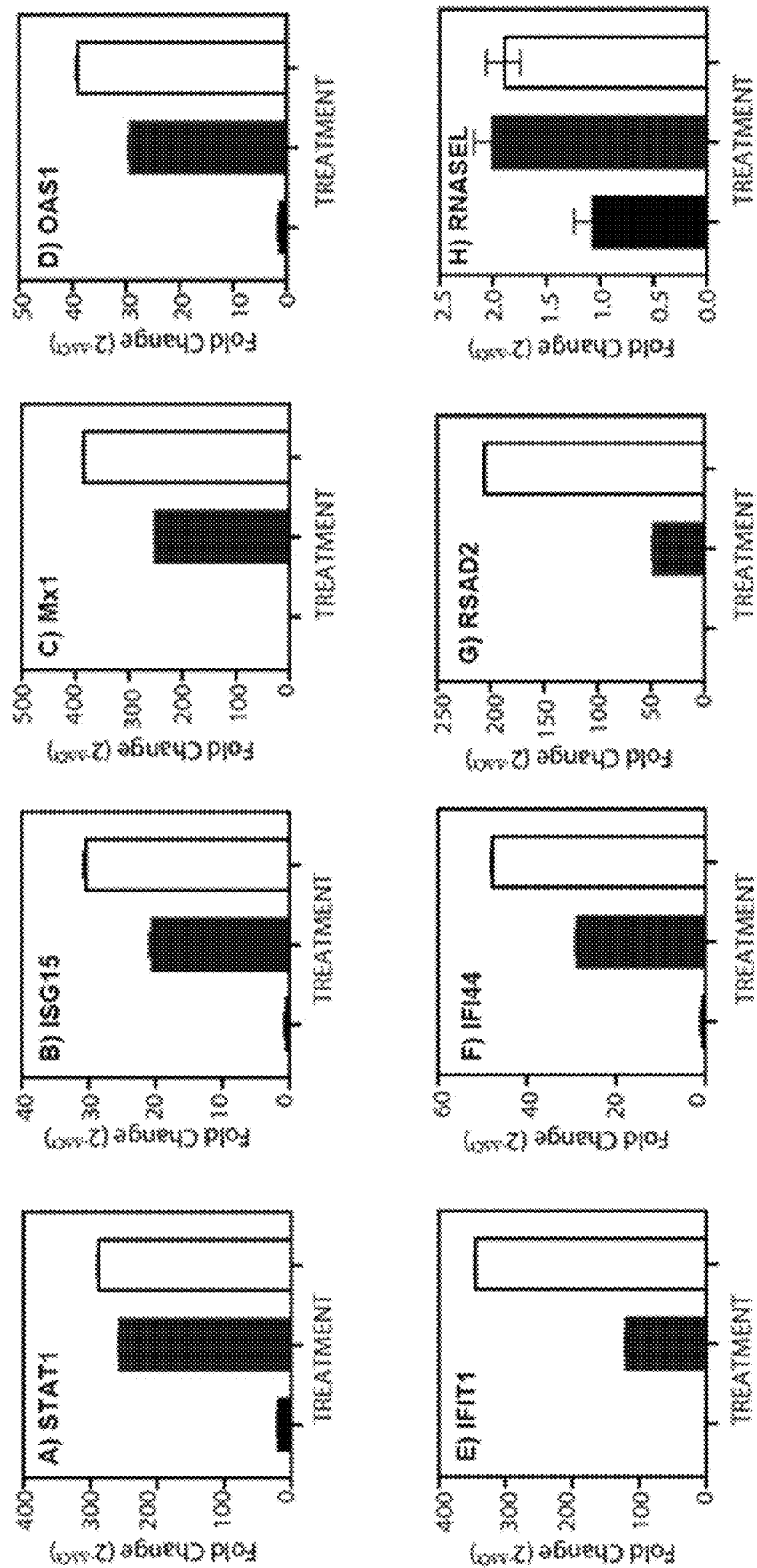
FIG. 17 illustrates plots characterizing IFN signaling of example genetically engineered effector cells in response to SARS-CoV-2-infected cells, in accordance with the present disclosure.

(xiv) FIG. 17 shows IFN signaling in Calu-3 cells treated with Type-I IFNs from activated effector cell. Differential gene expression was calculated using the ΔΔCT method by normalizing the sample Ct values to mean Ct values of 3 reference genes, and expressions are represented as fold changes over untreated cell samples. Error bars represent standard error means (SEM) from the three biological replicates.

Table 1 below provides difference sequences used to generate the effector cells.

TABLE 1

List of genes used

| GENETIC ELEMENT | SEQ ID NO |
| --- | --- |
| SARS-CoV-2 Sgp | SEQ ID NO: 1 |
| SARS-CoV-1 Sgp | SEQ ID NO: 2 |
| VHH-72 antibody | SEQ ID NO: 3 |
| Type-III Interferon (IFN-λ2) | SEQ ID NO: 4 |
| Type-III Interferon (IFN-λ1) | SEQ ID NO: 5 |
| Type-I Interferon (IFN-α2b) | SEQ ID NO: 6 |
| Type-I Interferon (IFN-β1a) | SEQ ID NO: 7 |
| Luc2 | SEQ ID NO: 8 |
| E2 Crimson | SEQ ID NO: 9 |
| Luc2-P2a-E2 Crimson | SEQ ID NO: 10 |
| GFP | SEQ ID NO: 11 |
| Nluc | SEQ ID NO: 12 |
| P2a | SEQ ID NO: 13 |
| GFP-P2a-Nluc | SEQ ID NO: 14 |
| Plasmid 1 (control) | SEQ ID NO: 15 |
| Plasmid 2 (SARS-CoV-2 Sgp) | SEQ ID NO: 16 |
| Plasmid 3 (SARS-CoV-1 Sgp) | SEQ ID NO: 17 |
| Plasmid 4 (VHH-72) | SEQ ID NO: 18 |
| Plasmid 5 (SARS-CoV-1 Sgp) | SEQ ID NO: 19 |
| Plasmid 6 (SARS-CoV-1 Sgp) | SEQ ID NO: 20 |
| Plasmid 7 (SARS-CoV-1 Sgp) | SEQ ID NO: 21 |
| Plasmid 8 (SARS-CoV-1 Sgp) | SEQ ID NO: 22 |
| Plasmid 9 (SARS-CoV-1 Sgp pseudoviral particles) | SEQ ID NO: 23 |
| Plasmid 8 (VHH-72) | SEQ ID NO: 24 |

Other experimental embodiments were directed to transforming T-cells to generated genetically modified diagnostic cells, which can be used to diagnose a host via an antigen test. Specific embodiments where directed to generating diagnostic cell, a type of effector cell, from immortalized human T-acute lymphoblastic leukemia (T-cell) cell line (Jurkat cells) and which are specific to the Sgp of SARS-CoV-2. The Sgp can be expressed by SARS-CoV-2 virions, and when the diagnostic cell encounters Sgp-presenting cells, such as infected host cells or virus particles or virions, the diagnostic cell is activated to express bioluminescent and fluorescent reporter proteins.

Referring back to FIG. 5B, FIG. 5B illustrates an example schematic of the mechanism of the diagnostic cell detecting Sgp antigens on infected cells. The Diagnostic cell uses an artificial cell-signaling pathway composed of two constant and two variable domains in cis, as described above and are shown in FIG. 5C. The constant domains provide functionality to the diagnostic cell and include a transmembrane molecule (receptor) that mobilizes the T-cell activation machinery (actuator) to upregulate the desired transgene. The variable domains include a camelid-derived, VHH binding domain, which is part of the transmembrane receptor element, that upon engaging the antigen biomarker, mobilizes the constant domains to synthesize the reporter proteins encoded by the effector element. Both variable domains can be exchanged to impart broad applicability to the diagnostic cell platform. In experimental embodiments, the VHH was used to develop a diagnostic cell with specificity either for both SARS viruses (SARS-CoV-2 and SARS-CoV-1), or for only SARS-CoV-2 without cross-reactivity to SARS-CoV-1. The reporter proteins used were a dual-reporter protein for fluorescence (GFP) and bioluminescence (NanoLuc® [Nluc], Promega, or GFP-2A-Nluc). A secretor peptide was not needed for the diagnostic cell.

To demonstrate the functionality of the diagnostic cell in a biosafety level 2 (BSL2) laboratory, Sgp-expressing cells were engineered to simulate target host cells with a SARS-CoV-2 infection, sometimes referred to as "antigen-producing cells". To demonstrate cell capability, the parental HEK293T/17 cell line was engineered to stably express the Sgp from SARS-CoV-2 (SARS-CoV-2-Sgp-cells). A non-engineered parental cell line was used as a negative control. The diagnostic cell was engineered to express GFP linked to Nluc through a self-cleavable 2A peptide linker (GFP-2A-Nluc) as target-inducible reporters for quantitative assessment of the infection. The binding domain of the diagnostic cell included the anti-Sgp VHH sequence (VHH-72; PDB: 6WAQ), which neutralizes zoonotic betacoronavirus infections (SARS-CoV-2 and SARS-CoV-1). The binding of Sgp on the target via the binding domain (see schematic in the FIG. 5B) results in the formation of immune synapse. The resulting activation of the diagnostic cell transcriptional machinery through intracellular calcium rise quantitatively informs on the infection burden by upregulation of the reporter proteins. The VHH portion can be replaced by the variable heavy-light (VH-VL) portion of the scFv of antibodies to provide specificity against any desired antigen. To further demonstrate the ability of the diagnostic cell to identify other SARS coronaviruses, a parallel validation of the VHH-72 diagnostic cell with target SARS-CoV-1-Sgp-cells (expressing the Sgp from SARS-CoV-1) was conducted. Data in FIGS. 21A-21D show that the SARS-CoV-1 antigen test exhibited a pattern similar to that observed with SARS-CoV-2 in FIGS. 18A-18D.

Figure 18B:
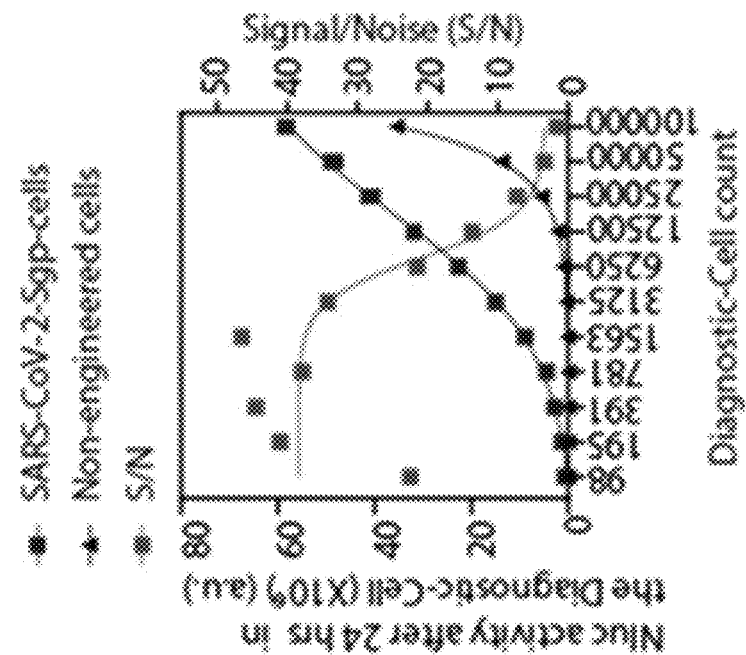
FIGS. 18A-18D illustrate plots characterizing activation of example genetically engineered diagnostic cells in response to antigen-presenting target cells, in accordance with the present disclosure.
Figure 18A:
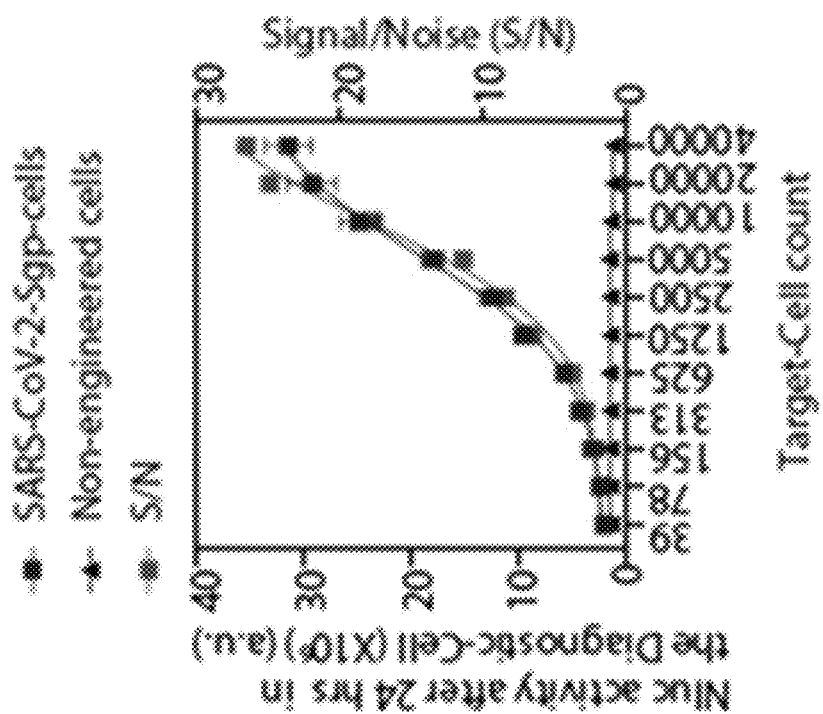
Figure 18D:
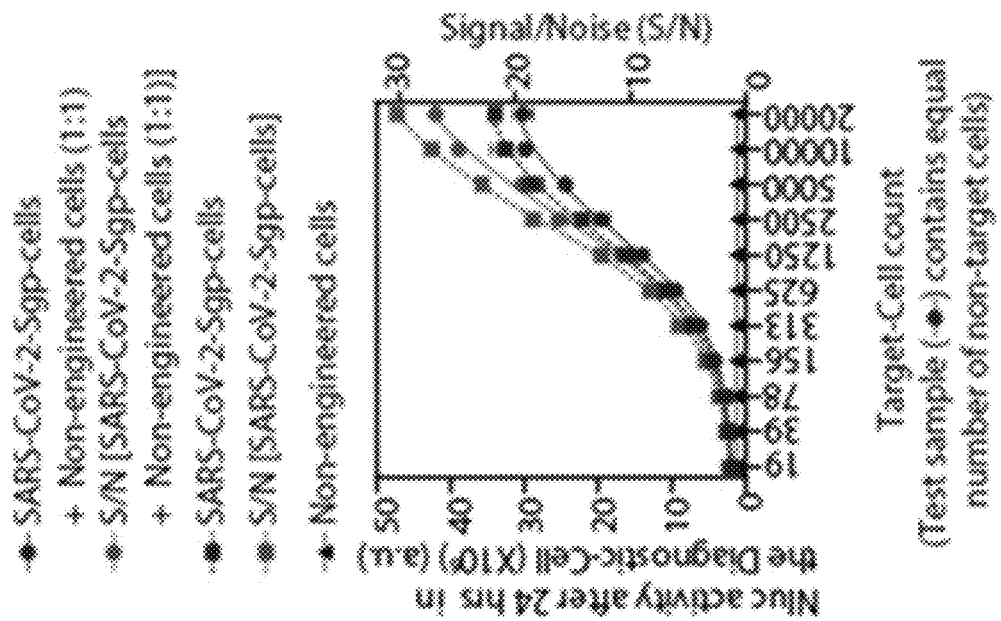
Figure 18C:
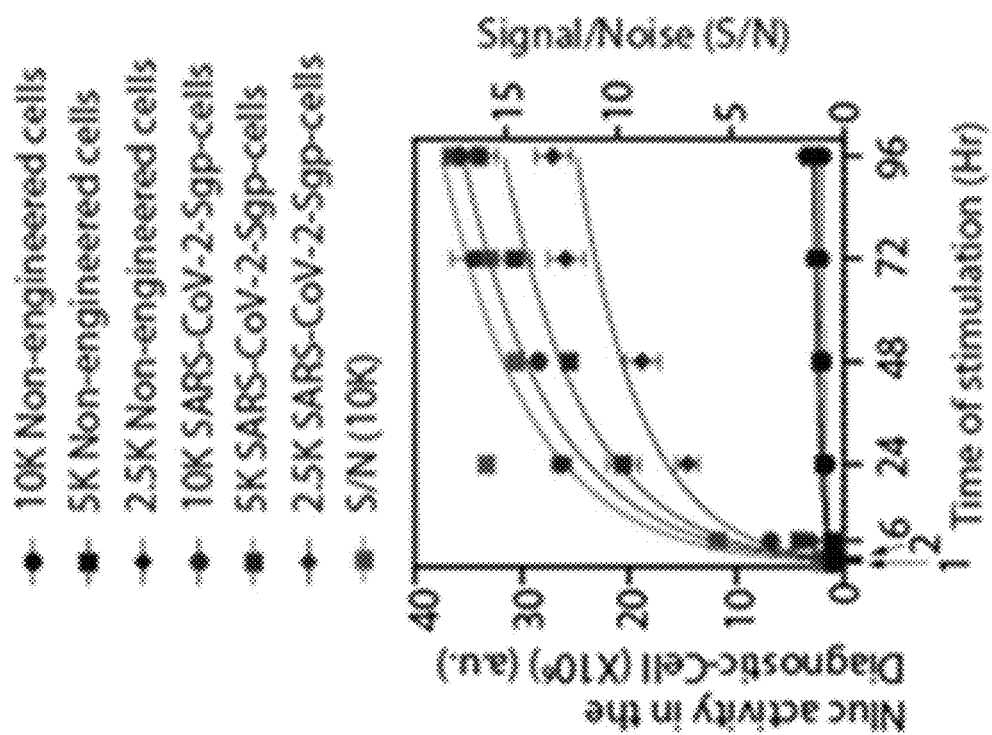

FIGS. 18A-18D illustrate plots characterizing activation of example genetically engineered diagnostic cells in response to antigen-presenting target cells, in accordance with the present disclosure. The Nluc activity in the VHH-72 diagnostic cell is proportional to the number of target SARS-CoV-2-Sgp-cells (as shown by FIG. 18A), proportional to the diagnostic cell count (target cells=2,500) (as shown by FIG. 18B), increased with respect to time and was significantly elevated within 1 hour ($p<0.02$; target cells=2, 500) when stimulated by the target SARS-CoV-2-Sgp-cells versus non-target cells (as shown by FIG. 18C), and not affected in presence of non-target cells (as shown by FIG. 18D). Nluc activity for all observations was measured using n=4, error bars indicate ±1 SD and can also be considered as one half the width of a 68% confidence interval for the mean. VHH-72 diagnostic cell (12,500 cells) were used for FIGS. 18A, 18C, and 18D.

The results in FIG. 18A demonstrate that, in addition to the qualitative detection of the infection, the Nluc activity of diagnostic cell provides a quantitative measure that is proportional to the infection burden. The signal-to-noise ratio (S/N), as defined in the figure legend, quantifies the sensitivity of the diagnostic cell. The S/N was around 1.5 at a low infection burden (e.g., around 40 target cells or diagnostic cell to target cell ratio [D:T]=320:1, p<0.002) and exponentially increased to around 25 at a high infection burden (e.g., at 40,000 target cells [D:T=1:3.2; p<0.002]). This corroborates computational findings by others regarding the efficacy of cell-based immune targeting at lower D:T ratios.

FIG. 18B shows that a lower diagnostic cell count offers more sensitive detection when stimulated by the same number of targets. This finding is supported by the observation that the S/N is around 1.6 at 100,000 diagnostic cells (D:T=40:1; p<0.0001) and increases to around 40 at a lower diagnostic cell count (D:T=1:12.5; p<0.0001). Although this result comes at the expense of longer test durations, the data shows reduced non-specific interference when lower diagnostic cell counts are used. This is important in the context of developing a sensitive diagnostic test where a higher S/N ratio reduces false negatives and false positives.

FIG. 18C illustrates the Nluc reporter kinetics of the diagnostic cell when it is stimulated by serially diluted antigen-expressing cells or engineered target cells, e.g., engineered target SARS-CoV-2-Sgp-cells, and compared to the control cells. While the Nluc activity was already increased when compared to the control sample at 1 hour (for 2,500 SARS-CoV-2-Sgp-cells, p<0.02), it continued to increase for at least 96 hours. This finding can help in developing an antigen test for mass screening, as the wide readout window will accommodate a large number of patient specimens for assessing the disease penetration in the population. A representative S/N curve is included for 10,000 SARS-CoV-2-Sgp-cells, which increased with the duration of assay (e.g., for D:T of 0.8:1, S/N was around 1 at 1 hour [p=0.8] and at ~17 at 96 hours [p<0.0001]). While the signal from the diagnostic cell was increased in correlation to a higher infection burden, as represented by the SARS-CoV-2-Sgp-cell count, the kinetics of the test was faster at a lower infection burden. For example, compared to the control cells, the signal was elevated at 1 hour, when 2,500 SARS-CoV-2-Sgp-cells (p<0.02, S/N around 1, D:T=5:1) were used, and at 6 hours, when 5,000 SARS-CoV-2-Sgp-cells (p<0.0001, S/N around 3.5, D:T=2.5:1) or 10,000 cells (p<0.0001, S/N around 5.5, D:T=1.2:1) were used. This also validates the previous observation that the Nluc activity of the diagnostic cell was proportional to the infection burden (FIG. 18A) and exhibited higher S/N at a limited engagement of the diagnostic cell with the targets (FIG. 18B).

To investigate the precision with which the samples should be prepared and any non-specific signal from the impurities, the genetically engineered Sgp-expressing target cells and non-engineered control cells in equal numbers were mixed (e.g., 1:1) and serially diluted the cell mixture to stimulate the diagnostic cell. Data in FIG. 18D show that, in comparison to stimulation by only engineered target cells, the loss in Nluc reporter activity of the diagnostic cell was insignificant (p>0.05 at all D:T). This confirms that there is no contribution of the background noise to the signal generated from the diagnostic cell. As observed in FIG. 18A, the Nluc reporter expression was again proportional to the target cell numbers. These findings demonstrate the sensitivity of the assay with a heightened reporter signal and provide the rationale for applying it to a large number of patient samples with minimal time for sample preparation and purification.

Various experiment were directed to developing and characterizing the diagnostic cell in a BSL2 containment facility using genetically engineered Sgp-expressing target cells including SARS-CoV-2-Sgp-cells (FIGS. 18A-18D) and SARS-CoV-1-Sgp-cells (FIGS. 21A-21D).

Figure 22:
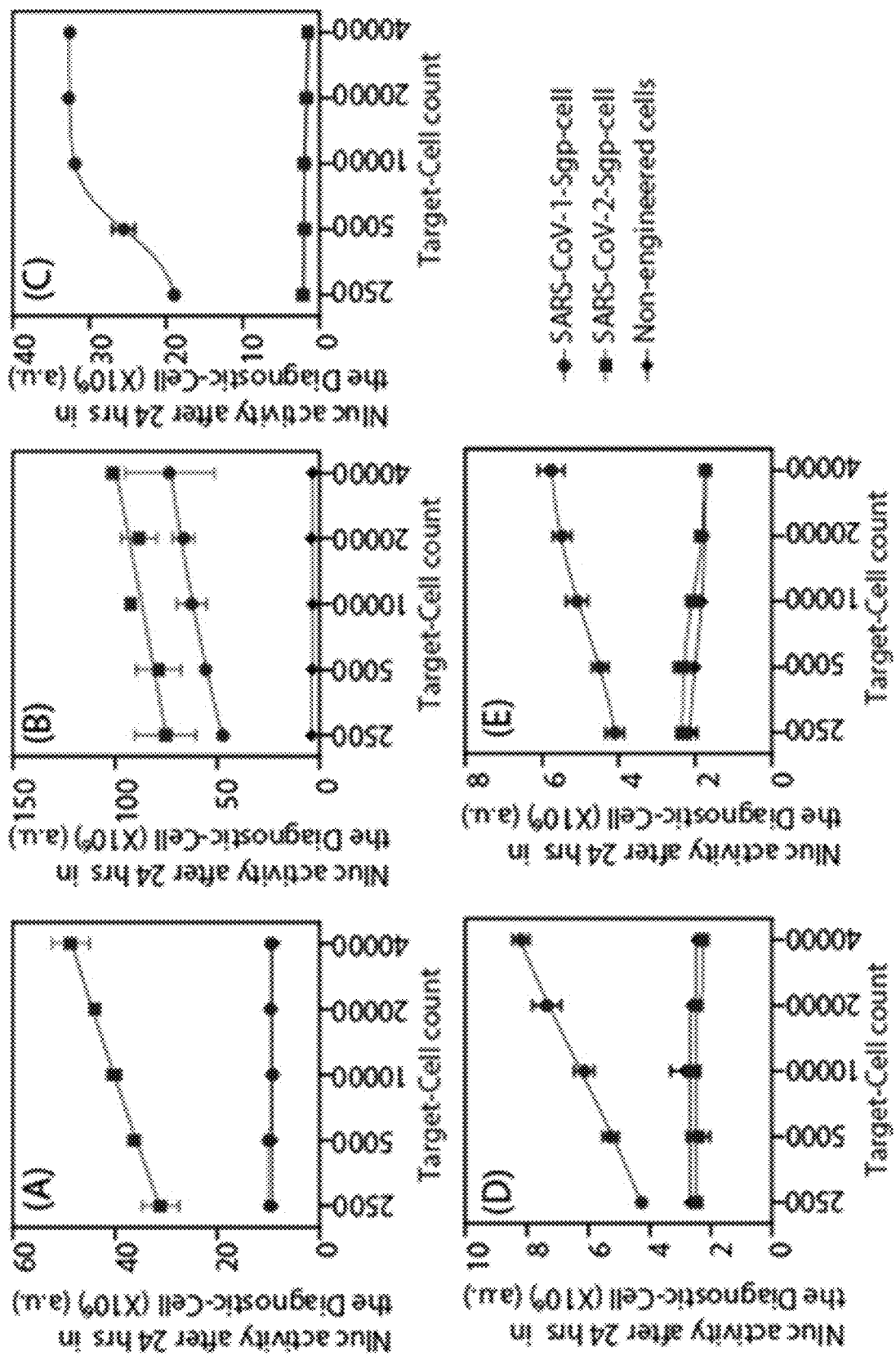
FIG. 22 illustrates example results of screening different diagnostic cells with specificity towards SARS-CoV-2 and SARS-CoV-1, in accordance with the present disclosure.

FIGS. 19A-19F show example data results of implementing an example diagnostic cell with infectious SARS-CoV-2 virus particles (Isolate: Hong Kong/VM20001061/2020) in a BSL3 containment facility, in accordance with the present disclosure. Toward this goal and to impart specificity to the diagnostic cell against the ongoing pandemic, the VHH-72 Sensor domain of diagnostic cell was exchanged with the VHH portion of another antibody (VHH-Ty1; PDB: 6ZXN) that is specific to the Sgp of SARS-CoV-2. The rationale for selecting VHH-Ty1 was that it can potentially reduce false positives because it does not cross-react with SARS-CoV-1 (see FIG. 22 for validation studies) or other seasonal human coronavirus strains (HKU1, OC43, 229E, and NL63). FIG. 22 describes experiments to identify the binding domain among multiple candidates for not cross-reacting with SARS-CoV-1. Initial investigations were conducted by assessing the target-inducible Nluc activity in the VHH-Ty1 diagnostic cell and were later validated by assessing the GFP signal. Negative control was composed of uninfected host cells or a diagnostic cell with abrogated specificity.

Figure 19B:
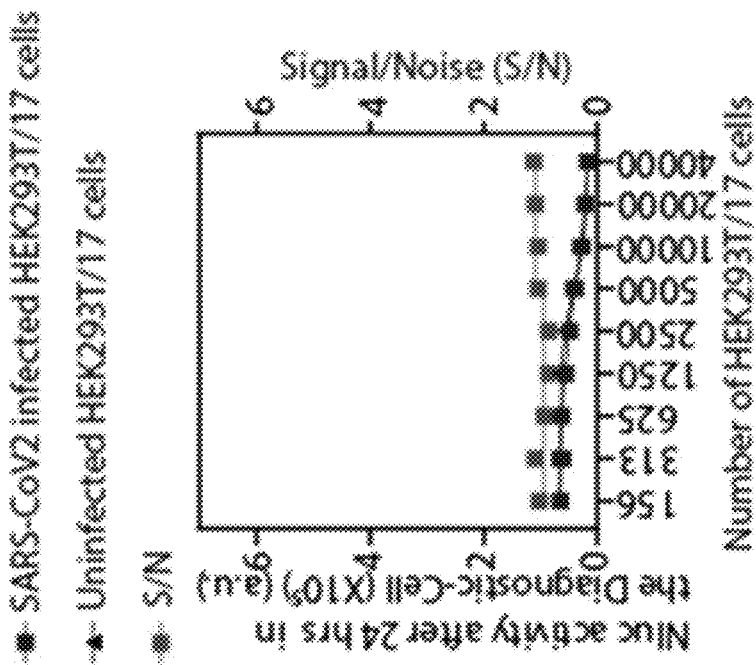
Figure 19A:
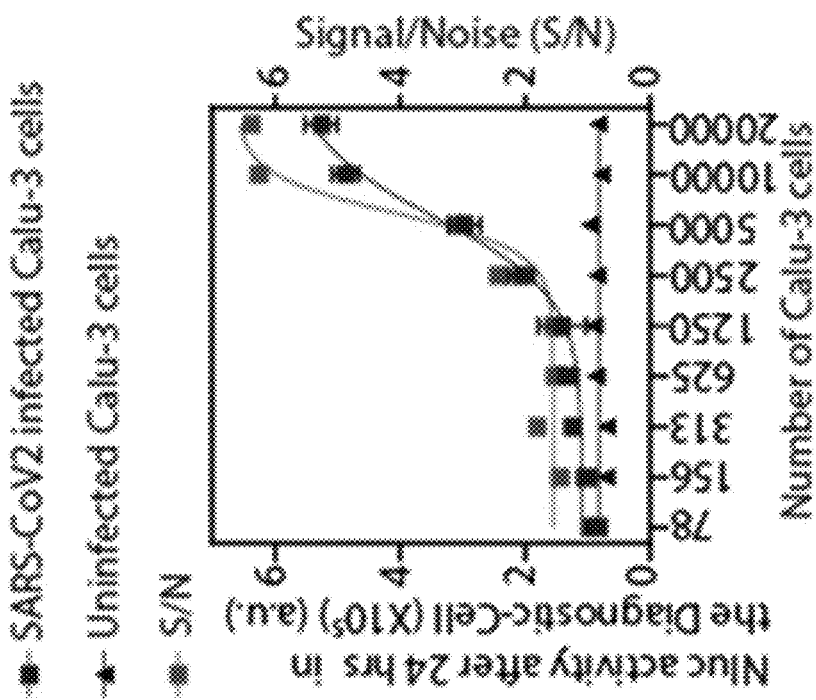
Figures 19C, 19D:
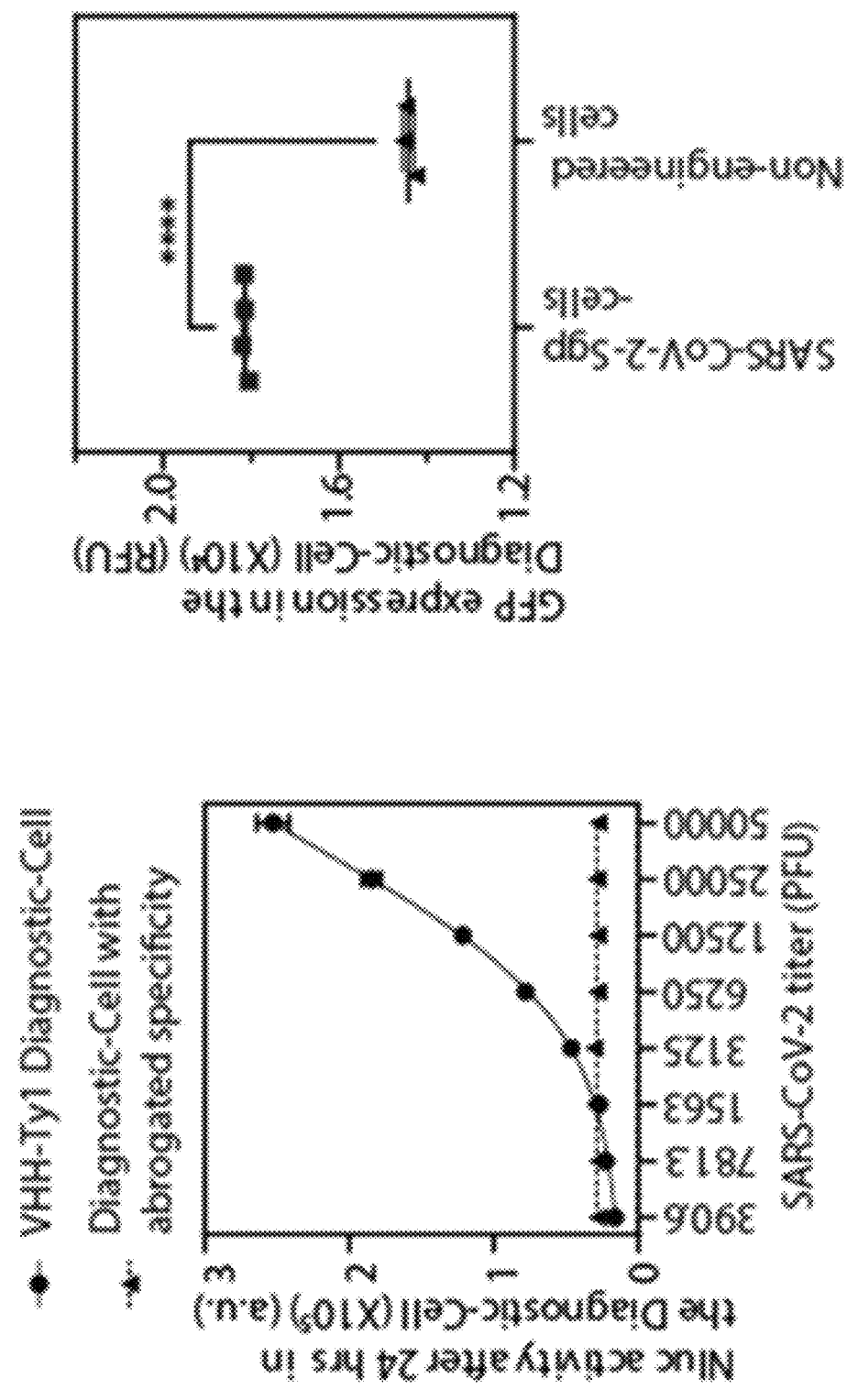
Figure 19E:
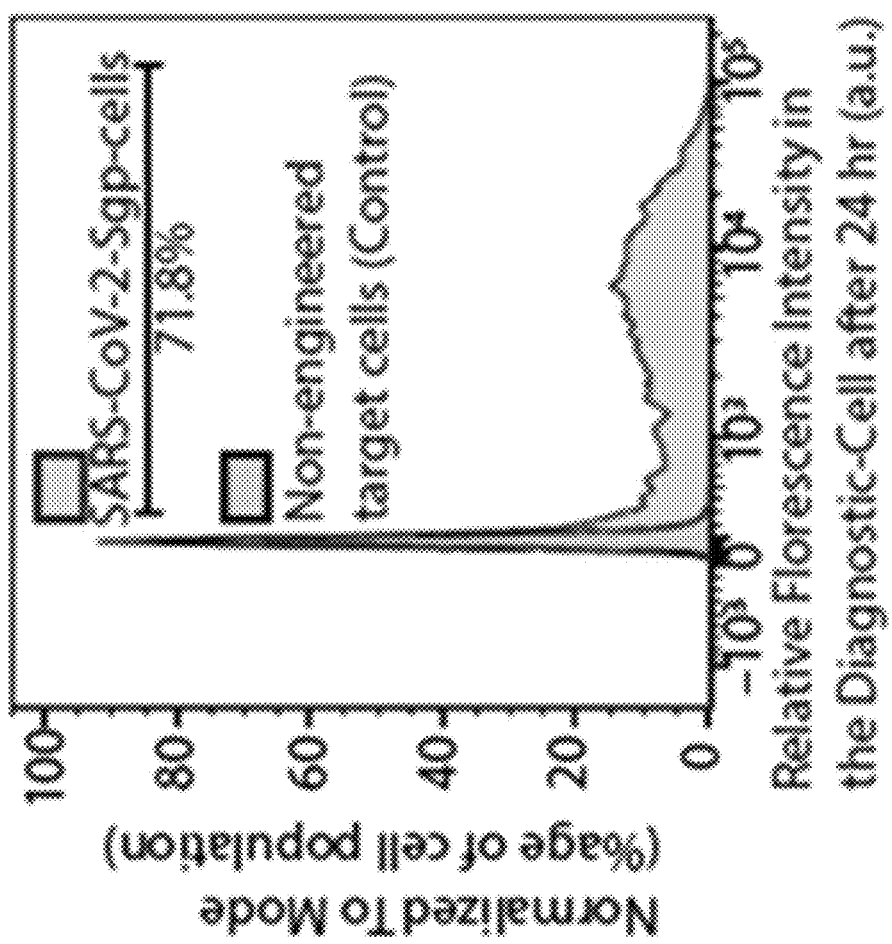
Figure 19F:
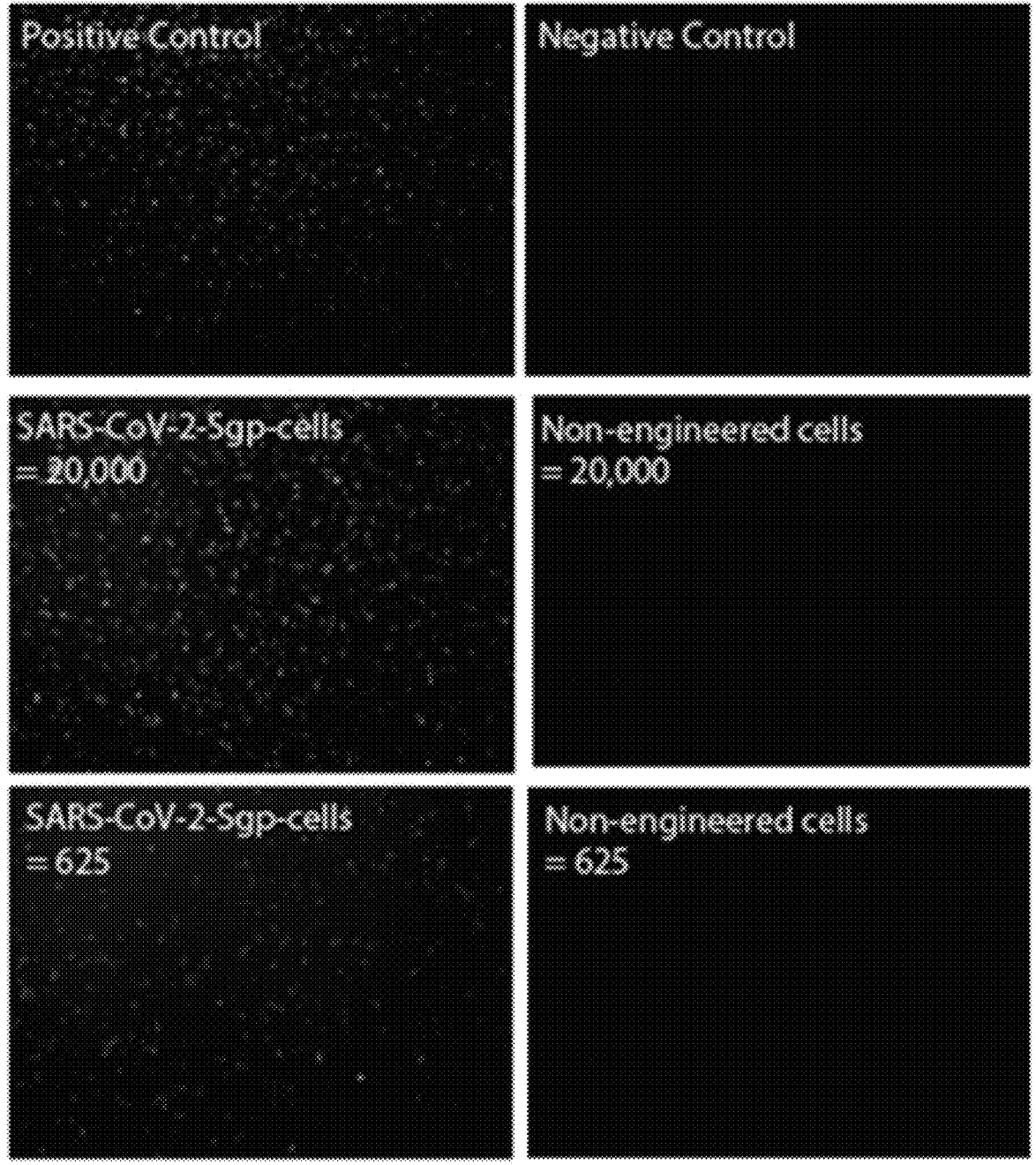

More particular, FIGS. 19A-19F show results from assessing a VHH-Ty1 diagnostic cell activation by infected host cells, SARS-CoV-2 virus or genetically engineered target SARS-CoV-2-Sgp-cells. FIG. 19A shows that the Nluc activity in the VHH-Ty1 diagnostic cell is proportional to the number of SARS-CoV-2-infected Calu-3 target cells (n=3). FIG. 19B shows that no Nluc activity was observed in the VHH-Ty1 diagnostic cell when SARS-CoV-2 treated HEK293T/17 cells (lacks receptors for SARS-CoV-2) were used as targets. FIG. 19C shows that the Nluc activity in the VHH-Ty1 diagnostic cell increased with respect to the number of viral particles present in solution. FIG. 19D shows that GFP expression in the VHH-Ty1 diagnostic cell was assessed using plate reader (target cells=2,500). FIG. 19E shows that GFP expression in the VHH-Ty1 diagnostic cell was assessed using flow-cytometry. FIG. 19F is a microscope image panel showing GFP expression in the VHH-Ty1 diagnostic cell at different D:T ratios. All images taken at 4× magnification. Positive control was prepared by chemically stimulating the diagnostic cell. Unstimulated diagnostic cell was used as negative control. Statistical significance was calculated using the two-tailed student's t-test test. Nluc activity for all observations was measured using n=4, error bars indicate ±1 SD. For FIGS. 19A, 19B, 19D, and 19F, VHH-Ty1 diagnostic cell=12,500 cells; for FIG. 19C VHH-Ty1 diagnostic cell=20,000.

FIG. 19A demonstrates the quantitative Nluc reporter response of the VHH-Ty1 diagnostic cell. The Nluc activity on engaging Calu-3 host cells infected with competent SARS-CoV-2 virus exhibited a trend similar to that observed with engineered SARS-CoV-2-Sgp-cells in FIG. 18A and was proportional to the infection burden. At a low infection burden, the S/N was around 1 (p=0.83; D:T ~160:1), which exponentially increased to around 6 at a high infection burden at 20,000 target cells (p<0.0001; D:T=1:1.6). FIG. 19B shows a similar assay conducted by replacing the Calu-3 cells with HEK293 cells. Lack of Nluc expression in the VHH-Ty1 diagnostic cell, when stimulated by HEK293T/17 cells treated with infectious SARS-CoV-2 virus correlates with lack of SARS-CoV-2 tropism for targeting HEK293T/17 cells that may not express receptors for virus attachment.

To develop an effective antigen test indicative of active infection, experiments were directed to confirming the diagnostic cell can detect virus particles. FIG. 19C shows the exponential increase of Nluc activity in the diagnostic cell after engaging serially diluted SARS-CoV-2 virion particles ranging from 112,500 PFU to 880 PFU (Nluc activity with respect to the viral titer). This finding is unique, as the lack of co-stimulatory molecules on virus particles, which are present on the mammalian host cell and are essential for stimulating the T-cells, challenges the possibility of diagnostic cell successfully detecting target virus particles. The fact that the diagnostic cell can detect virus particles may be explained by the cross-linking of multiple Sgp-specific VHH on the diagnostic cell surface assisted by the Sgp of SARS-CoV-2 particles. This initiates the intracellular activation-signaling cascade. Findings in FIG. 19C validate that it is, in fact, possible for the virions to directly activate the antigen-specific diagnostic cell.

To further reduce the operational cost of the diagnostic cell, the potential of target-inducible GFP expression in the diagnostic cell was explored to assess the status of active infection. The results of experiments performed using the engineered SARS-CoV-2-Sgp-cells (FIGS. 19D-19F) affirm GFP-based sensing of target cells using the VHH-Ty1 diagnostic cell. This finding reduces the reliance of diagnostic cell on a bioluminescent reporter (Nluc), which requires an additional step of substrate addition and contributes toward the cost of the test. To eliminate chances of infection during the handling of infected specimens, the use of diagnostic cell was validated with samples that underwent heat-inactivation (65° C. for 30 minutes). The Nluc signal from diagnostic cell is significantly elevated ($p<0.0001$, FIG. 23) and differentiates between engineered Sgp-expressing cells and non-engineered cells.

FIGS. 20A-20B illustrate results of detecting infection in mouse oropharyngeal swabs using an example diagnostic cell, in accordance with the present disclosure. The VHH-Ty1 diagnostic cell was further assessed to detect active infection in specimens obtained from both infected and healthy mice via oropharyngeal swabs. Results validate that the diagnostic cell can diagnose active COVID-19 infection via oropharyngeal swabs (FIG. 20A). For the proof-of-principle studies, the signal from the diagnostic cell after 24 hours was assessed. The results in FIG. 18C show that the test can be significantly faster with the potential to inform on the active infection within 1 hour (for 2,500 SARS-CoV-2-Sgp-cells). FIG. 20B shows results obtained by qPCR (as the gold standard) while using mouse lung tissues for comparison with the results from diagnostic cell. These results demonstrate that the diagnostic cell can be rapidly deployed at low cost toward emerging viruses and be used with oral specimens without any sample preparation or signal-amplification step.

FIG. 20A is a scatter plot that shows that the VHH-Ty1 diagnostic cell differentiates between infected and negative throat swab samples ($p<0.05$). (Infected mice, $n=8$ and Negative mice, $n=3$). Each data point represents average Nluc readings from 2 swabs. FIG. 20B is scatter plot that shows qPCR results for the lung tissues collected from the same mice (lung tissue for one infected mouse was not collected). Statistical significance was calculated using the two-tailed student's t-test with Welch's correction, error bars indicate ±1 SD.

The impact of this technology goes beyond the current COVID-19 pandemic. To show the expanded applicability of the diagnostic cell, multiple different diagnostic cells were generated to detect multiple viruses with the potential to cause the future pandemics. FIG. 24 shows the feasibility of the Diagnostic-Cell technology against Ebola, Marburg, West Nile Virus, Chikungunya, and Nipah using engineered Target Cells to present virus-specific envelope proteins. A fully matured approach will eliminate the long development periods needed to apply a separate, specific approach for each virus or its variants, which is currently the case for SARS-CoV-2, and rapidly deliver a diagnostic test for any pathogen in less than a month.

The experiments also confirmed the rapid scalability of the diagnostic cell for performing diagnostic antigen test. The doubling time of the VHH-Ty1 diagnostic cell was experimentally determined to be 24.3 (±6.8) hours. Further calculations show that with 10 million diagnostic cell, it is possible to scale up to meet the target for 30 million tests/day in less than 20 days.

FIGS. 21A-21D illustrate example results of assessing VHH-72 diagnostic cell activation by genetically engineered target SARS-CoV-1-Sgp-cells, in accordance with the present disclosure. As shown by FIG. 21A, the Nluc activity in the VHH-72 diagnostic cell is proportional to the number of target SARS-CoV-2-Sgp-cells. As shown by FIG. 21B, the Nluc activity in the VHH-72 diagnostic cell is proportional to the diagnostic cell count (target cells=2,500). As shown by FIG. 21C, the Nluc activity in the VHH-72 diagnostic cell increased with respect to time when stimulated by the target SARS-CoV-1-Sgp-cells versus non-target cells (target cells=2,500). As shown by FIG. 21D, the Nluc activity in the VHH-72 diagnostic cell is not affected in presence of non-target cells. Nluc activity for all observations was measured using $n=4$, error bars indicate ±1 SD and can also be considered as one half the width of an 68% confidence interval for that mean. VHH-72 diagnostic cell (12,500 cells) was used for FIGS. 21A, 21C, and 21D.

FIG. 22 illustrates example results of screening of different diagnostic cells with specificity towards SARS-CoV-2 and SARS-CoV-1, in accordance with the present disclosure. The Nluc activity in different diagnostic cell types is proportional to the number of target cells (SARS-CoV-2-Sgp-cells or SARS-CoV-1-Sgp-cells). The binding domain sequences were obtained from (A) VHH-Ty1, (B) S309 antibody, (C) S230 antibody, (D) m396 antibody, and (E) CR3022 antibody. In all experiments, diagnostic cell=12,500 and Nluc activity for all observations was measured using $n=4$; error bars indicate ±1 SD and can also be considered as one half the width of an 68% confidence interval for that mean.

FIG. 23 illustrates detection of heat-inactivated target cells by example VHH-Ty1 diagnostic cells, in accordance with the present disclosure. A scatter plot shows the Nluc activity in the VHH-Ty1 diagnostic cells (12,500 cells) upon interacting with engineered Sgp-expressing target cells (SARS-CoV-2-Sgp-cells=5,000 cells) heat-inactivated in air or on beads at 65° C. vs. non-engineered cells. Nluc activity for all observations was measured using $n=4$; error bars indicate ±1 SD.

FIG. 24 illustrates example assessment of different diagnostic cells generated with specificity to other emerging viruses, in accordance with the present disclosure. The Nluc activity the different types of diagnostic cells is specific to their targets and is proportional to the number of target cells engineered for surface expression with envelop proteins. The sequences for the envelop proteins were obtained from (A) Ebola virus; (B) Marburg virus; (C) Chikungunya virus; (D) Nipah virus; and (E) West-Nile virus. In all experiments, diagnostic cells=12,500 and Nluc activity for all observations was measured using $n=4$; error bars indicate ±1 SD and can also be considered as one half the width of a 68% confidence interval for that mean Table 2 below provides difference sequences used to generate the diagnostic cells.

TABLE 2

| Genetic Element | SEQ ID NO |
|---|---|
| SARS-CoV-2 Sgp | SEQ ID NO: 1 |
| SARS-CoV-1 Sgp | SEQ ID NO: 2 |
| VHH-72 antibody | SEQ ID NO: 3 |
| VHH-Ty1 antibody | SEQ ID NO: 25 |
| S309 antibody | SEQ ID NO: 26 |
| S230 antibody | SEQ ID NO: 27 |
| m396 antibody | SEQ ID NO: 28 |
| CR3022 antibody | SEQ ID NO: 29 |
| Ebola virus Egp | SEQ ID NO: 30 |
| Ebola virus Egp antibody | SEQ ID NO: 31 |
| Marburg virus Egp | SEQ ID NO: 32 |
| Marburg virus Egp antibody | SEQ ID NO: 33 |
| Chikungunya virus Egp | SEQ ID NO: 34 |
| Chikungunya virus Egp antibody | SEQ ID NO: 35 |
| Nipah virus Egp | SEQ ID NO: 36 |
| Nipah virus Egp antibody | SEQ ID NO: 37 |
| West-Nile virus Egp | SEQ ID NO: 38 |
| West-Nile virus Egp antibody | SEQ ID NO: 39 |
| Luc2 | SEQ ID NO: 8 |
| E2 Crimson | SEQ ID NO: 9 |
| Luc2-P2a-E2 Crimson | SEQ ID NO: 10 |
| GFP | SEQ ID NO: 11 |
| Nluc | SEQ ID NO: 12 |
| P2a | SEQ ID NO: 13 |
| GFP-P2a-Nluc | SEQ ID NO: 14 |
| Plasmid 2 (SARS-CoV-2 Egp) | SEQ ID NO: 16 |
| Plasmid 3 (SARS-CoV-1 Egp) | SEQ ID NO: 17 |
| Plasmid 4 (VHH-antibody) | SEQ ID NO: 18 |
| Plasmid 11 (VHH-Ty1 antibody) | SEQ ID NO: 40 |
| Plasmid 12 (S309 antibody) | SEQ ID NO: 41 |
| Plasmid 13 (S230 antibody) | SEQ ID NO: 42 |
| Plasmid 14 (m396 antibody) | SEQ ID NO: 43 |
| Plasmid 15 (CR2033 antibody) | SEQ ID NO: 44 |
| Plasmid 16 (Ebola virus Egp) | SEQ ID NO: 45 |
| Plasmid 17 (Ebola virus Egp antibody) | SEQ ID NO: 46 |
| Plasmid 18 (Marburg virus Egp) | SEQ ID NO: 47 |
| Plasmid 19 (Marburg virus Egp antibody) | SEQ ID NO: 48 |
| Plasmid 20 (Chikungunya virus Egp) | SEQ ID NO: 49 |
| Plasmid 21 (Chikungunya virus Egp antibody) | SEQ ID NO: 50 |
| Plasmid 22 (Nipah virus Egp) | SEQ ID NO: 51 |
| Plasmid 23 (Nipah virus Egp antibody) | SEQ ID NO: 52 |
| Plasmid 24 (West Nile virus Egp) | SEQ ID NO: 53 |
| Plasmid 25 (West Nile virus Egp antibody) | SEQ ID NO: 54 |

Synthesis and Experimental Information for Diagnostic Cell (1) Materials and reagents. Engineered Jurkat E6-1 (ATCC, Cat #TIB-152) cell lines were maintained in complete RPMI media [RPMI1640 (Corning, Cat #10-040-CV), 10% were heat-inactivated fetal bovine serum (FBS) (Sigma-Aldrich, Cat #F2442-500ML) and 1× Penicillin-Streptomycin solution (Corning, Cat #30-002-Cl)]. Parental and Engineered HEK293T/17 cells (ATCC, Cat #CRL-11268) were cultured in complete DMEM [DMEM growth media (Corning, Cat #10-013-CV) supplemented with 10% FBS (Sigma-Aldrich, Cat #F2442-500ML) and 1× Penicillin-Streptomycin solution (Corning, Cat #30-002-Cl)]. Calu-3 cells (ATCC Cat #HTB-55) were cultured in complete EMEM [EMEM growth media (Corning, Cat #10-009-CV) supplemented with 10% heat-inactivated fetal bovine serum (FBS) (Sigma-Aldrich, Cat #F2442-500ML) and 1× Penicillin-Streptomycin solution (Corning, Cat #30-002-Cl)]. All cells were expanded, and liquid nitrogen stocks were maintained using freezing media (50% FBS, 40% growth media and 10% DMSO). The SARS-CoV-2 virus culture [BEI Resources, NIH; Hong Kong/VM20001061/2020 (Cat #NR-52282)] was provided by SRI International. Plasmids encoding different genetic payloads (transfer plasmids) were designed in SnapGene software (GSL Biotech LLC) and sub-cloned into lentivirus vector plasmid (System Biosciences, Cat #CD510B-1) of piggyBac Transposon vector plasmid (System Biosciences, Cat #PB510B-1). Plasmids encoding $2^{nd}$ generation packaging genes (psPAX2—Cat #12260, pMD2.G—Cat #12259) were received from Didier Trono (Ecole Polytechnique Fédérale de Lausanne, Lausanne, Switzerland) through Addgene, while pAdvantage was obtained from Promega (Cat #E1711). piggyBac Transposase sequence was provided by Johns Hopkins University School of Medicine. All plasmid preparation services (chemical synthesis of DNA insert sequences, sub-cloning into respective vector backbones, and the amplification) were obtained from Epoch Life Science, Inc. (Missouri City, Tex.). Transporter 5™ reagent (Polysciences, Inc, Cat #26008-5) was used to transfect parental HEK293T/17 cells during lentivirus production. The collected lentivirus was transduced into Jurkat cells using Polybrene (Abm®, Cat #G062). TransIT®-2020 transfection reagent (Minis #MIR5400) was used to transfect piggyBac Transposon system plasmids into parental HEK293T/17 cells to engineer stable antigen-presenting cells (APCs) or Sgp-expressing target cells. Puromycin dihydrochloride (ThermoFisher Scientific, Cat #A1113803) was used for selecting stable cells. Nano-Glo® assay (Promega, Cat #N1120) was used to assess the NanoLuc® (Nluc) expression activity. Sterile mini-tip polyester swabs (Puritan, Cat #25-800-1PD) were used for collection of oropharyngeal swab samples from mice. For RNA preparations from lung tissues, Direct-zol RNA Mini-Prep Kit (Zymo Research, Cat #11-331) and reverse transcription by SuperScript III RT (Invitrogen, Cat #18080044) were used following the manufacturers' instructions. TaqMan Universal PCR Master Mix (Applied Biosystems, Cat #4305719) was used for RT-qPCR reactions.

(2) Lentivirus production. Lentivirus particles were prepared by packaging the transfer plasmid using $2^{nd}$ generation lentivirus system.

(3) Engineering of diagnostic cells. The Jurkat E6-1 suspension cell line was engineered with lentivirus particles carrying the genetic payload (FIG. 5B) with the artificial cell signaling pathway. The binding domain sequences were selected based on their specificities to the envelop proteins of the respective viruses. The cells were treated with lentivirus in the presence of 8 μg/mL Polybrene. After 48 hours, the engineered cells were placed in selection using 0.5 μg/mL of puromycin dihydrochloride. The unmodified parental cell line was also placed under selection as a positive control for cell killing by puromycin. Following selection, cells were expanded as required for different assays and frozen using freezing media. Sequences from the binding domain were obtained from the following sources: VHH-72 (PDB: 6WAQ), VHH-Ty1 (PDB: 6ZXN), S309 antibody (PDB: 6WPS), S230 antibody (PDB: 6NB8), m396 antibody (PDB: 2DD8), CR3022 antibody (PDB: 6W41), Ebola virus antibody (PDB: 6MAM), Marburg virus antibody (PDB: 5JRP), Chikungunya virus antibody (PDB: 4GQ9), Nipah virus antibody (PDB: 6U1T), and West-Nile virus antibody (PDB: 1ZTX). All gene sequences were codon optimized before expression using lentivirus plasmids.

(4) Engineering of target cells with surface expression of virus envelop protein. The parental HEK293T/17cells were engineered to stably express the virus envelop protein, using the piggyBac Transposon system, as previously described.

Two plasmids were designed with the piggyBac transposon vector backbone for cell surface expression of the envelop protein from the respective virus. A monolayer of HEK293T/17 cells were transfected with the transposon plasmid (carrying the gene of interest) and transposase plasmid, in a ratio of 2.5:1, respectively, using TransIT®-2020 transfection reagent. After 48 hours of transfection, the transfected cells were placed under selection using 0.5 μg/mL of Puromycin dihydrochloride. The unmodified parental HEK293T/17 cell line was placed under selection as a positive control for cell killing by the antibiotics. The generated stable cell lines were expanded as required for different assays. Sequences from the gene of interest (envelop proteins) were obtained from the following sources: SARS-CoV-2 (GenBank: QHD43416.1, position 1-1273), SARS-CoV-1 (GenBank: AAP13567.1, position 1-1255), Ebola virus (GenBank: AAB81004.1, position 33-676), Marburg virus (GenBank: CAA78117.1, position 19-681), Chikungunya (E1E2) virus (GenBank: AGX45493.1, 339-1247), Nipah virus Fusion gp (GenBank: Q9IH63.1, position 27-546), and West-Nile virus (GenBank: AAT11537.1, position 1-501). All gene sequences were codon optimized before expression in the piggyBac Transposon system.

(5) Method of use for the diagnostic cell [D] with genetically engineered target cells [T]. The diagnostic cell and target cells were co-cultured at different diagnostic cell to target cell (D:T) ratios in 100 μL of complete RPMI media in a single well of a 96-well plate. Phorbol myristate acetate (30 nM) and ionomycin (1 μM) solution mixed in 0.5% Dimethyl sulfoxide (DMSO) was used for unspecific stimulation of the diagnostic cell (positive control). Negative control comprised of stimulation by 0.5% DMSO. After the specified time in co-culture, NanoLuc® (Nluc) activity in the diagnostic cell was assessed using the Nano-Glo® assay following the manufacturer's instructions. The Nluc enzyme substrate was diluted in the cell lysis buffer provided with Nano-Glo® and added to the co-cultures in 96-well plate for assessing enzyme activity. Following a brief incubation period of 3 minutes, bioluminescence was read on a microplate reader (Perkin Elmer, EnVision™ Multilabel Plate Reader Model: 2104-0010A). Additionally, GFP expression in the diagnostic cell was assessed using the plate-reader, flow-cytometry (FACS Aria™ III, BD Biosciences), and fluorescence microscopy (EVOS FL Auto 2, Invitrogen).

(6) Method of use for the VHH-Ty1 diagnostic cell [D] with SARS-CoV-2-infected Calu-3 or HEK293T/17 epithelial cells as infected target cells [T]. Human lung epithelial cells, Calu-3 cells (or HEK293T/17 cells) were cultured in a 6-well plate ($1\times10^6$/well) overnight in complete EMEM media and infected as previously described. At about 70% confluency, the cells were infected with the SARS-CoV-2 virus culture at an MOI of 0.05 for 24 hours. The infected cells were harvested and then used as the antigen-presenting target cells in co-culture experiments. The virus-infected target cells were co-cultured at different D:T with the VHH-Ty1 diagnostic cell in 100 μL of complete RPMI media in a single well of a 96-well plate. Non-infected cells were used as the negative controls. After 24 hours of co-culture, Nluc activity in the VHH-Ty1 diagnostic cell was assessed using the Nano-Glo® assay.

(7) Method of use for the VHH-Ty1 diagnostic cell with SARS-CoV-2 viral particles. To test if the VHH-Ty1 diagnostic cell could be used to detect presence of SARS-CoV-2 viral particles in solution, the diagnostic cell was cultured in 100 μL per well of complete RPMI media containing varying concentrations of serially diluted SARS-CoV-2 viral particles in a 96-well plate (20,000/well). Another diagnostic cell with an abrogated sensor specificity was used as a negative control. The plate was incubated at 37° C. for 24 hours before Nluc activity was assessed using Nano-Glo assay.

(8) Method of use for the VHH-Ty1 diagnostic cell to detect SARS-CoV-2 infections in animal samples. To check if the diagnostic cell can detect active infection in animal samples, we used a mouse model. Eight (8) heterozygous female K18-hACE c57BL/6J mice (strain: 2B6.Cg-Tg(K18-ACE2) 2Prlmn/J, The Jackson Laboratory) were infected intranasally using 50 μL of virus culture (5,000 PFU) per animal, following protocols approved by the Institutional Animal Care and Use Committee at SRI International (#20003), while three (3) mice were not infected (negative controls). Eight days post infection (DPI-8), the mice were euthanized and two oropharyngeal swab samples were collected from each animal. The swabs were immediately placed into collection tubes containing 500 μL of complete RPMI media and transported to the BSL3 lab for processing. For each collected swab, the collection tube was vortexed for 10-15 seconds to release cells into the media before the swab was removed from the collection tubes. The collection tube was then centrifuged at 300 g for 5 minutes to collect cell pellets. The cell pellet was then resuspended into 50 μL of complete RPMI media. In a 96-well plate, each sample (cells in 50 μL) was co-cultured with 50 μL of 25,000 VHH-Ty1 diagnostic cell in complete RPMI media. The plate was incubated at 37° C. for 24 hours before Nluc activity was assessed using the Nano-Glo assay.

(9) Viral RNA extractions and RT-qPCR analysis. Total RNA was extracted from mouse lung tissue homogenates using the Direct-zol RNA MiniPrep Kit and reverse transcription was performed using SuperScript III RT, following the manufacturer's instructions. RT-qPCR reactions were performed using TaqMan Universal PCR Master Mix, in which samples were processed using the following cycling protocol in the ViiA 7 Thermocycler (Applied Biosystems): 50° C. for 2 minutes and 95° C. for 10 minutes, followed by 40 cycles at 95° C. for 15 seconds and 60° C. for 1 minute. The primer sequences used for RT-qPCR targeted the Nucleocapsid (NC) gene of SARS-CoV-2 and are as follows: Forward: 5'-GTTTGGTGGACCCTCAGATT-3', Reverse: 5'-GGTGAACCAAGACGCAGTAT-3' and Probe: 5'-/56-FAM/TAACCAGAA/ZEN/TG-GAGAACGCAGTGGG/3IABkFQ/-3'. Assay validation was performed using SARS-CoV-2 virus genome to create a standard curve, and the detection limit was determined to be from $5\times10^6$ to 0.5 viral RNA copies per mL. Results were expressed as $\log_{10}$(viral RNA copies/mL).

(10) Statistical analysis. The experimental design for each panel in the figures is described below. GraphPad Prism 9.2.0 (GraphPad Software, Inc) was used to conduct all statistical analyses.

(i) FIGS. 18A-18D (VHH-72 diagnostic cell activation by engineered target SARS-CoV-2-Sgp-cells). Statistical analysis for all panels (FIGS. 18A-18D) was based on an unpaired two-tailed student's t-test with common variance, and the p-value of <0.05 was considered statistically significant. Comparison of data points was done by the FDR multiple comparison approach, using the two-stage step-up procedure of Benjamini, Krieger, and Yekutieli with FDR=1%, and only p-values less than an FDR of 1% were reported. The SN is calculated as the ratio of the mean Nluc activity in the VHH-72 diagnostic cell when stimulated by the target cells (SARS-CoV-2-Sgp-cells) divided by the mean Nluc activity when stimulated by the negative controls (non-engineered parental HEK293T/17 cells). The error bars extend 1 SD above and below the mean and can also be considered as one half-width of a 68% confidence interval for the mean.

(ii) FIG. 18A (Nluc activity in diagnostic cell is proportional to the number of target cells). The Nluc activity in the diagnostic cell stimulated by the target (SARS-CoV-2-Sgp-cells) or non-target cells was fitted using a four-parameter logistic model for Nluc given by $Nluc(X)=Nluc_{min}+\{Nluc_{max}-Nluc_{min}\}/\{1+10^{\wedge}[b*(\log_{10}[X^*]-\log_{10}[X])]\}$; where $Nluc(X)$ is the value of Nluc at X, X is the Target-Cell count, $Nluc_{max}$ is an estimated parameter defining a upper asymptote for Nluc activity, $Nluc_{min}$ is an estimated parameter defining a lower asymptote for Nluc activity, b is a "Hill" parameter defining the slope at the inflection point of the fitted curve, and $X_{50}$ is an estimated parameter representing the X value corresponding to $(Nluc_{max}-Nluc_{min})/2$.

(iii) FIG. 18B (Nluc activity increases with respect to amount of VHH-72 diagnostic cell). The Nluc activity in the diagnostic cell stimulated by the target (SARS-CoV-2-Sgp-cells) or non-target cells was fitted using a four-parameter logistic model $Nluc(X)$ where X is the diagnostic cell count.

(iv) FIG. 18C (Nluc activity in diagnostic cell is a function of duration of stimulation). The Nluc activity in the diagnostic cell stimulated by the target (SARS-CoV-2-Sgp-cells) or non-engineered cells was fitted using the equation $Y=a+b*\log_{10}(X)$, where X is the stimulation time in hours.

(v) FIG. 18D (Sensitivity of diagnostic cell is unaffected by the presence of non-target cells). The Nluc activity in the diagnostic cell stimulated by the target (SARS-CoV-2-Sgp-cells) or non-target cells was fitted using a four-parameter logistic model $Nluc(X)$ where X is the target cell count.

(vi) FIGS. 19A-19F (VHH-Ty1 diagnostic cell activation by infected host cells, SARS-CoV-2 virus or engineered target SARS-CoV-2-Sgp-cells). Statistical analysis for all panels as based on an unpaired two-tailed student's t-test with common variance and the p-value of <0.05 was considered statistically significant. Comparison of data points was done by the FDR multiple-comparison approach, using the two-stage step-up procedure of Benjamini, Krieger, and Yekutieli with FDR=1%, and only p-values less than an FDR of 1% were reported. The S/N is calculated as the ratio of the mean Nluc activity in the diagnostic cell when stimulated by the targets (infected Calu-3 or infected HEK293T/17 cells) divided by the mean Nluc activity when stimulated by the non-infected parental Calu-3 or HEK293T/17 cells. The error bars extend 1 SD above and below the mean and can also be considered as one half-width of a 68% confidence interval for the mean.

(vii) FIG. 19A and FIG. 19B (Nluc activity in diagnostic cell is proportional to the number of SARS-CoV-2-infected epithelial cells). The Nluc activity in the diagnostic cell stimulated by the targets (infected Calu-3 or infected HEK293T/17 cells) or non-targets (non-infected Calu-3 or non-infected HEK293T/17 cells) was fitted using a four-parameter logistic model $Nluc(X)$ where X is the infected target cell count.

(viii) FIG. 19C (Nluc activity in diagnostic cell is proportional to the number of SARS-CoV-2 viral particles in solution). The Nluc activity in the VHH-Ty1 diagnostic cell (or diagnostic cell with an abrogated sensor specificity used as a negative control) stimulated by the SARS-CoV-2 viral particles was fitted using a four-parameter logistic model $Nluc(X)$ where X is the viral particle count (PFU).

(ix) FIG. 19D (Detection of GFP expression in the VHH-Ty1 diagnostic cell using a plate-reader). The scatter plot shows the Nluc activity when the diagnostic cell was stimulated by SARS-CoV-2-Sgp-cells or parental HEK293T/17 cells. An unpaired student's two-tailed t-test was used to determine the statistical difference between the two samples, assuming a common variance and a p-value of 0.05.

(x) FIG. 19E (Detection of GFP expression in the VHH-Ty1 diagnostic cell 1 using Flow-cytometry). Expression of GFP (Relative Fluorescence Intensity) in the diagnostic cell is analyzed using Flow-Jo software 10.8.0 (BD Biosciences) and the cell counts are normalized to the respective cell type.

Figure 20A:
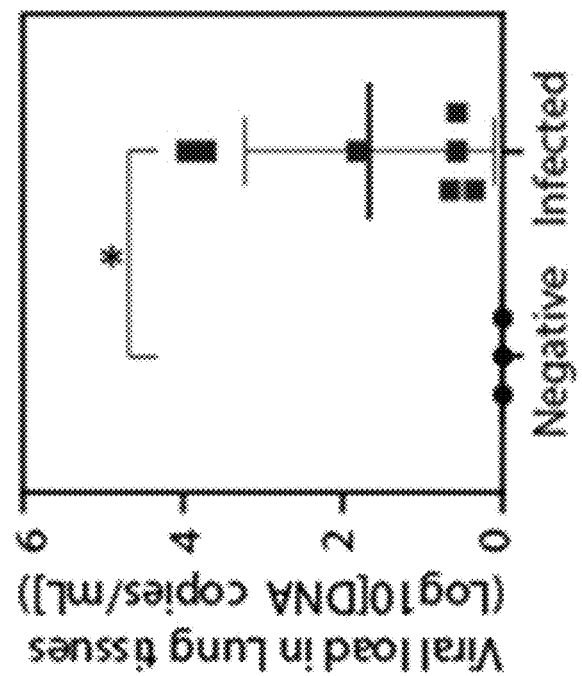
FIGS. 20A-20B illustrate results of detecting infection in mouse oropharyngeal swabs using an example diagnostic cell, in accordance with the present disclosure.

(xi) FIG. 20A (Detection of SARS-CoV-2 infection in mouse oropharyngeal swabs using the VHH-Ty1 diagnostic cell). A scatter plot (confidence interval of 95%) shows the difference between throat swabs collected from SAR-CoV-2-infected mice and non-infected mice, using an unpaired two-tailed student's t-test with Welch's correction and assuming Gaussian distribution.

Figure 20B:
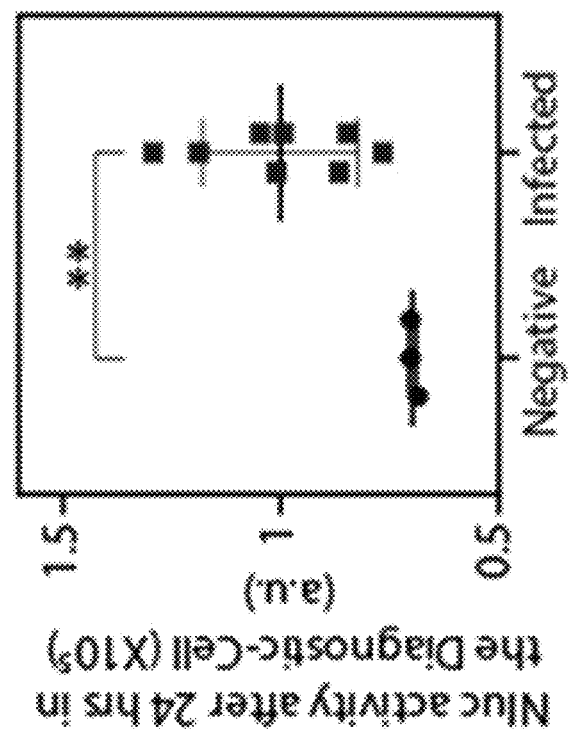

(xii) FIG. 20B (Diagnosis of SARS-CoV-2 infection in mouse lung tissues by qPCR). A scatter plot (confidence interval of 95%) shows the difference between viral loads of mouse lungs tissues collected from SAR-CoV-2-infected mice and non-infected mice, using an unpaired two-tailed students' t-test with Welch's correction and assuming Gaussian distribution.

Figure 21B:
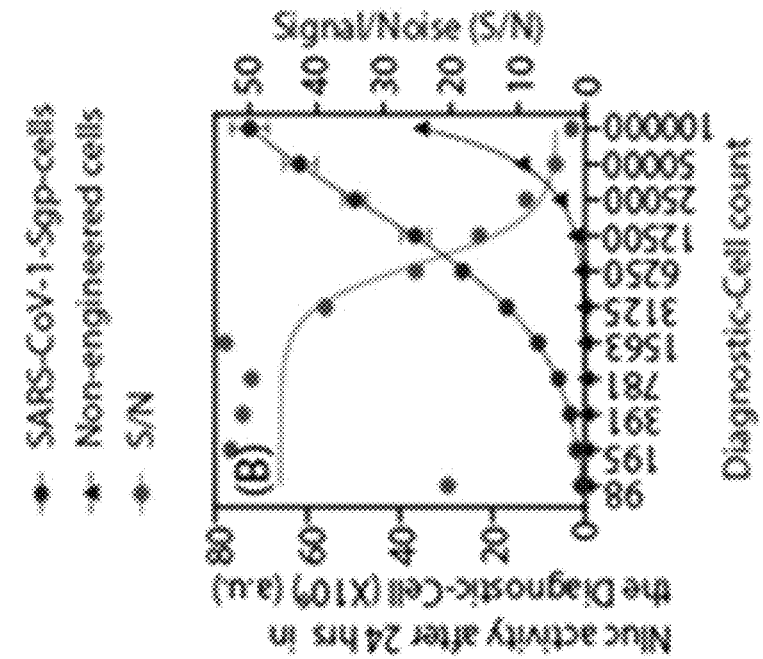
FIGS. 21A-21D illustrate example results of assessing VHH-72 diagnostic cell activation by genetically engineered target SARS-CoV-1-Sgp-cells, in accordance with the present disclosure.
Figure 21A:
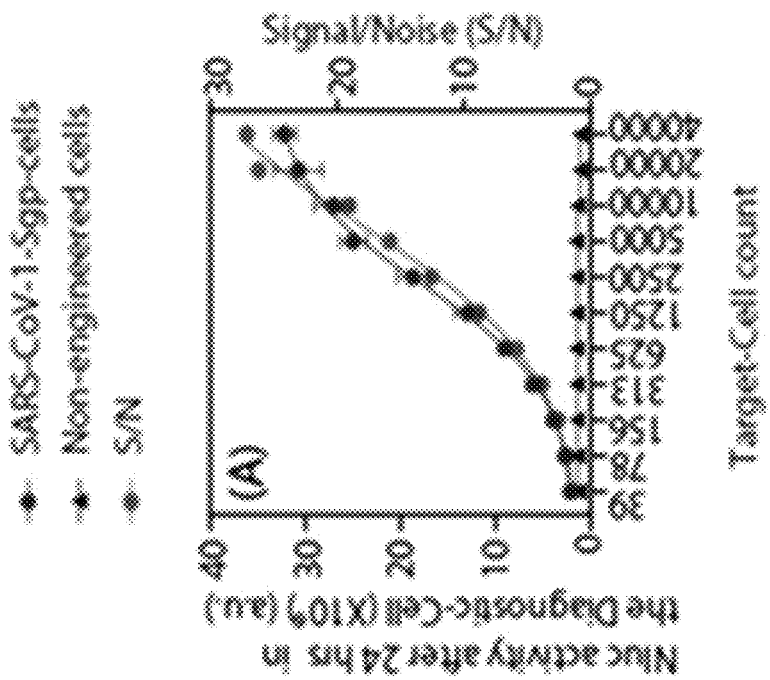
Figure 21D:
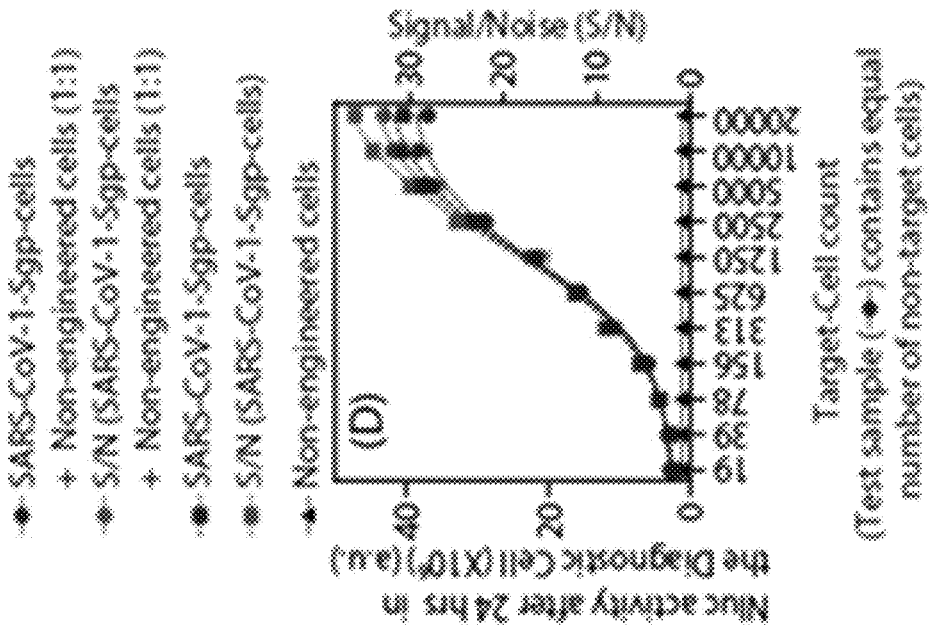
Figure 21C:
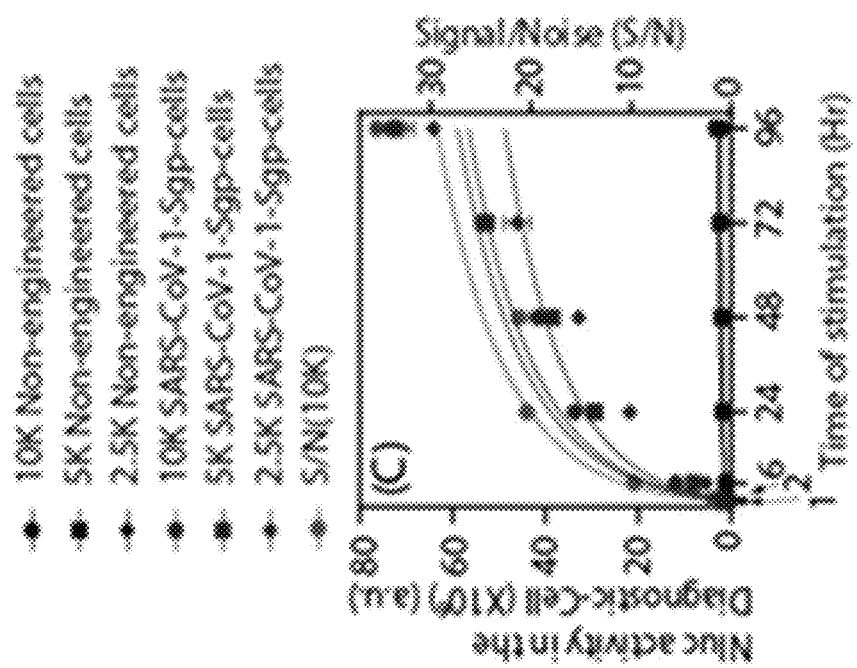

(xiii) FIGS. 21A-21B (VHH-72 diagnostic cell activation by engineered target SARS-CoV-1-Sgp-cells). Statistical analyses for SARS-CoV-1 related investigations reported in all panels (A-D) were similar to that employed for SARS-CoV-2 in the respective panels of FIG. 18A-18D.

(xiv) FIG. 22 (Screening of different diagnostic cells with specificity towards SARS-CoV-2 and SARS-CoV-1). The Nluc activity in the diagnostic cell stimulated by the target (SARS-CoV-2-Sgp-cells or SARS-CoV-1-Sgp-cells) or non-target cells was fitted using a four-parameter logistic model $Nluc(X)$ where X is the target cell count.

Figure 23:
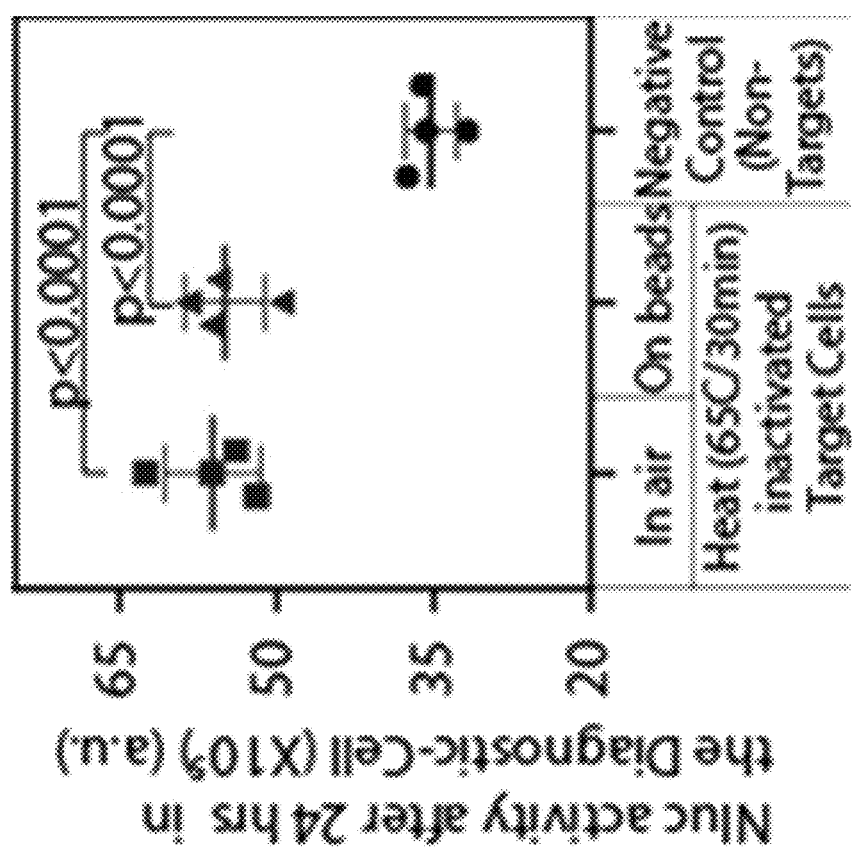
FIG. 23 illustrates detection of heat-inactivated target cells by example VHH-Ty1 diagnostic cells, in accordance with the present disclosure.

(xv) FIG. 23 (Detection of heat-inactivated target cells by the VHH-Ty1 diagnostic cell). A scatter plot (confidence interval of 95%) shows the difference in Nluc expression signal in the diagnostic cell by heat-inactivated engineered Sgp-presenting target cells (by air or beads at 65° C.) versus non-engineered cells, using an unpaired two-tailed students' t-test, assuming Gaussian distribution and that both sample means have the same standard deviations.

Figure 24:
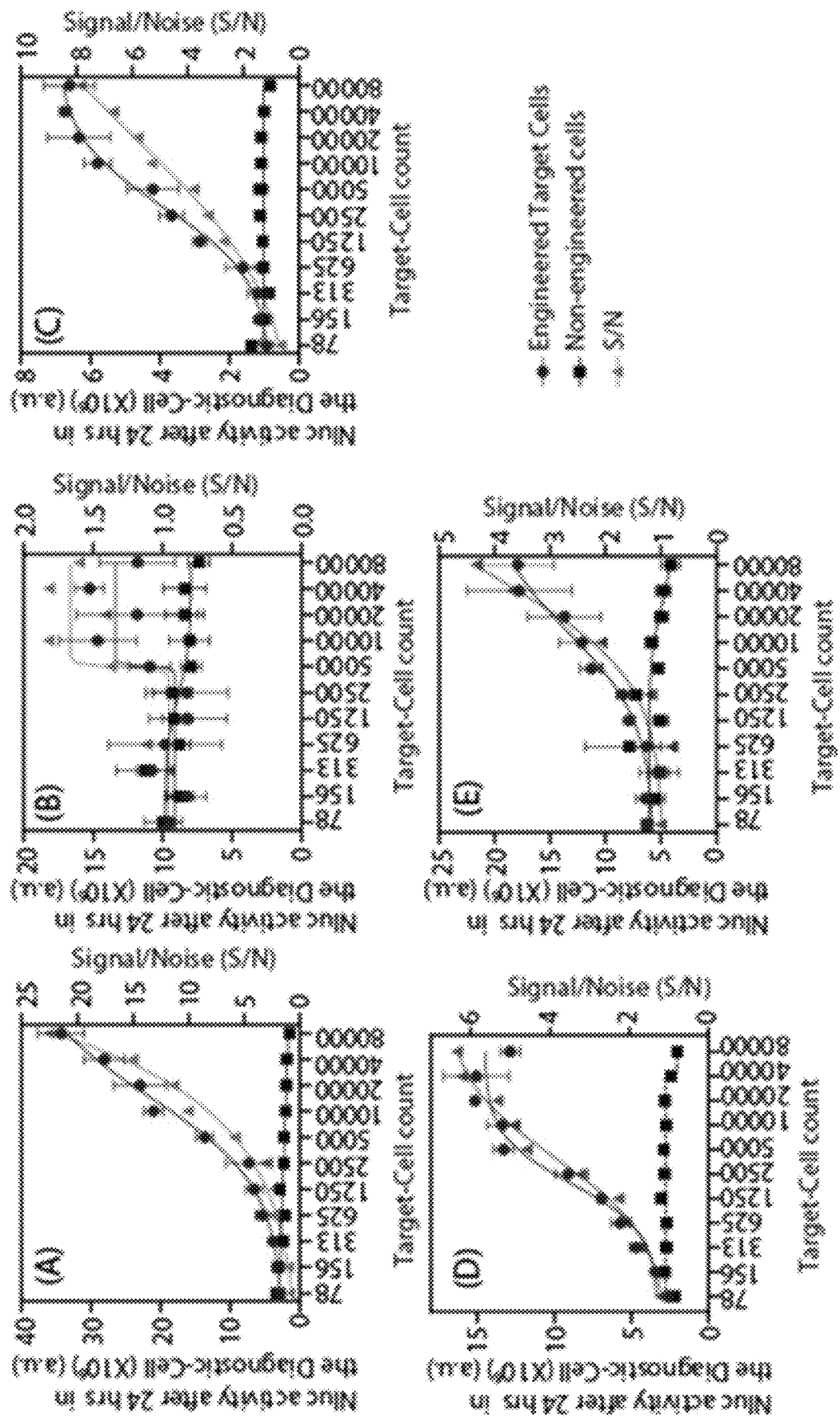
FIG. 24 illustrates example assessment of different diagnostic cells generated with specificity to other emerging viruses, in accordance with the present disclosure.

(xvi) FIG. 24 (Development of different diagnostic cells with specificity to other emerging viruses). The Nluc activity in the diagnostic cell stimulated by different target cell types (engineered target cells displaying the glycoproteins from (A) Ebola virus; (B) Marburg virus; (C) Chikungunya virus; (D) Nipah virus; and (E) West-Nile virus) or non-target (non-engineered parental HEK293T/17) control cells was fitted using a four-parameter logistic model $Nluc(X)$, where X is the target cell count.

Other experimental embodiments were directed to transforming T-cells to generated genetically modified reporter cells, which can be used to provide qualitative immunity information and/or assess immunity of a population via serology tests. For example, a sampling of hosts (e.g., subjects) of a population can be assessed to provide population status information on protective immunity, disease prevalence, and efficacy of vaccination programs. Such data can be gathered using serology tests that are scalable and have high-throughput with rapid turn-around time. In various experimental embodiments, a serology test platform was generated and assessed that used a pair of genetically engineered cells (e.g., reporter cell and test cell) to rapidly detect IgG antibodies with specificity for SARS-CoV-2. The serology test is a low-cost option for screening mass populations and has the potential for rapid scale-up. The serology test can be used to screen individuals for the presence of antibodies and measure their anti-viral immunity.

Various experimental embodiments were directed to generating and assessing the serology test platform, an antibody-specific reporter cell complex that can be used to identify individuals harboring antibodies against specific viral antigens. The test platform was validated by detecting antibodies against SARS-CoV-2 from clinical specimens. This platform can be quickly redirected to identify antibodies against any virus by generating different target cells. This technology is based on the ability of the T-cells to regulate its activation cascade on interaction with the genetically modified antigen-presenting cell. The complex is formed by engineering two cell types that compose the reporter cell complex, a T-cell-based reporter cell and an antigen-presenting target cell.

Figure 25B:
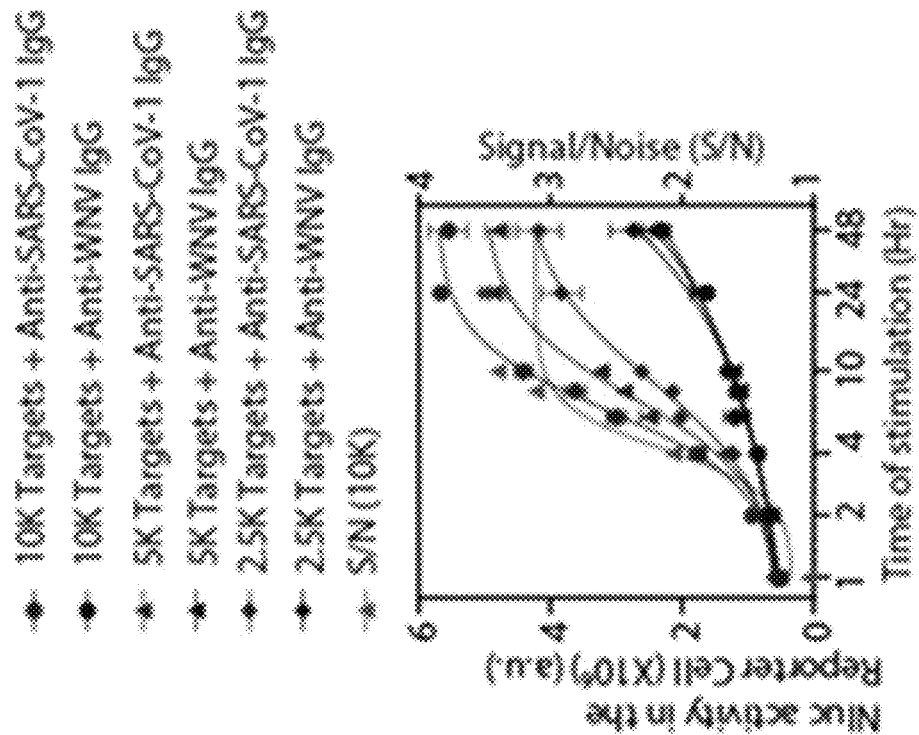
FIGS. 25A-25D illustrate plots characterizing assessment of example reporter cell complexes, in accordance with the present disclosure.
Figure 25A:
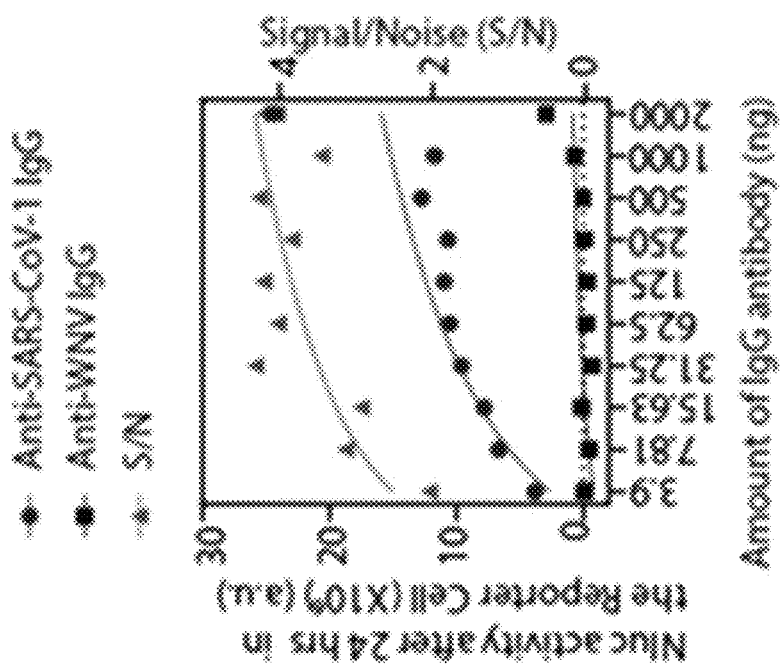
Figure 25D:
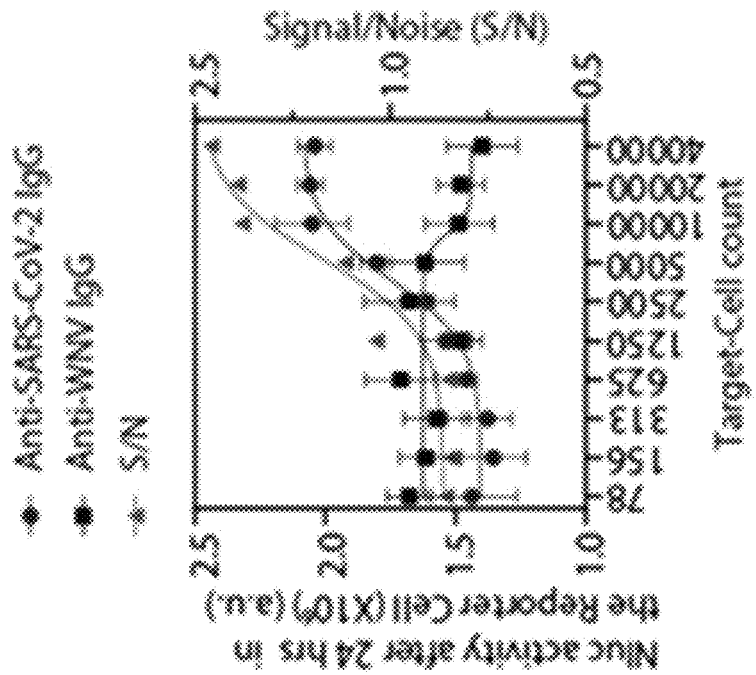
Figure 25C:
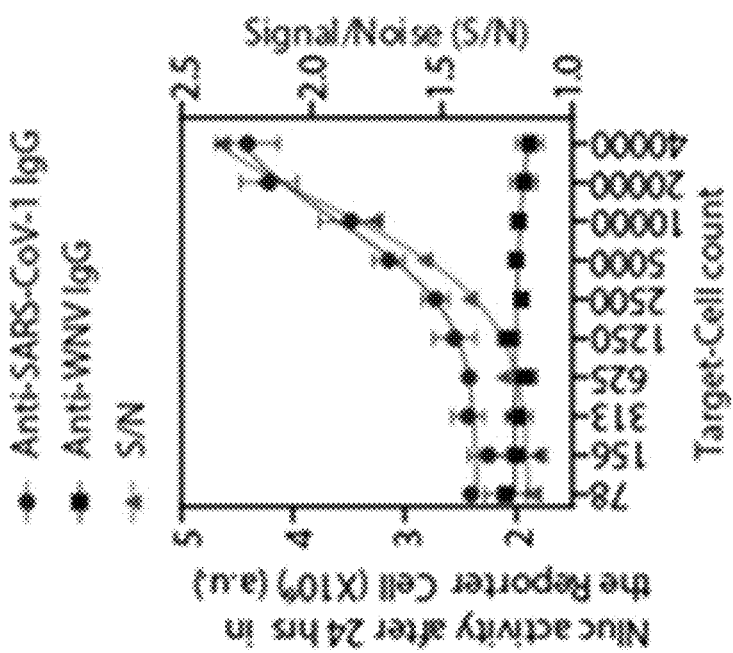

The target cell is a fast-growing clone of an easy-to-transfect cell line derived from the kidney cells of a human embryo (HEK293T/17) that has been genetically engineered to stably display the Sgp of the SARS-CoV-2 virus. The sequence of Sgp can be exchanged to present any other viral antigenic biomarker. The reporter cell is a fast-growing, immortalized human T-acute lymphoblastic leukemia (T-ALL) cell line (Jurkat cells, doubling time around 20 hours) genetically engineered to upregulate a dual reporter system that exhibits fluorescence (green fluorescent protein, GFP) and bioluminescence (NanoLuc® or Nluc) on recognizing the Fc region of an Sgp-specific immunoglobulin G (IgG) bound to Sgp on the target cell.

Referring back to FIG. 6B, FIG. 6B illustrates a schematic of the reporter cell complex that detects the anti-Sgp IgG antibodies. The target cell is composed of HEK293T/17 as the cellular chassis engineered to stably express the viral Sgp on its surface. The Sgp insert was sub-cloned into the PiggyBac system backbone and was then used for stable integration to generate the genetically modified target cell (see FIG. 6C). This approach transforms the reporter cell complex serology test technology into a broadly applicable platform because the Sgp sequence can be exchanged for any antigenic biomarker on the target cell, thereby redirecting the specificity of the complex toward the antibody of interest. This strategy was used to develop the reporter cell complex with specificity for SARS-CoV-2 or SARS-CoV-1. FIG. 6D details the gene insert that was used with the lentivirus transduction process to generate the reporter cell with specificity toward the Fc region of IgG antibodies. The reporter cell is encoded with an artificial cell-signaling pathway with the following three domains: the receptor element, a transmembrane molecule that includes an extracellular Fc-region binding portion (senor or binding domain) at its distal end and mobilizes; the actuator element, the T-cell's activation machinery that upregulates the effector protein, a dual reporter system (GFP-2A-Nluc) upregulated when the antibody is also bound to the Sgp on the target cell through its Fab portion.

To illustrate the function of the antibody-specific reporter cell complex for detecting the presence of virus-specific antibodies and identifying individuals with antibodies against viral infections, the parental HEK293T/17 cell line was transformed into two different types of target cells: 1) SARS-CoV-1-Sgp-cells and 2) SARS-CoV-2-Sgp-cells, which constitutively and stably express the Sgp from SARS-CoV-1 and SARS-CoV-2, respectively. The reporter cell was engineered to express GFP and Nluc transgenes as activation-inducible reporters (linked through a self-cleavable peptide linker) to quantitatively respond to the intensity of the stimulus. The sensor portion (part of the receptor element) of the reporter cell comprises the sequence of the Fc-region-binding domain from the bacterial Protein A (zz-domain; GenBank: M74186). The formation of immune synapse, assisted via the analyte antibody (see schematic in the FIG. 6B), results in transcriptional regulation of the reporter system (effector element) through intracellular calcium rise for quantitative assessment of the infection. To demonstrate the functionality of the reporter cell complex and its ability to identify different antibody (IgG) types, parallel validation assays were conducted using IgG antibodies with specificity for both SARS-CoV-1 and SARS-CoV-2; and, the assay were incubation with the two different target cells, SARS-CoV-1-Sgp-cell and SARS-CoV-2-Sgp-cell, respectively. Isotype IgG against the envelop glycoprotein of the West Nile Virus (Anti-WNV IgG) was used as a negative control in all panels and at the concentration similar to that of the analyte antibody.

FIGS. 25A-25D illustrate plots characterizing assessment of example reporter cell complexes, in accordance with the present disclosure. A reporter cell was incubated with the target cell to form the reporter cell complex in presence of target cell specific IgG antibody. The Nluc activity in the reporter cell (12,500 cells) is proportional to the Anti-SARS-CoV-1 IgG antibody titer, as shown by FIG. 25A, increased with respect to time, as shown by FIG. 25B, increased proportionally to the number of engineered target SARS-CoV-1-Sgp-cells, as shown by FIG. 25C, and increased proportionally to the number of engineered target SARS-CoV-2-Sgp-cells, as shown by FIG. 25D. A total of 10,000 target cells were used for FIGS. 25A-25B and were varied in FIGS. 25C-25D as represented along the x-axis. In all experiments, anti-WVN-Egp antibody was used as a negative control. Nluc activity for all observations was measured using n=4; error bars indicate ±1 SD and can also be considered as one half the width of an 68% confidence interval for the mean.

FIG. 25A demonstrates that, in addition to the qualitative detection of the infection, the reporter (Nluc) activity of the reporter cell complex also provides a quantitative measure proportional to the antibody titer. The SN, defined in the figure legend, quantifies the sensitivity of the reporter cell complex. The S/N was around 2 at low IgG antibody titer (around 4 ng) of the SARS-CoV-1-specific IgG ($p<0.0001$); the reporter cell—to—target cell ratio (R:T)=1.25:1 and logarithmically increases to around 4 at higher titers, a generally reported observation in serology tests. The data in FIG. 25B illustrates the reporter kinetics of the reporter cell complex upon engaging SARS-CoV-1-specific IgG and compared to the isotype control antibodies. The reporter cell complex, with serially diluted target cells (10,000; 5,000; and 2,500 SARS-CoV-1-Sgp-cells) was used. The Nluc activity from the reporter cell was detected as early as 2 hours (S/N=around 1.4, $p<0.002$) when a 10,000 target cells were used, and it increased steadily for the duration of the assay (at 48 hours, $p<0.0001$). The wide time window for the readout can assist mass screening efforts by accommodating a large test-sample size. A representative S/N curve is included for 10,000 SARS-CoV-1-Sgp-cells. Additionally, while the signal from the reporter cell was high in proportion to the higher target cell count, the kinetics of the test were faster at a lower target cell count. At 1 hour, a statistically significant increase in the signal was observed for 2,500 targets (S/N=around 1.16, $p<0.005$) and 5,000 targets (S/N=around 1.14, $p<0.005$), compared to 10,000 target cells (S/N=around 1.04, $p=0.16$).

FIGS. 25C-25D demonstrate the platform nature of the reporter cell complex and the effect of the target cell count on the sensitivity of the test. The data shows that, when using the same amount of target-specific IgG antibody, the reporter cell activity increases proportionately to the number of target cells. On the other hand, the signal from the reporter cell complex when incubated with the isotype-control antibody did not increase. FIG. 25C uses the SARS-CoV-1-Sgp-cells as target cells and detects SARS-CoV-1-specific IgG; the signal was statistically higher compared to isotype control ($p<0.02$ at all R:T<20:1). FIG. 25D uses the SARS-CoV-2-Sgp-cells to detect SARS-CoV-2-specific IgG; signal in this case was statistically higher at all R:T<1.25:1 ($p<0.002$), compared to the isotype control.

Figure 28:
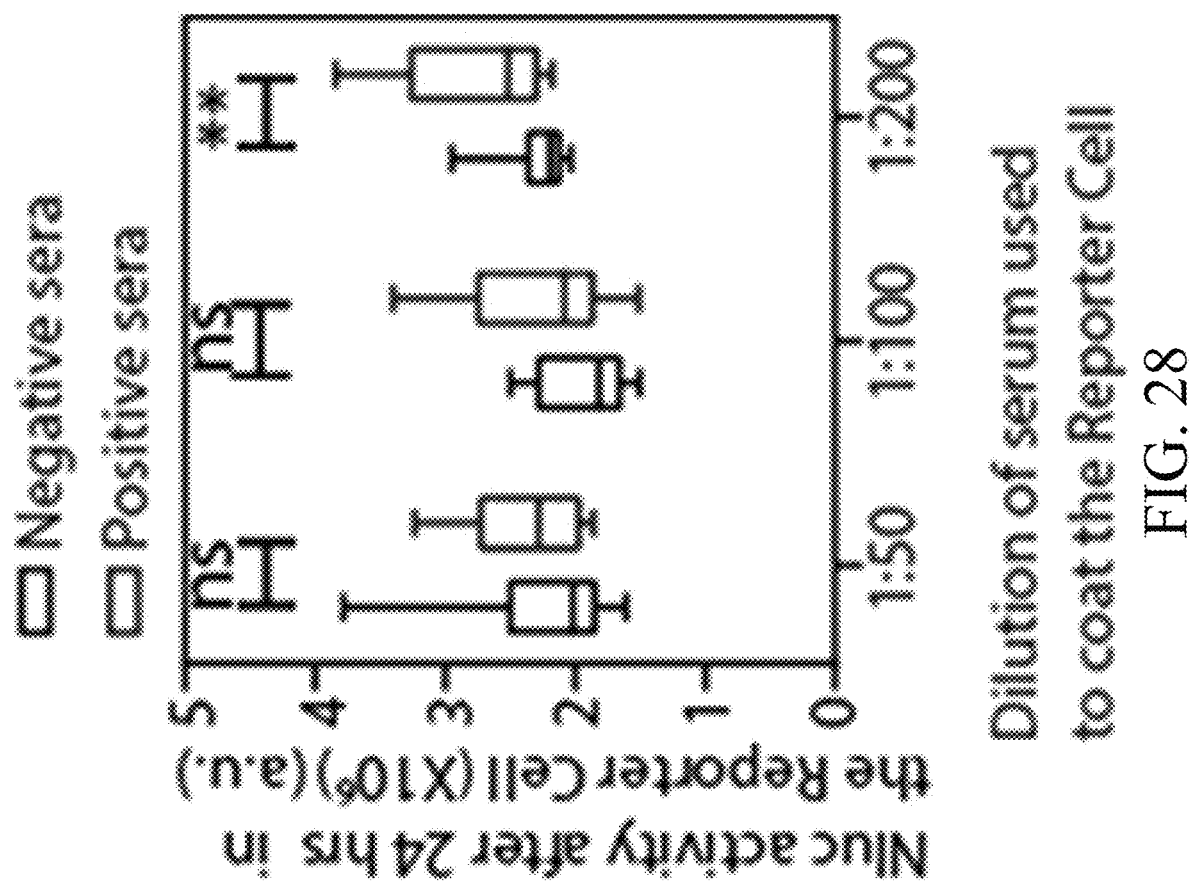
FIG. 28 illustrates a plot characterizing sensitivity of an example reporter cell complex using different sera dilutions, in accordance with the present disclosure.

To characterize the performance of the serology test platform for detecting SARS-CoV-2 IgG antibodies, a commercially available panel of serum samples from 10 COVID-19 patients and 10 negative controls was used. All specimens were previously examined using the Abbott Architect IgG assay for SARS-CoV-2 IgG antibodies. Similar procedures, as reported in FIGS. 25A-25D, were employed to create the reporter cell complex, and the results were assessed for sensitivity and specificity. Patient sera was initially serially diluted (1:50, 1:100, 1:200) in the cell-culture media to determine the optimal dilution for improved sensitivity (FIG. 28). The dilution of 1:200 ($p<0.05$) was selected for use in subsequent assays and can be further optimized.

Figures 26A, 26B:
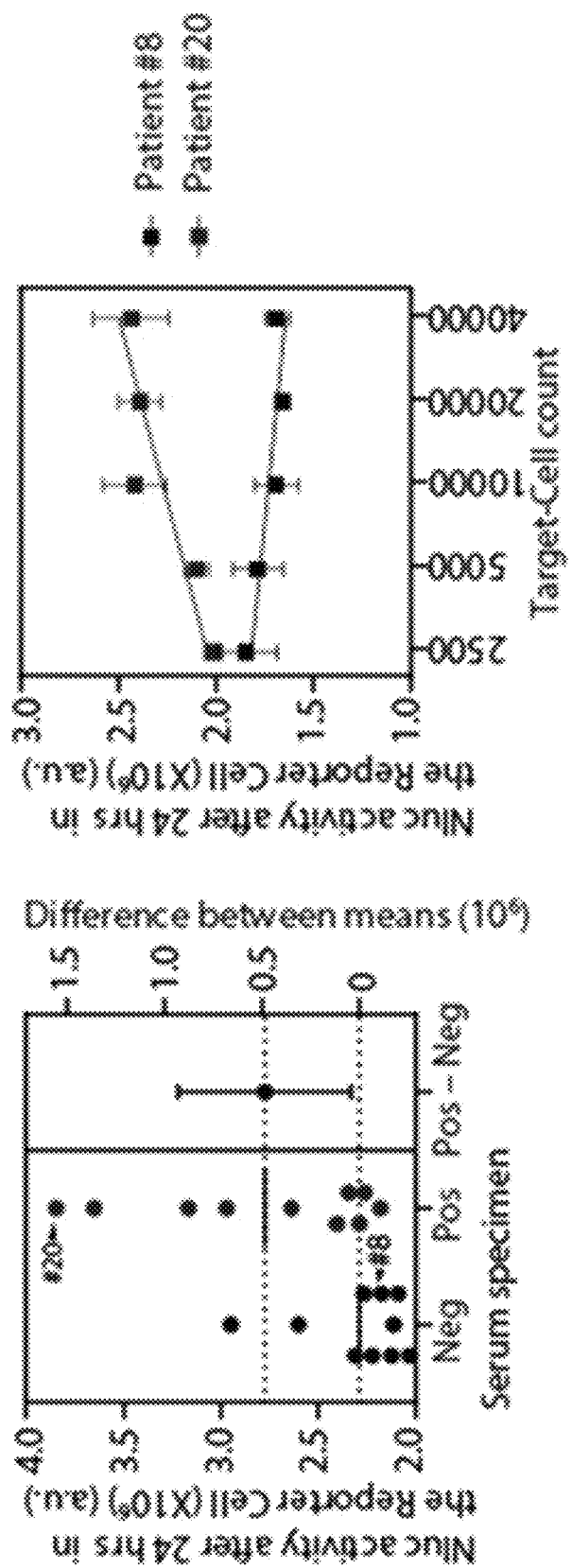
FIGS. 26A-26D illustrate plots characterizing assessment of use of an example reporter cell complex in a serology test using a commercial serum panel, in accordance with the present disclosure.
Figure 26D:
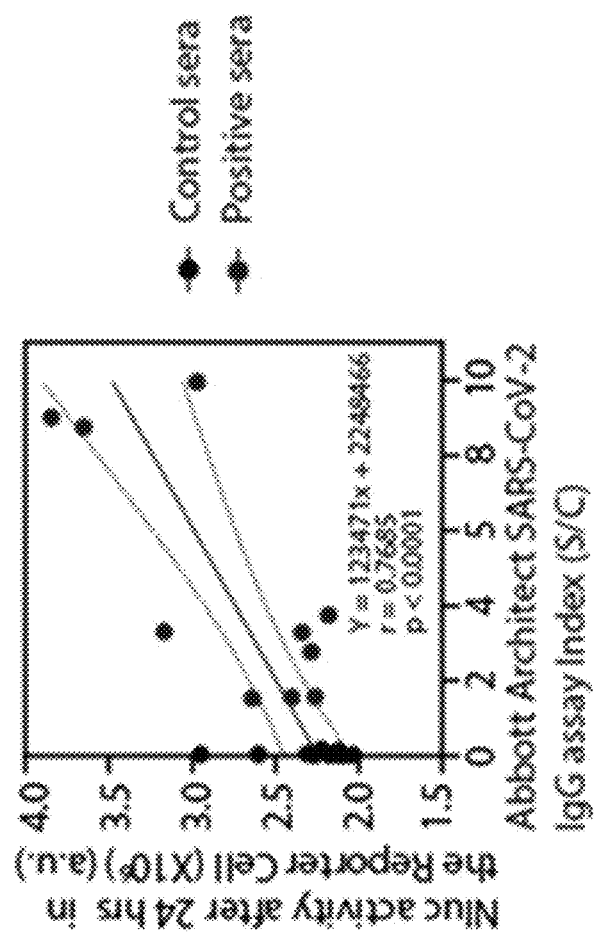
Figure 26C:
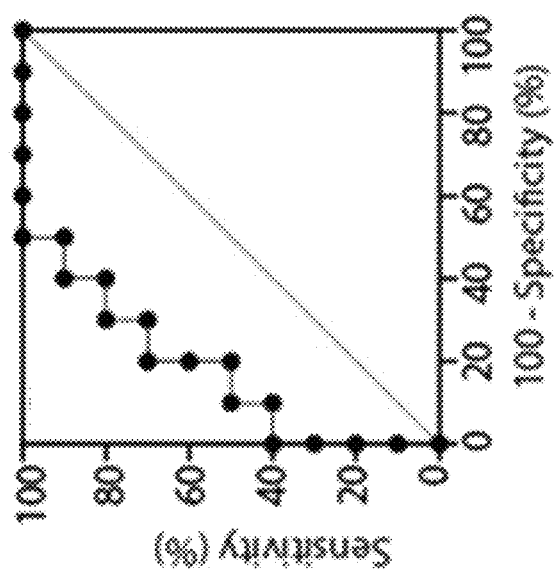

FIGS. 26A-26D illustrate plots characterizing assessment of use of an example reporter cell complex in a serology test using a commercial serum panel, in accordance with the present disclosure. FIG. 26A is an estimation plot that shows that the reporter cell complex significantly differentiates ($p<0.05$) between patient sera (positive, n=10) and control sera (negative, n=10) samples (1:200 sera dilution; 10,000 target SARS-CoV-2-Sgp-cells; 24 hours). The horizontal lines indicate the mean values for the respective groups. The p value was calculated using an unpaired two-tailed Student's t-test. FIG. 26B shows that the Nluc activity in the reporter cell (12,500 cells) increased proportionally to the target SARS-CoV-2-Sgp-cells (10,000 cells) with specimen #20 (positive) serum but not with specimen #8 (negative) serum. FIG. 26C shows an ROC analysis of the reporter cell complex, using the Abbott Architect IgG assay as the gold standard, with an AUC value of 0.830. FIG. 26D shows a correlation analysis of 20 SARS-CoV-2 sera panels with different levels of SARS-CoV-2 IgG antibodies analyzed by the Abbott Architect IgG assay verses the reporter cell complex. Correlation and linear regression analyses were performed using Pearson's correlation coefficients. Mean Nluc activity values of Diagnostic-Cell-Complex are plotted on the y-axis, while index values of the Abbott Architect IgG assay are shown on the x-axis. Statistical significance was calculated using the two-tailed test. The dashed lines indicate the standard deviations of the linear regression plots. Nluc activity for all observations was measured using n=4; error bars indicate ±1 SD.

The estimation plot in FIG. 26A demonstrates the magnitude of the difference in means of two clinical specimen groups (positive or negative for the SARS-CoV-2 antibodies) as assessed by a serology test. At the 95% confidence interval, the difference between the two means is greater than zero, demonstrating statistical significance ($p<0.05$) of the test. FIG. 26B illustrates an enhanced approach in context of the reporter cell complex, which was introduced to differentiate between the seropositive specimens at a low antibody titer from the seronegative specimens. It is believed that, unlike the seronegative specimen, incubation of the fixed quantity of seropositive specimen with serially diluted target cell count will proportionately reduce the stimulation of the reporter cell and show up as a slope of the reporter cell signal. This approach was confirmed as shown in FIG. 26B. The presence of slope in the reporter cell signal from the reporter cell complex, when incubated with a seropositive specimen differentiates it from the seronegative specimen ($p<0.004$ at all R:T<2.5:1) and offers to minimize the instances of false-negatives and false-positives. To determine the robustness of the serology test based on the reporter cell complex and its performance in clinical-sample testing, a receiver operating characteristics (ROC) curve analysis was used, as shown in FIG. 26C. Using the Abbott Architect IgG assay as the gold-standard test, the ROC curve showed an area-under-the-curve (AUC) value of 0.83 ($p<0.05$). At a cut-off value of 2276910 a.u., the serology assay showed an optimal sensitivity and specificity of 80% and 70%, respectively. Table 3 reports a complete analysis of the results, showing a positive predictive value of 72.7%, a negative predictive value of 77.8%, and a likelihood ratio of 2.667. FIG. 26D demonstrates the linear relationship between our reporter cell complex test benchmarked against the Abbott Architect IgG assay as the reference standard. Pearson-correlation analysis between results of the 20 serum samples using the reporter cell complex serology test and the gold standard produced a correlation coefficient of 0.77. Linear regression analysis indicated the R-squared value of 0.59 ($p<0.0001$) when reporter cell activity from the reporter cell complex-based serology test was plotted against the Abbott Architect IgG assay values.

TABLE 3

Contingency table analysis to determine the accuracy of the Diagnostic-Cell-Complex, using the Wilson-Brown method; Abbott Architect IgG assay used as the gold standard.

| Data analyzed | COVID-19 IgG positive | COVID-19 IgG negative | Total |
|---|---|---|---|
| Diagnostic-Cell-Complex Positive | 8 | 3 | 11 |
| Diagnostic-Cell-Complex Negative | 2 | 7 | 9 |
| Total | 10 | 10 | 20 |

| Effect size | Value | 95% CI |
|---|---|---|
| Sensitivity | 0.8 | 0.4902 to 0.9645 |
| Specificity | 0.7 | 0.3968 to 0.8922 |
| Positive Predictive Value | 0.7273 | 0.4344 to 0.9025 |
| Negative Predictive Value | 0.7778 | 0.4526 to 0.9605 |
| Likelihood Ratio | 2.667 | |

Figure 27A:
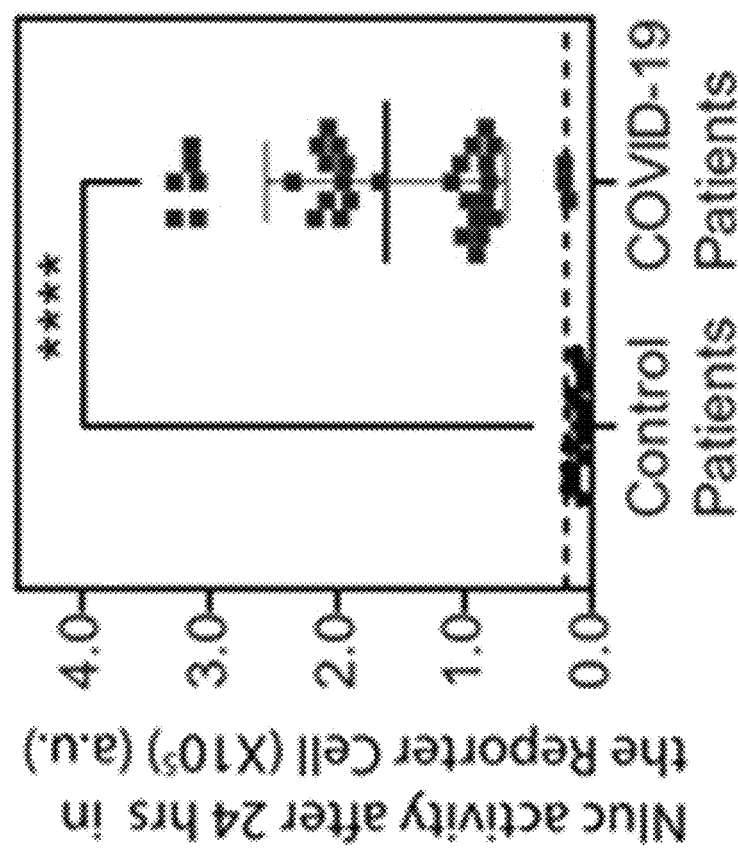
FIGS. 27A-27B illustrate plots characterizing clinical validation of an example reporter cell complex for detecting IgG antibodies specific to SARS-CoV-2, in accordance with the present disclosure.
Figure 27B:
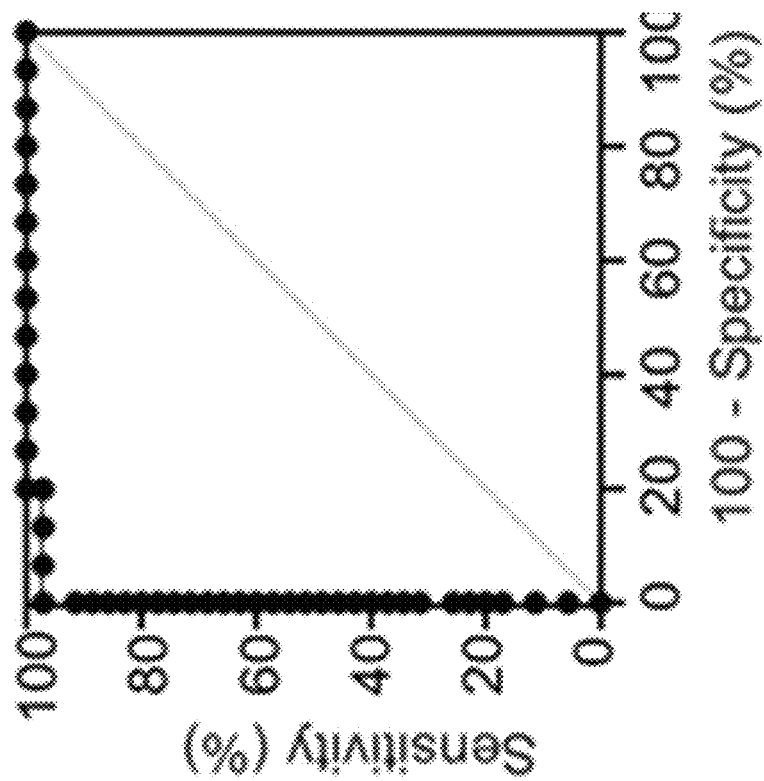

FIGS. 27A-27B illustrate plots characterizing clinical validation of an example reporter cell complex for detecting IgG antibodies specific to SARS-CoV-2, in accordance with the present disclosure. FIG. 27A is a scatter plot showing that the reporter cell complex significantly differentiates between control subjects and COVID-19 patients ($p<0.0001$). The dotted horizontal line represents a positive cut-off value based on the ROC analysis. The p value was calculated using an unpaired two-tailed student's t-test. FIG. 27B shows an ROC analysis of the reporter cell complex, based on qPCR results, with an AUC value of 0.9941. Patient sera was diluted at 1:200 and incubated with target SARS-CoV-2-Sgp-cells (10,000 cells) for 24 hours (COVID-19 patients, n=34 and control patients, n=15). Nluc activity for each serum sample was measured using n=4; error bars indicate ±1 SD of the mean.

To ensure reliability and reproducibility, FIGS. 27A-27B illustrates the results from the serology test conducted on another set of 49 serum samples (control subjects=15, COVID-19 patients=34) obtained from UC Davis Health. All serum samples used for validation were from patients with confirmed qPCR test results for SARS-CoV-2 RNA. FIG. 27A shows that the serology test detected Sgp-IgG antibodies in individuals with prior exposure to SARS-CoV-2 virus compared to the control subjects (p<0.0001). For the proof-of-principle studies, the signal from the reporter cell complex was assessed after 24 hours. The results in FIG. 27B show that the test can be significantly faster with the potential to inform on the seropositivity within 2 hours. Based on the clinical status (qPCR result), the ROC curve analysis in FIG. 27B further demonstrates the accuracy of the reporter cell complex serology assay with an AUC value of 0.9941 (p<0.0001). At a cut-off value of 18824 a.u., the serology assay showed an optimal sensitivity of 97.04% and specificity of 93.33% for detecting anti-Sgp IgG antibodies. Table 4 below shows a contingency-table analysis with a positive predictive value of 97.04%, a negative predictive value of 93.33%, and a likelihood ratio of 14.56.

TABLE 4

Contingency table analysis to determine the accuracy of the reporter cell complex, using the Wilson-Brown method; RT-qPCR used to determine clinical status of patients.

| Data analyzed | COVID-19 positive | COVID-19 negative | Total |
|---|---|---|---|
| Diagnostic-Cell-Complex Positive | 33 | 1 | 34 |
| Diagnostic-Cell-Complex Negative | 1 | 14 | 15 |
| Total | 34 | 15 | 49 |

| Effect size | Value | 95% CI |
|---|---|---|
| Sensitivity | 0.9706 | 0.8508 to 0.9985 |
| Specificity | 0.9333 | 0.7018 to 0.9966 |
| Positive Predictive Value | 0.9706 | 0.8508 to 0.9985 |
| Negative Predictive Value | 0.9333 | 0.7018 to 0.9966 |
| Likelihood Ratio | 14.56 | |

FIG. 28 illustrates a plot characterizing sensitivity of an example reporter cell complex using different sera dilutions, in accordance with the present disclosure. The Nluc activity in the reporter cell (12,500 cells) varied with respect to serum dilutions. SARS-CoV-2-Sgp-cells (10,000 cells) were used. Each data bar represents Nluc activity for observations measured using n=10; error bars indicate ±1 SD.

Synthesis and Experimental Information for Reporter Cell Complex (1) Materials and reagents. Jurkat E6-1 (ATCC, Cat #TIB-152) cell line was maintained in complete RPMI media (RPMI1640 [Corning, Cat #10-040-CV], 10% heat-inactivated fetal bovine serum or FBS [Sigma-Aldrich, Cat #F2442-500ML], and 1× Penicillin-Streptomycin solution [Corning, Cat #30-002-Cl]). HEK293T/17 cells (ATCC, Cat #CRL-11268) cultured in complete DMEM (DMEM growth media [Corning, Cat #10-013-CV] supplemented with 10% heat-inactivated FBS and 1× Penicillin-Streptomycin). Plasmids encoding different genetic payloads (transfer plasmids) were designed in SnapGene software (GSL Biotech LLC) and sub-cloned into lentivirus vector plasmid (System Biosciences, Cat #CD510B-1). 2nd generation packaging plasmids (psPAX2 [Cat #12260] and pMD2.G [Cat #12259]) were obtained from Didier Trono (Ecole Polytechnique Fédérale de Lausanne, Lausanne, Switzerland) through Addgene. pAdvantage was obtained from Promega (Cat #E1711). Johns Hopkins University School of Medicine provided the PiggyBac Transposase sequence. All plasmid preparation services (chemical synthesis of DNA insert sequences, sub-cloning into respective vector backbones, and the amplification) were obtained from Epoch Life Science, Inc. (Missouri City, Tex.). For lentivirus production, plasmid transfections into parental HEK293T/17 cells were performed using Transporter 5™ reagent (Polysciences, Inc., Cat #26008-5). Polybrene (Abm®, Cat #G062) was used for lentivirus transductions into Jurkat cells. TransIT®-2020 transfection reagent (Mirus #MIR5400) was used to transfect and make stable target cells. Puromycin dihydrochloride (ThermoFisher Scientific, Cat #A1113803) was used for selecting stable cells. Anti-SARS-CoV-1 Sgp monoclonal antibody or 5230 (Absolute Antibody, Cat #Ab00268), Anti-SARS-CoV-2 Sgp monoclonal antibody (SinoBiological, Cat #40150-R007), and Anti-West Nile virus envelop glycoprotein (WNV-Egp) monoclonal antibody (SinoBiological, Cat #40345-MM03) were used for characterization experiments of the reporter cell complex. Nano-Glo® assay kit (Promega, Cat #N1120) was used to assess expression of the Nluc protein.

(1.1) Source of COVID-19 patient sera samples. For the initial assay characterization, a commercially available panel of 20 COVID patient serum specimens (10 positive SARS-CoV-2-IgG and 10 negative SARS-CoV-2-IgG sera samples), confirmed using the Abbott Architect SARS-CoV-2-IgG assay, were obtained from Boca Biolistics (Cat #C0050-0001). The samples were heat-inactivated at 65° C. for 30 minutes to allow safe handling in a BSL2 laboratory, and stored in a −80° C. freezer until required. For clinical validation, 49 serum samples from individuals with confirmed qPCR results for presence/absence of SARS-CoV-2 RNA were obtained from UC Davis Health (University of California Davis) (control subjects, n=15 and COVID-19 confirmed patients, n=34).

(1.2) Lentivirus production. Lentivirus particles were prepared by packaging the transfer plasmid using $2^{nd}$ generation lentivirus system as detailed previously.

(1.3) Generation of the reporter cell (R) component of the reporter cell complex. The Jurkat E6-1 suspension cell line was engineered with lentivirus particles carrying the genetic payload (FIG. 6B), as detailed previously. The receptor domain was replaced with the synthetic sequence from the bacterial Protein A (zz-domain; GenBank: M74186), previously reported to bind to the Fc region of immunoglobulin G (IgG) antibodies. The cells were treated with lentivirus in the presence of 8 µg/mL Polybrene. After 48 hours, the engineered cells were placed in selection using 0.5 µg/ml of puromycin dihydrochloride. The unmodified parental cell line was also placed under selection as a positive control for determining the minimum lethal concentration of puromycin. Following selection, cells were expanded as required for different assays and frozen using freezing media.

(1.4) Generation of the target cell (T) component of the reporter cell complex. The HEK293T/17 adherent cells were engineered to stably express viral Sgp, using the PiggyBac Transposon system, as previously described. Two plasmids were designed with the piggyBac transposon backbone (System Biosciences, Cat #PB510B-1) to either express the Sgp of SARS-CoV-1 (SARS-CoV-1-Sgp; GenBank: AAP13567.1) or of SARS-CoV-2 (SARS-CoV-2-Sgp; GenBank: QHD43416.1) on the cell surface. A monolayer of HEK293T/17 cells were transfected with both the Transposon plasmid (carrying gene of interest) and Transposase plasmid, in a ratio of 2.5:1, using TransIT®-2020 transfection reagent. After 48 hours of transfection, the transfected cells were placed under selection using Puromycin dihydrochloride. The unmodified parental HEK293T/17 cell line was also placed under selection as a positive control to determine the minimum lethal concentration of puromycin. The generated stable cell lines were labeled as SARS-CoV-1-Sgp-cells (HEK293T/17 cells engineered to stably express the Sgp from SARS-CoV-1) and SARS-CoV-2-Sgp-cells (HEK293T/17 cells engineered to stably express the Sgp from SARS-CoV-2). The cells were then expanded for different assays.

(1.5) Method of use of reporter cell complex for serology test.

(i) With research-grade antibodies against SARS-CoV-1-Sgp or SARS-CoV-1-Sgp during technology development (FIGS. 25A-25D and 28). The reporter cell (12,500 in 50 μL of complete RPMI media) was incubated with varying concentrations (or as stated) of the Anti-SARS-CoV-1 IgG (S230) or Anti-SARS-CoV-2 IgG monoclonal antibodies for 30 minutes at 37° C., washed once, and then co-cultured with 10,000 target cells (SARS-CoV-1-Sgp-cells or SARS-CoV-2-Sgp-cells, respectively) in 100 μL of complete RPMI media per well of a 96-well plate. As a negative control, the reporter cell was coated using a non-specific Anti-WNV-Egp monoclonal antibody and co-cultured with the same target cells. After the specified time in co-culture, NanoLuc® (Nluc) activity in the reporter cell was assessed using Nano-Glo® assay kit, following the manufacturer's instructions. The Nluc enzyme substrate was diluted in the cell-lysis buffer provided with the Nano-Glo® and added to the co-cultures in 96-well plate for assessing enzyme activity. Following a brief incubation period of 3 minutes, bioluminescence was read on a microplate reader (Perkin Elmer, Envision™ Multilabel Plate Reader Model: 2104-0010A).

(ii) With COVID-19 patient serum (FIGS. 26A-26D and 27A-27B). For each serum sample, the reporter cell (12,500 in 50 μL of complete RPMI media) was incubated with the respective patient serum at different dilutions (or as stated) for 30 minutes at 37° C., washed once and then co-cultured with 10,000 (or varying numbers) of target SARS-CoV-2-Sgp-cells, in 100 μL of complete RPMI media per well of a 96-well plate. After the 24 hours in co-culture, NanoLuc® (Nluc) activity in the reporter cell was assessed using Nano-Glo® assay as described earlier.

(1.6) Statistical analysis. The experimental design for each panel in the figures is described below. GraphPad Prism 9.2.0 (GraphPad Software, Inc.) was used to conduct all statistical analysis.

(i) FIGS. 25A-25D (Development of method for using the reporter cell complex). Statistical analyses were based on multiple t-tests using a two-stage linear step-up procedure of Benjamini, Krieger, and Yekutieli with a FDR of 1%. There was no adjustment for multiple comparisons. The S/N is calculated as the ratio of the mean Nluc activity in the reporter cell when the reporter cell complex is incubated with Anti-SARS-CoV-1-Sgp-IgG or Anti-SARS-CoV-2-Sgp-IgG antibodies, divided by the mean Nluc activity in the reporter cell when the reporter cell complex is incubated with Anti-WNV-Egp-IgG antibodies. The error bars extend 1 SD above and below the mean and can also be considered as one half the width of a 68% confidence interval for the mean.

(ii) FIG. 25A (Nluc activity in the reporter cell is proportional to the concentration of antibodies). The Nluc activity in the reporter cell when stimulated by the target SARS-CoV-1-Sgp-cells was fitted using a semi-log logistic model $Y=a+b*\log 10(X)$, where X is the concentration (ng) of IgG antibodies used to coat the reporter cell, a=Y-intercept, and b=Slope.

(iii) FIG. 25B (Nluc activity in the reporter cell is a function of duration of stimulation). The Nluc activity in the Anti-SARS-CoV-1-Sgp-coated (or Anti-WNV-Egp-coated) reporter cell stimulated by the target cells (SARS-CoV-1-Sgp-cells) was fitted using a four-parameter logistic model $Nluc=Nluc_{min}+\{Nluc_{max}-Nluc_{min}\}/\{1+10\hat{}[b*(\log_{10}[Time_{50}]-X)]\}$; where X is the $\log_{10}$ of the duration of activation (hours) by the target cells, $Nluc_{max}$ is an estimated parameter defining a upper asymptote for Nluc activity, $Nluc_{min}$ is an estimated parameter defining a lower asymptote for Nluc activity, b is a "Hill" parameter defining the slope at the inflection point of the fitted curve, and $Time_{50}$ is an estimated parameter representing the X value corresponding to $(Nluc_{max}-Nluc_{min})/2$.

(iv) FIGS. 25C-25D (Nluc activity in the reporter cell is proportional to the target cell count). The Nluc activity in the reporter cell when stimulated by the target SARS-CoV-1-Sgp-cells or SARS-CoV-2-Sgp-cells was fitted using a four-parameter logistic model $Nluc=Nluc_{min}+\{Nluc_{max}-Nluc_{min}\}/\{1+10\hat{}[b*(\log_{10}[Target_{50}]-X)]\}$; where X is the $\log_{10}$ of the target cell count, $Nluc_{max}$ is an estimated parameter defining a upper asymptote for Nluc activity, $Nluc_{min}$ is an estimated parameter defining a lower asymptote for Nluc activity, b is a "Hill" parameter defining the slope at the inflection point of the fitted curve, and $Target_{50}$ is an estimated parameter representing the X value corresponding to $(Nluc_{max}-Nluc_{min})/2$. FIG. 25C shows results with Anti-SARS-CoV-1-IgG (S230) while FIG. 25D shows results with Anti-SARS-CoV-2-IgG (Anti-WNV-IgG as negative control in both experiments).

(v) FIGS. 26A-26D (Characterization of the reporter cell complex for serology test using a commercial serum panel). Statistical analysis was based on an unpaired two-tailed student's t-test with common variance and the p-value of <0.05 was considered statistically significant. Statistical analysis for FIG. 26B was based on multiple t-tests using a two-stage linear step-up procedure of Benjamini, Krieger, and Yekutieli with a FDR of 1%. The error bars extend 1 SD above and below the mean and can also be considered as one half the width of a 68% confidence interval for the mean.

(vi) FIG. 26A (Reporter cell complex differentiates between positive patient sera and negative sera samples). An estimation plot (confidence interval of 95%) shows the difference between positive patient sera and negative sera samples, using an unpaired two-tailed student's t-test, assuming Gaussian distribution and that both sample means have the same standard deviations.

(vii) FIG. 26B (Specificity of the reporter cell complex in differentiating sera samples with varying IgG antibody titers). The Nluc activity in the serum-coated reporter cell stimulated by the target SARS-CoV-2-Sgp-cells was fitted using a straight-line equation $Y=a+b*\log_{10}(X)$; where X is the target cell count used to activate the reporter cell, a=Y-intercept, and b=Slope.

(viii) FIG. 26C (ROC curve analysis). The ROC curve analysis was performed using the Wilson/Brown method at 95% Confidence Interval, and results on the ROC curve are expressed as percentages. Abbott Architect SARS-CoV-2-IgG assay was used to classify patient samples.

(ix) FIG. 26D (Correlation between the reporter cell complex serology test and the gold standard test). Simple linear regression was used to plot the goodness of fit between the two assays and determine the $R^2$ statistic, while the nonparametric Pearson-Spearman method was used to determine the correlation coefficient, R. A two-tailed p-value was used to determine if the correlation between the two assays is significant.

(x) FIG. 27A (Clinical validation of the reporter cell complex for detecting COVID-19 IgG antibodies in patients). A scatterplot shows the difference between COVID-19 patient sera and control sera samples, using an unpaired two-tailed student's t-test, assuming a Gaussian distribution with a Welch's correction since standard deviations are not assumed equal.

(xi) FIG. 27B (ROC curve analysis). The ROC curve analysis was performed using the Wilson/Brown method at 95% Confidence Interval, and results on the ROC curve are expressed as percentages. RT-qPCR results were used to determine clinical status and classify patient serum.

(xii) FIG. 28 (Sensitivity of the reporter cell complex while using serially diluted sera). The difference between the multiple box plots was determined using the Holm-Sidak method, assuming that all sample groups had similar standard deviations.

(xiii) Table 3 and Table 4 (Contingency table analysis for human COVID-19 sera samples). Confidence intervals for the specificities, sensitivities, and predictive values were calculated using the Wilson/Brown method. The p-values were calculated using the Fisher's exact t-test. Table 3 shows results using a commercial serum panel while Table 4 shows results using clinical samples from UC Davis Health.

Table 5 below provides a list of genes used to engineer example reporter cells and target cells.

TABLE 5

List of genes used to engineer the reporter cells and target cells

| GENETIC ELEMENT | SEQ ID NO |
|---|---|
| SARS-CoV-2 Sgp | SEQ ID NO: 1 |
| SARS-CoV-1 Sgp | SEQ ID NO: 2 |
| ZZ domain (Fc-region-binding domain from the bacterial Protein A) | SEQ ID NO: 55 |
| Luc2 | SEQ ID NO: 8 |
| E2 Crimson | SEQ ID NO: 9 |
| Luc2-P2a-E2 Crimson | SEQ ID NO: 10 |
| GFP | SEQ ID NO: 11 |
| Nluc | SEQ ID NO: 12 |
| P2a | SEQ ID NO: 13 |
| GFP-P2a-Nluc | SEQ ID NO: 14 |
| Plasmid 2 (SARS-CoV-2 Sgp) | SEQ ID NO: 16 |
| Plasmid 3 (SARS-CoV-1 Sgp) | SEQ ID NO: 17 |
| Plasmid 26 (ZZ domain) | SEQ ID NO: 56 |

Various embodiments are implemented in accordance with the underlying Provisional Applications: Ser. No. 63/142,315, entitled "SARS-CoV-2 Specific Therapeutic Cell Biofactory," filed Jan. 27, 2021; Ser. No. 63/222,784, entitled "Diagnostic-Cell Platform for Antigen Testing," filed Jul. 16, 2021; and Ser. No. 63/255,380, entitled "Cell-based Serological Test for Covid-19," filed Oct. 13, 2021, to which benefit is claimed and which are fully incorporated herein by reference for their general and specific teachings. For instance, embodiments herein and/or in the Provisional Applications can be combined in varying degrees (including wholly). Reference can also be made to the experimental teachings and underlying references provided in the underlying Provisional Applications. Further embodiments are implemented in accordance with the underlying U.S. application Ser. No. 15/263,078, entitled "Genetically Engineered Cells as a Modular Platform for Cell-based Medicine", filed on Sep. 12, 2016, to which benefit is claimed, as a continuation-in-part, and which is fully incorporated herein by reference for its general and specific teachings. Embodiments discussed in the Provisional Applications are not intended, in any way, to be limiting to the overall technical disclosure, or to any part of the claimed disclosure unless specifically noted. In some embodiments, the genetically modified effector cells, diagnostic cells, and/or reporter cells can include at least some of the components or features as described by Repellin C E, et al., entitled "Modular Antigen-Specific T-cell Biofactories for Calibrated In Vivo Synthesis of Engineered Proteins", Advanced Biosystems, 2(12):1800210 (2018), and Repellin C E, et al, entitled "NK-Cell Biofactory as an Off-the-Shelf Cell-based Vector for Targeted In Situ Synthesis of Engineered Proteins", Advanced BioSystems 5(7): 2000398 (2021), each of which are hereby incorporated in their entirety for their teaching.

Although specific embodiments have been illustrated and described herein, a variety of alternate and/or equivalent implementations can be substituted for the specific examples shown and described without departing from the scope of the present disclosure. This application is intended to cover any adaptations or variations of the specific embodiments and examples discussed herein.

The invention claimed is:

1. A genetically engineered effector cell comprising an exogenous polynucleotide sequence that includes, in operative association, and on a single construct:

a receptor element that encodes a chimeric antigen receptor (CAR) comprising an extracellular antigen binding domain operably linked to a transmembrane domain, and an intracellular signaling domain, wherein the extracellular antigen binding domain is a portion of an antibody that recognizes an antigen on a surface of a Severe Acute Respiratory Syndrome Coronavirus 2 (SARS-CoV-2)-infected cell, and wherein the CAR is configured to cause a rise in calcium in response to the antigen binding domain binding to the antigen of the SARS-CoV-2-infected cell;

an actuator element that encodes a transcription factor binding site that upregulates synthesis of an antiviral protein in response to the antigen binding domain of the CAR binding to the antigen of the SARS-CoV-2-infected cell, wherein the transcription factor binding site is configured to bind to a transcription factor protein that is triggered by the rise in calcium and is translocated into the nucleus of the genetically engineered cell; and an effector element that encodes the antiviral protein configured to provide a therapeutic effect for an infection associated with the SARS-CoV-2-infected cell, the antiviral protein comprising an interferon, wherein, in response to the antigen binding domain of the CAR binding to the antigen of the SARS-CoV-2-infected cell, the genetically engineered effector cell is configured to activate and, to synthesize and secrete the antiviral protein, wherein the genetically engineered effector cell is configured to synthesize and secrete an amount of the antiviral protein as a function of an amount of the SARS-CoV-2-infected cell present in a sample or in situ.

2. The effector cell of claim 1, wherein the amount of the antiviral protein is proportional to the amount of SARS-CoV-2-infected cell present in situ, and the antiviral protein is configured to neutralize the SARs-CoV-2 infected cell.

3. The effector cell of claim 1, wherein the effector element further encodes a signal peptide upstream of the antiviral protein, the signal peptide being non-native to the antiviral protein.

4. The effector cell of claim 1, wherein the antiviral protein is selected from the group consisting of:

a Type-1 interferon (IFN), a Type-3 IFN, and a combination thereof.

5. The effector cell of claim 1, wherein the activation of the genetically engineered effector cell is configured to regulate stimulation of cytokines in a host.

6. The effector cell of claim 1, wherein the genetically engineered effector cell comprises a T-cell, a natural killer cell, a pluripotent stem cell, a multipotent stem cell, an epithelial cell, or a K562 cell, and the exogenous polynucleotide sequence comprises a sequence with at least 80% sequence identity to a sequence selected from SEQ ID Nos: 18-22 and 24.

7. The genetically engineered effector cell of claim 1, wherein the antigen on the surface of the SARS-CoV-2-infected cell comprises the spike glycoprotein or envelope glycoprotein of SARS-CoV-2, and the extracellular antigen binding domain comprises a sequence with at least 80% sequence identity to a sequence selected from SEQ ID Nos: 3 and 25-29.

8. The genetically engineered effector cell of claim 1, wherein the intracellular signaling domain includes one or more of:

an intracellular signaling portion of a CD28, an intracellular signaling portion of a 4-1BB, and an intracellular signaling portion of a CD3 zeta.

9. The genetically engineered effector cell of claim 1, wherein;

the transcription factor binding site is selected from the group consisting of:

a nuclear factor of activated T-cell (NFAT) response element, a serum response element (SRE), and a cyclic AMP response element (CRE);

the intracellular signaling domain comprises:

an intracellular signaling portion of a CD28 and an intracellular signaling portion of a CD3 zeta; and the transmembrane domain is selected from the group consisting of:

T-cell receptor $\alpha$ or $\beta$ chain, a CD3$\zeta$ chain, CD28, CD3$\varepsilon$, CD45, CD4, CD5, CD8, CD9, CD16, CD22, CD33, CD37, CD64, CD80, CD86, CD134, CD137, ICOS, CD154, and a GITR.

10. A population of genetically engineered effector cells, each of the genetically engineered effector cells of the population comprising an exogenous polynucleotide sequence that includes an actuator element, an effector element, and a receptor element, wherein:

the receptor element encodes a chimeric antigen receptor (CAR) comprising an extracellular antigen binding domain operably linked to a transmembrane domain, and an intracellular signaling domain, wherein the extracellular antigen binding domain recognizes an antigen on a surface of a Severe Acute Respiratory Syndrome Coronavirus 2 (SARS-CoV-2)-infected cell, and wherein the CAR is configured to cause a rise in calcium in response to the antigen binding domain binding to the antigen of the SARS-CoV-2-infected cell;

the actuator element encodes a transcription factor binding site that upregulates synthesis of an antiviral protein in response to the antigen binding domain of the CAR binding to the antigen of the SARS-CoV-2-infected cell, wherein the transcription factor binding site is configured to bind to a transcription factor protein that is triggered by the rise in calcium and is translocated into the nucleus of the genetically engineered cell; and the effector element encodes the antiviral protein configured to provide a therapeutic effect for an infection associated with the SARS-CoV-2-infected cell, the antiviral protein comprising an interferon, wherein, in response to the antigen binding domain of the CAR binding to the antigen of the SARS-CoV-2-infected cell, the population of genetically engineered effector cells are configured to activate and, in response, to synthesize and secrete a calibrated amount of the antiviral protein based on a presence of the SARS-CoV-2-infected cell.

11. The population of genetically engineered effector cells of claim 10, wherein the antiviral protein includes a first antiviral protein and a second antiviral protein, and a first subset of the population includes the effector element that encodes the first antiviral protein and a second subset of the population includes the effector element that encodes the second antiviral protein or the effector element include the first antiviral protein bound to the second antiviral protein by a 2A linker peptide, wherein the first antiviral protein and the second antiviral protein comprise different interferons.

12. The population of genetically engineered effector cells of claim 11, wherein the first antiviral protein includes a Type-1 interferon (IFN) and the second antiviral protein includes a Type-3 IFN.

13. The population of genetically engineered effector cells of claim 11, wherein antigen includes the spike glycoprotein of SARS-CoV-2 and the antiviral protein is configured to cause action on the SARS-CoV-2-infected cell to treat or prevent a coronavirus infection, and wherein the spike glycoprotein comprises a sequence with at least 80% sequence identity to a sequence selected from SEQ ID Nos: 1-2.

14. The population of genetically engineered effector cells of claim 10, wherein the calibrated amount of the antiviral protein is a function of an amount of the SARS-CoV-2-infected cell present in a plurality of cells or in a sample.

15. A method comprising contacting a plurality of cells with a volume of the genetically engineered effector cell of claim 1.

16. The method of claim 15, further including detecting expression of the antiviral protein, wherein detectable expression of the antiviral protein indicates the presence of the SARS-CoV-2-infected cell.

17. The method of claim 15, further including, in response to the antigen binding domain of the CAR binding to the antigen of the SARS-CoV-2-infected cell, activating the effector cell and, in response, synthesizing and secreting a calibrated amount of the antiviral protein based on the presence of the SARS-CoV-2-infected cell.

18. The method of claim 17, wherein the calibrated amount of the antiviral protein is proportional to an amount of the SARS-CoV-2-infected cell present within the plurality of cells.

19. The method of claim 15, wherein the antiviral protein includes an interferon (IFN), and the method further includes neutralizing the SARS-CoV-2-infected cell by the IFN.

* * * * *